(12) United States Patent
Behnke et al.

(10) Patent No.: US 11,458,138 B2
(45) Date of Patent: Oct. 4, 2022

(54) 6-6 FUSED BICYCLIC HETEROARYL COMPOUNDS AND THEIR USE AS LATS INHIBITORS

(71) Applicant: Novartis AG, Basel (CH)

(72) Inventors: Dirk Behnke, Basel (CH); Frada Berenshteyn, Woburn, MA (US); Xueshi Hao, San Diego, CA (US); Timothy Hoffman, San Diego, CA (US); Qihui Jin, San Diego, CA (US); Arnaud Lacoste, Cambridge, MA (US); Cameron Lee, Cambridge, MA (US); Jun Liu, San Diego, CA (US); Yahu Liu, San Diego, CA (US); Juergen Klaus Maibaum, Basel (CH); Tingting Mo, Saratoga, CA (US); Jianfeng Pan, San Diego, CA (US); Xin Qu, Cambridge, MA (US); Jan Tchorz, Basel (CH); Yun Feng Xie, San Diego, CA (US); Shanshan Yan, San Diego, CA (US); Yefen Zou, San Diego, CA (US)

(73) Assignee: Novartis AG, Basel (CH)

( * ) Notice: Subject to any disclaimer, the term of this patent is extended or adjusted under 35 U.S.C. 154(b) by 932 days.

(21) Appl. No.: 15/963,816

(22) Filed: Apr. 26, 2018

(65) Prior Publication Data
US 2018/0344738 A1    Dec. 6, 2018

Related U.S. Application Data

(60) Provisional application No. 62/491,475, filed on Apr. 28, 2017, provisional application No. 62/491,484, (Continued)

(51) Int. Cl.
*A61K 31/4375*    (2006.01)
*A61K 31/519*    (2006.01)
*C07D 487/04*    (2006.01)
*C12N 5/079*    (2010.01)
*C07D 519/00*    (2006.01)
*A61P 17/02*    (2006.01)
*A61K 9/00*    (2006.01)
(Continued)

(52) U.S. Cl.
CPC .......... *A61K 31/519* (2013.01); *A61K 9/0048* (2013.01); *A61K 31/4375* (2013.01); *A61K 31/47* (2013.01); *A61K 31/506* (2013.01); *A61P 17/02* (2018.01); *C07D 487/04* (2013.01); *C07D 519/00* (2013.01); *C12N 5/0621* (2013.01); *A61K 35/30* (2013.01); *C12N 15/52* (2013.01); *C12N 15/8645* (2013.01); *C12N 2310/20* (2017.05); *C12N 2502/085* (2013.01); *C12N 2502/1352* (2013.01); *C12N 2502/27* (2013.01)

(58) Field of Classification Search
CPC .......................... A61K 31/4375; C07D 471/04
See application file for complete search history.

(56) References Cited

U.S. PATENT DOCUMENTS

2011/0319409 A1    12/2011    Cox et al.

FOREIGN PATENT DOCUMENTS

EP            2733201            5/2014
JP       2008531538 A           8/2008
(Continued)

OTHER PUBLICATIONS

Gain at el.: "Global Survey of Corneal Transplantation and Eye Banking", (2016), JAMA Ophthalmology, vol. 134, No. 2, pp. 167-173.
(Continued)

*Primary Examiner* — Timothy P Thomas
(74) *Attorney, Agent, or Firm* — Asha K. Nadipuram

(57) ABSTRACT

The present invention is related to 6-6 Fused Bicyclic Heteroaryl Compounds of the Formula A2 or A1 and their Use as LATS Inhibitors, or a salt, stereoisomer or pharmaceutical composition thereof; wherein the variables are as defined herein.

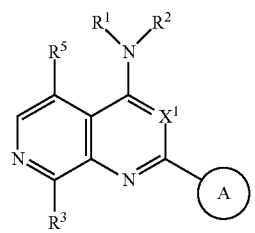

A2

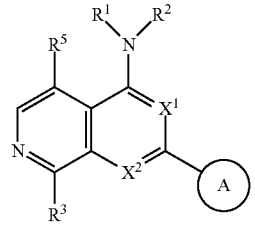

A1

The present invention further relates to a method of LATS inhibition in a cell population using a compound of Formula A1, or a salt, stereoisomer or pharmaceutical composition thereof. The present invention further provides a method for manufacturing compounds of the invention, and its therapeutic uses. The invention further provides methods to their preparation, to their medical use, their use in the treatment and management of diseases or disorders.

14 Claims, 40 Drawing Sheets

Specification includes a Sequence Listing.

Related U.S. Application Data filed on Apr. 28, 2017, provisional application No. 62/491,573, filed on Apr. 28, 2017, provisional application No. 62/491,526, filed on Apr. 28, 2017, provisional application No. 62/650,232, filed on Mar. 29, 2018.

(51) Int. Cl.

| | | |
|---|---|---|
| A61K 31/47 | (2006.01) | |
| A61K 31/506 | (2006.01) | |
| A61K 35/30 | (2015.01) | |
| C12N 15/52 | (2006.01) | |
| C12N 15/864 | (2006.01) | |

(56) References Cited

FOREIGN PATENT DOCUMENTS

| | | |
|---|---|---|
| JP | 2011529920 A | 12/2011 |
| RU | 2014114973 A | 11/2015 |
| WO | 2004/065392 A1 | 8/2004 |
| WO | 2006/090169 A1 | 8/2006 |
| WO | 2008/122614 A1 | 10/2008 |
| WO | 2010/014939 A1 | 2/2010 |
| WO | 2013/045461 A1 | 4/2013 |
| WO | 2014/052699 A1 | 4/2014 |
| WO | 2015/148597 | 10/2015 |
| WO | 2016/046768 A1 | 3/2016 |
| WO | 2017/023905 A1 | 2/2017 |
| WO | 2017/035116 A1 | 3/2017 |
| WO | 2018/198077 | 11/2018 |

OTHER PUBLICATIONS

Rama, P. et al.: "Limbal stem-cell therapy and long-term corneal regeneration" N Engl J Med., (2010), vol. 363, pp. 147-155.
Forbes SJ and Newsome PN: "Liver regeneration—mechanisms and models to clinical application", (2016), Nature Reviews Gastroenterology & Hepatology, vol. 13 No. 8, pp. 473-485.
Dutkowski, P. et al.: "Challenges to Liver Transplantation and Strategies to Improve Outcomes", (2015), Gastroenterology, 148(2):307-323.
Demidova-Rice, T. N. et al.: "Acute and impaired wound healing: pathophysiology and current methods for drug delivery, part 1: normal and chronic wounds: biology, causes, and approaches to care", (2012) Advances in Skin & Wound Care, 25(7):304-314.
Demidova-Rice, T. N. et al.: "Acute and impaired wound healing: pathophysiology and current methods for drug delivery, part 2: role of growth factors in normal and pathological wound healing: therapeutic potential and methods of delivery", (2012), Advances in Skin & Wound Care, 25(8):349-370.
Eaglstein, W. H. et al.: "Food and Drug Administration (FDA) drug approval end points for chronic cutaneous ulcer studies", (2012) Wound repair and regeneration: official publication of the Wound Healing Society [and] the European Tissue Repair Society, 20(6):793-796.
Panda et al.: "Fibrin glue in opthamology", Indian J Opthalmology, (Baxter AG, Vienna, Austria), Sep.-Oct. 2009; 57(5):371-379.
Barry, E.R. et al.: "The Hippo superhighway: signaling crossroads converging on the Hippo/Yap pathway in stem cells and development", (2013), Current opinion in cell biology, 25(2):247-253.
Mo, J.S. et al.: "The Hippo signaling pathway in stem cell biology and cancer", (2014), EMBO reports 15(6):642-656.
Pan, D.: "The hippo signaling pathway in development and cancer", (2010), Developmental cell, 19(4):491-505.
Nishio, M. et al.: "Hippo vs. Crab: tissue-specific functions of the mammalian Hippo pathway", (2017), Genes to Cells, vol. 22, pp. 6-31.
Kaufman et al.:"Optisol corneal storage medium", Arch Ophthalmol., Jun. 1991, 109(6): 864-8.
Kim, H. et al:"Therapeutic Cell Delivery for Regeneration of Corneal Endothelium", JSM Biotechnol. Bioeng., 2016, p. 1047.
Holland E.J. et al.: "Systemic immunosuppression in ocular surface stem cell transplantation: results of a 10-year experience". Cornea, Jun. 2012, 31(6):655-61.
Chen et al., 2016, Molecular Therapy, 24:447-457; Gornalusse et al., Nature Biotechnology, 2017, 35(8):765-772.
Flotte, T. R. et al.: "Adeno-associated virus-based gene therapy for inherited disorders", Pediatr Res., Dec. 2005, 58(6):1143-7.
Goncalves M. A. et al.:"Adeno-associated virus: from defective virus to effective vector", Virol J, May 6, 2005, 2:43.
Surace, E. and Auricchio, A.: "Adeno-associated viral vectors for retinal gene transfer", Prog Retin Eye Res., (2003), 22(6):705-19.
Mandel R. J. et al.: "Recombinant adeno-associated viral vectors as therapeutic agents to treat neurological disorders", Mol Ther., Mar. 2006, 13(3):463-83.
Zetsche et al.: "Cpf1 is a Single RNA-Guided Endonuclease of a Class 2 CRISPR-Cas System", Cell, (2015), 163:759-771.
Grissa et al.: "The CRISPRdb database and tools to display CRISPRs and to generate dictionaries of spacers and repeats", (2007), BMC Bioinformatics 8:172.
Barrangou et al. (2007) Science 315: 1709-1712; Marragini et al. (2008) Science 322: 1843-1845.
Wiedenheft et al.: "RNA-guided genetic silencing systems in bacteria and archaea", (2012), Nature, 482: 331-8.
Haft et al.: "A Guide of 45 CRISPR-Associated (Cas) Protein Families and Multiple CRISPR/Cas Subtypes Exist in Prokaryotic Genomes", (2005), PLoS Comput. Biol., 1: e60.
Kunin et al: "Evolutionary conservation of sequence and secondary structures in CRISPR repeats", (2007), Genome Biology, 8: R61.
Mojica et al.: "Intervening Sequences of Regularly Spaced Prokaryotic Repeats Derive from Foreign Genetic Elements," (2005), J. Mol. Evol., 60:174-182.
Bolotin et al.: "Clustered regularly interspaced short palindrome repeats (CRISPRs) have spacers of extrachromosal origin", (2005), Microbiol.,151: 2551-2561.
Pourcel et al.:"CRISPR elements in Yersinia pestis acquire new repeats by preferential uptake of bacteriophage DNA, and provide additional tools for evolutionary studies", (2005), Microbiol., 151: 653-663.
Stern et al.: "Self-targeting by CRISPR: gene regulation or autoimmunity?",(2010), Trends. Genet., 28:335-340.
Brouns et al.:"Small CRISPR RNAs Guide Anitviral Defense in Prokaryotes", (2008), Science, 321: 960-964.
Pennisi, Elizabeth: "The CRISPR Craze," (2013), Science, 341: 833-836.
Mali et al."RNA-Guided Human Genome Engineering via Cas9", Science, 2013, 339(6121): 823-826.
Horvath et al., Science 2010; 327(5962): 167-170.
Deveau et al, J Bacteriol 2008; 190(4): 1390-1400.
Ran F. et al., Nature, vol. 520, 2015, pp. 186-191.
Hou et al.: "Efficient genome engineering in human pluripotent stem cells using Cas9 from Neisseria meningitidis", PNAS Early Edition 2013, 1-6.
Jinek et al: A Programmable Dual-RNA-Guided DNA Endonuclease in Adaptive Bacterial Immunity, Science 2012, 337:816.
Slaymaker et al., Science Express, available online Dec. 1, 2015 at Science DOI: 10.1126/science.aad5227.
Kleinstiver et al.:High-fidelity CRISPR-Cas9 nucleases with no detectable genome-wide off-target effects, Nature, 529, 2016, pp. 490-495.
Sorokin, A.V. et al.:"Nucleocytoplasmic Transport of Proteins", Biochemistry (Moscow) (2007) 72:13, 1439-1457.
Lange J. et al, "Classical Nuclear Localization Signals: Definition, Function, and Interaction with Importin," Biol Chem., (2007), 282:8, pp. 5101-5105.
Loew et al.: "Improved Tet-responsive promoters with minimized background expression", (2010), BMC Biotechnol., 10:81.
Banaszynski et al: "A Rapid, Reversible, and Tunable Method to Regulate Protein Function in Living Cells Using Synthetic Small Molecules", (2016), Cell, 126: 995-1004.
Davis et al.: "Tamoxifen induced protein activation", (2015), Nat. Chem. Biol., 11: 316-318.

(56) References Cited

OTHER PUBLICATIONS

Rapamycin or optogenetic induced activation or dimerization of split Cas9 Zetsche (2015) Nature Biotechnol. 33(2): 139-142.
Nihongaki et al.:Photoactivatable CRISPR-Cas9 for optogenetic genome editing, (2015), Nature Biotechnol., 33(7): 755-760.
Polstein and Gersbach: "A light-inducible CRISPR-Cas9 system for control of endogenous gene activation",(2015), Nat. Chem. Biol., 11: 198-200.
Chung et al.: SMASh tag drug inducible degradation, (2015), Nat. Chem. Biol. 11: 713-720.
Zuker and Stiegler: "Optimal computer folding of RNA sequences using thermodynamics and auxiliary information", Nucleic Acids Res. 9, (1981), 133-148.
A.R. Gruber et al.: Genes and Mechanisms Related to RNA Interference Regulate Express of the Small Temporal RNAs that Control C. elegans Developmental Timing, (2008), Cell, 106(1): 23-34.
Carr, P.A. et al.: "Genome engineering", 2009, Nature Biotechnology, 27(12): 1151-62.
Boch J.: "TALEs fo genome targeting", (2011), Nature Biotech., 29:135-6.
Boch et al.: Breaking the Code of DNA Binding Specificity of TAL-Type III Effectors, (2009), Science, vol. 326, pp. 1509-1512.
Moscou et al.: A Simple Cipher Governs DNA Recognition by TAL Effectors, (2009), Science, 326: 3501.
Cermak et al.: Efficient design and assembly of custom TALEN and other TAL effector-based contstructs for DNA Targeting, (2011), Nucl. Acids Res., 39: e82.
Miller et al.: A TALE nuclease architecture for efficient genome editing, (2011), Nature Biotech., 29: 143-8.
Hockemeyer et al.: "Genetic engineering of human pluripotent cells using TALE nucleases", (2011), Nature Biotech., 29: 731-734.
Wood et al.:Targeted Gemone Editing Across Species Using ZFNs and TALENS, (2011), Science, 333(6040): 307.
Doyon et al.: Enhancing zinc-finger-nuclease activity with improved obligate heterodimeric architectures, (2011), Nature Methods, vol. 8, No. 1, pp. 74-79.
Szczepek et al.: "Structure-based redesign of the dimerization interface reduces the toxicity of zinc-finger nucleases", (2007), Nature Biotech., vol. 25, No. 7, pp. 786-793.
Guo et al.: Directed evolution of an enhanced and highly efficient Fok; cleavage domain for Zinc Finger Nucleases, (2010) ,J. Mol. Biol. 400: 96-107.
Zhang et al.: "Programmable Sequence-Specific Transcriptional Regulation of Mammalian Genome Using Designer TAL Effectors", (2011), Nature Biotech., 29:149-53.
Geibler et al., (2011) PLoS One, vol. 6, No. 5, e19509.
Carroll et al.: "Genome Engineering With Zinc-Finger Nucleases", (2011), Genetics Society of America 188: 773-782.
Kim et al.: "Hybrid restriction enzymes: Zinc finger fusions to Fok I cleavage domain", (1996), Proc. Natl. Acad. Sci. USA, 93: 1156-1160.
Bitinaite et al.: "FokI dimerization is required for DNA cleavage", (1998), Proc. Natl. Acad. Sci. USA, vol. 95, pp. 10570-10575.
Provasi et al.: "Editing T cell specificity towards leukemia by zinc finger nucleases and lentiviral gene transfer", (2011), Nature Med., vol. 18, No. 5, pp. 807-815.
Torikai, H. et al.: Toward eliminating HLA class I expression to generate universal cells from allogeneic donors, (2013),Blood, 122: 1341-1349.
Cathomen et al.:Zinc-finger Nucleases: The Next Generation Emerges, (2008), Mol. Ther. 16(7): 1200-7.
Fujise et al.: "Integration of Hepatitis B Virus DNA into Cells of Six Established Human Hepatoceullular Carcinoma Cell Lines", Hepatogastroenterology, Oct. 1990, 37(5):457-60.
Chevalier et al.: "Homing endonucleases: structural and functional insight into the catalysts of intron/intein mobility", (2001), Nucleic Acids Res., 29(18): 3757-3774.

Van Roey, P. et al.: "Catalytic domain structure and hypothesis for function of GIY-YIG intron endonuclease I-Tevl", (2002), Nature Struct. Biol., 9: 806-811.
Carpenter et al.: "CellProfiler: image analysis software for identifying and quantifying cell phenotypes", Genome Biol. 2006, vol. 7, Issue 10, Article R100.
Chevalier et al.: "Design, Activity, and Structure of a Highly Specific Artificial Endonuclease", (2002), Mol. Cell., 10:895-905.
Epinat et al.: "A novel engineered meganuclease induces homolgous recombination in yeast and mammalian cells", (2003), Nucleic Acids Res., 31: 2952-62.
Silva et al.: "From Monomeric to Homodimeric Endonucleases and Back: Engineering Novel Specificity of LAGLIDADG Enzmes", (2006), J Mol Biol, 361: 744-54.
Seligman et al.: "Mutations altering the cleavage specificity of a homing endonuclease", (2002), Nucleic Acids Res, vol. 30, No. 17, pp. 3870-3879.
Sussman et al.: "Isolation and Characterization of New Homing Endonuclease Specificities at Individual Target Site Positions", (2004), J Mol. Biol., 342: 31-41.
Rosen et al.: "Homing endonuclease I-CreI derivatives with novel DNA target specificities", (2006), Nucleic Acids Res., (2006), vol. 34, No. 17, pp. 4791-4800.
Doyon et al.: "Directed Evolution and Substrate Specificity Profile of Homing Endonuclease I-SceI", (2006), J. Am. Chem. Soc., 128: 2477-84.
Chen et al.: "Directed evolution of homing endonuclease I-SceI with altered sequence specificity", (2009), Protein Eng. Des. & Sel., vol. 22, No. 4, pp. 249-256.
Arnould, S. et al.: "Engineering of Large Numbers of Highly Specific Homing Endonucleases that Induce Recombination on Novel DNA Targets",(2006), J. Mol. Biol., 355: 443-58.
Smith (2006) Nucleic Acids Res. 363(2): 283-94.
Silva et al. (2011) Current Gene Therapy 11:11-27.
Van Den Bulcke et al.: "Structural and Rheological Properties of Methacrylamide Modified Gelatin Hydrogels", Biomacromolecules, (2000), vol. 1, p. 31-38.
Yue et al.: "Synthesis, properties, and biomedical applications of gelatin methacryloyl (GelMA) hydrogels", Biomaterials, (2015), vol. 73, p. 254-271.
Thomas, Merina M.D. et al.: "Contact Lens Use in Patients With Boston Keratoprosthesis Type 1: Fitting, Management, and Complications", Eye & Contact Lens, Nov. 2015, vol. 41, No. 6, pp. 334-340.
Moysidis, S.N. et al.: "Magnetic field-guided cell delivery with nanoparticle-loaded human corneal endothelial cells", Nanomedicine, Apr. 2015, 11(3):499-509.
Rzany, B. et al.: "Epidemiology of Erythema Multiforme Majus, Stevens-Johnson Syndrome, and Toxic Epidermal Necrolysis in Germany (1990-1992): Structure and Results of a Population-Based Registry", J. Clin. Epidemiol., vol. 49, pp. 769-773, (1996).
Lu, W. Y. et al.: "Hepatic progenitor cells of biliary origin with liver repopulation capacity", (2015), Nat. Cell Biol., vol. 17, No. 8, pp. 971-983.
Written Opinion of the International Searching Authority for PCT/IB2018/052919 dated Dec. 11, 2018.
Karabekian et al.: "HLA Class I Depleted hESC as a Source of Hypoimmunogenic Cells for Tissue Engineering Applications", Tissue Eng Part A. Oct. 2015;21(19-20):2559-71.
Hao et al.: "Tumor Suppressor LATS1 Is a Negative Regulator of Oncogene YAP", J. Biol. Chem., Feb. 29, 2008, 283(9):5496-5509.
Wang et al.: "Selective inhibition of ROCK kinase isoforms to promote neuroregeneration after brain surgery", Med Chem Res, 2016, 25(1): 40-50.
Loureiro et al.: "Comparison of culture media for ex vivo cultivation of limbal epithelial progenitor cells", Mol Vis. 2013;19:69-77.
Parekh et al.: "Concise Review: An Update on the Culture of Human Corneal Endothelial Cells for Transplantation: Corneal Endothelial Cell Culture", Stem Cells Transl Med. Feb. 2016;5(2):258-64.
Fuest et al.: "Advances in corneal cell therapy", Regen Med. Sep. 2016;11(6):601-15.

(56) References Cited

OTHER PUBLICATIONS

Albert et al.: "Cultivation and Characterization of Cornea Limbal Epithelial Stem Cells on Lens Capsule in Animal Material Free Medium", PLoS One. 2012;7(10):e47187.

Trcin et al.: "Synthetic vs natural scaffolds for human limbal stem cells", Croat Med J. Jun. 2015;56(3):246-56.

Torikai et al.: "Genetic editing of HLA expression in hematopoietic stem cells to broaden their human application", Sci Rep. Feb. 23, 2016;6:21757.

Qazi et al.: "Gene Therapy in Corneal Transplantation", Semin Ophthalmol. Sep.-Nov. 2013;28(5-6):287-300.

Van Eis, M. J. et al.: "2,6-Naphthyridines as potent and selective inhibitors of the novel protein kinase C isozymes", Bioorganic & Medicinal Chemistry Letters, (2011), vol. 21, pp. 7367-7372.

CAS Registry No. 1631030-22-2, STN Entry Date Oct. 31, 2014.

Shaharuddin et al., "A Human Corneal Epithelial Cell Line Model for Limbal Stem Cell Biology and Limbal Immunobiology," Stem Cells Transl Med. 6(3):761-66 (2017).

Viser et al., "LATS tumor suppressor: a new governor of cellular homeostasis," Cell Cycle. 9(19):3892-903 (2010).

Chen et al., "Engineered Viruses as Genome Editing Devices," Mol Ther. 24(3):447-457 (2016).

Marraffini et al., "CRISPR interference limits horizontal gene transfer in staphylococci by targeting DNA," Science. 322(5909):1843-5 (2008).

Cermak et al., "Efficient design and assembly of custom TALEN and other TAL effector-based constructs for DNA targeting," Nucleic Acids Res. 39(12):e82 (11 pages).

Silva et al., "Meganucleases and other tools for targeted genome engineering: perspectives and challenges for gene therapy," Curr Gene Ther. 11(1):11-27 (2011).

Kim et al., "Therapeutical Cell Delivery for Regeneration of Corneal Endothelium," JSM Biotechnol Bioeng. 3(1):1047 (6 pages) (2016).

Shaw et al., "Novel ROCK inhibitors for the treatment of pulmonary arterial hypertension," Bioorg Med Chem Lett. 24(20):4812-7 (2014).

Fig. 2A
Fig. 2B
Fig. 2C
Fig. 2D
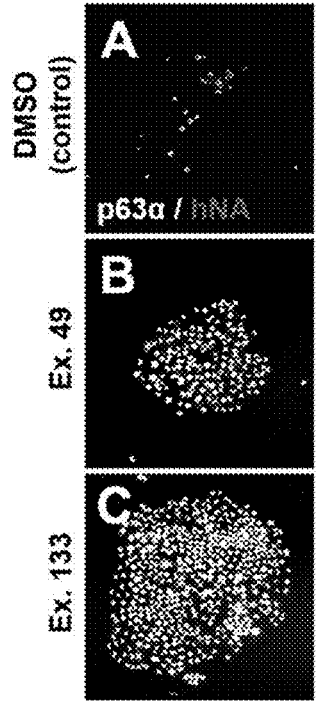
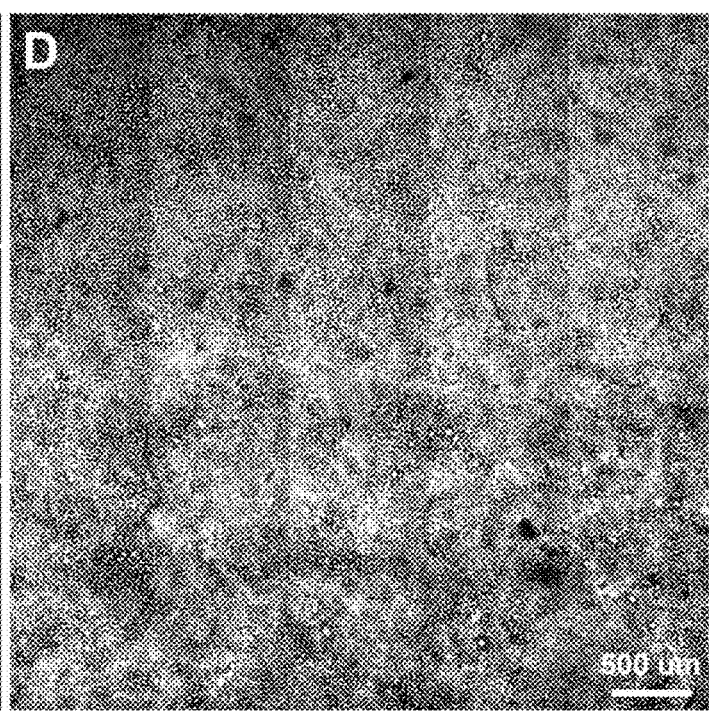

Fig. 7A
Fig. 7B
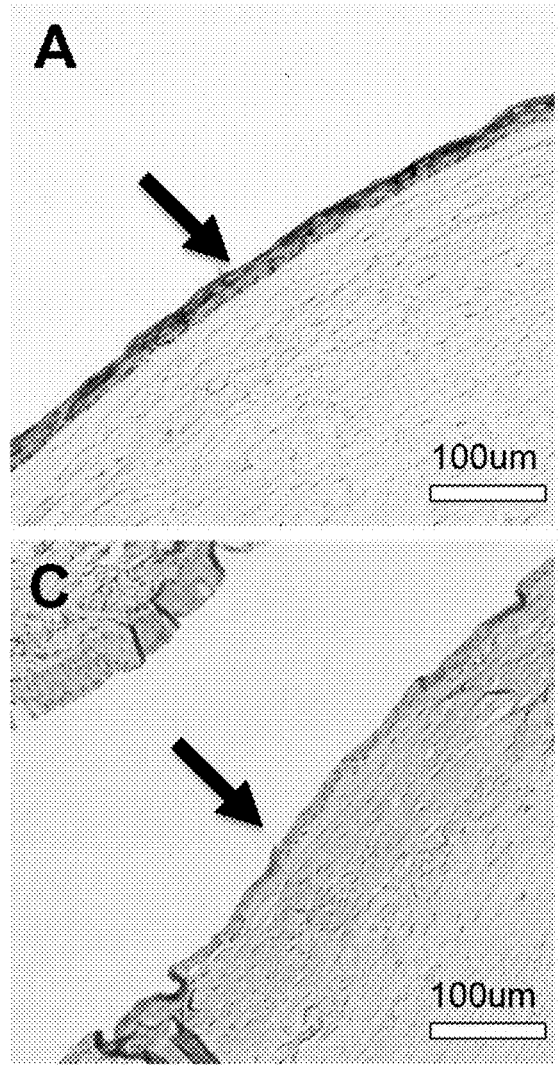
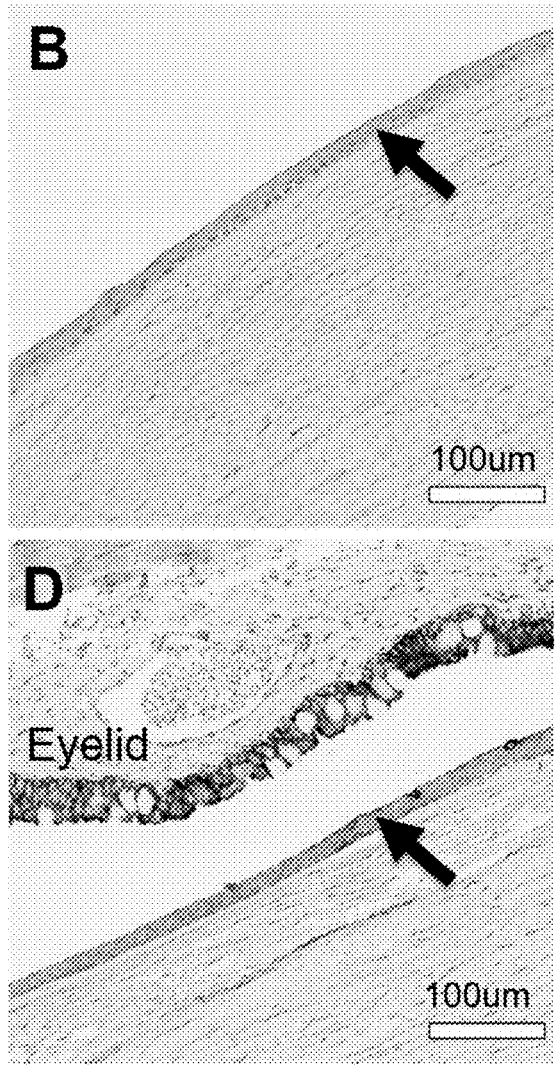
Fig. 7C
Fig. 7D

Fig. 18A
Fig. 18B
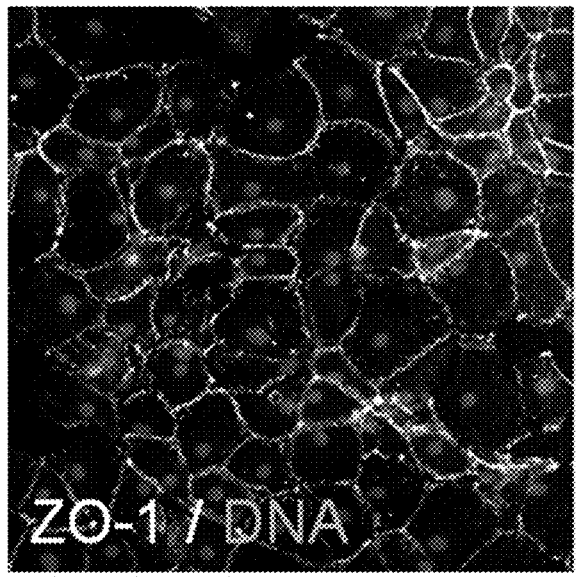
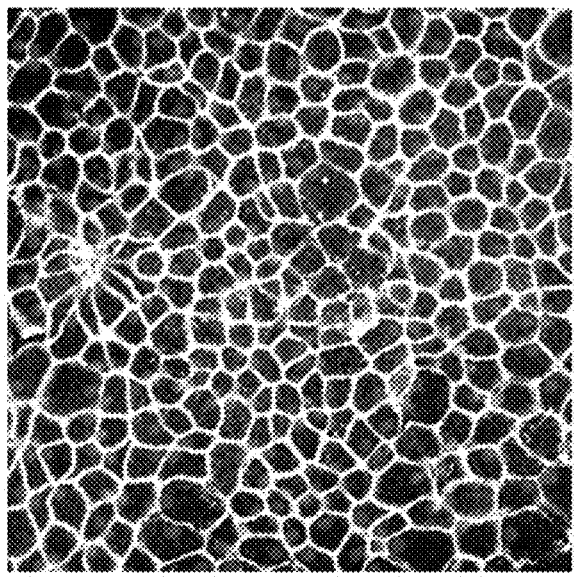

CD44

CD73

CD105

CD166

Light source does not penetrate mask

Thickness of cured layer limited by absorption siRNA Validation p: picomolar

Ex.133 Cellular

Ex 133 (uM):  -  9 pYAP→

ACTIN→

SEQUENCE LISTING

```
<160> NUMBER OF SEQ ID NOS: 31

<210> SEQ ID NO 1
<211> LENGTH: 1130
<212> TYPE: PRT
<213> ORGANISM: Homo sapiens

<400> SEQUENCE: 1

Met Lys Arg Ser Glu Lys Pro Glu Gly Tyr Arg Gln Met Arg Pro Lys
1               5                   10                  15

Thr Phe Pro Ala Ser Asn Tyr Thr Val Ser Ser Arg Gln Met Leu Gln
            20                  25                  30

Glu Ile Arg Glu Ser Leu Arg Asn Leu Ser Lys Pro Ser Asp Ala Ala
        35                  40                  45

Lys Ala Glu His Asn Met Ser Lys Met Ser Thr Glu Asp Pro Arg Gln
    50                  55                  60

Val Arg Asn Pro Pro Lys Phe Gly Thr His His Lys Ala Leu Gln Glu
65                  70                  75                  80

Ile Arg Asn Ser Leu Leu Pro Phe Ala Asn Glu Thr Asn Ser Ser Arg
                85                  90                  95

Ser Thr Ser Glu Val Asn Pro Gln Met Leu Gln Asp Leu Gln Ala Ala
            100                 105                 110

Gly Phe Asp Glu Asp Met Val Ile Gln Ala Leu Gln Lys Thr Asn Asn
        115                 120                 125

Arg Ser Ile Glu Ala Ala Ile Glu Phe Ile Ser Lys Met Ser Tyr Gln
    130                 135                 140

Asp Pro Arg Arg Glu Gln Met Ala Ala Ala Ala Ala Arg Pro Ile Asn
```

```
            145                 150                 155                 160
        Ala Ser Met Lys Pro Gly Asn Val Gln Gln Ser Val Asn Arg Lys Gln
                        165                 170                 175
        Ser Trp Lys Gly Ser Lys Glu Ser Leu Val Pro Gln Arg His Gly Pro
                        180                 185                 190
        Pro Leu Gly Glu Ser Val Ala Tyr His Ser Glu Ser Pro Asn Ser Gln
                        195                 200                 205
        Thr Asp Val Gly Arg Pro Leu Ser Gly Ser Gly Ile Ser Ala Phe Val
                        210                 215                 220
        Gln Ala His Pro Ser Asn Gly Gln Arg Val Asn Pro Pro Pro Pro Pro
        225                 230                 235                 240
        Gln Val Arg Ser Val Thr Pro Pro Pro Pro Arg Gly Gln Thr Pro
                                245                 250                 255
        Pro Pro Arg Gly Thr Thr Pro Pro Pro Ser Trp Glu Pro Asn Ser
                        260                 265                 270
        Gln Thr Lys Arg Tyr Ser Gly Asn Met Glu Tyr Val Ile Ser Arg Ile
                        275                 280                 285
        Ser Pro Val Pro Pro Gly Ala Trp Gln Glu Gly Tyr Pro Pro Pro Pro
                290                 295                 300
        Leu Asn Thr Ser Pro Met Asn Pro Asn Gln Gly Gln Arg Gly Ile
        305                 310                 315                 320
        Ser Ser Val Pro Val Gly Arg Gln Pro Ile Ile Met Gln Ser Ser Ser
                                325                 330                 335
        Lys Phe Asn Phe Pro Ser Gly Arg Pro Gly Met Gln Asn Gly Thr Gly
                        340                 345                 350
        Gln Thr Asp Phe Met Ile His Gln Asn Val Val Pro Ala Gly Thr Val
                        355                 360                 365
        Asn Arg Gln Pro Pro Pro Pro Tyr Pro Leu Thr Ala Ala Asn Gly Gln
                370                 375                 380
        Ser Pro Ser Ala Leu Gln Thr Gly Gly Ser Ala Ala Pro Ser Ser Tyr
        385                 390                 395                 400
        Thr Asn Gly Ser Ile Pro Gln Ser Met Met Val Pro Asn Arg Asn Ser
                                405                 410                 415
        His Asn Met Glu Leu Tyr Asn Ile Ser Val Pro Gly Leu Gln Thr Asn
                        420                 425                 430
        Trp Pro Gln Ser Ser Ser Ala Pro Ala Gln Ser Ser Pro Ser Ser Gly
                        435                 440                 445
        His Glu Ile Pro Thr Trp Gln Pro Asn Ile Pro Val Arg Ser Asn Ser
                        450                 455                 460
        Phe Asn Asn Pro Leu Gly Asn Arg Ala Ser His Ser Ala Asn Ser Gln
        465                 470                 475                 480
        Pro Ser Ala Thr Thr Val Thr Ala Ile Thr Pro Ala Pro Ile Gln Gln
                                485                 490                 495
        Pro Val Lys Ser Met Arg Val Leu Lys Pro Glu Leu Gln Thr Ala Leu
                        500                 505                 510
        Ala Pro Thr His Pro Ser Trp Ile Pro Gln Pro Ile Gln Thr Val Gln
                        515                 520                 525
        Pro Ser Pro Phe Pro Glu Gly Thr Ala Ser Asn Val Thr Val Met Pro
                        530                 535                 540
        Pro Val Ala Glu Ala Pro Asn Tyr Gln Gly Pro Pro Pro Tyr Pro
        545                 550                 555                 560
        Lys His Leu Leu His Gln Asn Pro Ser Val Pro Pro Tyr Glu Ser Ile
                                565                 570                 575
```

-continued

```
Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
        595                 600                 605

Gln Ile Thr Thr Ser Pro Ile Thr Val Arg Lys Asn Lys Lys Asp Glu
    610                 615                 620

Glu Arg Arg Glu Ser Arg Ile Gln Ser Tyr Ser Pro Gln Ala Phe Lys
625                 630                 635                 640

Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Gly
            660                 665                 670

Leu Ser Gln Asp Ala Gln Asp Gln Met Arg Lys Met Leu Cys Gln Lys
        675                 680                 685

Glu Ser Asn Tyr Ile Arg Leu Lys Arg Ala Lys Met Asp Lys Ser Met
    690                 695                 700

Phe Val Lys Ile Lys Thr Leu Gly Ile Gly Ala Phe Gly Glu Val Cys
705                 710                 715                 720

Leu Ala Arg Lys Val Asp Thr Lys Ala Leu Tyr Ala Thr Lys Thr Leu
                725                 730                 735

Arg Lys Lys Asp Val Leu Leu Arg Asn Gln Val Ala His Val Lys Ala
            740                 745                 750

Glu Arg Asp Ile Leu Ala Glu Ala Asp Asn Glu Trp Val Val Arg Leu
        755                 760                 765

Tyr Tyr Ser Phe Gln Asp Lys Asp Asn Leu Tyr Phe Val Met Asp Tyr
    770                 775                 780

Ile Pro Gly Gly Asp Met Met Ser Leu Leu Ile Arg Met Gly Ile Phe
785                 790                 795                 800

Pro Glu Ser Leu Ala Arg Phe Tyr Ile Ala Glu Leu Thr Cys Ala Val
                805                 810                 815

Glu Ser Val His Lys Met Gly Phe Ile His Arg Asp Ile Lys Pro Asp
            820                 825                 830

Asn Ile Leu Ile Asp Arg Asp Gly His Ile Lys Leu Thr Asp Phe Gly
        835                 840                 845

Leu Cys Thr Gly Phe Arg Trp Thr His Asp Ser Lys Tyr Tyr Gln Ser
    850                 855                 860

Gly Asp His Pro Arg Gln Asp Ser Met Asp Phe Ser Asn Glu Trp Gly
865                 870                 875                 880

Asp Pro Ser Ser Cys Arg Cys Gly Asp Arg Leu Lys Pro Leu Glu Arg
                885                 890                 895

Arg Ala Ala Arg Gln His Gln Arg Cys Leu Ala His Ser Leu Val Gly
            900                 905                 910

Thr Pro Asn Tyr Ile Ala Pro Glu Val Leu Leu Arg Thr Gly Tyr Thr
        915                 920                 925

Gln Leu Cys Asp Trp Trp Ser Val Gly Val Ile Leu Phe Glu Met Leu
    930                 935                 940

Val Gly Gln Pro Pro Phe Leu Ala Gln Thr Pro Leu Glu Thr Gln Met
945                 950                 955                 960

Lys Val Ile Asn Trp Gln Thr Ser Leu His Ile Pro Gln Ala Lys
                965                 970                 975

Leu Ser Pro Glu Ala Ser Asp Leu Ile Ile Lys Leu Cys Arg Gly Pro
            980                 985                 990
```

Glu Asp Arg Leu Gly Lys Asn Gly Ala Asp Glu Ile Lys Ala His Pro
    995                 1000                1005

Phe Phe Lys Thr Ile Asp Phe Ser Ser Asp Leu Arg Gln Gln Ser
    1010                1015                1020

Ala Ser Tyr Ile Pro Lys Ile Thr His Pro Thr Asp Thr Ser Asn
    1025                1030                1035

Phe Asp Pro Val Asp Pro Asp Lys Leu Trp Ser Asp Asp Asn Glu
    1040                1045                1050

Glu Glu Asn Val Asn Asp Thr Leu Asn Gly Trp Tyr Lys Asn Gly
    1055                1060                1065

Lys His Pro Glu His Ala Phe Tyr Glu Phe Thr Phe Arg Arg Phe
    1070                1075                1080

Phe Asp Asp Asn Gly Tyr Pro Tyr Asn Tyr Pro Lys Pro Ile Glu
    1085                1090                1095

Tyr Glu Tyr Ile Asn Ser Gln Gly Ser Glu Gln Gln Ser Asp Glu
    1100                1105                1110

Asp Asp Gln Asn Thr Gly Ser Glu Ile Lys Asn Arg Asp Leu Val
    1115                1120                1125

Tyr Val
    1130

<210> SEQ ID NO 2
<211> LENGTH: 690
<212> TYPE: PRT
<213> ORGANISM: Homo sapiens

<400> SEQUENCE: 2

Met Lys Arg Ser Glu Lys Pro Glu Gly Tyr Arg Gln Met Arg Pro Lys
1               5                   10                  15

Thr Phe Pro Ala Ser Asn Tyr Thr Val Ser Ser Arg Gln Met Leu Gln
                20                  25                  30

Glu Ile Arg Glu Ser Leu Arg Asn Leu Ser Lys Pro Ser Asp Ala Ala
            35                  40                  45

Lys Ala Glu His Asn Met Ser Lys Met Ser Thr Glu Asp Pro Arg Gln
        50                  55                  60

Val Arg Asn Pro Pro Lys Phe Gly Thr His His Lys Ala Leu Gln Glu
65                  70                  75                  80

Ile Arg Asn Ser Leu Leu Pro Phe Ala Asn Glu Thr Asn Ser Ser Arg
                85                  90                  95

Ser Thr Ser Glu Val Asn Pro Gln Met Leu Gln Asp Leu Gln Ala Ala
            100                 105                 110

Gly Phe Asp Glu Asp Met Val Ile Gln Ala Leu Gln Lys Thr Asn Asn
        115                 120                 125

Arg Ser Ile Glu Ala Ala Ile Glu Phe Ile Ser Lys Met Ser Tyr Gln
    130                 135                 140

Asp Pro Arg Arg Glu Gln Met Ala Ala Ala Ala Arg Pro Ile Asn
145                 150                 155                 160

Ala Ser Met Lys Pro Gly Asn Val Gln Gln Ser Val Asn Arg Lys Gln
                165                 170                 175

Ser Trp Lys Gly Ser Lys Glu Ser Leu Val Pro Gln Arg His Gly Pro
            180                 185                 190

Pro Leu Gly Glu Ser Val Ala Tyr His Ser Glu Ser Pro Asn Ser Gln
        195                 200                 205

Thr Asp Val Gly Arg Pro Leu Ser Gly Ser Gly Ile Ser Ala Phe Val
    210                 215                 220

```
Gln Ala His Pro Ser Asn Gly Gln Arg Val Asn Pro Pro Pro Pro
225                 230                 235                 240

Gln Val Arg Ser Val Thr Pro Pro Pro Arg Gly Gln Thr Pro
            245                 250                 255

Pro Pro Arg Gly Thr Thr Pro Pro Pro Ser Trp Glu Pro Asn Ser
            260                 265                 270

Gln Thr Lys Arg Tyr Ser Gly Asn Met Glu Tyr Val Ile Ser Arg Ile
            275                 280                 285

Ser Pro Val Pro Pro Gly Ala Trp Gln Glu Gly Tyr Pro Pro Pro
290                 295                 300

Leu Asn Thr Ser Pro Met Asn Pro Pro Asn Gln Gly Gln Arg Gly Ile
305                 310                 315                 320

Ser Ser Val Pro Val Gly Arg Gln Pro Ile Ile Met Gln Ser Ser
                325                 330                 335

Lys Phe Asn Phe Pro Ser Gly Arg Pro Gly Met Gln Asn Gly Thr Gly
                340                 345                 350

Gln Thr Asp Phe Met Ile His Gln Asn Val Val Pro Ala Gly Thr Val
            355                 360                 365

Asn Arg Gln Pro Pro Pro Tyr Pro Leu Thr Ala Ala Asn Gly Gln
370                 375                 380

Ser Pro Ser Ala Leu Gln Thr Gly Gly Ser Ala Ala Pro Ser Ser Tyr
385                 390                 395                 400

Thr Asn Gly Ser Ile Pro Gln Ser Met Met Val Pro Asn Arg Asn Ser
                405                 410                 415

His Asn Met Glu Leu Tyr Asn Ile Ser Val Pro Gly Leu Gln Thr Asn
            420                 425                 430

Trp Pro Gln Ser Ser Ser Ala Pro Ala Gln Ser Ser Pro Ser Ser Gly
            435                 440                 445

His Glu Ile Pro Thr Trp Gln Pro Asn Ile Pro Val Arg Ser Asn Ser
450                 455                 460

Phe Asn Asn Pro Leu Gly Asn Arg Ala Ser His Ser Ala Asn Ser Gln
465                 470                 475                 480

Pro Ser Ala Thr Thr Val Thr Ala Ile Thr Pro Ala Pro Ile Gln Gln
                485                 490                 495

Pro Val Lys Ser Met Arg Val Leu Lys Pro Glu Leu Gln Thr Ala Leu
            500                 505                 510

Ala Pro Thr His Pro Ser Trp Ile Pro Gln Pro Ile Gln Thr Val Gln
            515                 520                 525

Pro Ser Pro Phe Pro Glu Gly Thr Ala Ser Asn Val Thr Val Met Pro
            530                 535                 540

Pro Val Ala Glu Ala Pro Asn Tyr Gln Gly Pro Pro Pro Tyr Pro
545                 550                 555                 560

Lys His Leu Leu His Gln Asn Pro Ser Val Pro Pro Tyr Glu Ser Ile
                565                 570                 575

Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
            595                 600                 605

Gln Ile Thr Thr Ser Pro Ile Thr Val Arg Lys Asn Lys Lys Asp Glu
            610                 615                 620

Glu Arg Arg Glu Ser Arg Ile Gln Ser Tyr Ser Pro Gln Ala Phe Lys
625                 630                 635                 640
```

```
Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Lys
        660                 665                 670

Pro Phe Lys Met Ser Ile Phe Ile Leu Asn His Leu Phe Ala Trp Cys
            675                 680                 685

Leu Phe
    690

<210> SEQ ID NO 3
<211> LENGTH: 1088
<212> TYPE: PRT
<213> ORGANISM: Homo sapiens

<400> SEQUENCE: 3

Met Arg Pro Lys Thr Phe Pro Ala Thr Thr Tyr Ser Gly Asn Ser Arg
1               5                   10                  15

Gln Arg Leu Gln Glu Ile Arg Glu Gly Leu Lys Gln Pro Ser Lys Ser
            20                  25                  30

Ser Val Gln Gly Leu Pro Ala Gly Pro Asn Ser Asp Thr Ser Leu Asp
        35                  40                  45

Ala Lys Val Leu Gly Ser Lys Asp Ala Thr Arg Gln Gln Gln Gln Met
    50                  55                  60

Arg Ala Thr Pro Lys Phe Gly Pro Tyr Gln Lys Ala Leu Arg Glu Ile
65                  70                  75                  80

Arg Tyr Ser Leu Leu Pro Phe Ala Asn Glu Ser Gly Thr Ser Ala Ala
                85                  90                  95

Ala Glu Val Asn Arg Gln Met Leu Gln Glu Leu Val Asn Ala Gly Cys
            100                 105                 110

Asp Gln Glu Met Ala Gly Arg Ala Leu Lys Gln Thr Gly Ser Arg Ser
        115                 120                 125

Ile Glu Ala Ala Leu Glu Tyr Ile Ser Lys Met Gly Tyr Leu Asp Pro
    130                 135                 140

Arg Asn Glu Gln Ile Val Arg Val Ile Lys Gln Thr Ser Pro Gly Lys
145                 150                 155                 160

Gly Leu Met Pro Thr Pro Val Thr Arg Arg Pro Ser Phe Glu Gly Thr
                165                 170                 175

Gly Asp Ser Phe Ala Ser Tyr His Gln Leu Ser Gly Thr Pro Tyr Glu
            180                 185                 190

Gly Pro Ser Phe Gly Ala Asp Gly Pro Thr Ala Leu Glu Glu Met Pro
        195                 200                 205

Arg Pro Tyr Val Asp Tyr Leu Phe Pro Gly Val Gly Pro His Gly Pro
    210                 215                 220

Gly His Gln His Gln His Pro Pro Lys Gly Tyr Gly Ala Ser Val Glu
225                 230                 235                 240

Ala Ala Gly Ala His Phe Pro Leu Gln Gly Ala His Tyr Gly Arg Pro
                245                 250                 255

His Leu Leu Val Pro Gly Glu Pro Leu Gly Tyr Gly Val Gln Arg Ser
            260                 265                 270

Pro Ser Phe Gln Ser Lys Thr Pro Pro Glu Thr Gly Gly Tyr Ala Ser
        275                 280                 285

Leu Pro Thr Lys Gly Gln Gly Gly Pro Gly Ala Gly Leu Ala Phe
    290                 295                 300

Pro Pro Pro Ala Ala Gly Leu Tyr Val Pro His Pro His His Lys Gln
305                 310                 315                 320
```

```
Ala Gly Pro Ala Ala His Gln Leu His Val Leu Gly Ser Arg Ser Gln
                325                 330                 335

Val Phe Ala Ser Asp Ser Pro Gln Ser Leu Leu Thr Pro Ser Arg
            340                 345                 350

Asn Ser Leu Asn Val Asp Leu Tyr Glu Leu Gly Ser Thr Ser Val Gln
            355                 360                 365

Gln Trp Pro Ala Ala Thr Leu Ala Arg Arg Asp Ser Leu Gln Lys Pro
370                 375                 380

Gly Leu Glu Ala Pro Pro Arg Ala His Val Ala Phe Arg Pro Asp Cys
385                 390                 395                 400

Pro Val Pro Ser Arg Thr Asn Ser Phe Asn Ser His Gln Pro Arg Pro
                405                 410                 415

Gly Pro Pro Gly Lys Ala Glu Pro Ser Leu Pro Ala Pro Asn Thr Val
                420                 425                 430

Thr Ala Val Thr Ala Ala His Ile Leu His Pro Val Lys Ser Val Arg
            435                 440                 445

Val Leu Arg Pro Glu Pro Gln Thr Ala Val Gly Pro Ser His Pro Ala
            450                 455                 460

Trp Val Pro Ala Pro Ala Pro Ala Pro Ala Pro Ala Pro Ala Pro Ala
465                 470                 475                 480

Ala Glu Gly Leu Asp Ala Lys Glu His Ala Leu Ala Leu Gly Gly
                485                 490                 495

Ala Gly Ala Phe Pro Leu Asp Val Glu Tyr Gly Gly Pro Asp Arg Arg
            500                 505                 510

Cys Pro Pro Pro Tyr Pro Lys His Leu Leu Leu Arg Ser Lys Ser
                515                 520                 525

Glu Gln Tyr Asp Leu Asp Ser Leu Cys Ala Gly Met Glu Gln Ser Leu
530                 535                 540

Arg Ala Gly Pro Asn Glu Pro Glu Gly Gly Asp Lys Ser Arg Lys Ser
545                 550                 555                 560

Ala Lys Gly Asp Lys Gly Gly Lys Asp Lys Lys Gln Ile Gln Thr Ser
                565                 570                 575

Pro Val Pro Val Arg Lys Asn Ser Arg Asp Glu Glu Lys Arg Glu Ser
            580                 585                 590

Arg Ile Lys Ser Tyr Ser Pro Tyr Ala Phe Lys Phe Phe Met Glu Gln
            595                 600                 605

His Val Glu Asn Val Ile Lys Thr Tyr Gln Gln Lys Val Asn Arg Arg
610                 615                 620

Leu Gln Leu Glu Gln Glu Met Ala Lys Ala Gly Leu Cys Glu Ala Glu
625                 630                 635                 640

Gln Glu Gln Met Arg Lys Ile Leu Tyr Gln Lys Glu Ser Asn Tyr Asn
                645                 650                 655

Arg Leu Lys Arg Ala Lys Met Asp Lys Ser Met Phe Val Lys Ile Lys
            660                 665                 670

Thr Leu Gly Ile Gly Ala Phe Gly Glu Val Cys Leu Ala Cys Lys Val
            675                 680                 685

Asp Thr His Ala Leu Tyr Ala Met Lys Thr Leu Arg Lys Lys Asp Val
            690                 695                 700

Leu Asn Arg Asn Gln Val Ala His Val Lys Ala Glu Arg Asp Ile Leu
705                 710                 715                 720

Ala Glu Ala Asp Asn Glu Trp Val Val Lys Leu Tyr Tyr Ser Phe Gln
                725                 730                 735
```

```
Asp Lys Asp Ser Leu Tyr Phe Val Met Asp Tyr Ile Pro Gly Gly Asp
            740                 745                 750

Met Met Ser Leu Leu Ile Arg Met Glu Val Phe Pro Glu His Leu Ala
        755                 760                 765

Arg Phe Tyr Ile Ala Glu Leu Thr Leu Ala Ile Glu Ser Val His Lys
    770                 775                 780

Met Gly Phe Ile His Arg Asp Ile Lys Pro Asp Asn Ile Leu Ile Asp
785                 790                 795                 800

Leu Asp Gly His Ile Lys Leu Thr Asp Phe Gly Leu Cys Thr Gly Phe
                805                 810                 815

Arg Trp Thr His Asn Ser Lys Tyr Tyr Gln Lys Gly Ser His Val Arg
                820                 825                 830

Gln Asp Ser Met Glu Pro Ser Asp Leu Trp Asp Asp Val Ser Asn Cys
                835                 840                 845

Arg Cys Gly Asp Arg Leu Lys Thr Leu Glu Gln Arg Ala Arg Lys Gln
    850                 855                 860

His Gln Arg Cys Leu Ala His Ser Leu Val Gly Thr Pro Asn Tyr Ile
865                 870                 875                 880

Ala Pro Glu Val Leu Leu Arg Lys Gly Tyr Thr Gln Leu Cys Asp Trp
                885                 890                 895

Trp Ser Val Gly Val Ile Leu Phe Glu Met Leu Val Gly Gln Pro Pro
            900                 905                 910

Phe Leu Ala Pro Thr Pro Thr Glu Thr Gln Leu Lys Val Ile Asn Trp
        915                 920                 925

Glu Asn Thr Leu His Ile Pro Ala Gln Val Lys Leu Ser Pro Glu Ala
930                 935                 940

Arg Asp Leu Ile Thr Lys Leu Cys Cys Ser Ala Asp His Arg Leu Gly
945                 950                 955                 960

Arg Asn Gly Ala Asp Asp Leu Lys Ala His Pro Phe Phe Ser Ala Ile
                965                 970                 975

Asp Phe Ser Ser Asp Ile Arg Lys Gln Pro Ala Pro Tyr Val Pro Thr
            980                 985                 990

Ile Ser His Pro Met Asp Thr Ser Asn Phe Asp Pro Val Asp Glu Glu
        995                 1000                1005

Ser Pro Trp Asn Asp Ala Ser Glu Gly Ser Thr Lys Ala Trp Asp
    1010                1015                1020

Thr Leu Thr Ser Pro Asn Asn Lys His Pro Glu His Ala Phe Tyr
    1025                1030                1035

Glu Phe Thr Phe Arg Arg Phe Phe Asp Asp Asn Gly Tyr Pro Phe
    1040                1045                1050

Arg Cys Pro Lys Pro Ser Gly Ala Glu Ala Ser Gln Ala Glu Ser
    1055                1060                1065

Ser Asp Leu Glu Ser Ser Asp Leu Val Asp Gln Thr Glu Gly Cys
    1070                1075                1080

Gln Pro Val Tyr Val
    1085

<210> SEQ ID NO 4
<211> LENGTH: 5
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
```

```
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 4 nggng                                                                    5

<210> SEQ ID NO 5
<211> LENGTH: 7
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(2)
<223> OTHER INFORMATION: a, c, t, g, unknown or other

<400> SEQUENCE: 5 nnagaaw                                                                  7

<210> SEQ ID NO 6
<211> LENGTH: 5
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(2)
<223> OTHER INFORMATION: a, c, t, g, unknown or other

<400> SEQUENCE: 6 nngrr                                                                    5

<210> SEQ ID NO 7
<211> LENGTH: 8
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(4)
<223> OTHER INFORMATION: a, c, t, g, unknown or other

<400> SEQUENCE: 7 nnnngatt                                                                 8

<210> SEQ ID NO 8
<211> LENGTH: 7
<212> TYPE: PRT
<213> ORGANISM: Simian virus 40

<400> SEQUENCE: 8

Pro Lys Lys Lys Arg Lys Val
1               5

<210> SEQ ID NO 9
<211> LENGTH: 42
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 9
nnnnnnnnnn nnnnnnnnnn guuuuagagc uaugcuguuu ug                          42

<210> SEQ ID NO 10
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (80)..(86)
<223> OTHER INFORMATION: This region may encompass 1-7 nucleotides
<220> FEATURE:
<221> NAME/KEY: misc_feature
<222> LOCATION: (80)..(86)
<223> OTHER INFORMATION: This region may or may not be present
<220> FEATURE:
<223> OTHER INFORMATION: See specification as filed for detailed
      description of substitutions and preferred embodiments

<400> SEQUENCE: 10
aacuuaccaa ggaacagcau agcaaguuaa aauaaggcua guccguuauc aacuugaaaa        60
aguggcaccg agucggugcu uuuuuu                                            86

<210> SEQ ID NO 11
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (68)..(74)
<223> OTHER INFORMATION: This region may encompass 1-7 nucleotides
<220> FEATURE:
<221> NAME/KEY: misc_feature
<222> LOCATION: (68)..(74)
<223> OTHER INFORMATION: This region may or may not be present
<220> FEATURE:
<223> OTHER INFORMATION: See specification as filed for detailed
      description of substitutions and preferred embodiments

<400> SEQUENCE: 11
aacagcauag caaguuaaaa uaaggcuagu ccguuaucaa cuugaaaaag uggcaccgag        60
ucggugcuuu uuuu                                                         74

<210> SEQ ID NO 12
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: misc_feature
<222> LOCATION: (96)..(102)
<223> OTHER INFORMATION: This region may encompass 1-7 nucleotides

```
<220> FEATURE:
<221> NAME/KEY: misc_feature
<222> LOCATION: (96)..(102)
<223> OTHER INFORMATION: This region may or may not be present
<220> FEATURE:
<223> OTHER INFORMATION: See specification as filed for detailed
      description of substitutions and preferred embodiments

<400> SEQUENCE: 12
nnnnnnnnnn nnnnnnnnng uuuuagagcu agaaauagca aguuaaaaua aggcuagucc      60
guuaucaacu ugaaaaagug gcaccgaguc ggugcuuuuu uu                        102

<210> SEQ ID NO 13
<211> LENGTH: 21
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(18)
<223> OTHER INFORMATION: a, c, t, or g
<220> FEATURE:
<221> NAME/KEY: modified_base
<222> LOCATION: (19)..(19)
<223> OTHER INFORMATION: a, c, t, g, unknown or other

<400> SEQUENCE: 13
nnnnnnnnnn nnnnnnnng g                                                 21

<210> SEQ ID NO 14
<211> LENGTH: 19
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(16)
<223> OTHER INFORMATION: a, c, t, or g
<220> FEATURE:
<221> NAME/KEY: modified_base
<222> LOCATION: (17)..(17)
<223> OTHER INFORMATION: a, c, t, g, unknown or other

<400> SEQUENCE: 14
nnnnnnnnnn nnnnnnngg                                                   19

<210> SEQ ID NO 15
<211> LENGTH: 21
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(14)
<223> OTHER INFORMATION: a, c, t, or g
<220> FEATURE:
<221> NAME/KEY: modified_base
<222> LOCATION: (15)..(16)
<223> OTHER INFORMATION: a, c, t, g, unknown or other

<400> SEQUENCE: 15
nnnnnnnnnn nnnnnnagaa w                                                21

<210> SEQ ID NO 16
```

```
<211> LENGTH: 21
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(14)
<223> OTHER INFORMATION: a, c, t, or g
<220> FEATURE:
<221> NAME/KEY: modified_base
<222> LOCATION: (15)..(16)
<223> OTHER INFORMATION: a, c, t, g, unknown or other

<400> SEQUENCE: 16
nnnnnnnnnn nnnnnnagaa w                                              21

<210> SEQ ID NO 17
<211> LENGTH: 23
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(18)
<223> OTHER INFORMATION: a, c, t, or g
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 17
nnnnnnnnnn nnnnnnnng gng                                             23

<210> SEQ ID NO 18
<211> LENGTH: 16
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(11)
<223> OTHER INFORMATION: a, c, t, or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 18
nnnnnnnnnn nnggng                                                    16

<210> SEQ ID NO 19
<211> LENGTH: 8
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
```

```
<222> LOCATION: (1)..(4)
<223> OTHER INFORMATION: a, c, t, g, unknown or other

<400> SEQUENCE: 19 nnnngatt                                                                 8

<210> SEQ ID NO 20
<211> LENGTH: 8
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(4)
<223> OTHER INFORMATION: a, c, t, g, unknown or other

<400> SEQUENCE: 20 nnnngctt                                                                 8

<210> SEQ ID NO 21
<211> LENGTH: 6
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(2)
<223> OTHER INFORMATION: a, c, t, g, unknown or other

<400> SEQUENCE: 21 nngrrt                                                                   6

<210> SEQ ID NO 22
<211> LENGTH: 6
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(2)
<223> OTHER INFORMATION: a, c, t, g, unknown or other

<400> SEQUENCE: 22 nngrrv                                                                   6

<210> SEQ ID NO 23
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 23

Leu Ala Gly Leu Ile Asp Ala Asp Gly
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 24

Lys Lys Leu Arg Arg Thr Leu Ser Val Ala
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 26

His His His His His His His His
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norvaline

<400> SEQUENCE: 27

Xaa Lys Lys Arg Asn Arg Arg Leu Ser Val Ala
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Tyr Lys Asp Asp Asp Asp Lys
1               5

<210> SEQ ID NO 29
<211> LENGTH: 13
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(6)
<223> OTHER INFORMATION: a, c, t, or g
```

```
<220> FEATURE:
<221> NAME/KEY: modified_base
<222> LOCATION: (7)..(8)
<223> OTHER INFORMATION: a, c, t, g, unknown or other

<400> SEQUENCE: 29 nnnnnnnag aaw                                                         13

<210> SEQ ID NO 30
<211> LENGTH: 18
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(11)
<223> OTHER INFORMATION: a, c, t, or g
<220> FEATURE:
<221> NAME/KEY: modified_base
<222> LOCATION: (12)..(13)
<223> OTHER INFORMATION: a, c, t, g, unknown or other

<400> SEQUENCE: 30
nnnnnnnnnn nnnagaaw                                                   18

<210> SEQ ID NO 31
<211> LENGTH: 25
<212> TYPE: DNA
<213> ORGANISM: Unknown
<220> FEATURE:
<223> OTHER INFORMATION: Description of Unknown:
      Target sequence
<220> FEATURE:
<221> NAME/KEY: modified_base
<222> LOCATION: (1)..(20)
<223> OTHER INFORMATION: a, c, t, or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 31
nnnnnnnnnn nnnnnnnnnn nggng                                           25
```

US 11,458,138 B2

6-6 FUSED BICYCLIC HETEROARYL COMPOUNDS AND THEIR USE AS LATS INHIBITORS

The present application claims priority to U.S. Provisional Application Ser. No. 62/491,475, filed on Apr. 28, 2017, and to U.S. Provisional Application Ser. No. 62/491,484, filed on Apr. 28, 2017, and to U.S. Provisional Application Ser. No. 62/491,573, filed on Apr. 28, 2017, and to U.S. Provisional Application Ser. No. 62/491,526, filed on Apr. 28, 2017, and to U.S. Provisional Application Ser. No. 62/650,232, filed on Mar. 29, 2018, the disclosures of which are entirely and specifically incorporated by reference herein.

SEQUENCE LISTING

The instant application contains a Sequence Listing which has been submitted electronically in ASCII format and is hereby incorporated by reference in its entirety. Said ASCII copy, created on Apr. 23, 2018, is named PAT057699-US-NP_SL.txt and is 35,072 bytes in size.

INTRODUCTION

The present invention relates to LATS (large tumor suppressor kinase) inhibitors. The present invention further relates to 6-6 fused bicyclic heteroaryl compounds and compositions comprising such compounds.

The present invention also relates to ex-vivo use of such compounds to produce cellular material for cell therapy/transplantation. The present invention further relates to methods of generating an expanded population of cells, such as an expanded population of ocular cells for example comprising limbal stem cells (LSCs) or corneal endothelial cells (CECs) involving the use of a LATS inhibitor, as well as the population of cells such as ocular cells comprising for example limbal stem cells (LSCs) or corneal endothelial cells (CECs) and preparations, uses and methods of therapy comprising said cells.

The present invention also relates to 6-6 fused bicyclic heteroaryl compounds, compositions comprising such compounds, and their use in promoting wound healing, particularly for treatment of burns, acute and chronic skin ulcers, including vascular, diabetic and pressure ulcers, such as venous leg ulcers, diabetic foot ulcers, pressure ulcers.

The present invention additionally relates to 6-6 fused bicyclic heteroaryl compounds, compositions comprising such compounds, and their use in liver regeneration and liver regrowth as well as in the prevention of damage and in the maintenance or improvement of function of organs ex-vivo, with or without perfusion devices.

BACKGROUND OF THE INVENTION

Organ regeneration and/or healing is an issue crucial to treat many serious health issues.

For example in the eye, it is known that corneal blindness is the third leading cause of blindness worldwide. Approximately half of all the cornea transplants worldwide are performed for treatment of corneal endothelial dysfunction.

The cornea is a transparent tissue comprising different layers: corneal epithelium, Bowman's membrane, stroma, Descemet's Membrane and endothelium. The corneal endothelium also comprises a monolayer of human corneal endothelial cells and helps maintain corneal transparency via its barrier and ionic pump functions. It plays a crucial role in maintaining the balance of fluid, nutrients and salts between the corneal stroma and the aqueous humor. To maintain transparency, endothelial cell density must be maintained, however endothelial cell density can be significantly decreased as a result of trauma, disease or endothelial dystrophies. The density of the cells also decreases with aging. Human corneal endothelium has a limited propensity to proliferate in vivo. If the density of cells falls too low, the barrier function may be compromised. Loss of endothelial barrier function results in corneal edema and loss of visual acuity. The clinical condition of bullous keratopathy may be one resulting complication.

Currently the only treatment for blindness caused by corneal endothelial dysfunction is corneal transplantation. Although corneal transplantation is one of the most common forms of organ transplantation, the availability of donor corneas required is extremely limited. A 2012-2013 global survey quantified the considerable shortage of corneal graft tissue, finding that only one cornea is available for every 70 needed (Gain at el., (2016) Global Survey of Corneal Transplantation and Eye Banking. JAMA Ophthalmol. 134: 167-173).

New therapeutic approaches to supply corneal endothelial cells for the treatment of corneal endothelial dysfunction are thus greatly needed.

The corneal epithelium also needs to be maintained in the eye. The corneal epithelium is composed of a layer of basal cells and multiple layers of a non-keratinized, stratified, squamous epithelium. It is essential in maintaining the clarity and the regular refractive surface of the cornea. It acts as a transparent, renewable protective layer over the corneal stroma and is replenished by a stem cell population located in the limbus. In limbal stem cell deficiency, a condition in which limbal stem cells are diseased or absent, a decrease in the number of healthy limbal stem cells results in a decreased capacity for corneal epithelium renewal.

Limbal stem cell deficiency may arise as a result of injuries from chemical or thermal burns, ultraviolet and ionizing radiation, or even as a result of contact lens wear; genetic disorders like aniridia, and immune disorders such as Stevens Johnson syndrome and ocular cicatricial pemphigoid. Loss of limbal stem cells can be partial or total; and may be unilateral or bilateral. Symptoms of limbal stem cell deficiency include pain, photophobia, non healing painful corneal epithelial defects, corneal neovascularization, replacement of the corneal epithelium by conjunctival epithelium, loss of corneal transparency and decreased vision that can eventually lead to blindness.

A product for use in treating limbal stem cell deficiency was granted a conditional marketing authorisation in the European Union in 2015 (under the name Holoclar®), making it the first Advanced Therapy Medicinal Product (ATMP) containing stem cells in Europe. Holoclar is an ex vivo expanded preparation of autologous human corneal epithelial cells containing stem cells. A biopsy of healthy limbal tissue is taken from the patient, expanded ex vivo and frozen until surgery. For administration to the patient the thawed cells are grown on a membrane comprising fibrin, and then surgically implanted onto the eye of the patient. The therapy is intended for use in adults with moderate to severe limbal stem cell deficiency due to physical or chemical ocular burns. (Rama P, Matuska S, Paganoni G, Spinelli A, De Luca M, Pellegrini G. (2010) Limbal stem-cell therapy and long-term corneal regeneration. N Engl J Med. 363:147-155). However the method is limited in that it is for autologous use only and there must be enough surviving limbus in one eye to allow a minimum of 1-2 square millimeters of undamaged tissue to be extracted from the patient. There is also the risk that for each specific patient the culture of his/her cells may not be successful and the patient cannot receive this treatment. Furthermore also feeder cells of murine origin are used to prepare the Holoclar cell preparation, which introduces potential safety concerns, due to the risk of disease transmission and potential immunogenicity into the preparation for use in humans. Moreover the Holoclar cell preparation only contains approximately 5% of limbal stem cells, as identified by p63alpha staining.

New therapeutic approaches to supply limbal stem cells for the treatment of limbal stem cell deficiency are thus greatly needed.

Functional liver regeneration during homeostasis and in disease conditions is critical to maintaining essential physiological processes. Despite the liver's marked potential to regenerate, this process can be impaired following severe acute or chronic liver injury. Liver damage and impaired liver regeneration often result in serious morbidity and mortality and therefore require life-saving liver transplantation. Unfortunately, the need for liver transplants currently far eclipses the supply of available donor organs. As a result, many patients continue to die while awaiting a life-saving transplant. The use of split-liver transplants from deceased donors or partial-liver transplants from living donors is limited by graft size constraints. Transplantation of a partial liver that has an inadequate graft-to-recipient weight ratio (GRWR) increases the incidence of graft dysfunction and failure. Therapies that increase liver regrowth may allow transplantation of partial livers that otherwise would be deemed inadequate for transplantation based on size. Alternatively, regenerating livers by inhibiting liver cell death, improving liver function and repairing the aberrant liver architecture could normalize liver function, preventing the need for transplantation (Forbes S J and Newsome P N (2016) Liver regeneration—mechanisms and models to clinical application. Nature Reviews Gastroenterology & Hepatology, 13(8):473-485; Dutkowski P, Linecker M, DeOliveira M L, Millhaupt B, Clavien P A (2015) Challenges to Liver Transplantation and Strategies to Improve Outcomes. Gastroenterology, 148(2):307-323).

Hence, there remains an urgent need for more efficacious therapeutics to promote liver regrowth.

Chronic skin ulcers, including vascular, diabetic and pressure ulcers, constitute a major public health issue. The increased demand for wound care is reflected in the association of wounds with comorbidities, increased mortality and patient's quality of life (Demidova-Rice T N, Hamblin M R, & Herman I M (2012) Acute and impaired wound healing: pathophysiology and current methods for drug delivery, part 1: normal and chronic wounds: biology, causes, and approaches to care. Advances in skin & wound care 25(7):304-314; Demidova-Rice T N, Hamblin M R, & Herman I M (2012) Acute and impaired wound healing: pathophysiology and current methods for drug delivery, part 2: role of growth factors in normal and pathological wound healing: therapeutic potential and methods of delivery. Advances in skin & wound care 25(8):349-370). The health care cost of patients with chronic wounds is around 25 billion dollars per year in the US alone. No new chemical entities have been approved by the FDA since the approval of Regranex (PDGF) in 1997, which has limited efficacy (Eaglstein W H, Kirsner R S, & Robson M C (2012) Food and Drug Administration (FDA) drug approval end points for chronic cutaneous ulcer studies. Wound repair and regeneration: official publication of the Wound Healing Society [and] the European Tissue Repair Society 20(6):793-796). Intrinsically, growth factors are not stable in the proteolytic environment of wound bed. Growth factor therapy could also suffer from low expression of its corresponding receptors in the wounds, as demonstrated in the clinic patient samples (Demidova-Rice T N, Hamblin M R, & Herman I M (2012) Acute and impaired wound healing: pathophysiology and current methods for drug delivery, part 2: role of growth factors in normal and pathological wound healing: therapeutic potential and methods of delivery. Advances in skin & wound care 25(8):349-370).

Hence, there remains an urgent need for more efficacious therapeutics to promote wound healing in patients with chronic wounds.

New therapeutic approaches to promote cell proliferation are thus greatly needed for conditions affecting a range of organs throughout the body, such as the eye, liver and skin.

SUMMARY OF THE INVENTION

The present invention relates to compounds, salts thereof, and compositions thereof, wherein the compounds are LATS (large tumor suppressor kinase) inhibitors. These compounds have use in therapies for the conditions and purposes detailed above.

Various aspects of the invention are described herein.

The present invention relates to a compound of Formula A2 or a subformulae thereof, or a salt, or stereoisomer thereof,

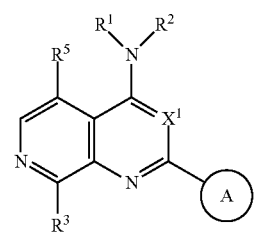

wherein $X^1$, ring A, $R^1$, $R^2$, $R^3$, and $R^5$ are as defined in the detailed description infra.

In a preferred embodiment, the compound is according to Formula I or Formula II, or subformulae thereof, or a salt thereof:

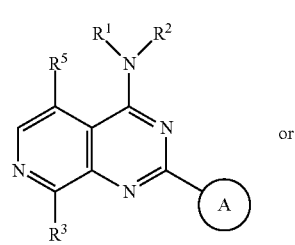

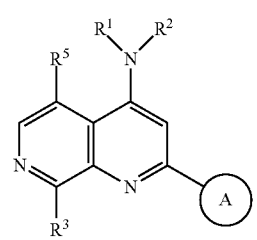

wherein ring A, $R^1$, $R^2$, $R^3$, and $R^5$ are as defined in the detailed description infra.

In another aspect, the invention relates to a pharmaceutical composition comprising a therapeutically effective amount of a compound according to the definition of Formula A2 or subformulae thereof, or a pharmaceutically acceptable salt thereof, or subformulae thereof and one or more pharmaceutically acceptable carriers.

In another aspect, the invention relates to a combination, in particular a pharmaceutical combination, comprising a therapeutically effective amount of the compound according to the definition of Formula A2 or subformulae thereof, or a pharmaceutically acceptable salt thereof, and one or more therapeutically active agent.

In another aspect, the invention relates to compounds and compositions that may be used in therapy.

In an embodiment the present invention relates to a method of LATS inhibition in a cell or cell population using a compound of Formula A1 or subformulae thereof or a salt thereof, or a stereoisomer thereof:

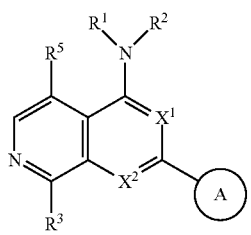

A1 wherein $X^1$, $X^2$, ring A, $R^1$, $R^2$, $R^3$, and $R^5$ are as defined in the detailed description infra. Preferably the salt is a pharmaceutically acceptable salt. In a specific embodiment of the method of LATS inhibition in a cell population according to the invention, the compound, or a salt thereof, is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; 2-(pyridin-4-yl)-4-(3-(trifluoromethyl)piperazin-1-yl)pyrido[3,4-d]pyrimidine. In another specific embodiment of the method of LATS inhibition in a cell population according to the invention, the compound, or a salt thereof, is selected from N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

In another embodiment the present invention relates to a method of LATS inhibition in an ocular cell population using a compound of Formula A1 or subformulae thereof or a salt thereof, or a stereoisomer thereof. In yet another embodiment the present invention relates to a method of LATS inhibition in a cell population comprising limbal stem cells using a compound of Formula A1 or subformulae thereof or a salt thereof, or a stereoisomer thereof. In yet a further embodiment the present invention relates to a method of LATS inhibition in a cell population comprising corneal endothelial cells using a compound of Formula A1 or subformulae thereof or a salt thereof, or a stereoisomer thereof.

Also preferably the method of LATS inhibition in a cell population is performed ex vivo. In yet another preferred embodiment said compound is present in a concentration of 0.5 to 100 micromolar, preferably 0.5 to 25 micromolar, more preferably 1 to 20 micromolar, particularly preferably of about 3 to 10 micromolar. In one preferred embodiment of the method of LATS inhibition in a cell population comprising limbal stem cells the compound is present for 12 to 16 days, particularly preferably the compound is present for 14 days. In another embodiment of the method of LATS inhibition in a cell population comprising corneal endothelial cells the compound is present for one to two weeks and subsequently the cells are cultured for a period in growth medium without supplementation with said compound, preferably wherein the period is one to two weeks. In an embodiment of the invention of the method of LATS inhibition in a cell population the LATS inhibitor inhibits LATS1 or LATS2, or LATS1 and LATS2. In a more preferred embodiment the LATS inhibitor inhibits LATS1 and LATS2. In another preferred embodiment of the method of LATS inhibition in a cell population comprising limbal stem cells said method further comprises genetically modifying said limbal stem cells. In another preferred embodiment of the method of LATS inhibition in a cell population comprising corneal endothelial cells said method further comprises genetically modifying said corneal endothelial cells. Preferably said genetically modifying comprises introducing into said cell a gene editing system which specifically targets a gene associated with facilitating a host versus graft immune response. In yet another preferred embodiment the method of LATS inhibition in a cell population, the method comprises the further step after generation of an expanded population of cells of rinsing those cells to substantially remove the compound according to the invention. In one aspect the invention relates to an expanded cell population comprising limbal stem cells obtainable by the method of LATS inhibition in a cell population comprising limbal stem cells according to the invention. In another aspect the invention relates to a an expanded cell population comprising limbal stem cells obtained by the method of LATS inhibition in a cell population comprising limbal stem cells according to the invention. In one aspect the invention relates to a population of corneal endothelial cells obtainable by the method of LATS inhibition in a cell population comprising corneal endothelial cells according to the invention. In another aspect the invention relates to a population of corneal endothelial cells obtained by the method of LATS inhibition according to the invention. In yet another aspect the invention relates to an ocular cell delivery preparation, comprising a cell population obtainable or obtained by the method of LATS inhibition according to the invention and a composition suitable for ocular delivery which is a localising agent. In a specific embodiment the localising agent is GelMa (which is methacrylamide modified gelatin, and is also known as gelatin methacrylate). In another specific embodiment the localising agent is fibrin or fibrin glue. Preferably the cell delivery preparation of limbal stem cells has greater than 20% limbal stem cells. Also preferably the cell delivery preparation of limbal stem cells has greater than 20% p63alpha positive cells. In certain preferred aspects the cell population obtainable or obtained by the method of LATS inhibition according to the invention or cell delivery preparation according to the invention has only trace levels of the compound according to the invention. Preferably, in the cell delivery preparation of corneal endothelial cells, corneal endothelial cells are present in the cell delivery preparation at a density greater than 500 cells per $mm^2$ (area). In certain preferred aspects the cell population obtainable or obtained by the method of LATS inhibition according to the invention or cell delivery preparation according to the invention has only trace levels of the compound according to the invention.

In another aspect the invention relates to a method of culturing cells comprising culturing a population of cells in the presence of a LATS inhibitor. The cells can be a cell population as described and/or as provided herein. Preferably the cells are ocular cells or liver cells. In a preferred embodiment the cells are ocular cells. In a further aspect the invention relates to a method of culturing cells comprising culturing a population of cells comprising limbal stem cells in the presence of a LATS inhibitor. In another aspect the invention relates to a method of culturing cells comprising culturing a population of cells comprising corneal endothelial cells in the presence of a LATS inhibitor. In a preferred embodiment the invention relates to a method of culturing cells comprising culturing a cell population comprising limbal stem cells, wherein the LATS inhibitor is a compound of Formula A1 or subformulae thereof or salt thereof according to the invention. In another preferred embodiment the invention relates to a method of culturing cells comprising culturing a population comprising corneal endothelial cells, wherein the LATS inhibitor is a compound of Formula A1 or subformulae thereof or salt thereof according to the invention. Preferably the salt is a pharmaceutically acceptable salt. In a preferred embodiment said compound is present in a concentration of 0.5 to 100 micromolar, preferably 0.5 to 25 micromolar, more preferably 1 to 20 micromolar, particularly preferably of about 3 to 10 micromolar. In one preferred embodiment of the method of culturing cells comprising culturing a cell population comprising limbal stem cells, the compound is present for 12 to 16 days, particularly preferably the compound is present for 14 days. In another preferred embodiment of the method of culturing cells comprising culturing a cell population comprising corneal endothelial cells, the compound is present for one to two weeks and subsequently the cells are cultured for a period in growth medium without supplementation with said compound, preferably wherein the period is one to two weeks. In an embodiment of the invention the LATS inhibitor inhibits LATS1 or LATS2, or LATS1 and LATS2. In a more a preferred embodiment the LATS inhibitor inhibits LATS1 and LATS2. In one embodiment said method further comprises genetically modifying cells. Preferably said genetically modifying comprises introducing into said cell a gene editing system which specifically targets a gene associated with facilitating a host versus graft immune response. Preferably the cells are ocular cells. In one embodiment said method further comprises genetically modifying limbal stem cells. In another preferred embodiment said method further comprises genetically modifying corneal endothelial cells. In yet another preferred embodiment the method of culturing cells comprises the further step after generation of an expanded population of cells of rinsing those cells to substantially remove the compound according to the invention. In one aspect the invention relates to an expanded cell population obtainable by the method of culturing cells according to the invention. In another aspect the invention relates to an expanded cell population obtained by the method of culturing cells according to the invention. Preferably the cells are ocular cells. In one aspect the invention relates to an expanded cell population comprising limbal stem cells obtainable by the method of culturing cells comprising limbal stem cells according to the invention. In another aspect the invention relates to an expanded cell population comprising limbal stem cells obtained by the method of culturing cells comprising limbal stem cells according to the invention. In one aspect the invention relates to a population of corneal endothelial cells obtainable by the method of culturing cells comprising corneal endothelial cells according to the invention. In another aspect the invention relates to a population of corneal endothelial cells obtained by the method of culturing cells comprising corneal endothelial cells according to the invention. In another aspect the invention relates to an ocular cell delivery preparation, comprising a cell population obtainable or obtained by the method of culturing cells according to the invention and a composition suitable for ocular delivery which is a localising agent. In a specific embodiment the localising agent is GelMa. In another specific embodiment the localising agent is fibrin or fibrin glue. Preferably the cell delivery preparation of limbal stem cells has greater than 20% limbal stem cells. Also preferably the cell delivery preparation of limbal stem cells has greater than 20% p63alpha positive cells. Preferably corneal endothelial cells are present in the cell delivery preparation of corneal endothelial cells, at a density greater than 500 cells per $mm^2$ (area). In certain preferred aspects the cell population obtainable or obtained by the method of culturing cells according to the invention or cell delivery preparation according to the invention has only trace levels of the compound according to the invention.

In another aspect the invention relates to a method of cell population expansion comprising the step of a) culturing a seeding population of cells in the presence of a LATS inhibitor to generate an expanded population of cells. In a preferred embodiment the method of cell population expansion is performed ex vivo. Preferably the cells are ocular cells or liver cells. In a preferred embodiment the cells are ocular cells. In yet another aspect the invention relates to a method of cell population expansion comprising the step of a) culturing a seeding population of cells comprising limbal stem cells in the presence of a LATS inhibitor to generate an expanded population of cells comprising limbal stem cells. Preferably the LATS inhibitor is a compound of Formula A1 or subformulae thereof or salt thereof, according to the invention. In a further aspect the invention relates to a method of cell population expansion comprising the step of a) culturing a seeding population of cells comprising limbal stem cells in the presence of a compound of Formula A1 or subformulae thereof, or a salt thereof to generate an expanded population of cells comprising limbal stem cells. In another embodiment of the invention said compound is selected from Formula A2 or subformulae thereof or a salt thereof. In another aspect the invention relates to a method of cell population expansion comprising the step of a) culturing a seeding population of cells comprising corneal endothelial cells in the presence of a LATS inhibitor to generate an expanded population of cells comprising corneal endothelial cells. Preferably the LATS inhibitor is a compound of Formula A1 or subformulae thereof or salt thereof, according to the invention. In a further aspect the invention relates to a method of cell population expansion comprising the step of a) culturing a seeding population of cells comprising corneal endothelial cells in the presence of a compound of Formula A1 or subformulae thereof, or a pharmaceutically acceptable salt thereof to generate an expanded population of cells comprising corneal endothelial cells. Preferably said compound is selected from Formula A2 or subformulae thereof. Also preferably the salt is a pharmaceutically acceptable salt. Preferably said compound is selected from the group of compounds consisting of N-methyl-2-(pyridin-4-yl)-N-(1,1,1-trifluoropropan-2-yl) pyrido[3,4-d]pyrimidin-4-amine; 2-methyl-1-(2-methyl-2-((2-(pyridin-4-yl)pyrido[3,4-d]pyrimidin-4-yl)amino) propoxy)propan-2-ol; 2,4-dimethyl-4-((2-(pyridin-4-yl) pyrido[3,4-d]pyrimidin-4-yl)amino)pentan-2-ol; N-(tert-butyl)-2-(pyridin-4-yl)-1,7-naphthyridin-4-amine; 2-(pyridin-4-yl)-N-(1-(trifluoromethyl)cyclobutyl)pyrido[3,4-d]pyrimidin-4-amine; N-propyl-2-(pyridin-4-yl)pyrido[3,4-d]pyrimidin-4-amine; N-isopropyl-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; 2-methyl-2-((2-(pyridin-4-yl)pyrido[3,4-d]pyrimidin-4-yl)amino)propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methyl propan-2-yl)pyrido[3,4-d]pyrimidin-4-amine; 2-(2-methyl-2-((2-(pyridin-4-yl)pyrido[3,4-d]pyrimidin-4-yl)amino) propoxy)ethan-1-ol; N-(1-methylcyclopropyl)-7-(pyridin-4-yl)isoquinolin-5-amine; and 2-(3-methyl-1H-pyrazol-4-yl)-N-(1-methylcyclopropyl)pyrido[3,4-d]pyrimidin-4-amine.

Also preferably said compound or a salt thereof, is selected from N-(tert-butyl)-2-(pyridin-4-yl)-1,7-naphthyridin-4-amine and (S)—N-methyl-2-(pyridin-4-yl)-N-(1,1,1-trifluoropropan-2-yl)pyrido[3,4-d]pyrimidin-4-amine.

In a preferred embodiment of the method of cell population expansion said compound is present in a concentration of 0.5 to 100 micromolar, preferably 0.5 to 25 micromolar, more preferably 1 to 20 micromolar, particularly preferably of about 3 to 10 micromolar. In one preferred embodiment of the method of cell population expansion relating to limbal stem cells in step a) the compound is present for 12 to 16 days, particularly preferably the compound is present for 14 days. In another preferred embodiment of the method of cell population expansion relating to corneal endothelial cells in step a) the compound is present for one to two weeks and subsequently step b) is performed wherein the cells are cultured for a period in growth medium without supplementation with said compound, preferably wherein the period is one to two weeks. In a specific embodiment of the method of cell population expansion relating to limbal stem cells the compounds according to Formula A1 or subformulae thereof produce greater than 30 fold expansion of the seeded amount of cells. In another specific embodiment of the method of cell population expansion relating to limbal stem cells the compounds according to Formula A1 and subformulae thereof produce 100 fold to 2200 fold, preferably 600 fold to 2200 fold expansion of the seeded amount of cells. In an embodiment of the method of cell population expansion relating to limbal stem cells, the method according to the invention produces a cell population with greater than 20% limbal stem cells. In another embodiment of the method of cell population expansion relating to limbal stem cells, the method according to the invention produces a cell population with greater than 50% limbal stem cells. In another aspect the method of cell population expansion relating to limbal stem cells according to the invention produces a cell population with greater than 20% expressing p63alpha. In yet another aspect the method of cell population expansion relating to limbal stem cells according to the invention produces a cell population with greater than 50% expressing p63alpha. In a specific embodiment of the method of cell population expansion relating to corneal endothelial cells the compounds according to Formula A1 or subformulae thereof produce greater than 10 fold expansion of the seeded amount of cells. In another specific embodiment of the method of cell population expansion relating to corneal endothelial cells the compounds according to Formula A1 or subformulae thereof produce 15 fold to 600 fold, preferably 20 fold to 550 fold expansion of the seeded amount of cells. In an embodiment of the invention the LATS inhibitor inhibits LATS1 or LATS2, or LATS1 and LATS2. In a more preferred embodiment the LATS inhibitor inhibits LATS1 and LATS2. In another preferred embodiment said method of cell population expansion further comprises use of a gene editing system. Preferably said method comprises use of a gene editing system which specifically targets a gene associated with facilitating a host versus graft immune response. Also preferably the cells are ocular cells or liver cells. In a preferred embodiment the cells are ocular cells. In another preferred embodiment said method of cell population expansion further comprises genetically modifying limbal stem cells, preferably wherein said genetically modifying comprises introducing into said cell a gene editing system which specifically targets a gene associated with facilitating a host versus graft immune response. In another preferred embodiment said method further comprises genetically modifying corneal endothelial cells, preferably wherein said genetically modifying comprises introducing into said cell a gene editing system which specifically targets a gene associated with facilitating a host versus graft immune response. In yet another preferred embodiment, the method of cell population expansion further comprises step c) rinsing the expanded population of cells to substantially remove the compound according to the invention.

In one aspect the invention relates to a kit comprising a LATS inhibitor, growth medium and instructions for cell population expansion. In another aspect the invention relates to a cell population obtainable by the method of cell population expansion according to the invention. In yet another aspect the invention relates to a cell population obtained by the method of cell population expansion according to the invention. In another aspect the invention relates to an ocular cell population obtainable by the method of cell population expansion according to the invention. In another aspect the invention relates to an ocular cell population obtained by the method of cell population expansion according to the invention. In one aspect the invention relates to a cell population comprising limbal stem cells obtainable by the method of cell population expansion relating to limbal stem cells according to the invention. In another aspect the invention relates to a cell population comprising limbal stem cells obtained by the method of cell population expansion relating to limbal stem cells according to the invention. In one aspect the invention relates to a cell population comprising corneal endothelial cells obtainable by the method of cell population expansion relating to corneal endothelial cells according to the invention. In another aspect the invention relates to a cell population comprising corneal endothelial cells obtained by the method of cell population expansion relating to corneal endothelial cells according to the invention. In yet another aspect the invention relates to an ocular cell delivery preparation, comprising a cell population obtainable or obtained by the method of cell population expansion according to the invention and a composition suitable for ocular delivery which is a localising agent. In a specific embodiment the localising agent is GelMa. In another specific embodiment the localising agent is fibrin or fibrin glue. Preferably the cell delivery preparation of limbal stem cells has greater than 20% limbal stem cells. Also preferably the cell delivery preparation of limbal stem cells has greater than 20% p63alpha positive cells. Preferably corneal endothelial cells are present in the cell delivery preparation of corneal endothelial cells, at a density greater than 500 cells per mm$^2$ (area). In certain preferred aspects the cell population obtainable or obtained by the method of cell population expansion or cell delivery preparation according to the invention has only trace levels of the compound according to the invention.

In some aspects of the method of cell population expansion, the method further comprises use of a gene editing system. Preferably the gene editing system is used for genetically modifying cells. In embodiments of methods according to the invention genetically modifying comprises reducing or eliminating the expression and/or function of a gene associated with facilitating a host versus graft immune response. Also preferably the gene editing system specifically targets a gene associated with facilitating a host versus graft immune response. Preferably said gene editing system is selected from the group consisting of a CRISPR gene editing system, a TALEN gene editing system, a zinc finger nuclease gene editing system, a meganuclease gene editing system, AAV vector driven homologous recombination and lentiviral vectors-based genome editing technologies.

In one aspect the invention relates to an isolated cell population, wherein greater than 10%, 20%, 30%, 40%, 50%, 60%, 70%, 80%, or 90% of cells are limbal stem cells. Preferably greater than 20% are limbal stem cells. More preferably greater than 50% are limbal stem cells. In another preferred embodiment greater than 70% are limbal stem cells. Particularly preferably greater than 90% are limbal stem cells. In one embodiment the cells have been gene edited.

In another aspect the invention relates to an isolated cell population, wherein greater than 10%, 20%, 30%, 40%, 50%, 60%, 70%, 80%, or 90% of cells are p63alpha expressing cells. Preferably greater than 20% are p63alpha positive. More preferably greater than 50% are p63alpha positive. In another preferred embodiment greater than 70% are p63alpha positive. Particularly preferably greater than 90% are p63alpha positive. In one embodiment the cells have been gene edited.

In a further aspect the invention relates to a cell population comprising limbal stem cells or the cell population according to the invention, wherein one or more of said cells comprises a non-naturally occurring insertion or deletion of one or more nucleic acid residues of a gene associated with facilitating a host vs graft immune response, wherein insertion and/or deletion results in reduced or eliminated expression or function of said gene. In a preferred embodiment said gene is selected from the group consisting of B2M, HLA-A, HLA-B and HLA-C. In a specific embodiment the cells have genetically modified levels of B2M expression.

In a further aspect the invention relates to a cell population comprising corneal endothelial cells or the cell population according to the invention, wherein one or more of said cells comprises a non-naturally occurring insertion or deletion of one or more nucleic acid residues of a gene associated with facilitating a host vs graft immune response, wherein insertion and/or deletion results in reduced or eliminated expression or function of said gene. In a preferred embodiment said gene is selected from the group consisting of B2M, HLA-A, HLA-B and HLA-C. In a specific embodiment the cells have genetically modified levels of B2M expression.

In a further aspect the invention relates to a cell population comprising limbal stem cells or corneal endothelial cells which have been gene edited. In a further aspect the invention relates to a cell population comprising limbal stem cells which have been gene edited. Preferably the gene editing was performed by CRISPR. Preferably also the B2M gene was edited.

In one aspect the invention relates to a growth promoting agent of cells comprising a LATS inhibitor. In one embodiment the invention relates to a growth promoting agent of ocular cells comprising a LATS inhibitor. In one aspect the invention relates to a growth promoting agent of limbal stem cells comprising a LATS inhibitor. Preferably the LATS inhibitor is a compound of Formula A1 or subformulae thereof or salt thereof. In another aspect the invention relates to a growth promoting agent of limbal stem cells comprising a compound of Formula A1 or subformulae thereof or salt thereof. In one aspect the invention relates to a growth promoting agent of corneal endothelial cells comprising a LATS inhibitor. Preferably the LATS inhibitor is a compound of Formula A1 or subformulae thereof or a salt thereof. In another aspect the invention relates to a growth promoting agent of corneal endothelial cells comprising a compound of Formula A1 or subformulae thereof or a salt thereof.

In one aspect the invention relates to a pharmaceutical composition comprising a compound of Formula A2 or subformulae thereof, or a pharmaceutically acceptable salt, or stereoisomer thereof, according to the invention and at least one pharmaceutically acceptable excipient. Preferably the composition further comprises a preservation or cryopreservation solution.

In another aspect the invention relates to a cell proliferation medium comprising a LATS inhibitor and a growth medium. Preferably the LATS inhibitor is a compound of Formula A1 or subformulae thereof according to the invention. In one aspect the invention relates to a cell proliferation medium comprising a compound of Formula A1 or subformulae thereof according to the invention and a growth medium. In one embodiment the cell proliferation medium additionally comprises cells as provided herein. Preferably the cell proliferation medium additionally comprises ocular cells. In another embodiment the cell proliferation medium additionally comprises limbal stem cells. Preferably the limbal stem cells are in suspension. In yet another embodiment the cell proliferation medium comprises corneal endothelial cells. Preferably the corneal endothelial cells are in suspension.

In one aspect the invention relates to a cell preparation comprising a LATS inhibitor and cells of a cell population as described and/or provided herein. In another aspect the invention relates to a cell preparation comprising a LATS inhibitor and ocular cells. In another aspect the invention relates to a cell preparation comprising a LATS inhibitor and limbal stem cells. In yet another aspect the invention relates to a cell preparation comprising a LATS inhibitor and corneal endothelial cells. Preferably the LATS inhibitor is a compound of Formula A1 or subformulae thereof according to the invention. In another aspect the invention relates to a cell preparation comprising a compound of Formula A1 according to the invention and limbal stem cells. In an alternative aspect the invention relates to a cell preparation comprising a compound of Formula A1 according to the invention and corneal endothelial cells. Preferably the cell preparation further comprises a growth medium. Particularly preferably the cell preparation further comprises a preservation or cryopreservation solution.

In another aspect the invention relates to an ocular cell delivery preparation, comprising a cell preparation according to the invention and a composition suitable for ocular delivery which is a localising agent. In a specific embodiment the localising agent is GelMa. In another specific embodiment the localising agent is fibrin or fibrin glue. In another aspect the invention relates to an ocular cell delivery preparation, comprising a cell preparation according to the invention and a composition suitable for ocular delivery which is a localising agent. In a specific embodiment the localising agent is GelMa. In another specific embodiment the localising agent is fibrin or fibrin glue. In certain preferred aspects the cell preparation according to the invention has only trace levels of the compound according to the invention. In yet another specific embodiment greater than 20% of the cells in the cell delivery preparation are limbal stem cells. In a further specific embodiment greater than 20% of the cells in the cell delivery preparation are p63alpha expressing cells.

In yet another aspect the invention relates to an ocular cell delivery preparation, comprising a cell preparation according to the invention and a composition suitable for ocular delivery which is a localising agent. In a specific embodiment the localising agent is GelMa. Preferably the corneal endothelial cells are in suspension. In an alternative embodiment the corneal endothelial cells are present in the cell delivery preparation at a density greater than 500 cells per $mm^2$ (area). Particularly preferably the corneal endothelial cells are present at a density of 1000 to 3500 cells/$mm^2$ (area), more preferably 2000 to about 3000 cells/$mm^2$ (area). In certain preferred aspects the cell preparation according to the invention has only trace levels of the compound according to the invention.

Preferably the growth medium in the methods or cell preparation according to the invention is selected from the group consisting of Dulbecco's Modified Eagle's Medium (DMEM) supplemented with Fetal Bovine Serum (FBS), human endothelial Serum Free (SF) Medium with human serum, X-VIVO15 medium and DMEM/F12 which is optionally supplemented with calcium chloride; preferably X-VIVO15 medium.

Preferably the preservation or cryopreservation solution according to the invention comprises a solution which is Optisol or PBS (phosphate buffered saline) and the cryopreservation solution additionally comprises glycerol, dimethyl sulfoxide, propylene glycol or acetamide.

In another aspect the invention relates to a kit comprising a composition suitable for ocular delivery and a LATS inhibitor. Preferably the LATS inhibitor is a compound of Formula A2 or subformulae thereof according to the invention. In another aspect the invention relates to a kit comprising a composition suitable for ocular delivery and compound of Formula A2 or subformulae thereof according to the invention. Preferably the kit has instructions for use. In an embodiment the composition suitable for ocular delivery is a localising agent or topical eye drops. Preferably the composition suitable for ocular delivery is a localising agent. In a specific embodiment the kit further comprises limbal stem cells. In another specific embodiment of the kit the composition suitable for ocular delivery is a localising agent which is GelMa. In an alternative specific embodiment of the kit the composition suitable for ocular delivery is a localising agent which is fibrin or fibrin glue. In yet another specific embodiment, greater than 20% of the cells in the kit are limbal stem cells. In a further specific embodiment, greater than 20% of the cells in the kit are p63alpha expressing cells. In an alternative specific embodiment the kit comprises corneal endothelial cells. In another specific embodiment the composition suitable for ocular delivery of corneal endothelial cells is a localising agent which is GelMa. In yet another specific embodiment corneal endothelial cells are present in a monolayer. Preferably the corneal endothelial cells are present at a density greater than 500 cells per $mm^2$ (area). Particularly preferably the corneal endothelial cells are present at a density of 1000 to 3500 cells/$mm^2$ (area), more preferably 2000 to about 3000 cells/$mm^2$ (area).

In preferred embodiments according to the invention the composition suitable for ocular delivery is a localising agent which is a biomatrix. Preferably the composition suitable for ocular delivery according to the invention is a localising agent selected from the group consisting of fibrin, collagen, gelatin, cellulose, amniotic membrane, fibrin glue, polyethylene (glycol) diacrylate (PEGDA), GelMA, localising agents comprising a polymer, cross-linked polymer, or hydrogel comprising one or more of hyaluronic acid, polyethylene glycol, polypropylene glycol, polyethylene oxide, polypropylene oxide, poloxamer, polyvinyl alcohol, polyacrylic acid, polymethacrylic acid, polyvinyl pyrrolidone, poly(lactide-co-glycolide), alginate, gelatin, collagen, fibrinogen, cellulose, methylcellulose, hydroxyethylcellulose, hydroxypropyl cellulose, hydroxypropylmethylcellulose, hydroxypropyl-guar, gellan gum, guar gum, xanthan gum and carboxymethylcellulose, as well as derivatives thereof, co-polymers thereof, and combinations thereof. In preferred embodiments according to the invention the composition suitable for ocular delivery is a localising agent which is GelMa, fibrin or fibrin glue. In specific embodiments according to the invention the composition suitable for ocular delivery is a localising agent which is GelMa. In other specific embodiments according to the invention the composition suitable for ocular delivery is a localising agent which is fibrin or fibrin glue. Preferably the localising agent is fibrin glue. Fibrin glues are known in the art, including, for example, TISSEEL VH Fibrin sealant (Baxter AG, Vienna, Austria) (Panda et al., 2009, Indian J Ophthalmol. September-October; 57(5): 371-379). In one embodiment fibrin glue is used for the delivery of limbal stem cells. In another embodiment GelMa is used for the delivery of corneal endothelial cells.

In more preferred embodiments according to the invention wherein limbal stem cells are present in combination with the localising agent, greater than 10%, 20%, 30%, 40%, 50%, 60%, 70%, 80%, or 90% of cells are limbal stem cells. Preferably greater than 20% are limbal stem cells. More preferably greater than 50% are limbal stem cells. In another preferred embodiment greater than 70% are limbal stem cells. Particularly preferably greater than 90% are limbal stem cells.

In further preferred embodiments according to the invention wherein cells are present in combination with the localising agent, greater than 10%, 20%, 30%, 40%, 50%, 60%, 70%, 80%, or 90% of cells are p63alpha expressing cells. Preferably greater than 20% are p63alpha positive cells. More preferably greater than 50% are p63alpha positive cells. In another preferred embodiment greater than 70% are p63alpha positive cells. Particularly preferably greater than 90% are p63alpha positive cells.

In more preferred embodiments according to the invention corneal endothelial cells are present in combination with the localising agent. Preferably the corneal endothelial cells are in a monolayer. More preferably the corneal endothelial cells are present at a density greater than 500 cells per $mm^2$ (area). Particularly preferably the corneal endothelial cells are present at a density of 1000 to 3500 cells/$mm^2$ (area), more particularly preferably 2000 to about 3000 cells/$mm^2$ (area).

In further particularly preferred embodiments of the invention the LATS inhibitor inhibits LATS1 or LATS2, or LATS1 and LATS2. In a more particularly preferred embodiments according to the invention the LATS inhibitor inhibits LATS1 and LATS2.

In preferred embodiments according to the invention the compound is selected from the group consisting of 2-methyl-1-(2-methyl-2-((2-(pyridin-4-yl)pyrido[3,4-d]pyrimidin-4-yl)amino)propoxy)propan-2-ol; N-(tert-butyl)-2-(pyridin-4-yl)-1,7-naphthyridin-4-amine; N-methyl-2-(pyridin-4-yl)-N-(1,1,1-trifluoropropan-2-yl)pyrido[3,4-d]pyrimidin-4-amine; (S)—N-methyl-2-(pyridin-4-yl)-N-(1,1,1-trifluoropropan-2-yl)pyrido[3,4-d]pyrimidin-4-amine; 2,4-dimethyl-4-((2-(pyridin-4-yl)pyrido[3,4-d]pyrimidin-4-yl)amino)pentan-2-ol; N-isopropyl-N-methyl-2-(pyridin-4-yl)pyrido[3,4-d]pyrimidin-4-amine; 2-(pyridin-4-yl)-N-(1-(trifluoromethyl)cyclobutyl)pyrido[3,4-d]pyrimidin-4-amine; N-isopropyl-2-(pyridin-4-yl)pyrido[3,4-d]pyrimidin-4-amine; N-propyl-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; 2-methyl-2-((2-(pyridin-4-yl)pyrido[3,4-d]pyrimidin-4-yl)amino)propan-1-ol; 2-(3-methyl-1H-pyrazol-4-yl)-N-(1-methylcyclopropyl)pyrido[3,4-d]pyrimidin-4-amine; N-propyl-2-(3-(trifluoromethyl)-1H-pyrazol-4-yl)pyrido[3,4-d]pyrimidin-4-amine; 2-(pyridin-4-yl)-4-(3-(trifluoromethyl) piperazin-1-yl)pyrido[3,4-d]pyrimidine; N-cyclopentyl-2-(pyridin-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; N-(1-methylcyclopropyl)-7-(pyridin-4-yl)isoquinolin-5-amine; 2-(2-methyl-2-((2-(pyridin-4-yl)pyrido[3,4-d]pyrimidin-4-yl)amino)propoxy)ethan-1-ol; and (R)—N-methyl-2-(pyridin-4-yl)-N-(1,1,1-trifluoropropan-2-yl)pyrido[3,4-d]pyrimidin-4-amine.

Also preferably said compound or a salt thereof, is selected from N-(tert-butyl)-2-(pyridin-4-yl)-1,7-naphthyridin-4-amine and (S)—N-methyl-2-(pyridin-4-yl)-N-(1,1,1-trifluoropropan-2-yl)pyrido[3,4-d]pyrimidin-4-amine. Preferably said compound or a salt thereof, is N-(tert-butyl)-2-(pyridin-4-yl)-1,7-naphthyridin-4-amine.

In particularly preferred embodiments according to the invention the compound according to the invention is present in a concentration of 0.5 to 100 micromolar, preferably 0.5 to 25 micromolar, more preferably 1 to 20 micromolar, particularly preferably of about 3 to 10 micromolar.

The invention relates in one aspect to a method of transplanting a population of cells to a subject, said method comprising administering the population of cells obtainable or obtained by the method of cell population expansion or method of culturing cells or method of LATS inhibition according to the invention.

The invention further relates to a method of transplanting a population of ocular cells onto the eye of a subject, said method comprising administering the population of cells obtainable or obtained by the method of cell population expansion or method of culturing cells or method of LATS inhibition according to the invention, wherein the cells are ocular cells.

Preferably ocular cells are limbal stem cells or corneal endothelial cells. The invention relates in another aspect to a method of transplanting a population of ocular cells onto the cornea of a subject, said method comprising administering the cell delivery preparation according to the invention.

The invention relates in another aspect to a method of transplanting a population of cells comprising limbal stem cells onto the cornea of a subject, said method comprising administering the population of cells comprising limbal stem cells obtainable or obtained by the method of cell population expansion or method of culturing cells or method of LATS inhibition according to the invention. The invention relates in another aspect to a method of transplanting a population of cells comprising limbal stem cells onto the cornea of a subject, said method comprising administering the cell delivery preparation according to the invention.

The invention relates in another aspect to a method of transplanting a cell population comprising limbal stem cells onto the cornea of a subject, said method comprising expanding a cell population comprising limbal stem cells by culturing said population with cell proliferation medium comprising a LATS inhibitor according to the invention, preferably rinsing the expanded cell population to substantially remove the LATS inhibitor, and administering said cells onto the cornea of said subject. Preferably said cell population is combined with a biomatrix prior to said administration. In a specific embodiment said cell population is combined with a biomatrix which is GelMA prior to said administration. In a another specific embodiment said cell population is combined with fibrin glue prior to said administration. In an embodiment said cell population is combined with a carrier which is a contact lens. In a specific embodiment the cell population comprising limbal stem cells is combined with a biomatrix which is GelMA and the GelMA is polymerized on a carrier which is a contact lens. In another specific embodiment the cell population comprising limbal stem cells is combined with fibrin glue and a contact lens.

The invention relates in one aspect to a method of transplanting a population of corneal endothelial cells onto the cornea of a subject, said method comprising administering the population of corneal endothelial cells obtainable or obtained by the method of cell population expansion or method of culturing cells or method of LATS inhibition according to the invention. The invention relates in another aspect to a method of transplanting a population of corneal endothelial cells onto the cornea of a subject, said method comprising administering the cell delivery preparation according to the invention.

The invention relates in another aspect to a method of transplanting a population of cells comprising corneal endothelial cells onto the cornea of a subject, said method comprising expanding a population of cells comprising corneal endothelial cells by culturing said population with cell proliferation medium comprising a LATS inhibitor according to the invention, rinsing the expanded population of cells to substantially remove the LATS inhibitor, and administering said cells onto the cornea of said subject. Preferably said cells are combined with a biomatrix prior to said administration. In a specific embodiment said cells are combined with a biomatrix which is GelMA prior to said administration. In a more specific embodiment said corneal endothelial cells are combined with a biomatrix which is bioprinted onto the ocular surface. Particularly preferably said corneal endothelial cells are combined with a biomatrix which is GelMA and bioprinted onto the ocular surface by polymerising the GelMA by a light triggered reaction.

The invention relates in another aspect to a method of transplanting a population of cells to the eye of a subject, comprising combining the cells with a biomatrix to form a cell/biomatrix mixture, injecting the mixture into the eye of the subject or applying the mixture onto the surface of the eye of the subject, and bioprinting the cells in or on the eye by guiding and fixing the cells, such as on the cornea, using a light source, such as an Ultraviolet A or white light source.

In certain embodiments, the light source produces light of a wavelength that is at least 350 nm. In certain embodiments, the light source produces light in the 350 nm to 420 nm range. For example, an LED light source can be used to produce a light having a wavelength of 365 nm or 405 nm, or any other wavelength above 350 nm, or a mercury lamp with a bandpass filter can be used to produce a light having a wavelength of 350 nm to 700 nm, for example a wavelength of 365 nm or 405 nm. In another embodiment, the light source produces visible, white light having a wavelength, for example, in the 400 nm to 700 nm range. In certain embodiments, the cells are ocular cells, such as corneal cells, for example corneal endothelial cells.

The invention relates in another aspect to a method of transplanting a population of corneal endothelial cells to the eye of a subject, comprising culturing a population of corneal endothelial cells in a cell proliferation medium that comprises a LATS inhibitor, combining the corneal endothelial cells with a biomatrix to form a cell/biomatrix mixture, injecting the mixture into the eye of the subject, and bioprinting the cells in the eye by guiding and fixing the cells on the cornea using a light source, such a UVA or LED or visible light source.

The invention relates in a further aspect to a method of prophylaxis or treatment of an ocular disease or disorder using a LATS inhibitor. Preferably the LATS inhibitor is a compound of Formula A1 or subformulae thereof according to the invention. The invention relates in yet a further aspect to a method of prophylaxis or treatment of an ocular disease or disorder using a compound according to Formula A2 or subformulae thereof according to the invention. In preferred specific embodiments the method of prophylaxis or treatment of an ocular disease or disorder further comprises the method of LATS inhibition in a cell population or the method of cell population expansion according to the invention, wherein said cells are ocular cells. Preferably the method of prophylaxis or treatment of an ocular disease or disorder comprises administering to a subject in need thereof of a therapeutically effective amount of a cell population obtainable or obtained by the method of cell population expansion according to the invention, wherein said cells are ocular cells. In another preferred embodiment the method of prophylaxis or treatment of an ocular disease or disorder comprises administering to a subject in need thereof of a therapeutically effective amount of the cell delivery preparation according to the invention, wherein said cells are ocular cells. In yet another preferred embodiment the method of prophylaxis or treatment of an ocular disease or disorder the method comprises the steps of the method of transplanting a population of cells comprising ocular cells to the eye of a subject according to the invention. Preferably the ocular cells are limbal stem cells or corneal endothelial cells. In yet another preferred embodiment the method of prophylaxis or treatment of an ocular disease or disorder the method comprises the steps of the method of transplanting a population of cells comprising limbal stem cells onto the cornea of a subject according to the invention. In an alternatively preferred embodiment the method of prophylaxis or treatment of an ocular disease or disorder the method comprises the steps of the method of transplanting a population of corneal endothelial cells onto the cornea of a subject according to the invention. In a specific embodiment of the method of prophylaxis or treatment of an ocular disease or disorder according to the invention the cell population obtainable or obtained by the method of cell population expansion according to the invention or cell delivery preparation according to the invention is administered simultaneously or sequentially with an agent or agents selected from the group consisting of dexamethasone, cyclosporine, tobramycin, and cefazolin.

In one aspect the invention relates to a YAP (yes associated protein) modulator for use in a method of transplanting a population of cells to a subject, which comprises administering to a subject in need thereof of a therapeutically effective amount of a cell population obtainable or obtained by the method of cell population expansion according to the invention or cell delivery preparation according to the invention. Preferably said YAP modulator is a LATS inhibitor. Preferably the cells are ocular cells.

In one aspect the invention relates to a YAP (yes associated protein) modulator for use in a method of transplanting a population of cells comprising limbal stem cells onto the cornea of a subject, which comprises administering to a subject in need thereof of a therapeutically effective amount of a cell population obtainable or obtained by the method of cell population expansion according to the invention or cell delivery preparation according to the invention. Preferably said YAP modulator is a LATS inhibitor.

In another aspect the invention relates to a YAP modulator for use in a method of treating limbal stem cell deficiency, comprising administering to a subject in need thereof of a therapeutically effective amount of a cell population obtainable or obtained by the method of cell population expansion according to the invention or cell delivery preparation according to the invention. Preferably said YAP modulator is a LATS inhibitor.

In one aspect the invention relates to a YAP (yes associated protein) modulator for use in a method of transplanting a population of corneal endothelial cells onto the cornea of a subject, which comprises administering to a subject in need thereof of a therapeutically effective amount of a cell population obtainable or obtained by the method of cell population expansion according to the invention or cell delivery preparation according to the invention. Preferably said YAP modulator is a LATS inhibitor.

In another aspect the invention relates to a YAP modulator for use in a method of treating corneal endothelial dysfunction, comprising administering to a subject in need thereof of a therapeutically effective amount of a cell population obtainable or obtained by the method of cell population expansion according to the invention or cell delivery preparation according to the invention. Preferably said YAP modulator is a LATS inhibitor.

In yet another embodiment, the present invention relates to a method of treatment of a disease or disorder comprising administering to a subject in need thereof a cell population, wherein the population has been grown in the presence of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a pharmaceutically acceptable salt thereof. Preferably the cells are ocular cells.

In one aspect the invention relates to a compound according to Formula A2 or subformulae thereof, or a pharmaceutically acceptable salt thereof according to the invention for use in therapy or as a medicament. Preferably the compound is for use in an ocular disease or disorder.

In another aspect the invention relates to a LATS inhibitor for use in an ocular disease or disorder, preferably wherein the LATS inhibitor is a compound. Preferably the compound is a compound of Formula A1 or subformulae thereof, or a pharmaceutically acceptable salt thereof according to the invention.

In yet another aspect the invention relates to the use of a compound of Formula A2 or subformulae thereof, or a pharmaceutically acceptable salt thereof according to the invention in the manufacture of a medicament. In a further aspect the invention relates to the use of a compound of Formula A1 or subformulae thereof, or a pharmaceutically acceptable salt thereof according to the invention in the manufacture of a medicament to treat an ocular disease or disorder.

In preferred specific embodiments of the compound for use according to the invention or LATS inhibitor for use according to the invention or use of the compound in a manufacture of a medicament according to the invention, the use further comprises the method of LATS inhibition in a cell population or the method of cell population expansion according to the invention.

In further preferred specific embodiments of the compound for use according to the invention or LATS inhibitor for use according to the invention or use of the compound in a manufacture of a medicament according to the invention, the use comprises administering to a subject in need thereof a therapeutically effective amount of a cell population obtainable or obtained by the method of cell population expansion according to the invention. In yet further preferred embodiments of the compound for use according to the invention or LATS inhibitor for use according to the invention or use of the compound in a manufacture of a medicament according to the invention, the use comprises administering to a subject in need thereof of a therapeutically effective amount of the cell delivery preparation according to the invention. In one preferred embodiment of the compound for use according to the invention or LATS inhibitor for use according to the invention or use of the compound in a manufacture of a medicament according to the invention, the use comprises the steps of the method of transplanting a population of cells comprising ocular cells onto the cornea of a subject according to the invention. In yet more preferred embodiments of the compound for use according to the invention or LATS inhibitor for use according to the invention or use of the compound in a manufacture of a medicament according to the invention, the use comprises the steps of the method of transplanting a population of cells comprising limbal stem cells onto the cornea of a subject according to the invention. In yet more preferred embodiments of the compound for use according to the invention or LATS inhibitor for use according to the invention or use of the compound in a manufacture of a medicament according to the invention, the use comprises the steps of the method of transplanting a population of cells comprising corneal endothelial cells onto the cornea of a subject according to the invention. In specific embodiments of the compound for use according to the invention or LATS inhibitor for use according to the invention or use of the compound in a manufacture of a medicament according to the invention, the cell population obtainable or obtained by the method of cell population expansion according to the invention or cell delivery preparation according to the invention is administered simultaneously or sequentially with an agent or agents selected from the group consisting of dexamethasone, cyclosporine, tobramycin, and cefazolin.

In preferred embodiments according to the invention, the ocular disease or disorder is associated with limbal stem cell deficiency. In more preferred embodiments the ocular disease or disorder is limbal stem cell deficiency. More preferably the ocular disease or disorder is limbal stem cell deficiency which arises due to an injury or disorder selected from the group consisting of chemical burns, thermal burns, radiation injury, aniridia, sclerocornea, multiple endocrine neoplasia, Stevens Johnson syndrome, ocular cicatricial pemphigoid, collagen vascular diseases; chronic non-auto-immune inflammatory disorders arising from contact lens use, dry eye disease, rosacea, staph marginal, keratitis (including bacterial, fungal & viral keratitis), pterygia or neoplasm, limbal stem cell deficiency arising after multiple eye surgeries, excision of pterygia or neoplasm or cryotherapy; and limbal stem cell deficiency arising as a result of medication toxicity from a medication selected from the group consisting of preservatives (thimerosal, benzalkonium), topical anesthetics, pilocarpine, beta blockers, mitomycin, 5-fluorouracil, silver nitrate, and oral medications causing Stevens Johnson syndrome. Particularly preferably the ocular disease or disorder is limbal stem cell deficiency which arises due to an injury or disorder selected from the group consisting of chemical burns, aniridia, Stevens Johnson Syndrome and contact lens use.

In preferred embodiments according to the invention, the ocular disease or disorder is associated with decreased corneal endothelial cell density. In more preferred embodiments the ocular disease or disorder is corneal endothelial dysfunction. More preferably the ocular disease or disorder is corneal endothelial dysfunction which is selected from the group consisting of Fuchs endothelial corneal dystrophy, bullous keratopathy (including pseudophakic bullous keratopathy and aphakic bullous keratopathy), corneal transplant failure, posterior polymorphous corneal dystrophy, congenital hereditary endothelial dystrophy, X-linked endothelial corneal dystrophy, aniridia, and corneal endothelitis. In a specific embodiment the ocular disease or disorder is selected from the group consisting of Fuchs endothelial corneal dystrophy, bullous keratopathy (including pseudophakic bullous keratopathy and aphakic bullous keratopathy) and corneal transplant failure.

The invention further relates to methods of promoting wound healing, particularly for treating or ameliorating the symptoms of burns, acute and chronic skin ulcers, comprising administering to a subject in need thereof an effective amount of a LATS inhibitor.

Within certain other aspects, the invention relates to a method of promoting wound healing comprising administering a therapeutically effective amount of a compound of Formula A1 or subformulae thereof, or a pharmaceutically acceptable salt, or a stereoisomer thereof.

In another aspect, the invention relates to compounds and compositions that may be used in promoting wound healing. In another aspect, the invention relates to compounds and compositions that may be used for the manufacture of a medicament for promoting wound healing.

The present invention also relates to a method of promoting wound healing, particularly for treating or ameliorating the symptoms of burns, acute skin ulcers, and chronic skin ulcers, comprising administering to a subject in need thereof a therapeutically effective amount of a compound of Formula A1 or subformulae thereof, and optionally with a second therapeutic agent that is another compound of the invention or one other type of therapeutic agent.

The present invention also relates to a method of promoting ocular wound healing comprising administering to an eye of a subject a therapeutically effective amount of a compound of the invention. In one embodiment, the ocular wound is a corneal wound. In other embodiments, the ocular wound is an injury or surgical wound.

In another aspect, the invention relates to compounds and compositions that may be used in liver regeneration and liver regrowth. Within certain other aspects, the invention relates to a method of promoting liver regeneration and liver regrowth comprising administering a therapeutically effective amount of a compound of Formula A1 or subformulae thereof, or a pharmaceutically acceptable salt thereof, or a stereoisomer thereof. In another aspect, the invention relates to compounds and compositions that may be used for the manufacture of a medicament for liver regeneration and liver regrowth.

The present invention also relates to a method for liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution, comprising administering to a subject in need thereof a therapeutically effective amount of a compound of the present invention and optionally with a second therapeutic agent that is another compound of the invention or one other type of therapeutic agent.

In certain embodiments, the invention relates to a method of generating cellular material for cell therapy and/or transplantation comprising the ex-vivo use of a compound of Formula A1 or subformulae thereof, or a pharmaceutically acceptable salt thereof, or a stereoisomer thereof. The cellular material may comprise ocular, liver or skin cells.

Furthermore, in certain embodiments, the invention relates to a method of promoting liver regeneration and liver regrowth comprising the ex-vivo use of a compound of Formula A1 or subformulae thereof, or a pharmaceutically acceptable salt thereof, or a stereoisomer thereof.

The present invention also relates to an ex-vivo method for liver cell population expansion, comprising use of a compound of the present invention or a pharmaceutically acceptable salt thereof, or a stereoisomer thereof.

Other features and advantages of the present invention will be apparent from the following detailed description and claims.

BRIEF DESCRIPTION OF THE FIGURES

FIG. 2: Immunolabelling of p63-alpha in limbal stem cell cultures indicates that the LSC population can be expanded when it is maintained in medium comprising the LATS inhibitors (compound ex. 49 and ex. 133). FIG. 2A: In the presence of growth medium and DMSO, only a few isolated cells attach to the culture dish and survive up to 6 days. Most cells expressed the human nuclear marker, but few expressed p63alpha. FIGS. 2B and 2C: In contrast, in the presence of LATS inhibitors: compound example no. 49 and example no. 133, the cells formed colonies and expressed p63alpha. This result indicated that the LATS inhibitors promote the expansion of the population of cells with the p63alpha-positive phenotype. FIG. 2D: Passaging cells and culturing them in the presence of LATS inhibitor compound example no. 49 for two weeks enabled cell population expansion and the formation of confluent cultures expressing p63alpha.

FIG. 7: FIG. 7A: Transplanted eye, keratin-12 staining; FIG. 7B: Transplanted eye, keratin-19 staining; FIG. 7C: non-transplanted control eye, keratin-12 staining; FIG. 7D: non-transplanted control eye, keratin-19 staining. These figures show that in a rabbit model of limbal stem cell deficiency, a population of LSCs expanded in medium comprising compound example no. 12, combined with GelMA and delivered via a contact lens in vivo to the rabbit's corneal surface, lead to regeneration of a keratin-12-positive corneal epithelium (FIG. 7A) and prevented conjunctivalization by keratin-19-positive conjunctival cells in the transplanted eye. FIG. 7B: Arrow is pointing to absence of keratin 19 staining. In contrast, non-transplanted rabbit eyes showed absence of keratin-12-positive corneal epithelium restoration. FIG. 7C: Arrow is pointing to absence of keratin-12 staining. Instead, signs of conjunctivalization were observed, as showed by the presence of keratin-19 staining. FIG. 7D: Arrow is pointing to areas of positive keratin-19 staining.

FIG. 8.

FIG. 15: LATS inhibitors (compound ex. 133 and ex. 49) induce YAP dephosphorylation in CECs within one hour of treatment.

FIG. 18: Zonula Occludens-1 (ZO-1) immunolabelling indicates that CECs proliferated in the presence of the LATS inhibitor, compound ex. 49, (FIG. 18b) form tight junctions, an endothelial structure and retain a normal cell size and morphology characteristic of functional CECs. CECs proliferated in the presence of the vehicle alone (DMSO) show signs of polymegatism characteristic of dysfunctional CECs (FIG. 18a).

FIG. 22: Bubble depression method depicting method 1 as described further under the "bio-printing section", in which a biomatrix is applied to an eye to deliver a cell preparation according to the invention.

FIG. 23: Subtractive method using femtosecond (FS) laser, depicting method 2 as described further under the "bio-printing section", in which a biomatrix is applied to an eye to deliver a cell preparation according to the invention.

FIG. 24: Dye mask method, depicting method 3 as described further under the "bio-printing section", in which a biomatrix is applied to an eye to deliver a cell preparation according to the invention.

FIG. 25: Dry dispense method, depicting method 4 as described further under the "bio-printing section", in which a biomatrix is applied to an eye to deliver a cell preparation according to the invention.

FIG. 28 CECs bioprinted on the posterior side of the cornea can rebuild a corneal endothelium in a rabbit model of corneal endothelium dystrophy. Results indicated that in experimental rabbits, the corneal endothelium structure can be detected using ZO-1 immunohistochemistry (FIG. 28A). In the right eye of a rabbit where the corneal endothelium was surgically removed and no CEC was bioprinted, the ZO-1 staining is absent, indicating an absence of normal corneal endothelium structure (FIG. 28B). In the right eye of a rabbit where the corneal endothelium was surgically removed and CEC were bioprinted, the ZO-1 staining is present, indicating that a corneal endothelium structure has been rebuilt (FIG. 28C).

(FIG. 30 discloses SEQ ID NO: 28).

FIG. 33A is a western blot of pYAP in lysate of human HaCaT cells that were untreated or treated by 40 pM each of siRNA against MST1/2 or LATS1/2; actin was used as control.

FIG. 33B is a western blot of pYAP in lysate of human HaCaT cells that were untreated or treated by 9 pM of Example 133; actin was used as control.

FIG. 33C is a graph of the relative inhibitory activity against LATS1 versus concentration of Example 133 ranging from ~$10^{-4}$ to 1 μm. The calculated $IC_{50}$ of Example 133 against LATS1 was 1.3 nM.

FIG. 35A shows micrographs of mouse skin treated topically with vehicle or Example 133.

FIG. 35B is a scatter plot comparing the percentage of Ki67+ cells in mouse skin treated with vehicle or Example 133.

DETAILED DESCRIPTION OF THE INVENTION

LATS

Figure 1:
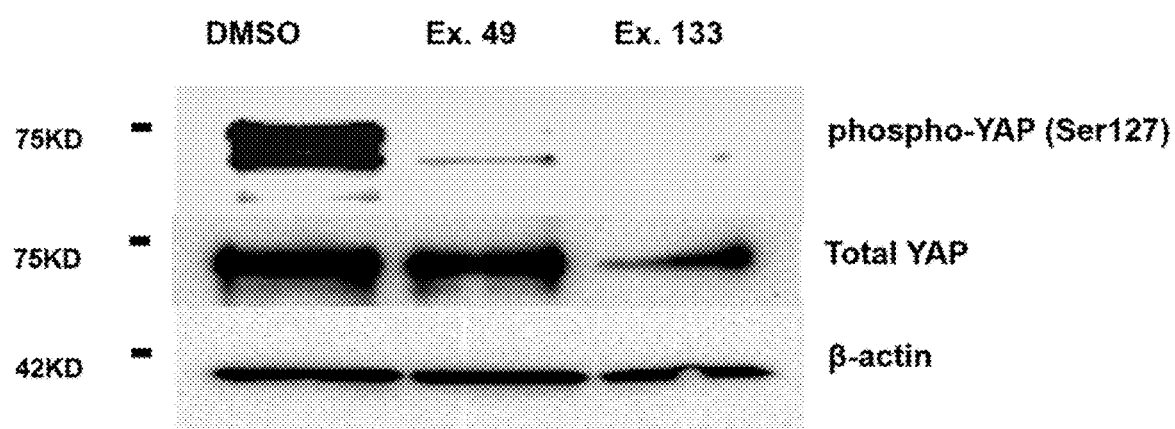
FIG. 1: LATS inhibitors (compound ex. 49 and ex. 133) induce YAP dephosphorylation in LSCs within one hour of treatment as shown by Western blot.

LATS is the abbreviated name of the large tumor suppressor kinase. LATS as used herein refers to LATS1 and/or LATS2. LATS1 as used herein refers to the large tumor suppressor kinase 1 and LATS2 refers to the large tumor suppressor kinase 2. LATS1 and LATS2 both have serine/threonine protein kinase activity. LATS1 and LATS2 have been given the Human Genome Organisation (HUGO) Gene Nomenclature Committee identifiers: HGNC ID 6514 and HGNC ID 6515 respectively. LATS1 is sometimes also referred to in the art as WARTS or wts, and LATS2 is sometimes referred to in the art as KPM. Representative LATS sequences, include, but are not limited to, the protein sequences available from the National Center for Biotechnology Information protein database with the accession numbers NP_004681.1 (LATS1) and NP_001257448.1 (LATS1) and NP_055387.2 (LATS 2), as shown below.

```
LATS1: NP_004681.1 (Serine/threonine-protein kinase LATS1 isoform 1,
homo sapiens) (SEQ ID NO: 1:)
   1    mkrsekpegy rqmrpktfpa snytvssrqm lqeireslrn lskpsdaaka ehnmskmste
  61    dprqvrnppk fgthhkalqe irnsllpfan etnssrstse vnpqmlqdlq aagfdedmvi
 121    qalqktnnrs ieaaiefisk msyqdprreq maaaaarpin asmkpgnvqq svnrkqswkg
 181    skeslvpqrh gpplgesvay hsespnsqtd vgrplsgsgi safvqahpsn gqrvnppppp
 241    qvrsvtpppp prgqtppprg ttppppswep nsqtkrysgn meyvisrisp vppgawqegy
 301    ppplntspm nppnqgqrgi ssvpvgrqpi imqssskfnf psgrpgmqng tgqtdfmihq
 361    nvvpagtvnr qppppyplta angqspsalq tggsaapssy tngsipqsmm vpnrnshnme
 421    lynisvpglq tnwpqsssap aqsspssghe iptwqpnipv rsnsfnnplg nrashsansq
 481    psattvtait papiqqpvks mrvlkpelqt alapthpswi pqpiqtvqps pfpegtasnv
 541    tvmppvaeap nyqgppppyp khllhqnpsv ppyesiskps kedqpslpke deseksyenv
 601    dsgdkekkqi ttspitvrkn kkdeerresr iqsyspqafk ffmeqhvenv lkshqqrlhr
 661    kkqlenemmr vglsqdaqdq mrkmlcqkes nyirlkrakm dksmfvkikt lgigafgevc
 721    larkvdtkal yatktlrkkd vllrnqvahv kaerdilaea dnewvvrlyy sfqdkdnlyf
 781    vmdyipggdm msllirmgif peslarfyia eltcavesvh kmgfihrdik pdnilidrdg
 841    hikltdfglc tgfrwthdsk yyqsgdhprq dsmdfsnewg dpsscrcgdr lkplerraar
 901    qhqrclahsl vgtpnyiape vllrtgytql cdwwsvgvil femlvgqppf laqtpletqm
 961    kvinwqtslh ippqaklspe asdliiklcr gpedrlgkng adeikahpff ktidfssdlr
1021    qqsasyipki thptdtsnfd pvdpdklwsd dneeenvndt lngwykngkh pehafyeftf
1081    rrffddngyp ynypkpieye yinsqgseqq sdeddqntgs eiknrdlvyv LATS1: serine/threonine-protein kinase LATS1 isoform 2 [Homo sapiens]
NCBI Reference Sequence: NP_001257448.1 (SEQ ID NO: 2:)
   1    mkrsekpegy rqmrpktfpa snytvssrqm lqeireslrn lskpsdaaka ehnmskmste
  61    dprqvrnppk fgthhkalqe irnsllpfan etnssrstse vnpqmlqdlq aagfdedmvi
 121    qalqktnnrs ieaaiefisk msyqdprreq maaaaarpin asmkpgnvqq svnrkqswkg
 181    skeslvpqrh gpplgesvay hsespnsqtd vgrplsgsgi safvqahpsn gqrvnppppp
 241    qvrsvtpppp prgqtppprg ttppppswep nsqtkrysgn meyvisrisp vppgawqegy
 301    pppintspm nppnqgqrgi ssvpvgrqpi imqssskfnf psgrpgmqng tgqtdfmihq
```

-continued

```
 361        nvvpagtvnr  qppppyplta  angqspsalq  tggsaapssy  tngsipqsmm  vpnrnshnme 421        lynisvpglq  tnwpqsssap  aqsspssghe  iptwqpnipv  rsnsfnnplg  nrashsansq 481        psattvtait  papiqqpvks  mrvlkpelqt  alapthpswi  pqpiqtvqps  pfpegtasnv 541        tvmppvaeap  nyqgppppyp  khllhqnpsv  ppyesiskps  kedqpslpke  deseksyenv 601        dsgdkekkqi  ttspitvrkn  kkdeerresr  iqsyspqafk  ffmeqhvenv  lkshqqrlhr 661        kkqlenemmr  vkpfkmsifi  lnhlfawclf
```

LATS 2: NP_055387.2 serine/threonine-protein kinase LATS2 [*Homo sapiens*].
((SEQ ID NO: 3:)

```
   1        mrpktfpatt  ysgnsrqrlq  eireglkqps  kssvqglpag  pnsdtsldak  vlgskdatrq 61        qqqmratpkf  gpyqkalrei  ryslLpfane  sgtsaaaevn  rqmlqelvna  gcdqemagra 121        Ikqtgsrsie  aaleyiskmg  yldprneqiv  rvikqtspgk  glmptpvtrr  psfegtgdsf 181        asyhqlsgtp  yegpsfgadg  ptaleemprp  yvdylfpgvg  phgpghqhqh  ppkgygasve 241        aagahfplqg  ahygrphllv  pgeplgygvq  rspsfqsktp  petggyaslp  tkgqggppga 301        glafpppaag  lyvphphhkq  agpaahqlhv  lgsrsqvfas  dsppqslltp  srnslnvdly 361        elgstsvqqw  paatlarrds  lqkpgleapp  rahvafrpdc  pvpsrtnsfn  shqprpgppg 421        kaepslpapn  tvtavtaahi  Ihpyksvrvl  rpepqtavgp  shpawvpapa  papapapapa 481        aegldakeeh  alalggagaf  pldveyggpd  rrcppppypk  hlllrskseq  ydldslcagm 541        eqslragpne  peggdksrks  akgdkggkdk  kqiqtspvpv  rknsrdeekr  esriksyspy 601        afkffmeqhv  enviktyqqk  vnrrlqleqe  makaglceae  qeqmrkilyq  kesnynrlkr 661        akmdksmfvk  iktlgigafg  evclackvdt  halyamktlr  kkdvinrnqv  ahvkaerdil 721        aeadnewvvk  lyysfqdkds  lyfvmdyipg  gdmmsllirm  evfpehlarf  yiaeltlaie 781        svhkmgfihr  dikpdnilid  Idghikltdf  glctgfrwth  nskyyqkgsh  vrqdsmepsd 841        lwddvsncrc  gdrlktleqr  arkqhqrcla  hslvgtpnyi  apevllrkgy  tqlcdwwsvg 901        vilfemlvgq  ppflaptpte  tqlkvinwen  tlhipaqvkl  speardlitk  lccsadhrlg 961        rngaddlkah  pffsaidfss  dirkqpapyv  ptishpmdts  nfdpvdeesp  wndasegstk 1021        awdtltspnn  khpehafyef  tfrrffddng  ypfrcpkpsg  aeasqaessd  lessdlvdqt 1081        egcqpvyv
```

LATS is thought to negatively regulate YAP1 activity. "YAP1" refers to the yes-associated protein 1, also known as YAP or YAP65, which is a protein that acts as a transcriptional regulator of genes involved in cell proliferation. LATS kinases are serine/threonine protein kinases that have been shown to directly phosphorylate YAP which results in its cytoplasmic retention and inactivation. Without phosphorylation by LATS, YAP translocates into the nucleus, forming a complex with a DNA binding protein, TEAD, and results in downstream gene expression. (Barry E R & Camargo F D (2013) The Hippo superhighway: signaling crossroads converging on the Hippo/Yap pathway in stem cells and development. Current opinion in cell biology 25(2):247-253; Mo J S, Park H W, & Guan K L (2014) The Hippo signaling pathway in stem cell biology and cancer. EMBO reports 15(6):642-656; Pan D (2010) The hippo signaling pathway in development and cancer. Developmental cell 19(4):491-505.)

The Hippo/YAP pathway is involved in numerous cell types and tissues in mammalian systems, including various cancers. In particular, the Hippo pathway is evidently involved in the intestine, stomach and esophagus, pancreas, salivary gland, skin, mammary gland, ovary, prostate, brain and nervous system, bone, chrondrocytes, adipose cells, myocytes, T lymphocytes, B lymphocytes, myeloid cells, kidney, and lung. See Nishio et al., 2017, *Genes to Cells* 22:6-31.

LATS1 and LATS2 Inhibition

Compounds of Formula A1 or subformulae thereof, in free form or in salt form are potent inhibitors of LATS1 and/or LATS2.

In a preferred embodiment the compounds of Formula A2 or subformulae thereof, in free form or in salt form are potent inhibitors of LATS1 and LATS2.

The inhibition efficacy of the compounds against LATS1 were assayed by the LATS1 Biochemical HTRF Assay as described in Example A1 below. The inhibition efficacy of the compounds of the invention against LATS1 (LATS1 $IC_{50}$ in micromolar) in this assay are reported in Table 1A. It should be noted that compounds with $IC_{50}$ greater than 1 micromolar are considered inactive in this assay.

The inhibition efficacy of selected compounds against LATS2 were assayed by the LATS2 Biochemical Caliper Assay as described in Example A3 below. The inhibition efficacy of the compounds of the invention against LATS2 (LATS2 IC$_{50}$ in micromolar) in this assay are also reported in Table 1A. It should be noted that compounds with IC$_{50}$ greater than 1 micromolar are considered inactive in this assay.

LATS Inhibitors

The invention therefore relates to a compound of Formula A2:

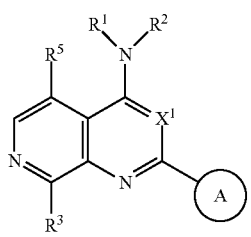

or a salt, or stereoisomer thereof, wherein
X$^1$ is CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or a 9-membered fused bicyclic heteroaryl that is selected from

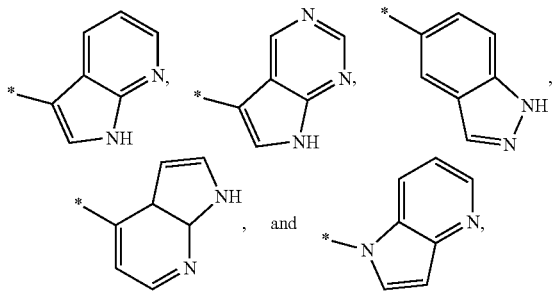

wherein "*" represents the point of attachment of ring A to the remainder of the molecule; and
wherein ring A is unsubstituted or substituted by 1 to 2 substituents independently selected from halogen, cyano, C$_{1-6}$alkyl, C$_{1-6}$haloalkyl, —NH$_2$, C$_{1-6}$alkylamino, di-(C$_{1-6}$alkyl)amino, C$_{3-6}$cycloalkyl, and phenylsulfonyl;
R$^0$ is hydroxyl or C$_{1-6}$alkoxy;
R$^1$ is hydrogen or C$_{1-6}$alkyl;
R$^2$ is selected from
(a) C$_{1-8}$alkyl that is unsubstituted or substituted by 1 to 3 substituents independently selected from
  (i) halogen;
  (ii) cyano;
  (iii) oxo;
  (iv) C$_2$alkenyl;
  (v) C$_2$alkynyl;
  (vi) C$_{1-6}$haloalkyl;
  (vii) —OR$^6$, wherein R$^6$ is selected from hydrogen, C$_{1-6}$alkyl that is unsubstituted or substituted by R$^0$ or —C(O)R$^0$;
  (viii) —NR$^{7a}$R$^{7b}$, wherein R$^{7a}$ is hydrogen or C$_{1-6}$alkyl, and R$^{7b}$ is selected from hydrogen, —C(O)R$^0$, C$_{1-6}$alkyl that is unsubstituted or substituted by —C(O)R$^0$;
  (ix) —C(O)R$^8$, wherein R$^8$ is R$^0$ or —NH—C$_{1-6}$alkyl-C(O)R$^0$;
  (x) —S(O)$_2$C$_{1-6}$alkyl;
  (xi) monocyclic C$_{3-6}$cycloalkyl or polycyclic C$_{7-10}$cycloalkyl that are each unsubstituted or substituted by 1 to 2 substituents independently selected from halogen, C$_{1-6}$alkyl, hydroxyC$_{1-6}$alkyl, C$_{1-6}$haloalkyl, R$^0$, —NH$_2$, C$_{1-6}$alkylamino, and di-(C$_{1-6}$ alkyl)amino;
  (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, C$_{1-6}$alkyl, C$_{1-6}$alkylamino, and di-(C$_{1-6}$alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from N and O; and
  (xv) 9- or 10-membered fused bicyclic heteroaryl comprising, as ring member, 1 to 2 heteroatoms independently selected from N and O;
(b) —S(O)$_2$C$_{1-6}$alkyl;
(c) phenyl that is unsubstituted or substituted by 1 to 2 substituents independently selected from halogen, C$_{1-6}$alkyl and R$^0$;
(d) C$_{3-6}$cycloalkyl that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$ alkyl that is unsubstituted or substituted by R$^0$ or —C(O)R$^0$; and
(e) 4-membered heterocycloalkyl comprising, as ring members, 1 to 2 heteroatoms selected from N, O and S and that is unsubstituted or substituted by 1 to 2 substituents independently selected from C$_{1-6}$haloalkyl, R$^0$, C$_{1-6}$alkylamino, di-(C$_{1-6}$ alkyl)amino, —C(O)R$^0$, and C$_{1-6}$alkyl that is unsubstituted or substituted by R$^0$ or —C(O)R$^0$;
or, provided that when X$^1$ is CH, R$^1$ and R$^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by R$^1$ and R$^2$ taken together with the nitrogen atom to which both are bound is unsubstituted or substituted by 1 to 3 substituents independently selected from halogen, C$_{1-6}$alkyl, C$_{1-6}$haloalkyl, and R$^0$;
R$^3$ is selected from hydrogen, halogen and C$_{1-6}$alkyl; and
R$^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by R$^0$;
with the proviso that:
(1) when X$^1$ is N, ring A is 4-primidinyl or 3-fluoro-4-primidinyl, R$^1$ is H or methyl, R$^3$ is H or Cl and R$^5$ is H; then R$^2$ is not C$_{2-4}$alkyl that is substituted with a substituent selected from —NH$_2$, C$_{1-6}$alkylamino or t-butylcarbamoyl-amino and that is optionally further substituted with unsubstituted phenyl; and
(2) when X$^1$ is N, ring A is indazol-5-yl, R$^1$, R$^3$ and R$^5$ are H; then R$^2$ is not C$_4$alkyl that is substituted with —NH$_2$.

Unless specified otherwise, the term "compounds of the present invention" refers to compounds of Formula A2 or subformulae thereof, or salts thereof, as well as all stereoisomers (including diastereoisomers and enantiomers), rotamers, tautomers and isotopically labeled compounds (including deuterium substitutions), as well as inherently formed moieties.

Various (enumerated) embodiments of the invention are described herein. It will be recognized that features specified in each embodiment may be combined with other specified features to provide further embodiments of the present invention. When an embodiment is described as being "according to" a previous embodiment, the previous embodiment includes sub-embodiments thereof, for example such that when Embodiment 20 is described as being "according to" embodiments 1 to 19, embodiments 1 to 19 includes embodiments 19 and 19A.

Embodiment 1

A compound of Formula A2 or a salt thereof, as described above.

Embodiment 2

A compound of Formula A2 according to embodiment 1, or a salt thereof,
wherein
Ring A is
(a) a 5- or 6-membered monocyclic heteroaryl that is linked to the remainder of the molecule through a carbon ring member and comprises, as ring member, 1 to 2 heteroatoms that are selected from N, provided that at least one of the nitrogen atom ring member is an unsubstituted nitrogen (—N=) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

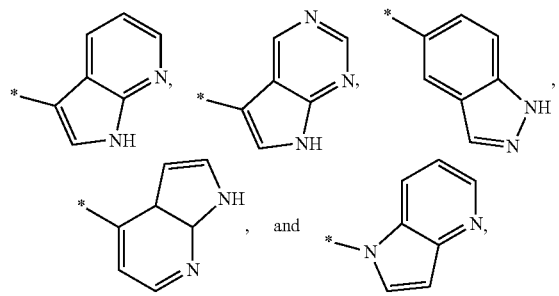

wherein "*" represents the point of attachment of ring A to the remainder of the molecule; and
wherein ring A is unsubstituted or substituted by 1 to 2 substituents independently selected from halogen, cyano, $C_{1-6}$alkyl, $C_{1-6}$haloalkyl, —$NH_2$ and $C_{3-6}$cycloalkyl.

Embodiment 3

A compound of Formula A2, or a salt thereof, according to embodiment 1, wherein ring A is selected from

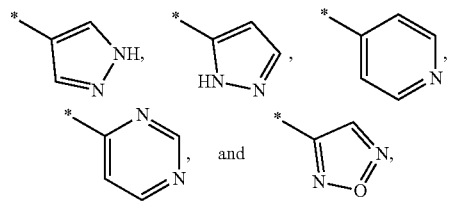

which are each unsubstituted or substituted by 1 to 2 substituents independently selected from cyano, halogen, $C_{1-6}$alkyl, $C_{1-6}$haloalkyl, $NH_2$, and $C_{3-6}$cycloalkyl;
or from

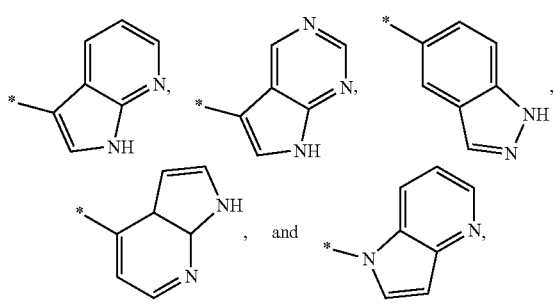

which are each unsubstituted or substituted by $C_{1-6}$alkyl.

Embodiment 4

A compound of Formula A2, or a salt thereof, according to any one of embodiments 1 to 3, wherein ring A is selected from

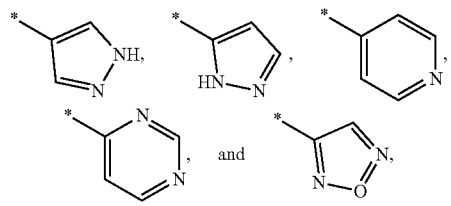

which are each unsubstituted or substituted by a substituent selected from halogen, cyano, $C_{1-6}$alkyl, $C_{1-6}$ haloalkyl, and —$NH_2$;
or is

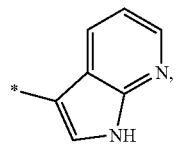

which is unsubstituted or substituted by $C_{1-6}$alkyl.

Embodiment 5

A compound of Formula A2, or a salt thereof, according to any one of embodiments 1 to 3, wherein ring A is selected from

Embodiment 6

A compound of Formula A2, or a salt thereof, according to any one of embodiments 1 to 5, wherein ring A is selected from

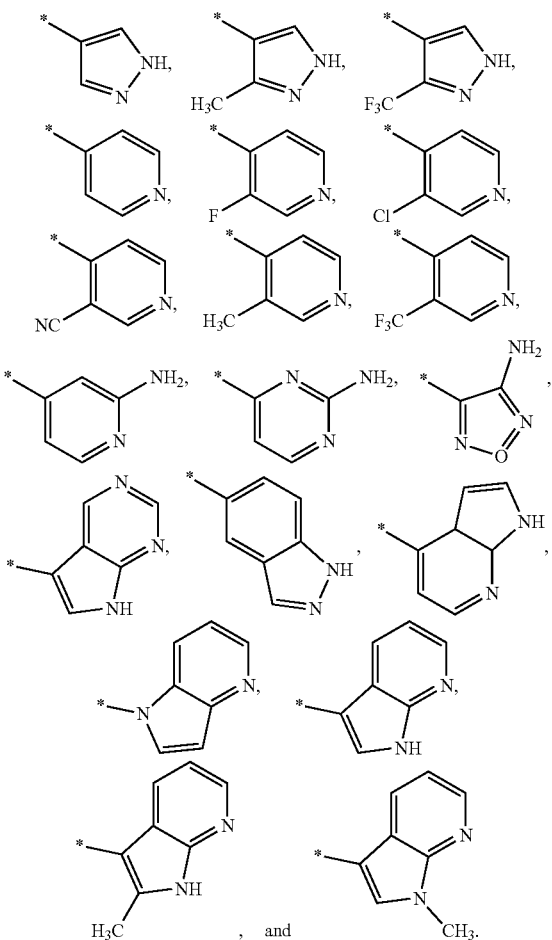

Embodiment 7

A compound of Formula A2, or a salt thereof, according to any one of embodiments 1 to 6, wherein ring A is selected from

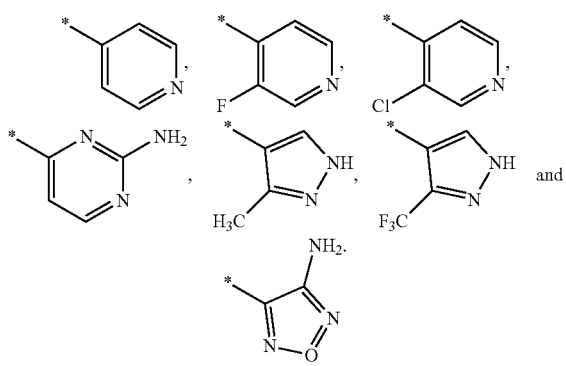

Embodiment 8

A compound of Formula A2, or a salt thereof, according to any one of embodiments 1 to 7, wherein ring A is

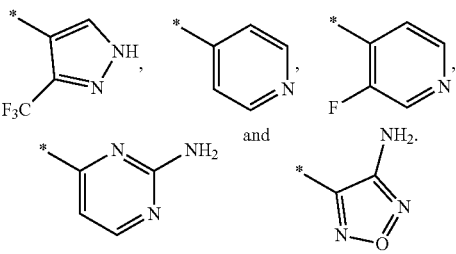

Embodiment 9

A compound of Formula A2, or a salt thereof, according to any one of embodiments 1 to 7, wherein ring A is

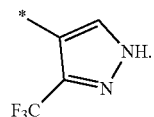

Embodiment 10

A compound of Formula A2, or a salt thereof, according to any one of embodiments 1 to 7, wherein ring A is

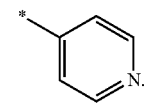

Embodiment 11

A compound of Formula A2, or a salt thereof, according to any one of embodiments 1 to 7, wherein ring A is

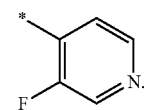

Embodiment 12

A compound of Formula A2, or a salt thereof, according to any one of embodiments 1 to 7, wherein ring A is

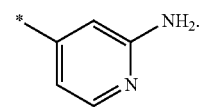 [SMILES: *c1ccnc(N)c1]

Embodiment 13

A compound of Formula A2, or a salt thereof, according to any one of embodiments 1 to 5, wherein ring A is

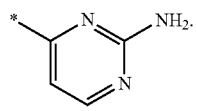

Embodiment 14

A compound of Formula A2, or a salt thereof, according to any one of embodiments 1 to 5, wherein ring A is

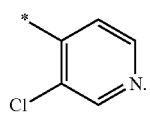

Embodiment 15

A compound of Formula A2, or a salt thereof, according to any one of embodiments 1 to 6, wherein ring A is

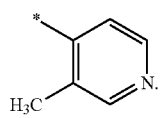

Embodiment 16

A compound of Formula A2, or a salt thereof, according to any one of embodiments 1 to 3, wherein ring A is

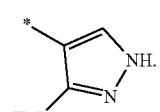

Embodiment 17

A compound of Formula A2, or a salt thereof, according to any one of embodiments 1 to 4, wherein ring A is

Embodiment 18

A compound of Formula A2, or a salt thereof, according to any one of embodiments 1 to 5, wherein ring A is

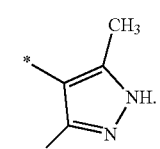

Embodiment 18A

A compound of Formula A2, or a salt thereof, according to any one of embodiments 1 to 5, wherein ring A is

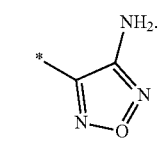

Embodiment 19

A compound of Formula A2, or a salt thereof, according to any one of embodiments 1 to 3, wherein ring A is selected from

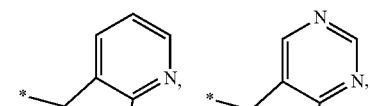

which are each unsubstituted or substituted by 1 to 2 substituents independently selected from cyano, halogen, $C_{1-6}$alkyl, $C_{1-6}$haloalkyl, $NH_2$, and $C_{3-6}$cycloalkyl; or from

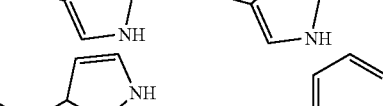

which are each unsubstituted or substituted by $C_{1-6}$alkyl.

Embodiment 20

A compound of Formula A2, or a salt thereof, according to any one of embodiments 1 to 19, wherein $R^1$ is selected from hydrogen, methyl and ethyl.

Embodiment 21

A compound of Formula A2, or a salt thereof, according to any one of embodiments 1 to 20, wherein $R^1$ is methyl.

Embodiment 22

A compound of Formula A2, or a salt thereof, according to any one of embodiments 1 to 20, wherein $R^1$ is hydrogen.

Embodiment 23

A compound of Formula A2, or a salt thereof, according to any one of embodiments 1 to 22, wherein
$R^2$ is selected from
(a) $C_{1-8}$alkyl that is unsubstituted or substituted by 1 to 3 substituents independently selected from
  (i) cyano;
  (ii) $C_2$alkynyl;
  (iii) $C_{1-6}$haloalkyl;
  (iv) —$OR^6$, wherein $R^6$ is selected from hydrogen, $C_{1-6}$alkyl that is unsubstituted or substituted by $R^0$ or —C(O)$R^0$;
  (v) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (vi) —C(O)$R^8$, wherein $R^8$ is $R^0$;
  (vii) —S(O)$_2C_{1-6}$alkyl;
  (viii) monocyclic $C_{3-6}$cycloalkyl that is unsubstituted or substituted by a substituent selected from $C_{1-6}$alkyl, hydroxy$C_{1-6}$alkyl and $R^0$;
  (ix) 6-membered heterocycloalkyl comprising, as ring members, 1 to 2 heteroatoms independently selected from N and O and that is unsubstituted or substituted by $C_{1-6}$alkyl; and
  (x) phenyl that is unsubstituted or substituted by halogen;
(b) $C_{3-6}$cycloalkyl that is unsubstituted or substituted by 1 to 2 substituents independently selected from $C_{1-6}$haloalkyl, $R^0$, $C_{1-6}$alkylamino, —C(O)$R^0$, and $C_{1-6}$alkyl that is unsubstituted or substituted by $R^0$ or —C(O)$R^0$; and
(c) 4-membered heterocycloalkyl comprising, as ring member, a heteroatom selected from N and O and that is unsubstituted or substituted by 1 to 2 substituents independently selected from $C_{1-6}$haloalkyl, $R^0$, $C_{1-6}$alkylamino, —C(O)$R^0$, and $C_{1-6}$alkyl that is unsubstituted or substituted by $R^0$ or —C(O)$R^0$.

Embodiment 24

A compound of Formula A2, or a salt thereof, according to any one of embodiments 1 to 22, wherein
$R^2$ is selected from
(a) $C_{1-8}$alkyl that is unsubstituted or substituted by 1 to 3 substituents independently selected from
  (i) cyano;
  (ii) $C_2$alkynyl;
  (iii) $C_{1-6}$haloalkyl;
  (iv) —$OR^6$, wherein $R^6$ is selected from hydrogen, $C_{1-6}$alkyl that is unsubstituted or substituted by $R^0$ or —C(O)$R^0$;
  (v) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (vi) —C(O)$R^8$, wherein $R^8$ is $R^0$;
  (vii) —S(O)$_2C_{1-6}$alkyl;
  (viii) monocyclic $C_{3-6}$cycloalkyl that is unsubstituted or substituted by a substituent selected from $C_{1-6}$alkyl, hydroxy$C_{1-6}$alkyl and $R^0$;
  (ix) 6-membered heterocycloalkyl comprising, as ring members, 1 to 2 heteroatoms independently selected from N and O and that is unsubstituted or substituted by $C_{1-6}$alkyl; and
  (x) phenyl that is unsubstituted or substituted by halogen;
  and wherein the C atom of the $C_{1-8}$alkyl that is unsubstituted or substituted by 1 to 3 substituents (i) to (x) that is the point of attachment of $R^2$ to the remainder of the molecule is not a —CH$_2$— group;
(b) $C_{3-6}$cycloalkyl that is unsubstituted or substituted by 1 to 2 substituents independently selected from $C_{1-6}$haloalkyl, $R^0$, $C_{1-6}$alkylamino, —C(O)$R^0$, and $C_{1-6}$alkyl that is unsubstituted or substituted by $R^0$ or —C(O)$R^0$; and
(c) 4-membered heterocycloalkyl comprising, as ring member, a heteroatom selected from N and O and that is unsubstituted or substituted by 1 to 2 substituents independently selected from $C_{1-6}$haloalkyl, $R^0$, $C_{1-6}$alkylamino, —C(O)$R^0$, and $C_{1-6}$alkyl that is unsubstituted or substituted by $R^0$ or —C(O)$R^0$.

Embodiment 25

A compound of Formula A2, or a salt thereof, according to any one of embodiments 1 to 23, wherein
$R^2$ is selected from
(a) $C_{1-8}$alkyl that is unsubstituted or substituted by 1 to 2 substituents independently selected from
  (i) cyano;
  (ii) $C_2$alkynyl;
  (iii) $C_{1-6}$haloalkyl;
  (iv) —$OR^6$, wherein $R^6$ is selected from hydrogen, $C_{1-6}$alkyl that is unsubstituted or substituted by hydroxyl or —C(O)H;
  (v) —$NR^{7a}R^{7b}$, wherein $R^{7a}$ is hydrogen or $C_{1-6}$alkyl, and $R^{7b}$ is selected from hydrogen, —C(O)—$C_{1-6}$alkoxy, and $C_{1-6}$alkyl that is unsubstituted or substituted by —C(O)OH; and
  (vi) monocyclic $C_{3-6}$cycloalkyl that is unsubstituted or substituted by hydroxyl; and
(b) $C_{3-6}$cycloalkyl that is unsubstituted or substituted by 1 to 2 substituents independently selected from $C_{1-6}$haloalkyl, $R^0$, $C_{1-6}$alkylamino, and $C_{1-6}$alkyl that is unsubstituted or substituted by hydroxyl or —C(O)—$C_{1-6}$alkoxy.

Embodiment 26

A compound of Formula A2, or a salt thereof, according to any one of embodiments 1 to 25, wherein
$R^2$ is selected from
(a) $C_{1-8}$alkyl that is unsubstituted or substituted by 1 to 2 substituents independently selected from
  (i) $C_{1-6}$haloalkyl;
  (ii) —$OR^6$, wherein $R^6$ is selected from hydrogen, and $C_{1-6}$alkyl that is unsubstituted or substituted by hydroxyl; and (iii) monocyclic $C_{3-6}$cycloalkyl that is unsubstituted or substituted by hydroxyl; and (b) $C_{3-6}$cycloalkyl that is unsubstituted or substituted by 1 to 2 substituents independently selected from $C_{1-6}$haloalkyl, $R^0$, $C_{1-6}$alkylamino, and $C_{1-6}$alkyl that is unsubstituted or substituted by hydroxyl.

Embodiment 27

A compound of Formula A2, or a salt thereof, according to any one of embodiments 1 to 26, wherein $R^2$ is $C_{1-8}$alkyl that is unsubstituted or substituted by 1 to 2 substituent independently selected from $C_{1-6}$haloalkyl and —$OR^6$, wherein $R^6$ is selected from hydrogen, and $C_{1-6}$alkyl that is unsubstituted or substituted by hydroxyl.

Embodiment 28

A compound of Formula A2, or a salt thereof, according to any one of embodiments 1 to 27, wherein $R^2$ is $C_{1-8}$alkyl that is unsubstituted or substituted by hydroxyl.

Embodiment 29

A compound of Formula A2, or a salt thereof, according to any one of embodiments 1 to 27, wherein $R^2$ is $C_{1-6}$alkyl that is unsubstituted or substituted by $C_{1-6}$haloalkyl.

Embodiment 30

A compound of Formula A2, or a salt thereof, according to any one of embodiments 1 to 27, wherein $R^2$ is $C_{1-6}$alkyl that is unsubstituted or substituted by —O—$C_{1-6}$alkyl-OH.

Embodiment 31

A compound of Formula A2, or a salt thereof, according to any one of embodiments 1 to 26, wherein $R^2$ is $C_{3-6}$cycloalkyl that is unsubstituted or substituted by a substituent selected from $C_{1-6}$haloalkyl, $C_{1-6}$alkylamino, $R^0$, and $C_{1-6}$alkyl that is unsubstituted or substituted by hydroxyl.

Embodiment 32

A compound of Formula A2, or a salt thereof, according to any one of embodiments 1 to 26 and 31, wherein $R^2$ is unsubstituted $C_{3-6}$cycloalkyl.

Embodiment 33

A compound of Formula A2, or a salt thereof, according to any one of embodiments 1 to 26 and 31, wherein $R^2$ is $C_{3-6}$cycloalkyl that is substituted by $C_{1-6}$alkyl or $C_{1-6}$haloalkyl.

Embodiment 34

A compound of Formula A2, or a salt thereof, according to any one of embodiments 1 to 25, wherein $R^2$ is selected from isopropyl, s-butyl, t-butyl, 2-methyl-but-2-yl, 2,4,4-trimethylpentan-2-yl,

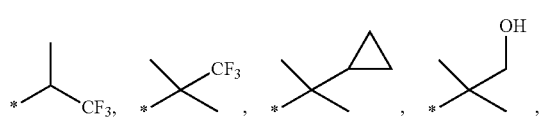

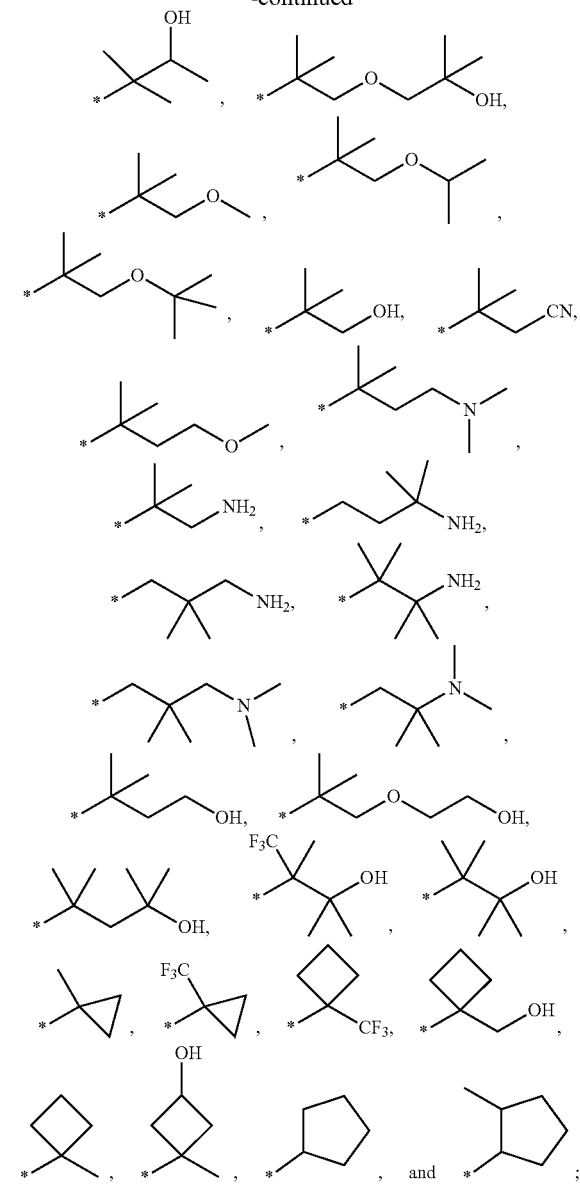

wherein "*" represents the point of attachment of $R^2$ to the remainder of the molecule.

Embodiment 34A

A compound of Formula A2, or a salt thereof, according to any one of embodiments 1 to 25, wherein $R^2$ is selected from

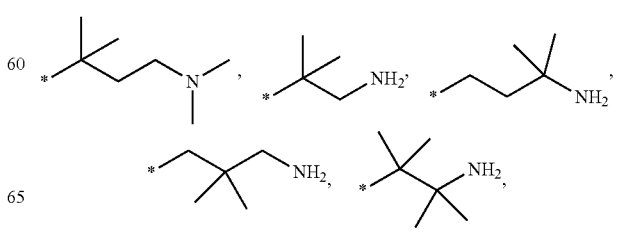

Embodiment 35

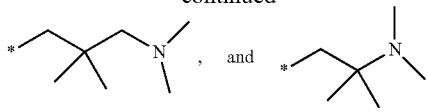

A compound of Formula A2, or a salt thereof, according to any one of embodiments 1 to 23 and 25 to 27, wherein $R^2$ is selected from n-propyl, isopropyl, t-butyl,

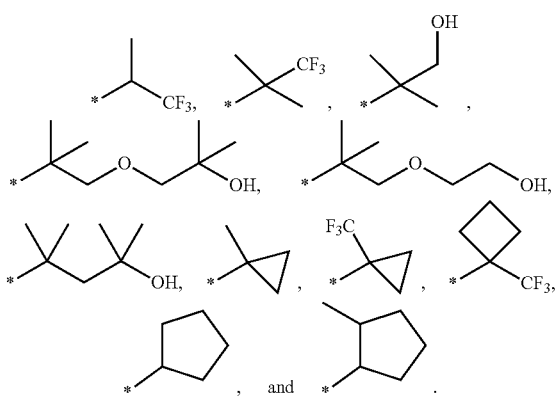

Embodiment 36

A compound of Formula A2, or a salt thereof, according to any one of embodiments 1 to 27, 34 and 35, wherein $R^2$ is selected from

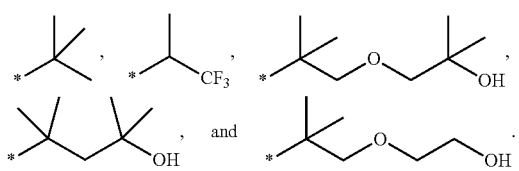

Embodiment 37

A compound of Formula A2, or a salt thereof, according to any one of embodiments 1 to 27, 29, and 34 to 36, wherein $R^2$ is

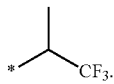

Embodiment 38

A compound of Formula A2, or a salt thereof, according to any one of embodiments 1 to 27, 30, and 34 to 36 wherein $R^2$ is

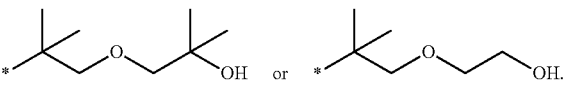

Embodiment 39

A compound of Formula A2, or a salt thereof, according to any one of embodiments 1 to 27, 31, and 34 to 36 wherein $R^2$ is

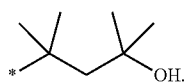 [SMILES: *C(C)(C)CC(C)(C)O]

Embodiment 40

A compound of Formula A2, or a salt thereof, according to any one of embodiments 1 to 26, 31, 34 and 35 wherein $R^2$ is selected from

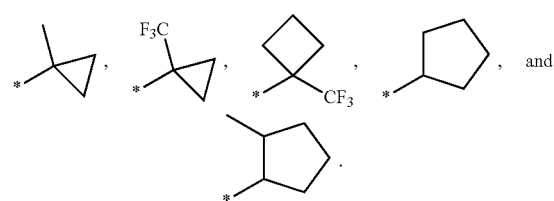

Embodiment 41

A compound of Formula A2, or a salt thereof, according to any one of embodiments 1 to 26, 31, 33 to 35 and 40, wherein $R^2$ is selected from

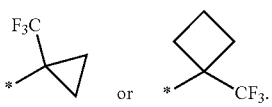

Embodiment 42

A compound of Formula A2, or a salt thereof, according to any one of embodiments 1 to 26, 31, 33 to 35 and 40, wherein $R^2$ is

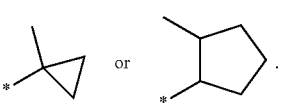

Embodiment 43

A compound of Formula A2, or a salt thereof, according to any one of embodiments 1 to 26, 31, 32, 34, 35 and 40 wherein $R^2$ is

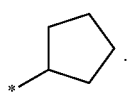

Embodiment 44

A compound of Formula A2, or a salt thereof, according to any one of embodiments 1 to 23, 25 to 30, and 35 wherein $R^2$ is selected from n-propyl, isopropyl and t-butyl.

Embodiment 45

A compound of Formula A2, or a salt thereof, according to any one of embodiments 1 to 23, 25 to 30, 35, and 44 wherein $R^2$ is n-propyl.

Embodiment 46

A compound of Formula A2, or a salt thereof, according to any one of embodiments 1 to 30, 35, and 44, wherein $R^2$ is isopropyl.

Embodiment 47

A compound of Formula A2, or a salt thereof, according to any one of embodiments 1 to 30, 35, and 44, wherein $R^2$ is t-butyl.

Embodiment 48

A compound of Formula A2, or a salt thereof, according to any one of embodiments 1 to 19, wherein
$X^1$ is CH; and
$R^1$ and $R^2$ taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$.

Embodiment 49

A compound of Formula A2, or a salt thereof, according to any one of embodiments 1 to 19, and 48 wherein
$X^1$ is CH; and
$R^1$ and $R^2$ are taken together with the nitrogen atom to which both are bound to form a 5- or 6-membered heterocycloalkyl that can include, as ring member, 1 to 2 additional heteroatom selected from N, O and S, wherein the 5- or 6-membered heterocycloalkyl formed by $R^1$ and $R^2$ taken together with the nitrogen atom to which both are bound is unsubstituted or substituted by 1 to 3 substituents independently selected from hydroxyl, $C_{1-4}$alkyl and $C_{1-4}$haloalkyl.

Embodiment 50

A compound of Formula A2, or a salt thereof, according to any one of embodiments 1 to 19, 48 and 49 wherein
$X^1$ is CH; and
$R^1$ and $R^2$ are taken together with the nitrogen atom to which both are bound to form a 6-membered heterocycloalkyl that can include, as ring member, an additional heteroatom selected from N and O, wherein the 6-membered heterocycloalkyl formed by $R^1$ and $R^2$ taken together with the nitrogen atom to which both are bound is unsubstituted or substituted by 1 to 3 substituents independently selected from hydroxyl, $C_{1-6}$alkyl and $C_{1-6}$haloalkyl.

Embodiment 51

A compound of Formula A2, or a salt thereof, according to any one of embodiments 1 to 19, and 48 to 50 wherein
$X^1$ is CH; and
$R^1$ and $R^2$ are taken together with the nitrogen atom to which both are bound to form a 6-membered heterocycloalkyl selected from piperidinyl, piperazinyl and morpholinyl, wherein the piperidinyl, piperazinyl or morpholinyl is unsubstituted or substituted by 1 to 3 substituents independently selected from hydroxyl and $C_{1-6}$alkyl.

Embodiment 52

A compound of Formula A2, or a salt thereof, according to any one of embodiments 1 to 51, wherein $R^3$ is selected from hydrogen, chloro and methyl.

Embodiment 53

A compound of Formula A2, or a salt thereof, according to any one of embodiments 1 to 52, wherein $R^3$ is hydrogen.

Embodiment 53A

A compound of Formula A2, or a salt thereof, according to any one of embodiments 1 to 52, wherein $R^3$ is chloro.

Embodiment 53B

A compound of Formula A2, or a salt thereof, according to any one of embodiments 1 to 52, wherein $R^3$ is methyl.

Embodiment 54

A compound of the Formula A2, or a salt thereof, according to any one of embodiments 1 to 53, wherein $R^5$ is selected from hydrogen and chloro.

Embodiment 55

A compound of Formula A2, or a salt thereof, according to any one of embodiments 1 to 54, wherein $R^5$ is hydrogen.

Embodiment 56

A compound of Formula A2, or a salt thereof, according to embodiment 1, wherein the compound is of Formula A3:

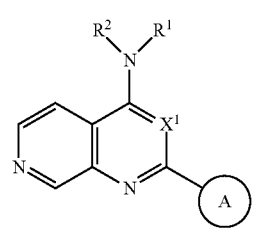

wherein
X¹ is CH or N;
Ring A is

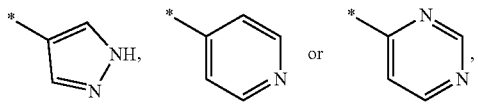 [SMILES: *c1cn[nH]c1 ; *c1ccncc1 ; *c1ccncn1]

each of which is unsubstituted or substituted by a substituent selected from halogen, $C_{1-6}$alkyl, $C_{1-6}$haloalkyl, and —$NH_2$;
R¹ is hydrogen or unsubstituted $C_{1-6}$alkyl; and
R² is
(a) $C_{1-8}$alkyl that is unsubstituted or substituted by 1 substituents selected from
 (i) $C_{1-4}$haloalkyl and
 (ii) —$OR^6$, wherein $R^6$ is selected from hydrogen and $C_{1-6}$alkyl that is unsubstituted or substituted by hydroxyl; or
(b) monocyclic $C_{3-6}$cycloalkyl that is unsubstituted or substituted by $C_{1-6}$alkyl or $C_{1-6}$haloalkyl.

Embodiment 57

A compound of Formula A2, or a salt thereof, according to embodiment 56, wherein ring A is

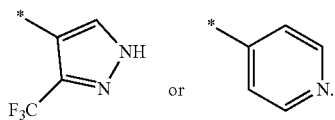 [SMILES: *c1c[nH]nc1C(F)(F)F ; "or" ; *c1ccncc1]

Embodiment 58

A compound of Formula A2, or a salt thereof, according to embodiment 56 or embodiment 57, wherein R² is

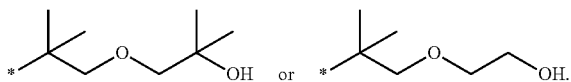

Embodiment 59

A compound of Formula A2, or a salt thereof, according to embodiment 56 or embodiment 57, wherein R² is n-propyl or tert-butyl that is unsubstituted or substituted by trifluromethyl.

Embodiment 60

A compound of the Formula A2, or a salt thereof, according to embodiment 1, selected from: N-(2-cyclopropylpropan-2-yl)-2-(pyridin-4-yl)pyrido[3,4-d]pyrimidin-4-amine; N,N-diethyl-2-(pyridin-4-yl)pyrido[3,4-d]pyrimidin-4-amine; N-ethyl-N-(propan-2-yl)-2-(pyridin-4-yl)pyrido[3,4-d]pyrimidin-4-amine; 2-(pyridin-4-yl)-N-(1,1,1-trifluoropropan-2-yl)pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; N-(1-methoxy-2-methylpropan-2-yl)-2-(pyridin-4-yl)pyrido[3,4-d]pyrimidin-4-amine; N-(4-methoxy-2-methylbutan-2-yl)-2-(pyridin-4-yl)pyrido[3,4-d]pyrimidin-4-amine; N-butyl-N-methyl-2-(pyridin-4-yl)pyrido[3,4-d]pyrimidin-4-amine; N-ethyl-N-methyl-2-(pyridin-4-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; 2-methyl-1-(2-methyl-2-{[2-(pyridin-4-yl)pyrido[3,4-d]pyrimidin-4-yl]amino}propoxy)propan-2-ol; N-ethyl-2-(pyridin-4-yl)pyrido[3,4-d]pyrimidin-4-amine; N-propyl-2-(pyridin-4-yl)pyrido[3,4-d]pyrimidin-4-amine; N-(2-cyclohexylpropan-2-yl)-2-(pyridin-4-yl)pyrido[3,4-d]pyrimidin-4-amine; N-(3-methyloxetan-3-yl)-2-(pyridin-4-yl)pyrido[3,4-d]pyrimidin-4-amine; N-(2-methylcyclopentyl)-2-(pyridin-4-yl)pyrido[3,4-d]pyrimidin-4-amine; 3-methyl-3-{[2-(pyridin-4-yl)pyrido[3,4-d]pyrimidin-4-yl]amino}butan-2-ol; N-butyl-2-(pyridin-4-yl)pyrido[3,4-d]pyrimidin-4-amine; N-(2-methyl-4-phenylbutan-2-yl)-2-(pyridin-4-yl)pyrido[3,4-d]pyrimidin-4-amine; N-cyclopropyl-2-(pyridin-4-yl)pyrido[3,4-d]pyrimidin-4-amine; N-(4-methanesulfonyl-2-methylbutan-2-yl)-2-(pyridin-4-yl)pyrido[3,4-d]pyrimidin-4-amine; 2-methyl-2-{[2-(pyridin-4-yl)pyrido[3,4-d]pyrimidin-4-yl]amino}propane-1,3-diol; 3-{[2-(pyridin-4-yl)pyrido[3,4-d]pyrimidin-4-yl]amino}butan-2-ol; 2-(2-methyl-2-{[2-(pyridin-4-yl)pyrido[3,4-d]pyrimidin-4-yl]amino}propoxy)acetic acid; (1R,2S)-2-{[2-(pyridin-4-yl)pyrido[3,4-d]pyrimidin-4-yl]amino}cyclopentan-1-ol; 4,4,4-trifluoro-3-{[2-(pyridin-4-yl)pyrido[3,4-d]pyrimidin-4-yl]amino}butan-1-ol; N-(1-methanesulfonyl-2-methylpropan-2-yl)-2-(pyridin-4-yl)pyrido[3,4-d]pyrimidin-4-amine; (2S)-3,3,3-trifluoro-2-methyl-2-{[2-(pyridin-4-yl)pyrido[3,4-d]pyrimidin-4-yl]amino}propanoic acid; 2-[(2-methyl-2-{[2-(pyridin-4-yl)pyrido[3,4-d]pyrimidin-4-yl]amino}propyl)amino]acetic acid; (2R)-3,3,3-trifluoro-2-methyl-2-{[2-(pyridin-4-yl)pyrido[3,4-d]pyrimidin-4-yl]amino}propanoic acid; methyl 2-methyl-2-{[2-(pyridin-4-yl)pyrido[3,4-d]pyrimidin-4-yl]amino}propanoate; (1S,2S)-2-{[2-(pyridin-4-yl)pyrido[3,4-d]pyrimidin-4-yl]amino}cyclopentan-1-ol; 2-methyl-2-{[2-(pyridin-4-yl)pyrido[3,4-d]pyrimidin-4-yl]amino}propanoic acid; 2-(2-{[2-(pyridin-4-yl)pyrido[3,4-d]pyrimidin-4-yl]amino}ethoxy)ethan-1-ol; 2-(hydroxymethyl)-2-{[2-(pyridin-4-yl)pyrido[3,4-d]pyrimidin-4-yl]amino}propane-1,3-diol; 3-methyl-3-(3-methyl-3-{[2-(pyridin-4-yl)pyrido[3,4-d]pyrimidin-4-yl]amino}butanamido)butanoic acid; 2-(pyridin-4-yl)-N-(1,1,1-trifluoro-3-phenylpropan-2-yl)pyrido[3,4-d]pyrimidin-4-amine; N-{[4-(dimethylamino)oxan-4-yl]methyl}-2-(pyridin-4-yl)pyrido[3,4-d]pyrimidin-4-amine; 3-methyl-3-{[2-(pyridin-4-yl)pyrido[3,4-d]pyrimidin-4-yl]amino}butanoic acid; N-(2-methanesulfonylethyl)-2-(pyridin-4-yl)pyrido[3,4-d]pyrimidin-4-amine; N-[2-(adamantan-1-yl)propan-2-yl]-2-(pyridin-4-yl)pyrido[3,4-d]pyrimidin-4-amine; 2-methyl-N-[2-(pyridin-4-yl)pyrido[3,4-d]pyrimidin-4-yl]propanamide; 4,4,4-trifluoro-3-{[2-(pyridin-4-yl)pyrido[3,4-d]pyrimidin-4-yl]amino}butanoic acid; N-[2-(pyridin-4-yl)pyrido[3,4-d]pyrimidin-4-yl]propane-2-sulfonamide; 2-(pyridin-4-yl)-N-[3-(1H-1,2,3,4-tetrazol-5-yl)propyl]pyrido[3,4-d]pyrimidin-4-amine; N-methyl-2-(pyridin-4-yl)-N-[1,1,1-trifluoropropan-2-yl]pyrido[3,4-d]pyrimidin-4-amine; N-methyl-2-(pyridin-4-yl)-N-[(2S)-1,1,1-trifluoropropan-2-yl]pyrido[3,4-d]pyrimidin-4-amine; N-methyl-2-(pyridin-4-yl)-N-[(2R)-1,1,1-trifluoropropan-2-yl]pyrido[3,4-d]pyrimidin-4-amine; 2,4-dimethyl-4-{[2-(pyridin-4-yl)pyrido[3,4-d]pyrimidin-4-yl]amino}pentan-2-ol; 4,4,4-trifluoro-2,3-dimethyl-3-{[2-(pyridin-4-yl)pyrido[3,4-d]pyrimidin-4-yl]amino}butan-2-ol; (1-{[2-(pyridin-4-yl)pyrido[3,4-d]pyrimidin-4-yl]

amino}cyclopentyl)methanol; N-(3-methoxycyclobutyl)-2-(pyridin-4-yl)pyrido[3,4-d]pyrimidin-4-amine; (1R,2R)-1-N,2-N-dimethyl-1-N-[2-(pyridin-4-yl)pyrido[3,4-d]pyrimidin-4-yl]cyclohexane-1,2-diamine; methyl (1 s,3s)-3-{[2-(pyridin-4-yl)pyrido[3,4-d]pyrimidin-4-yl]amino}cyclobutane-1-carboxylate; ethyl 1-{[2-(pyridin-4-yl)pyrido[3,4-d]pyrimidin-4-yl]amino}cyclobutane-1-carboxylate; 1-{[2-(pyridin-4-yl)pyrido[3,4-d]pyrimidin-4-yl]amino}cyclobutane-1-carboxylic acid; (1 s,3s)-3-{[2-(pyridin-4-yl)pyrido[3,4-d]pyrimidin-4-yl]amino}cyclobutane-1-carboxylic acid; 2-(pyridin-4-yl)-N-(1,1,1-trifluoro-2-methylpropan-2-yl)pyrido[3,4-d]pyrimidin-4-amine; N-tert-butyl-2-(pyridin-4-yl)pyrido[3,4-d]pyrimidin-4-amine; N-(1-methylcyclobutyl)-2-(pyridin-4-yl)pyrido[3,4-d]pyrimidin-4-amine; 3-methyl-3-{[2-(pyridin-4-yl)pyrido[3,4-d]pyrimidin-4-yl]amino}butan-1-ol; 2-(pyridin-4-yl)-N-[1-(trifluoromethyl)cyclobutyl]pyrido[3,4-d]pyrimidin-4-amine; N-(2-methylbutan-2-yl)-2-(pyridin-4-yl)pyrido[3,4-d]pyrimidin-4-amine; 2-(pyridin-4-yl)-N-[1-(trifluoromethyl)cyclopropyl]pyrido[3,4-d]pyrimidin-4-amine; N-cyclopentyl-2-(pyridin-4-yl)pyrido[3,4-d]pyrimidin-4-amine; 2-methyl-2-{[2-(pyridin-4-yl)pyrido[3,4-d]pyrimidin-4-yl]amino}propan-1-ol; 3,3,3-trifluoro-2-methyl-2-{[2-(pyridin-4-yl)pyrido[3,4-d]pyrimidin-4-yl]amino}propan-1-ol; N-(butan-2-yl)-2-(pyridin-4-yl)pyrido[3,4-d]pyrimidin-4-amine; N-(2-methylbut-3-yn-2-yl)-2-(pyridin-4-yl)pyrido[3,4-d]pyrimidin-4-amine; (1 r,3s)-3-methyl-3-{[2-(pyridin-4-yl)pyrido[3,4-d]pyrimidin-4-yl]amino}cyclobutan-1-ol; 2,3-dimethyl-3-{[2-(pyridin-4-yl)pyrido[3,4-d]pyrimidin-4-yl]amino}butan-2-ol; 2-(pyridin-4-yl)-N-(2,4,4-trimethylpentan-2-yl)pyrido[3,4-d]pyrimidin-4-amine; N-(pentan-3-yl)-2-(pyridin-4-yl)pyrido[3,4-d]pyrimidin-4-amine; N-[2-methyl-1-(morpholin-4-yl)propan-2-yl]-2-(pyridin-4-yl)pyrido[3,4-d]pyrimidin-4-amine; N-[1-(tert-butoxy)-2-methylpropan-2-yl]-2-(pyridin-4-yl)pyrido[3,4-d]pyrimidin-4-amine; 4,4,4-trifluoro-2-{[2-(pyridin-4-yl)pyrido[3,4-d]pyrimidin-4-yl]amino}butan-1-ol; N-pentyl-2-(pyridin-4-yl)pyrido[3,4-d]pyrimidin-4-amine; 2-{[2-(pyridin-4-yl)pyrido[3,4-d]pyrimidin-4-yl]amino}butan-1-ol; N-[1-(1H-indol-3-yl)-2-methylpropan-2-yl]-2-(pyridin-4-yl)pyrido[3,4-d]pyrimidin-4-amine; N-[1-(4-fluorophenyl)-2-methylpropan-2-yl]-2-(pyridin-4-yl)pyrido[3,4-d]pyrimidin-4-amine; N-(2-phenylpropan-2-yl)-2-(pyridin-4-yl)pyrido[3,4-d]pyrimidin-4-amine; N-(2-fluorophenyl)-2-(pyridin-4-yl)pyrido[3,4-d]pyrimidin-4-amine; N-[2-(4-fluorophenyl)propan-2-yl]-2-(pyridin-4-yl)pyrido[3,4-d]pyrimidin-4-amine; 3,3,3-trifluoro-2-methyl-2-{[2-(pyridin-4-yl)pyrido[3,4-d]pyrimidin-4-yl]amino}propanoic acid; 2-{[2-(pyridin-4-yl)pyrido[3,4-d]pyrimidin-4-yl]amino}ethan-1-ol; N-methyl-2-(pyridin-4-yl)pyrido[3,4-d]pyrimidin-4-amine; 1-({[2-(pyridin-4-yl)pyrido[3,4-d]pyrimidin-4-yl]amino}methyl)cyclopentan-1-ol; N,N-dimethyl-2-(pyridin-4-yl)pyrido[3,4-d]pyrimidin-4-amine; N-(2-methylphenyl)-2-(pyridin-4-yl)pyrido[3,4-d]pyrimidin-4-amine; N-(4-methylphenyl)-2-(pyridin-4-yl)pyrido[3,4-d]pyrimidin-4-amine; N-(4-methoxyphenyl)-2-(pyridin-4-yl)pyrido[3,4-d]pyrimidin-4-amine; N-phenyl-2-(pyridin-4-yl)pyrido[3,4-d]pyrimidin-4-amine; N-(3-methylphenyl)-2-(pyridin-4-yl)pyrido[3,4-d]pyrimidin-4-amine; 6-{[2-(pyridin-4-yl)pyrido[3,4-d]pyrimidin-4-yl]amino}hexanoic acid; N-(3-fluorophenyl)-2-(pyridin-4-yl)pyrido[3,4-d]pyrimidin-4-amine; N-(4-fluorophenyl)-2-(pyridin-4-yl)pyrido[3,4-d]pyrimidin-4-amine; 4-{[2-(pyridin-4-yl)pyrido[3,4-d]pyrimidin-4-yl]amino}butanoic acid; N-(1-phenylethyl)-2-(pyridin-4-yl)pyrido[3,4-d]pyrimidin-4-amine; N-(1-methylcyclopropyl)-2-(pyridin-4-yl)pyrido[3,4-d]pyrimidin-4-amine; tert-butyl N-(2-methyl-2-{[2-(pyridin-4-yl)pyrido[3,4-d]pyrimidin-4-yl]amino}propyl)carbamate; (1-{[2-(pyridin-4-yl)pyrido[3,4-d]pyrimidin-4-yl]amino}cyclobutyl)methanol; methyl 2-(1-{[2-(pyridin-4-yl)pyrido[3,4-d]pyrimidin-4-yl]amino}cyclopropyl)acetate; N-(2-methylpropyl)-2-(pyridin-4-yl)pyrido[3,4-d]pyrimidin-4-amine; 3-methyl-3-{[2-(pyridin-4-yl)pyrido[3,4-d]pyrimidin-4-yl]amino}butanenitrile; N-(6-aminohexyl)-2-(pyridin-4-yl)pyrido[3,4-d]pyrimidin-4-amine; N-(4-aminobutyl)-2-(pyridin-4-yl)pyrido[3,4-d]pyrimidin-4-amine; 2-methyl-2-{[2-(pyridin-4-yl)pyrido[3,4-d]pyrimidin-4-yl]amino}propanenitrile; N-[2-methyl-1-(2-methylpiperidin-1-yl)propan-2-yl]-2-(pyridin-4-yl)pyrido[3,4-d]pyrimidin-4-amine; dimethyl(3-methyl-3-{[2-(pyridin-4-yl)pyrido[3,4-d]pyrimidin-4-yl]amino}butyl)amine; N-(1-amino-2-methylpropan-2-yl)-2-(pyridin-4-yl)pyrido[3,4-d]pyrimidin-4-amine; N-cyclopentyl-2-[3-(trifluoromethyl)-1H-pyrazol-4-yl]pyrido[3,4-d]pyrimidin-4-amine; 4-[4-(tert-butylamino)pyrido[3,4-d]pyrimidin-2-yl]pyridin-2-amine; 2-[1-(benzenesulfonyl)-2-methyl-1H-pyrrolo[2,3-b]pyridin-3-yl]-N-tert-butylpyrido[3,4-d]pyrimidin-4-amine; N-tert-butyl-2-{2-methyl-1H-pyrrolo[2,3-b]pyridin-3-yl}pyrido[3,4-d]pyrimidin-4-amine; N-tert-butyl-2-[3-(trifluoromethyl)-1H-pyrazol-4-yl]pyrido[3,4-d]pyrimidin-4-amine; N-tert-butyl-2-(3-chloropyridin-4-yl)pyrido[3,4-d]pyrimidin-4-amine; N-tert-butyl-2-(3-methylpyridin-4-yl)pyrido[3,4-d]pyrimidin-4-amine; 2-(3-chloropyridin-4-yl)-N-(2-methylbutan-2-yl)pyrido[3,4-d]pyrimidin-4-amine; 2,4-dimethyl-4-({2-[3-(trifluoromethyl)-1H-pyrazol-4-yl]pyrido[3,4-d]pyrimidin-4-yl}amino)pentan-2-ol; N-ethyl-2-(3-fluoropyridin-4-yl)-N-(propan-2-yl)pyrido[3,4-d]pyrimidin-4-amine; 2-methyl-1-[2-methyl-2-({2-[3-(trifluoromethyl)-1H-pyrazol-4-yl]pyrido[3,4-d]pyrimidin-4-yl}amino) propoxy]propan-2-ol; 2-(3-fluoropyridin-4-yl)-N-methyl-N-(propan-2-yl)pyrido[3,4-d]pyrimidin-4-amine; N-ethyl-2-(3-methylpyridin-4-yl)-N-(propan-2-yl)pyrido[3,4-d]pyrimidin-4-amine; 2-(3-chloropyridin-4-yl)-N-(1-methoxy-2-methylpropan-2-yl)pyrido[3,4-d]pyrimidin-4-amine; 4-{[2-(3-chloropyridin-4-yl)pyrido[3,4-d]pyrimidin-4-yl]amino}-2,4-dimethylpentan-2-ol; 2-(3-chloropyridin-4-yl)-N-cyclopentylpyrido[3,4-d]pyrimidin-4-amine; 1-(2-{[2-(3-chloropyridin-4-yl)pyrido[3,4-d]pyrimidin-4-yl]amino}-2-methylpropoxy)-2-methylpropan-2-ol; N-methyl-2-(3-methylpyridin-4-yl)-N-(propan-2-yl)pyrido[3,4-d]pyrimidin-4-amine; 2-(3-chloropyridin-4-yl)-N-(4-methanesulfonyl-2-methylbutan-2-yl)pyrido[3,4-d]pyrimidin-4-amine; N-tert-butyl-2-[3-(trifluoromethyl)pyridin-4-yl]pyrido[3,4-d]pyrimidin-4-amine; N-tert-butyl-2-[2-chloro-5-(trifluoromethyl)pyridin-4-yl]pyrido[3,4-d]pyrimidin-4-amine; 2-(3-chloropyridin-4-yl)-N-[3-(1H-1,2,3,4-tetrazol-5-yl)propyl]pyrido[3,4-d]pyrimidin-4-amine; 2-(3-methyl-1H-pyrazol-4-yl)-N-(1-methylcyclopropyl)pyrido[3,4-d]pyrimidin-4-amine; 2-(3-fluoropyridin-4-yl)-N-(1,1,1-trifluoro-2-methylpropan-2-yl)pyrido[3,4-d]pyrimidin-4-amine; 2-(3-methyl-1H-pyrazol-4-yl)-N-(1,1,1-trifluoro-2-methylpropan-2-yl)pyrido[3,4-d]pyrimidin-4-amine; 2-(3-fluoropyridin-4-yl)-N-methyl-N-[(2S)-1,1,1-trifluoropropan-2-yl]pyrido[3,4-d]pyrimidin-4-amine; 2-(3-fluoropyridin-4-yl)-N-methyl-N-[(2R)-1,1,1-trifluoropropan-2-yl]pyrido[3,4-d]pyrimidin-4-amine; 4-{4-[(1-methylcyclopropyl)amino]pyrido[3,4-d]pyrimidin-2-yl}pyridin-2-amine; 2-(3-chloropyridin-4-yl)-N-(1,1,1-trifluoro-2-methylpropan-2-yl)pyrido[3,4-d]pyrimidin-4-amine; 2,4-dimethyl-4-{[2-(3-methyl-1H-pyrazol-4-yl)pyrido[3,4-d]pyrimidin-4-yl]amino}pentan-2-ol; 4-{4-[(1-methylcyclopropyl)amino]pyrido[3,4-d]pyrimidin-2- yl}pyridine-3-carbonitrile; 2-{2-methyl-1H-pyrrolo[2,3-b]pyridin-3-yl}-N-propylpyrido[3,4-d]pyrimidin-4-amine; 2-(1H-indazol-5-yl)-N-(1-methylcyclopropyl)pyrido[3,4-d]pyrimidin-4-amine; 2-(3,5-dimethyl-1H-pyrazol-4-yl)-N-(1,1,1-trifluoro-2-methylpropan-2-yl)pyrido[3,4-d]pyrimidin-4-amine; N-(1,1,1-trifluoro-2-methylpropan-2-yl)-2-[3-(trifluoromethyl)-1H-pyrazol-4-yl]pyrido[3,4-d]pyrimidin-4-amine; 4-{4-[(4-hydroxy-2,4-dimethylpentan-2-yl)amino]pyrido[3,4-d]pyrimidin-2-yl}pyridine-3-carbonitrile; 2-(3,5-difluoropyridin-4-yl)-N-(1-methylcyclopropyl)pyrido[3,4-d]pyrimidin-4-amine; 2-(2,3-difluoropyridin-4-yl)-N-(1-methylcyclopropyl)pyrido[3,4-d]pyrimidin-4-amine; N-(1-methylcyclopropyl)-2-(1,3-thiazol-5-yl)pyrido[3,4-d]pyrimidin-4-amine; N-(1-methylcyclopropyl)-2-[2-(trifluoromethyl)pyridin-4-yl]pyrido[3,4-d]pyrimidin-4-amine; 4-{4-[(1-methylcyclopropyl)amino]pyrido[3,4-d]pyrimidin-2-yl}pyridine-2-carbonitrile; N-(1-methylcyclopropyl)-2-(1,2-oxazol-4-yl)pyrido[3,4-d]pyrimidin-4-amine; 2-(dimethyl-1,2-oxazol-4-yl)-N-(1-methylcyclopropyl)pyrido[3,4-d]pyrimidin-4-amine; N-(1-methylcyclopropyl)-2-{1H-pyrrolo[2,3-b]pyridin-4-yl}pyrido[3,4-d]pyrimidin-4-amine; N-propyl-2-{1H-pyrrolo[2,3-b]pyridin-3-yl}pyrido[3,4-d]pyrimidin-4-amine; N-propyl-2-{1H-pyrrolo[3,2-b]pyridin-1-yl}pyrido[3,4-d]pyrimidin-4-amine; 2-(3-methylpyridin-4-yl)-N-(1,1,1-trifluoro-2-methylpropan-2-yl)pyrido[3,4-d]pyrimidin-4-amine; N-(1-methylcyclobutyl)-2-(1H-pyrazol-4-yl)pyrido[3,4-d]pyrimidin-4-amine; N-(1-methylcyclopropyl)-2-(pyrimidin-4-yl)pyrido[3,4-d]pyrimidin-4-amine; 4-{[2-(3,5-dimethyl-1H-pyrazol-4-yl)pyrido[3,4-d]pyrimidin-4-yl]amino}-2,4-dimethylpentan-2-ol; N-propyl-2-{7H-pyrrolo[2,3-d]pyrimidin-5-yl}pyrido[3,4-d]pyrimidin-4-amine; 2-(3-chloropyridin-4-yl)-N-propylpyrido[3,4-d]pyrimidin-4-amine; 2-(3-cyclopropyl-1H-pyrazol-4-yl)-N-propylpyrido[3,4-d]pyrimidin-4-amine; 2-(3-methylpyridin-4-yl)-N-propylpyrido[3,4-d]pyrimidin-4-amine; 2-{1-methyl-1H-pyrrolo[2,3-b]pyridin-3-yl}-N-propylpyrido[3,4-d]pyrimidin-4-amine; 2,4-dimethyl-4-{[2-(1H-pyrazol-4-yl)pyrido[3,4-d]pyrimidin-4-yl]amino}pentan-2-ol; N-[(1R)-1-phenylethyl]-2-(1H-pyrazol-4-yl)pyrido[3,4-d]pyrimidin-4-amine; 2-(5-methyl-1H-pyrazol-4-yl)-N-[(1R)-1-phenylethyl]pyrido[3,4-d]pyrimidin-4-amine; N-methyl-2-(1-methyl-1H-pyrazol-5-yl)-N-(1-methylcyclopropyl)pyrido[3,4-d]pyrimidin-4-amine; 2-(1-methyl-1H-pyrazol-5-yl)-N-[(1R)-1-phenylethyl]pyrido[3,4-d]pyrimidin-4-amine; N-methyl-N-(1-methylcyclopropyl)-2-(1H-pyrazol-4-yl)pyrido[3,4-d]pyrimidin-4-amine; 2-(1-methyl-1H-pyrazol-5-yl)-N-(1-methylcyclopropyl)pyrido[3,4-d]pyrimidin-4-amine; 2-(1-ethyl-1H-pyrazol-5-yl)-N-(1-methylcyclopropyl)pyrido[3,4-d]pyrimidin-4-amine; N-(1-methylcyclopropyl)-2-(pyridazin-4-yl)pyrido[3,4-d]pyrimidin-4-amine; N-(1-methylcyclopropyl)-2-(1,3-oxazol-5-yl)pyrido[3,4-d]pyrimidin-4-amine; N-(1-methylcyclopropyl)-2-(1H-pyrazol-5-yl)pyrido[3,4-d]pyrimidin-4-amine; 2-(1H-imidazol-5-yl)-N-(1-methylcyclopropyl)pyrido[3,4-d]pyrimidin-4-amine; 2-(1-methyl-1H-imidazol-5-yl)-N-(1-methylcyclopropyl)pyrido[3,4-d]pyrimidin-4-amine; N-(1-methylcyclopropyl)-2-{1H-pyrrolo[3,2-b]pyridin-1-yl}pyrido[3,4-d]pyrimidin-4-amine; N-(1-methylcyclopropyl)-2-(1H-1,2,3-triazol-4-yl)pyrido[3,4-d]pyrimidin-4-amine; 2-(3-methyl-1,2-oxazol-5-yl)-N-(1-methylcyclopropyl)pyrido[3,4-d]pyrimidin-4-amine; N-(1-methylcyclopropyl)-2-(2H-1,2,3,4-tetrazol-5-yl)pyrido[3,4-d]pyrimidin-4-amine; 2-(1H-pyrazol-4-yl)-N-[1-(pyridin-4-yl)ethyl]pyrido[3,4-d]pyrimidin-4-amine; N-tert-butyl-2-(1-methyl-1H-pyrazol-5-yl)pyrido[3,4-d]pyrimidin-4-amine; (1-{[2-(3-methyl-1H-pyrazol-4-yl)pyrido[3,4-d]pyrimidin-4-yl]amino}cyclobutyl)methanol; 2-(1-methyl-1H-pyrazol-5-yl)-N-(1-methylcyclobutyl)pyrido[3,4-d]pyrimidin-4-amine; (1-{[2-(1-methyl-1H-pyrazol-5-yl)pyrido[3,4-d]pyrimidin-4-yl]amino}cyclobutyl)methanol; 2-(1H-pyrazol-4-yl)-N-[1-(trifluoromethyl)cyclopropyl]pyrido[3,4-d]pyrimidin-4-amine; 2-(1-methyl-1H-pyrazol-5-yl)-N-[1-(trifluoromethyl)cyclopropyl]pyrido[3,4-d]pyrimidin-4-amine; 2-(3-methyl-1H-pyrazol-4-yl)-N-[1-(pyridin-4-yl)ethyl]pyrido[3,4-d]pyrimidin-4-amine; (1-{[2-(1H-pyrazol-4-yl)pyrido[3,4-d]pyrimidin-4-yl]amino}cyclobutyl)methanol; (1-{[2-(1H-pyrazol-4-yl)pyrido[3,4-d]pyrimidin-4-yl]amino}cyclopropyl)methanol; 2-(1-methyl-1H-pyrazol-5-yl)-N-[1-(pyridin-4-yl)ethyl]pyrido[3,4-d]pyrimidin-4-amine; N-(1-methylcyclopropyl)-2-(1H-pyrazol-4-yl)pyrido[3,4-d]pyrimidin-4-amine; 2-(1-ethyl-1H-pyrazol-4-yl)-N-(2-methylpropyl)pyrido[3,4-d]pyrimidin-4-amine; 2-(1-methyl-1H-pyrazol-4-yl)-N-(1-methylcyclopropyl)pyrido[3,4-d]pyrimidin-4-amine; N-(1-amino-2-methylpropan-2-yl)-2-(1H-pyrazol-4-yl)pyrido[3,4-d]pyrimidin-4-amine; 8-chloro-N-(1-methylcyclopropyl)-2-(pyridin-4-yl)pyrido[3,4-d]pyrimidin-4-amine; 8-methyl-N-(1-methylcyclopropyl)-2-(pyridin-4-yl)pyrido[3,4-d]pyrimidin-4-amine; N-tert-butyl-5-chloro-2-(pyridin-4-yl)pyrido[3,4-d]pyrimidin-4-amine; 5-chloro-N-(1-methylcyclopropyl)-2-(pyridin-4-yl)pyrido[3,4-d]pyrimidin-4-amine; 2-(2-{[4-(tert-butylamino)-2-(pyridin-4-yl)pyrido[3,4-d]pyrimidin-5-yl]amino}ethoxy)ethan-1-ol; N-(4-methoxy-2-methylbutan-2-yl)-2-(pyridin-4-yl)-1,7-naphthyridin-4-amine; N-[2-methyl-1-(propan-2-yloxy)propan-2-yl]-2-(pyridin-4-yl)-1,7-naphthyridin-4-amine; N-[(2S)-butan-2-yl]-2-(pyridin-4-yl)-1,7-naphthyridin-4-amine; N-[(2R)-butan-2-yl]-2-(pyridin-4-yl)-1,7-naphthyridin-4-amine; N-(1-methoxy-2-methylpropan-2-yl)-2-(pyridin-4-yl)-1,7-naphthyridin-4-amine; N-methyl-N-(propan-2-yl)-2-(pyridin-4-yl)-1,7-naphthyridin-4-amine; 3-methyl-3-{[2-(pyridin-4-yl)-1,7-naphthyridin-4-yl]amino}butan-1-ol; N-tert-butyl-2-(pyridin-4-yl)-1,7-naphthyridin-4-amine; 2,2-dimethyl-1-[2-(pyridin-4-yl)-1,7-naphthyridin-4-yl]piperidin-4-ol; 2,4-dimethyl-4-{[2-(pyridin-4-yl)-1,7-naphthyridin-4-yl]amino}pentan-2-ol; N-cyclopentyl-2-(pyridin-4-yl)-1,7-naphthyridin-4-amine; dimethyl(3-methyl-3-{[2-(pyridin-4-yl)-1,7-naphthyridin-4-yl]amino}butyl)amine; N,N-diethyl-2-(pyridin-4-yl)-1,7-naphthyridin-4-amine; 2-methyl-1-(2-methyl-2-{[2-(pyridin-4-yl)-1,7-naphthyridin-4-yl]amino}propoxy)propan-2-ol; N-propyl-2-(pyridin-4-yl)-1,7-naphthyridin-4-amine; N-tert-butyl-2-(3-methyl-1H-pyrazol-4-yl)-1,7-naphthyridin-4-amine; N-tert-butyl-2-(pyrimidin-4-yl)-1,7-naphthyridin-4-amine; 2-(2-aminopyrimidin-4-yl)-N-tert-butyl-1,7-naphthyridin-4-amine; N-tert-butyl-2-{1H-pyrrolo[2,3-b]pyridin-4-yl}-1,7-naphthyridin-4-amine; N-tert-butyl-2-(pyridazin-4-yl)-1,7-naphthyridin-4-amine; 2-(2-aminopyridin-4-yl)-N-tert-butyl-1,7-naphthyridin-4-amine; N,N-diethyl-2-(3-fluoropyridin-4-yl)-1,7-naphthyridin-4-amine; (3-{[2-(3-fluoropyridin-4-yl)-1,7-naphthyridin-4-yl]amino}-3-methylbutyl)dimethylamine; 2-(3-fluoropyridin-4-yl)-N-methyl-N-(propan-2-yl)-1,7-naphthyridin-4-amine; 2-(3-fluoropyridin-4-yl)-4-(piperidin-1-yl)-1,7-naphthyridine; 2-(3-fluoropyridin-4-yl)-4-(morpholin-4-yl)-1,7-naphthyridine; N-tert-butyl-2-(3-fluoropyridin-4-yl)-1,7-naphthyridin-4-amine; 2-(3-fluoropyridin-4-yl)-N-(2-methylbutan-2-yl)-1,7-naphthyridin-4-amine; 2-{[2-(3-fluoropyridin-4-yl)-1,7-naphthyridin-4-yl]amino}-2-methylpropan-1-ol; 1-[2-(3-chloropyridin-4-yl)-1,7-naphthyridin-4-yl]-2,2-dimethylpiperidin-4-ol; 2-(3-fluoropyridin-4-yl)-N-[2-methyl-1-(morpholin-4-yl)propan-2-yl]-1,7-naphthyridin-4-amine; 4-(4-methylpiperazin-1-yl)-2-(pyridin-4-yl)-1,7- naphthyridine; 4-(piperazin-1-yl)-2-(pyridin-4-yl)-1,7-naphthyridine; 4-(2-methylpiperidin-1-yl)-2-(pyridin-4-yl)-1,7-naphthyridine; 2-(pyridin-4-yl)-N-(1-(trifluoromethyl)cyclobutyl)-1,7-naphthyridin-4-amine; 2-methyl-N1-(2-(pyridin-4-yl)-1,7-naphthyridin-4-yl)propane-1,2-diamine; N-(oxetan-3-yl)-2-(pyridin-4-yl)-1,7-naphthyridin-4-amine; N-(1-methylcyclopropyl)-2-(pyridin-4-yl)-1,7-naphthyridin-4-amine; 4-(3,3-dimethylpiperazin-1-yl)-2-(pyridin-4-yl)-1,7-naphthyridine; 2,2-dimethyl-4-(2-(pyridin-4-yl)-1,7-naphthyridin-4-yl)morpholine; N-(1-methylcyclobutyl)-2-(pyridin-4-yl)-1,7-naphthyridin-4-amine; 2,2-dimethyl-N1-(2-(pyridin-4-yl)-1,7-naphthyridin-4-yl)propane-1,3-diamine; $N^2,N^2$,2-trimethyl-$N^1$-(2-(pyridin-4-yl)-1,7-naphthyridin-4-yl)propane-1,2-diamine; 4-(2-methylpiperazin-1-yl)-2-(pyridin-4-yl)-1,7-naphthyridine; 2-methyl-$N^1$-(2-(pyridin-4-yl)-1,7-naphthyridin-4-yl)propane-1,3-diamine; (R)-2-(pyridin-4-yl)-4-(3-(trifluoromethyl)piperazin-1-yl)-1,7-naphthyridine; N-(tert-butyl)-N-methyl-2-(pyridin-4-yl)-1,7-naphthyridin-4-amine; N-(1-methylcyclobutyl)-2-(pyrimidin-4-yl)-1,7-naphthyridin-4-amine; $N^1,N^1$,3-trimethyl-$N^3$-(2-(pyrimidin-4-yl)pyrido[3,4-d]pyrimidin-4-yl)butane-1,3-diamine; $N^1,N^1$,3-trimethyl-$N^3$-(2-(3-methyl-1H-pyrazol-4-yl)pyrido[3,4-d]pyrimidin-4-yl)butane-1,3-diamine; tert-butyl (2-methyl-1-((2-(pyridin-4-yl)pyrido[3,4-d]pyrimidin-4-yl)amino)propan-2-yl)carbamate; tert-butyl (2-((2-(pyridin-4-yl)pyrido[3,4-d]pyrimidin-4-yl)amino)ethyl)carbamate; 2-methyl-$N^1$-(2-(pyridin-4-yl)pyrido[3,4-d]pyrimidin-4-yl)propane-1,2-diamine; $N^1$-(2-(pyridin-4-yl)pyrido[3,4-d]pyrimidin-4-yl)ethane-1,2-diamine; N,N,2-trimethyl-2-((2-(pyridin-4-yl)pyrido[3,4-d]pyrimidin-4-yl)amino)propanamide; $N^1$,3-dimethyl-$N^1$-(2-(pyridin-4-yl)pyrido[3,4-d]pyrimidin-4-yl)butane-1,3-diamine; tert-butyl (2,2-dimethyl-3-((2-(pyridin-4-yl)pyrido[3,4-d]pyrimidin-4-yl)amino)propyl)carbamate; 2,2-dimethyl-$N^1$-(2-(pyridin-4-yl)pyrido[3,4-d]pyrimidin-4-yl)propane-1,3-diamine; 3-methyl-3-((2-(pyridin-4-yl)pyrido[3,4-d]pyrimidin-4-yl)amino)butanamide; (R)-2-(pyridin-4-yl)-4-(3-(trifluoromethyl)piperazin-1-yl)pyrido[3,4-d]pyrimidine; 2,3-dimethyl-$N^2$-(2-(pyridin-4-yl)pyrido[3,4-d]pyrimidin-4-yl)butane-2,3-diamine; (S)-2-(pyridin-4-yl)-4-(3-(trifluoromethyl)piperazin-1-yl)pyrido[3,4-d]pyrimidine; ethyl 2-methyl-2-((2-(pyridin-4-yl)pyrido[3,4-d]pyrimidin-4-yl)amino)propanoate; $N^1,N^1$,2,2-tetramethyl-$N^3$-(2-(pyridin-4-yl)pyrido[3,4-d]pyrimidin-4-yl)propane-1,3-diamine; 4-(4-(tert-butylamino)pyrido[3,4-d]pyrimidin-2-yl)-1,2,5-oxadiazol-3-amine; $N^2,N^2$,2-trimethyl-$N^1$-(2-(pyridin-4-yl)pyrido[3,4-d]pyrimidin-4-yl) propane-1,2-diamine; 2-methyl-2-((2-(pyridin-4-yl)pyrido[3,4-d]pyrimidin-4-yl)amino)propanamide; (S)-1,1,1-trifluoro-2-methyl-3-((2-(pyridin-4-yl)-1,7-naphthyridin-4-yl)amino)propan-2-ol; N-tert-butyl-2-(3-chloropyridin-4-yl)-1,7-naphthyridin-4-amine; 2-(3-chloropyridin-4-yl)-N,N-diethyl-1,7-naphthyridin-4-amine; N-((1R,2S)-2-methylcyclopentyl)-2-(pyridin-4-yl)pyrido[3,4-d]pyrimidin-4-amine; (S)—N-(sec-butyl)-2-(pyridin-4-yl)pyrido[3,4-d]pyrimidin-4-amine; N-((1S,2R)-2-methylcyclopentyl)-2-(pyridin-4-yl)pyrido[3,4-d]pyrimidin-4-amine; (R)—N-(sec-butyl)-2-(pyridin-4-yl)pyrido[3,4-d]pyrimidin-4-amine; N-((1S,2S)-2-methylcyclopentyl)-2-(pyridin-4-yl)pyrido[3,4-d]pyrimidin-4-amine; N-((1R,2R)-2-methylcyclopentyl)-2-(pyridin-4-yl)pyrido[3,4-d]pyrimidin-4-amine; N-(tert-butyl)-2-(pyridin-4-yl)-1,7-naphthyridin-4-amine; N-propyl-2-(3-(trifluoromethyl)-1H-pyrazol-4-yl)pyrido[3,4-d]pyrimidin-4-amine; tert-butyl (3-methyl-3-((2-(pyridin-4-yl)pyrido[3,4-d]pyrimidin-4-yl)amino)butyl)carbamate; $N^1,N^1,N^3$,2,2-pentamethyl-$N^3$-(2-(pyridin-4-yl)pyrido[3,4-d]pyrimidin-4-yl)propane-1,3-diamine; $N^1,N^1$-diethyl-3-methyl-$N^3$-(2-(pyridin-4-yl)pyrido[3,4-d]pyrimidin-4-yl)butane-1,3-diamine; $N^3$-(2-(2-fluoropyridin-4-yl)pyrido[3,4-d]pyrimidin-4-yl)-$N^1,N^1$,3-trimethylbutane-1,3-diamine; $N^3$-(2-(3,5-dimethyl-1H-pyrazol-4-yl)pyrido[3,4-d]pyrimidin-4-yl)-$N^1,N^1$,3-trimethylbutane-1,3-diamine; $N^1,N^1$,3-trimethyl-$N^3$-(2-(3-(trifluoromethyl)-1H-pyrazol-4-yl)pyrido[3,4-d]pyrimidin-4-yl)butane-1,3-diamine; $N^3$-(2-(2-aminopyridin-4-yl)pyrido[3,4-d]pyrimidin-4-yl)-$N^1,N^1$,3-trimethylbutane-1,3-diamine; and 3-methyl-$N^1$-(2-(pyridin-4-yl)pyrido[3,4-d]pyrimidin-4-yl)butane-1,3-diamine.

Embodiment 60A

A compound of the Formula A2, or a salt thereof, according to embodiment 1, selected from: N-methyl-2-(pyridin-4-yl)-N-(1,1,1-trifluoropropan-2-yl)pyrido[3,4-d]pyrimidin-4-amine; 2-methyl-1-(2-methyl-2-{[2-(pyridin-4-yl)pyrido[3,4-d]pyrimidin-4-yl]amino}propoxy)propan-2-ol; 2,4-dimethyl-4-{[2-(pyridin-4-yl)pyrido[3,4-d]pyrimidin-4-yl]amino}pentan-2-ol; N-tert-butyl-2-(pyrimidin-4-yl)-1,7-naphthyridin-4-amine; 2-(pyridin-4-yl)-N-[1-(trifluoromethyl)cyclobutyl]pyrido[3,4-d]pyrimidin-4-amine; N-propyl-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; 2-(3-methyl-1H-pyrazol-4-yl)-N-(1-methylcyclopropyl)pyrido[3,4-d]pyrimidin-4-amine; 2-methyl-2-{[2-(pyridin-4-yl)pyrido[3,4-d]pyrimidin-4-yl]amino}propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; N-(1-methylcyclopropyl)-7-(pyridin-4-yl)isoquinolin-5-amine; (1S,2S)-2-{[2-(pyridin-4-yl)pyrido[3,4-d]pyrimidin-4-yl]amino}cyclopentan-1-ol; N-methyl-2-(pyridin-4-yl)-N-[(2S)-1,1,1-trifluoropropan-2-yl]pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; N-(tert-butyl)-2-(pyridin-4-yl)-1,7-naphthyridin-4-amine; and N-methyl-2-(pyridin-4-yl)-N-[(2R)-1,1,1-trifluoropropan-2-yl]pyrido[3,4-d]pyrimidin-4-amine.

Embodiment 60B

A compound of the Formula A2, or a salt thereof, according to embodiment 1, selected from: N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 60C

A compound of the Formula A2, or a salt thereof, according to embodiment 1, wherein the compound is N-(tert-butyl)-2-(pyridin-4-yl)-1,7-naphthyridin-4-amine.

53

Embodiment 61

A compound of Formula I, or a salt thereof

I wherein
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —NH$_2$, $C_{1-6}$alkylamino, di-($C_{1-6}$ alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
 (i) halogen;
 (ii) cyano;
 (iii) oxo;
 (iv) $C_2$alkenyl;
 (v) $C_2$alkynyl;
 (vi) $C_{1-6}$haloalkyl;
 (vii) —OR$^6$, wherein R$^6$ is selected from hydrogen, $C_{1-6}$alkyl that is unsubstituted or substituted by R$^0$ or —C(O)R$^0$;
 (viii) —NR$^{7a}$R$^{7b}$, wherein R$^{7a}$ is hydrogen or $C_{1-6}$alkyl, and R$^{7b}$ is selected from hydrogen, —C(O)R$^0$, $C_{1-6}$alkyl that is unsubstituted or substituted by —C(O)R$^0$;

54

(ix) —C(O)R$^8$, wherein R$^8$ is R$^0$ or —NH—$C_{1-6}$alkyl-C(O)R$^0$;
 (x) —S(O)$_2C_{1-6}$alkyl;
 (xi) monocyclic $C_{3-6}$cycloalkyl or polycyclic $C_{7-10}$cycloalkyl that are each unsubstituted or substituted by 1 to 2 substituents independently selected from halogen, $C_{1-6}$ alkyl, hydroxy$C_{1-6}$alkyl, $C_{1-6}$haloalkyl, R$^0$, —NH$_2$, $C_{1-6}$alkylamino, and di-($C_{1-6}$ alkyl)amino;
 (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
 (xiii) phenyl that is unsubstituted or substituted by halogen;
 (xiv) 5- or 6-membered monocyclic heteroaryl comprising, as ring members, 1 to 4 heteroatoms independently selected from N and O; and
 (xv) 9- or 10-membered fused bicyclic heteroaryl comprising, as ring member, 1 to 2 heteroatoms independently selected from N and O;
(b) —S(O)$_2C_{1-6}$alkyl;
(c) phenyl that is unsubstituted or substituted by 1 to 2 substituents independently selected from halogen, $C_{1-6}$alkyl and R$^0$;
(d) $C_{3-6}$cycloalkyl that is unsubstituted or substituted by 1 to 2 substituents independently selected from $C_{1-6}$haloalkyl, R$^0$, $C_{1-6}$alkylamino, di-($C_{1-6}$alkyl)amino, —C(O)R$^0$, and $C_{1-6}$alkyl that is unsubstituted or substituted by R$^0$ or —C(O)R$^0$; and
(e) 4-membered heterocycloalkyl comprising, as ring members, 1 to 2 heteroatoms selected from N, O and S and that and that is unsubstituted or substituted by 1 to 2 substituents independently selected from $C_{1-6}$haloalkyl, R$^0$, $C_{1-6}$alkylamino, di-($C_{1-6}$ alkyl)amino, —C(O)R$^0$, and $C_{1-6}$alkyl that is unsubstituted or substituted by R$^0$ or —C(O)R$^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by R$^0$;
with the proviso that:
(1) when ring A is 4-primidinyl or 3-fluoro-4-primidinyl, R$^1$ is H or methyl, R$^3$ is H or Cl and R$^5$ is H; then R$^2$ is not $C_{2-4}$alkyl that is substituted with a substituent selected from —NH$_2$, $C_{1-6}$alkylamino or t-butyl-carbamoyl-amino and that and that is optionally further substituted with unsubstituted phenyl; and
(2) when ring A is indazol-5-yl, R$^1$, R$^3$ and R$^5$ are H; then R$^2$ is not $C_4$alkyl that is substituted with —NH$_2$.

Embodiment 62

A compound of Formula I according to embodiment 61, or a salt thereof,
wherein
Ring A is
(a) a 5- or 6-membered monocyclic heteroaryl that is linked to the remainder of the molecule through a carbon ring member and comprises, as ring member, 1 to 2 heteroatoms that are selected from N, provided that at least one of the nitrogen atom ring member is an unsubstituted nitrogen (—N═) positioned at the 3- or the 5-position relative to the linking carbon ring member of the 5-membered heteroaryl or at the para ring position of the 6-membered heteroaryl; or
(b) a 9-membered fused bicyclic heteroaryl that is selected from

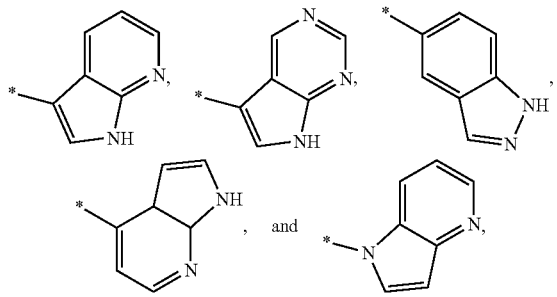

wherein "*" represents the point of attachment of ring A to the remainder of the molecule and ring A is unsubstituted or substituted by 1 to 2 substituents independently selected from halogen, cyano, $C_{1-6}$alkyl, $C_{1-6}$haloalkyl, —$NH_2$ and $C_{1-6}$cycloalkyl.

Embodiment 63

A compound of Formula I, or a salt thereof, according to embodiment 61 or embodiment 62, wherein ring A is selected from

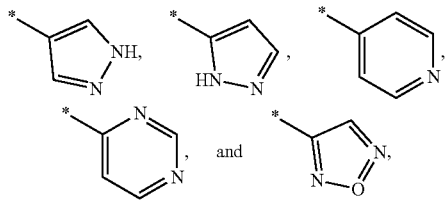

which are each unsubstituted or substituted by 1 to 2 substituents independently selected from cyano, halogen, $C_{1-6}$alkyl, $C_{1-6}$haloalkyl, $NH_2$, and $C_{3-6}$cycloalkyl; or from

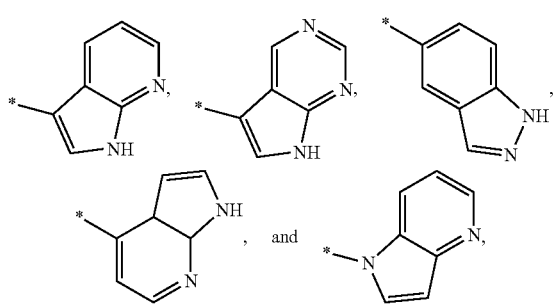

which are each unsubstituted or substituted by $C_{1-6}$alkyl.

Embodiment 64

A compound of Formula I, or a salt thereof, according to any one of embodiments 61 to 63, wherein ring A is selected from

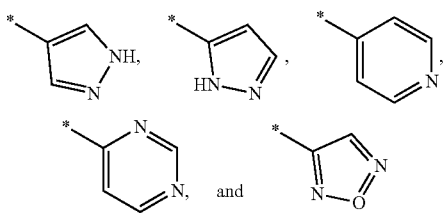

that are each unsubstituted or substituted by a substituent selected from halogen, cyano, $C_{1-6}$alkyl, $C_{1-6}$haloalkyl, and —$NH_2$;
or

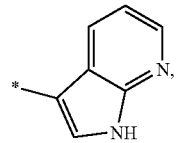

that is unsubstituted or substituted by $C_{1-6}$alkyl.

Embodiment 65

A compound of Formula I, or a salt thereof, according to any one of embodiments 61 to 63, wherein ring A is selected from

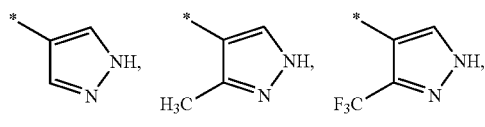
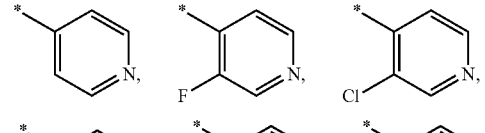
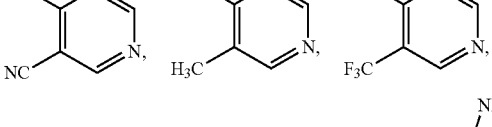
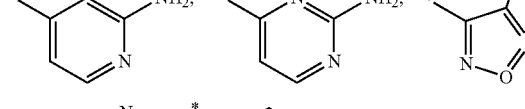
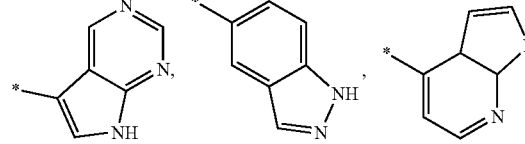
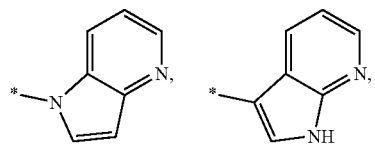

-continued

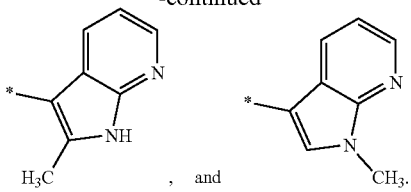

Embodiment 66

A compound of Formula I, or a salt thereof, according to any one of embodiments 61 to 65, wherein ring A is selected from

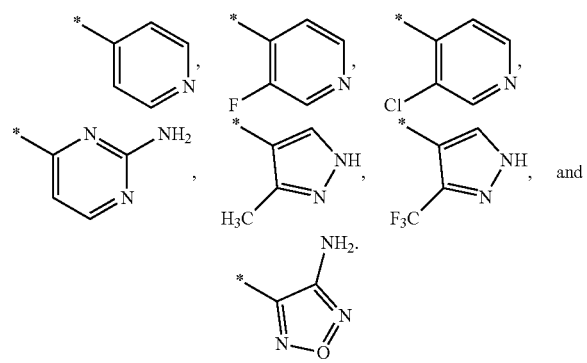

Embodiment 67

A compound of Formula I, or a salt thereof, according to any one of embodiments 61 to 66, wherein ring A is selected from

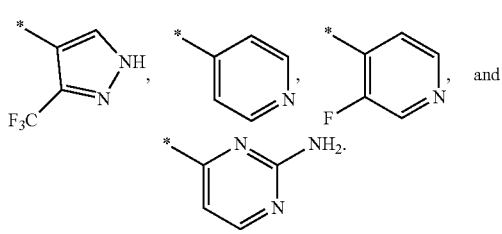

Embodiment 68

A compound of Formula I, or a salt thereof, according to any one of embodiments 61 to 67, wherein ring A is

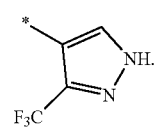

Embodiment 69

A compound of Formula I, or a salt thereof, according to any one of embodiments 61 to 67, wherein ring A is

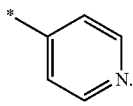

Embodiment 70

A compound of Formula I, or a salt thereof, according to any one of embodiments 61 to 67, wherein ring A is

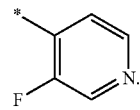

Embodiment 71

A compound of Formula I, or a salt thereof, according to any one of embodiments 61 to 67, wherein ring A is

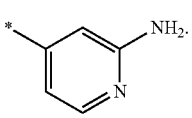 [SMILES: *c1ccnc(N)c1]

Embodiment 72

A compound of Formula I, or a salt thereof, according to any one of embodiments 61 to 67, wherein ring A is

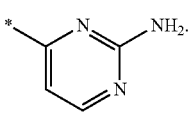

Embodiment 73

A compound of Formula I, or a salt thereof, according to any one of embodiments 61 to 65, wherein ring A is

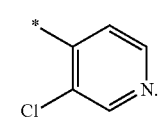

Embodiment 74

A compound of Formula I, or a salt thereof, according to any one of embodiments 61 to 65, wherein ring A is

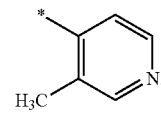

Embodiment 75

A compound of Formula I, or a salt thereof, according to any one of embodiments 61 to 66, wherein ring A is

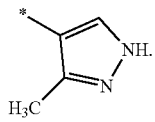

Embodiment 76

A compound of Formula I, or a salt thereof, according to any one of embodiments 61 to 63, wherein ring A is

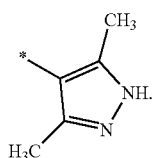

Embodiment 77

A compound of Formula I, or a salt thereof, according to any one of embodiments 61 to 64, wherein ring A is

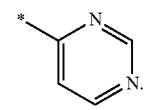

Embodiment 78

A compound of Formula I, or a salt thereof, according to any one of embodiments 61 to 65, wherein ring A is

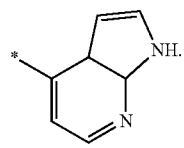 [SMILES: *C1=CC=NC2NC=CC12]

Embodiment 78A

A compound of Formula I, or a salt thereof, according to any one of embodiments 61 to 65, wherein ring A is

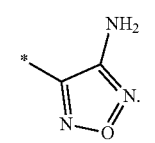

Embodiment 79

A compound of Formula I, or a salt thereof, according to any one of embodiments 61 to 63, wherein ring A is selected from

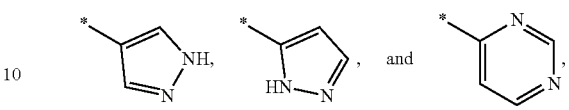

which are each unsubstituted or substituted by 1 to 2 substituents independently selected from cyano, halogen, $C_{1-6}$alkyl, $C_{1-6}$haloalkyl, $NH_2$, and $C_{3-6}$cycloalkyl; or from

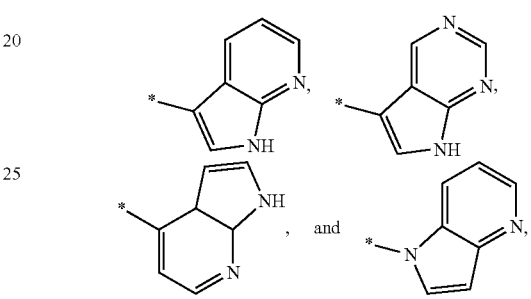

which are each unsubstituted or substituted by $C_{1-6}$alkyl.

Embodiment 80

A compound of Formula I, or a salt thereof, according to any one of embodiments 61 to 79, wherein $R^1$ is selected from hydrogen, methyl and ethyl.

Embodiment 81

A compound of Formula I, or a salt thereof, according to any one of embodiments 61 to 80, wherein $R^1$ is methyl.

Embodiment 82

A compound of Formula I, or a salt thereof, according to any one of embodiments 61 to 80, wherein $R^1$ is hydrogen.

Embodiment 83

A compound of Formula I, or a salt thereof, according to any one of embodiments 61 to 82, wherein
$R^2$ is selected from
(a) $C_{1-8}$alkyl that is unsubstituted or substituted by 1 to 3 substituents independently selected from
  (i) cyano;
  (ii) $C_2$alkynyl;
  (iii) $C_{1-6}$haloalkyl;
  (iv) —$OR^6$, wherein $R^6$ is selected from hydrogen, $C_{1-6}$alkyl that is unsubstituted or substituted by $R^0$ or —C(O)$R^0$;
  (v) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (vi) —C(O)$R^8$, wherein $R^8$ is $R^0$;
  (vii) —S(O)$_2$$C_{1-6}$alkyl;

(viii) monocyclic $C_{3-6}$cycloalkyl that is unsubstituted or substituted by a substituent selected from $C_{1-6}$alkyl, hydroxy$C_{1-6}$alkyl and $R^o$;
(ix) 6-membered heterocycloalkyl comprising, as ring members, 1 to 2 heteroatoms independently selected from N and O and that and that is unsubstituted or substituted by $C_{1-6}$alkyl; and
(x) phenyl that is unsubstituted or substituted by halogen;
(b) $C_{3-6}$cycloalkyl that is unsubstituted or substituted by 1 to 2 substituents independently selected from $C_{1-6}$haloalkyl, $R^o$, $C_{1-6}$alkylamino, —C(O)$R^o$, and $C_{1-6}$alkyl that is unsubstituted or substituted by $R^o$ or —C(O)$R^o$; and
(c) 4-membered heterocycloalkyl comprising, as ring member, a heteroatom selected from N and O and that and that is unsubstituted or substituted by 1 to 2 substituents independently selected from $C_{1-6}$haloalkyl, $R^o$, $C_{1-6}$alkylamino, —C(O)$R^o$, and $C_{1-6}$alkyl that is unsubstituted or substituted by $R^o$ or —C(O)$R^o$.

Embodiment 84

A compound of Formula I, or a salt thereof, according to any one of embodiments 61 to 82, wherein
$R^2$ is selected from
(a) $C_{1-8}$alkyl that is unsubstituted or substituted by 1 to 3 substituents independently selected from
(i) cyano;
(ii) $C_2$alkynyl;
(iii) $C_{1-6}$haloalkyl;
(iv) —OR$^6$, wherein $R^6$ is selected from hydrogen, $C_{1-6}$alkyl that is unsubstituted or substituted by $R^o$ or —C(O)$R^o$;
(v) —NR$^{7a}$R$^{7b}$, wherein R$^{7a}$ is hydrogen or $C_{1-6}$alkyl, and R$^{7b}$ is selected from hydrogen, —C(O)$R^o$, $C_{1-6}$alkyl that is unsubstituted or substituted by —C(O)$R^o$;
(vi) —C(O)$R^8$, wherein $R^8$ is $R^o$;
(vii) —S(O)$_2$$C_{1-6}$alkyl;
(viii) monocyclic $C_{3-6}$cycloalkyl that is unsubstituted or substituted by a substituent selected from $C_{1-6}$alkyl, hydroxy$C_{1-6}$alkyl and $R^o$;
(ix) 6-membered heterocycloalkyl comprising, as ring members, 1 to 2 heteroatoms independently selected from N and O and that and that is unsubstituted or substituted by $C_{1-6}$alkyl; and
(x) phenyl that is unsubstituted or substituted by halogen; and wherein the C atom of the $C_{1-8}$alkyl that is unsubstituted or substituted by 1 to 3 substituents (i) to (x) that is the point of attachment of $R^2$ to the remainder of the molecule is not a —CH$_2$— group.
(b) $C_{3-6}$cycloalkyl that is unsubstituted or substituted by 1 to 2 substituents independently selected from $C_{1-6}$haloalkyl, $R^o$, $C_{1-6}$alkylamino, —C(O)$R^o$, and $C_{1-6}$alkyl that is unsubstituted or substituted by $R^o$ or —C(O)$R^o$; and
(c) 4-membered heterocycloalkyl comprising, as ring member, a heteroatom selected from N and O and that and that is unsubstituted or substituted by 1 to 2 substituents independently selected from $C_{1-6}$haloalkyl, $R^o$, $C_{1-6}$alkylamino, —C(O)$R^o$, and $C_{1-6}$alkyl that is unsubstituted or substituted by $R^o$ or —C(O)$R^o$.

Embodiment 85

A compound of Formula I, or a salt thereof, according to any one of embodiments 61 to 83, wherein
$R^2$ is selected from
(a) $C_{1-8}$alkyl that is unsubstituted or substituted by 1 to 2 substituents independently selected from
(i) cyano;
(ii) $C_2$alkynyl;
(iii) $C_{1-6}$haloalkyl;
(iv) —OR$^6$, wherein $R^6$ is selected from hydrogen, $C_{1-6}$alkyl that is unsubstituted or substituted by hydroxyl or —C(O)H;
(v) —NR$^{7a}$R$^{7b}$, wherein R$^{7a}$ is hydrogen or $C_{1-6}$alkyl, and R$^{7b}$ is selected from hydrogen, —C(O)—$C_{1-6}$alkoxy, and $C_{1-6}$alkyl that is unsubstituted or substituted by —C(O)OH; and
(vi) monocyclic $C_{3-6}$cycloalkyl that is unsubstituted or substituted by one hydroxyl; and
(b) $C_{3-6}$cycloalkyl that is unsubstituted or substituted by 1 to 2 substituents independently selected from $C_{1-6}$haloalkyl, $R^o$, $C_{1-6}$alkylamino, and $C_{1-6}$alkyl that is unsubstituted or substituted by hydroxyl or —C(O)—$C_{1-6}$alkoxy.

Embodiment 86

A compound of Formula I, or a salt thereof, according to any one of embodiments 61 to 85, wherein
$R^2$ is selected from
(a) $C_{1-8}$alkyl that is unsubstituted or substituted by 1 to 2 substituents independently selected from
(i) $C_{1-6}$haloalkyl;
(ii) —OR$^6$, wherein $R^6$ is selected from hydrogen, and $C_{1-6}$alkyl that is unsubstituted or substituted by hydroxyl; and
(iii) monocyclic $C_{3-6}$cycloalkyl that is unsubstituted or substituted by hydroxyl; and
(b) $C_{3-6}$cycloalkyl that is unsubstituted or substituted by 1 to 2 substituents independently selected from $C_{1-6}$haloalkyl, $R^o$, $C_{1-6}$alkylamino, and $C_{1-6}$alkyl that is unsubstituted or substituted by hydroxyl.

Embodiment 87

A compound of Formula I, or a salt thereof, according to any one of embodiments 61 to 86, wherein $R^2$ is $C_{1-6}$alkyl that is unsubstituted or substituted by 1 to 2 substituent independently selected from $C_{1-6}$haloalkyl and —OR$^6$, wherein $R^6$ is selected from hydrogen, and $C_{1-6}$alkyl that is unsubstituted or substituted by hydroxyl.

Embodiment 88

A compound of Formula I, or a salt thereof, according to any one of embodiments 61 to 87, wherein $R^2$ is $C_{1-6}$alkyl that is unsubstituted or substituted by hydroxyl.

Embodiment 89

A compound of Formula I, or a salt thereof, according to any one of embodiments 61 to 87, wherein $R^2$ is $C_{1-6}$alkyl that is unsubstituted or substituted by $C_{1-6}$ haloalkyl.

Embodiment 90

A compound of Formula I, or a salt thereof, according to any one of embodiments 61 to 87, wherein $R^2$ is $C_{1-6}$alkyl that is unsubstituted or substituted by —O—$C_{1-6}$alkyl-OH.

Embodiment 91

A compound of Formula I, or a salt thereof, according to any one of embodiments 61 to 86, wherein $R^2$ is $C_{3-6}$cycloalkyl that is unsubstituted or substituted by a substituent selected from $C_{1-6}$haloalkyl, $C_{1-6}$alkylamino, $R^0$, and $C_{1-6}$alkyl that is unsubstituted or substituted by hydroxyl.

Embodiment 92

A compound of Formula I, or a salt thereof, according to any one of embodiments 61 to 86 and 91, wherein $R^2$ is unsubstituted $C_{3-6}$cycloalkyl.

Embodiment 93

A compound of the Formula I, or a salt thereof, according to any one of embodiments 61 to 86 and 91, wherein $R^2$ is $C_{3-6}$cycloalkyl that is substituted by $C_{1-6}$alkyl or $C_{1-6}$haloalkyl.

Embodiment 94

A compound of the Formula I, or a salt thereof, according to any one of embodiments 61 to 85, wherein $R^2$ is selected from n-propyl, isopropyl, s-butyl, t-butyl, 2-methyl-but-2-yl, 2,4,4-trimethylpentan-2-yl,

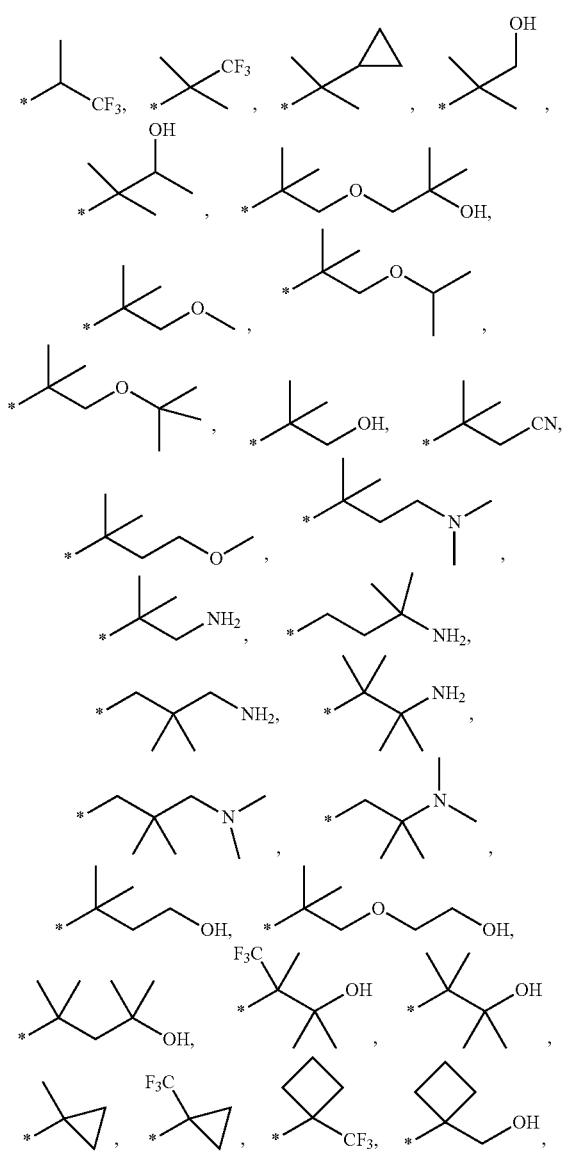

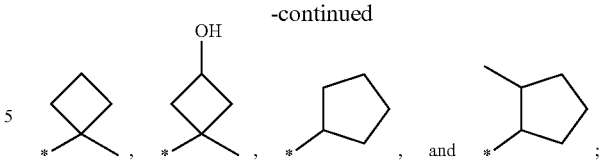

wherein "*" represents the point of attachment of $R^2$ to the remainder of the molecule.

Embodiment 94A

A compound of the Formula I, or a salt thereof, any one of according to embodiments 61 to 85, wherein $R^2$ is selected from

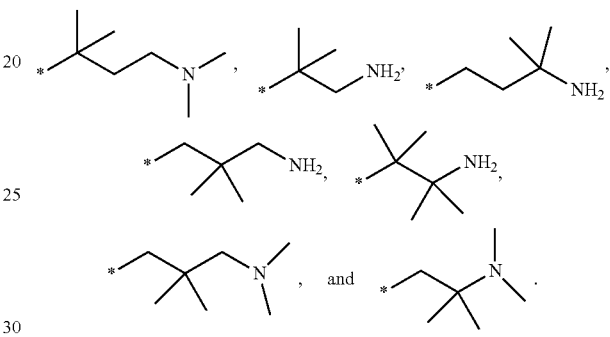

Embodiment 95

A compound of Formula I, or a salt thereof, according to any one of embodiments 61 to 83 and 85 to 87, wherein $R^2$ is selected from n-propyl, isopropyl, t-butyl,

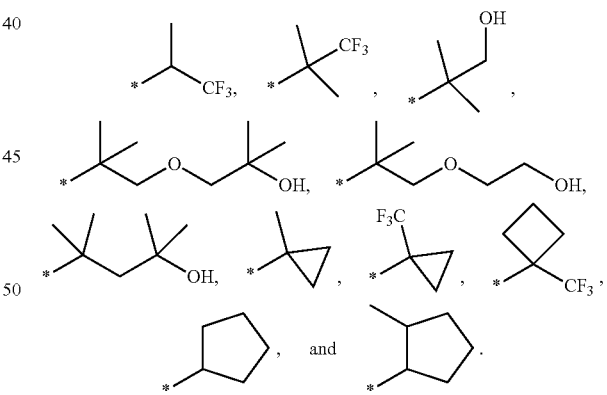

Embodiment 96

A compound of Formula I, or a salt thereof, according to any one of embodiments 61 to 87, 94 and 95, wherein $R^2$ is selected from

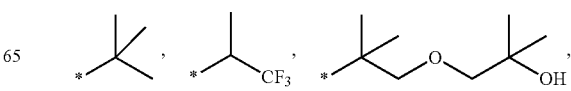

-continued

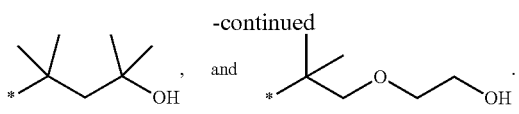

Embodiment 97

A compound of Formula I, or a salt thereof, according to any one of embodiments 61 to 87, 89, and 94 to 96, wherein $R^2$ is

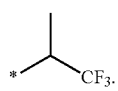

Embodiment 98

A compound of Formula I, or a salt thereof, according to any one of embodiments 61 to 87, 90, and 94 to 96 wherein $R^2$ is OH

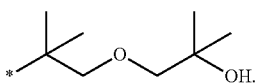 [SMILES: *C(C)(C)COCC(C)(C)O]

Embodiment 99

A compound of Formula I, or a salt thereof, according to any one of embodiments 61 to 87, 91, and 94 to 96, wherein $R^2$ is

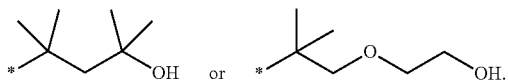

Embodiment 100

A compound of Formula I, or a salt thereof, according to any one of embodiments 61 to 86, 91, 94 and 95 wherein $R^2$ is selected from

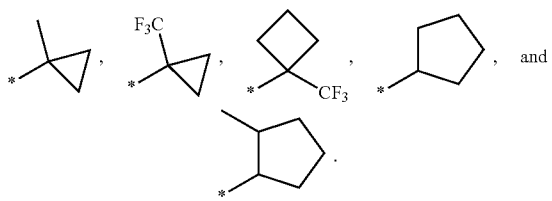

Embodiment 101

A compound of Formula I, or a salt thereof, according to any one of embodiments 61 to 86, 91, 93 to 95 and 100, wherein $R^2$ is

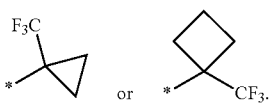

Embodiment 102

A compound of Formula I, or a salt thereof, according to any one of embodiments 61 to 86, 91, 93 to 95 and 100, wherein $R^2$ is

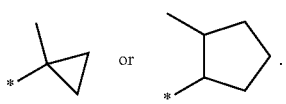

Embodiment 103

A compound of Formula I, or a salt thereof, according to any one of embodiments 61 to 86, 91 to 95, 100 and 102, wherein $R^2$ is

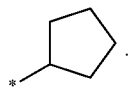

Embodiment 104

A compound of Formula I, or a salt thereof, according to any one of embodiments 61 to 83, 85 to 90, and 95, wherein $R^2$ is selected from n-propyl, isopropyl and t-butyl.

Embodiment 105

A compound of Formula I, or a salt thereof, according to any one of embodiments 61 to 83, 85 to 90, 95, and 104, wherein $R^2$ is n-propyl.

Embodiment 106

A compound of the Formula I, or a salt thereof, according to any one of embodiments 61 to 90, 95, and 104, wherein $R^2$ is isopropyl.

Embodiment 107

A compound of Formula I, or a salt thereof, according to any one of embodiments 61 to 90, 95, and 104, wherein $R^2$ is t-butyl.

Embodiment 108

A compound of Formula I, or a salt thereof, according to any one of embodiments 61 to 107, wherein $R^3$ is selected from hydrogen, chloro and methyl.

Embodiment 109

A compound of Formula I, or a salt thereof, according to any one of embodiments 61 to 108, wherein $R^3$ is hydrogen.

Embodiment 109A

A compound of Formula I, or a salt thereof, according to any one of embodiments 61 to 108, wherein $R^3$ is chloro.

Embodiment 109B

A compound of Formula I, or a salt thereof, according to any one of embodiments 61 to 108, wherein $R^3$ is methyl.

Embodiment 110

A compound of the Formula I, or a salt thereof, according to any one of embodiments 61 to 109, wherein $R^5$ is selected from hydrogen, and chloro.

Embodiment 111

A compound of Formula I, or a salt thereof, according to any one of embodiments 61 to 110, wherein $R^5$ is hydrogen.

Embodiment 112

A compound of Formula I, or a salt thereof, according to embodiment 61, wherein the compound is of Formula V:

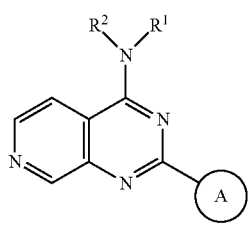

wherein
Ring A is

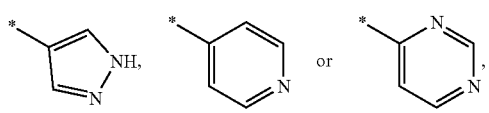 [SMILES: *c1cn[nH]c1 ; *c1ccncc1 ; *c1ccncn1]

each of which is unsubstituted or substituted by a substituent selected from halogen, $C_{1-6}$alkyl, $C_{1-6}$haloalkyl, and $-NH_2$;
$R^1$ is hydrogen or unsubstituted $C_{1-6}$alkyl; and
$R^2$ is
(a) $C_{1-8}$alkyl that is unsubstituted or substituted by 1 substituents selected from
  (i) $C_{1-4}$haloalkyl or
  (ii) $-OR^6$, wherein $R^6$ is selected from hydrogen and $C_{1-6}$alkyl that is unsubstituted or substituted by hydroxyl; or
(b) monocyclic $C_{3-6}$cycloalkyl that is unsubstituted or substituted by $C_{1-6}$alkyl or $C_{1-6}$haloalkyl.

Embodiment 113

A compound of Formula I, or a salt thereof, according to embodiment 112, wherein ring A is selected from

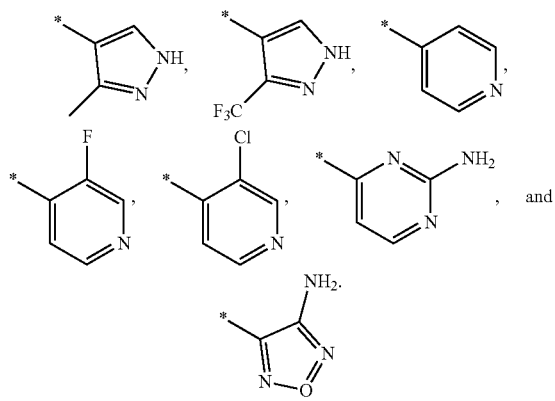

Embodiment 114

A compound of Formula I, or a salt thereof, according to embodiment 112 or embodiment 113, wherein ring A is

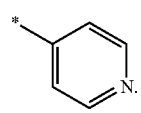

Embodiment 115

A compound of Formula I, or a salt thereof, according to embodiment 112 or embodiment 113, wherein ring A is

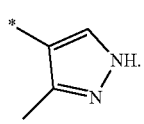

Embodiment 116

A compound of Formula I, or a salt thereof, according to any one of embodiments 112 to 115, wherein $R^2$ is selected from

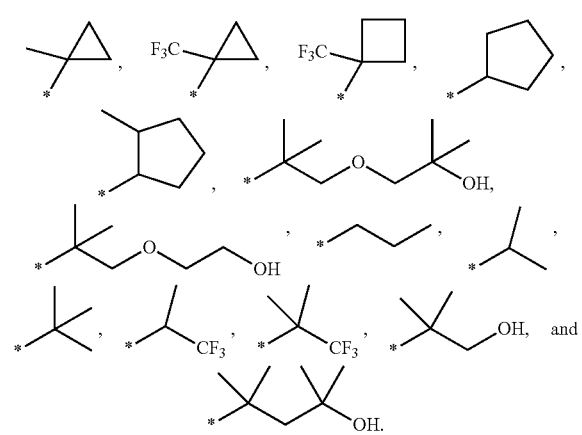

Embodiment 116A

A compound of Formula I, or a salt thereof, according to any one of embodiments 112 to 115, wherein R² is selected from

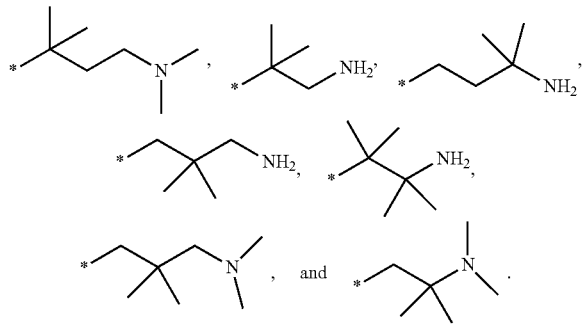

Embodiment 117

A compound of Formula I, or a salt thereof, according to any one of embodiments 112 to 116, wherein R² is

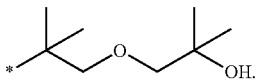 [SMILES: *C(C)(C)COCC(C)(C)O]

Embodiment 118

A compound of Formula I or a salt thereof, according to any one of embodiments 112 to 116, wherein R² is

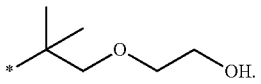

Embodiment 119

A compound of Formula I, or a salt thereof, according to any one of embodiments 112 to 116, wherein R² is

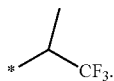

Embodiment 120

A compound of the Formula I, or a salt thereof, according to embodiment 61, selected from: N-(2-cyclopropylpropan-2-yl)-2-(pyridin-4-yl)pyrido[3,4-d]pyrimidin-4-amine; N,N-diethyl-2-(pyridin-4-yl)pyrido[3,4-d]pyrimidin-4-amine; N-ethyl-N-(propan-2-yl)-2-(pyridin-4-yl)pyrido[3,4-d]pyrimidin-4-amine; 2-(pyridin-4-yl)-N-(1,1,1-trifluoropropan-2-yl)pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; N-(1-methoxy-2-methylpropan-2-yl)-2-(pyridin-4-yl)pyrido[3,4-d]pyrimidin-4-amine; N-(4-methoxy-2-methylbutan-2-yl)-2-(pyridin-4-yl)pyrido[3,4-d]pyrimidin-4-amine; N-butyl-N-methyl-2-(pyridin-4-yl)pyrido[3,4-d]pyrimidin-4-amine; N-ethyl-N-methyl-2-(pyridin-4-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; 2-methyl-1-(2-methyl-2-{[2-(pyridin-4-yl)pyrido[3,4-d]pyrimidin-4-yl]amino}propoxy)propan-2-ol; N-ethyl-2-(pyridin-4-yl)pyrido[3,4-d]pyrimidin-4-amine; N-propyl-2-(pyridin-4-yl)pyrido[3,4-d]pyrimidin-4-amine; N-(2-cyclohexylpropan-2-yl)-2-(pyridin-4-yl)pyrido[3,4-d]pyrimidin-4-amine; N-(3-methyloxetan-3-yl)-2-(pyridin-4-yl)pyrido[3,4-d]pyrimidin-4-amine; N-(2-methylcyclopentyl)-2-(pyridin-4-yl)pyrido[3,4-d]pyrimidin-4-amine; 3-methyl-3-{[2-(pyridin-4-yl)pyrido[3,4-d]pyrimidin-4-yl]amino}butan-2-ol; N-butyl-2-(pyridin-4-yl)pyrido[3,4-d]pyrimidin-4-amine; N-(2-methyl-4-phenylbutan-2-yl)-2-(pyridin-4-yl)pyrido[3,4-d]pyrimidin-4-amine; N-cyclopropyl-2-(pyridin-4-yl)pyrido[3,4-d]pyrimidin-4-amine; N-(4-methanesulfonyl-2-methylbutan-2-yl)-2-(pyridin-4-yl)pyrido[3,4-d]pyrimidin-4-amine; 2-methyl-2-{[2-(pyridin-4-yl)pyrido[3,4-d]pyrimidin-4-yl]amino}propane-1,3-diol; 3-{[2-(pyridin-4-yl)pyrido[3,4-d]pyrimidin-4-yl]amino}butan-2-ol; 2-(2-methyl-2-{[2-(pyridin-4-yl)pyrido[3,4-d]pyrimidin-4-yl]amino}propoxy)acetic acid; (1R,2S)-2-{[2-(pyridin-4-yl)pyrido[3,4-d]pyrimidin-4-yl]amino}cyclopentan-1-ol; 4,4,4-trifluoro-3-{[2-(pyridin-4-yl)pyrido[3,4-d]pyrimidin-4-yl]amino}butan-1-ol; N-(1-methanesulfonyl-2-methylpropan-2-yl)-2-(pyridin-4-yl)pyrido[3,4-d]pyrimidin-4-amine; (2S)-3,3,3-trifluoro-2-methyl-2-{[2-(pyridin-4-yl)pyrido[3,4-d]pyrimidin-4-yl]amino}propanoic acid; 2-[(2-methyl-2-{[2-(pyridin-4-yl)pyrido[3,4-d]pyrimidin-4-yl]amino}propyl)amino]acetic acid; (2R)-3,3,3-trifluoro-2-methyl-2-{[2-(pyridin-4-yl)pyrido[3,4-d]pyrimidin-4-yl]amino}propanoic acid; methyl 2-methyl-2-{[2-(pyridin-4-yl)pyrido[3,4-d]pyrimidin-4-yl]amino}propanoate; (1S,2S)-2-{[2-(pyridin-4-yl)pyrido[3,4-d]pyrimidin-4-yl]amino}cyclopentan-1-ol; 2-methyl-2-{[2-(pyridin-4-yl)pyrido[3,4-d]pyrimidin-4-yl]amino}propanoic acid; 2-(2-{[2-(pyridin-4-yl)pyrido[3,4-d]pyrimidin-4-yl]amino}ethoxy)ethan-1-ol; 2-(hydroxymethyl)-2-{[2-(pyridin-4-yl)pyrimidin-4-yl]amino}propane-1,3-diol; 3-methyl-3-(3-methyl-3-{[2-(pyridin-4-yl)pyrido[3,4-d]pyrimidin-4-yl]amino}butanamido)butanoic acid; 2-(pyridin-4-yl)-N-(1,1,1-trifluoro-3-phenylpropan-2-yl)pyrido[3,4-d]pyrimidin-4-amine; N-{[4-(dimethylamino)oxan-4-yl]methyl}-2-(pyridin-4-yl)pyrido[3,4-d]pyrimidin-4-amine; 3-methyl-3-{[2-(pyridin-4-yl)pyrido[3,4-d]pyrimidin-4-yl]amino}butanoic acid; N-(2-methanesulfonylethyl)-2-(pyridin-4-yl)pyrido[3,4-d]pyrimidin-4-amine; N-[2-(adamantan-1-yl)propan-2-yl]-2-(pyridin-4-yl)pyrido[3,4-d]pyrimidin-4-amine; 2-methyl-N-[2-(pyridin-4-yl)pyrido[3,4-d]pyrimidin-4-yl]propanamide; 4,4,4-trifluoro-3-{[2-(pyridin-4-yl)pyrido[3,4-d]pyrimidin-4-yl]amino}butanoic acid; N-[2-(pyridin-4-yl)pyrido[3,4-d]pyrimidin-4-yl]propane-2-sulfonamide; 2-(pyridin-4-yl)-N-[3-(1H-1,2,3,4-tetrazol-5-yl)propyl]pyrido[3,4-d]pyrimidin-4-amine; N-methyl-2-(pyridin-4-yl)-N-[1,1,1-trifluoropropan-2-yl]pyrido[3,4-d]pyrimidin-4-amine; N-methyl-2-(pyridin-4-yl)-N-[(2S)-1,1,1-trifluoropropan-2-yl]pyrido[3,4-d]pyrimidin-4-amine; N-methyl-2-(pyridin-4-yl)-N-[(2R)-1,1,1-trifluoropropan-2-yl]pyrido[3,4-d]pyrimidin-4-amine; 2,4-dimethyl-4-{[2-(pyridin-4-yl)pyrido[3,4-d]pyrimidin-4-yl]amino}pentan-2-ol; 4,4,4-trifluoro-2,3-dimethyl-3-{[2-

(pyridin-4-yl)pyrido[3,4-d]pyrimidin-4-yl]amino}butan-2-ol; (1-{[2-(pyridin-4-yl)pyrido[3,4-d]pyrimidin-4-yl] amino}cyclopentyl)methanol; N-(3-methoxycyclobutyl)-2-(pyridin-4-yl)pyrido[3,4-d]pyrimidin-4-amine; (1R,2R)-1-N,2-N-dimethyl-1-N-[2-(pyridin-4-yl)pyrido[3,4-d] pyrimidin-4-yl]cyclohexane-1,2-diamine; methyl (1 s,3s)-3-{[2-(pyridin-4-yl)pyrido[3,4-d]pyrimidin-4-yl] amino}cyclobutane-1-carboxylate; ethyl 1-{[2-(pyridin-4-yl)pyrido[3,4-d]pyrimidin-4-yl]amino}cyclobutane-1-carboxylate; 1-{[2-(pyridin-4-yl)pyrido[3,4-d]pyrimidin-4-yl]amino}cyclobutane-1-carboxylic acid; (1 s,3s)-3-{[2-(pyridin-4-yl)pyrido[3,4-d]pyrimidin-4-yl] amino}cyclobutane-1-carboxylic acid; 2-(pyridin-4-yl)-N-(1,1,1-trifluoro-2-methylpropan-2-yl)pyrido[3,4-d] pyrimidin-4-amine; N-tert-butyl-2-(pyridin-4-yl)pyrido[3,4-d]pyrimidin-4-amine; N-(1-methylcyclobutyl)-2-(pyridin-4-yl)pyrido[3,4-d]pyrimidin-4-amine; 3-methyl-3-{[2-(pyridin-4-yl)pyrido[3,4-d]pyrimidin-4-yl]amino}butan-1-ol; 2-(pyridin-4-yl)-N-[1-(trifluoromethyl)cyclobutyl] pyrido[3,4-d]pyrimidin-4-amine; N-(2-methylbutan-2-yl)-2-(pyridin-4-yl)pyrido[3,4-d]pyrimidin-4-amine; 2-(pyridin-4-yl)-N-[1-(trifluoromethyl)cyclopropyl]pyrido [3,4-d]pyrimidin-4-amine; N-cyclopentyl-2-(pyridin-4-yl)pyrido[3,4-d]pyrimidin-4-amine; 2-methyl-2-{[2-(pyridin-4-yl)pyrido[3,4-d]pyrimidin-4-yl]amino}propan-1-ol; 3,3,3-trifluoro-2-methyl-2-{[2-(pyridin-4-yl)pyrido[3,4-d] pyrimidin-4-yl]amino}propan-1-ol; N-(butan-2-yl)-2-(pyridin-4-yl)pyrido[3,4-d]pyrimidin-4-amine; N-(2-methylbut-3-yn-2-yl)-2-(pyridin-4-yl)pyrido[3,4-d] pyrimidin-4-amine; (1 r,3s)-3-methyl-3-{[2-(pyridin-4-yl) pyrido[3,4-d]pyrimidin-4-yl]amino}cyclobutan-1-ol; 2,3-dimethyl-3-{[2-(pyridin-4-yl)pyrido[3,4-d]pyrimidin-4-yl] amino}butan-2-ol; 2-(pyridin-4-yl)-N-(2,4,4-trimethylpentan-2-yl)pyrido[3,4-d]pyrimidin-4-amine; N-(pentan-3-yl)-2-(pyridin-4-yl)pyrido[3,4-d]pyrimidin-4-amine; N-[2-methyl-1-(morpholin-4-yl)propan-2-yl]-2-(pyridin-4-yl)pyrido[3,4-d]pyrimidin-4-amine; N-[1-(tert-butoxy)-2-methylpropan-2-yl]-2-(pyridin-4-yl)pyrido[3,4-d]pyrimidin-4-amine; 4,4,4-trifluoro-2-{[2-(pyridin-4-yl) pyrido[3,4-d]pyrimidin-4-yl]amino}butan-1-ol; N-pentyl-2-(pyridin-4-yl)pyrido[3,4-d]pyrimidin-4-amine; 2-{[2-(pyridin-4-yl)pyrido[3,4-d]pyrimidin-4-yl]amino}butan-1-ol; N-[1-(1H-indol-3-yl)-2-methylpropan-2-yl]-2-(pyridin-4-yl)pyrido[3,4-d]pyrimidin-4-amine; N-[1-(4-fluorophenyl)-2-methylpropan-2-yl]-2-(pyridin-4-yl)pyrido [3,4-d]pyrimidin-4-amine; N-(2-phenylpropan-2-yl)-2-(pyridin-4-yl)pyrido[3,4-d]pyrimidin-4-amine; N-(2-fluorophenyl)-2-(pyridin-4-yl)pyrido[3,4-d]pyrimidin-4-amine; N-[2-(4-fluorophenyl)propan-2-yl]-2-(pyridin-4-yl) pyrido[3,4-d]pyrimidin-4-amine; 3,3,3-trifluoro-2-methyl-2-{[2-(pyridin-4-yl)pyrido[3,4-d]pyrimidin-4-yl] amino}propanoic acid; 2-{[2-(pyridin-4-yl)pyrido[3,4-d] pyrimidin-4-yl]amino}ethan-1-ol; N-methyl-2-(pyridin-4-yl)pyrido[3,4-d]pyrimidin-4-amine; 1-({[2-(pyridin-4-yl) pyrido[3,4-d]pyrimidin-4-yl]amino}methyl)cyclopentan-1-ol; N,N-dimethyl-2-(pyridin-4-yl)pyrido[3,4-d]pyrimidin-4-amine; N-(2-methylphenyl)-2-(pyridin-4-yl)pyrido[3,4-d] pyrimidin-4-amine; N-(4-methylphenyl)-2-(pyridin-4-yl) pyrido[3,4-d]pyrimidin-4-amine; N-(4-methoxyphenyl)-2-(pyridin-4-yl)pyrido[3,4-d]pyrimidin-4-amine; N-phenyl-2-(pyridin-4-yl)pyrido[3,4-d]pyrimidin-4-amine; N-(3-methylphenyl)-2-(pyridin-4-yl)pyrido[3,4-d]pyrimidin-4-amine; 6-{[2-(pyridin-4-yl)pyrido[3,4-d]pyrimidin-4-yl] amino}hexanoic acid; N-(3-fluorophenyl)-2-(pyridin-4-yl) pyrido[3,4-d]pyrimidin-4-amine; N-(4-fluorophenyl)-2-(pyridin-4-yl)pyrido[3,4-d]pyrimidin-4-amine; 4-{[2-(pyridin-4-yl)pyrido[3,4-d]pyrimidin-4-yl]amino}butanoic acid; N-(1-phenylethyl)-2-(pyridin-4-yl)pyrido[3,4-d]pyrimidin-4-amine; N-(1-methylcyclopropyl)-2-(pyridin-4-yl) pyrido[3,4-d]pyrimidin-4-amine; tert-butyl N-(2-methyl-2-{[2-(pyridin-4-yl)pyrido[3,4-d]pyrimidin-4-yl] amino}propyl)carbamate; (1-{[2-(pyridin-4-yl)pyrido[3,4-d]pyrimidin-4-yl]amino}cyclobutyl)methanol; methyl 2-(1-{[2-(pyridin-4-yl)pyrido[3,4-d]pyrimidin-4-yl] amino}cyclopropyl)acetate; N-(2-methylpropyl)-2-(pyridin-4-yl)pyrido[3,4-d]pyrimidin-4-amine; 3-methyl-3-{[2-(pyridin-4-yl)pyrido[3,4-d]pyrimidin-4-yl] amino}butanenitrile; N-(6-aminohexyl)-2-(pyridin-4-yl) pyrido[3,4-d]pyrimidin-4-amine; N-(4-aminobutyl)-2-(pyridin-4-yl)pyrido[3,4-d]pyrimidin-4-amine; 2-methyl-2-{[2-(pyridin-4-yl)pyrido[3,4-d]pyrimidin-4-yl] amino}propanenitrile; N-[2-methyl-1-(2-methylpiperidin-1-yl)propan-2-yl]-2-(pyridin-4-yl)pyrido[3,4-d]pyrimidin-4-amine; dimethyl (3-methyl-3-{[2-(pyridin-4-yl)pyrido[3,4-d]pyrimidin-4-yl]amino}butyl)amine; N-(1-amino-2-methylpropan-2-yl)-2-(pyridin-4-yl)pyrido[3,4-d] pyrimidin-4-amine; N-cyclopentyl-2-[3-(trifluoromethyl)-1H-pyrazol-4-yl]pyrido[3,4-d]pyrimidin-4-amine; 4-[4-(tert-butylamino)pyrido[3,4-d]pyrimidin-2-yl]pyridin-2-amine; 2-[1-(benzenesulfonyl)-2-methyl-1H-pyrrolo[2,3-b] pyridin-3-yl]-N-tert-butylpyrido[3,4-d]pyrimidin-4-amine; N-tert-butyl-2-{2-methyl-1H-pyrrolo[2,3-b]pyridin-3-yl}pyrido[3,4-d]pyrimidin-4-amine; N-tert-butyl-2-[3-(trifluoromethyl)-1H-pyrazol-4-yl]pyrido[3,4-d]pyrimidin-4-amine; N-tert-butyl-2-(3-chloropyridin-4-yl)pyrido[3,4-d] pyrimidin-4-amine; N-tert-butyl-2-(3-methylpyridin-4-yl) pyrido[3,4-d]pyrimidin-4-amine; 2-(3-chloropyridin-4-yl)-N-(2-methylbutan-2-yl)pyrido[3,4-d]pyrimidin-4-amine; 2,4-dimethyl-4-({2-[3-(trifluoromethyl)-1H-pyrazol-4-yl] pyrido[3,4-d]pyrimidin-4-yl}amino)pentan-2-ol; N-ethyl-2-(3-fluoropyridin-4-yl)-N-(propan-2-yl)pyrido[3,4-d]pyrimidin-4-amine; 2-methyl-1-[2-methyl-2-({2-[3-(trifluoromethyl)-1H-pyrazol-4-yl]pyrido[3,4-d]pyrimidin-4-yl}amino) propoxy]propan-2-ol; 2-(3-fluoropyridin-4-yl)-N-methyl-N-(propan-2-yl)pyrido[3,4-d]pyrimidin-4-amine; N-ethyl-2-(3-methylpyridin-4-yl)-N-(propan-2-yl)pyrido[3,4-d]pyrimidin-4-amine; 2-(3-chloropyridin-4-yl)-N-(1-methoxy-2-methylpropan-2-yl)pyrido[3,4-d]pyrimidin-4-amine; 4-{[2-(3-chloropyridin-4-yl)pyrido[3,4-d]pyrimidin-4-yl]amino}-2,4-dimethylpentan-2-ol; 2-(3-chloropyridin-4-yl)-N-cyclopentylpyrido[3,4-d]pyrimidin-4-amine; 1-(2-{[2-(3-chloropyridin-4-yl)pyrido[3,4-d]pyrimidin-4-yl] amino}-2-methylpropoxy)-2-methylpropan-2-ol; N-methyl-2-(3-methylpyridin-4-yl)-N-(propan-2-yl)pyrido[3,4-d]pyrimidin-4-amine; 2-(3-chloropyridin-4-yl)-N-(4-methanesulfonyl-2-methylbutan-2-yl)pyrido[3,4-d] pyrimidin-4-amine; N-tert-butyl-2-[3-(trifluoromethyl) pyridin-4-yl]pyrido[3,4-d]pyrimidin-4-amine; N-tert-butyl-2-[2-chloro-5-(trifluoromethyl)pyridin-4-yl]pyrido[3,4-d] pyrimidin-4-amine; 2-(3-chloropyridin-4-yl)-N-[3-(1H-1,2,3,4-tetrazol-5-yl)propyl]pyrido[3,4-d]pyrimidin-4-amine; 2-(3-methyl-1H-pyrazol-4-yl)-N-(1-methylcyclopropyl) pyrido[3,4-d]pyrimidin-4-amine; 2-(3-fluoropyridin-4-yl)-N-(1,1,1-trifluoro-2-methylpropan-2-yl)pyrido[3,4-d]pyrimidin-4-amine; 2-(3-methyl-1H-pyrazol-4-yl)-N-(1,1,1-trifluoro-2-methylpropan-2-yl)pyrido[3,4-d]pyrimidin-4-amine; 2-(3-fluoropyridin-4-yl)-N-methyl-N-[(2S)-1,1,1-trifluoropropan-2-yl]pyrido[3,4-d]pyrimidin-4-amine; 2-(3-fluoropyridin-4-yl)-N-methyl-N-[(2R)-1,1,1-trifluoropropan-2-yl]pyrido[3,4-d]pyrimidin-4-amine; 4-{4-[(1-methylcyclopropyl)amino]pyrido[3,4-d]pyrimidin-2-yl}pyridin-2-amine; 2-(3-chloropyridin-4-yl)-N-(1,1,1-trifluoro-2-methylpropan-2-yl)pyrido[3,4-d]pyrimidin-4-amine; 2,4-dimethyl-4-{[2-(3-methyl-1H-pyrazol-4-yl)

pyrido[3,4-d]pyrimidin-4-yl]amino}pentan-2-ol; 4-{4-[(1-methylcyclopropyl)amino]pyrido[3,4-d]pyrimidin-2-yl}pyridine-3-carbonitrile; 2-{2-methyl-1H-pyrrolo[2,3-b]pyridin-3-yl}-N-propylpyrido[3,4-d]pyrimidin-4-amine; 2-(1H-indazol-5-yl)-N-(1-methylcyclopropyl)pyrido[3,4-d]pyrimidin-4-amine; 2-(3,5-dimethyl-1H-pyrazol-4-yl)-N-(1,1,1-trifluoro-2-methylpropan-2-yl)pyrido[3,4-d]pyrimidin-4-amine; N-(1,1,1-trifluoro-2-methylpropan-2-yl)-2-[3-(trifluoromethyl)-1H-pyrazol-4-yl]pyrido[3,4-d]pyrimidin-4-amine; 4-{4-[(4-hydroxy-2,4-dimethylpentan-2-yl)amino]pyrido[3,4-d]pyrimidin-2-yl}pyridine-3-carbonitrile; 2-(3,5-difluoropyridin-4-yl)-N-(1-methylcyclopropyl)pyrido[3,4-d]pyrimidin-4-amine; 2-(2,3-difluoropyridin-4-yl)-N-(1-methylcyclopropyl)pyrido[3,4-d]pyrimidin-4-amine; N-(1-methylcyclopropyl)-2-(1,3-thiazol-5-yl)pyrido[3,4-d]pyrimidin-4-amine; N-(1-methylcyclopropyl)-2-[2-(trifluoromethyl)pyridin-4-yl]pyrido[3,4-d]pyrimidin-4-amine; 4-{4-[(1-methylcyclopropyl)amino]pyrido[3,4-d]pyrimidin-2-yl}pyridine-2-carbonitrile; N-(1-methylcyclopropyl)-2-(1,2-oxazol-4-yl)pyrido[3,4-d]pyrimidin-4-amine; 2-(dimethyl-1,2-oxazol-4-yl)-N-(1-methylcyclopropyl)pyrido[3,4-d]pyrimidin-4-amine; N-(1-methylcyclopropyl)-2-{1H-pyrrolo[2,3-b]pyridin-4-yl}pyrido[3,4-d]pyrimidin-4-amine; N-propyl-2-{1H-pyrrolo[2,3-b]pyridin-3-yl}pyrido[3,4-d]pyrimidin-4-amine; N-propyl-2-{1H-pyrrolo[3,2-b]pyridin-1-yl}pyrido[3,4-d]pyrimidin-4-amine; 2-(3-methylpyridin-4-yl)-N-(1,1,1-trifluoro-2-methylpropan-2-yl)pyrido[3,4-d]pyrimidin-4-amine; N-(1-methylcyclobutyl)-2-(1H-pyrazol-4-yl)pyrido[3,4-d]pyrimidin-4-amine; N-(1-methylcyclopropyl)-2-(pyrimidin-4-yl)pyrido[3,4-d]pyrimidin-4-amine; 4-{[2-(3,5-dimethyl-1H-pyrazol-4-yl)pyrido[3,4-d]pyrimidin-4-yl]amino}-2,4-dimethylpentan-2-ol; N-propyl-2-{7H-pyrrolo[2,3-d]pyrimidin-5-yl}pyrido[3,4-d]pyrimidin-4-amine; 2-(3-chloropyridin-4-yl)-N-propylpyrido[3,4-d]pyrimidin-4-amine; 2-(3-cyclopropyl-1H-pyrazol-4-yl)-N-propylpyrido[3,4-d]pyrimidin-4-amine; 2-(3-methylpyridin-4-yl)-N-propylpyrido[3,4-d]pyrimidin-4-amine; 2-{1-methyl-1H-pyrrolo[2,3-b]pyridin-3-yl}-N-propylpyrido[3,4-d]pyrimidin-4-amine; 2,4-dimethyl-4-{[2-(1H-pyrazol-4-yl)pyrido[3,4-d]pyrimidin-4-yl]amino}pentan-2-ol; N-[(1R)-1-phenylethyl]-2-(1H-pyrazol-4-yl)pyrido[3,4-d]pyrimidin-4-amine; 2-(5-methyl-1H-pyrazol-4-yl)-N-[(1R)-1-phenylethyl]pyrido[3,4-d]pyrimidin-4-amine; N-methyl-2-(1-methyl-1H-pyrazol-5-yl)-N-(1-methylcyclopropyl)pyrido[3,4-d]pyrimidin-4-amine; 2-(1-methyl-1H-pyrazol-5-yl)-N-[(1R)-1-phenylethyl]pyrido[3,4-d]pyrimidin-4-amine; N-methyl-N-(1-methylcyclopropyl)-2-(1H-pyrazol-4-yl)pyrido[3,4-d]pyrimidin-4-amine; 2-(1-methyl-1H-pyrazol-5-yl)-N-(1-methylcyclopropyl)pyrido[3,4-d]pyrimidin-4-amine; 2-(1-ethyl-1H-pyrazol-5-yl)-N-(1-methylcyclopropyl)pyrido[3,4-d]pyrimidin-4-amine; N-(1-methylcyclopropyl)-2-(pyridazin-4-yl)pyrido[3,4-d]pyrimidin-4-amine; N-(1-methylcyclopropyl)-2-(1,3-oxazol-5-yl)pyrido[3,4-d]pyrimidin-4-amine; N-(1-methylcyclopropyl)-2-(1H-pyrazol-5-yl)pyrido[3,4-d]pyrimidin-4-amine; 2-(1H-imidazol-5-yl)-N-(1-methylcyclopropyl)pyrido[3,4-d]pyrimidin-4-amine; 2-(1-methyl-1H-imidazol-5-yl)-N-(1-methylcyclopropyl)pyrido[3,4-d]pyrimidin-4-amine; N-(1-methylcyclopropyl)-2-{1H-pyrrolo[3,2-b]pyridin-1-yl}pyrido[3,4-d]pyrimidin-4-amine; N-(1-methylcyclopropyl)-2-(1H-1,2,3-triazol-4-yl)pyrido[3,4-d]pyrimidin-4-amine; 2-(3-methyl-1,2-oxazol-5-yl)-N-(1-methylcyclopropyl)pyrido[3,4-d]pyrimidin-4-amine; N-(1-methylcyclopropyl)-2-(2H-1,2,3,4-tetrazol-5-yl)pyrido[3,4-d]pyrimidin-4-amine; 2-(1H-pyrazol-4-yl)-N-[1-(pyridin-4-yl)ethyl]pyrido[3,4-d]pyrimidin-4-amine; N-tert-butyl-2-(1-methyl-1H-pyrazol-5-yl)pyrido[3,4-d]pyrimidin-4-amine; (1-{[2-(3-methyl-1H-pyrazol-4-yl)pyrido[3,4-d]pyrimidin-4-yl]amino}cyclobutyl)methanol; 2-(1-methyl-1H-pyrazol-5-yl)-N-(1-methylcyclobutyl)pyrido[3,4-d]pyrimidin-4-amine; (1-{[2-(1-methyl-1H-pyrazol-5-yl)pyrido[3,4-d]pyrimidin-4-yl]amino}cyclobutyl)methanol; 2-(1H-pyrazol-4-yl)-N-[1-(trifluoromethyl)cyclopropyl]pyrido[3,4-d]pyrimidin-4-amine; 2-(1-methyl-1H-pyrazol-5-yl)-N-[1-(trifluoromethyl)cyclopropyl]pyrido[3,4-d]pyrimidin-4-amine; 2-(3-methyl-1H-pyrazol-4-yl)-N-[1-(pyridin-4-yl)ethyl]pyrido[3,4-d]pyrimidin-4-amine; (1-{[2-(1H-pyrazol-4-yl)pyrido[3,4-d]pyrimidin-4-yl]amino}cyclobutyl)methanol; (1-{[2-(1H-pyrazol-4-yl)pyrido[3,4-d]pyrimidin-4-yl]amino}cyclopropyl)methanol; 2-(1-methyl-1H-pyrazol-5-yl)-N-[1-(pyridin-4-yl)ethyl]pyrido[3,4-d]pyrimidin-4-amine; N-(1-methylcyclopropyl)-2-(1H-pyrazol-4-yl)pyrido[3,4-d]pyrimidin-4-amine; 2-(1-ethyl-1H-pyrazol-4-yl)-N-(2-methylpropyl)pyrido[3,4-d]pyrimidin-4-amine; 2-(1-methyl-1H-pyrazol-4-yl)-N-(1-methylcyclopropyl)pyrido[3,4-d]pyrimidin-4-amine; N-(1-amino-2-methylpropan-2-yl)-2-(1H-pyrazol-4-yl)pyrido[3,4-d]pyrimidin-4-amine; 8-chloro-N-(1-methylcyclopropyl)-2-(pyridin-4-yl)pyrido[3,4-d]pyrimidin-4-amine; 8-methyl-N-(1-methylcyclopropyl)-2-(pyridin-4-yl)pyrido[3,4-d]pyrimidin-4-amine; N-tert-butyl-5-chloro-2-(pyridin-4-yl)pyrido[3,4-d]pyrimidin-4-amine; $N^1,N^1$,3-trimethyl-$N^3$-(2-(pyrimidin-4-yl)pyrido[3,4-d]pyrimidin-4-yl)butane-1,3-diamine; $N^1,N^1$,3-trimethyl-$N^3$-(2-(3-methyl-1H-pyrazol-4-yl)pyrido[3,4-d]pyrimidin-4-yl)butane-1,3-diamine; tert-butyl (2-methyl-1-((2-(pyridin-4-yl)pyrido[3,4-d]pyrimidin-4-yl)amino)propan-2-yl)carbamate; tert-butyl (2-((2-(pyridin-4-yl)pyrido[3,4-d]pyrimidin-4-yl)amino)ethyl)carbamate; 2-methyl-$N^1$-(2-(pyridin-4-yl)pyrido[3,4-d]pyrimidin-4-yl)propane-1,2-diamine; $N^1$-(2-(pyridin-4-yl)pyrido[3,4-d]pyrimidin-4-yl)ethane-1,2-diamine; N,N,2-trimethyl-2-((2-(pyridin-4-yl)pyrido[3,4-d]pyrimidin-4-yl)amino)propanamide; $N^1$,3-dimethyl-$N^1$-(2-(pyridin-4-yl)pyrido[3,4-d]pyrimidin-4-yl)butane-1,3-diamine; tert-butyl (2,2-dimethyl-3-((2-(pyridin-4-yl)pyrido[3,4-d]pyrimidin-4-yl)amino)propyl)carbamate; 2,2-dimethyl-$N^1$-(2-(pyridin-4-yl)pyrido[3,4-d]pyrimidin-4-yl)propane-1,3-diamine; 3-methyl-3-((2-(pyridin-4-yl)pyrido[3,4-d]pyrimidin-4-yl)amino)butanamide; (R)-2-(pyridin-4-yl)-4-(3-(trifluoromethyl)piperazin-1-yl)pyrido[3,4-d]pyrimidine; 2,3-dimethyl-$N^2$-(2-(pyridin-4-yl)pyrido[3,4-d]pyrimidin-4-yl)butane-2,3-diamine; (S)-2-(pyridin-4-yl)-4-(3-(trifluoromethyl)piperazin-1-yl)pyrido[3,4-d]pyrimidine; ethyl 2-methyl-2-((2-(pyridin-4-yl)pyrido[3,4-d]pyrimidin-4-yl)amino)propanoate; $N^1,N^1$,2,2-tetramethyl-$N^3$-(2-(pyridin-4-yl)pyrido[3,4-d]pyrimidin-4-yl)propane-1,3-diamine; 4-(4-(tert-butylamino)pyrido[3,4-d]pyrimidin-2-yl)-1,2,5-oxadiazol-3-amine; $N^2,N^2$,2-trimethyl-$N^1$-(2-(pyridin-4-yl)pyrido[3,4-d]pyrimidin-4-yl)propane-1,2-diamine; 2-methyl-2-((2-(pyridin-4-yl)pyrido[3,4-d]pyrimidin-4-yl)amino)propanamide; (S)-1,1,1-trifluoro-2-methyl-3-((2-(pyridin-4-yl)-1,7-naphthyridin-4-yl)amino)propan-2-ol; 5-chloro-N-(1-methylcyclopropyl)-2-(pyridin-4-yl)pyrido[3,4-d]pyrimidin-4-amine; 2-(2-{[4-(tert-butylamino)-2-(pyridin-4-yl)pyrido[3,4-d]pyrimidin-5-yl]amino}ethoxy)ethan-1-ol; N-((1R,2S)-2-methylcyclopentyl)-2-(pyridin-4-yl)pyrido[3,4-d]pyrimidin-4-amine; (S)—N-(sec-butyl)-2-(pyridin-4-yl)pyrido[3,4-d]pyrimidin-4-amine; N-((1S,2R)-2-methylcyclopentyl)-2-(pyridin-4-yl)pyrido[3,4-d]pyrimidin-4-amine; (R)—N-(sec-butyl)-2-(pyridin-4-yl)pyrido[3,4-d]pyrimidin-4-amine; N-((1S,2S)-2-methylcyclopentyl)-2-(pyridin-4-yl)pyrido[3,4-d]pyrimidin-4-amine; N-((1R,2R)-2-methylcyclopentyl)-2-

(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; tert-butyl (3-methyl-3-((2-(pyridin-4-yl)pyrido[3,4-d]pyrimidin-4-yl)amino)butyl)carbamate; $N^1,N^1,N^3,2,2$-pentamethyl-$N^3$-(2-(pyridin-4-yl)pyrido[3,4-d]pyrimidin-4-yl)propane-1,3-diamine; $N^1,N^1$-diethyl-3-methyl-$N^3$-(2-(pyridin-4-yl)pyrido[3,4-d]pyrimidin-4-yl)butane-1,3-diamine; $N^3$-(2-(2-fluoropyridin-4-yl)pyrido[3,4-d]pyrimidin-4-yl)-$N^1,N^1$,3-trimethylbutane-1,3-diamine; $N^3$-(2-(3,5-dimethyl-1H-pyrazol-4-yl)pyrido[3,4-d]pyrimidin-4-yl)-$N^1,N^1$,3-trimethylbutane-1,3-diamine; $N^1,N^1$,3-trimethyl-$N^3$-(2-(3-(trifluoromethyl)-1H-pyrazol-4-yl)pyrido[3,4-d]pyrimidin-4-yl)butane-1,3-diamine; $N^3$-(2-(2-aminopyridin-4-yl)pyrido[3,4-d]pyrimidin-4-yl)-$N^1,N^1$,3-trimethylbutane-1,3-diamine; and 3-methyl-$N^1$-(2-(pyridin-4-yl)pyrido[3,4-d]pyrimidin-4-yl)butane-1,3-diamine.

Embodiment 120A

A compound of the Formula I, or a salt thereof, according to embodiment 61, selected from: N-methyl-2-(pyridin-4-yl)-N-(1,1,1-trifluoropropan-2-yl)pyrido[3,4-d]pyrimidin-4-amine; 2-methyl-1-(2-methyl-2-{[2-(pyridin-4-yl)pyrido[3,4-d]pyrimidin-4-yl]amino}propoxy)propan-2-ol; 2,4-dimethyl-4-{[2-(pyridin-4-yl)pyrido[3,4-d]pyrimidin-4-yl]amino}pentan-2-ol; 2-(pyridin-4-yl)-N-[1-(trifluoromethyl)cyclobutyl]pyrido[3,4-d]pyrimidin-4-amine; N-propyl-2-(pyridin-4-yl)pyrido[3,4-d]pyrimidin-4-amine; N-(propan-2-yl)-2-(pyridin-4-yl)pyrido[3,4-d]pyrimidin-4-amine; 2-(3-methyl-1H-pyrazol-4-yl)-N-(1-methylcyclopropyl)pyrido[3,4-d]pyrimidin-4-amine; 2-methyl-2-{[2-(pyridin-4-yl)pyrido[3,4-d]pyrimidin-4-yl]amino}propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; N-(1-methylcyclopropyl)-7-(pyridin-4-yl)isoquinolin-5-amine; (1S,2S)-2-{[2-(pyridin-4-yl)pyrido[3,4-d]pyrimidin-4-yl]amino}cyclopentan-1-ol; N-methyl-2-(pyridin-4-yl)-N-[(2S)-1,1,1-trifluoropropan-2-yl]pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; and N-methyl-2-(pyridin-4-yl)-N-[(2R)-1,1,1-trifluoropropan-2-yl]pyrido[3,4-d]pyrimidin-4-amine.

Embodiment 120B

A compound of the Formula I, or a salt thereof, according to embodiment 61, wherein the compound is N-methyl-2-(pyridin-4-yl)-N-[(2S)-1,1,1-trifluoropropan-2-yl]pyrido[3,4-d]pyrimidin-4-amine.

Embodiment 121

A compound of Formula II, or a salt thereof,

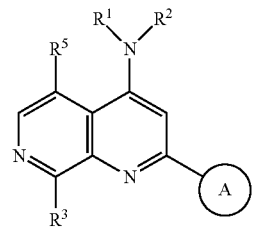

II wherein
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

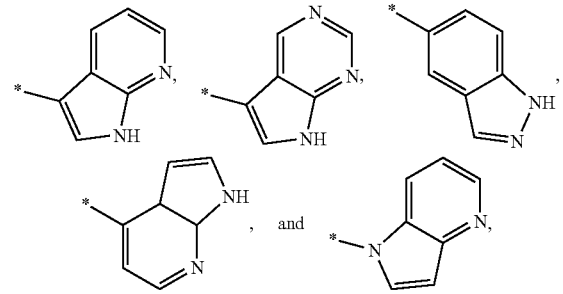

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —NH$_2$, $C_{1-6}$alkylamino, di-($C_{1-6}$ alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
 (i) halogen;
 (ii) cyano;
 (iii) oxo;
 (iv) $C_2$alkenyl;
 (v) $C_2$alkynyl;
 (vi) $C_{1-6}$haloalkyl;
 (vii) —OR$^6$, wherein R$^6$ is selected from hydrogen, $C_{1-6}$alkyl that is unsubstituted or substituted by R$^0$ or —C(O)R$^0$;
 (viii) —NR$^{7a}$R$^{7b}$, wherein R$^{7a}$ is hydrogen or $C_{1-6}$alkyl, and R$^{7b}$ is selected from hydrogen, —C(O)R$^0$, $C_{1-6}$alkyl that is unsubstituted or substituted by —C(O)R$^0$;

(ix) —C(O)R$^8$, wherein R$^8$ is R$^0$ or —NH—C$_{1-6}$alkyl-C(O)R$^0$;
(x) —S(O)$_2$C$_{1-6}$alkyl;
(xi) monocyclic C$_{3-6}$cycloalkyl or polycyclic C$_{7-10}$cycloalkyl that are each unsubstituted or substituted by 1 to 2 substituents independently selected from halogen, C$_{1-6}$alkyl, hydroxyC$_{1-6}$alkyl, C$_{1-6}$haloalkyl, R$^0$, —NH$_2$, C$_{1-6}$alkylamino, and di-(C$_{1-6}$ alkyl)amino;
(xii) 6-membered heterocycloalkyl comprising, as ring members, 1 to 2 heteroatoms independently selected from N, O and S and that is unsubstituted or substituted by 1 to 2 substituents independently selected from hydroxyl, halogen, C$_{1-6}$alkyl, C$_{1-6}$alkylamino, and di-(C$_{1-6}$alkyl)amino;
(xiii) phenyl that is unsubstituted or substituted by halogen;
(xiv) 5- or 6-membered monocyclic heteroaryl comprising, as ring members, 1 to 4 heteroatoms independently selected from N and O; and
(xv) 9- or 10-membered fused bicyclic heteroaryl comprising, as ring member, 1 to 2 heteroatoms independently selected from N and O;
(b) —S(O)$_2$C$_{1-6}$alkyl;
(c) phenyl that is unsubstituted or substituted by 1 to 2 substituents independently selected from halogen, C$_{1-6}$alkyl and R$^0$;
(d) C$_{3-6}$cycloalkyl that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$; and
(e) 4-membered heterocycloalkyl comprising, as ring members, 1 to 2 heteroatoms selected from N, O and S and that is unsubstituted or substituted by 1 to 2 substituents independently selected from C$_{1-6}$haloalkyl, R$^0$, C$_{1-6}$alkylamino, di-(C$_{1-6}$ alkyl)amino, —C(O)R$^0$, and C$_{1-6}$alkyl that is unsubstituted or substituted by R$^0$ or —C(O)R$^0$; or
or R$^1$ and R$^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by R$^1$ and R$^2$ taken together with the nitrogen atom to which both are bound is unsubstituted or substituted by 1 to 3 substituents independently selected from halogen, C$_{1-6}$alkyl, C$_{1-6}$haloalkyl, and R$^0$;
R$^3$ is selected from hydrogen, halogen and C$_{1-6}$alkyl; and
R$^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by R$^0$.

Embodiment 122

A compound of formula II according to embodiment 121, or a salt thereof, wherein
Ring A is
(a) a 5- or 6-membered monocyclic heteroaryl that is linked to the remainder of the molecule through a carbon ring member and comprises, as ring member, 1 to 2 heteroatoms that are selected from N, provided that at least one of the nitrogen atom ring member is an unsubstituted nitrogen (—N=) positioned at the 3- or the 4-position relative to the linking carbon ring member of the 5-membered heteroaryl or at the para ring position of the 6-membered heteroaryl; or (b) a 9-membered fused bicyclic heteroaryl that is selected from

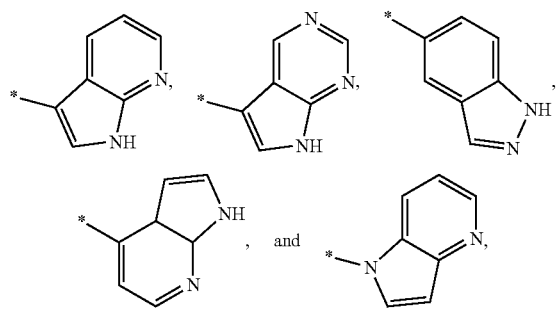

wherein "*" represents the point of attachment of ring A to the remainder of the molecule and that is unsubstituted or substituted by 1 to 2 substituents independently selected from halogen, cyano, C$_{1-6}$alkyl, C$_{1-6}$haloalkyl, —NH$_2$ and C$_{3-6}$cycloalkyl.

Embodiment 123

A compound of Formula II, or a salt thereof, according to embodiment 121 or embodiment 122, wherein ring A is selected from

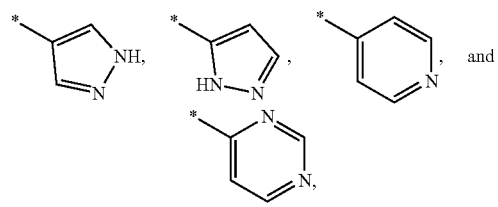

which are each unsubstituted or substituted by 1 to 2 substituents independently selected from cyano, halogen, C$_{1-6}$alkyl, C$_{1-6}$haloalkyl, NH$_2$, and C$_{3-6}$cycloalkyl; or from

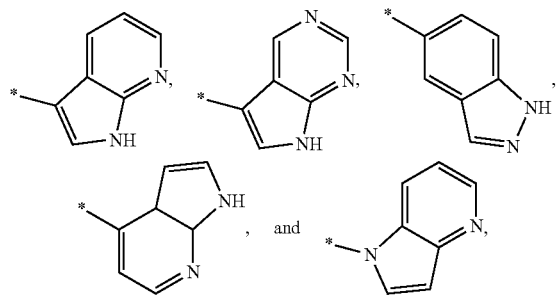

which are each unsubstituted or substituted by C$_{1-6}$alkyl.

Embodiment 124

A compound of Formula II, or a salt thereof, according to any one of embodiments 121 to 123, wherein ring A is selected from

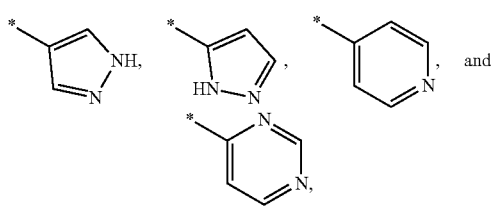

which are each unsubstituted or substituted by a substituent selected from halogen, cyano, C$_{1-6}$alkyl, C$_{1-6}$haloalkyl, and —NH$_2$; or is

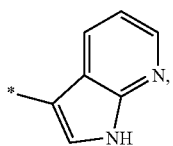 [SMILES: *c1c[nH]c2ncccc12]

which is unsubstituted or substituted by C$_{1-6}$alkyl.

Embodiment 125

A compound of Formula II, or a salt thereof, according to any one of embodiments 121 to 123, wherein ring A is selected from

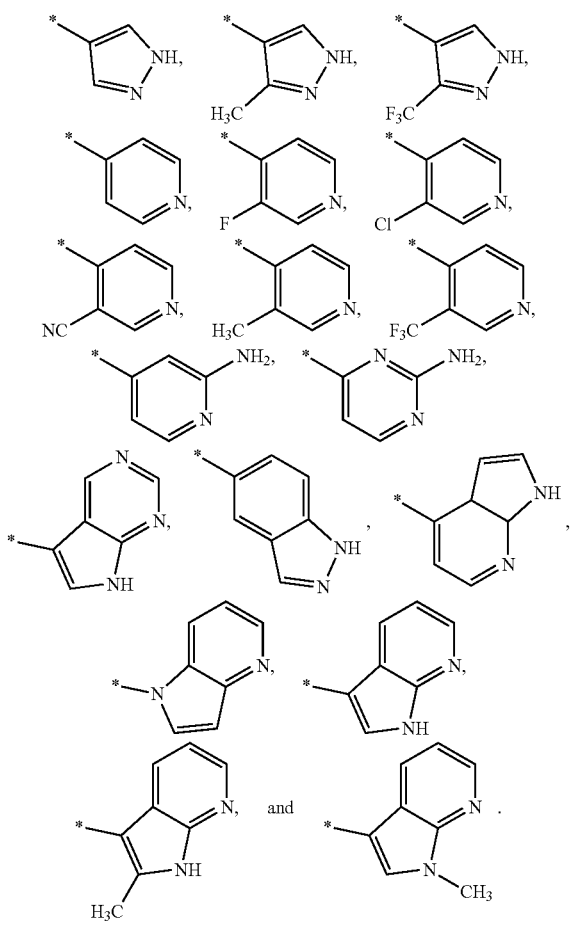

Embodiment 126

A compound of Formula II, or a salt thereof, according to any one of embodiments 121 to 125, wherein ring A is selected from

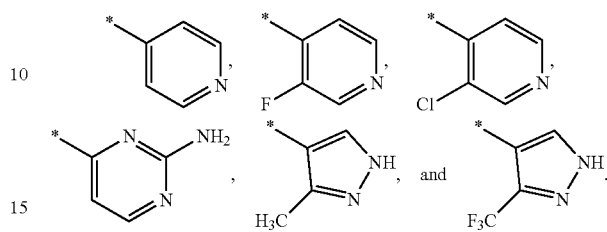

Embodiment 127

A compound of Formula II, or a salt thereof, according to any one of embodiments 121 to 126, wherein ring A is selected from

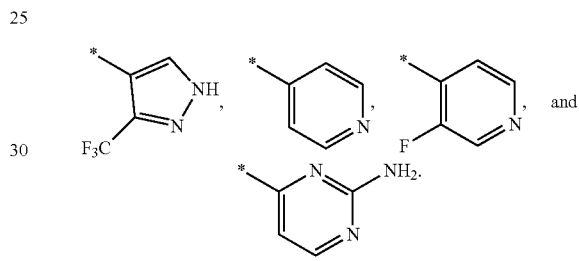

Embodiment 128

A compound of Formula II, or a salt thereof, according to any one of embodiments 121 to 127, wherein ring A is

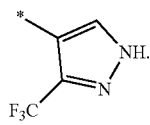

Embodiment 129

A compound of Formula II, or a salt thereof, according to any one of embodiments 121 to 127, wherein ring A is

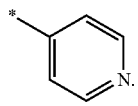

Embodiment 130

A compound of Formula II, or a salt thereof, according to any one of embodiments 121 to 127, wherein ring A is

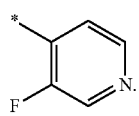

Embodiment 131

A compound of Formula II, or a salt thereof, according to any one of embodiments 121 to 127, wherein ring A is

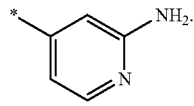

Embodiment 132

A compound of Formula II, or a salt thereof, according to any one of embodiments 121 to 127, wherein ring A is

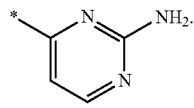

Embodiment 133

A compound of Formula II, or a salt thereof, according to any one of embodiments 121 to 125, wherein ring A is

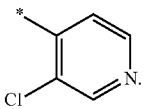

Embodiment 134

A compound of Formula II, or a salt thereof, according to any one of embodiments 121 to 125, wherein ring A is

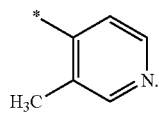

Embodiment 135

A compound of Formula II, or a salt thereof, according to any one of embodiments 121 to 126, wherein ring A is

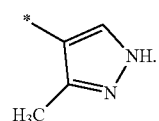

Embodiment 136

A compound of Formula II, or a salt thereof, according to any one of embodiments 121 to 123, wherein ring A is

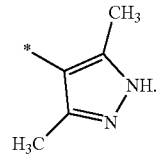

Embodiment 137

A compound of Formula II, or a salt thereof, according to any one of embodiments 121 to 124, wherein ring A is

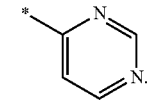

Embodiment 138

A compound of Formula II, or a salt thereof, according to any one of embodiments 121 to 125, wherein ring A is

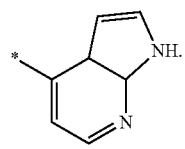 [SMILES: *C1=CC=NC2NC=CC12]

Embodiment 139

A compound of Formula II, or a salt thereof, according to any one of embodiments 121 to 123, wherein ring A is selected from

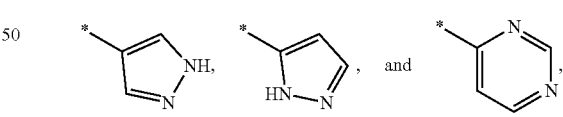

which are each unsubstituted or substituted by 1 to 2 substituents independently selected from cyano, halogen, $C_{1-6}$alkyl, $C_{1-6}$haloalkyl, $NH_2$, and $C_{3-6}$cycloalkyl; or from

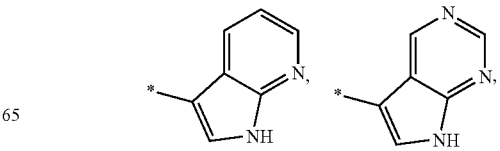

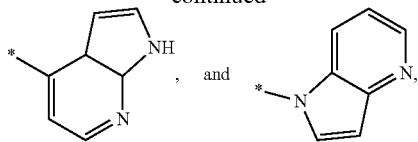

which are each unsubstituted or substituted by $C_{1-6}$alkyl.

Embodiment 140

A compound of Formula II, or a salt thereof, according to any one of embodiments 121 to 139, wherein $R^1$ is selected from hydrogen, methyl and ethyl.

Embodiment 141

A compound of Formula II, or a salt thereof, according to any one of embodiments 121 to 140, wherein $R^1$ is methyl.

Embodiment 142

A compound of Formula II, or a salt thereof, according to any one of embodiments 121 to 140, wherein $R^1$ is hydrogen.

Embodiment 143

A compound of Formula II, or a salt thereof, according to any one of embodiments 121 to 142, wherein
$R^2$ is selected from
(a) $C_{1-8}$alkyl that is unsubstituted or substituted by 1 to 3 substituents independently selected from
  (i) cyano;
  (ii) $C_2$alkynyl;
  (iii) $C_{1-6}$haloalkyl;
  (iv) —OR$^6$, wherein R$^6$ is selected from hydrogen, $C_{1-6}$alkyl that is unsubstituted or substituted by R$^0$ or —C(O)R$^0$;
  (v) —NR$^{7a}$R$^{7b}$, wherein R$^{7a}$ is hydrogen or $C_{1-6}$alkyl, and R$^{7b}$ is selected from hydrogen, —C(O)R$^0$, $C_{1-6}$alkyl that is unsubstituted or substituted by —C(O)R$^0$;
  (vi) —C(O)R$^8$, wherein R$^8$ is R$^0$;
  (vii) —S(O)$_2$C$_{1-6}$alkyl;
  (viii) monocyclic $C_{3-6}$cycloalkyl that is unsubstituted or substituted by a substituent selected from $C_{1-6}$alkyl, hydroxyC$_{1-6}$alkyl and R$^0$;
  (ix) 6-membered heterocycloalkyl comprising, as ring members, 1 to 2 heteroatoms independently selected from N and O and that is unsubstituted or substituted by $C_{1-6}$alkyl; and
  (x) phenyl that is unsubstituted or substituted by halogen;
(b) $C_{3-6}$cycloalkyl that is unsubstituted or substituted by 1 to 2 substituents independently selected from $C_{1-6}$haloalkyl, R$^0$, $C_{1-6}$alkylamino, —C(O)R$^0$, and $C_{1-6}$alkyl that is unsubstituted or substituted by R$^0$ or —C(O)R$^0$; and
(c) 4-membered heterocycloalkyl comprising, as ring member, a heteroatom selected from N and O and that is unsubstituted or substituted by 1 to 2 substituents independently selected from $C_{1-6}$haloalkyl, R$^0$, $C_{1-6}$alkylamino, —C(O)R$^0$, and $C_{1-6}$alkyl that is unsubstituted or substituted by R$^0$ or —C(O)R$^0$.

Embodiment 144

A compound of Formula II, or a salt thereof, according to any one of embodiments 121 to 142, wherein
$R^2$ is selected from
(a) $C_{1-8}$alkyl that is unsubstituted or substituted by 1 to 3 substituents independently selected from
  (i) cyano;
  (ii) $C_2$alkynyl;
  (iii) $C_{1-6}$haloalkyl;
  (iv) —OR$^6$, wherein R$^6$ is selected from hydrogen, $C_{1-6}$alkyl that is unsubstituted or substituted by R$^0$ or —C(O)R$^0$;
  (v) —NR$^{7a}$R$^{7b}$, wherein R$^{7a}$ is hydrogen or $C_{1-6}$alkyl, and R$^{7b}$ is selected from hydrogen, —C(O)R$^0$, $C_{1-6}$alkyl that is unsubstituted or substituted by —C(O)R$^0$;
  (vi) —C(O)R$^8$, wherein R$^8$ is R$^0$;
  (vii) —S(O)$_2$C$_{1-6}$alkyl;
  (viii) monocyclic $C_{3-6}$cycloalkyl that is unsubstituted or substituted by a substituent selected from $C_{1-6}$alkyl, hydroxyC$_{1-6}$alkyl and R$^0$;
  (ix) 6-membered heterocycloalkyl comprising, as ring members, 1 to 2 heteroatoms independently selected from N and O and that is unsubstituted or substituted by $C_{1-6}$alkyl; and
  (x) phenyl that is unsubstituted or substituted by halogen;
  wherein the C atom of the $C_{1-8}$alkyl that is unsubstituted or substituted by 1 to 3 substituents (i) to (x) that is the point of attachment of $R^2$ to the remainder of the molecule is not a —CH$_2$— group;
(b) $C_{3-6}$cycloalkyl that is unsubstituted or substituted by 1 to 2 substituents independently selected from $C_{1-6}$haloalkyl, R$^0$, $C_{1-6}$alkylamino, —C(O)R$^0$, and $C_{1-6}$alkyl that is unsubstituted or substituted by R$^0$ or —C(O)R$^0$; and
(c) 4-membered heterocycloalkyl comprising, as ring member, a heteroatom selected from N and O and that is unsubstituted or substituted by 1 to 2 substituents independently selected from $C_{1-6}$haloalkyl, R$^0$, $C_{1-6}$alkylamino, —C(O)R$^0$, and $C_{1-6}$alkyl that is unsubstituted or substituted by R$^0$ or —C(O)R$^0$.

Embodiment 145

A compound of Formula II, or a salt thereof, according to any one of embodiments 121 to 143, wherein
$R^2$ is selected from
(a) $C_{1-8}$alkyl that is unsubstituted or substituted by 1 to 2 substituents independently selected from
  (i) cyano;
  (ii) $C_2$alkynyl;
  (iii) $C_{1-6}$haloalkyl;
  (iv) —OR$^6$, wherein R$^6$ is selected from hydrogen, $C_{1-6}$alkyl that is unsubstituted or substituted by hydroxyl or —C(O)H;
  (v) —NR$^{7a}$R$^{7b}$, wherein R$^{7a}$ is hydrogen or $C_{1-6}$alkyl, and R$^{7b}$ is selected from hydrogen, —C(O)—C$_{1-6}$alkoxy, and $C_{1-6}$alkyl that is unsubstituted or substituted by —C(O)OH; and
  (vi) monocyclic $C_{3-6}$cycloalkyl that is unsubstituted or substituted by a hydroxyl; and
(b) $C_{3-6}$cycloalkyl that is unsubstituted or substituted by 1 to 2 substituents independently selected from $C_{1-6}$haloalkyl, R$^0$, $C_{1-6}$alkylamino, and $C_{1-6}$alkyl that is unsubstituted or substituted by hydroxyl or —C(O)—C$_{1-6}$alkoxy.

Embodiment 146

A compound of Formula II, or a salt thereof, according to any one of embodiments 121 to 145, wherein $R^2$ is selected from
(a) $C_{1-8}$alkyl that is unsubstituted or substituted by 1 to 2 substituents independently selected from
  (i) $C_{1-6}$haloalkyl;
  (ii) —$OR^6$, wherein $R^6$ is selected from hydrogen, and $C_{1-6}$alkyl that is unsubstituted or substituted by hydroxyl; and
  (iii) monocyclic $C_{3-6}$cycloalkyl that is unsubstituted or substituted by hydroxyl; and
(b) $C_{3-6}$cycloalkyl that is unsubstituted or substituted by 1 to 2 substituents independently selected from $C_{1-6}$haloalkyl, $R^0$, $C_{1-6}$alkylamino, and $C_{1-6}$alkyl that is unsubstituted or substituted by hydroxyl.

Embodiment 147

A compound of Formula II, or a salt thereof, according to any one of embodiments 121 to 146, wherein $R^2$ is $C_{1-6}$alkyl that is unsubstituted or substituted by 1 to 2 substituent independently selected from $C_{1-6}$haloalkyl and —$OR^6$, wherein $R^6$ is selected from hydrogen, and $C_{1-6}$alkyl that is unsubstituted or substituted by hydroxyl.

Embodiment 148

A compound of Formula II, or a salt thereof, according to any one of embodiments 121 to 147, wherein $R^2$ is $C_{1-6}$alkyl that is unsubstituted or substituted by hydroxyl.

Embodiment 149

A compound of Formula II, or a salt thereof, according to any one of embodiments 121 to 147, wherein $R^2$ is $C_{1-6}$alkyl that is unsubstituted or substituted by $C_{1-6}$haloalkyl.

Embodiment 150

A compound of Formula II, or a salt thereof, according to any one of embodiments 121 to 147, wherein $R^2$ is $C_{1-6}$alkyl that is unsubstituted or substituted by —O—$C_{1-6}$alkyl-OH.

Embodiment 151

A compound of the Formula II, or a salt thereof, according to any one of embodiments 121 to 146, wherein $R^2$ is $C_{3-6}$cycloalkyl that is unsubstituted or substituted by a substituent selected from $C_{1-6}$haloalkyl, $C_{1-6}$alkylamino, $R^0$, and $C_{1-6}$alkyl that is unsubstituted or substituted by hydroxyl.

Embodiment 152

A compound of Formula II, or a salt thereof, according to any one of embodiments 121 to 146 and 151, wherein $R^2$ is unsubstituted $C_{3-6}$cycloalkyl.

Embodiment 153

A compound of Formula II, or a salt thereof, according to any one of embodiments 121 to 146 and 151, wherein $R^2$ is $C_{3-6}$cycloalkyl that is substituted by $C_{1-6}$alkyl or $C_{1-6}$haloalkyl.

Embodiment 154

A compound of Formula II, or a salt thereof, according to any one of embodiments 121 to 145, wherein $R^2$ is selected from n-propyl, isopropyl, s-butyl, t-butyl, 2-methyl-but-2-yl, 2,4,4-trimethylpentan-2-yl,

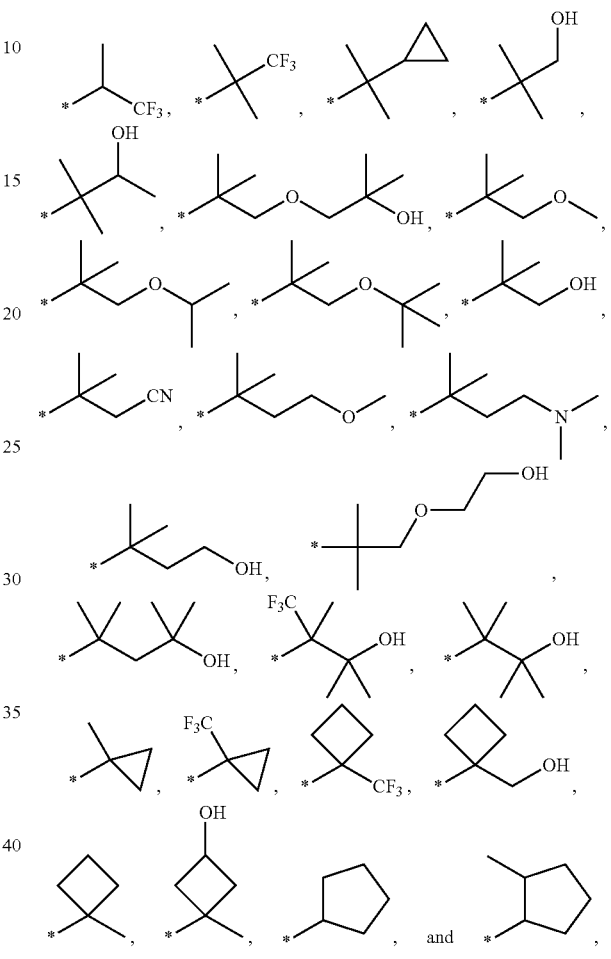

wherein "*" represents the point of attachment of $R^2$ to the remainder of the molecule.

Embodiment 155

A compound of Formula II, or a salt thereof, according to any one of embodiments 121 to 143 and 145 to 147, wherein $R^2$ is selected from n-propyl, isopropyl, t-butyl,

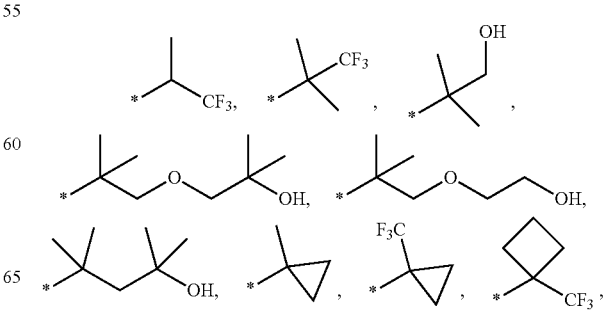

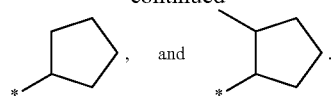

Embodiment 156

A compound of Formula II, or a salt thereof, according to any one of embodiments 121 to 147, 154 and 155, wherein $R^2$ is selected from

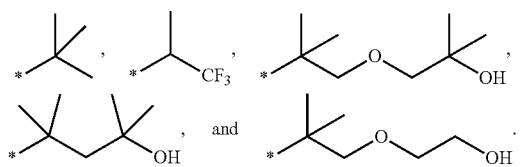

Embodiment 157

A compound of Formula II, or a salt thereof, according to any one of embodiments 121 to 147, 149, and 154 to 156, wherein $R^2$ is

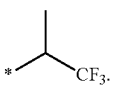

Embodiment 158

A compound of Formula II, or a salt thereof, according to any one of embodiments 121 to 147, 150, and 154 to 156, wherein $R^2$ is

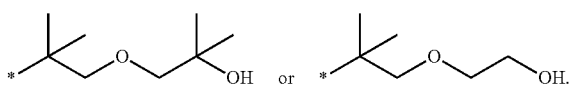

Embodiment 159

A compound of Formula II, or a salt thereof, according to any one of embodiments 121 to 147, 151, and 154 to 156, wherein $R^2$ is

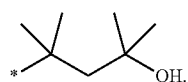 [SMILES: *C(C)(C)CC(C)(C)O]

Embodiment 160

A compound of Formula II, or a salt thereof, according to any one of embodiments 121 to 146, 151, 154 and 155, wherein $R^2$ is selected from

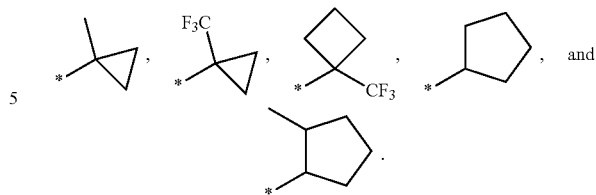

Embodiment 161

A compound of Formula II, or a salt thereof, according to any one of embodiments 121 to 146, 151, 153 to 155 and 160, wherein $R^2$ is

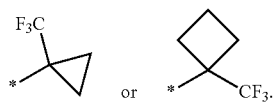

Embodiment 162

A compound of Formula II, or a salt thereof, according to any one of embodiments 121 to 136, 151, 153 to 155 and 160, wherein $R^2$ is

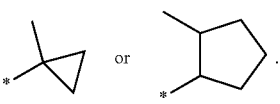

Embodiment 163

A compound of Formula II, or a salt thereof, according to any one of embodiments 121 to 136, 151, 152, 154, 155, and 160, wherein $R^2$ is

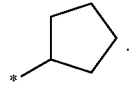

Embodiment 164

A compound of Formula II, or a salt thereof, according to any one of embodiments 121 to 133, 135 to 150, and 155, wherein $R^2$ is selected from n-propyl, isopropyl and t-butyl.

Embodiment 165

A compound of Formula II, or a salt thereof, according to any one of embodiments 121 to 143, 145 to 150, 155, and 164, wherein $R^2$ is n-propyl.

Embodiment 166

A compound of Formula II, or a salt thereof, according to any one of embodiments 121 to 150, 155, and 164, wherein $R^2$ is isopropyl.

Embodiment 167

A compound of Formula II, or a salt thereof, according to any one of embodiments 121 to 150, 155, and 164, wherein $R^2$ is t-butyl.

Embodiment 168

A compound of Formula II, or a salt thereof, according to any one of embodiments 121 to 139, wherein $R^1$ and $R^2$ taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$.

Embodiment 169

A compound of Formula II, or a salt thereof, according to any one of embodiments 121 to 139, and 168, wherein $R^1$ and $R^2$ are taken together with the nitrogen atom to which both are bound to form a 5- or 6-membered heterocycloalkyl that can include, as ring member, 1 to 2 additional heteroatom selected from N, O and S, wherein the 5- or 6-membered heterocycloalkyl formed by $R^1$ and $R^2$ taken together with the nitrogen atom to which both are bound is unsubstituted or substituted by 1 to 3 substituents independently selected from hydroxyl, $C_{1-4}$alkyl and $C_{1-4}$haloalkyl.

Embodiment 170

A compound of Formula II, or a salt thereof, according to any one of embodiments 121 to 139, 168, and 169, wherein $R^1$ and $R^2$ are taken together with the nitrogen atom to which both are bound to form a 6-membered heterocycloalkyl that can include, as ring member, an additional heteroatom selected from N and O, wherein the 6-membered heterocycloalkyl formed by $R^1$ and $R^2$ taken together with the nitrogen atom to which both are bound is unsubstituted or substituted by 1 to 3 substituents independently selected from hydroxyl, $C_{1-6}$alkyl and $C_{1-6}$haloalkyl.

Embodiment 171

A compound of Formula II, or a salt thereof, according to any one of embodiments 121 to 139, and 168 to 170, wherein $R^1$ and $R^2$ are taken together with the nitrogen atom to which both are bound to form a 6-membered heterocycloalkyl selected from piperidinyl, piperazinyl and morpholinyl, wherein the piperidinyl, piperazinyl or morpholinyl is unsubstituted or substituted by 1 to 3 substituents independently selected from hydroxyl and $C_{1-6}$alkyl.

Embodiment 172

A compound of Formula II, or a salt thereof, according to any one of embodiments 121 to 171, wherein $R^3$ is selected from hydrogen, chloro and methyl.

Embodiment 173

A compound of Formula II, or a salt thereof, according to any one of embodiments 121 to 172, wherein $R^3$ is hydrogen.

Embodiment 174

A compound of the Formula II, or a salt thereof, according to any one of embodiments 121 to 173, wherein $R^5$ is selected from hydrogen, and chloro.

Embodiment 175

A compound of Formula II, or a salt thereof, according to any one of embodiments 121 to 174, wherein $R^5$ is hydrogen.

Embodiment 176

A compound of the Formula II, or a salt thereof, according to embodiment 121, wherein the compound is of Formula VI:

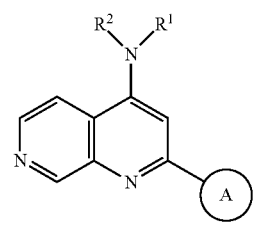

VI wherein

Ring A is

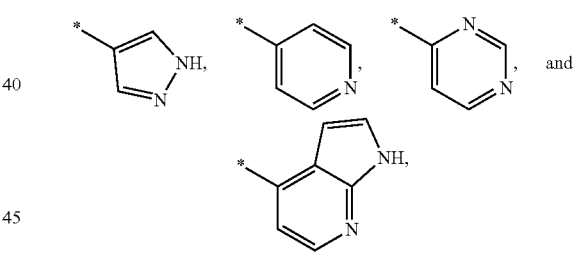

and each unsubstituted or substituted by a substituent selected from halogen, $C_{1-6}$alkyl, $C_{1-6}$haloalkyl, and —$NH_2$;

$R^1$ is hydrogen or unsubstituted $C_{1-6}$alkyl; and $R^2$ is (a) $C_{1-8}$alkyl that is unsubstituted or substituted by a substituent selected from
  (i) di-$C_{1-6}$alkylamino;
  (ii) $C_{1-6}$haloalkyl;
  (iii) —$OR^6$, wherein $R^6$ is selected from hydrogen, $C_{1-6}$alkyl that is unsubstituted or substituted by $R^0$; or (b) monocyclic $C_{3-6}$cycloalkyl that is unsubstituted or substituted by $C_{1-6}$alkyl or $C_{1-6}$haloalkyl;

or $R^1$ and $R^2$ may be taken together with the nitrogen to which they are bound to form a 6-membered heterocycloalkyl, which is unsubstituted or substituted by 1 to 3 substituted selected from $C_{1-6}$alkyl and hydroxyl.

Embodiment 177

A compound of the Formula II, or a salt thereof, according to embodiment 176, wherein ring A is

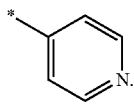

Embodiment 178

A compound of the Formula II, or a salt thereof, according to embodiment 176 or embodiment 177, wherein $R^2$ is selected from ethyl,

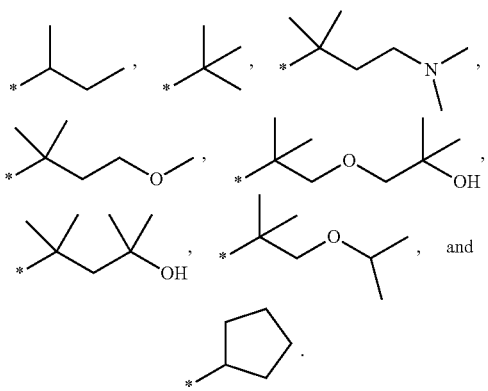

Embodiment 179

A compound of the Formula II, or a salt thereof, according to any one of embodiments 176 to 178, wherein $R^2$ is tert-butyl.

Embodiment 180

A compound of the Formula II, or a salt thereof, according to embodiment 121, selected from: N-(4-methoxy-2-methylbutan-2-yl)-2-(pyridin-4-yl)-1,7-naphthyridin-4-amine; N-[2-methyl-1-(propan-2-yloxy)propan-2-yl]-2-(pyridin-4-yl)-1,7-naphthyridin-4-amine; N-[(2S)-butan-2-yl]-2-(pyridin-4-yl)-1,7-naphthyridin-4-amine; N-[(2R)-butan-2-yl]-2-(pyridin-4-yl)-1,7-naphthyridin-4-amine; N-(1-methoxy-2-methylpropan-2-yl)-2-(pyridin-4-yl)-1,7-naphthyridin-4-amine; N-methyl-N-(propan-2-yl)-2-(pyridin-4-yl)-1,7-naphthyridin-4-amine; 3-methyl-3-{[2-(pyridin-4-yl)-1,7-naphthyridin-4-yl]amino}butan-1-ol; N-tert-butyl-2-(pyridin-4-yl)-1,7-naphthyridin-4-amine; 2,2-dimethyl-1-[2-(pyridin-4-yl)-1,7-naphthyridin-4-yl]piperidin-4-ol; 2,4-dimethyl-4-{[2-(pyridin-4-yl)-1,7-naphthyridin-4-yl]amino}pentan-2-ol; N-cyclopentyl-2-(pyridin-4-yl)-1,7-naphthyridin-4-amine; dimethyl(3-methyl-3-{[2-(pyridin-4-yl)-1,7-naphthyridin-4-yl]amino}butyl)amine; N,N-diethyl-2-(pyridin-4-yl)-1,7-naphthyridin-4-amine; 2-methyl-1-(2-methyl-2-{[2-(pyridin-4-yl)-1,7-naphthyridin-4-yl]amino}propoxy)propan-2-ol; N-propyl-2-(pyridin-4-yl)-1,7-naphthyridin-4-amine; N-tert-butyl-2-(3-methyl-1H-pyrazol-4-yl)-1,7-naphthyridin-4-amine; N-tert-butyl-2-(pyrimidin-4-yl)-1,7-naphthyridin-4-amine; 2-(2-aminopyrimidin-4-yl)-N-tert-butyl-1,7-naphthyridin-4-amine; N-tert-butyl-2-{1H-pyrrolo[2,3-b]pyridin-4-yl}-1,7-naphthyridin-4-amine; N-tert-butyl-2-(pyridazin-4-yl)-1,7-naphthyridin-4-amine; 2-(2-aminopyridin-4-yl)-N-tert-butyl-1,7-naphthyridin-4-amine; N,N-diethyl-2-(3-fluoropyridin-4-yl)-1,7-naphthyridin-4-amine; (3-{[2-(3-fluoropyridin-4-yl)-1,7-naphthyridin-4-yl]amino}-3-methylbutyl)dimethylamine; 2-(3-fluoropyridin-4-yl)-N-methyl-N-(propan-2-yl)-1,7-naphthyridin-4-amine; 2-(3-fluoropyridin-4-yl)-4-(piperidin-1-yl)-1,7-naphthyridine; 2-(3-fluoropyridin-4-yl)-4-(morpholin-4-yl)-1,7-naphthyridine; N-tert-butyl-2-(3-fluoropyridin-4-yl)-1,7-naphthyridin-4-amine; 2-(3-fluoropyridin-4-yl)-N-(2-methylbutan-2-yl)-1,7-naphthyridin-4-amine; 2-{[2-(3-fluoropyridin-4-yl)-1,7-naphthyridin-4-yl]amino}-2-methylpropan-1-ol; 1-[2-(3-chloropyridin-4-yl)-1,7-naphthyridin-4-yl]-2,2-dimethylpiperidin-4-ol; 2-(3-fluoropyridin-4-yl)-N-[2-methyl-1-(morpholin-4-yl)propan-2-yl]-1,7-naphthyridin-4-amine; N-tert-butyl-2-(pyrimidin-4-yl)-1,7-naphthyridin-4-amine; 2-(pyridin-4-yl)-N-[1-(trifluoromethyl)cyclobutyl]pyrido[3,4-d]pyrimidin-4-amine; N-tert-butyl-2-(3-chloropyridin-4-yl)-1,7-naphthyridin-4-amine; and 2-(3-chloropyridin-4-yl)-N,N-diethyl-1,7-naphthyridin-4-amine.

Embodiment 180a

A compound of the Formula II, or a salt thereof, according to embodiment 121, wherein the compound is N-(tert-butyl)-2-(pyridin-4-yl)-1,7-naphthyridin-4-amine.

Embodiment 181

A compound of Formula A1, or a salt thereof,

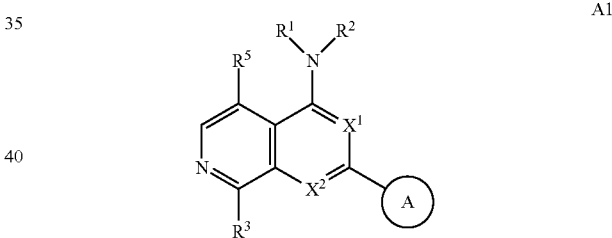

for use in ocular diseases or disorders, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

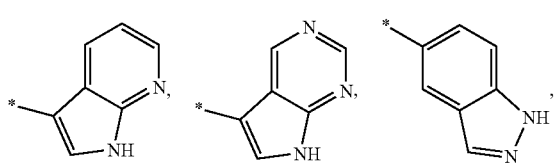

-continued

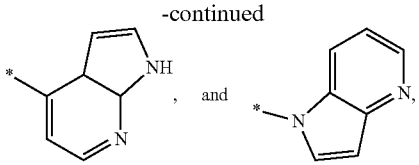

wherein "*" represents the point of attachment of ring A to the remainder of the molecule, wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$cycloalkyl, and phenylsulfonyl;

$R^0$ is hydroxyl or $C_{1-6}$alkoxy;

$R^1$ is hydrogen or $C_{1-6}$alkyl;

$R^2$ is selected from (a) $C_{1-8}$alkyl that is unsubstituted or substituted by 1 to 3 substituents independently selected from
  (i) halogen;
  (ii) cyano;
  (iii) oxo;
  (iv) $C_2$alkenyl;
  (v) $C_2$alkynyl;
  (vi) $C_{1-6}$haloalkyl;
  (vii) —$OR^6$, wherein $R^6$ is selected from hydrogen, $C_{1-6}$alkyl that is unsubstituted or substituted by $R^0$ or —C(O)$R^0$;
  (viii) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (ix) —C(O)$R^8$, wherein $R^8$ is $R^0$ or —NH—$C_{1-6}$alkyl-C(O)$R^0$;
  (x) —$S(O)_2C_{1-6}$alkyl;
  (xi) monocyclic $C_{3-6}$cycloalkyl or polycyclic $C_{7-10}$cycloalkyl that are each unsubstituted or substituted by 1 to 2 substituents independently selected from halogen, $C_{1-6}$ alkyl, hydroxy$C_{1-6}$alkyl, $C_{1-6}$haloalkyl, $R^0$, —$NH_2$, $C_{1-6}$alkylamino, and di-($C_{1-6}$ alkyl)amino;
  (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from N and O; and
  (xv) 9- or 10-membered fused bicyclic heteroaryl comprising, as ring member, 1 to 2 heteroatoms independently selected from N and O;

(b) —$S(O)_2C_{1-6}$alkyl;

(c) phenyl that is unsubstituted or substituted by 1 to 2 substituents independently selected from halogen, $C_{1-6}$alkyl and $R^0$;

(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$; and (e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$ alkyl)amino, —C(O)$R^0$, and $C_{1-6}$alkyl that is unsubstituted or substituted by $R^0$ or —C(O)$R^0$;

or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;

$R^3$ is selected from hydrogen, halogen and $C_{1-6}$alkyl; and $R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 182

A compound of Formula A1 or a salt thereof, for use in ocular diseases or disorders according to embodiment 181, wherein the compound is of the formula selected from Formulae I to IV:

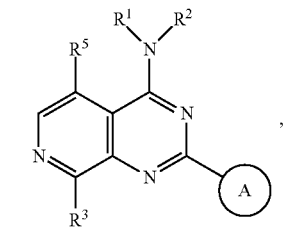

I

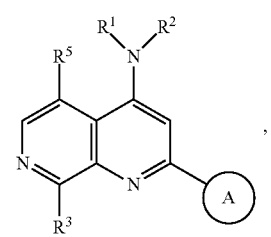

II

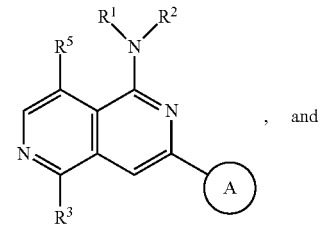

, and

III

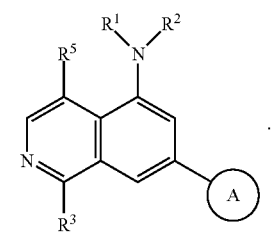

IV

Embodiment 183

A compound of Formula A1 or a salt thereof, for use in ocular diseases or disorders according to embodiment 181, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; 2-(pyridin-4-yl)-4-(3-(trifluoromethyl)piperazin-1-yl)pyrido[3,4-d]pyrimidine; N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 184

A compound of the Formula A1 or a salt thereof, for use in ocular diseases or disorders according to embodiment 181, wherein the compound is according to any one of embodiments 1 to 180.

Embodiment 185

Use of a compound of the Formula A1, or a salt thereof,

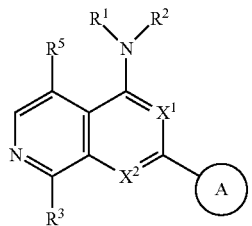

A1

In a method of generating an expanded population of limbal stem cells, preferably ex vivo,
wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

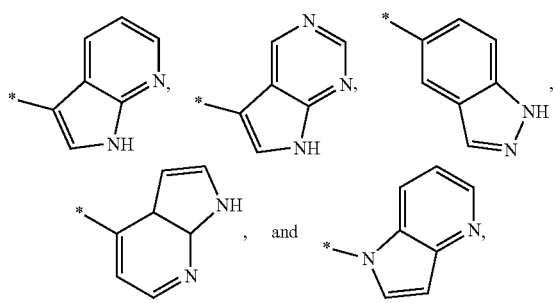

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$ alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
  (i) halogen;
  (ii) cyano;
  (iii) oxo;
  (iv) $C_2$alkenyl;
  (v) $C_2$alkynyl;
  (vi) $C_{1-6}$haloalkyl;
  (vii) —$OR^6$, wherein $R^6$ is selected from hydrogen, $C_{1-6}$alkyl that is unsubstituted or substituted by $R^0$ or —C(O)$R^0$;
  (viii) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (ix) —C(O)$R^8$, wherein $R^8$ is $R^0$ or —NH—$C_{1-6}$alkyl-C(O)$R^0$;
  (x) —S(O)$_2C_{1-6}$alkyl;
  (xi) monocyclic $C_{3-6}$cycloalkyl or polycyclic $C_{7-10}$cycloalkyl that are each unsubstituted or substituted by 1 to 2 substituents independently selected from halogen, $C_{1-6}$ alkyl, hydroxy$C_{1-6}$alkyl, $C_{1-6}$haloalkyl, $R^0$, —$NH_2$, $C_{1-6}$alkylamino, and di-($C_{1-6}$ alkyl)amino;
  (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from N and O; and
  (xv) 9- or 10-membered fused bicyclic heteroaryl comprising, as ring member, 1 to 2 heteroatoms independently selected from N and O;
(b) —S(O)$_2C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$ alkyl)amino, —C(O)$R^0$, and $C_{1-6}$alkyl that is unsubstituted or substituted by $R^0$ or —C(O)$R^0$;
or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^O$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by $R^O$.

Embodiment 186

Use of a compound of the Formula A1, or a salt thereof,

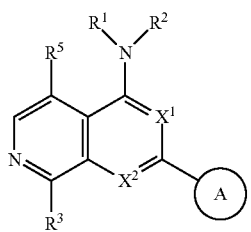

in a method of generating an expanded corneal endothelial cell population, preferably ex vivo, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

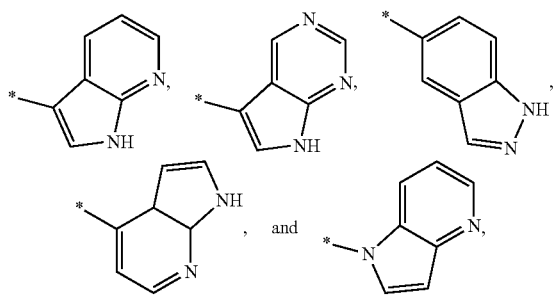

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —NH$_2$, $C_{1-6}$alkylamino, di-($C_{1-6}$alkyl)amino, $C_{3-6}$cycloalkyl, and phenylsulfonyl;
$R^O$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
  (i) halogen;
  (ii) cyano;
  (iii) oxo;
  (iv) $C_2$alkenyl;
  (v) $C_2$alkynyl;
  (vi) $C_{1-6}$haloalkyl;
  (vii) —OR$^6$, wherein $R^6$ is selected from hydrogen, $C_{1-6}$alkyl that is unsubstituted or substituted by $R^O$ or —C(O)R$^O$;
  (viii) —NR$^{7a}$R$^{7b}$, wherein $R^{7a}$ is hydrogen or $C_{1-6}$alkyl, and $R^{7b}$ is selected from hydrogen, —C(O)R$^O$, $C_{1-6}$alkyl that is unsubstituted or substituted by —C(O)R$^O$;
  (ix) —C(O)R$^8$, wherein $R^8$ is $R^O$ or —NH—$C_{1-6}$alkyl-C(O)R$^O$;
  (x) —S(O)$_2$C$_{1-6}$alkyl;
  (xi) monocyclic $C_{3-6}$cycloalkyl or polycyclic $C_{7-10}$cycloalkyl that are each unsubstituted or substituted by 1 to 2 substituents independently selected from halogen, $C_{1-6}$ alkyl, hydroxyC$_{1-6}$alkyl, $C_{1-6}$haloalkyl, $R^O$, —NH$_2$, $C_{1-6}$alkylamino, and di-($C_{1-6}$ alkyl)amino;
  (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from N and O; and
  (xv) 9- or 10-membered fused bicyclic heteroaryl comprising, as ring member, 1 to 2 heteroatoms independently selected from N and O;
(b) —S(O)$_2$C$_{1-6}$alkyl;
(c) phenyl that is unsubstituted or substituted by 1 to 2 substituents independently selected from halogen, $C_{1-6}$alkyl and $R^O$;
(d) $C_{3-6}$cycloalkyl that is unsubstituted or substituted by 1 to 2 substituents independently selected from $C_{1-6}$haloalkyl, $R^O$, $C_{1-6}$alkylamino, di-($C_{1-6}$alkyl)amino, —C(O)R$^O$, and $C_{1-6}$ alkyl that is unsubstituted or substituted by $R^O$ or —C(O)R$^O$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^O$, $C_{1-6}$alkylamino, di-($C_{1-6}$ alkyl)amino, —C(O)R$^O$, and $C_{1-6}$alkyl that is unsubstituted or substituted by $R^O$ or —C(O)R$^O$;
or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^O$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by $R^O$.

Embodiment 187

Use of a compound of the Formula A1 or a salt thereof, according to embodiment 185 or 186, wherein the compound is of the formula selected from Formulae I to IV:

99

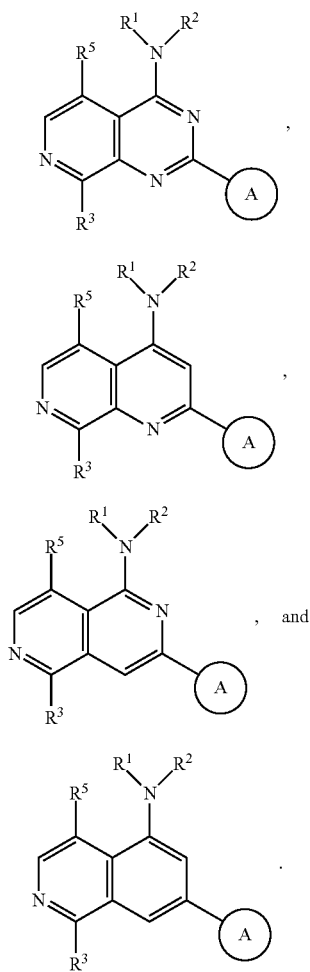

I, II, III, and IV

Embodiment 188

Use of a compound of Formula A1 or a salt thereof, according to embodiment 185 or 186, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; and 2-(pyridin-4-yl)-4-(3-(trifluoromethyl) piperazin-1-yl)pyrido[3,4-d]pyrimidine.

Embodiment 188A

Use of a compound of the Formula A1, or a salt thereof, according to embodiment 185 or 186, wherein the compound is selected from: N-methyl-2-(pyridin-4-yl)-N-(1,1,1-trifluoropropan-2-yl)pyrido[3,4-d]pyrimidin-4-amine; 2-methyl-1-(2-methyl-2-{[2-(pyridin-4-yl)pyrido[3,4-d]pyrimidin-4-yl]amino}propoxy)propan-2-ol; 2,4-dimethyl-4-{[2-(pyridin-4-yl)pyrido[3,4-d]pyrimidin-4-yl]amino}pentan-2-ol; N-tert-butyl-2-(pyrimidin-4-yl)-1,7-naphthyridin-4-amine; 2-(pyridin-4-yl)-N-[1-(trifluoromethyl)cyclobutyl]pyrido[3,4-d]pyrimidin-4-amine; N-propyl-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; 2-(3-methyl-1H-pyrazol-4-yl)-N-(1-methylcyclopropyl)pyrido[3,4-d]pyrimidin-4-amine; 2-methyl-2-{[2-(pyridin-4-yl)pyrido[3,4-d]pyrimidin-4-yl]amino}propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; N-(1-methylcyclopropyl)-7-(pyridin-4-yl)isoquinolin-5-amine; (1S,2S)-2-{[2-(pyridin-4-yl)pyrido[3,4-d]pyrimidin-4-yl]amino}cyclopentan-1-ol; N-methyl-2-(pyridin-4-yl)-N-[(2S)-1,1,1-trifluoropropan-2-yl]pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine and N-methyl-2-(pyridin-4-yl)-N-[(2R)-1,1,1-trifluoropropan-2-yl]pyrido[3,4-d]pyrimidin-4-amine.

Embodiment 188B

Use of a compound of the Formula A1, or a salt thereof, according to embodiment 185 or 186, wherein the compound is selected from: N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 188C

Use of a compound of the Formula A1, or a salt thereof, according to embodiment 185 or 186, wherein the compound is compound is N-(tert-butyl)-2-(pyridin-4-yl)-1,7-naphthyridin-4-amine.

Embodiment 189

Use of a compound of Formula A1 or a salt thereof, according to embodiment 185 or 186, wherein the compound is according to any one of embodiments 1 to 180.

Embodiment 190

A method of treatment of an ocular disease or disorder comprising administering to a subject in need thereof a cell population, wherein the cell population has been grown in the presence of a compound of Formula A1, or a salt thereof,

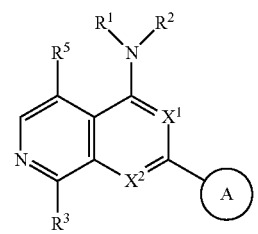

A1 wherein
X¹ and X² are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

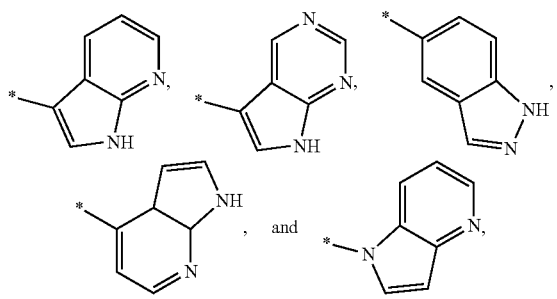

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —NH₂, $C_{1-6}$alkylamino, di-($C_{1-6}$ alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
(i) halogen;
(ii) cyano;
(iii) oxo;
(iv) $C_2$alkenyl;
(v) $C_2$alkynyl;
(vi) $C_{1-6}$haloalkyl;
(vii) —$OR^6$, wherein $R^6$ is selected from hydrogen, $C_{1-6}$alkyl that is unsubstituted or substituted by $R^0$ or —C(O)$R^0$;
(viii) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
(ix) —C(O)$R^8$, wherein $R^8$ is $R^0$ or —NH—$C_{1-6}$alkyl-C(O)$R^0$;
(x) —S(O)₂$C_{1-6}$alkyl;
(xi) monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —NH₂, $C_{1-6}$alkylamino, and di-($C_{1-6}$alkyl)amino;
(xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
(xiii) phenyl that is unsubstituted or substituted by halogen;
(xiv) 5- or 6-membered monocyclic heteroaryl comprising, as ring members, 1 to 4 heteroatoms independently selected from N and O; and
(xv) 9- or 10-membered fused bicyclic heteroaryl comprising, as ring member, 1 to 2 heteroatoms independently selected from N and O;
(b) —S(O)₂$C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$ alkyl that is unsubstituted or substituted by $R^0$ or —C(O)$R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$ alkyl)amino, —C(O)$R^0$, and $C_{1-6}$alkyl that is unsubstituted or substituted by $R^0$ or —C(O)$R^0$;
or, $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by $R^0$.

Embodiment 190A

A method of treatment of an ocular disease or disorder comprising administering to a subject in need thereof a limbal stem cell population, wherein said population has been grown in the presence of a compound of Formula A1, or a salt thereof,

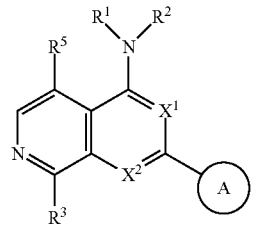

wherein
X¹ and X² are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or (b) a 9-membered fused bicyclic heteroaryl that is selected from

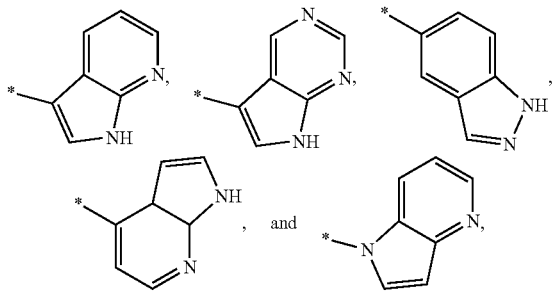

wherein "*" represents the point of attachment of ring A to the remainder of the molecule;

wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$ alkyl)amino, $C_{3-6}$cycloalkyl, and phenylsulfonyl;

$R^0$ is hydroxyl or $C_{1-6}$alkoxy;

$R^1$ is hydrogen or $C_{1-6}$alkyl;

$R^2$ is selected from (a) $C_{1-8}$alkyl that is unsubstituted or substituted by 1 to 3 substituents independently selected from
  (i) halogen;
  (ii) cyano;
  (iii) oxo;
  (iv) $C_2$alkenyl;
  (v) $C_2$alkynyl;
  (vi) $C_{1-6}$haloalkyl;
  (vii) —$OR^6$, wherein $R^6$ is selected from hydrogen, $C_{1-6}$alkyl that is unsubstituted or substituted by $R^0$ or —C(O)$R^0$;
  (viii) —$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
  (ix) —C(O)$R^8$, wherein $R^8$ is $R^0$ or —NH—$C_{1-6}$alkyl-C(O)$R^0$;
  (x) —$S(O)_2C_{1-6}$alkyl;
  (xi) monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
  (xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$ alkylamino, and di-($C_{1-6}$alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from N and O; and
  (xv) 9- or 10-membered fused bicyclic heteroaryl comprising, as ring member, 1 to 2 heteroatoms independently selected from N and O;

(b) —$S(O)_2C_{1-6}$alkyl;

(c) phenyl that is unsubstituted or substituted by 1 to 2 substituents independently selected from $C_{1-6}$alkyl and $R^0$;

(d) $C_{1-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$; and (e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$ alkyl)amino, —C(O)$R^0$, and $C_{1-6}$alkyl that is unsubstituted or substituted by $R^0$ or —C(O)$R^0$;

or, $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;

$R^3$ is selected from hydrogen, halogen and $C_{1-6}$alkyl; and $R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 191

A method of treatment of an ocular disease or disorder comprising administering to a subject in need thereof a corneal endothelial cell population, wherein the population has been grown in the presence of a compound of Formula A1, or a salt thereof,

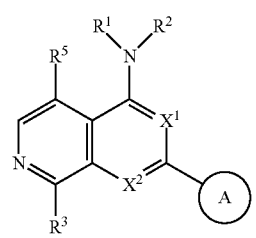

wherein $X^1$ and $X^2$ are each independently CH or N;

Ring A is (a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or (b) a 9-membered fused bicyclic heteroaryl that is selected from

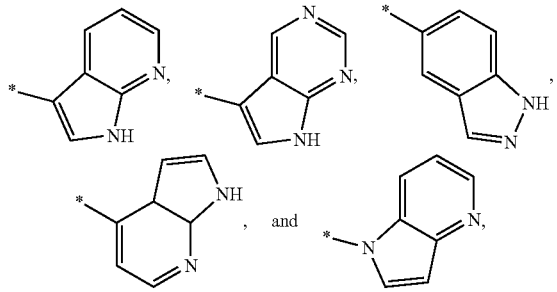

, and wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$ alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
(i) halogen;
(ii) cyano;
(iii) oxo;
(iv) $C_2$alkenyl;
(v) $C_2$alkynyl;
(vi) $C_{1-6}$haloalkyl;
(vii) —$OR^6$, wherein $R^6$ is selected from hydrogen, $C_{1-6}$alkyl that is unsubstituted or substituted by $R^0$ or —$C(O)R^0$;
(viii) —$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;
(ix) —$C(O)R^8$, wherein $R^8$ is $R^0$ or —NH—$C_{1-6}$alkyl-$C(O)R^0$;
(x) —$S(O)_2C_{1-6}$alkyl;
(xi) monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
(xii) 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
(xiii) phenyl that is unsubstituted or substituted by halogen;
(xiv) 5- or 6-membered monocyclic heteroaryl comprising, as ring members, 1 to 4 heteroatoms independently selected from N and O; and
(xv) 9- or 10-membered fused bicyclic heteroaryl comprising, as ring member, 1 to 2 heteroatoms independently selected from N and O;
(b) —$S(O)_2C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$ alkyl)amino, —$C(O)R^0$, and $C_{1-6}$alkyl that is unsubstituted or substituted by $R^0$ or —$C(O)R^0$;
or, $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by $R^0$.

Embodiment 192

A method of treatment of an ocular disease or disorder according to embodiment 190 or 191, wherein the compound is of the formula selected from Formulae I to IV:

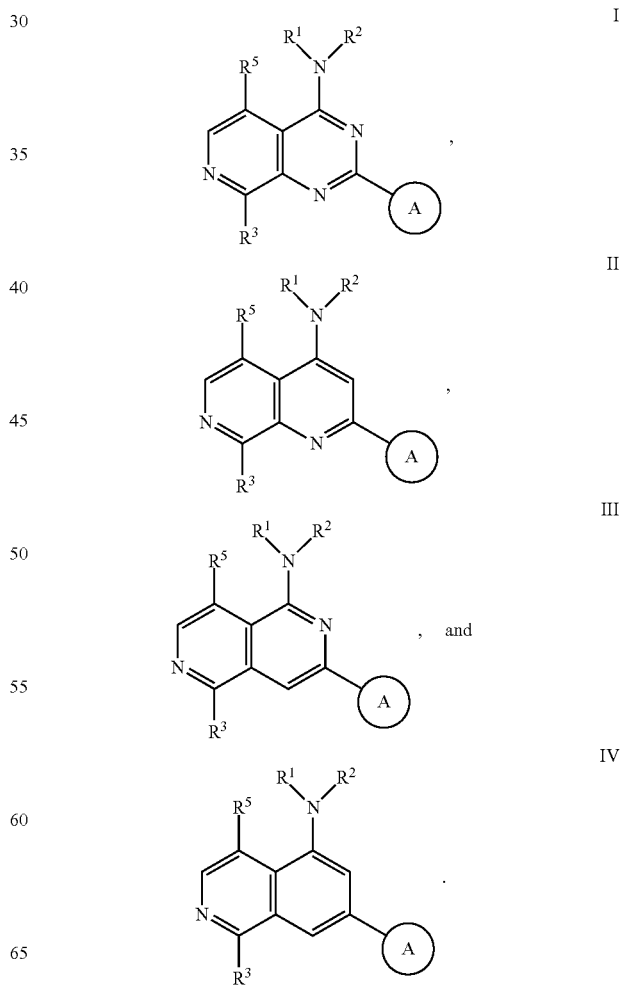

Embodiment 193

A method of treatment of an ocular disease or disorder according to embodiment 190 or 191, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; 2-(pyridin-4-yl)-4-(3-(trifluoromethyl)piperazin-1-yl)pyrido[3,4-d]pyrimidine; N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 193A

A method of treatment of an ocular disease or disorder according to embodiment 190 or 191, wherein the compound is selected from: N-methyl-2-(pyridin-4-yl)-N-(1,1,1-trifluoropropan-2-yl)pyrido[3,4-d]pyrimidin-4-amine; 2-methyl-1-(2-methyl-2-{[2-(pyridin-4-yl)pyrido[3,4-d]pyrimidin-4-yl]amino}propoxy)propan-2-ol; 2,4-dimethyl-4-{[2-(pyridin-4-yl)pyrido[3,4-d]pyrimidin-4-yl]amino}pentan-2-ol; N-tert-butyl-2-(pyrimidin-4-yl)-1,7-naphthyridin-4-amine; 2-(pyridin-4-yl)-N-[1-(trifluoromethyl)cyclobutyl]pyrido[3,4-d]pyrimidin-4-amine; N-propyl-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine; 2-(3-methyl-1H-pyrazol-4-yl)-N-(1-methylcyclopropyl)pyrido[3,4-d]pyrimidin-4-amine; 2-methyl-2-{[2-(pyridin-4-yl)pyrido[3,4-d]pyrimidin-4-yl]amino}propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl)pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; 2-(2-methyl-2-{[2-(pyridin-4-yl)pyrido[3,4-d]pyrimidin-4-yl]amino}propoxy)ethan-1-ol; N-(1-methylcyclopropyl)-7-(pyridin-4-yl)isoquinolin-5-amine; (1S,2S)-2-{[2-(pyridin-4-yl)pyrido[3,4-d]pyrimidin-4-yl]amino}cyclopentan-1-ol; N-methyl-2-(pyridin-4-yl)-N-[(2S)-1,1,1-trifluoropropan-2-yl]pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine and N-methyl-2-(pyridin-4-yl)-N-[(2R)-1,1,1-trifluoropropan-2-yl]pyrido[3,4-d]pyrimidin-4-amine.

Embodiment 193B

A method of treatment of an ocular disease or disorder according to embodiment 190 or 191, wherein the compound is selected from: N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 193C

A method of treatment of an ocular disease or disorder according to embodiment 190 or 191, wherein the compound is N-(tert-butyl)-2-(pyridin-4-yl)-1,7-naphthyridin-4-amine.

Embodiment 194

A method of promoting cell proliferation according to embodiment 190 or 191, wherein the compound is according to any one of embodiments 1 to 180.

Embodiment 195

Use of a compound of Formula A1, or a salt thereof,

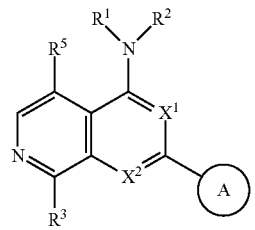

in the manufacture of a medicament for an ocular disease or disorder, wherein $X^1$ and $X^2$ are each independently CH or N;

Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

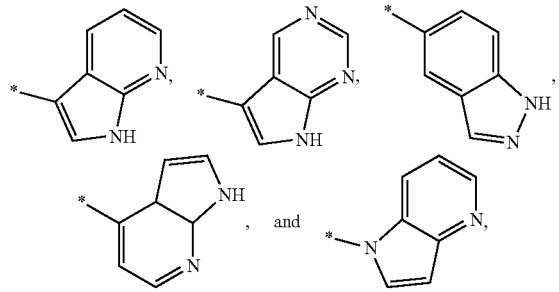

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
  (i) halogen;
  (ii) cyano;
  (iii) oxo;
  (iv) $C_2$alkenyl;
  (v) $C_2$alkynyl;

(vi) C$_{1-6}$haloalkyl;
(vii) —OR$^6$, wherein R$^6$ is selected from hydrogen, C$_{1-6}$alkyl that is unsubstituted or substituted by R$^0$ or —C(O)R$^0$;
(viii) —NR$^{7a}$R$^{7b}$, wherein R$^{7a}$ is hydrogen or C$_{1-6}$alkyl, and R$^{7b}$ is selected from hydrogen, —C(O)R$^0$, C$_{1-6}$alkyl that is unsubstituted or substituted by —C(O)R$^0$;
(ix) —C(O)R$^8$, wherein R$^8$ is R$^0$ or —NH—C$_{1-6}$alkyl-C(O)R$^0$;
(x) —S(O)$_2$C$_1$-6alkyl;
(xi) monocyclic C$_{3-6}$cycloalkyl or polycyclic C$_{7-10}$cycloalkyl that are each unsubstituted or substituted by 1 to 2 substituents independently selected from halogen, C$_{1-6}$alkyl, hydroxyC$_{1-6}$alkyl, C$_{1-6}$haloalkyl, R$^0$, —NH$_2$, C$_{1-6}$alkylamino, and di-(C$_{1-6}$ alkyl)amino;
(xii) 6-membered heterocycloalkyl comprising, as ring members, 1 to 2 heteroatoms independently selected from N, O and S and that is unsubstituted or substituted by 1 to 2 substituents independently selected from hydroxyl, halogen, C$_{1-6}$alkyl, C$_{1-6}$alkylamino, and di-(C$_{1-6}$alkyl)amino;
(xiii) phenyl that is unsubstituted or substituted by halogen;
(xiv) 5- or 6-membered monocyclic heteroaryl comprising, as ring members, 1 to 4 heteroatoms independently selected from N and O; and
(xv) 9- or 10-membered fused bicyclic heteroaryl comprising, as ring member, 1 to 2 heteroatoms independently selected from N and O;
(b) —S(O)$_2$C$_{1-6}$alkyl;
(c) phenyl that is unsubstituted or substituted by 1 to 2 substituents independently selected from halogen, C$_{1-6}$alkyl and R$^0$;
(d) C$_{3-6}$cycloalkyl that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$; and
(e) 4-membered heterocycloalkyl comprising, as ring members, 1 to 2 heteroatoms selected from N, O and S and that is unsubstituted or substituted by 1 to 2 substituents independently selected from C$_{1-6}$haloalkyl, R$^0$, C$_{1-6}$alkylamino, di-(C$_{1-6}$ alkyl)amino, —C(O)R$^0$, and C$_{1-6}$alkyl that is unsubstituted or substituted by R$^0$ or —C(O)R$^0$;
or, R$^1$ and R$^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by R$^1$ and R$^2$ taken together with the nitrogen atom to which both are bound is unsubstituted or substituted by 1 to 3 substituents independently selected from halogen, C$_{1-6}$alkyl, C$_{1-6}$haloalkyl, and R$^0$;
R$^3$ is selected from hydrogen, halogen and C$_{1-6}$alkyl; and R$^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by R$^0$.

Embodiment 196

Use of a compound of Formula A1 or a salt thereof, in the manufacture of a medicament for an ocular disease or disorder according to embodiment 195, wherein the compound is of the formula selected from Formulae I to IV:

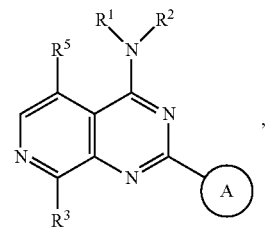

I

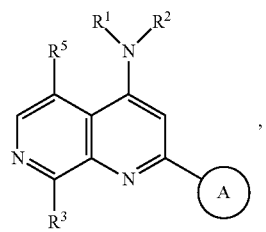

II

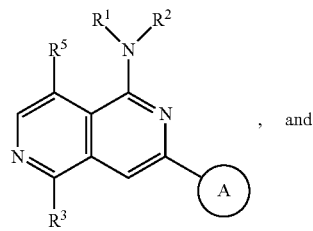

III, and

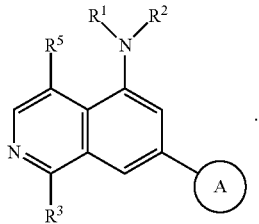

IV

Embodiment 197

Use of a compound of Formula A1 or a salt thereof, in the manufacture of a medicament for an ocular disease or disorder according to embodiment 195, wherein the compound is selected from 3-(pyridin-4-yl)-N-(1-(trifluoromethyl)cyclopropyl)-2,6-naphthyridin-1-amine; N-(1-methyl-cyclopropyl)-7-(pyridin-4-yl)isoquinolin-5-amine; and 2-(pyridin-4-yl)-4-(3-(trifluoromethyl)piperazin-1-yl)pyrido[3,4-d]pyrimidine.

Embodiment 197A

Use of a compound of the Formula A1, or a salt thereof, in the manufacture of a medicament for an ocular disease or disorder according to embodiment 195, wherein the compound is selected from: N-methyl-2-(pyridin-4-yl)-N-(1,1,1-trifluoropropan-2-yl)pyrido[3,4-d]pyrimidin-4-amine; 2-methyl-1-(2-methyl-2-{[2-(pyridin-4-yl)pyrido[3,4-d]pyrimidin-4-yl]amino}propoxy) propan-2-ol; 2,4-dimethyl-4-{[2-(pyridin-4-yl)pyrido[3,4-d]pyrimidin-4-yl]amino}pentan-2-ol; N-tert-butyl-2-(pyridin-4-yl)-1,7-naphthyridin-4-amine; 2-(pyridin-4-yl)-N-[1-(trifluoromethyl)cyclobutyl]pyrido[3,4-d]pyrimidin-4-amine; N-propyl-2-(pyridin-4-yl)pyrido[3,4-d]pyrimidin-4-amine; N-(propan-2-yl)-2-(pyridin-4-yl)pyrido[3,4-d]

pyrimidin-4-amine; 3-(pyridin-4-yl)-N-(1-(trifluoromethyl) cyclopropyl)-2,6-naphthyridin-1-amine; 2-(3-methyl-1H-pyrazol-4-yl)-N-(1-methylcyclopropyl)pyrido[3,4-d]pyrimidin-4-amine; 2-methyl-2-{[2-(pyridin-4-yl)pyrido[3,4-d]pyrimidin-4-yl]amino}propan-1-ol; 2-(pyridin-4-yl)-4-(3-(trifluoromethyl)piperazin-1-yl)pyrido[3,4-d]pyrimidine; N-cyclopentyl-2-(pyridin-4-yl)pyrido[3,4-d]pyrimidin-4-amine; N-propyl-2-(3-(trifluoromethyl)-1H-pyrazol-4-yl) pyrido[3,4-d]pyrimidin-4-amine; N-(2-methylcyclopentyl)-2-(pyridin-4-yl)pyrido[3,4-d]pyrimidin-4-amine; 2-(3-chloropyridin-4-yl)-N-(1,1,1-trifluoro-2-methylpropan-2-yl)pyrido[3,4-d]pyrimidin-4-amine; 2-(2-methyl-2-{[2-(pyridin-4-yl)pyrido[3,4-d]pyrimidin-4-yl]amino}propoxy) ethan-1-ol; N-(1-methylcyclopropyl)-7-(pyridin-4-yl) isoquinolin-5-amine; (1S,2S)-2-{[2-(pyridin-4-yl)pyrido[3,4-d]pyrimidin-4-yl]amino}cyclopentan-1-ol; N-methyl-2-(pyridin-4-yl)-N-[(2S)-1,1,1-trifluoropropan-2-yl]pyrido[3,4-d]pyrimidin-4-amine; N-methyl-N-(propan-2-yl)-2-(pyridin-4-yl)pyrido[3,4-d]pyrimidin-4-amine; N-(propan-2-yl)-2-(pyridin-4-yl)pyrido[3,4-d]pyrimidin-4-amine; 3-(pyridin-4-yl)-N-(1-(trifluoromethyl)cyclopropyl)-2,6-naphthyridin-1-amine and N-methyl-2-(pyridin-4-yl)-N-[(2R)-1,1,1-trifluoropropan-2-yl]pyrido[3,4-d]pyrimidin-4-amine.

Embodiment 197B

Use of a compound of the Formula A1, or a salt thereof, in the manufacture of a medicament for an ocular disease or disorder according to embodiment 195, wherein the compound is selected from: N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 197C

Use of a compound of the Formula A1, or a salt thereof, in the manufacture of a medicament for an ocular disease or disorder according to embodiment 195, wherein the compound is compound is N-(tert-butyl)-2-(pyridin-4-yl)-1,7-naphthyridin-4-amine.

Embodiment 198

Use of a compound of Formula A1 or a salt thereof, in the manufacture of a medicament for an ocular disease or disorder according to embodiment 195, wherein the compound is according to any one of embodiments 1 to 180.

Embodiment 199

A compound of Formula A1, or a pharmaceutically acceptable salt thereof,

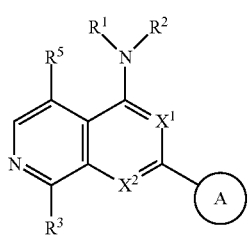

A1 for use in promoting liver regeneration and liver regrowth, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

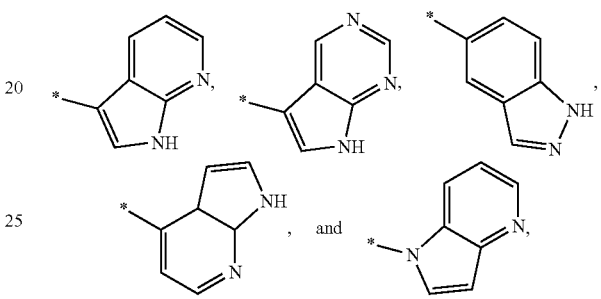

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —NH$_2$, $C_{1-6}$alkylamino, di-($C_{1-6}$ alkyl)amino, $C_{3-6}$ cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—OR$^6$, wherein R$^6$ is selected from hydrogen, $C_{1-6}$alkyl that is unsubstituted or substituted by R$^0$ or —C(O)R$^0$;
—NR$^{7a}$R$^{7b}$, wherein R$^{7a}$ is hydrogen or $C_{1-6}$alkyl, and R$^{7b}$ is selected from hydrogen, —C(O)R$^0$, $C_{1-6}$alkyl that is unsubstituted or substituted by —C(O)R$^0$;
—C(O)R$^8$, wherein R$^8$ is R$^0$ or —NH—$C_{1-6}$alkyl-C(O)R$^0$;
—S(O)$_2$C$_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxyC$_{1-6}$alkyl, $C_{1-6}$haloalkyl, R$^0$, —NH$_2$, $C_{1-6}$alkylamino, and di-($C_{1-6}$alkyl)amino;
6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and 9- or 10-membered fused bicyclic heteroaryl comprising, as ring member, 1 to 2 heteroatoms independently selected from N and O;

(b) —S(O)$_2$C$_{1-6}$alkyl;

(c) phenyl that is unsubstituted or substituted by 1 to 2 substituents independently selected from halogen, C$_{1-6}$alkyl and R$^0$;

(d) C$_{3-6}$cycloalkyl that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$; and (e) 4-membered heterocycloalkyl comprising, as ring members, 1 to 2 heteroatoms selected from N, O and S and that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$;

or R$^1$ and R$^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by R$^1$ and R$^2$ taken together with the nitrogen atom to which both are bound is unsubstituted or substituted by 1 to 3 substituents independently selected from halogen, C$_{1-6}$alkyl, C$_{1-6}$haloalkyl, and R$^0$;

R$^3$ is selected from hydrogen, halogen and C$_{1-6}$alkyl; and

R$^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by R$^0$.

Embodiment 200

A compound of Formula A1 or a pharmaceutically acceptable salt thereof, for use in promoting liver regeneration and liver regrowth according to embodiment 199, wherein the compound is of the formula selected from Formulae I to IV:

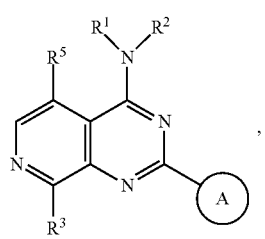

I

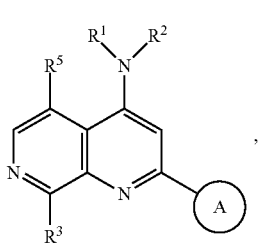

II

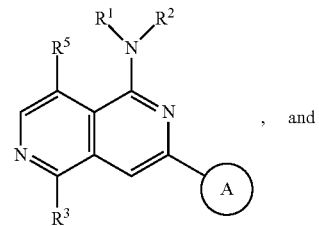

III

, and

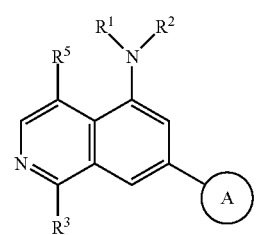

IV

Embodiment 201

A compound of Formula A1 or a pharmaceutically acceptable salt thereof, for use in promoting liver regeneration and liver regrowth according to embodiment 199, wherein the compound is selected from:
2-methyl-1-(2-methyl-2-{[2-(pyridin-4-yl)pyrido[3,4-d]pyrimidin-4-yl]amino}propoxy)propan-2-ol;
dimethyl(3-methyl-3-{[2-(pyridin-4-yl)pyrido[3,4-d]pyrimidin-4-yl]amino}butyl)amine;
N-(1-amino-2-methylpropan-2-yl)-2-(pyridin-4-yl)pyrido[3,4-d]pyrimidin-4-amine;
8-chloro-N-(1-methylcyclopropyl)-2-(pyridin-4-yl)pyrido[3,4-d]pyrimidin-4-amine;
8-methyl-N-(1-methylcyclopropyl)-2-(pyridin-4-yl)pyrido[3,4-d]pyrimidin-4-amine;
N-(tert-butyl)-5-chloro-2-(pyridin-4-yl)pyrido[3,4-d]pyrimidin-4-amine;
5-chloro-N-(1-methylcyclopropyl)-2-(pyridin-4-yl)pyrido[3,4-d]pyrimidin-4-amine;
N-tert-butyl-2-(pyrimidin-4-yl)-1,7-naphthyridin-4-amine;
N-tert-butyl-2-(3-methyl-1H-pyrazol-4-yl)-1,7-naphthyridin-4-amine;
N-tert-butyl-2-(pyrimidin-4-yl)-1,7-naphthyridin-4-amine;
2-(2-aminopyrimidin-4-yl)-N-tert-butyl-1,7-naphthyridin-4-amine;
N$^1$,N$^1$,3-trimethyl-N$^3$-(2-(3-methyl-1H-pyrazol-4-yl)pyrido[3,4-d]pyrimidin-4-yl)butane-1,3-diamine;
N$^1$,N$^1$,3-trimethyl-N$^3$-(2-(3-methyl-1H-pyrazol-4-yl)pyrido[3,4-d]pyrimidin-4-yl)butane-1,3-diamine;
2,2-dimethyl-N$^1$-(2-(pyridin-4-yl)pyrido[3,4-d]pyrimidin-4-yl)propane-1,3-diamine;
2,3-dimethyl-N$^2$-(2-(pyridin-4-yl)pyrido[3,4-d]pyrimidin-4-yl)butane-2,3-diamine;
N$^1$,N$^1$,2,2-tetramethyl-N$^3$-(2-(pyridin-4-yl)pyrido[3,4-d]pyrimidin-4-yl)propane-1,3-diamine;
4-(4-(tert-butylamino)pyrido[3,4-d]pyrimidin-2-yl)-1,2,5-oxadiazol-3-amine; and
N$^2$,N$^2$,2-trimethyl-N$^1$-(2-(pyridin-4-yl)pyrido[3,4-d]pyrimidin-4-yl)propane-1,2-diamine.

Embodiment 202

A compound of the Formula A1 or a pharmaceutically acceptable salt thereof, for use in promoting liver regeneration and liver regrowth according to embodiment 199, wherein the compound is according to any one of embodiments 1 to 180.

Embodiment 203

Use of a compound of the Formula A1, or a pharmaceutically acceptable salt thereof,

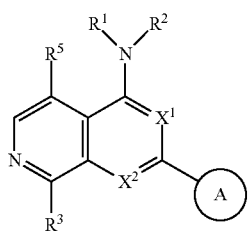

for promoting liver regeneration and liver regrowth, wherein $X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N=) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

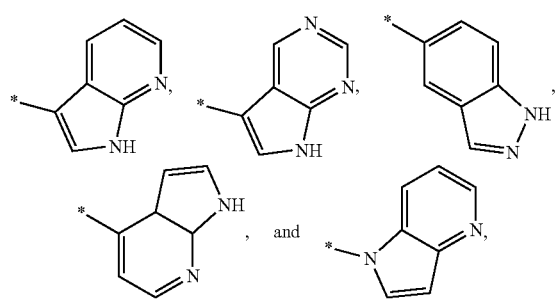

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_1$-6alkylamino, di-($C_{1-6}$alkyl)amino, $C_{3-6}$ cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by $R^0$ or —C(O)$R^0$;

—$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
—C(O)$R^8$, wherein $R^8$ is $R^0$ or —NH—$C_{1-6}$alkyl-C(O)$R^0$;
—S(O)$_2$$C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino; 6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and
9- or 10-membered fused bicyclic heteroaryl comprising, as ring member, 1 to 2 heteroatoms independently selected from N and O;
(b) —S(O)$_2$$C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$;
or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 204

Use of a compound of the Formula A1 or a pharmaceutically acceptable salt thereof, for promoting liver regeneration and liver regrowth according to embodiment 203, wherein the compound is of the formula selected from Formulae I to IV:

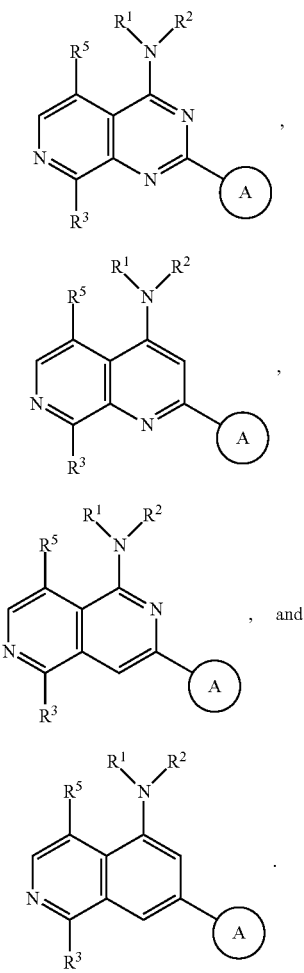

Embodiment 205

Use of a compound of Formula A1 or a pharmaceutically acceptable salt thereof, for promoting liver regeneration and liver regrowth according to embodiment 203, wherein the compound is selected from:
2-methyl-1-(2-methyl-2-{[2-(pyridin-4-yl)pyrido[3,4-d]pyrimidin-4-yl]amino}propoxy)propan-2-ol;
dimethyl(3-methyl-3-{[2-(pyridin-4-yl)pyrido[3,4-d]pyrimidin-4-yl]amino}butyl)amine;
N-(1-amino-2-methylpropan-2-yl)-2-(pyridin-4-yl)pyrido[3,4-d]pyrimidin-4-amine;
8-chloro-N-(1-methyl cyclopropyl)-2-(pyridin-4-yl)pyrido[3,4-d]pyrimidin-4-amine;
8-methyl-N-(1-methylcyclopropyl)-2-(pyridin-4-yl)pyrido[3,4-d]pyrimidin-4-amine;
N-(tert-butyl)-5-chloro-2-(pyridin-4-yl)pyrido[3,4-d]pyrimidin-4-amine;
5-chloro-N-(1-methyl cyclopropyl)-2-(pyridin-4-yl)pyrido[3,4-d]pyrimidin-4-amine;
N-tert-butyl-2-(pyrimidin-4-yl)-1,7-naphthyridin-4-amine;
N-tert-butyl-2-(3-methyl-1H-pyrazol-4-yl)-1,7-naphthyridin-4-amine;
N-tert-butyl-2-(pyrimidin-4-yl)-1,7-naphthyridin-4-amine;
2-(2-aminopyrimidin-4-yl)-N-tert-butyl-1,7-naphthyridin-4-amine;
$N^1,N^1$,3-trimethyl-$N^3$-(2-(3-methyl-1H-pyrazol-4-yl)pyrido[3,4-d]pyrimidin-4-yl)butane-1,3-diamine;
$N^1,N^1$, 3-trimethyl-$N^3$-(2-(3-methyl-1H-pyrazol-4-yl)pyrido[3,4-d]pyrimidin-4-yl)butane-1,3-diamine;
2,2-dimethyl-$N^1$-(2-(pyridin-4-yl)pyrido[3,4-d]pyrimidin-4-yl)propane-1,3-diamine;
2,3-dimethyl-$N^2$-(2-(pyridin-4-yl)pyrido[3,4-d]pyrimidin-4-yl)butane-2,3-diamine;
$N^1,N^1$,2,2-tetramethyl-$N^3$-(2-(pyridin-4-yl)pyrido[3,4-d]pyrimidin-4-yl)propane-1,3-diamine;
4-(4-(tert-butylamino)pyrido[3,4-d]pyrimidin-2-yl)-1,2,5-oxadiazol-3-amine; and
$N^2,N^2$,2-trimethyl-N-(2-(pyridin-4-yl)pyrido[3,4-d]pyrido[3,4-d]pyrimidin-4-yl)propane-1,2-diamine.

Embodiment 206

Use of a compound of Formula A1 or a pharmaceutically acceptable salt thereof, for promoting liver regeneration and liver regrowth according to embodiment 203, wherein the compound is according to any one of embodiments 1 to 180.

Embodiment 207

A method of promoting liver regeneration and liver regrowth, comprising administering to a subject in need thereof a therapeutically effective amount of a compound of Formula A1, or a pharmaceutically acceptable salt thereof,

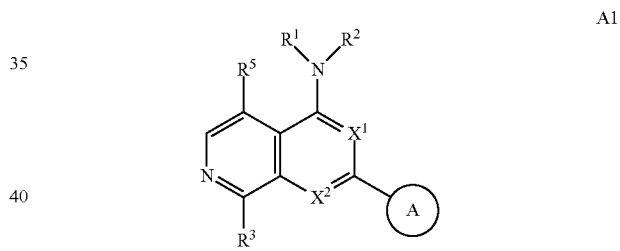

wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

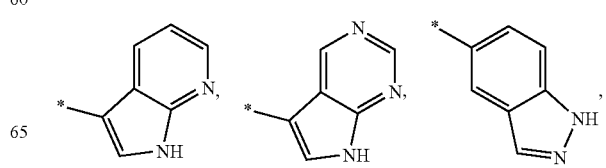

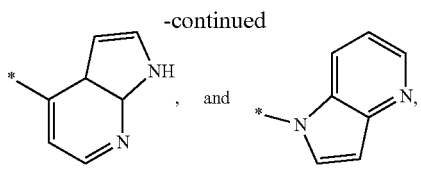

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$ cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by $R^0$ or —$C(O)R^0$;
—$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;
—$C(O)R^8$, wherein $R^8$ is $R^0$ or —NH—$C_{1-6}$alkyl-$C(O)R^0$;
—$S(O)_2C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$ alkyl, $C_{1-6}$haloalkyl, $R^0$, —$NH_2$, $C_{1-6}$alkylamino, and di-($C_{1-6}$alkyl)amino;
6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and
9- or 10-membered fused bicyclic heteroaryl comprising, as ring member, 1 to 2 heteroatoms independently selected from N and O;
(b) —$S(O)_2C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$;
or, $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 208

A method of promoting liver regeneration and liver regrowth, according to embodiment 207, wherein the compound is of the formula selected from Formulae I to IV:

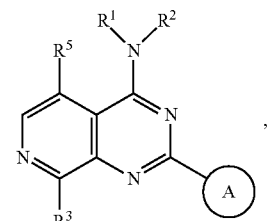

I

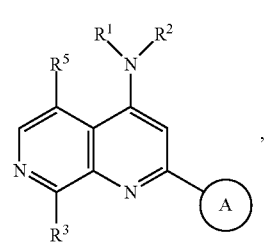

II

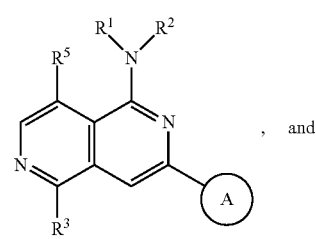

, and

III

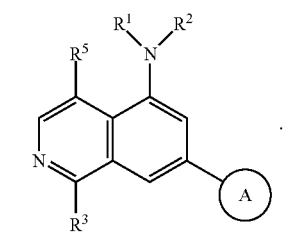

IV

Embodiment 209

A method of promoting liver regeneration and liver regrowth according to embodiment 207, wherein the compound is selected from:
2-methyl-1-(2-methyl-2-{[2-(pyridin-4-yl)pyrido[3,4-d]pyrimidin-4-yl]amino}propoxy)propan-2-ol;

dimethyl(3-methyl-3-{[2-(pyridin-4-yl)pyrido[3,4-d]py-rimidin-4-yl]amino}butyl)amine;
N-(1-amino-2-methylpropan-2-yl)-2-(pyridin-4-yl)pyrido[3,4-d]pyrimidin-4-amine;
8-chloro-N-(1-methylcyclopropyl)-2-(pyridin-4-yl)pyrido[3,4-d]pyrimidin-4-amine;
8-methyl-N-(1-methylcyclopropyl)-2-(pyridin-4-yl)pyrido[3,4-d]pyrimidin-4-amine;
N-(tert-butyl)-5-chloro-2-(pyridin-4-yl)pyrido[3,4-d]pyrimidin-4-amine;
5-chloro-N-(1-methylcyclopropyl)-2-(pyridin-4-yl)pyrido[3,4-d]pyrimidin-4-amine;
N-tert-butyl-2-(pyrimidin-4-yl)-1,7-naphthyridin-4-amine;
N-tert-butyl-2-(3-methyl-1H-pyrazol-4-yl)-1,7-naphthyridin-4-amine;
N-tert-butyl-2-(pyrimidin-4-yl)-1,7-naphthyridin-4-amine;
2-(2-aminopyrimidin-4-yl)-N-tert-butyl-1,7-naphthyridin-4-amine;
$N^1,N^1$,3-trimethyl-$N^3$-(2-(3-methyl-1H-pyrazol-4-yl)pyrido[3,4-d]pyrimidin-4-yl)butane-1,3-diamine;
$N^1,N^1$,3-trimethyl-$N^3$-(2-(3-methyl-1H-pyrazol-4-yl)pyrido[3,4-d]pyrimidin-4-yl)butane-1,3-diamine;
2,2-dimethyl-$N^1$-(2-(pyridin-4-yl)pyrido[3,4-d]pyrimidin-4-yl)propane-1,3-diamine;
2,3-dimethyl-$N^2$-(2-(pyridin-4-yl)pyrido[3,4-d]pyrimidin-4-yl)butane-2,3-diamine;
$N^1,N^1$,2,2-tetramethyl-$N^3$-(2-(pyridin-4-yl)pyrido[3,4-d]pyrimidin-4-yl)propane-1,3-diamine;
4-(4-(tert-butylamino)pyrido[3,4-d]pyrimidin-2-yl)-1,2,5-oxadiazol-3-amine; and
$N^2,N^2$,2-trimethyl-$N^1$-(2-(pyridin-4-yl)pyrido[3,4-d]pyrimidin-4-yl)propane-1,2-diamine.

Embodiment 210

A method of promoting liver regeneration and liver regrowth according to embodiment 207, wherein the compound is according to any one of embodiments 1 to 180.

Embodiment 211

Use of a compound of Formula A1, or a pharmaceutically acceptable salt thereof,

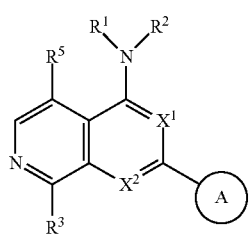

in the manufacture of a medicament for promoting liver regeneration and liver regrowth, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

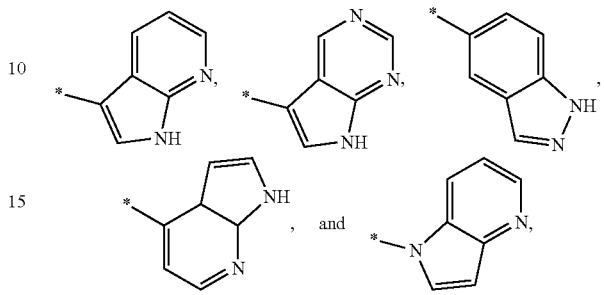

wherein "*" represents the point of attachment of ring A to the remainder of the molecule,
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by
$R^0$ or —$C(O)R^0$;
—$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;
—$C(O)R^8$, wherein $R^8$ is $R^0$ or —NH—$C_{1-6}$alkyl-$C(O)R^0$;
—$S(O)_2C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and
9- or 10-membered fused bicyclic heteroaryl comprising, as ring member, 1 to 2 heteroatoms independently selected from N and O;
(b) —$S(O)_2C_{1-6}$alkyl;
(c) phenyl that is unsubstituted or substituted by 1 to 2 substituents independently selected from halogen, $C_{1-6}$alkyl and $R^0$;

(d) C$_{3-6}$cycloalkyl that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$; and (e) 4-membered heterocycloalkyl comprising, as ring members, 1 to 2 heteroatoms selected from N, O and S and that is unsubstituted or substituted by 1 to 2 substituents independently selected from C$_{1-6}$haloalkyl, R$^0$, C$_{1-6}$alkylamino, di-(C$_{1-6}$alkyl)amino, —C(O)R$^0$, and C$_{1-6}$alkyl that is unsubstituted or substituted by R$^0$ or —C(O)R$^0$;

or R$^1$ and R$^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by R$^1$ and R$^2$ taken together with the nitrogen atom to which both are bound is unsubstituted or substituted by 1 to 3 substituents independently selected from halogen, C$_{1-6}$alkyl, C$_{1-6}$haloalkyl, and R$^0$;

R$^3$ is selected from hydrogen, halogen and C$_{1-6}$alkyl; and

R$^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by R$^0$.

Embodiment 212

Use of a compound of Formula A1 or a pharmaceutically acceptable salt thereof, in the manufacture of a medicament for promoting liver regeneration and liver regrowth according to embodiment 211, wherein the compound is of the formula selected from Formulae I to IV:

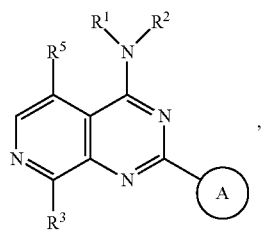

I

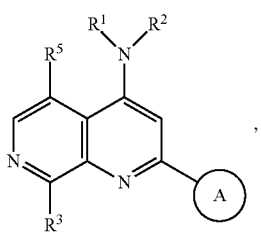

II

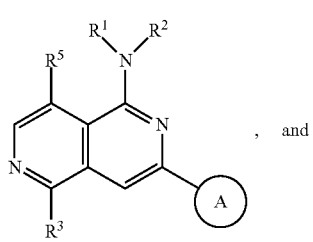

III, and

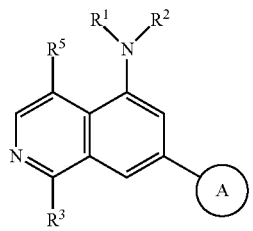

IV

Embodiment 213

Use of a compound of Formula A1 or a pharmaceutically acceptable salt thereof, in the manufacture of a medicament for promoting liver regeneration and liver regrowth according to embodiment 211, wherein the compound is selected from:

2-methyl-1-(2-methyl-2-{[2-(pyridin-4-yl)pyrido[3,4-d]pyrimidin-4-yl]amino}propoxy)propan-2-ol;
dimethyl(3-methyl-3-{[2-(pyridin-4-yl)pyrido[3,4-d]pyrimidin-4-yl]amino}butyl)amine;
N-(1-amino-2-methylpropan-2-yl)-2-(pyridin-4-yl)pyrido[3,4-d]pyrimidin-4-amine;
8-chloro-N-(1-methyl cyclopropyl)-2-(pyridin-4-yl)pyrido[3,4-d]pyrimidin-4-amine;
8-methyl-N-(1-methylcyclopropyl)-2-(pyridin-4-yl)pyrido[3,4-d]pyrimidin-4-amine;
N-(tert-butyl)-5-chloro-2-(pyridin-4-yl)pyrido[3,4-d]pyrimidin-4-amine;
5-chloro-N-(1-methyl cyclopropyl)-2-(pyridin-4-yl)pyrido[3,4-d]pyrimidin-4-amine;
N-tert-butyl-2-(pyrimidin-4-yl)-1,7-naphthyridin-4-amine;
N-tert-butyl-2-(3-methyl-1H-pyrazol-4-yl)-1,7-naphthyridin-4-amine;
N-tert-butyl-2-(pyrimidin-4-yl)-1,7-naphthyridin-4-amine;
2-(2-aminopyrimidin-4-yl)-N-tert-butyl-1,7-naphthyridin-4-amine;
N$^1$,N$^1$,3-trimethyl-N$^3$-(2-(3-methyl-1H-pyrazol-4-yl)pyrido[3,4-d]pyrimidin-4-yl)butane-1,3-diamine;
N$^1$,N$^1$, 3-trimethyl-N$^3$-(2-(3-methyl-1H-pyrazol-4-yl)pyrido[3,4-d]pyrimidin-4-yl)butane-1,3-diamine;
2,2-dimethyl-N$^1$-(2-(pyridin-4-yl)pyrido[3,4-d]pyrimidin-4-yl)propane-1,3-diamine;
2,3-dimethyl-N$^2$-(2-(pyridin-4-yl)pyrido[3,4-d]pyrimidin-4-yl)butane-2,3-diamine;
N$^1$,N$^1$,2,2-tetramethyl-N$^3$-(2-(pyridin-4-yl)pyrido[3,4-d]pyrimidin-4-yl)propane-1,3-diamine;
4-(4-(tert-butylamino)pyrido[3,4-d]pyrimidin-2-yl)-1,2,5-oxadiazol-3-amine; and
N$^2$,N$^2$,2-trimethyl-N-(2-(pyridin-4-yl)pyrido[3,4-d]pyrido[3,4-d]pyrimidin-4-yl)propane-1,2-diamine.

Embodiment 214

Use of a compound of Formula A1 or a pharmaceutically acceptable salt thereof, in the manufacture of a medicament for promoting liver regeneration and liver regrowth according to embodiment 211, wherein the compound is according to any one of embodiments 1 to 180.

In another embodiment, the present invention relates to a pharmaceutical composition comprising at least one of the compounds of the present invention or a pharmaceutically acceptable salt thereof.

In another embodiment, the present invention relates a pharmaceutical composition comprising at least one of the compounds of the present invention or a pharmaceutically acceptable salt thereof and at least one pharmaceutically acceptable carrier, diluent or excipient.

In another embodiment, the present invention relates to a compound of the present invention, or a pharmaceutically acceptable salt thereof, or a pharmaceutical composition for use as a medicament.

In another embodiment, the present invention relates to a pharmaceutical composition for use in promoting liver regeneration and liver regrowth, comprising a compound of Formula A1 or subformulae thereof, or a pharmaceutically acceptable salt thereof.

In another embodiment, the present invention also relates the use of a compound of Formula A1 or subformulae thereof, or a pharmaceutically acceptable salt thereof for the manufacture of a medicament for promoting liver regeneration and liver regrowth alone, or optionally in combination with another compound of Formula A1 or subformulae thereof, or a pharmaceutically acceptable salt thereof and/or at least one other type of therapeutic agent.

In another embodiment, the present invention relates to a method for promoting liver regeneration and liver regrowth comprising administering to a subject in need thereof a therapeutically effective amount of a compound of Formula A1 or subformulae thereof, or a pharmaceutically acceptable salt thereof.

In another embodiment, the present invention relates to a method for promoting liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution.

In another embodiment, the present invention relates to a method for promoting liver regeneration and liver regrowth comprising administering to a subject in need thereof a therapeutically effective amount of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a pharmaceutically acceptable salt thereof.

In another embodiment, the present invention relates to a method for promoting liver regeneration and liver regrowth comprising administering to a subject in need thereof a therapeutically effective amount of an agent capable of inhibiting the activity of LATS kinases; thereby inducing YAP translocation and driving downstream gene expression for cell proliferation. In a preferred embodiment, the agent is a compound according to any one of embodiments 1 to 180.

In another embodiment, the present invention relates to a method for expanding a population of liver cells ex vivo which comprises contacting the liver cells with a compound according to any one of embodiments 1 to 180. In a preferred embodiment, the method further comprises gene editing said liver cells. Preferably said gene editing targets a gene involved in the host versus graft immune response.

In another embodiment, the present invention relates to a method for expanding a population of liver progenitor cells ex vivo which comprises contacting the liver progenitor cells with a compound according to any one of embodiments 1 to 180. In a preferred embodiment, the method further comprises gene editing said liver progenitor cells.

Preferably said gene editing targets a gene involved in the host versus graft immune response.

In another embodiment, the present invention relates to a population of liver cells obtained by contacting liver cells with a compound according to any one of embodiments 1 to 180. In a preferred embodiment, the liver cells obtained by contacting liver cells with a compound according to any one of embodiments 1 to 180 have been gene edited. Preferably said gene editing targets a gene involved in the host versus graft immune response.

In another embodiment, the present invention relates to a population of liver progenitor cells obtained by contacting liver progenitor cells with a compound according to any one of embodiments 1 to 180. In a preferred embodiment, the liver progenitor cells obtained by contacting liver progenitor cells with a compound according to any one of embodiments 1 to 180 have been gene edited. Preferably said gene editing targets a gene involved in the host versus graft immune response.

Embodiment 215

A compound of Formula A1, or a pharmaceutically acceptable salt thereof,

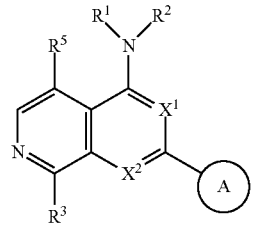

A1 for use in promoting wound healing, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

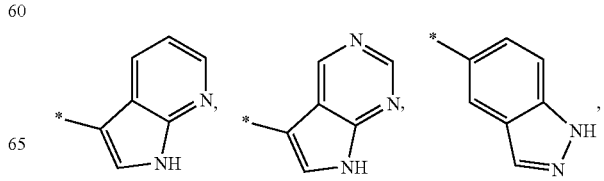

-continued

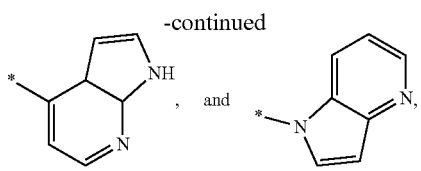

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$ cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by $R^0$ or —$C(O)R^0$;
—$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;
—$C(O)R^8$, wherein $R^8$ is $R^0$ or —NH—$C_{1-6}$alkyl-$C(O)R^0$;
—$S(O)_2C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and
9- or 10-membered fused bicyclic heteroaryl comprising, as ring member, 1 to 2 heteroatoms independently selected from N and O;
(b) —$S(O)_2C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$;
or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered heteroC$_{3-8}$alkyl of the —NH-(3- to 8-membered heteroalkyl) comprises 1 to 2 oxygen atoms as chain members and is unsubstituted or substituted by $R^0$.

Embodiment 216

A compound of Formula A1 or a pharmaceutically acceptable salt thereof, for use in promoting wound healing according to embodiment 215, wherein the compound is of the formula selected from Formulae I to IV:

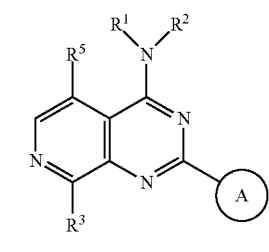
I

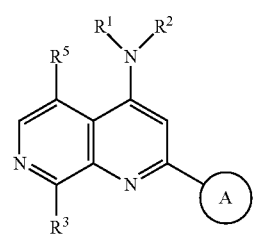
II

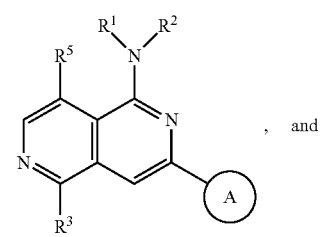
, and
III

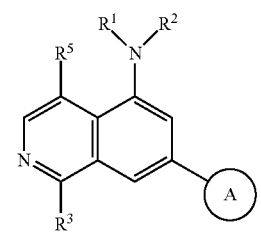
IV

Embodiment 217

A compound of Formula A1 or a pharmaceutically acceptable salt thereof, for use in promoting wound healing according to embodiment 215, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; 2-(pyridin-4-yl)-4-(3-(trifluoromethyl)piperazin-1-yl)pyrido[3,4-d]pyrimidine; N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 218

A compound of the Formula A1 or a pharmaceutically acceptable salt thereof, for use in promoting wound healing according to embodiment 215, wherein the compound is according to any one of embodiments 1 to 180.

Embodiment 219

Use of a compound of the Formula A1, or a pharmaceutically acceptable salt thereof,

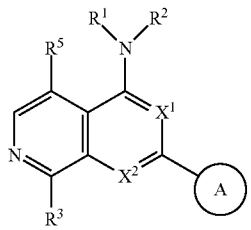

A1 for promoting wound healing, wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

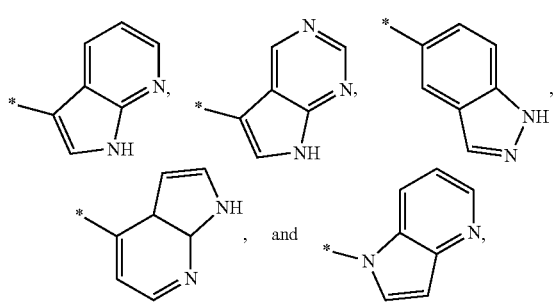

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$ cycloalkyl, and phenylsulfonyl;
$R^0$ is hydroxyl or $C_{1-6}$alkoxy;

$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by $R^0$ or —C(O)$R^0$;
—$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
—C(O)$R^8$, wherein $R^8$ is $R^0$ or —NH—$C_{1-6}$alkyl-C(O)$R^0$;
—S(O)$_2C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;
phenyl that is unsubstituted or substituted by halogen;
5- or 6-membered monocyclic heteroaryl comprising, as ring members, 1 to 4 heteroatoms independently selected from N and O; and
9- or 10-membered fused bicyclic heteroaryl comprising, as ring member, 1 to 2 heteroatoms independently selected from N and O;
(b) —S(O)$_2C_{1-6}$alkyl;
(c) phenyl that is unsubstituted or substituted by 1 to 2 substituents independently selected from halogen, $C_{1-6}$alkyl and $R^0$;
(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$; and
(e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$alkyl)amino, —C(O)$R^0$, and $C_{1-6}$alkyl that is unsubstituted or substituted by $R^0$ or —C(O)$R^0$;
or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;
$R^3$ is selected from hydrogen, halogen and $C_{1-6}$alkyl; and
$R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 220

Use of a compound of the Formula A1 or a pharmaceutically acceptable salt thereof, for promoting wound healing according to embodiment 219, wherein the compound is of the formula selected from Formulae I to IV:

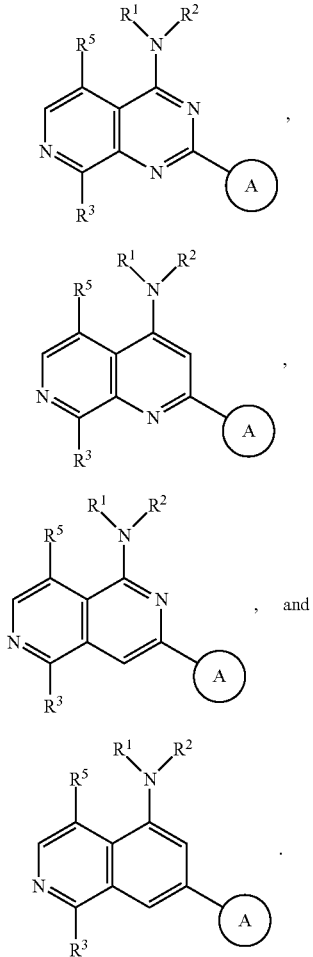

I, II, III, and IV

Embodiment 221

Use of a compound of Formula A1 or a pharmaceutically acceptable salt thereof, for promoting wound healing according to embodiment 219, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; and 2-(pyridin-4-yl)-4-(3-(trifluoromethyl) piperazin-1-yl)pyrido[3,4-d]pyrimidine.

Embodiment 222

Use of a compound of Formula A1 or a pharmaceutically acceptable salt thereof, for promoting wound healing according to embodiment 219, wherein the compound is according to any one of embodiments 1 to 180.

Embodiment 223

A method of promoting wound healing, comprising administering to a subject in need thereof a therapeutically effective amount of a compound of Formula A1, or a pharmaceutically acceptable salt thereof,

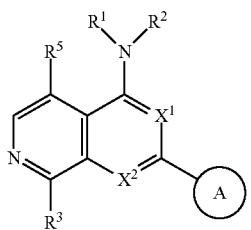

A1 wherein
$X^1$ and $X^2$ are each independently CH or N;
Ring A is
(a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or
(b) a 9-membered fused bicyclic heteroaryl that is selected from

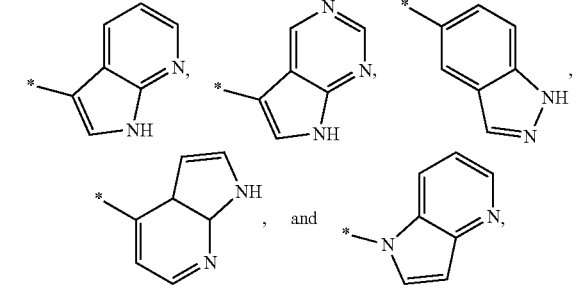

wherein "*" represents the point of attachment of ring A to the remainder of the molecule;
wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$ cycloalkyl, and phenylsulfonyl;
$R^0$ is hydroxyl or $C_{1-6}$alkoxy;
$R^1$ is hydrogen or $C_{1-6}$alkyl;
$R^2$ is selected from
(a) $C_{1-8}$alkyl that is unsubstituted or substituted by 1 to 3 substituents independently selected from
halogen;
cyano;
oxo;
$C_2$alkenyl;
$C_2$alkynyl;
$C_{1-6}$haloalkyl;
—$OR^6$, wherein $R^6$ is selected from hydrogen, $C_{1-6}$alkyl that is unsubstituted or substituted by $R^0$ or —C(O)$R^0$;
—$NR^{7a}R^{7b}$, wherein $R^{7a}$ is hydrogen or $C_{1-6}$alkyl, and $R^{7b}$ is selected from hydrogen, —C(O)$R^0$, $C_{1-6}$alkyl that is unsubstituted or substituted by —C(O)$R^0$;
—C(O)$R^8$, wherein $R^8$ is $R^0$ or —NH—$C_{1-6}$alkyl-C(O)$R^0$;
—S(O)$_2C_{1-6}$alkyl;
monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^O$, —$NH_2$, $C_{1-6}$alkylamino, and di-($C_{1-6}$alkyl)amino;

6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;

phenyl that is unsubstituted or substituted by halogen;

5- or 6-membered monocyclic heteroaryl comprising, as ring members, 1 to 4 heteroatoms independently selected from N and O; and 9- or 10-membered fused bicyclic heteroaryl comprising, as ring member, 1 to 2 heteroatoms independently selected from N and O;

(b) —$S(O)_2C_{1-6}$alkyl;

(c) phenyl that is unsubstituted or substituted by 1 to 2 substituents independently selected from halogen, $C_{1-6}$alkyl and $R^O$;

(d) $C_{3-6}$cycloalkyl that is unsubstituted or substituted by 1 to 2 substituents independently selected from $C_{1-6}$haloalkyl, $R^O$, $C_{1-6}$alkylamino, di-($C_{1-6}$alkyl)amino, —$C(O)R^O$, and $C_{1-6}$alkyl that is unsubstituted or substituted by $R^O$ or —$C(O)R^O$; and (e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^O$, $C_{1-6}$alkylamino, di-($C_{1-6}$alkyl)amino, —$C(O)R^O$, and $C_{1-6}$alkyl that is unsubstituted or substituted by $R^O$ or —$C(O)R^O$;

or, $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^O$;

$R^3$ is selected from hydrogen, halogen and $C_{1-6}$alkyl; and $R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^O$.

Embodiment 224

A method of promoting wound healing, according to embodiment 223, wherein the compound is of the formula selected from Formulae I to IV:

I

II

III, and

IV

Embodiment 225

A method of promoting wound healing according to embodiment 223, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; 2-(pyridin-4-yl)-4-(3-(trifluoromethyl)piperazin-1-yl)pyrido[3,4-d]pyrimidine; N-(tert-butyl)-2-(pyridin-4-yl)-1,7-naphthyridin-4-amine; and N-methyl-2-(pyridin-4-yl)-N-[(2S)-1,1,1-trifluoropropan-2-yl]pyrido[3,4-d]pyrimidin-4-amine.

Embodiment 226

A method of promoting wound healing according to embodiment 223, wherein the compound is according to any one of embodiments 1 to 180.

Embodiment 227

Use of a compound of Formula A1, or a pharmaceutically acceptable salt thereof,

A1 in the manufacture of a medicament for promoting wound healing, wherein $X^1$ and $X^2$ are each independently CH or N;

Ring A is (a) a 5- or 6-membered monocyclic heteroaryl that is linked to the remainder of the molecule through a carbon ring member and comprises, as ring member, 1 to 4 heteroatoms that are independently selected from N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or (b) a 9-membered fused bicyclic heteroaryl that is selected from

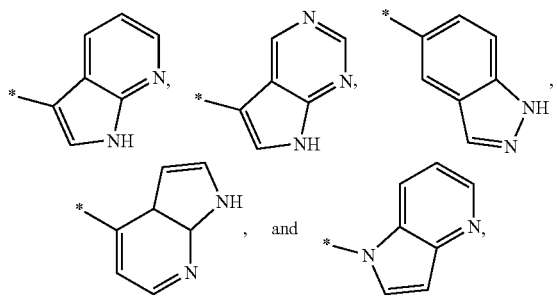

wherein "*" represents the point of attachment of ring A to the remainder of the molecule;

wherein ring A is unsubstituted or substituted by 1 to 2 substituents independently selected from halogen, cyano, $C_{1-6}$alkyl, $C_{1-6}$haloalkyl, —$NH_2$, $C_{1-6}$alkylamino, di-($C_{1-6}$alkyl)amino, $C_{3-6}$ cycloalkyl, and phenylsulfonyl;

$R^0$ is hydroxyl or $C_{1-6}$alkoxy;

$R^1$ is hydrogen or $C_{1-6}$alkyl;

$R^2$ is selected from (a) $C_{1-8}$alkyl that is unsubstituted or substituted by 1 to 3 substituents independently selected from halogen;

cyano;

oxo;

$C_2$alkenyl;

$C_2$alkynyl;

$C_{1-6}$haloalkyl;

—$OR^6$, wherein $R^6$ is selected from hydrogen, $C_{1-6}$alkyl that is unsubstituted or substituted by $R^0$ or —$C(O)R^0$;

—$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;

—$C(O)R^8$, wherein $R^8$ is $R^0$ or —NH—$C_{1-6}$alkyl-$C(O)R^0$;

—$S(O)_2C_{1-6}$alkyl;

monocyclic $C_{3-6}$cycloalkyl or polycyclic $C_{7-10}$cycloalkyl that are each unsubstituted or substituted by 1 to 2 substituents independently selected from halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;

6-membered heterocycloalkyl comprising, as ring members, 1 to 2 heteroatoms independently selected from N, O and S and that is unsubstituted or substituted by 1 to 2 substituents independently selected from hydroxyl, halogen, $C_{1-6}$alkyl, $C_{1-6}$alkylamino, and di-($C_{1-6}$alkyl)amino;

phenyl that is unsubstituted or substituted by halogen;

5- or 6-membered monocyclic heteroaryl comprising, as ring members, 1 to 4 heteroatoms independently selected from N and O; and 9- or 10-membered fused bicyclic heteroaryl comprising, as ring member, 1 to 2 heteroatoms independently selected from N and O;

(b) —$S(O)_2C_{1-6}$alkyl;

(c) phenyl that is unsubstituted or substituted by 1 to 2 substituents independently selected from halogen, $C_{1-6}$alkyl and $R^0$;

(d) $C_{3-6}$cycloalkyl that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$; and (e) 4-membered heterocycloalkyl comprising, as ring members, 1 to 2 heteroatoms selected from N, O and S and that is unsubstituted or substituted by 1 to 2 substituents independently selected from $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$;

or $R^1$ and $R^2$ can be taken together with the nitrogen atom to which both are bound to form a 4- to 6-membered heterocycloalkyl that can include, as ring members, 1 to 2 additional heteroatoms independently selected from N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from halogen, $C_{1-6}$alkyl, $C_{1-6}$haloalkyl, and $R^0$;

$R^3$ is selected from hydrogen, halogen and $C_{1-6}$alkyl; and $R^5$ is selected from hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

Embodiment 228

Use of a compound of Formula A1 or a pharmaceutically acceptable salt thereof, in the manufacture of a medicament for promoting wound healing according to embodiment 227, wherein the compound is of the formula selected from Formulae I to IV:

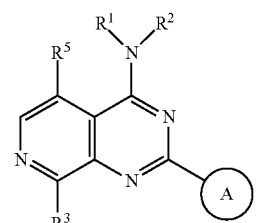

I

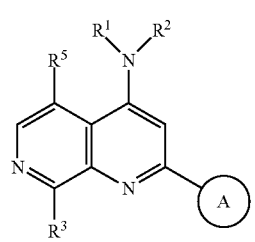

II

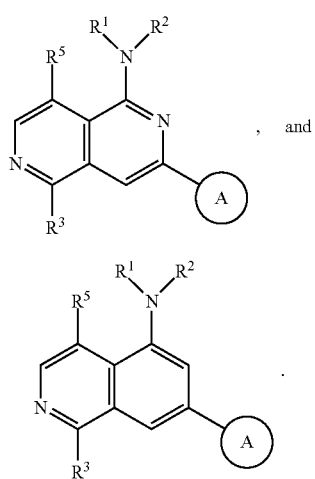

Embodiment 229

Use of a compound of Formula A1 or a pharmaceutically acceptable salt thereof, in the manufacture of a medicament for promoting wound healing according to embodiment 227, wherein the compound is selected from 3-(pyridin-4-yl)-N-(1-(trifluoromethyl)cyclopropyl)-2,6-naphthyridin-1-amine; N-(1-methylcyclopropyl)-7-(pyridin-4-yl)isoquinolin-5-amine; and 2-(pyridin-4-yl)-4-(3-(trifluoromethyl)piperazin-1-yl)pyrido[3,4-d]pyrimidine.

Embodiment 230

Use of a compound of Formula A1 or a pharmaceutically acceptable salt thereof, in the manufacture of a medicament for promoting wound healing according to embodiment 227, wherein the compound is according to any one of embodiments 1 to 180.

In another embodiment, the present invention relates to a composition comprising at least one of the compounds of Formula A2 or subformulae thereof or a pharmaceutically acceptable salt thereof.

In another embodiment, the present invention relates a pharmaceutical composition comprising at least one of the compounds of Formula A2 or subformulae thereof, or a pharmaceutically acceptable salt thereof and at least one pharmaceutically acceptable carrier, diluent or excipient.

In another embodiment, the present invention relates to a compound of Formula A2 or subformulae thereof, or a pharmaceutically acceptable salt thereof, or a pharmaceutical composition for use as a medicament.

In another embodiment, the present invention relates to a pharmaceutical composition for use in promoting liver regeneration and liver regrowth, comprising a compound of Formula A1 or subformulae thereof, or a pharmaceutically acceptable salt thereof.

In another embodiment, the present invention also relates the use of a compound of Formula A1 or subformulae thereof, or a pharmaceutically acceptable salt thereof for the manufacture of a medicament for promoting liver regeneration and liver regrowth alone, or optionally in combination with another compound of Formula A1 or subformulae thereof, or a pharmaceutically acceptable salt thereof and/or at least one other type of therapeutic agent.

In another embodiment, the present invention relates to a method for promoting liver regeneration and liver regrowth comprising administering to a subject in need thereof a therapeutically effective amount of a compound of Formula A1 or subformulae thereof, or a pharmaceutically acceptable salt thereof.

In another embodiment, the present invention relates to a method for promoting liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution.

In another embodiment, the present invention related to a method for promoting liver regeneration and liver regrowth comprising administering to a subject in need thereof a therapeutically effective amount of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a pharmaceutically acceptable salt thereof.

In another embodiment, the present invention relates to a pharmaceutical composition for use in promoting wound healing, comprising a compound of Formula A1 or subformulae thereof, or a pharmaceutically acceptable salt thereof.

In another embodiment, the present invention also relates to the use of a compound of Formula A1 or subformulae thereof, or a pharmaceutically acceptable salt thereof for the manufacture of a medicament for promoting wound healing alone, or optionally in combination with another compound of Formula A1 or subformulae thereof, or a pharmaceutically acceptable salt thereof and/or at least one other type of therapeutic agent.

In another embodiment, the present invention relates to a method of promoting wound healing comprising administering to a subject in need thereof a therapeutically effective amount of a compound of Formula A1 or subformulae thereof, or a pharmaceutically acceptable salt thereof.

In another embodiment, the present invention relates to a method of promoting wound healing comprising treating or ameliorating the symptomology of burns, acute and chronic skin ulcers, wherein the skin ulcers include, but are not limited to vascular ulcers, diabetic ulcers, and pressure ulcers.

In another embodiment, the present invention related to a method of promoting wound healing comprising administering to a subject in need thereof a therapeutically effective amount of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a pharmaceutically acceptable salt thereof.

In another embodiment, the present invention relates to a method of treatment of an ocular disease or disorder comprising administering to a subject in need thereof a cell population, wherein the population has been grown in the presence of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a salt thereof.

In another embodiment, the present invention relates to a method of treatment of an ocular disease or disorder comprising administering to a subject in need thereof a limbal stem cell population, wherein the population has been grown in the presence of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a salt thereof.

In another embodiment, the present invention relates to a method of treatment of an ocular disease or disorder comprising administering to a subject in need thereof a corneal endothelial cell population, wherein the population has been grown in the presence of an agent capable of inhibiting the activity of LATS1 and LATS2 kinases; thereby inducing YAP translocation and driving downstream gene expression for cell proliferation. In a further embodiment, the agent is a compound of Formula A1 or subformulae thereof, or a pharmaceutically acceptable salt thereof.

In another embodiment, the present invention relates to a method of promoting ocular wound healing comprising administering to an eye of a subject a therapeutically effective amount of a compound of the invention. In one embodiment, the ocular wound is a corneal wound. In other embodiments, the ocular wound is an injury or surgical wound.

DEFINITIONS

The general terms used hereinbefore and hereinafter preferably have within the context of this invention the following meanings, unless otherwise indicated, where more general terms wherever used may, independently of each other, be replaced by more specific definitions or remain, thus defining more detailed embodiments of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "a," "an," "the" and similar terms used in the context of the present invention (especially in the context of the claims) are to be construed to cover both the singular and plural unless otherwise indicated herein or clearly contradicted by the context.

As used herein, the term "$C_{1-8}$alkyl" refers to a straight or branched hydrocarbon chain radical consisting solely of carbon and hydrogen atoms, containing no unsaturation, having from one to eight carbon atoms, and which is attached to the rest of the molecule by a single bond. The term "$C_{1-4}$alkyl" is to be construed accordingly. As used herein, the term "n-alkyl" refers to straight chain (unbranced) alkyl radical as defined herein. Examples of $C_{1-8}$alkyl include, but are not limited to, methyl, ethyl, n-propyl, 1-methylethyl (iso-propyl), n-butyl, n-pentyl, 1,1-dimethylethyl (t-butyl), —$C(CH_3)_2CH_2CH(CH_3)_2$ and —$C(CH_3)_2CH_3$.

As used herein, the term "$C_{2-6}$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "$C_{2-4}$alkenyl" is to be construed accordingly. Examples of $C_{2-6}$alkenyl include, but are not limited to, ethenyl, prop-1-enyl, but-1-enyl, pent-1-enyl, pent-4-enyl and penta-1,4-dienyl.

The term "alkylene" refers to a divalent alkyl group. For example, the term "$C_{1-6}$alkylene" or "$C_1$ to $C_6$ alkylene" refers to a divalent, straight, or branched aliphatic group containing 1 to 6 carbon atoms. Examples of alkylene include, but are not limited to methylene (—$CH_2$—), ethylene (—$CH_2CH_2$—), n-propylene (—$CH_2CH_2CH_2$—), iso-propylene (—$CH(CH_3)CH_2$—), n-butylene, sec-butylene, iso-butylene, tert-butylene, n-pentylene, isopentylene, neopentylene and n-hexylene.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$alkynyl" is to be construed accordingly. Examples of $C_{2-6}$ alkynyl include, but are not limited to, ethynyl, prop-1-ynyl, but-1-ynyl, pent-1-ynyl, pent-4-ynyl and penta-1,4-diynyl.

As used herein, the term "$C_{1-6}$alkoxy" refers to a radical of the formula —$OR_a$, where $R_a$ is a $C_{1-6}$alkyl radical as generally defined above. "$C_{1-6}$ alkoxy" or "$C_1$ to $C_6$ alkoxy" is intended to include $C_1$, $C_2$, $C_3$, $C_4$, $C_5$, and $C_6$ alkoxy groups (that is 1 to 6 carbons in the alkyl chain). Examples of $C_{1-6}$alkoxy include, but are not limited to, methoxy, ethoxy, propoxy, isopropoxy, butoxy, isobutoxy, pentoxy, and hexoxy.

As used herein, the term "$C_{1-6}$alkylamino" refers to a radical of the formula —NH—$R_a$, where $R_a$ is a $C_{1-4}$alkyl radical as defined above.

As used herein, the term "di-($C_{1-6}$alkyl)amino" refers to a radical of the formula —N($R_a$)—$R_a$, where each $R_a$ is a $C_{1-4}$alkyl radical, which may be the same or different, as defined above.

As used herein, the term "cyano" means the radical *—C≡N. The term "cycloalkyl" refers to nonaromatic carbocyclic ring that is a fully hydrogenated ring, including mono-, bi- or poly-cyclic ring systems. "$C_{3-10}$cycloalkyl" or "$C_3$ to $C_{10}$ cycloalkyl" is intended to include $C_3$, $C_4$, $C_5$, $C_6$, $C_7$, $C_8$, $C_9$ and $C_{10}$ cycloalkyl groups that is 3 to 10 carbon ring members). Example cycloalkyl groups include, but are not limited to, cyclopropyl, cyclobutyl, cyclopentyl, cyclohexyl and norbornyl.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halogen" refers to bromo, chloro, fluoro or iodo; preferably fluoro, chloro or bromo.

As used herein, the term "haloalkyl" is intended to include both branched and straight-chain saturated alkyl groups as defined above having the specified number of carbon atoms, substituted with one or more halogens. For example, "$C_{1-6}$ haloalkyl" or "$C_1$ to $C_6$ haloalkyl" is intended to include $C_1$, $C_2$, $C_3$, $C_4$, $C_5$, and $C_6$ alkyl chain. Examples of haloalkyl include, but are not limited to, fluoromethyl, difluoromethyl, trifluoromethyl, trichloromethyl, pentafluoroethyl, pentachloroethyl, 2,2,2-trifluoroethyl, 1,3-dibromopropan-2-yl, 3-bromo-2-fluoropropyl and 1,4,4-trifluorobutan-2-yl, heptafluoropropyl, and heptachloropropyl.

"Heteroalkyl", as used herein, refers to an alkyl, as defined herein, where one or more of the carbon atoms within the alkyl chain are replaced by heteroatoms independently selected from N, O and S. In $C_{X-Y}$heteroalkyl or x- to y-membered heteroalkyl, as used herein, x-y describe the number of chain atoms (carbon and heteroatoms) on the heteroalkyl. For example $C_{3-8}$heteroalkyl refers to an alkyl chain with 3 to 8 chain atoms. Further, heteroalkyl as defined herein the atom linking the radical to the remainder of the molecule must be a carbon. Representative example of 3- to 8-membered heteroalkyl include, but are not limited to —(CH$_2$)OCH$_3$, —(CH$_2$)$_2$OCH(CH$_3$)$_2$, —(CH$_2$)$_2$—O—(CH$_2$)$_2$—OH and —(CH$_2$)$_2$—(O—(CH$_2$)$_2$)$_2$—OH.

The term "heteroaryl" refers to aromatic moieties containing at least one heteroatom (e.g., oxygen, sulfur, nitrogen or combinations thereof) within a 5- to 10-membered aromatic ring system Examples of heteroaryl include, but are not limited to pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl and 1H-benzo[d][1,2,3]triazolyl. The heteroaromatic moiety may consist of a single or fused ring system. A typical single heteroaryl ring is a 5- to 6-membered ring containing one to four heteroatoms independently selected from N, O and S and a typical fused heteroaryl ring system is a 9- to 10-membered ring system containing one to four heteroatoms independently selected from N, O and S. The fused heteroaryl ring system may consist of two heteroaryl rings fused together or a heteroaryl fused to an aryl (e.g., phenyl).

As used herein, the term "heteroatoms" refers to nitrogen (N), oxygen (O) or sulfur (S) atoms. Unless otherwise indicated, any heteroatom with unsatisfied valences is assumed to have hydrogen atoms sufficient to satisfy the valences, and when the heteroatom is sulfur, it can be unoxidized (S) or oxidized to S(O) or S(O)$_2$.

The term "hydroxyl" or "hydroxy", as used herein, refers to the radical —OH.

"Heterocycloalkyl" means cycloalkyl, as defined in this application, provided that one or more of the ring carbons indicated, are replaced by a moiety selected from —O—, —N═, —NH—, —S—, —S(O)— and —S(O)$_2$—, Examples of 3 to 8 membered heterocycloalkyl include, but are not limited to oxiranyl, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholinyl, piperazinyl, piperidinyl, pyrazolidinyl, hexahydropyrimidinyl, 1,4-dioxa-8-aza-spiro[4.5]dec-8-yl, thiomorpholinyl, sulfanomorpholinyl, sulfonomorpholinyl and octahydropyrrolo[3,2-b]pyrrolyl.

The term "oxo", as used herein, refers to the divalent radical ═O.

As referred to herein, the term "substituted" means that at least one hydrogen atom is replaced with a non-hydrogen group, provided that normal valencies are maintained and that the substitution results in a stable compound. When a substituent is oxo (i.e., ═O), then 2 hydrogens on the atom are replaced. In cases wherein there are nitrogen atoms (e.g., amines) present in compounds of the present invention, these may be converted to N-oxides by treatment with an oxidizing agent (e.g., mCPBA and/or hydrogen peroxides) to afford other compounds of the invention.

As used herein, the term "unsubstituted nitrogen" refers to a nitrogen ring atom that has no capacity for substitution due to its linkage to its adjacent ring atoms by a double bond and a single bond (—N═). For example, the nitrogen at the para position of the 4-pyridyl

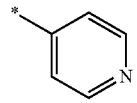

is an "unsubstituted" nitrogen, and the nitrogen at the 4-position, in reference to the linking C-ring atom, of 1H-pyrazol-4-yl,

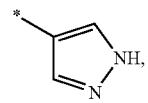

is an "unsubstituted" nitrogen.

As a person of ordinary skill in the art would be able to understand, for example, a ketone (—CH—C(═O)—) group in a molecule may tautomerize to its enol form (—C═C(OH)—). Thus, this invention is intended to cover all possible tautomers even when a structure depicts only one of them.

As used herein,

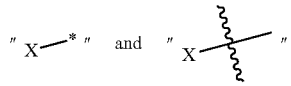

are symbols denoting the point of attachment of X, to other part of the molecule.

When any variable occurs more than one time in any constituent or formula for a compound, its definition at each occurrence is independent of its definition at every other occurrence. Thus, for example, if a group is shown to be substituted with 0-3 R groups, then said group may be unsubstituted or substituted with up to three R groups, and at each occurrence R is selected independently from the definition of R.

Unless specified otherwise, the term "compound of the present invention" or "compounds of the present invention" refers to compounds of Formula A2 and subformulae thereof, as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g, (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)—.

Geometric isomers may occur when a compound contains a double bond or some other feature that gives the molecule a certain amount of structural rigidity. If the compound contains a double bond, the substituent may be E or Z configuration. If the compound contains a disubstituted cycloalkyl, the cycloalkyl substituent may have a cis- or trans-configuration.

Conformational isomers (or conformers) are isomers that can differ by rotations about one or more a bonds. Rotamers are conformers that differ by rotation about only a single a bond.

The term "atropisomer" refers to a structural isomer based on axial or planar chirality resulting from restricted rotation in the molecule.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation).

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

As used herein, the term "LATS" is the abbreviated name of the large tumor suppressor protein kinase. LATS as used herein refers to LATS1 and/or LATS2. LATS1 as used herein refers to the large tumor suppressor kinase 1 and LATS2 refers to the large tumor suppressor kinase 2. LATS1 and LATS2 both have serine/threonine protein kinase activity.

As used herein, the term "YAP1" refers to the yes-associated protein 1, also known as YAP or YAP65, which is a protein that acts as a transcriptional regulator of genes involved in cell proliferation.

As used herein, the term "MST1/2" refers to mammalian sterile 20-like kinase-1 and -2.

As used herein, the term "pharmaceutical composition" refers to a compound of the invention, or a pharmaceutically acceptable salt thereof, together with at least one pharmaceutically acceptable carrier. In one embodiment pharmaceutical composition is in a form suitable for topical, parenteral or injectable administration.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by LATS activity, or (ii) characterized by activity (normal or abnormal) of LATS; or (2) reduce or inhibit the activity of LATS; or (3) reduce or inhibit the expression of LATS. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of LATS; or at least partially reducing or inhibiting the expression of LATS.

The term "subject" includes human and non-human animals. Non-human animals include vertebrates, e.g., mammals and non-mammals, such as non-human primates, sheep, cats, horses, cows, chickens, dog, mouse, rat, goat, rabbit, and pig. Preferably, the subject is human. Except when noted, the terms "patient" or "subject" are used herein interchangeably.

The term "$IC_{50}$", as used herein, refers to the molar concentration of an inhibitor that produces 50% of the inhibition effect.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, a subject is "in need of" a treatment if such subject would benefit biologically, medically or in quality of life from such treatment.

Depending on the process conditions the compounds of the present invention are obtained either in free (neutral) or salt form. Both the free form and salt form, and particularly "pharmaceutically acceptable salts" of these compounds are within the scope of the invention.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of the invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of Formula A2 in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/di hydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the Formula A1 or sub-formulae thereof. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of Formula A2 can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final compounds or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein.

The term "isolated" means altered or removed from the natural state. For example, a nucleic acid or a peptide or cell naturally present in a living animal is not "isolated," but the same nucleic acid or peptide or cell partially or completely separated from the coexisting materials of its natural state is "isolated."

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

A "cell population" or "population of cells" as used herein comprises cells that proliferate in the presence of a LATS1 and/or LATS2 inhibitor in vivo or ex vivo. In such cells, Hippo signaling typically suppresses cell growth, but will proliferate when the pathway is disrupted by LATS inhibition. In certain embodiments, a cell population useful in a method, preparation, medium, agent, or kit of the invention comprises cells from tissues described above or cells described or provided herein. Such cells include, but are not limited to ocular cells (e.g., limbal stem cells, corneal endothelial cells), epithelial cells (e.g., from skin), neural stem cells, mesenchymal stem cells, basal stem cells of the lungs, embryonic stem cells, adult stem cells, induced pluripotent stem cells and liver progenitor cells.

Pharmacology and Utility

In one embodiment the present invention relates to small molecule LATS kinase inhibitors for all indications where cell proliferation would be favorable in vivo and/or ex vivo.

Ex vivo cell therapies generally involve expansion of a cell population isolated from a patient or healthy donor to be transplanted to a patient to establish a transient or stable graft of the expanded cells. Ex vivo cell therapies can be used to deliver a gene or biotherapeutic molecule to a patient, wherein gene transfer or expression of the biotherapeutic molecule is achieved in the isolated cells. Non-limiting examples of ex vivo cell therapies include, but are not limited to, stem cell transplantation (e.g., hematopoietic stem cell transplantation, autologous stem cell transplantation, or cord blood stem cell transplantation), tissue regeneration, cellular immunotherapy, and gene therapy. See for example, Naldini, 2011, Nature Reviews Genetics volume 12, pages 301-315.

In one specific aspect the invention relates to small molecule LATS inhibitors, which are capable of activating the YAP pathway to promote skin cell proliferation, and thereby are useful in promoting wound healing.

Further examples of the uses of the compounds of the present invention are inter alia 1) in the treatment of insufficient liver regrowth following transplantation of marginal grafts (organs that are felt inadequate and thus frequently discarded for reasons that include but not limited to excessive fatty content, small for body size and older age of donor);
2) to support enhanced regrowth of the remnant liver mass following extensive hepatectomy, for example in the setting of primary and metastatic tumors of the liver, traumatic liver injury, and resection of other space occupying lesions of the liver such as vascular malformations and liver abscesses;
3) to promote growth of hepatic cells (e.g. hepatic progenitor cells (HPCs)) in culture (ex vivo expansion) and possible subsequent transplantation;
4) to regenerate livers of patients with acute liver failure from viral hepatitis, drug-induced liver injury, autoimmune hepatitis, ischemic and congestive liver disease;
5) to support treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution; or 6) to prevent damage and maintain or improve function of organs ex vivo, with or without perfusion devices.

The YAP/Hippo pathway regulates tissue growth and regeneration in skin and other tissues. The Hippo (MST) kinase cascade, with LATS being the terminal kinases, negatively regulates YAP activity. LATS kinases are serine/threonine protein kinases that have been shown to directly phosphorylate YAP which results in its cytoplasmic retention and inactivation. Without phosphorylation by LATS, YAP translocates to the nucleus, forming a complex with TEAD and driving the downstream gene expression for cell proliferation and survival.

The activity of a compound according to the present invention can be assessed by the following in vitro & in vivo methods.

LATS1 and LATS2 Inhibition

Compounds of Formula A1 or subformulae thereof, in free form or in pharmaceutically acceptable salt form are potent inhibitors of LATS1 and LATS2.

The inhibition efficacy of the compounds against LATS1 were assayed by the LATS1 Biochemical HTRF Assay as described in the Examples Section A. The inhibition efficacy of the compounds of the invention against LATS1 (LATS1 $IC_{50}$ in μM) are reported in Table 1A.

The LATS1 $IC_{50}$ of the compounds ranged from >10 μM to less than 1 nM, with the majority of the compounds having $IC_{50}$ below 1 μM. It should be noted that compounds with $IC_{50}$ greater than 1 μM are considered inactive in this assy.

The inhibition efficacy of selected compounds against LATS2 were assayed by the LATS2 Biochemical Caliper Assay as described in the Examples Section A. The inhibition efficacy of the compounds of the invention against LATS2 (LATS2 $IC_{50}$ in μM) are also reported in Table 1A.

pYAP Suppression (HaCaT Cells)

By the inhibition of LATS1 and LATS2 kinases, compounds of Formula A1 suppress phosphorylation of YAP. The ability of the compounds to reduce phosphorylation of YAP in human HaCaT cells (a keratinocytes cell line) was measured by the pYAP HTRF Assay as described in the Examples. The assay results are reported in Table 1C. The data demonstrated that treatment by compounds of Formula A1 reduced phosphorylation of YAP.

The ability of the compounds of Formula A1 in reducing phosphorylation of YAP can be demonstrated in similar fashion in JHH-5 cells (Fujise et al., Hepatogastroenterology. 1990 October; 37(5):457-60).

YAP Nuclear Translocation (HaCaT Cells)

Without phosphorylation by LATS, YAP translocates to the nucleus. The effect of the compounds of Formula A1, or subformulae thereof, on YAP translocation in human HaCaT cells were assessed by the YAP Nuclear Translocation Assay as described in the Examples Section A. The resulted $EC_{50}$ values are reported in Table 1C. The nuclear translocation $EC_{50}$ ranged from >20 μM to 0.3 μM, and selected compounds having $EC_{50}$ values about 1 μM or below. The data supports that treatment by selected compounds of Formula A1 activate the translocation of YAP from the cytoplasma into the nucleus.

The effect of the compounds of Formula A1, or subformulae thereof, on YAP translocation can be demonstrated in similar fashion in JHH-5 cells (Fujise et al., Hepatogastroenterology. 1990 October; 37(5):457-60).

Target Identification

Compounds of Formula A1, or subformulae thereof, selectively target LATS1/2 versus MST1/2 kinases. To identify the target of the hits from the YAP translocation assay screen, the Target Identification Assay as described in the Examples Section A was performed. The results of the assay are described in FIGS. 33A to 33C.

Figure 33A:
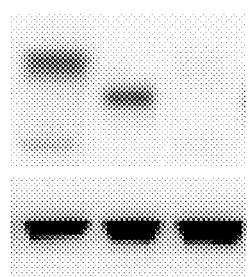
FIG. 33A.

FIG. 33A shows the western blot analyses for pYAP (Ser127) in lysates of human HaCaT cell, treated with vehicle, or transfected with 40 μM of siRNA against MST1/2 or LATS1/2. siRNA against LATS1/2 eliminated pYAP signal whereas siRNA against MST1/2 had minimal impact. It is consistent with the consensus in the field that LATS is responsible for YAP phosphorylation.

Figure 33B:
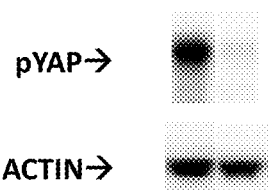
FIG. 33B.

FIG. 33B shows the western blot analysis of cell lysates of human HaCaT cells that were untreated or treated with 9 μM of Example 133 for 1 hour in the presence of 0.5 μM Okadaic acid. pYAP was dramatically inhibited. The result is similar to the study of siRNA against LATS and MSTS (FIG. 33A), which suggests Example 133 targets the LATS kinases.

Figure 33C:
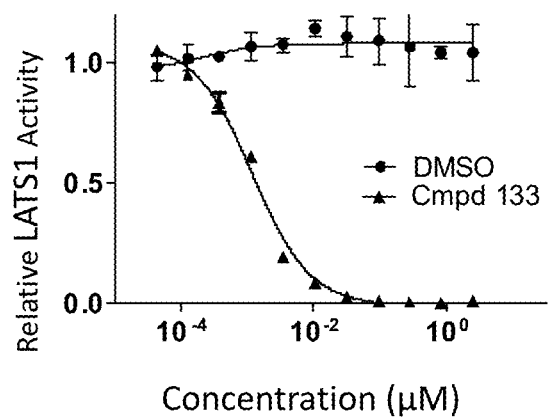
FIG. 33C.

FIG. 33C shows the inhibition of LATS1 activity (relative to DMSO control) in response to concentration of Example 133 ranging from about $10^{-4}$ to 1 μM. The data show that Example 133 strongly inhibited LATS1 in this assay with an $IC_{50}$ of 1.3 nM. The result further confirmed that the compounds of the invention are potent inhibitors of the LATS kinases.

Mouse In Vivo Pharmacodynamics (PD): Use in Wound Healing

The compounds of the invention also activate the YAP pathway in vivo. A study of YAP pathway target gene expression was conducted in an in vivo mouse model as described in the In Vivo PD Assay in the Examples Section A. Two full-thickness excisional wounds on the dorsum of an anesthetized mouse were treated topically with vehicle, or 0.2 and 2 mg/mL of Example 133. After two daily doses, the skin samples around the wound edge were collected and Taqman analyses were performed using Cyr61 and Gapdh probes. mRNA expression levels for the target genes were normalized to Gapdh mRNA levels and plotted against the concentration of Example 133 in FIG. 34. The data shows that Example 133 significantly up-regulated the YAP target gene Cyr61 when compared to vehicle, and in a dose-dependent manner. The result is consistent with known LATS biology for activation of the YAP pathway.

In Vivo Skin Cell Proliferation

Further, the compounds of the invention increase skin cell proliferation in vivo when applied topically. The study was conducted as described the "In Vivo Histology and Ki67 Staining Assay" in the Examples Section A. Example 133 or vehicle were applied to intact mouse dorsal skin. After three days of twice-a-day dosing, the skin samples were collected and subjected to immunohistology staining for Ki67. The sections were evaluated visually for cell proliferation and for the abundance of Ki67 positive cells. The study results are documented in FIGS. 35A and 35B.

Figure 35A:
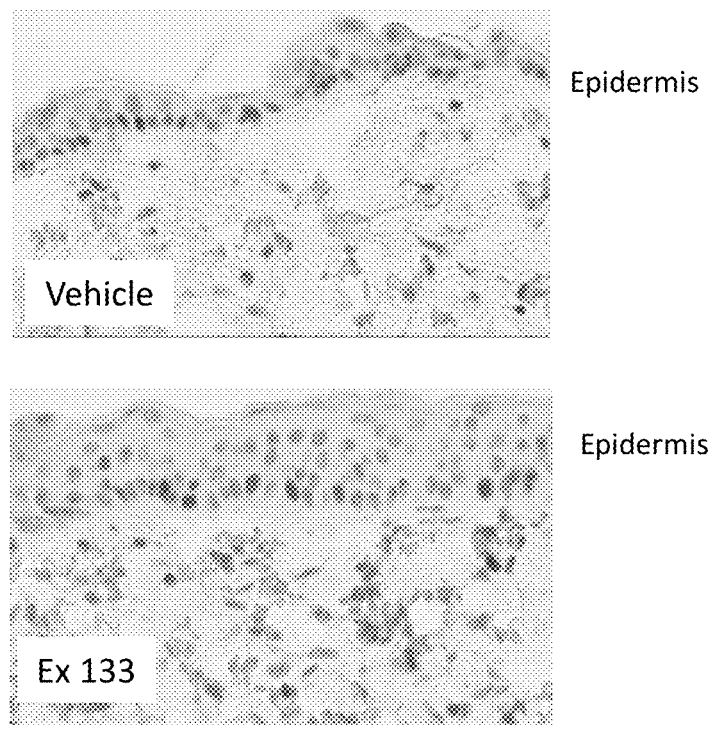
FIG. 35A.
Figure 35B:
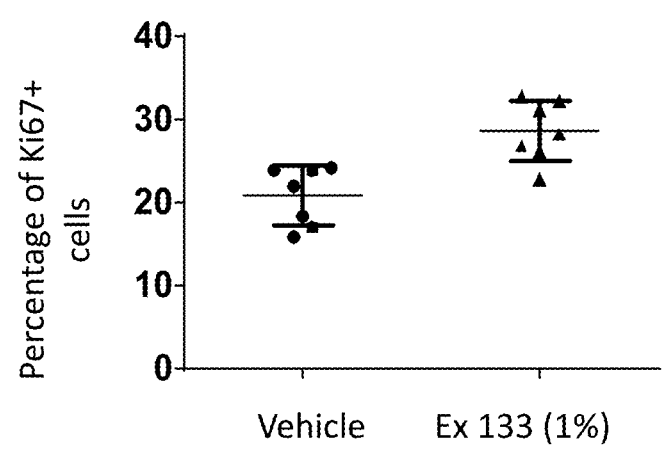
FIG. 35B.

FIG. 35A shows representative micrographs of the Ki67 stained mouse skin treated by either vehicle or Example 133. Mouse skin treated by Example 133 shows significant increase in basal cell proliferation and epidermal thickness as compared to vehicle. FIG. 35B compares the abundance of Ki67 positive cell in untreated and treated mouse skin. The data shows a 10% higher abundance of Ki67 positive cells in skin treated by Example 133, which is indicative of a statistically significant induction of Ki67 positive cells. Accordingly, Example 133 significantly increased skin cell proliferation in mice in vivo. In summary, from high-content imaging-based phenotypic HTS, compounds of the invention have been shown to be potent LATS inhibitors, which was confirmed by both cellular and biochemical LATS assays. Also, by using siRNA to knockdown both LATS1 and LATS2, LATS as a negative regulator of the YAP pathway has also been validated.

Further, it has been shown, in vitro, that Example 133 activated the YAP pathway, promoted cell proliferation in human keratinocytes (HaCaT). LATS inhibitors induced YAP target gene expression in wounded mouse PD models. Topical treatment of Example 133 in mice induced YAP target gene expression and increased basal layer skin cell growth as evidenced by Ki67 staining. Accordingly, Example 133 is useful in promoting skin regeneration.

Compounds of Formula A1 or subformulae thereof, in free form or in pharmaceutically acceptable salt form, therefore may be useful as a therapy for a disease or condition which can benefit from proliferation of cells as described herein. For example, where regeneration of injured or diseased tissue and organs would benefit a subject, including but not limited to skin, liver and the cornea. Additionally, the compounds of Formula A2, or subformulae thereof, may also be used as research chemicals, e.g. as tool compounds.

Thus, as a further aspect, the present invention provides the use of a compound of Formula A2 or subformulae thereof, or a pharmaceutically acceptable salt thereof, or a stereoisomer thereof, in therapy.

In a one embodiment, the present invention provides the use of a compound of Formula A1, or subformulae thereof, or a pharmaceutically acceptable salt thereof, or a stereoisomer thereof, for treating and ameliorating the symptomology of burns, acute skin ulcers and chronic skin ulcers. In one embodiment, the chronic skin ulcer is selected from vascular, diabetic and pressure ulcers. In a further embodiment, the chronic skin ulcer is selected from venous leg ulcers, diabetic foot ulcers, and bed sores.

In another aspect, the invention provides a method of treating a disease or condition, which is treated by inhibition of LATS kinases, comprising administration of a therapeutically acceptable amount of a compound of Formula A2, or subformulae thereof, or a pharmaceutically acceptable salt thereof, or a stereoisomer thereof.

In one embodiment, the disease or condition is selected from burns, acute skin ulcer or chronic skin ulcer. In a further embodiment, the chronic skin ulcer is selected from vascular, diabetic, and pressure ulcers. In a further embodiment, the chronic skin ulcer is selected from venous leg ulcers, diabetic foot ulcers, and bed sores.

Thus, as a further aspect, the present invention provides the use of a compound of Formula A2, or subformulae thereof, or a pharmaceutically acceptable salt thereof, or a stereoisomer thereof, for the manufacture of a medicament.

In a further embodiment, the present invention provides the use of a compound of Formula A1 or subformulae thereof, or a pharmaceutically acceptable salt thereof, or a stereoisomer thereof, for the manufacture of a medicament for promoting wound healing, or for the treatment of a disease which may be treated by inhibition of LATS kinases. In another embodiment, the disease is burns, acute or chronic skin ulcer. In another embodiment, the chronic skin ulcer is selected from diabetic ulcers, pressure ulcers and vascular ulcers. In another embodiment, the chronic skin ulcer is selected from venous leg ulcers, diabetic foot ulcers and bed sores.

Thus, as a further aspect, the present invention provides a compound of Formula A2 or subformulae thereof, or a pharmaceutically acceptable salt thereof, or a stereoisomer thereof, for use as a medicament.

In a further embodiment, the present invention provides a compound of Formula A1 or subformulae thereof, or a pharmaceutically acceptable salt thereof, or a stereoisomer thereof, for use as a medicament for promoting wound healing, or for the treatment of a disease which may be treated by inhibition of LATS kinases. In another embodiment, the disease is burns, acute skin ulcer or chronic skin ulcer. In another embodiment, the chronic skin ulcer is selected from diabetic ulcers, pressure ulcers and vascular ulcers. In another embodiment, the chronic skin ulcer is selected from venous leg ulcers, diabetic foot ulcers and bed sores.

In Vivo Treatment of Mice: Use in Liver

The ability of the compounds of Formula A1 to induce liver regeneration and liver regrowth was measured by treating mice with the compounds as described in the in vivo Assay as described in the Biologic Assay section infra. The assay results are reported in Table 1C. The results show that the tested compounds reduce pYAP levels in mouse livers when compared to vehicle control treated mice, indicating LATS kinase inhibition in vivo in the liver 2 hours post dosing. Increased mRNA expression of YAP target genes Cyr61 and Ctgf indicates activation of YAP signaling 2 hours post dosing. Immunohistochemistry staining for the proliferation marker Ki67 further indicates increased liver cell proliferation 24 hours post dosing.

Thus, as a further aspect, the present invention provides the use of a compound of Formula A2 or subformulae thereof, or a pharmaceutically acceptable salt thereof, or a stereoisomer thereof, in therapy.

In a one embodiment, the present invention provides the use of a compound of Formula A1 or subformulae thereof, or a pharmaceutically acceptable salt thereof, or a stereoisomer thereof, for promoting liver regeneration and liver regrowth, particularly for the treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution.

In another aspect, the invention provides a method of treating a disease which is treated by inhibition of LATS kinases comprising administration of a therapeutically acceptable amount of a compound of Formula A1 or subformulae thereof, or a pharmaceutically acceptable salt thereof, or a stereoisomer thereof.

In a further embodiment, the invention provides a method of promoting liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution, comprising administration of a therapeutically acceptable amount of a compound of Formula A1 or subformulae thereof, or a pharmaceutically acceptable salt thereof, or a stereoisomer thereof.

Thus, as a further aspect, the present invention provides the use of a compound of Formula A2 or subformulae thereof, or a pharmaceutically acceptable salt thereof, or a stereoisomer thereof, for the manufacture of a medicament.

In a further embodiment, the medicament is for promoting liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution Thus, as a further aspect, the present invention provides a compound of Formula A2 or subformulae thereof, or a pharmaceutically acceptable salt thereof, or a stereoisomer thereof, for use as a medicament. In a further embodiment, the medicament is for promoting liver regeneration and liver regrowth, particularly for treatment of insufficient liver regrowth following transplantation of marginal grafts; for supporting enhanced regrowth of the remnant liver mass following extensive hepatectomy; for regeneration of patients' of livers following acute liver failure from viral hepatitis, drug-induced liver injury, autoimmune hepatitis, ischemic- and congestive liver disease; and for treatment of patients with chronic liver injury and underlying liver fibrosis, from non-alcoholic steatohepatitis, alcoholic steatohepatitis, chronic viral hepatitis B and C, hemochromatosis, alpha-1 anti-trypsin deficiency, Wilson's disease and drug-induced liver fibrosis to enhance both regenerative capacity and accelerate fibrosis resolution.

In another aspect, the present invention provides the use of a compound of Formula A1 or subformulae thereof, or a salt thereof, or a stereoisomer thereof, for promoting growth of hepatic cells in culture outside the donor (ex-vivo expansion) or for induction of liver regeneration ex-vivo.

In another aspect, the present invention provides the method for promoting growth of hepatic cells in culture outside the donor (ex-vivo expansion) or for induction of liver regeneration ex-vivo using a compound of Formula A1 or subformulae thereof, or a salt thereof, or a stereoisomer thereof.

Pharmaceutical Composition and Administration

In another aspect, in embodiments of the invention relating to in vivo use, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. In embodiments of the invention relating to topical uses of the compounds of the invention, the pharmaceutical composition is formulated in a way that is suitable for topical administration such as aqueous solutions, suspensions, ointments, creams, gels or sprayable formulations, e.g., for delivery by aerosol or the like, comprising the active ingredient together with one or more of solubilizers, stabilizers, tonicity enhancing agents, buffers and preservatives that are known to those skilled in the art.

In embodiments of the invention relating to in vivo use, the compound of the present invention is typically formulated into pharmaceutical dosage forms to provide an easily controllable dosage of the drug and to give the patient an elegant and easily handleable product. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In embodiments of the invention relating to in vivo use, the compounds of the invention may be administered in a single daily dose, or the total daily dosage may be administered in divided doses of two, three, or four times daily.

In embodiments of the invention relating to in vivo use, the pharmaceutical composition or combination of the present invention can be in unit dosage of about 1-1000 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The compounds of the present invention can be applied topically in the form of aqueous solutions, suspensions, ointments, creams, lotion, gels or sprayable formulations, e.g., for delivery by aerosol or the like. The dosage may range between about $10^{-3}$ molar and $10^{-9}$ molar concentrations. A therapeutically effective amount in vivo may range depending on the route of administration, between about 1-100 mg/kg.

In certain instances, it may be advantageous to administer the compound of the present invention in combination with at least one additional pharmaceutical (or therapeutic) agent, such as a pain killer, and combinations thereof. In particular, compositions will either be formulated together as a combination therapeutic or administered separately.

In certain instances, it may be advantageous to administer the compound of the present invention in combination with at least one additional pharmaceutical (or therapeutic) agent, such as an immunosuppressant for example corticosteroids, cyclosporine, tacrolimus, and combinations of immunosuppressants. In particular, compositions will either be formulated together as a combination therapeutic or administered separately.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of Formula A1 or subformulae thereof, and at least one other therapeutic agent as a combined preparation for simultaneous, separate or sequential use in therapy. In one embodiment, the therapy is the treatment of a disease or condition mediated by LATS1/2. Products provided as a combined preparation include a composition comprising the compound of Formula A1 and the other therapeutic agent(s) together in the same pharmaceutical composition, or the compound of Formula A1 and the other therapeutic agent(s) in separate form, e.g. in the form of a kit.

In one embodiment, the invention provides a pharmaceutical composition comprising a compound of Formula A2 or subformulae thereof and another therapeutic agent(s). Optionally, the pharmaceutical composition may comprise a pharmaceutically acceptable carrier, as described above.

In one embodiment related to in vivo use, the invention provides a kit comprising two or more separate pharmaceutical compositions, at least one of which contains a compound of Formula A2 or subformulae thereof. In one embodiment, the kit comprises means for separately retaining said compositions, such as a container, divided bottle, divided tube, or divided foil packet. An example of such a kit is a foil packet, as typically used for deliver gel or ointment, and the like.

The kit of an embodiment of the invention related to in vivo use may be used for administering different dosage forms of the active agents, for example, oral and topical, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, for embodiments of the invention related to in vivo use, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention relates to the use of a compound of Formula A1 or subformulae thereof for treating a disease or condition mediated by inhibition of LATS, wherein the medicament is prepared for administration with another therapeutic agent. The invention also relates to the use of another therapeutic agent for treating a disease or condition mediated by inhibition of LATS, wherein the medicament is administered with a compound of Formula A1 or subformulae thereof.

The invention also relates to a compound of formula A1 or subformulae thereof for use in a method of treating a disease or condition mediated by inhibition of LATS, wherein the compound of Formula A1 or subformulae thereof is prepared for administration with another therapeutic agent. The invention also relates to another therapeutic agent for use in a method of treating a disease or condition mediated inhibition of LATS, wherein the other therapeutic agent is prepared for administration with a compound of Formula A1 or subformulae thereof.

The invention also relates to a compound of Formula A1 or subformulae thereof for use in a method of treating a disease or condition mediated by inhibition of LATS, wherein the compound is administered with another therapeutic agent. The invention also provides another therapeutic agent for use in a method of treating a disease or condition mediated by inhibition of LATS, wherein the other therapeutic agent is administered with a compound of Formula A1 or subformulae thereof.

The invention also relates to the use of a compound of Formula A1 or subformulae thereof for treating a disease or condition mediated by LATS1/2, wherein the patient has previously (e.g. within 24 hours) been treated with another therapeutic agent. The invention also provides the use of another therapeutic agent for treating a disease or condition mediated by LATS, wherein the patient has previously (e.g. within 24 hours) been treated with a compound of Formula A1 or subformulae thereof.

PREPARATION OF COMPOUNDS

The compounds of the present invention can be prepared in a number of ways known to one skilled in the art of organic synthesis in view of the methods, reaction schemes and examples provided herein. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, $2^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis,* 4th Ed., Wiley (2007). Protecting groups incorporated in making of the compounds of the present invention, such as the trityl protecting group, may be shown as one regioisomer but may also exist as a mixture of regioisomers.

Abbreviations

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "nm" for nanometer or nanometers, "L" for liter or liters, "mL" or "ml" for milliliter or milliliters, "ul", "uL", "µl", or "µL" for microliter or microliters, "nL" or "nl" for nanoliter or nanoliters," "N" for normal, "uM" or "µM" micromolar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "aq" for aqueous, "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "1H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:

AC Active Control
AIBN azobisisobutyronitrile
ATP adenosine triphosphate
Bn benzyl
Boc tert-butoxy carbonyl
Boc$_2$O di-tert-butyl dicarbonate
BSA bovine serum albumin
Bu butyl
Cs$_2$CO$_3$ cesium carbonate anhydrous
CHCl$_3$ chloroform
DAST diethylaminosulfurtrifluoride
DBU 2,3,4,6,7,8,9,10-octahydropyrimido[1,2-a]azepine
DCM dichloromethane
DMAP 4-dimethylaminopyridine
DMEM Dulbecco's modified Eagle's medium
DMF dimethylformamide
DMSO dimethylsulfoxide
DPPA diphenylphosphoryl azide
DTT dithiolthreitol
EA ethyl acetate
EDTA ethylenediaminetetraacetic acid
Equiv. equivalence
Et ethyl
Et$_2$O diethyl ether
EtOH ethanol
EtOAc ethyl acetate
FBS fetal bovine serum HATU 2-(7-Aza-1H-benzotriazole-1-yl)-1,1,3,3-tetramethyluronium hexafluorophosphate
HCl hydrochloric acid
HEPES (4-(2-hydroxyethyl)-1-piperazineethanesulfonic acid
HPMC (hydroxypropyl)methyl cellulose
HTRF homogeneous time resolved fluorescence
i-Bu isobutyl
i-Pr isopropyl
KOAc potassium acetate
LiAlH$_4$ lithium aluminium hydride
Me methyl
mCPBA 3-chloroperoxybenzoic acid
MeCN acetonitrile
MnO$_2$ manganese dioxide
N$_2$ nitrogen
NaBH$_4$ sodium borohydride
NaHCO$_3$ sodium bicarbonate
Na$_2$SO$_4$ sodium sulfate
NBS N-Bromosuccinimide
NC Neutral Control
PBS phosphate buffered saline
PFA paraformaldehyde
Ph phenyl
PPh$_3$ triphenylphosphine
Ph$_3$P=O triphenylphosphine oxide
pYAP phospho-YAP
R$_f$ retention factor
RT room temperature (° C.)
Ser serine
t-Bu or Bu$^t$ tert-butyl
T3P® Propane phosphonic acid anhydride
TEA triethylamine
TFA trifluoroacetic acid
TH F tetrahydrofuran
UVA Ultraviolet A
YAP Yes associated protein (NCBI Gene ID: 10413; official symbol: (YAP1)

I. General Synthetic Routes

Compounds of Formulae I to VI can be prepared as illustrated in the General Schemes I to III and in greater details in Schemes 1 to 6 below. Detailed description for the synthesis of the intermediates and exemplified compounds are also disclosed below.

General Scheme I for the Preparation of Compounds of Formula I or II

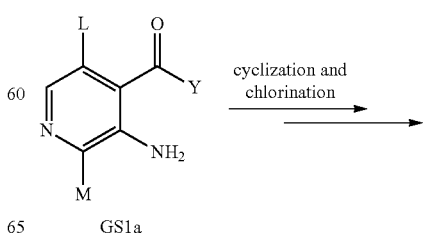

GS1a

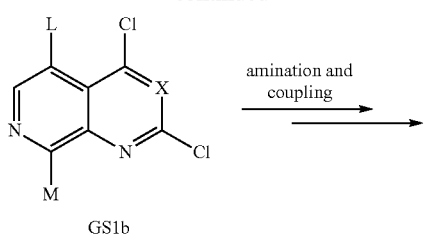

GS1b

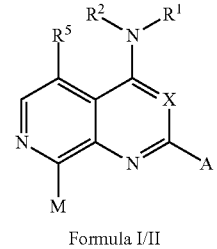

Formula I/II

M, L = halide, alky, —CN, etc
Y = OH, NH$_2$

The bicyclic dichloride GS1b could be commercially available when X=C or could be prepared from aminoisonicotinic acid/amide GS1a through cyclization and chlorination. The dichloride of GS1b could be aminated and coupled with the appropriate agents to form GS1c, which further functionalized to yield Formula I or Formula II through any necessary functionalization, such as but not limited to protection and de-protection steps, reduction, hydrolysis, alkylation, amination, coupling, etc General Scheme II for the Preparation of
Compounds of Formula III

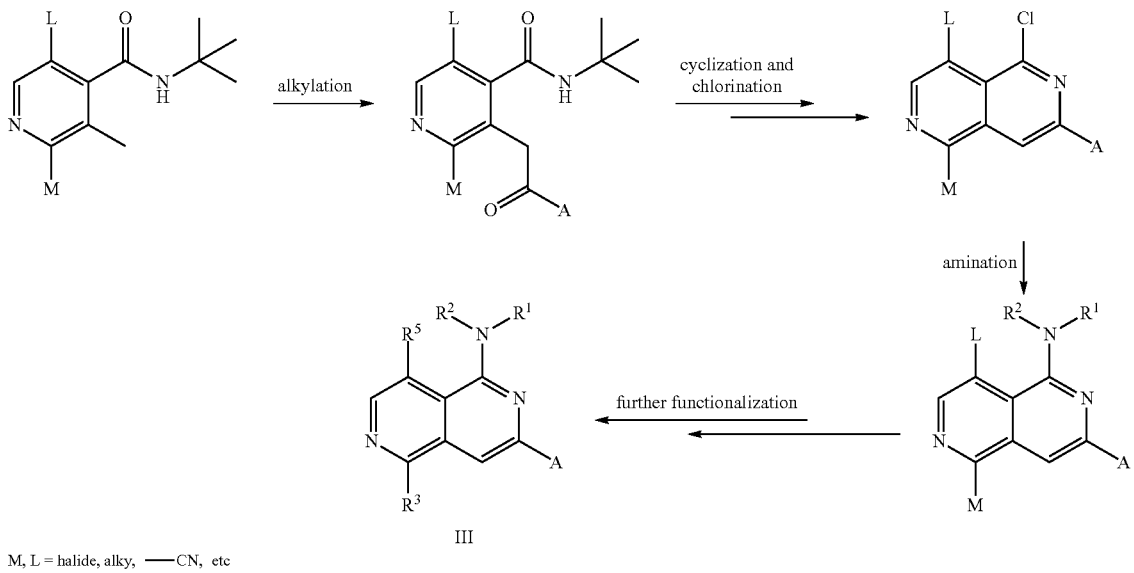

M, L = halide, alky, —CN, etc

General Scheme III for the Preparation of
Compounds of Formula IV

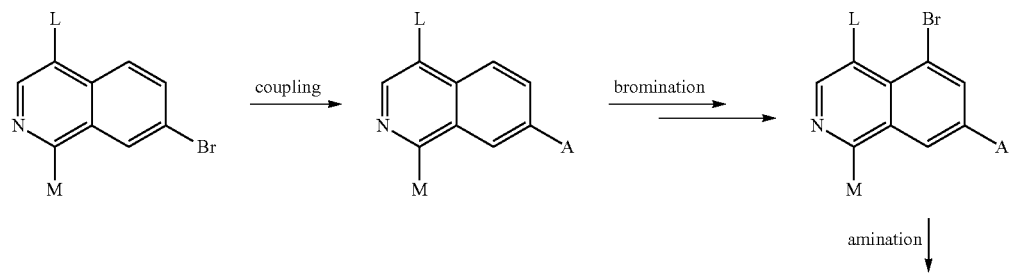

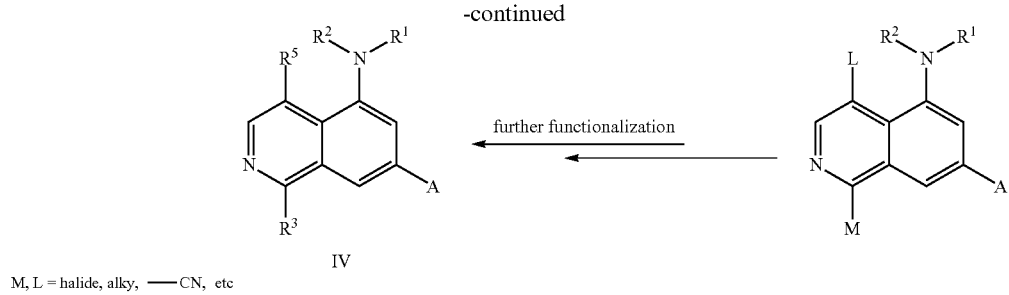

IV

M, L = halide, alky, —CN, etc

Scheme 1.

Compounds of Formula V can be prepared as illustrated in Scheme 1 below. Step C could include amination and any necessary functionalization, such as but not limited to protection and de-protection steps, reduction, hydrolysis, alkylation, etc.

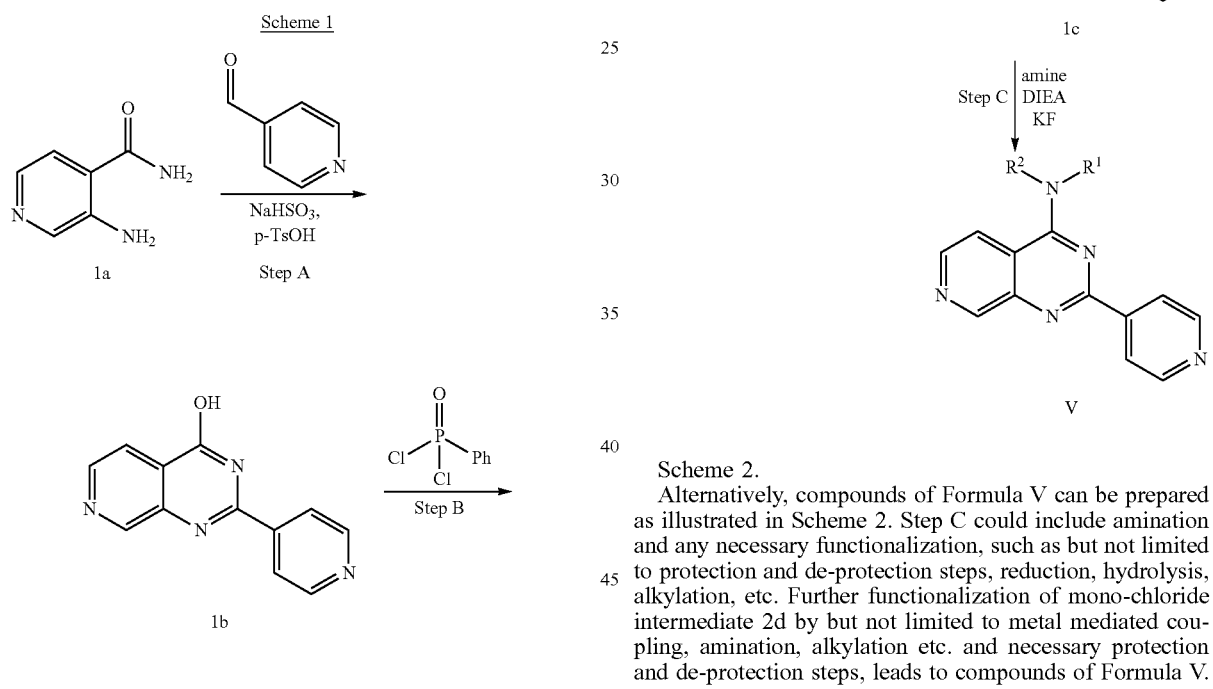

Scheme 2.

Alternatively, compounds of Formula V can be prepared as illustrated in Scheme 2. Step C could include amination and any necessary functionalization, such as but not limited to protection and de-protection steps, reduction, hydrolysis, alkylation, etc. Further functionalization of mono-chloride intermediate 2d by but not limited to metal mediated coupling, amination, alkylation etc. and necessary protection and de-protection steps, leads to compounds of Formula V.

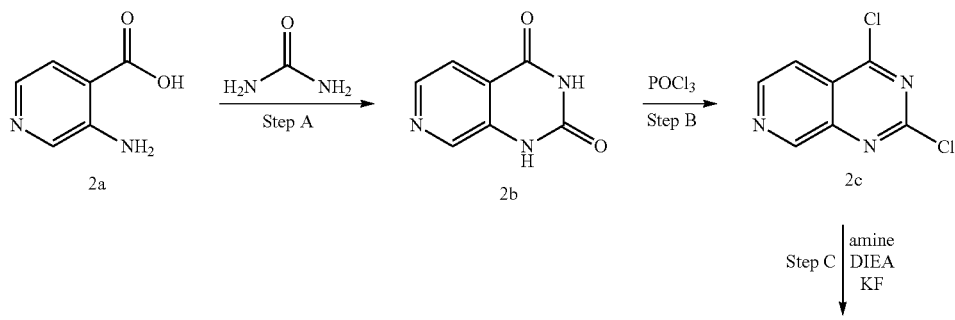

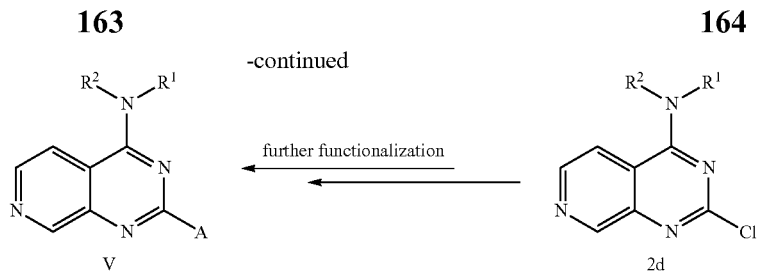

Scheme 3.

Compounds of Formula I where $R^5$ is hydrogen can be prepared as illustrated in Scheme 3. Step C could include amination and any necessary functionalization, such as but not limited to protection and de-protection steps, reduction, hydrolysis, alkylation, etc. Further functionalization of mono-chloride intermediate 3d by but not limited to metal mediated coupling, amination, alkylation etc. and necessary protection and de-protection steps, leads to compounds of Formula (I) where $R^5$ is hydrogen.

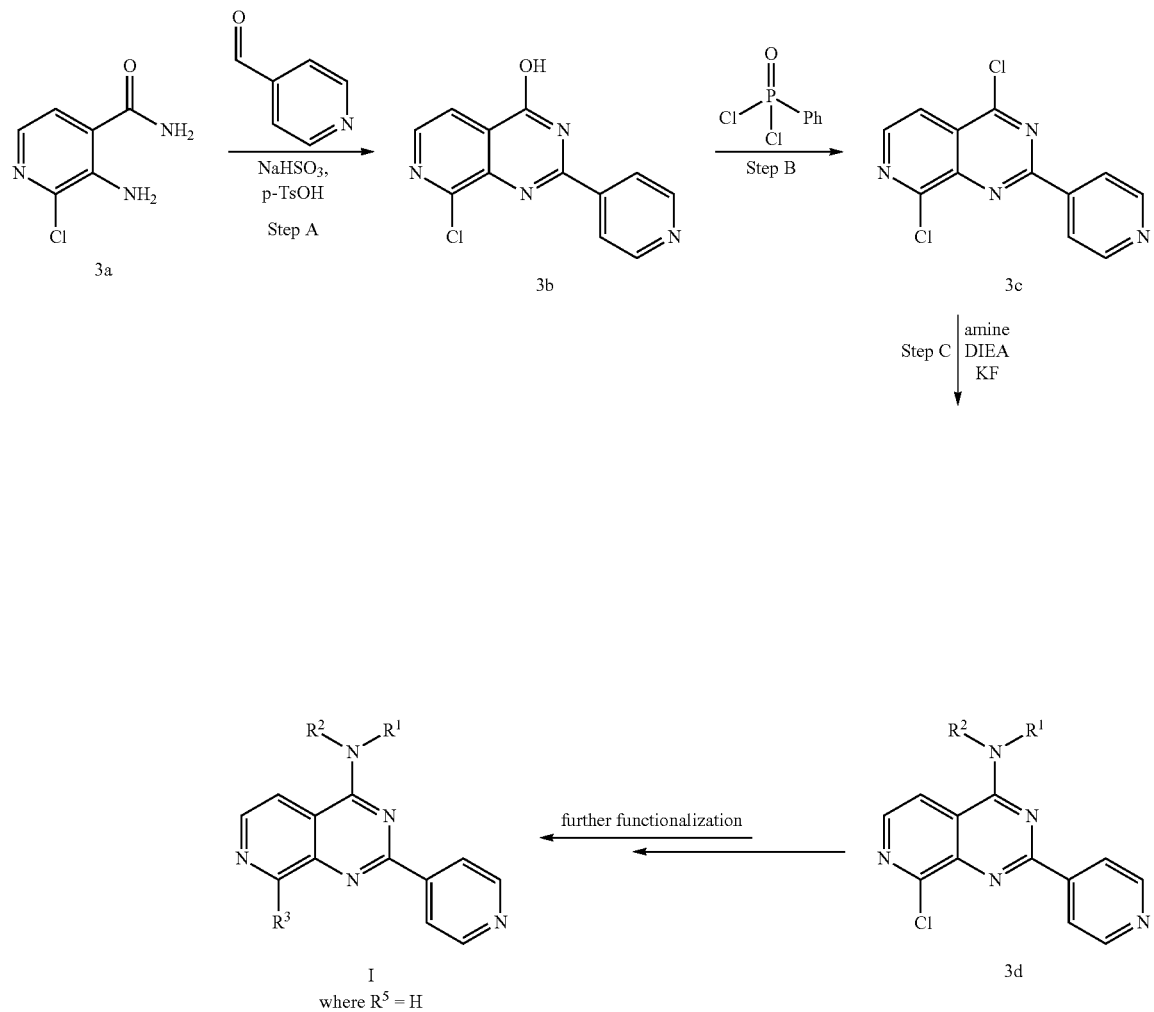

Scheme 4.

Compounds of Formula I, where $R^3$ and $R^5$ are both hydrogen, can be prepared as illustrated in Scheme 4. Step C could include amination and any necessary functionalization, such as but not limited to protection and de-protection steps, reduction, hydrolysis, alkylation, etc. leads to compounds of Formula I where $R^3$ and $R^5$ are both hydrogen.

Scheme 4

Scheme 5.

Compounds of Formula I, where R³ is hydrogen, can be prepared as illustrated in Scheme 5. Step D could include amination and any necessary functionalization, such as but not limited to protection and de-protection steps, reduction, hydrolysis, alkylation, etc. Further functionalization of mono-chloride intermediate 5d by, but not limited to, metal mediated coupling, amination, alkylation etc. and necessary protection and de-protection steps, leads to compounds of Formula I where R³ is hydrogen,

Scheme 5

Scheme 6.

Compounds of Formula VI can be prepared from commercially available dichloride 6a' (2,4-dichloro-1,7-naphthyridine, Aquila Pharmatech) as illustrated in Scheme 6. Step A could include metal mediated coupling and any necessary functionalization, such as but not limited to protection and de-protection steps, cyclization, reduction, hydrolysis, alkylation, etc. Step B could include amination and any necessary functionalization, such as but not limited to protection and de-protection steps, reduction, hydrolysis, alkylation, etc.

Scheme 6

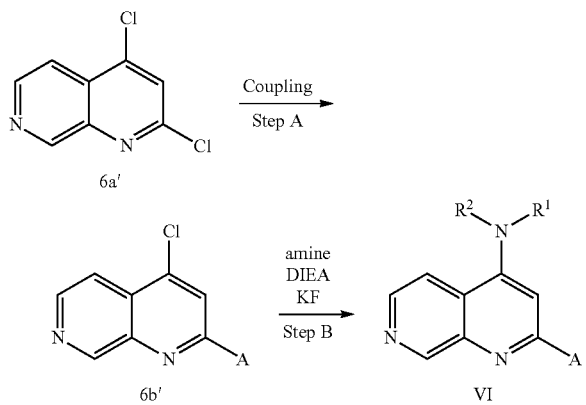

Preparation of Exemplified Examples

The following Examples have been prepared, isolated and characterized using the methods disclosed herein. The following examples demonstrate a partial scope of the invention and are not meant to be limiting of the scope of the invention.

Unless specified otherwise, starting materials are generally available from a non-excluding commercial sources such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia).

LCMS Methods Employed in Characterization of Examples 1-290

Analytical LC/MS is carried out on Agilent systems using ChemStation software. The systems consist of:
Agilent G1312 Binary Pump
Agilent G1367 Well Plate Autosampler
Agilent G1316 Thermostated Column Compartment
Agilent G1315 Diode Array Detector
Agilent 6140/6150 Mass Spectrometer
SOFTA Evaporative Light Scattering Detector
Typical method conditions are as follows:
Flow Rate: 0.9 mL/min
Column: 1.8 micrometres 2.1×50 mm Waters Acquity HSS T3 $C_{1-8}$ column
Mobile Phase A: Water+0.05% TFA
Mobile Phase B: Acetonitrile+0.035% TFA
Run Time: 2.25 minutes
The system runs a gradient from 10% B to 90% B in 1.35 minutes. A 0.6 minute wash at 100% B follows the gradient. The remaining duration of the method returns the system to initial conditions.

Typical mass spectrometer Scan range is 100 to 1000 amu.

LCMS Methods Employed in Characterization of Examples 291-335

LC-MS (method 1):
System: Waters Acquity UPLC with Waters SQ detector.
Column: Acquity HSS T3 1.8 μm 2.1×50 mm.
Flow: 1.0 ml/min. Column temperature: 60° C.
Gradient: from 5 to 98% B in 1.4 min, A=water+0.05% formic acid+3.75 mM ammonium acetate, B=acetonitrile+0.04% formic acid.
LC-MS (method 2):
System: Waters Acquity H-Class UPLC with Waters SQ detector.
Column: BEH C18 1.7 μm 2.1×50 mm
Flow: 3.0 ml/min. Column temperature: 30° C.
Gradient: from 2 to 100% B in 2.7 min, A=2 mM ammonium acetate/water+0.1% formic acid, B=acetonitrile+0.1% formic acid.

NMR Employed in Characterization of Examples 1-290

Proton spectra are recorded on a Bruker AVANCE II 400 MHz with 5 mm QNP Cryoprobe or a Bruker AVANCE III 500 MHz with 5 mm QNP probe unless otherwise noted. Chemical shifts are reported in ppm relative to dimethyl sulfoxide (δ 2.50), chloroform (δ 7.26), methanol (δ 3.34), or dichloromethane (δ 5.32). A small amount of the dry sample (2-5 mg) is dissolved in an appropriate deuterated solvent (1 mL).

NMR Employed in Characterization of Examples 291-335

Proton spectra are recorder on a Bruker Avance 400 NMR spectrometer (400 MHz) equipped with a cryo probe or a Bruker Avance 600 NMR spectrometer (600 MHz) equipped with a cryo probe. Chemical shifts (δ-values) are reported in ppm downfield from tetramethylsilane, spectra splitting pattern are designated as singlet (s), doublet (d), triplet (t), quartet (q), pentet (p) multiplet, unresolved or more overlapping signals (m), broad signal (br). Solvents are given in parentheses.

Reagents and Materials

Solvents and reagents were purchased from suppliers and used without any further purification. Basic ion exchange resin cartridges PoraPak™ Rxn CX 20 cc (2 g) were purchased from Waters. Phase separator cartridges (Isolute Phase Separator) were purchased from Biotage. Isolute absorbant (Isolute HM-N) was purchased from Biotage.
ISCO Methods Employed in Purification of Examples
ISCO flash chromatography is carried on Teledyne COMBIFLASH® system with prepacked silica RediSep® column.

Preparative HPLC Methods Employed in Purification of Examples

Preparative HPLC is carried out on Waters Autoprep systems using MassLynx and FractionLynx software. The systems consist of:

Waters 2767 Autosampler/Fraction Collector

Waters 2525 Binary Pump

Waters 515 Makeup pump

Waters 2487 Dual Wavelength UV Detector

Waters ZQ Mass Spectrometer

Typical method conditions are as follows:

Flow Rate: 100 mL/min

Column: 10 micrometres 19×50 mm Waters Atlantis T3 C18 column

Injection Volume: 0-1000 microlitres

Mobile Phase A: Water+0.05% TFA

Mobile Phase B: Acetonitrile+0.035% TFA

Run Time: 4.25 minutes

The system runs a gradient from x % B to y % B as appropriate for the examples in 3 minutes following a 0.25 minute hold at initial conditions. A 0.5 minute wash at 100% B follows the gradient. The remaining duration of the method returns the system to initial conditions.

Fraction collection is triggered by mass detection through FractionLynx software.

Chiral Preparative HPLC Methods Employed in Purification of Examples

SFC chiral screening is carried out on a Thar Instruments Prep Investigator system coupled to a Waters ZQ mass spectrometer. The Thar Prep Investigator system consists of:

Leap HTC PAL autosampler

Thar Fluid Delivery Module (0 to 10 mL/min)

Thar SFC 10 position column oven

Waters 2996 PDA

Jasco CD-2095 Chiral Detector

Thar Automated Back Pressure Regulator.

All of the Thar components are part of the SuperPure Discovery Series line.

The system flows at 2 mL/min (4 mL/min for the WhelkO-1 column) and is kept at 30 degrees C. The system back pressure is set to 125 bar. Each sample is screened through a battery of six 3 micrometre columns:

3 micrometre 4.6×50 mm ChiralPak AD 3 micrometre 4.6×50 mm ChiralCel OD 3 micrometre 4.6×50 mm ChiralCel OJ 3 micrometre 4.6×250 mm Whelk O-1

3 micrometre 4.6×50 mm ChiralPak AS 3 micrometre 4.6×50 mm Lux-Cellulose-2

The system runs a gradient from 5% co-solvent to 50% co-solvent in 5 minutes followed by a 0.5 minute hold at 50% co-solvent, a switch back to 5% co-solvent and a 0.25 minute hold at initial conditions. In between each gradient there is a 4 minute equilibration method the flows at 5% co-solvent through the next column to be screened. The typical solvents screened are MeOH, MeOH+20 mM $NH_3$, MeOH+0.5% DEA, IPA, and IPA+20 mM $NH_3$.

Once separation is detected using one of the gradient methods an isocratic method will be developed and, if necessary, scaled up for purification on the Thar Prep80 system.

Synthesis of Intermediates

Intermediate 1c (Scheme 1): 4-chloro-2-(pyridin-4-yl)pyrido[3,4-d]pyrimidine

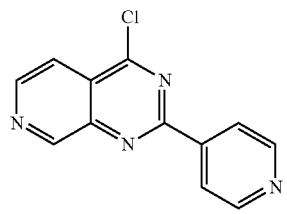 [SMILES: Clc1nc(-c2ccncc2)nc2cnccc12]

Step A

In a 20 mL microwave vial was added 3-aminoisonicotinamide (1a, 2 g, 14.58 mmol), isonicotinaldehyde (1.521 mL, 16.04 mmol), sodium bisulfite (1.821 g, 17.50 mmol) and 4-methylbenzenesulfonic acid hydrate (0.277 g, 1.458 mmol) in DMA (Volume: 5 mL) to give an orange suspension. The reaction was well stirred and heated in microwave at 160° C. for 12 min. The reaction mixture was diluted with water and filtered. The solid was washed with water, MeOH and ether to give 2.03 g off white solid as the product 1b (59%). 1H NMR (400 MHz, DMSO-d6) δ 9.18 (d, J=0.9 Hz, 1H), 8.88-8.78 (m, 2H), 8.73 (d, J=5.2 Hz, 1H), 8.16-8.08 (m, 2H), 8.03 (dd, J=5.2, 0.9 Hz, 1H).

Step B

In a 5 mL microwave reactor was 2-(pyridin-4-yl)pyrido[3,4-d]pyrimidin-4-ol (1b, 500 mg, 2.230 mmol) and phenylphosphonic dichloride (1564 microlitre, 11.15 mmol) to give a brown suspension. The reaction mixture was stirred at 170° C. for 30 min when LCMS indicated full conversion. The reaction mixture was quenched with ice/water and neutralized with saturated $Na_2CO_3$, then extracted with DCM×3 and give the product 1c (74%). 1H NMR (500 MHz, DMSO-d6) δ 9.65 (d, J=1.0 Hz, 1H), 8.96 (d, J=5.6 Hz, 1H), 8.87 (s, 2H), 8.47-8.30 (m, 2H), 8.18 (dd, J=5.6, 1.0 Hz, 1H). LCMS (m/z [M+H]$^+$): 243.1.

Intermediate 2c (Scheme 2): 2,4-dichloropyrido[3,4-d]pyrimidine

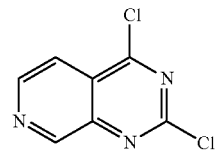

Step A

A mixture of urea (40.00 g, 666.00 mmol) and 3-aminoisonicotinic acid (2a, 18.40 g, 133.20 mmol) was heated at 210° C. for 1 hr (NOTE: no solvent was used). NaOH (2N, 320 mL) was added, and the mixture was stirred at 90° C. for 1 h. The solid was collected by filtration, and washed with water. The crude product thus obtained was suspended in HOAc (400 mL), and stirred at 100° C. for 1 h. The mixture was cooled to RT, filtered, and the solid was washed with a large amount of water, and then dried under the vacuum to give pyrido[3,4-d]pyrimidine-2,4(1H,3H)-dione (2b, 17.00 g, 78% yield) without further purification. LCMS (m/z [M+H]⁺): 164.0.

Step B

To a mixture of pyrido[3,4-d]pyrimidine-2,4(1H,3H)-dione (2b, 20.00 g, 122.60 mmol) and POCl₃ (328.03 g, 2.14 mol) in toluene (200 mL) was added DIEA (31.69 g, 245.20 mmol) dropwise and this reaction mixture stirred at 25° C. overnight (18 hr) to give suspension.

The solvent and POCl₃ was removed under vacuum, diluted with DCM (50 mL), neutralized with DIEA to pH=7 at −20° C. and concentrated again, the residue was purified by column (20-50% EA/PE) to give the product (2c, 20.00 g, 99.99 mmol, 82% yield) as a yellow solid. 1H NMR (400 MHz, CHLOROFORM-d) δ 9.52 (s, 1H), 8.92 (d, J=5.6 Hz, 1H), 8.04 (d, J=5.6 Hz, 1H). LCMS (m/z [M+H]⁺): 200.0.

Intermediate 3c (Scheme 3): 4,8-dichloro-2-(pyridin-4-yl)pyrido[3,4-d]pyrimidine

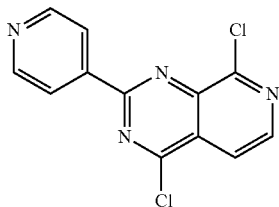 [SMILES: Clc1nc(-c2ccncc2)nc2c(Cl)nccc12]

Step A

In a 20 mL microwave reactor was added 3-aminoisonicotinamide (3a, 650 mg, 3.79 mmol), and isonicotinaldehyde (487 mg, 4.55 mmol), sodium bisulfite (788 mg, 7.58 mmol) in DMA (Volume: 10 mL) to give a yellow suspension. The reaction mixture was stirred under microwave at 160° C. for 10 min. The reaction mixture was diluted with water, filtered and washed with MeOH and ether. The solid was collected to give the product 3b (8-chloro-2-(pyridin-4-yl)pyrido[3,4-d]pyrimidin-4-ol, 300 mg, 29%). 1H NMR (400 MHz, DMSO-d6) δ 8.86-8.80 (m, 2H), 8.45 (d, J=5.1 Hz, 1H), 8.18-8.12 (m, 2H), 8.00 (d, J=5.1 Hz, 1H).

Step B

In a 20 mL microwave reactor was mixed (8-chloro-2-(pyridin-4-yl)pyrido[3,4-d]pyrimidin-4-ol (3b, 300 mg, 1.160 mmol), and phenylphosphonic dichloride (1 mL, 7.13 mmol) to give a yellow suspension. The reaction mixture was stirred under microwave at 170° C. for 60 min. The reaction mixture was diluted with water and filtered. The solid was washed with water, MeOH and ether to give the title product 3c (78%). 1H NMR (400 MHz, DMSO-d6) δ 9.05-8.96 (m, 2H), 8.52 (d, J=5.1 Hz, 1H), 8.46-8.38 (m, 2H), 8.05 (d, J=5.1 Hz, 1H). (NMR sample was added 1 drop of TFA, otherwise, 2 set of peaks were observed). LCMS (m/z [M+H]⁺): 277.0.

Intermediate 4c (Scheme 4, intermediate 4c, wherein X is F and A is 4-pyridinyl): 4-chloro-6-fluoro-2-(pyridin-4-yl)pyrido[3,4-d]pyrimidine

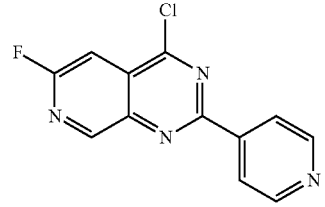 [SMILES: Fc1cc2c(Cl)nc(-c3ccncc3)nc2cn1]

Step A

A solution of isonicotinonitrile (800 mg, 7.69 mmol) in MeOH (30 ml) was treated with sodium methoxide (0.474 ml, 5.4M, 2.56 mmol) at r.t for 1 hr. Then 5-amino-2-fluoroisonicotinic acid (1.0 g, 6.41 mmol) was added and the resulting mixture was refluxed for 24 hours. After cooling to r.t, the solid product was collected by filtration. It was washed with EtOAc, then dried under vacuum to afford 6-fluoro-2-(pyridin-4-yl)pyrido[3,4-d]pyrimidin-4-ol (4b, 756 mg, 48.7%). 1H NMR (600 MHz, DMSO-d6) δ 8.89 (s, 1H), 8.81 (d, J=5.6 Hz, 2H), 8.14-8.06 (m, 2H), 7.74 (d, J=2.3 Hz, 1H). LCMS (m/z [M+H]⁺): 243.10.

Step B

To a mixture of 6-fluoro-2-(pyridin-4-yl)pyrido[3,4-d]pyrimidin-4-ol (4b, 750 mg, 3.1 mmol) in DCE (40 ml) was added thionyl chloride (1.81 ml, 24.8 mmol) and DMF (0.1 ml). The mixture was then stirred for 3 hours at 85° C. The reaction mixture was concentrated under reduced pressure and dried under vacuum overnight. The crude product (950 mg) was used for next step reaction without further work up or purification. LCMS (m/z [M+H]⁺): 261.10.

Intermediate 5d (Scheme 5): 4,5-dichloro-2-(pyridin-4-yl)pyrido[3,4-d]pyrimidine

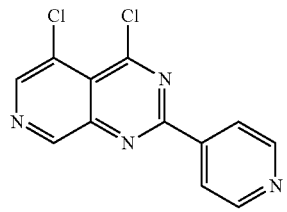 [SMILES: Clc1cncc2nc(-c3ccncc3)nc(Cl)c12]

Step A

A mixture of 3-bromo-5-fluoroisonicotinic acid (5a, 1.87 g, 8.5 mmol) and HATU (4.85 g, 12.75 mmol) in DMF (30 ml) was added DIEA (4.5 ml), the mixture was stirred at r.t for 20 minutes, then isonicotinimidamide (1.236 g, 10.2 mmol) was added. Stirring was continued for another 15 hours at r.t. The reaction mixture was concentrated under reduced pressure. The light brown syrup crude mixture was then dissolved in DCM and purified by silica gel chromatography (eluted with 0-10% MeOH/solvent A, solvent A is mixture of 4 liter DCM and 8 ml of 7N ammonia solution in MeOH), fractions 66-80 were pooled and concentrated to afford the desired product 3-bromo-5-fluoro-N-(imino(pyridin-4-yl)methyl)isonicotinamide 5b (566 mg, 20.6%). 1H NMR (500 MHz, DMSO-d6) δ 10.27 (s, 1H), 10.09 (s, 1H), 8.79-8.73 (m, 2H), 8.71 (s, 2H), 7.95-7.89 (m, 2H). LCMS (m/z [M+H]$^+$): 323.0.

Step B

A mixture of 3-bromo-5-fluoro-N-(imino(pyridin-4-yl)methyl)isonicotinamide (5b, 600 mg, 1.857 mmol), DIEA (0.33 ml, 1.857 mmol), potassium carbonate (257 mg, 1.857 mmol) and DBU (0.28 ml, 1.857 mmol) in DMA (8 ml) in a 20 ml microwave reaction vessel was heated at 150° C. for 45 minutes (microwave irradiation). The reaction mixture was diluted with water (20 ml), extracted with EtOAc (3×60 ml), the desired product remained in the aqueous phase. The aqueous phase was then purified by reverse phase ISCO (10-50% CH3CN/Water) to afford the desired product 5-bromo-2-(pyridin-4-yl)pyrido[3,4-d]pyrimidin-4-ol 5c (520 mg, 80% purity, 74%). LCMS (m/z [M+H]$^+$): 303.0.

Step C 5-bromo-2-(pyridin-4-yl)pyrido[3,4-d]pyrimidin-4-ol (5c, 150 mg, 0.495 mmol) was dissolved in anhydrous CH$_3$CN (2 ml) and followed by addition of POCl$_3$ (759 mg, 4.95 mmol). The reaction mixture was then heated at 100° C. for 16 hrs. LCMS showed the reaction was complete. The reaction was cooled to rt and the solvent was evaporated. The residue was diluted with ice water (40 ml), and was then extracted with EtOAc (3×40 ml). The combined organic layers were dried over Na$_2$SO$_4$, filtered and evaporated to dryness to afford the desired product 4,5-dichloro-2-(pyridin-4-yl)pyrido[3,4-d]pyrimidine 5d (86%) The product was used directly for next step without further purification. 1H NMR (400 MHz, DMSO-d$_6$) δ 9.05 (s, 1H), 8.87 (s, 2H), 8.68 (s, 1H), 8.16 (d, J=4.9 Hz, 2H). LCMS (m/z [M+H]$^+$): 277.0.

Intermediate 6b (Scheme 6, intermediate 6b', wherein A is 4-pyridinyl): 4-chloro-2-(pyridin-4-yl)-1,7-naphthyridine

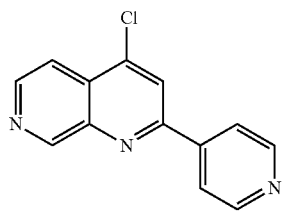 [SMILES: Clc1cc(-c2ccncc2)nc2cnccc12]

Step A

In a 20 mL microwave reactor was added PalladiumTetrakis (58.1 mg, 0.050 mmol), potassium carbonate (1.256 mL, 2.51 mmol), and 2,4-dichloro-1,7-naphthyridine (6a, 200 mg, 1.005 mmol) and pyridin-4-ylboronic acid (130 mg, 1.055 mmol) in acetonitrile (2 mL) to give an orange suspension. The reaction mixture was stirred at 120° C. for 60 min under microwave. The crude mixture was diluted with DCM, H$_2$O, separated and extracted with DCM×3. Combined the organic layers and dried Na$_2$SO$_4$, filtered and concentrated. The residue was purified by flash chromatography on a COMBIFLASH® system (ISCO) using 0-10% MeOH/DCM to give the product (62%). 1H NMR (400 MHz, DMSO-d6) δ 9.58 (d, J=0.9 Hz, 1H), 8.85-8.78 (m, 4H), 8.32-8.29 (m, 2H), 8.11 (dd, J=5.8, 0.9 Hz, 1H). LCMS (m/z [M+H]$^+$): 242.1.

Synthesis of Compounds of Formula A1

Example 1: N-(2-cyclopropylpropan-2-yl)-2-(pyridin-4-yl)pyrido[3,4-d]pyrimidin-4-amine (Compound 1)

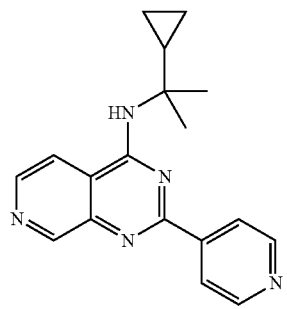 [SMILES: CC(C)(Nc1nc(-c2ccncc2)nc2cnccc12)C1CC1]

Title compound was prepared from 4-chloro-2-(pyridin-4-yl)pyrido[3,4-d]pyrimidine (Intermediate 1c) using step C as in Scheme 1.

Step C

In a 20 mL vial 4-chloro-2-(pyridin-4-yl)pyrido[3,4-d]pyrimidine (30 mg, 0.12 mmol) was stirred in DMF (0.7 mL) at room temperature and degassed with N$_2$. TEA (19 uL, 0.14 mmol) was added and stirred for 5 minutes then KF (7 mg, 0.12 mmol). This mixture was stirred at room temperature for 15 minutes then 2-cyclopropylpropan-2-amine (0.013 mL, 0.12 mmol) was added and degassed then stirred at 80° C. for two hrs. The reaction was then concentrated and purified by flash chromatography on a COMBIFLASH® system (ISCO) using 0-10% MeOH/DCM to afford the product N-(2-cyclopropylpropan-2-yl)-2-(pyridin-4-yl)pyrido[3,4-d]pyrimidin-4-amine (50%). 1H NMR (400 MHz, DMSO-d6) δ 9.19 (d, J=0.8 Hz, 1H), 8.80 (d, J=6.1 Hz, 2H), 8.64 (d, J=5.6 Hz, 1H), 8.40 (dd, J=5.7, 0.9 Hz, 1H), 8.29 (m, 2H), 7.74 (s, 1H), 1.94 (m, 1H), 1.52 (s, 6H), 0.49 (m, 4H). LCMS (m/z [M+H]$^+$): 306.2.

Examples 2-110

Examples 2-110 described infra were synthesized according to the protocol described for Example 1 using 4-chloro-2-(pyridin-4-yl)pyrido[3,4-d]pyrimidine (Intermediate 1c) and various amines respectively except specially stated.

Example 2: N-(2-cyclopropylpropan-2-yl)-2-(pyridin-4-yl)pyrido[3,4-d]pyrimidin-4-amine

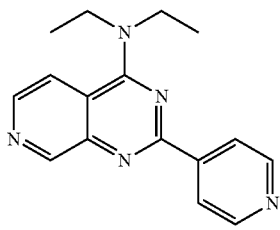 [SMILES: CCN(CC)c1nc(-c2ccncc2)nc2cnccc12]

1H NMR (400 MHz, DMSO-d6) δ 9.21 (d, J=0.8 Hz, 1H), 8.78 (m, 2H), 8.58 (d, J=5.9 Hz, 1H), 8.31 (m, 2H), 7.89 (dd, J=5.9, 0.9 Hz, 1H), 3.90 (q, J=7.0 Hz, 4H), 1.40 (t, J=7.0 Hz, 6H). LCMS (m/z [M+H]⁺): 280.1.

Example 3: N-ethyl-N-(propan-2-yl)-2-(pyridin-4-yl)pyrido[3,4-d]pyrimidin-4-amine

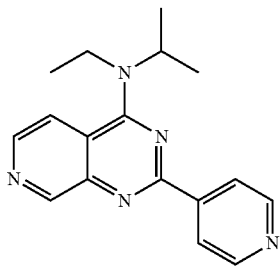 [SMILES: CCN(c1nc(-c2ccncc2)nc2cnccc12)C(C)C]

1H NMR (400 MHz, DMSO-d6) δ 9.22 (d, J=0.8 Hz, 1H), 8.78 (m, 2H), 8.58 (d, J=5.8 Hz, 1H), 8.30 (m, 2H), 7.88 (dd, J=5.8, 0.8 Hz, 1H), 4.95-4.90 (m, 1H), 3.81 (q, J=6.9 Hz, 2H), 1.40 (s, 3H), 1.38 (s, 3H), 1.35 (m, 3H). LCMS (m/z [M+H]⁺): 294.2.

Example 4: 2-(pyridin-4-yl)-N-(1,1,1-trifluoropropan-2-yl)pyrido[3,4-d]pyrimidin-4-amine

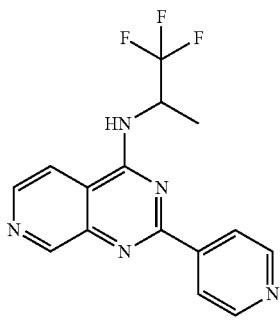 [SMILES: CC(Nc1nc(-c2ccncc2)nc2cnccc12)C(F)(F)F]

1H NMR (400 MHz, CDCl3) δ 9.45 (d, J=0.9 Hz, 1H), 8.83 (m, 2H), 8.78 (d, J=5.5 Hz, 1H), 8.70-8.60 (m, 2H), 7.63 (s, 1H), 5.98-5.92 (m, 1H), 5.80-5.75 (m, 1H), 1.81 (d, J=7.0 Hz, 3H). LCMS (m/z [M+H]⁺): 320.1.

Example 5: N-methyl-N-(propan-2-yl)-2-(pyridin-4-yl)pyrido[3,4-d]pyrimidin-4-amine

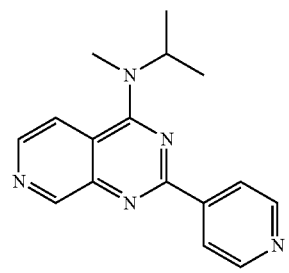 [SMILES: CC(C)N(C)c1nc(-c2ccncc2)nc2cnccc12]

1H NMR (400 MHz, DMSO-d6) δ 9.20 (d, J=0.8 Hz, 1H), 8.78 (m, 2H), 8.55 (d, J=5.8 Hz, 1H), 8.31 (m, 2H), 8.03 (dd, J=5.8, 0.9 Hz, 1H), 5.15-5.10 (m, 1H), 3.34 (s, 3H), 1.35 (d, J=6.6 Hz, 6H). LCMS (m/z [M+H]⁺): 280.2.

Example 6: N-(propan-2-yl)-2-(pyridin-4-yl)pyrido[3,4-d]pyrimidin-4-amine

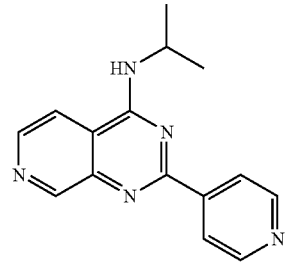 [SMILES: CC(C)Nc1nc(-c2ccncc2)nc2cnccc12]

1H NMR (400 MHz, DMSO-d6) δ 9.18 (d, J=0.8 Hz, 1H), 8.76 (m, 2H), 8.64 (d, J=5.6 Hz, 1H), 8.50 (d, J=7.5 Hz, 1H), 8.32 (m, 2H), 8.28 (dd, J=5.7, 0.9 Hz, 1H), 4.74-4.67 (d, J=6.7 Hz, 1H), 1.36 (d, J=6.6 Hz, 6H). LCMS (m/z [M+H]⁺): 266.1.

Example 7: N-(1-methoxy-2-methylpropan-2-yl)-2-(pyridin-4-yl)pyrido[3,4-d]pyrimidin-4-amine

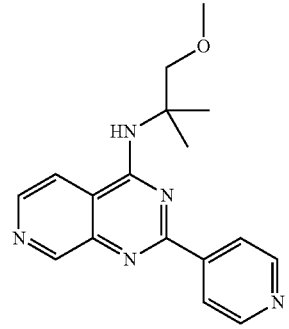 [SMILES: COCC(C)(C)Nc1nc(-c2ccncc2)nc2cnccc12]

1H NMR (400 MHz, DMSO-d6) δ 9.19 (d, J=0.8 Hz, 1H), 8.80 (m, 2H), 8.64 (d, J=5.8 Hz, 1H), 8.40 (dd, J=5.7, 0.9 Hz, 1H), 8.29 (m, 2H), 7.74 (s, 1H), 3.85 (s, 2H), 3.28 (s, 3H), 1.60 (s, 6H). LCMS (m/z [M+H]⁺): 310.2.

Example 8: N-(4-methoxy-2-methylbutan-2-yl)-2-(pyridin-4-yl)pyrido[3,4-d]pyrimidin-4-amine

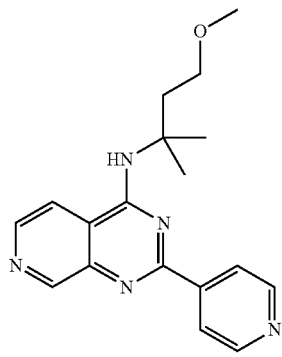 [SMILES: COCCC(C)(C)Nc1nc(-c2ccncc2)nc2cnccc12]

1H NMR (400 MHz, DMSO-d6) δ 9.19 (d, J=0.9 Hz, 1H), 8.80 (m, 2H), 8.65 (d, J=5.6 Hz, 1H), 8.30 (m, 2H), 8.28 (m, 1H), 7.85 (s, 1H), 3.48 (t, J=6.7 Hz, 2H), 3.20 (s, 3H), 2.35 (t, J=6.8 Hz, 2H), 1.64 (s, 6H). LCMS (m/z [M+H]+): 324.2.

Example 9: N-butyl-N-methyl-2-(pyridin-4-yl)pyrido[3,4-d]pyrimidin-4-amine

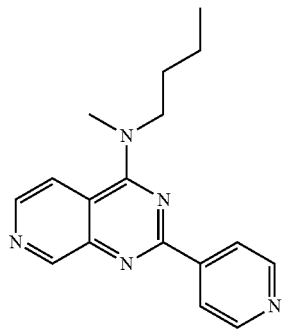 [SMILES: CCCCN(C)c1nc(-c2ccncc2)nc2cnccc12]

1H NMR (400 MHz, DMSO-d6) δ 9.21 (d, J=0.8 Hz, 1H), 8.77 (m, 2H), 8.55 (d, J=5.9 Hz, 1H), 8.31 (m, 2H), 8.08 (dd, J=5.8, 0.9 Hz, 1H), 3.92 (m, 2H), 3.54 (s, 3H), 1.82-1.75 (m, 2H), 1.48-1.36 (m, 2H), 0.98 (t, J=7.4 Hz, 3H). LCMS (m/z [M+H]+): 294.2.

Example 10: N-ethyl-N-methyl-2-(pyridin-4-yl)pyrido[3,4-d]pyrimidin-4-amine

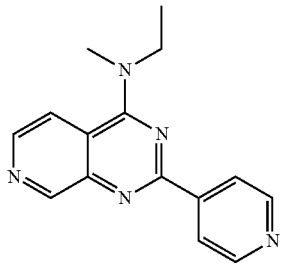 [SMILES: CCN(C)c1nc(-c2ccncc2)nc2cnccc12]

1H NMR (400 MHz, DMSO-d6) δ 9.21 (d, J=0.8 Hz, 1H), 8.78 (m, 2H), 8.55 (d, J=5.8 Hz, 1H), 8.31 (m, 2H), 8.05 (dd, J=5.9, 0.9 Hz, 1H), 3.94 (q, J=7.1 Hz, 2H), 3.50 (s, 3H), 1.39 (t, J=7.0 Hz, 3H). LCMS (m/z [M+H]+): 266.1.

Example 11: 2-(2-methyl-2-{[2-(pyridin-4-yl)pyrido[3,4-d]pyrimidin-4-yl]amino}propoxy)ethan-1-ol

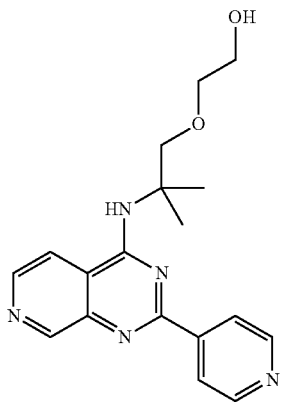

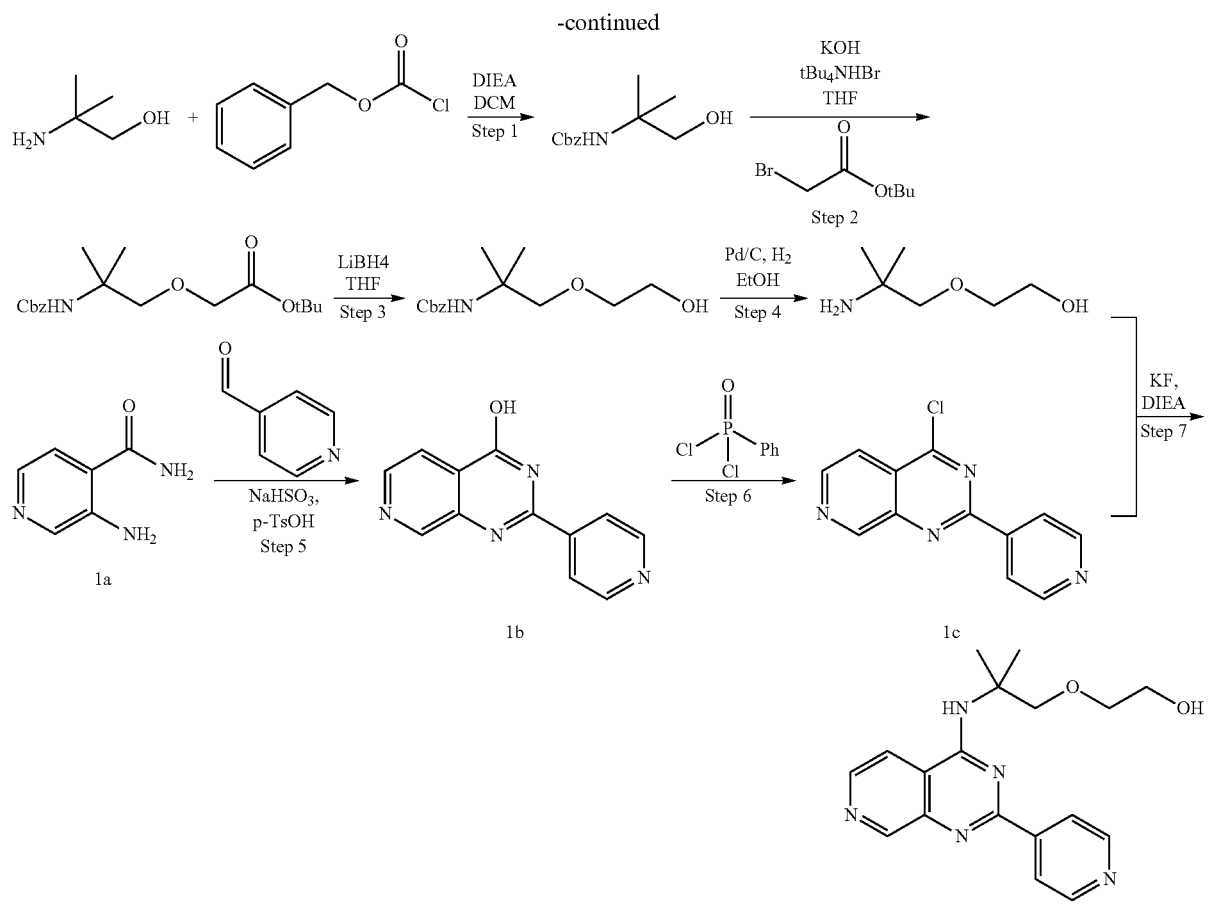

Step 1:

In a 40 mL vial at 0° C. was added 2-amino-2-methyl-propan-1-ol (1.5 g, 16.8 mmol) in 8 mL of dry DCM. DIEA (3.2 mL, 18.5 mmol) was added then benzyl carbonochloridate (2.37 mL, 16.8 mmol) in portions. The reaction mixture was stirred for two hrs slowly warming to room temperature. Solvent was evaporated under air flow. The residue was purified by flash chromatography on a COMBIFLASH® system (ISCO) using 0-50% EtOAc/Hexane to afford the product benzyl-(1-hydroxy-2-methylpropan-2-yl)carbamate (90%). LCMS (m/z [M+H]$^+$): 224.3.

Step 2

In a 20 mL vial was added benzyl-(1-hydroxy-2-methylpropan-2-yl)carbamate (0.63 g, 2.8 mmol) in 5 mL of dry THF. Potassium hydroxide (0.16 g, 2.8 mmol) was added in 0.5 mL of H$_2$O, then tert-butyl 2-bromoacetate (0.62 mL, 4.2 mmol) and tetrabutylammonium bromide (90 mg, 0.28 mmol). The reaction mixture was stirred overnight at 30° C. Solvent was evaporated under air flow. The residue was purified by flash chromatography on a COMBIFLASH® system (ISCO) using 0-40% EtOAc/Hexane to afford the product tert-butyl 2-(2-(((benzyloxy)carbonyl)amino)-2-methylpropoxy)acetate (35%). LCMS (m/z [M+H]$^+$): 338.4.

Step 3:

In a 20 mL vial at 0° C. was added tert-butyl 2-(2-(((benzyloxy)carbonyl)amino)-2-methylpropoxy) acetate (0.14 g, 0.17 mmol) in 1 mL of dry DMF. Lithium borohydride (0.45 mL, 0.91 mmol) was added in portions and stirred for 4 hrs at room temperature then quenched with water. DCM was used for extraction and the solvent evaporated under air flow. The residue was purified by flash chromatography on a COMBIFLASH® system (ISCO) using 0-70% EtOAc/Hexane to afford the product benzyl-(1-(2-hydroxyethoxy)-2-methylpropan-2-yl)carbamate (35%). LCMS (m/z [M+H]$^+$): 268.3.

Step 4

In a 20 mL septa sealed vial was added benzyl-(1-(2-hydroxyethoxy)-2-methylpropan-2-yl)carbamate (0.03 g, 0.11 mmol) in 1.2 mL of EtOH. The vial was vigorously purged with N$_2$ at room temperature. A small scoop of Pd/C (30%, cat. amount) was carefully added and the reaction maintained under N$_2$. A H$_2$ balloon was then used to flush the reaction vessel thoroughly and then stirred under H$_2$ pressure for four hrs. The H$_2$ was removed from the reaction then the vessel was purged with N$_2$. The material was then filtered through Na$_2$SO$_4$ and celite and the solvent evaporated under air flow. No further purification of the residue was necessary. 2-(2-amino-2-methylpropoxy)ethanol (95%). 1H NMR (500 MHz, Chloroform-d) b 3.76-3.73 (m, 2H), 3.62-3.59 (m, 2H), 3.26 (s, 2H), 1.27 (s, 2H), 1.20 (d, J=4.6 Hz, 1H), 1.11 (s, 6H). LCMS (m/z [M+H]$^+$): 134.2.

Step 5

In a 20 mL microwave vial was added 3-aminoisonicotinamide (1a, 2 g, 14.58 mmol), isonicotinaldehyde (1.521 mL, 16.04 mmol), sodium bisulfite (1.821 g, 17.50 mmol) and 4-methylbenzenesulfonic acid hydrate (0.277 g, 1.458 mmol) in DMA (Volume: 5 mL) to give an orange suspension. The reaction was well stirred and heated in microwave at 160° C. for 12 min. The reaction mixture was diluted with water and filtered. The solid was washed with water, MeOH and ether to give 2.03 g off white solid as the product 1b (59%). 1H NMR (400 MHz, DMSO-d6) δ 9.18 (d, J=0.9 Hz, 1H), 8.88-8.78 (m, 2H), 8.73 (d, J=5.2 Hz, 1H), 8.16-8.08 (m, 2H), 8.03 (dd, J=5.2, 0.9 Hz, 1H).

Step 6

In a 5 mL microwave reactor was 2-(pyridin-4-yl)pyrido[3,4-d]pyrimidin-4-ol (1b, 500 mg, 2.230 mmol) and phenylphosphonic dichloride (1564 microlitre, 11.15 mmol) to give a brown suspension. The reaction mixture was stirred at 170° C. for 30 min when LCMS indicated full conversion. The reaction mixture was quenched with ice/water and neutralized with saturated Na$_2$CO$_3$, then extracted with DCM×3 and give the product 1c (74%). 1H NMR (500 MHz, DMSO-d6) δ 9.65 (d, J=1.0 Hz, 1H), 8.96 (d, J=5.6 Hz, 1H), 8.87 (s, 2H), 8.47-8.30 (m, 2H), 8.18 (dd, J=5.6, 1.0 Hz, 1H). LCMS (m/z [M+H]$^+$): 243.1.

Step 7

In a 20 mL vial 4-chloro-2-(pyridin-4-yl)pyrido[3,4-d]pyrimidine (intermediate 1c) (150 mg, 0.618 mmol) was stirred in DMSO (1.5 mL) at room temperature and degassed with N$_2$. DIEA (324 microlitre, 1.85 mmol) was added and stirred for 5 minutes then KF (36 mg, 0.618 mmol). This mixture was stirred at room temperature for 15 minutes then 2-(2-amino-2-methylpropoxy)ethanol (99 mg, 0.74 mmol) was added and degassed then stirred at 60° C. for 30 min. The reaction was then concentrated and purified by flash chromatography on a COMBIFLASH® system (ISCO) using 0-10% MeOH/DCM to afford the title compound (25%). 1H NMR (400 MHz, DMSO-d6) δ 9.19 (d, J=0.8 Hz, 1H), 8.80 (m, 2H), 8.64 (d, J=5.6 Hz, 1H), 8.35 (m, 1H), 8.29 (m, 2H), 7.76 (s, 1H), 4.64-4.59 (m, 1H), 3.90 (s, 2H), 3.50-3.44 (m, 4H), 1.61 (s, 6H). LCMS (m/z [M+H]$^+$): 340.2

Example 12: 2-methyl-1-(2-methyl-2-{[2-(pyridin-4-yl)pyrido[3,4-d]pyrimidin-4-yl]amino}propoxy)propan-2-ol

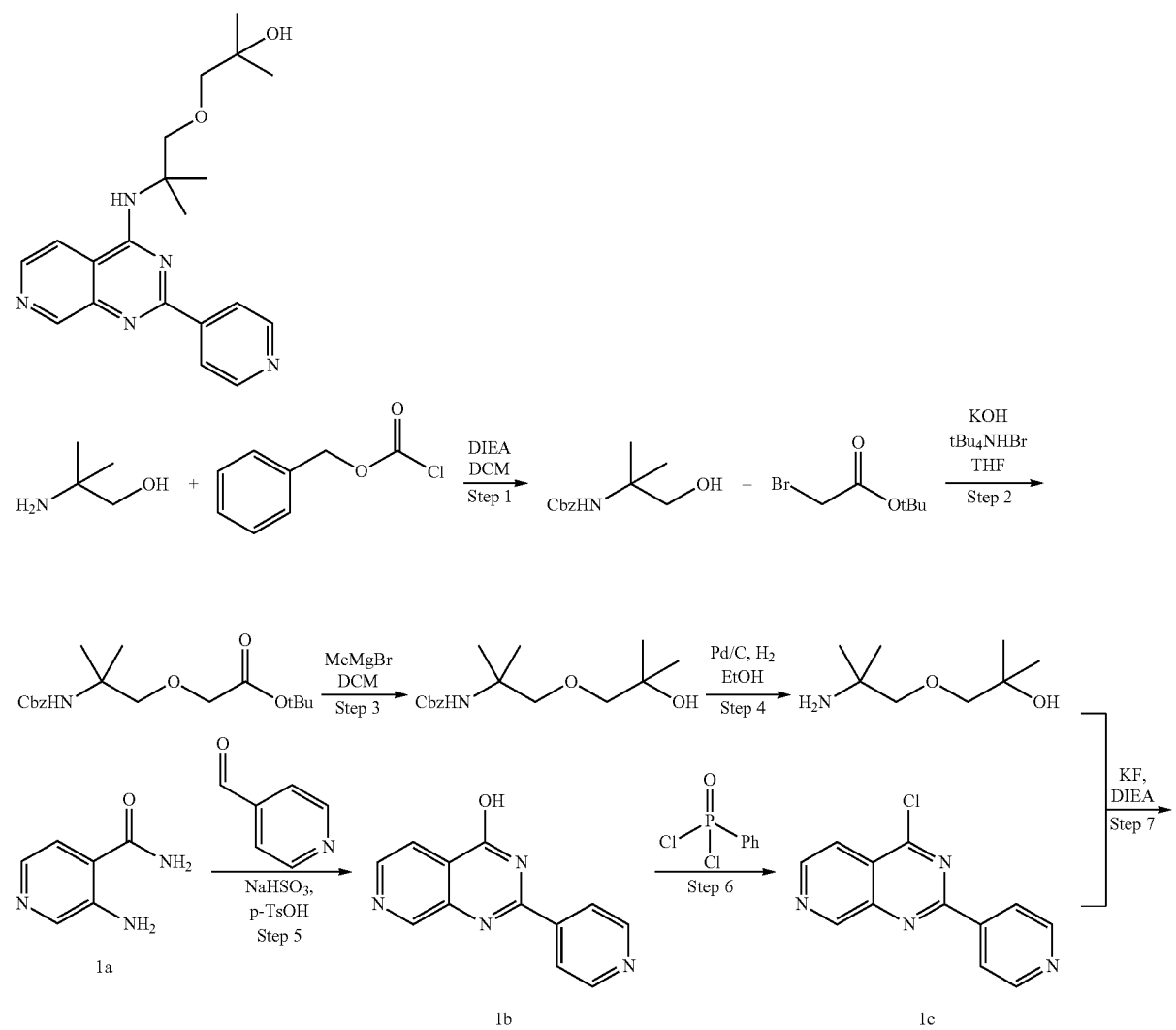

-continued

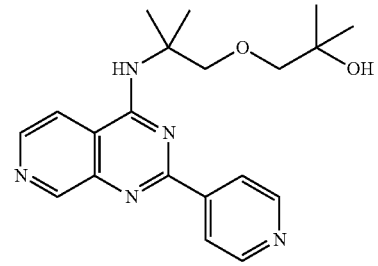

Step 1:

In a 40 ml vial at 0° C. was added 2-amino-2-methylpropan-1-ol (1.5 g, 16.8 mmol) in 8 mL of dry DCM. DIEA (3.2 mL, 18.5 mmol) was added then benzyl carbonochloridate (2.37 mL, 16.8 mmol) in portions. The reaction mixture was stirred for two hrs slowly warming to room temperature. Solvent was evaporated under air flow. The residue was purified by flash chromatography on a COMBIFLASH® system (ISCO) using 0-50% EtOAc/Hexane to afford the product benzyl-(1-hydroxy-2-methylpropan-2-yl)carbamate (90%). 1H NMR (400 MHz, Chloroform-d) δ 7.41-7.29 (m, 5H), 5.06 (s, 2H), 4.97-4.83 (m, 1H), 4.70 (s, 1H), 3.62 (s, 2H), 1.34-1.19 (m, 6H). LCMS (m/z [M+H]$^+$): 224.3.

Step 2

In a 20 mL vial was added benzyl-(1-hydroxy-2-methylpropan-2-yl)carbamate (0.63 g, 2.8 mmol) in 5 mL of dry THF. Potassium hydroxide (0.16 g, 2.8 mmol) was added in 0.5 mL of H$_2$O, then tert-butyl 2-bromoacetate (0.62 mL, 4.2 mmol) and tetrabutylammonium bromide (90 mg, 0.28 mmol). The reaction mixture was stirred overnight at 30° C. Solvent was evaporated under air flow. The residue was purified by flash chromatography on a COMBIFLASH® system (ISCO) using 0-40% EtOAc/Hexane to afford the product tert-butyl 2-(2-(((benzyloxy)carbonyl)amino)-2-methylpropoxy)acetate (35%). 1H NMR (500 MHz, Chloroform-d) b 7.39-7.28 (m, 5H), 5.52 (s, 1H), 5.06 (s, 2H), 3.96 (s, 2H), 3.45 (s, 2H), 1.48 (s, 9H), 1.36 (s, 6H). LCMS (m/z [M+H]$^+$): 338.4.

Step 3

Tert-butyl 2-(2-(((benzyloxy)carbonyl)amino)-2-methylpropoxy) acetate (700 mg, 4.15 mmol) was stirred in DCM (5 mL) in an ice bath for 10 minutes. Methyl magnesium bromide (30 mL, 42 mmol) was slowly added in portions then stirred while warming to room temp over two hrs. The reaction was then quenched with water and extracted three times with DCM. The organic layers were combined, concentrated and purified by flash chromatography on a COMBIFLASH® system (ISCO) using 0-50% EtOAc/Hexane to afford the product benzyl (1-(2-hydroxy-2 methylpropoxy)-2-methylpropan-2-yl)carbamate (55%). LCMS [M+H]= 296.4.

Step 4

In a 20 mL Septa Sealed Vial was Added Benzyl (1-(2-Hydroxy-2-methylpropoxy)-2-methylpropan-2-yl)carbamate (0.03 g, 0.11 mmol) in 1.2 mL of EtOH. The vial was vigorously purged with N$_2$ at room temperature. A small scoop of Pd/C (30%, cat. amount) was carefully added and the reaction maintained under N$_2$. A H$_2$ balloon was then used to flush the reaction vessel thoroughly and then stirred under H$_2$ pressure for four hrs. The H$_2$ was removed from the reaction then the vessel was purged with N$_2$. The material was then filtered through Na$_2$SO$_4$ and celite and the solvent evaporated under air flow. No further purification of the residue was necessary to afford (1-(2-amino-2-methylpropoxy)-2-methylpropan-2-ol) (95%). 1H NMR (500 MHz, Chloroform-d) b 3.32 (s, 2H), 3.26 (s, 2H), 1.22 (s, 6H), 1.12 (s, 6H). LCMS (m/z [M+H]$^+$): 162.2.

Step 5

In a 20 mL microwave vial was added 3-aminoisonicotinamide (1a, 2 g, 14.58 mmol), isonicotinaldehyde (1.521 mL, 16.04 mmol), sodium bisulfite (1.821 g, 17.50 mmol) and 4-methylbenzenesulfonic acid hydrate (0.277 g, 1.458 mmol) in DMA (Volume: 5 mL) to give an orange suspension. The reaction was well stirred and heated in microwave at 160° C. for 12 min. The reaction mixture was diluted with water and filtered. The solid was washed with water, MeOH and ether to give 2.03 g off white solid as the product 1b (59%). 1H NMR (400 MHz, DMSO-d6) δ 9.18 (d, J=0.9 Hz, 1H), 8.88-8.78 (m, 2H), 8.73 (d, J=5.2 Hz, 1H), 8.16-8.08 (m, 2H), 8.03 (dd, J=5.2, 0.9 Hz, 1H).

Step 6

In a 5 mL microwave reactor was 2-(pyridin-4-yl)pyrido [3,4-d]pyrimidin-4-ol (1b, 500 mg, 2.230 mmol) and phenylphosphonic dichloride (1564 microlitre, 11.15 mmol) to give a brown suspension. The reaction mixture was stirred at 170° C. for 30 min when LCMS indicated full conversion. The reaction mixture was quenched with ice/water and neutralized with saturated Na$_2$CO$_3$, then extracted with DCM×3 and give the product 1c (74%). 1H NMR (500 MHz, DMSO-d6) δ 9.65 (d, J=1.0 Hz, 1H), 8.96 (d, J=5.6 Hz, 1H), 8.87 (s, 2H), 8.47-8.30 (m, 2H), 8.18 (dd, J=5.6, 1.0 Hz, 1H). LCMS (m/z [M+H]$^+$): 243.1.

Step 7

In a 20 mL vial 4-chloro-2-(pyridin-4-yl)pyrido[3,4-d] pyrimidine (intermediate 1c) (25 mg, 0.10 mmol) was stirred in DMSO (0.7 mL) at room temperature and degassed with N$_2$. DIEA (43 uL, 0.25 mmol) was added and stirred for 5 minutes then KF (6 mg, 0.10 mmol). This mixture was stirred at room temperature for 15 minutes then 2(1-(2-amino-2-methylpropoxy)-2-methylpropan-2-ol) (0.013 mL, 0.12 mmol) was added and degassed then stirred at 60° C. for 30 min. The reaction was then concentrated and purified by flash chromatography on a COMBIFLASH® system (ISCO) using 0-10% MeOH/DCM to afford the title compound (50%). 1H NMR (400 MHz, DMSO-d6) δ 9.18 (d, J=0.8 Hz, 1H), 8.79 (m, 2H), 8.64 (d, J=5.6 Hz, 1H), 8.37 (dd, 5.7, 0.9 Hz, 1H), 8.30 (m, 2H), 7.80 (s, 1H), 4.40 (s, 1H), 3.90 (s, 2H), 3.17 (s, 2H), 1.61 (s, 6H), 0.99 (s, 6H). LCMS (m/z [M+H]$^+$): 368.2.

Example 13: N-ethyl-2-(pyridin-4-yl)pyrido[3,4-d]pyrimidin-4-amine

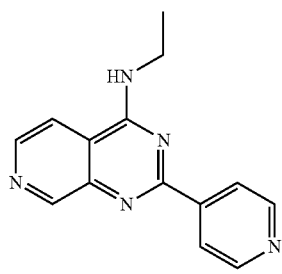 [SMILES: CCNc1nc(-c2ccncc2)nc2cnccc12]

1H NMR (400 MHz, DMSO-d6) δ 9.19 (d, J=0.9 Hz, 1H), 8.84 (m, 1H), 8.76 (m, 2H), 8.65 (d, J=5.6 Hz, 1H), 8.34 (m, 2H), 8.18 (dd, J=5.6, 0.9 Hz, 1H), 3.77-3.69 (qd, J=7.2, 5.4 Hz, 2H), 1.31 (t, J=7.2 Hz, 3H). LCMS (m/z [M+H]$^+$): 252.1.

Example 14: N-propyl-2-(pyridin-4-yl)pyrido[3,4-d]pyrimidin-4-amine

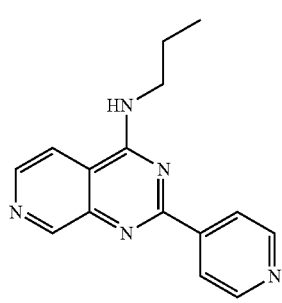 [SMILES: CCCNc1nc(-c2ccncc2)nc2cnccc12]

1H NMR (400 MHz, DMSO-d6) δ 9.19 (d, J=0.8 Hz, 1H), 8.82 (t, J=5.5 Hz, 1H), 8.78 (m, 2H), 8.64 (d, J=5.5 Hz, 1H), 8.33 (m, 2H), 8.19 (dd, J=5.6, 0.9 Hz, 1H), 3.70-3.62 (td, J=7.0, 5.7 Hz, 2H), 1.80-1.70 (m, 2H), 1.00 (t, J=7.4 Hz, 3H). LCMS (m/z [M+H]$^+$): 266.1.

Example 15: N-(2-cyclohexylpropan-2-yl)-2-(pyridin-4-yl)pyrido[3,4-d]pyrimidin-4-amine

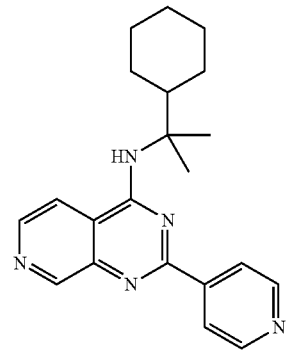 [SMILES: CC(C)(Nc1nc(-c2ccncc2)nc2cnccc12)C1CCCCC1]

1H NMR (400 MHz, DMSO-d6) δ 9.16 (d, J=0.9 Hz, 1H), 8.80 (m, 2H), 8.62 (d, J=5.6 Hz, 1H), 8.40 (dd, J=5.7, 0.9 Hz, 1H), 8.28 (m, 2H), 7.62 (s, 1H), 1.76-1.70 (m, 4H), 1.62-1.59 (m, 1H), 1.52 (s, 6H), 1.18-1.04 (q, J=11.8, 10.9 Hz, 6H). LCMS (m/z [M+H]$^+$): 348.2.

Example 16: N-(3-methyloxetan-3-yl)-2-(pyridin-4-yl)pyrido[3,4-d]pyrimidin-4-amine

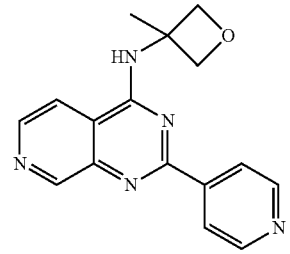

1H NMR (400 MHz, DMSO-d6) δ 9.21 (d, J=0.9 Hz, 1H), 9.14 (s, 1H), 8.76 (m, 2H), 8.68 (d, J=5.5 Hz, 1H), 8.25 (m, 2H), 8.16 (dd, J=5.6 Hz, 1H), 4.90 (d, J=6.3 Hz, 2H), 4.64 (d, J=6.5 Hz, 2H), 1.82 (s, 3H)). LCMS (m/z [M+H]$^+$): 294.1.

Example 17: N-(2-methylcyclopentyl)-2-(pyridin-4-yl)pyrido[3,4-d]pyrimidin-4-amine

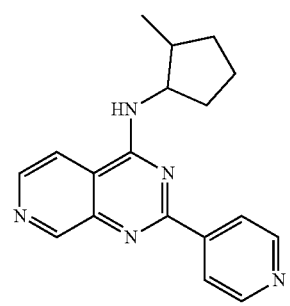 [SMILES: CC1CCCC1Nc1nc(-c2ccncc2)nc2cnccc12]

1H NMR (400 MHz, DMSO-d6) δ 9.19 (d, J=1.0 Hz, 1H), 8.78 (m, 2H), 8.66 (m, 1H), 8.33 (m, 2H), 8.32 (m, 1H), 7.91

(m, 1H), 4.45-4.42 (m, 1H), 2.20-2.14 (m, 1H), 1.98-1.82 (m, 2H), 1.80-1.72 (m, 2H), 1.70-1.62 (m, 1H), 1.50-1.42 (m, 1H), 0.91 (d, J=7.0 Hz, 3H). LCMS (m/z [M+H]$^+$): 306.2.

Example 17b: N-((1R,2S)-2-methylcyclopentyl)-2-(pyridin-4-yl)pyrido[3,4-d]pyrimidin-4-amine (17a) and N-((1S,2R)-2-methylcyclopentyl)-2-(pyridin-4-yl)pyrido[3,4-d]pyrimidin-4-amine (17b)

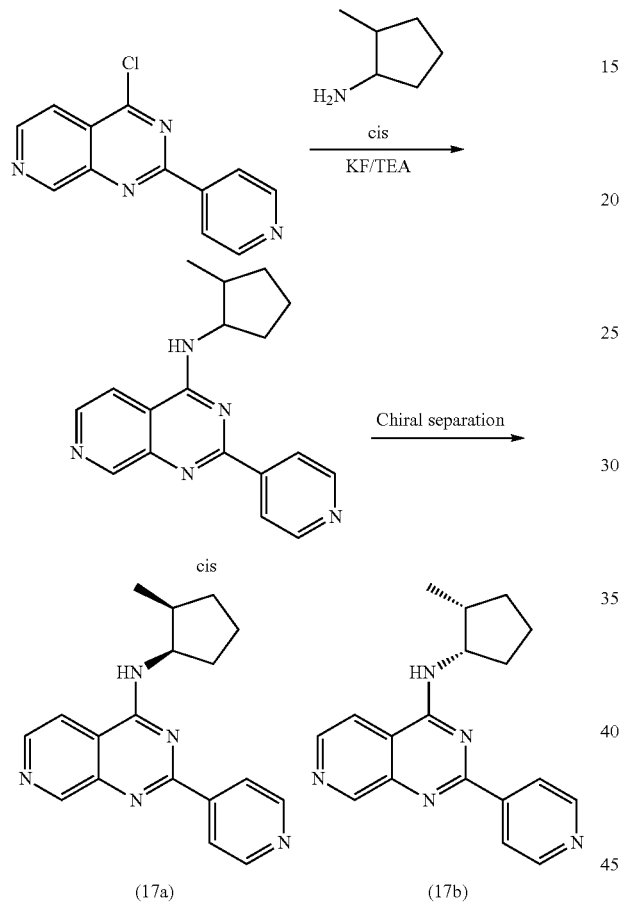

(17a)     (17b)

To a solution of 4-chloro-2-(pyridin-4-yl)pyrido[3,4-d]pyrimidine (130 mg, 0.536 mmol) in DMF (10 ml) was added TEA (0.23 ml, 1.61 mmol) and KF (32.7 mg, 0.56 mmol). The mixture was stirred for 5 minute before cis-2-methylcyclopentanamine hydrochloride (72.7 mg, 0.536 mmol) was added. The resulting mixture was then stirred for 2 hours at 50° C. The crude mixture was then purified by silica gel chromatography to afford 109 mg product. 100 mg of this material was subjected to chiral separation to afford two cis isomers, peak 1 (T$_R$=1.46 min) isomer 35 mg, peak 2 (T$_R$=1.95 min) isomer 46 mg. Chiral center assignments are tentative chiral separation conditions: solvent A CO$_2$ (80%), solvent B MeOH+0.1% NH$_4$Cl (20%), flow rate 2 ml/min, column 21×250 mm AD-H, run time 6 minute stacked injections, 10 minute elution time.

Peak 1 (T$_R$=1.46 min) isomer: 1H NMR (500 MHz, DMSO-d6) δ 9.19 (s, 1H), 8.77 (d, J=5.8 Hz, 2H), 8.66 (d, J=5.6 Hz, 1H), 8.40 (dd, J=5.7, 0.8 Hz, 1H), 8.36-8.29 (m, 3H), 4.86 (p, J=7.5 Hz, 1H), 2.09 (dtd, J=11.7, 8.1, 3.4 Hz, 1H), 1.89 (dddq, J=29.7, 12.7, 8.4, 3.8 Hz, 3H), 1.66-1.53 (m, 1H), 1.51-1.41 (m, 1H), 0.83 (d, J=7.1 Hz, 3H). LCMS (m/z [M+H]$^+$): 306.2.

Peak 2 (T$_R$=1.95 min) isomer: 1H NMR (500 MHz, DMSO-d6) δ 9.19 (d, J=0.7 Hz, 1H), 8.80-8.74 (m, 2H), 8.66 (d, J=5.6 Hz, 1H), 8.40 (dd, J=5.7, 0.8 Hz, 1H), 8.36-8.29 (m, 3H), 4.86 (p, J=7.6 Hz, 1H), 2.09 (dp, J=12.4, 4.6, 4.2 Hz, 1H), 1.98-1.79 (m, 3H), 1.66-1.54 (m, 1H), 1.50-1.41 (m, 1H), 0.83 (d, J=7.1 Hz, 3). LCMS (m/z [M+H]$^+$): 306.2.

Example 18: 3-methyl-3-{[2-(pyridin-4-yl)pyrido[3,4-d]pyrimidin-4-yl]amino}butan-2-ol

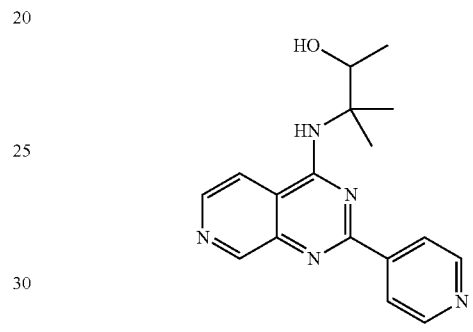

1H NMR (400 MHz, DMSO-d6) δ 9.17 (d, J=5.4 Hz, 1H), 8.79 (m, 2H), 8.63 (m, 1H), 8.33 (m, 1H), 8.28 (dd, J=5.4, 0.8 Hz, 2H), 7.58 (s, 1H), 5.00 (d, J=5.6 Hz, 1H), 4.30-4.26 (m, 1H), 1.29 (s, 3H), 1.27 (s, 3H), 1.05 (d, J=6.7 Hz, 3H). LCMS (m/z [M+H]$^+$): 310.2.

Example 19: N-butyl-2-(pyridin-4-yl)pyrido[3,4-d]pyrimidin-4-amine

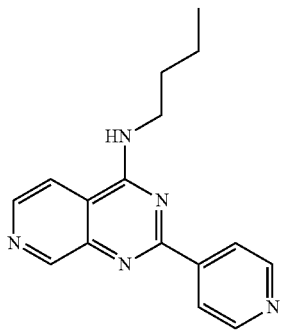 [SMILES: CCCCNc1nc(-c2ccncc2)nc2cnccc12]

1H NMR (400 MHz, DMSO-d6) δ 9.19 (d, J=0.9 Hz, 1H), 8.82 (m, 1H), 8.78 (m, 2H), 8.65 (d, J=5.6 Hz, 1H), 8.34 (m, 2H), 8.20 (dd, J=5.6, 0.9 Hz, 1H), 3.75-3.68 (td, 7.2, 5.6 Hz, 2H), 1.78-1.69 (m, 2H), 1.50-1.40 (m, 2H), 0.98 (t, J=7.4 Hz, 3H). LCMS (m/z [M+H]$^+$): 280.2.

Example 20: N-(2-methyl-4-phenylbutan-2-yl)-2-(pyridin-4-yl)pyrido[3,4-d]pyrimidin-4-amine

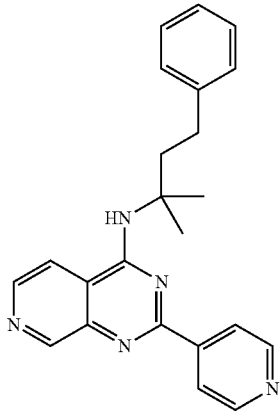 [SMILES: CC(C)(CCc1ccccc1)Nc1nc(-c2ccncc2)nc2cnccc12]

1H NMR (400 MHz, DMSO-d6) δ 9.19 (d, J=0.8 Hz, 1H), 8.78 (m, 2H), 8.63 (d, J=5.6 Hz, 1H), 8.40 (dd, J=5.7, 0.9 Hz, 1H), 8.30 (m, 2H), 7.79 (s, 1H), 7.13-7.04 (m, 5H), 2.61-2.56 (dd, J=10.7, 6.0 Hz, 2H), 2.48-2.43 (m, 2H), 1.65 (s, 6H). LCMS (m/z [M+H]+): 370.2.

Example 21: N-cyclopropyl-2-(pyridin-4-yl)pyrido[3,4-d]pyrimidin-4-amine

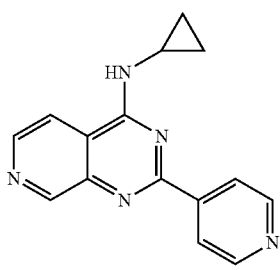 [SMILES: c1cc(-c2nc(NC3CC3)c3ccncc3n2)ccn1]

1H NMR (400 MHz, DMSO-d6) δ 9.21 (d, J=0.9 Hz, 1H), 8.83 (m, 1H), 8.78 (m, 2H), 8.64 (d, J=5.6 Hz, 1H), 8.40 (m, 2H), 8.18 (dd, J=5.6 1.0 Hz, 1H), 3.30-3.22 (m, 1H), 0.98-0.94 (m, 2H), 0.80-0.76 (m, 2H). LCMS (m/z [M+H]+): 264.1.

Example 22: N-(4-methanesulfonyl-2-methylbutan-2-yl)-2-(pyridin-4-yl)pyrido[3,4-d]pyrimidin-4-amine

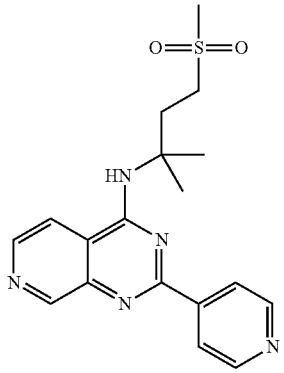 [SMILES: CC(C)(CCS(C)(=O)=O)Nc1nc(-c2ccncc2)nc2cnccc12]

1H NMR (400 MHz, DMSO-d6) δ 9.20 (d, J=0.8 Hz, 1H), 8.79 (m, 2H), 8.65 (d, J=5.6 Hz, 1H), 8.39 (dd, J=5.7, 0.9 Hz, 1H), 8.30 (m, 2H), 7.76 (s, 1H), 3.15-3.10 (m, 2H), 2.90 (s, 3H), 2.65-2.60 (m, 2H), 1.61 (s, 6H). LCMS (m/z [M+H]+): 372.1.

Example 23: 2-methyl-2-{[2-(pyridin-4-yl)pyrido[3,4-d]pyrimidin-4-yl]amino}propane-1,3-diol

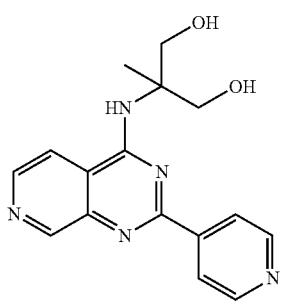 [SMILES: CC(CO)(CO)Nc1nc(-c2ccncc2)nc2cnccc12]

1H NMR (400 MHz, DMSO-d6) δ 9.18 (d, J=0.8 Hz, 1H), 8.79 (m, 2H), 8.63 (d, J=5.6 Hz, 1H), 8.32 (dd, J=5.7, 0.9 Hz, 1H), 8.29 (m, 2H), 7.38 (s, 1H), 4.81 (t, J=6.0 Hz, 2H), 3.97-3.94 (dd, J=10.8, 6.0 Hz, 2H), 3.90-3.82 (dd, J=10.9, 6.2 Hz, 2H), 1.52 (s, 3H). LCMS (m/z [M+H]+): 312.1.

Example 24: 3-{[2-(pyridin-4-yl)pyrido[3,4-d]pyrimidin-4-yl]amino}butan-2-ol

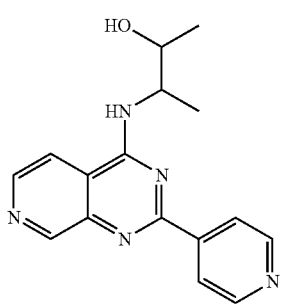 [SMILES: CC(O)C(C)Nc1nc(-c2ccncc2)nc2cnccc12]

1H NMR (400 MHz, DMSO-d6) δ 9.18 (d, J=0.8 Hz, 1H), 8.77 (m, 2H), 8.64 (d, J=5.6 Hz, 1H), 8.38 (m, 1H), 8.32 (m, 2H), 8.30 (s, 1H), 4.80 (d, J=5.5 Hz, 1H), 4.76-4.72 (m, 1H), 3.93-3.88 (m, 1H), 1.31 (d, J=6.7 Hz, 3H), 1.19 (d, J=6.3 Hz, 3H). LCMS (m/z [M+H]⁺): 296.2.

Example 25: 2-(2-methyl-2-{[2-(pyridin-4-yl)pyrido[3,4-d]pyrimidin-4-yl]amino}propoxy)acetic acid

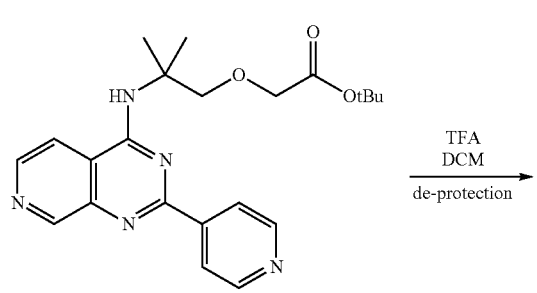

TFA
DCM
de-protection

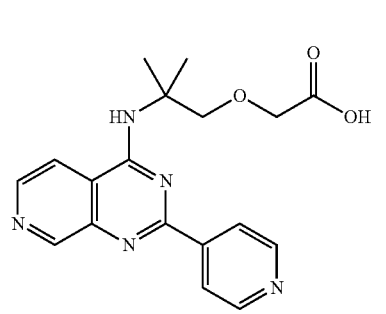

Title compound was prepared from tert-butyl 2-(2-amino-2-methylpropoxy)acetate and 4-chloro-2-(pyridin-4-yl)pyrido[3,4-d]pyrimidine as described in Step C, Example 1, followed by de-protection of the tert-butyl ester.

De-Protection:

tert-butyl 2-(2-methyl-2-((2-(pyridin-4-yl)pyrido[3,4-d]pyrimidin-4-yl)amino) propoxy)yl)amino)propoxy)acetate (25 mg, 0.061 mmol) was stirred in a 40% mixture of TFA in DCM at room temperature for two hours. No starting material was observed by TLC or LCMS. The reaction was diluted with DCM and concentrated using N₂ and mild heat then repeated three times and put on high vacuum overnight. Intermediates under these conditions were typically used without further purification. Title compounds under these conditions were then also purified by flash chromatography. 1H NMR (400 MHz, DMSO-d6) δ 9.20 (d, 0.8 Hz, 1H), 8.80 (m, 2H), 8.63 (d, J=5.6 Hz, 1H), 8.33 (ddd, J=10.8, 5.1, 1.2 Hz, 2H), 8.30 (m, 1H), 8.19 (s, 1H), 4.14 (s, 2H), 3.80 (s, 2H), 3.16 (s, 1H), 1.62 (s, 6H). LCMS (m/z [M+H]⁺): 354.2.

Example 26: (1R,2S)-2-{[2-(pyridin-4-yl)pyrido[3,4-d]pyrimidin-4-yl]amino}cyclopentan-1-ol

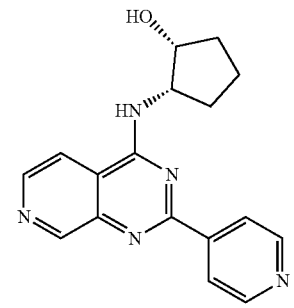 [SMILES: O[C@@H]1CCC[C@@H]1Nc1nc(-c2ccncc2)nc2cnccc12]

1H NMR (400 MHz, DMSO-d6) δ 9.19 (d, J=0.8 Hz, 1H), 8.78 (m, 1H), 8.65 (m, 1H), 8.40 (m, 1H), 8.37 (m, 1H), 8.32 (m, 2H), 4.72 (d, J=3.7 Hz, 1H), 4.60-4.52 (ddd, J=15.9, 9.2, 4.4 Hz, 1H), 4.44-4.40 (m, 1H), 2.04-1.98 (m, 3H), 1.90-1.82 (m, 1H), 1.74-1.56 (m, 2H). LCMS (m/z [M+H]⁺): 308.1.

Example 27: 4,4,4-trifluoro-3-{[2-(pyridin-4-yl)pyrido[3,4-d]pyrimidin-4-yl]amino}butan-1-ol

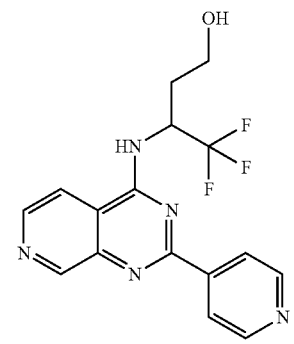 [SMILES: OCCC(Nc1nc(-c2ccncc2)nc2cnccc12)C(F)(F)F]

1H NMR (400 MHz, DMSO-d6) δ 9.30 (d, J=0.8 Hz, 1H), 8.85 (m, 1H), 8.80 (m, 2H), 8.74 (m, 1H), 8.39 (d, J=4.3 Hz, 1H), 8.33 (dd, J=5.7, 0.9 Hz, 2H), 5.76-5.70 (m, 1H), 4.77-4.70 (m, 1H), 3.61-3.55 (m, 2H), 2.11-2.08 (m, 2H). LCMS (m/z [M+H]⁺): 350.1.

193

Example 28: N-(1-methanesulfonyl-2-methylpropan-2-yl)-2-(pyridin-4-yl)pyrido[3,4-d]pyrimidin-4-amine

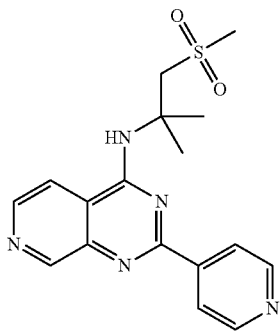 [SMILES: CC(C)(CS(C)(=O)=O)Nc1nc(-c2ccncc2)nc2cnccc12]

1H NMR (400 MHz, DMSO-d6) δ 9.20 (d, J=0.9 Hz, 1H), 8.79 (m, 2H), 8.67 (dd, J=5.9, 4.7 Hz, 1H), 8.40 (dd, J=5.7, 0.9 Hz, 1H), 8.30 (m, 2H), 8.08 (s, 1H), 4.13 (s, 2H), 2.90 (s, 3H), 1.80 (s, 6H). LCMS (m/z [M+H]$^+$): 358.1.

Example 29: (2S)-3,3,3-trifluoro-2-methyl-2-{[2-(pyridin-4-yl)pyrido[3,4-d]pyrimidin-4-yl]amino}propanoic acid

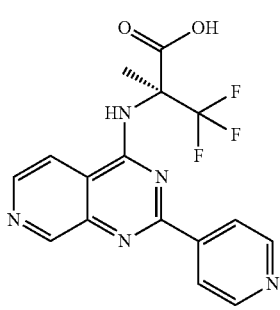 [SMILES: C[C@](Nc1nc(-c2ccncc2)nc2cnccc12)(C(=O)O)C(F)(F)F]

1H NMR (400 MHz, DMSO-d6) δ 9.23 (d, J=0.8 Hz, 1H), 8.79 (m, 2H), 8.76 (m, 1H), 8.70 (m, 1H), 8.30 (dd, J=5.6, 0.8 Hz, 2H), 7.81 (s, 1H), 2.02 (s, 3H). LCMS (m/z [M+H]$^+$): 364.1.

194

Example 30: 2-[(2-methyl-2-{[2-(pyridin-4-yl)pyrido[3,4-d]pyrimidin-4-yl]amino}propyl)amino]acetic acid

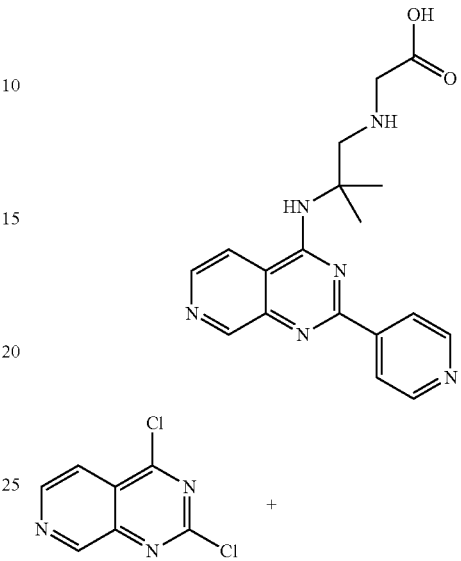

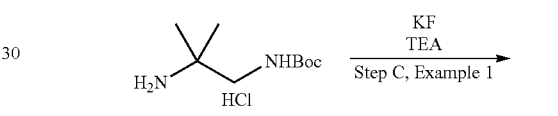

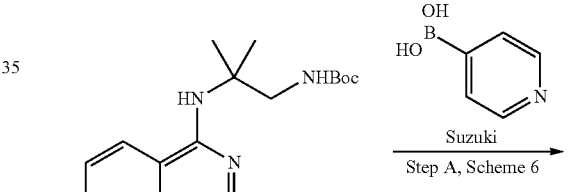

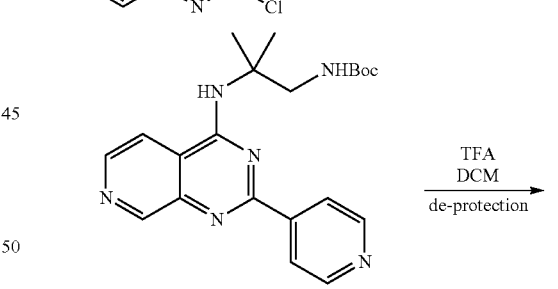

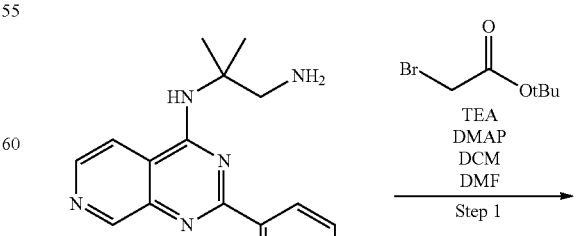

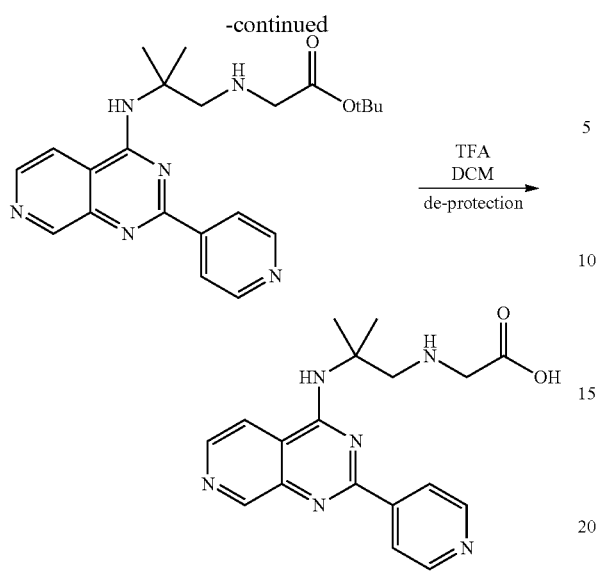

Title compound was prepared using tert-butyl 2-((2-methyl-2-((2-(pyridin-4-yl)pyrido [3,4-d]pyrimidin-4-yl)amino)propyl)amino)acetate as described in the above scheme. 1H NMR (400 MHz, DMSO-d6) δ 9.25 (m, 1H), 8.82 (m, 2H), 8.70 (m, 1H), 8.40 (m, 1H), 8.35 (m, 2H), 7.84 (d, J=9.4 Hz, 1H), 3.89-3.80 (d, J=6.2 Hz, 1H), 3.60-3.56 (d, J=11.0 Hz, 4H), 1.70 (s, 6H). LCMS (m/z [M+H]$^+$): 353.2.

Step 1

2-methyl-N2-(2-(pyridin-4-yl)pyrido[3,4-d]pyrimidin-4-yl)propane-1,2-diamine (20 mg, 0.068 mmol) was stirred in DCM/DMF at room temperature. 21 microlitre of TEA (21 microlitre, 0.149 mmol) was added and stirred for three minutes. tert-butyl 2-bromoacetate (11 microlitre, 0.071 mmol) and a catalytic amount of DMAP was then added and stirred at room temperature for four hrs. Reaction was then concentrated and purified by flash chromatography on a COMBIFLASH® system (ISCO) using 0-10% MeOH/DCM to afford the product tert-butyl 2-((2-methyl-2-((2-(pyridin-4-yl)pyrido[3,4-d]pyrimidin-4-yl)amino)propyl)amino)acetate (35%). LCMS (m/z [M+H]$^+$): 409.5.

Example 31: (2R)-3,3,3-trifluoro-2-methyl-2-{[2-(pyridin-4-yl)pyrido[3,4-d]pyrimidin-4-yl]amino}propanoic acid

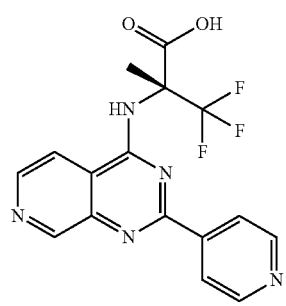 [SMILES: C[C@@](Nc1nc(-c2ccncc2)nc2cnccc12)(C(=O)O)C(F)(F)F]

1H NMR (400 MHz, DMSO-d6) δ 9.23 (d, J=0.8 Hz, 1H), 8.79 (m, 2H), 8.77 (m, 1H), 8.70 (m, 1H), 8.30 (m, 2H), 7.83 (s, 1H), 2.02 (s, 3H). LCMS (m/z [M+H]$^+$): 364.1.

Example 32: Methyl 2-methyl-2-{[2-(pyridin-4-yl)pyrido[3,4-d]pyrimidin-4-yl]amino}propanoate

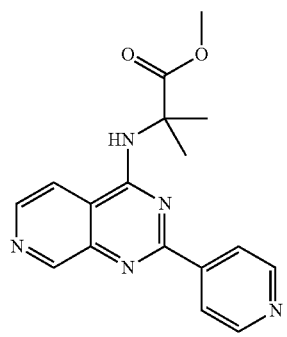 [SMILES: COC(=O)C(C)(C)Nc1nc(-c2ccncc2)nc2cnccc12]

1H NMR (400 MHz, DMSO-d6) δ 9.24 (d, J=0.8 Hz, 1H), 8.85 (s, 1H), 8.79 (m, 2H), 8.70 (d, J=5.5 Hz, 1H), 8.39 (dd, J=5.7, 1.0 Hz, 1H), 8.25 (m, 2H), 3.51 (s, 3H), 1.69 (s, 6H). LCMS (m/z [M+H]$^+$): 324.1.

Example 33: (1S,2S)-2-{[2-(pyridin-4-yl)pyrido[3,4-d]pyrimidin-4-yl]amino}cyclopentan-1-ol

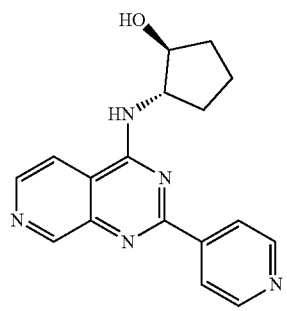 [SMILES: O[C@H]1CCC[C@@H]1Nc1nc(-c2ccncc2)nc2cnccc12]

1H NMR (400 MHz, DMSO-d6) δ 9.19 (d, J=0.8 Hz, 1H), 8.78 (m, 2H), 8.65 (d, J=5.6 Hz, 1H), 8.51 (d, J=7.0 Hz, 1H), 8.38 (m, 1H), 8.36 (m, 1H), 8.31 (dd, J=5.6, 0.9, Hz, 1H), 4.92 (d, J=4.6 Hz, 1H), 4.60-4.54 (d, J=7.0 Hz, 1H), 4.26-4.20 (m, 1H), 2.32-2.22 (ddt, J=13.2, 8.2, 4.3 Hz, 1H), 2.00-1.92 (m, 1H), 1.85-1.72 (m, 2H), 1.70-1.56 (m, 2H). LCMS (m/z [M+H]$^+$): 308.1.

Example 34: 2-methyl-2-{[2-(pyridin-4-yl)pyrido[3,4-d]pyrimidin-4-yl]amino}propanoic acid

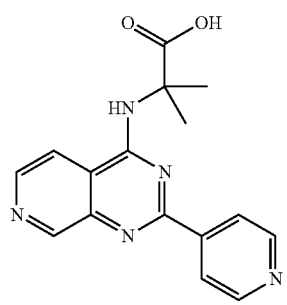 [SMILES: CC(C)(Nc1nc(-c2ccncc2)nc2cnccc12)C(=O)O]

Title compound was prepared from de-protection of methyl 2-methyl-2-((2-(pyridin-4-yl)pyrido[3,4-d]pyrimidin-4-yl)amino)propanoate as described in Step A, Example 25.

1H NMR (400 MHz, DMSO-d6) δ 12.61 (s, 1H), 9.20 (d, J=0.8 Hz, 1H), 8.86-8.80 (s, 1H), 8.75 (m, 2H), 8.67 (d, J=5.6 Hz, 1H), 8.30 (m, 2H), 8.28 (m, 1H), 1.66 (s, 6H). LCMS (m/z [M+H]+): 310.1.

Example 35: 2-(2-{[2-(pyridin-4-yl)pyrido[3,4-d]pyrimidin-4-yl]amino}ethoxy)ethan-1-ol

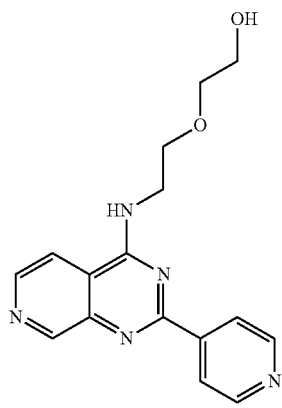 [SMILES: OCCOCCNc1nc(-c2ccncc2)nc2cnccc12]

1H NMR (400 MHz, DMSO-d6) δ 9.20 (d, J=0.9 Hz, 1H), 8.89 (t, J=5.5 Hz, 1H), 8.76 (m, 2H), 8.65 (d, J=5.5 Hz, 1H), 8.32 (m, 2H), 8.20 (dd, J=5.7, 0.9 Hz, 1H), 4.60-4.57 (m, 1H), 3.89 (q, J=5.7 Hz, 2H), 3.78 (t, J=5.8 Hz, 2H), 3.51-3.48 (d, J=2.9 Hz, 4H). LCMS (m/z [M+H]+): 312.1.

Example 36: 2-(hydroxymethyl)-2-{[2-(pyridin-4-yl)pyrido[3,4-d]pyrimidin-4-yl]amino}propane-1,3-diol

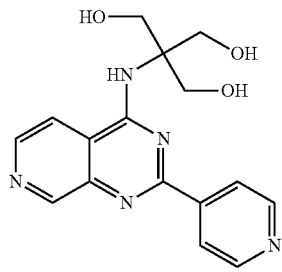 [SMILES: OCC(CO)(CO)Nc1nc(-c2ccncc2)nc2cnccc12]

1H NMR (400 MHz, DMSO-d6) δ 9.20 (d, J=0.8 Hz, 1H), 8.80 (m, 2H), 8.65 (d, J=5.6 Hz, 1H), 8.30 (ddd, J=19.4, 5.1, 1.3 Hz, 1H), 8.26 (m, 2H), 7.19 (s, 1H), 4.72 (t, J=6.0 Hz, 3H), 4.00 (d, J=6.0 Hz, 6H). LCMS (m/z [M+H]+): 328.1.

Example 37: 3-methyl-3-(3-methyl-3-{[2-(pyridin-4-yl)pyrido[3,4-d]pyrimidin-4-yl]amino}butanamido) butanoic acid

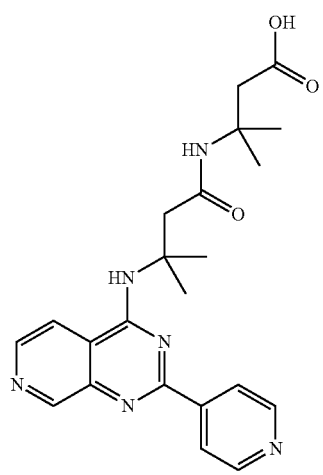 [SMILES: CC(C)(CC(=O)O)NC(=O)CC(C)(C)Nc1nc(-c2ccncc2)nc2cnccc12]

1H NMR (400 MHz, DMSO-d6) δ 9.20 (d, J=0.9 Hz, 1H), 8.80 (dt, J=4.5, 1.1 Hz, 2H), 8.64 (m, 1H), 8.33 (m, 2H), 8.30 (m, 1H), 7.90 (s, 1H), 1.72 (s, 6H), 1.70 (s, 2H), 1.30 (s, 2H), 1.00 (s, 6H). LCMS (m/z [M+H]+): 423.2.

Example 38: 2-(pyridin-4-yl)-N-(1,1,1-trifluoro-3-phenylpropan-2-yl)pyrido[3,4-d]pyrimidin-4-amine

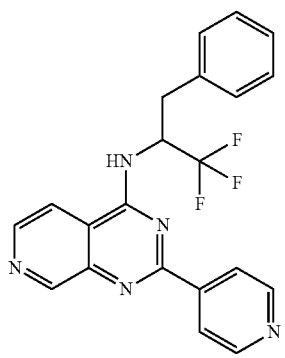 [SMILES: FC(F)(F)C(Cc1ccccc1)Nc1nc(-c2ccncc2)nc2cnccc12]

1H NMR (400 MHz, DMSO-d6) δ 9.21 (d, J=0.9 Hz, 1H), 8.99 (d, J=9.0 Hz, 1H), 8.75 (m, 2H), 8.71 (d, J=5.6 Hz, 1H), 8.33 (m, 1H), 8.30 (m, 2H), 7.41 (m, 2H), 7.11 (m, 2H), 7.02 (m, 1H), 5.95-5.86 (t, J=8.2 Hz, 1H), 3.38-3.34 (m, 1H), 3.24-3.17 (ddt, J=13.8, 11.7, 0.7 Hz, 1H). LCMS (m/z [M+H]+): 396.1.

Example 39: N-{[4-(dimethylamino)oxan-4-yl]methyl}-2-(pyridin-4-yl)pyrido[3,4-d]pyrimidin-4-amine

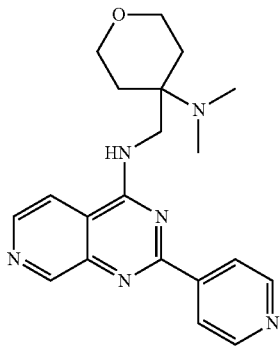 [SMILES: CN(C)C1(CNc2nc(-c3ccncc3)nc3cnccc23)CCOCC1]

1H NMR (400 MHz, DMSO-d6) δ 9.20 (s, 1H), 8.78 (m, 2H), 8.67 (d, J=5.5 Hz, 1H), 8.52 (s, 1H), 8.33 (m, 2H), 8.28 (m, 1H), 3.62 (t, J=10.6 Hz, 2H), 3.53 (d, J=10.7 Hz, 2H), 3.27 (d, J=5.3 Hz, 2H), 2.41 (s, 6H), 1.80 (d, J=14.1 Hz, 2H), 1.63 (t, J=11.5 Hz, 2H). LCMS (m/z [M+H]+): 365.2.

Example 40: 3-methyl-3-{[2-(pyridin-4-yl)pyrido[3,4-d]pyrimidin-4-yl]amino}butanoic acid

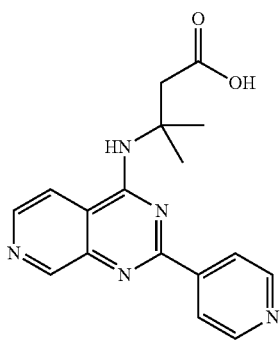 [SMILES: CC(C)(CC(=O)O)Nc1nc(-c2ccncc2)nc2cnccc12]

1H NMR (400 MHz, DMSO-d6) δ 12.02 (s, 1H), 9.20 (d, J=0.8 Hz, 1H), 8.80 (m, 2H), 8.66 (m, 1H), 8.40 (m, 1H), 8.30 (m, 2H), 7.99 (m, 1H), 3.12-3.08 (q, J=7.3 Hz, 2H), 1.70 (s, 6H. LCMS (m/z [M+H]+): 324.1.

Example 41: N-(2-methanesulfonylethyl)-2-(pyridin-4-yl)pyrido[3,4-d]pyrimidin-4-amine

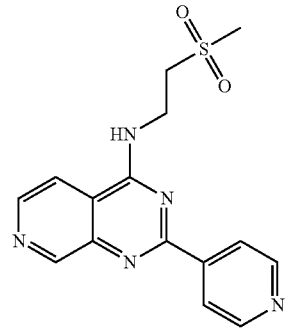 [SMILES: CS(=O)(=O)CCNc1nc(-c2ccncc2)nc2cnccc12]

1H NMR (400 MHz, DMSO-d6) δ 9.23 (s, 1H), 9.10 (t, J=5.6 Hz, 1H), 8.78 (m, 2H), 8.69 (d, J=5.7 Hz, 1H), 8.39 (m, 2H), 8.14 (d, J=5.7 Hz, 1H), 4.13-4.09 (q, J=6.4 Hz, 2H), 3.62 (t, J=6.7 Hz, 2H), 3.09 (s, 3H). LCMS (m/z [M+H]+): 330.1.

Example 42: N-[2-(adamantan-1-yl)propan-2-yl]-2-(pyridin-4-yl)pyrido[3,4-d]pyrimidin-4-amine

[Structure]

1H NMR (400 MHz, DMSO-d6) δ 9.16 (d, J=0.8 Hz, 1H), 8.78 (m, 2H), 8.63 (d, J=5.6 Hz, 1H), 8.45 (m, 1H), 8.25 (m, 2H), 7.06 (s, 1H), 1.99-1.96 (d, J=7.5 Hz, 3H), 1.80-1.76 (m, 6H), 1.67-1.64 (m, 6H), 1.64-1.60 (m, 6H). LCMS (m/z [M+H]+): 400.2.

Example 43: 2-methyl-N-[2-(pyridin-4-yl)pyrido[3,4-d]pyrimidin-4-yl]propanamide

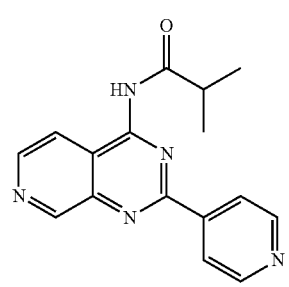 [SMILES: CC(C)C(=O)Nc1nc(-c2ccncc2)nc2cnccc12]

1H NMR (400 MHz, DMSO-d6) δ 11.08 (s, 1H), 9.49 (m, 1H), 8.84 (m, 2H), 8.80 (m, 1H), 8.40 (m, 2H), 8.25 (dd, J=5.8, 1.0 Hz, 1H), 3.29-3.18 (m, 1H), 1.26 (d, J=6.8 Hz, 6H). LCMS (m/z [M+H]⁺): 294.1.

Example 44: 4,4,4-trifluoro-3-{[2-(pyridin-4-yl)pyrido[3,4-d]pyrimidin-4-yl]amino}butanoic acid

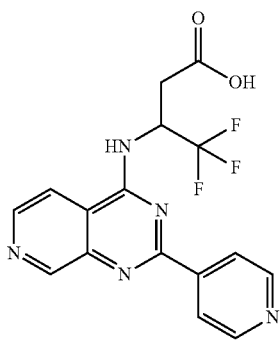 [SMILES: O=C(O)CC(Nc1nc(-c2ccncc2)nc2cnccc12)C(F)(F)F]

1H NMR (400 MHz, DMSO-d6) δ 9.29 (d, J=0.9 Hz, 1H), 8.80 (m, 2H), 8.71 (t, J=4.9 Hz, 1H), 8.34 (m, 2H), 8.23 (d, J=5.7 Hz, 1H), 5.84-5.79 (m, 1H), 3.65-3.55 (d, J=4.8 Hz, 1H), 2.45-2.41 (d, J=4.7 Hz, 1H), 2.32-2.26 (m, 1H). LCMS (m/z [M+H]⁺): 364.1.

Example 45: N-[2-(pyridin-4-yl)pyrido[3,4-d]pyrimidin-4-yl]propane-2-sulfonamide

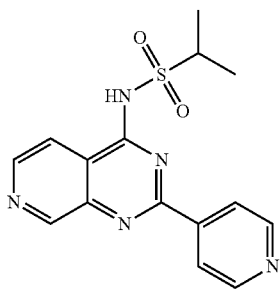 [SMILES: CC(C)S(=O)(=O)Nc1nc(-c2ccncc2)nc2cnccc12]

1H NMR (400 MHz, DMSO-d6) δ 9.38 (s, 1H), 8.88 (m, 2H), 8.76 (d, J=5.6 Hz, 1H), 8.40-8.30 (m, 3H), 4.20-4.10 (q, J=7.1 Hz, 1H), 1.40 (d, J=6.9 Hz, 6H). LCMS (m/z [M+H]⁺): 330.1.

Example 46: 2-(pyridin-4-yl)-N-[3-(1H-1,2,3,4-tetrazol-5-yl)propyl]pyrido[3,4-d]pyrimidin-4-amine

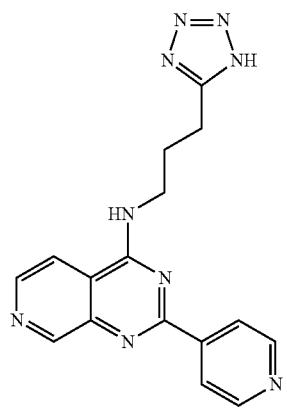 [SMILES: c1cc(-c2nc(NCCCc3nnn[nH]3)c3ccncc3n2)ccn1]

1H NMR (400 MHz, DMSO-d6) δ 9.21 (m, 1H), 9.18 (s, 1H), 8.75 (m, 2H), 8.64 (d, J=5.6 Hz, 1H), 8.30 (m, 2H), 8.21 (dd, J=5.6, 1.0 Hz, 1H), 3.81-3.75 (td, J=6.9, 5.3 Hz, 2H), 2.95 (t, J=7.2 Hz, 2H), 2.18-2.10 (m, 2H). LCMS (m/z [M+H]⁺): 334.2.

Example 47: N-methyl-2-(pyridin-4-yl)-N-(1,1,1-trifluoropropan-2-yl)pyrido[3,4-d]pyrimidin-4-amine

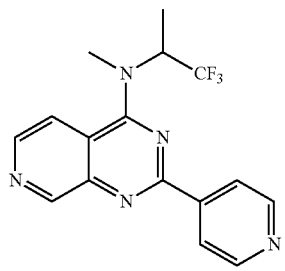

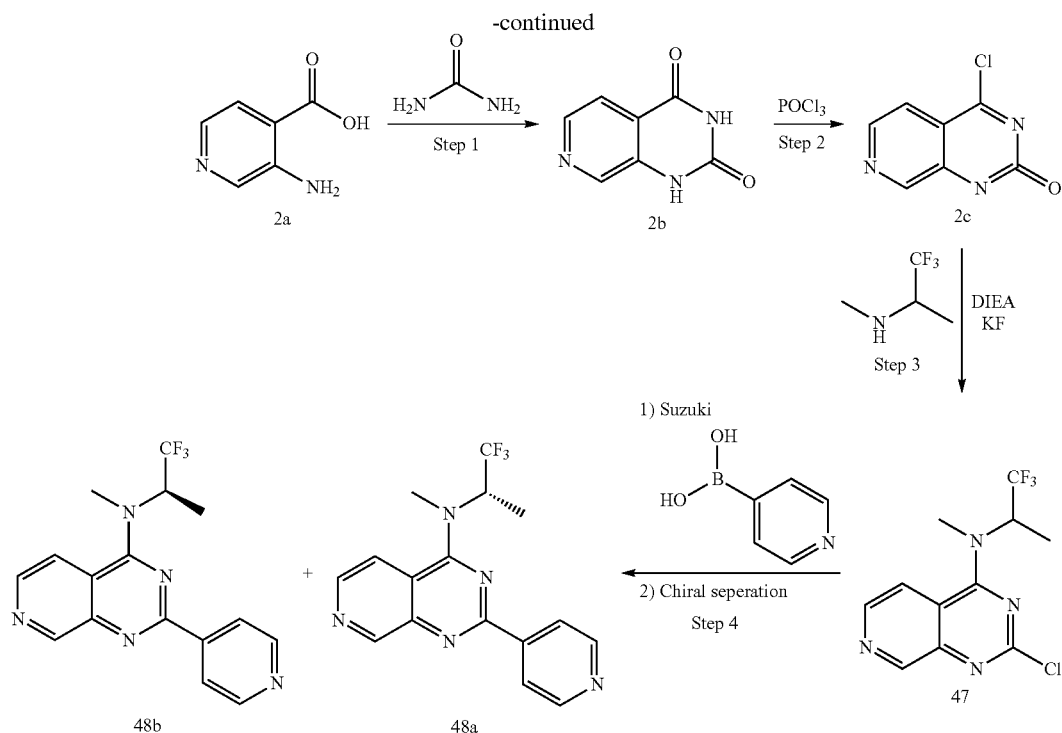

Step 1

A mixture of urea (40.00 g, 666.00 mmol) and 3-aminoisonicotinic acid (2a, 18.40 g, 133.20 mmol) was heated at 210° C. for 1 hr (NOTE: no solvent was used). NaOH (2N, 320 mL) was added, and the mixture was stirred at 90° C. for 1 h. The solid was collected by filtration, and washed with water. The crude product thus obtained was suspended in HOAc (400 mL), and stirred at 100° C. for 1 h. The mixture was cooled to RT, filtered, and the solid was washed with a large amount of water, and then dried under the vacuum to give pyrido[3,4-d]pyrimidine-2,4(1H,3H)-dione (2b, 17.00 g, 78% yield) without further purification. LCMS (m/z [M+H]$^+$): 164.0.

Step 2

To a mixture of pyrido[3,4-d]pyrimidine-2,4(1H,3H)-dione (2b, 20.00 g, 122.60 mmol) and POCl$_3$ (328.03 g, 2.14 mol) in toluene (200 mL) was added DIEA (31.69 g, 245.20 mmol) dropwise and this reaction mixture stirred at 25° C. overnight (18 hr) to give suspension.

The solvent and POCl$_3$ was removed under vacuum, diluted with DCM (50 mL), neutralized with DIEA to pH=7 at −20° C. and concentrated again, the residue was purified by column (20-50% EA/PE) to give 2,4-dichloropyrido[3,4-d]pyrimidine (2c, 20.00 g, 99.99 mmol, 82% yield) as a yellow solid. 1H NMR (400 MHz, CHLOROFORM-d) b 9.52 (s, 1H), 8.92 (d, J=5.6 Hz, 1H), 8.04 (d, J=5.6 Hz, 1H). LCMS (m/z [M+H]$^+$): 200.0.

Step 3

In a 20 mL vial 2,4-dichloropyrido[3,4-d]pyrimidine (600 mg, 3.0 mmol) was stirred in DMSO (0.7 mL) at room temperature and degassed with N$_2$. DIEA (1 mL, 6 mmol) was added and stirred for 5 minutes then KF (174 mg, 3 mmol). This mixture was stirred at room temperature for 15 minutes then racemic 1,1,1-trifluoro-N-methylpropan-2-amine (419 mg, 3.3 mmol) was added and degassed then stirred at 60° C. for 4 hours. The reaction was then concentrated and purified by flash chromatography on a COMBIFLASH® system (ISCO) using 0-10% MeOH/DCM to afford 2-chloro-N-methyl-N-(1,1,1-trifluoropropan-2-yl)pyrido[3,4-d]pyrimidin-4-amine (680 mg, 74%). 1H NMR (500 MHz, Acetone-d6) δ 9.09 (d, J=0.9 Hz, 1H), 8.59 (d, J=5.9 Hz, 1H), 8.22 (dd, J=5.9, 0.9 Hz, 1H), 5.93 (dddd, J=15.3, 8.3, 7.0, 1.2 Hz, 1H), 3.61 (q, J=1.0 Hz, 3H), 1.63 (d, J=7.0 Hz, 3H). LCMS (m/z [M+H]$^+$): 291.7.

Step 4

In a 20 mL microwave reactor was added PalladiumTetrakis (99 mg, 0.086 mmol), potassium carbonate (2.15 mL, 4.3 mmol), and 2 chloro-N-methyl-N-(1,1,1-trifluoropropan-2-yl)pyrido[3,4-d]pyrimidin-4-amine (500 mg, 1.72 mmol) and pyridin-4-ylboronic acid (233 mg, 1.89 mmol) in acetonitrile (8 mL) to give an yellow suspension. The reaction mixture was stirred at 130° C. for 30 min under microwave. The crude mixture was diluted with DCM, H$_2$O, separated and extracted with DCM×3. Combined the organic layers and dried Na$_2$SO$_4$, filtered and concentrated. The residue was purified by flash chromatography on a COMBIFLASH® system (ISCO) using 0-10% MeOH/DCM to give Example 47, the racemic product, then followed by chiral HPLC (21×250 mm OJ-H column with 85% CO$_2$ as phase A and 15% MeOH as phase B, flow rate 2 mL/min, 30° C., 3.5 min elution time) to separate the enantiomers to afford Examples 4ba and 48b.

205

Example 48a: N-methyl-2-(pyridin-4-yl)-N-[(2S)-1,1,1-trifluoropropan-2-yl]pyrido[3,4-d]pyrimidin-4-amine

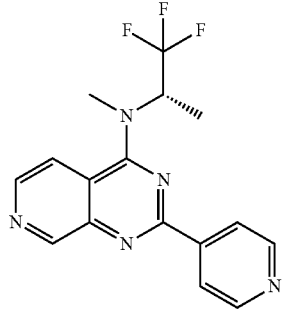 [SMILES: C[C@H](N(C)c1nc(-c2ccncc2)nc2cnccc12)C(F)(F)F]

1H NMR (500 MHz, DMSO-d6) δ 9.33 (d, J=0.8 Hz, 1H), 8.86-8.75 (m, 2H), 8.63 (d, J=5.9 Hz, 1H), 8.38-8.30 (m, 2H), 8.20 (dd, J=6.0, 0.9 Hz, 1H), 6.11 (qt, J=8.5, 7.4 Hz, 1H), 3.50 (d, J=1.1 Hz, 3H), 1.61 (d, J=7.0 Hz, 3H). LCMS (m/z [M+H]+): 334.1. Chiral HPLC T$_R$=1.73 min. Absolute stereochemistry was confirmed by X-ray crystal structure.

Example 48b: N-methyl-2-(pyridin-4-yl)-N-[(2R)-1,1,1-trifluoropropan-2-yl]pyrido[3,4-d]pyrimidin-4-amine

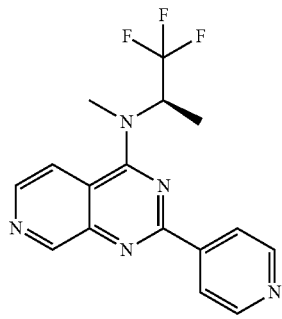 [SMILES: C[C@@H](N(C)c1nc(-c2ccncc2)nc2cnccc12)C(F)(F)F]

1H NMR (500 MHz, DMSO-d6) δ 9.33 (d, J=0.8 Hz, 1H), 8.86-8.75 (m, 2H), 8.63 (d, J=5.9 Hz, 1H), 8.38-8.30 (m, 2H), 8.20 (dd, J=6.0, 0.9 Hz, 1H), 6.11 (qt, J=8.5, 7.4 Hz, 1H), 3.50 (d, J=1.1 Hz, 3H), 1.61 (d, J=7.0 Hz, 3H). LCMS (m/z [M+H]+): 334.1. Chiral HPLC T$_R$=1.25 min. Absolute stereochemistry was confirmed by X-ray crystal structure.

206

Example 49: 2,4-dimethyl-4-{[2-(pyridin-4-yl)pyrido[3,4-d]pyrimidin-4-yl]amino}pentan-2-ol

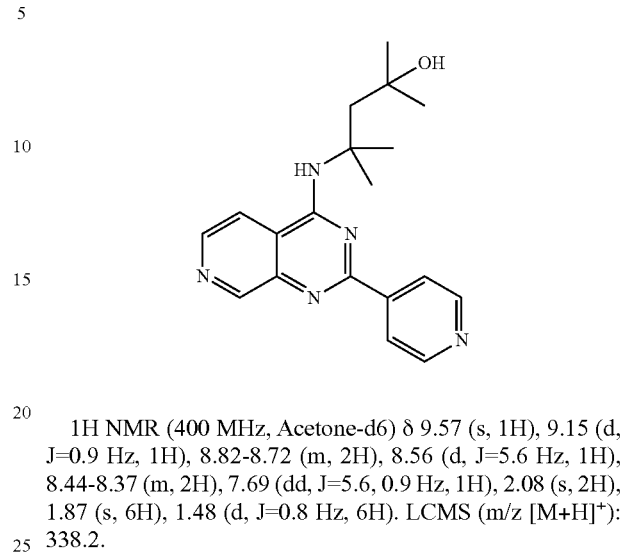

1H NMR (400 MHz, Acetone-d6) δ 9.57 (s, 1H), 9.15 (d, J=0.9 Hz, 1H), 8.82-8.72 (m, 2H), 8.56 (d, J=5.6 Hz, 1H), 8.44-8.37 (m, 2H), 7.69 (dd, J=5.6, 0.9 Hz, 1H), 2.08 (s, 2H), 1.87 (s, 6H), 1.48 (d, J=0.8 Hz, 6H). LCMS (m/z [M+H]+): 338.2.

Example 50: 4,4,4-trifluoro-2,3-dimethyl-3-{[2-(pyridin-4-yl)pyrido[3,4-d]pyrimidin-4-yl]amino}butan-2-ol

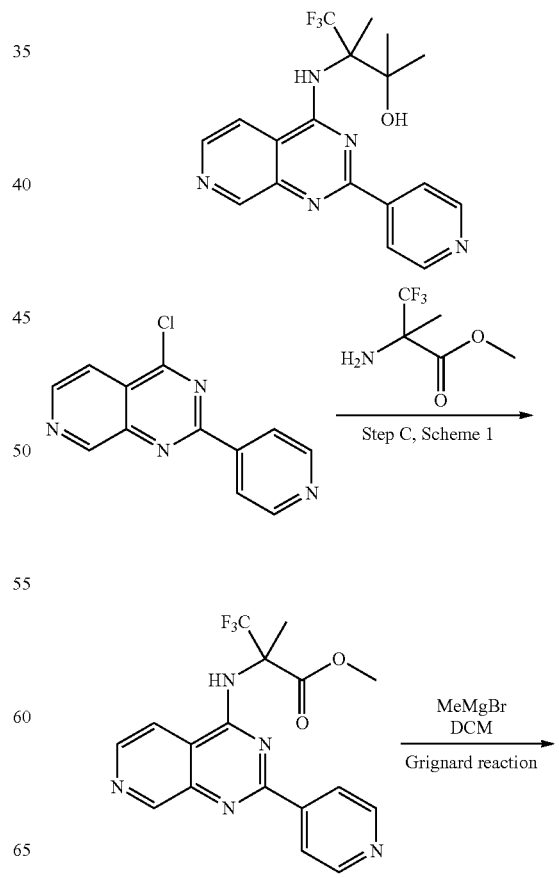

-continued

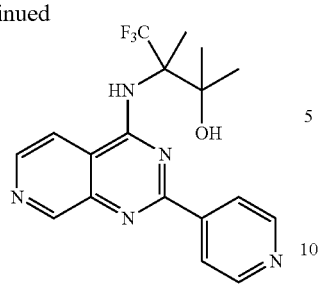

The title compound was prepared from methyl 2-amino-3,3,3-trifluoro-2-methylpropanoate hydrochloride and 4-chloro-2-(pyridin-4-yl)pyrido[3,4-d]pyrimidine as described in Step C, Example 1, followed by Grignard reaction with methylmagnesium bromide.

Grignard reaction: methyl 3,3,3-trifluoro-2-methyl-2-((2-(pyridin-4-yl)pyrido[3,4-d]pyrimidin-4-yl)amino)propanoate (7 mg, 0.019 mmol) was stirred with methylmagnesium bromide (1.4 M in hexanes, 0.133 mL) in DCM at 0° C. for 1 hour. No starting material was observed by TLC or LCMS. The reaction was quenched by MeOH and concentrated. The residue was purified by flash chromatography on a COMBIFLASH® system (ISCO) using 0-10% MeOH/DCM to give the title compound (66%). 1H NMR (500 MHz, Methanol-d4) b 9.28 (d, J=0.9 Hz, 1H), 8.77-8.71 (m, 2H), 8.67 (d, J=5.7 Hz, 1H), 8.44-8.38 (m, 2H), 7.85 (dd, J=5.7, 0.9 Hz, 1H), 2.09 (d, J=1.4 Hz, 3H), 1.55 (t, J=2.2 Hz, 3H), 1.37 (s, 3H). LCMS (m/z [M+H]$^+$): 378.2.

Example 51: (1-{[2-(pyridin-4-yl)pyrido[3,4-d]pyrimidin-4-yl]amino}cyclopentyl)methanol

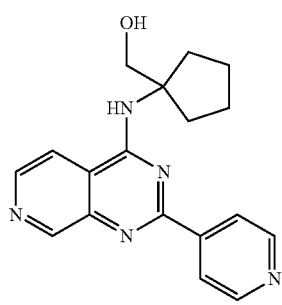 [SMILES: OCC1(Nc2nc(-c3ccncc3)nc3cnccc23)CCCC1]

1H NMR (500 MHz, Chloroform-d) δ 9.35 (d, J=0.9 Hz, 1H), 8.82-8.75 (m, 2H), 8.65 (d, J=5.6 Hz, 1H), 8.30-8.24 (m, 2H), 7.49 (dd, J=5.8, 0.9 Hz, 1H), 3.99 (d, J=4.0 Hz, 2H), 2.19 (td, J=7.3, 6.7, 2.5 Hz, 4H), 1.94-1.78 (m, 4H). LCMS (m/z [M+H]$^+$): 322.2.

Example 52: N-(3-methoxycyclobutyl)-2-(pyridin-4-yl)pyrido[3,4-d]pyrimidin-4-amine

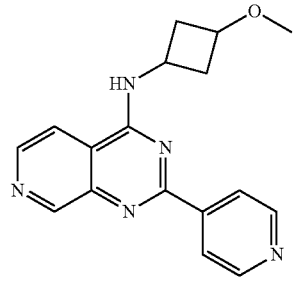 [SMILES: COC1CC(Nc2nc(-c3ccncc3)nc3cnccc23)C1]

1H NMR (500 MHz, DMSO-d6) δ 9.19 (d, J=0.9 Hz, 1H), 8.87 (d, J=6.4 Hz, 1H), 8.80-8.72 (m, 2H), 8.66 (d, J=5.5 Hz, 1H), 8.37-8.32 (m, 2H), 8.25 (dd, J=5.6, 0.9 Hz, 1H), 4.53-4.42 (m, 1H), 3.84-3.74 (m, 1H), 3.20 (s, 3H), 2.89-2.79 (m, 2H), 2.11 (tdd, J=9.0, 7.5, 2.8 Hz, 2H). LCMS (m/z [M+H]$^+$): 308.1.

Example 53: (1R,2R)-1-N,2-N-dimethyl-1-N-[2-(pyridin-4-yl)pyrido[3,4-d]pyrimidin-4-yl]cyclohexane-1,2-diamine

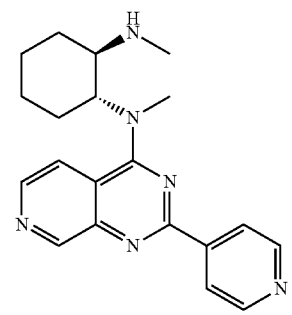 [SMILES: CN[C@@H]1CCCC[C@H]1N(C)c1nc(-c2ccncc2)nc2cnccc12]

1H NMR (500 MHz, Methanol-d4) δ 9.23 (d, J=0.8 Hz, 1H), 8.73-8.68 (m, 2H), 8.53 (d, J=5.9 Hz, 1H), 8.46-8.41 (m, 2H), 8.22 (dd, J=5.8, 0.9 Hz, 1H), 3.47 (s, 3H), 2.91 (dd, J=13.0, 9.0 Hz, 1H), 2.39 (s, 3H), 2.30 (dtt, J=12.6, 5.1, 2.5 Hz, 1H), 2.04 (dp, J=12.4, 3.1 Hz, 1H), 1.90 (dddd, J=23.1, 13.0, 5.6, 3.0 Hz, 2H), 1.84-1.74 (m, 1H), 1.58 (qt, J=12.7, 3.5 Hz, 1H), 1.42 (qt, J=13.2, 3.3 Hz, 1H), 1.33-1.23 (m, 1H). LCMS (m/z [M+H]$^+$): 349.2.

Example 54: methyl (1s,3s)-3-{[2-(pyridin-4-yl)pyrido[3,4-d]pyrimidin-4-yl]amino}cyclobutane-1-carboxylate

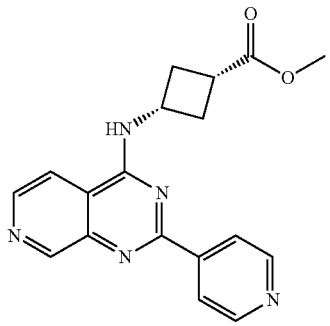 [SMILES: COC(=O)[C@H]1C[C@@H](Nc2nc(-c3ccncc3)nc3cnccc23)C1]

1H NMR (500 MHz, DMSO-d6) δ 9.20 (d, J=0.9 Hz, 1H), 8.95 (d, J=6.0 Hz, 1H), 8.82-8.72 (m, 2H), 8.67 (d, J=5.5 Hz, 1H), 8.34-8.28 (m, 2H), 8.25 (dd, J=5.6, 1.0 Hz, 1H), 4.95 (h, J=7.3 Hz, 1H), 3.71 (s, 3H), 3.27-3.21 (m, 1H), 2.72 (dddd, J=10.7, 8.2, 4.3, 2.5 Hz, 2H), 2.62-2.51 (m, 2H). LCMS (m/z [M+H]+): 336.1.

Example 55: ethyl 1-{[2-(pyridin-4-yl)pyrido[3,4-d]pyrimidin-4-yl]amino}cyclobutane-1-carboxylate

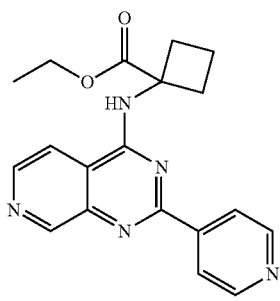 [SMILES: CCOC(=O)C1(Nc2nc(-c3ccncc3)nc3cnccc23)CCC1]

1H NMR (400 MHz, Chloroform-d) δ 9.27 (dd, J=12.0, 4.4 Hz, 1H), 8.83-8.74 (m, 2H), 8.54-8.40 (m, 1H), 8.40-8.31 (m, 2H), 7.56-7.49 (m, 1H), 4.32-4.16 (m, 2H), 3.03-2.85 (m, 2H), 2.49 (dddd, J=11.8, 9.4, 7.1, 2.3 Hz, 2H), 2.31-2.11 (m, 2H), 1.22 (dtd, J=9.6, 7.5, 7.0, 1.8 Hz, 3H). LCMS (m/z [M+H]+): 350.2.

Example 56: 1-{[2-(pyridin-4-yl)pyrido[3,4-d]pyrimidin-4-yl]amino}cyclobutane-1-carboxylic acid

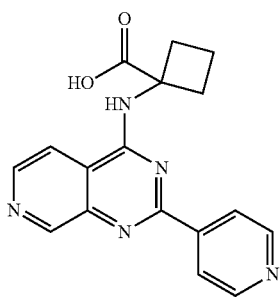 [SMILES: O=C(O)C1(Nc2nc(-c3ccncc3)nc3cnccc23)CCC1]

The title compound was prepared by hydrolysis of the ethyl ester of Example 55.

Hydrolysis: a suspension of example 55 (27 mg, 0.077 mmol) and lithium hydroxide (0.077 mL, 0.077 mmol) in MeOH (2 mL) was stirred at 90° C. for 3 hr until LCMS indicated no starting material left. The reaction mixture was neutralized with 2 mL 1M HCl. The aqueous layer was back extracted with DCM×5. The combined organic layer was washed with brine, dried and concentrated. The residue was washed with DCM/ether to give the title compound (92%). 1H NMR (500 MHz, DMSO-d6) δ 12.49 (s, 1H), 9.35 (s, 1H), 9.23 (d, J=0.9 Hz, 1H), 8.80-8.72 (m, 2H), 8.70 (d, J=5.5 Hz, 1H), 8.34 (dd, J=5.6, 1.0 Hz, 1H), 8.32-8.21 (m, 2H), 2.82 (ddd, J=13.3, 8.8, 4.9 Hz, 2H), 2.49-2.43 (m, 2H), 2.12-1.96 (m, 2H). LCMS (m/z [M+H]+): 322.1.

Example 57: (1s,3s)-3-{[2-(pyridin-4-yl)pyrido[3,4-d]pyrimidin-4-yl]amino}cyclobutane-1-carboxylic acid

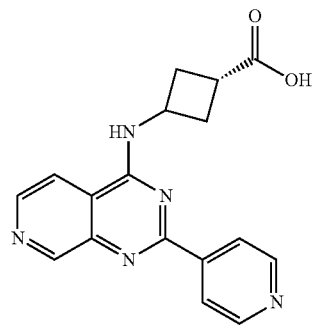

The title compound was prepared by hydrolysis of the ethyl ester of Example 54 using the procedure as described in Example 56. 1H NMR (500 MHz, DMSO-d6) δ 9.26 (d, J=0.9 Hz, 1H), 9.21 (d, J=6.0 Hz, 1H), 9.02-8.93 (m, 2H), 8.73 (d, J=5.6 Hz, 1H), 8.66 (d, J=5.7 Hz, 2H), 8.38 (dd, J=5.7, 0.9 Hz, 1H), 4.92 (q, J=7.4 Hz, 1H), 3.19-3.11 (m, 1H), 2.76-2.68 (m, 2H), 2.56 (ddd, J=12.9, 6.5, 2.7 Hz, 2H). LCMS (m/z [M+H]+): 322.1.

Example 58: 2-(pyridin-4-yl)-N-(1,1,1-trifluoro-2-methylpropan-2-yl)pyrido[3,4-d]pyrimidin-4-amine

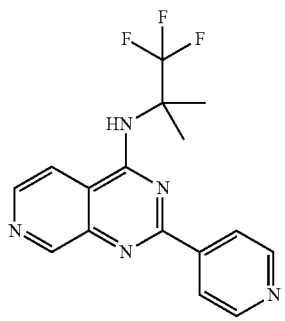 [SMILES: CC(C)(Nc1nc(-c2ccncc2)nc2cnccc12)C(F)(F)F]

1H NMR (400 MHz, DMSO-d6) δ 9.27 (d, J=0.8 Hz, 1H), 8.84-8.77 (m, 2H), 8.72 (d, J=5.7 Hz, 1H), 8.51 (dd, J=5.7, 0.9 Hz, 1H), 8.30-8.24 (m, 2H), 7.98 (s, 1H), 1.91 (s, 6H). LCMS (m/z [M+H]+): 334.1.

Example 59: N-tert-butyl-2-(pyridin-4-yl)pyrido[3,4-d]pyrimidin-4-amine

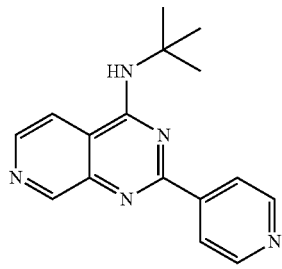 [SMILES: CC(C)(C)Nc1nc(-c2ccncc2)nc2cnccc12]

1H NMR (500 MHz, DMSO-d6) δ 9.18 (d, J=0.8 Hz, 1H), 8.82-8.77 (m, 2H), 8.64 (d, J=5.6 Hz, 1H), 8.39 (dd, J=5.7, 0.9 Hz, 1H), 8.34-8.29 (m, 2H), 7.88 (s, 1H), 1.66 (s, 9H). LCMS (m/z [M+H]$^+$): 280.2.

Example 60: N-(1-methylcyclobutyl)-2-(pyridin-4-yl)pyrido[3,4-d]pyrimidin-4-amine

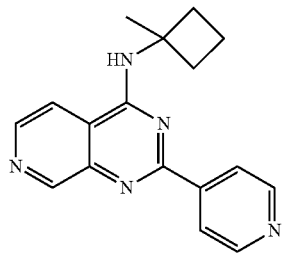 [SMILES: CC1(Nc2nc(-c3ccncc3)nc3cnccc23)CCC1]

1H NMR (400 MHz, DMSO-d6) δ 9.17 (d, J=0.8 Hz, 1H), 8.77 (dd, J=6.3, 1.9 Hz, 2H), 8.63 (d, J=5.6 Hz, 1H), 8.33-8.29 (m, 2H), 8.27 (dd, J=5.7, 0.9 Hz, 1H), 2.70-2.64 (m, 1H), 2.58-2.53 (m, 1H), 2.35-2.26 (m, 2H), 2.04-1.81 (m, 2H), 1.71 (s, 3H). LCMS (m/z [M+H]$^+$): 292.2.

Example 61: 3-methyl-3-{[2-(pyridin-4-yl)pyrido[3,4-d]pyrimidin-4-yl]amino}butan-1-ol

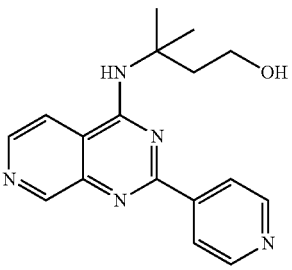 [SMILES: CC(C)(CCO)Nc1nc(-c2ccncc2)nc2cnccc12]

1H NMR (500 MHz, DMSO-d6) δ 9.19 (d, J=0.8 Hz, 1H), 8.83-8.77 (m, 2H), 8.65 (d, J=5.6 Hz, 1H), 8.34-8.29 (m, 2H), 8.17 (s, 1H), 8.12 (dd, J=5.7, 0.9 Hz, 1H), 4.86 (s, 1H), 3.68-3.61 (m, 2H), 2.19 (t, J=6.6 Hz, 2H), 1.66 (s, 6H). LCMS (m/z [M+H]$^+$): 310.2.

Example 62: 2-(pyridin-4-yl)-N-[1-(trifluoromethyl)cyclobutyl]pyrido[3,4-d]pyrimidin-4-amine

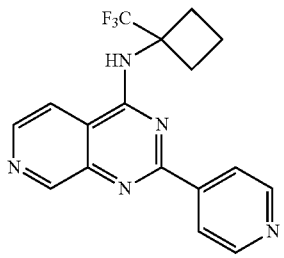 [SMILES: FC(F)(F)C1(Nc2nc(-c3ccncc3)nc3cnccc23)CCC1]

1H NMR (500 MHz, DMSO-d6) δ 9.26 (d, J=0.9 Hz, 1H), 8.98 (s, 1H), 8.81-8.76 (m, 2H), 8.71 (d, J=5.6 Hz, 1H), 8.39 (dd, J=5.8, 0.9 Hz, 1H), 8.30-8.25 (m, 2H), 2.91-2.76 (m, 4H), 2.11-1.96 (m, 2H). LCMS (m/z [M+H]$^+$): 346.1.

Example 63: N-(2-methylbutan-2-yl)-2-(pyridin-4-yl)pyrido[3,4-d]pyrimidin-4-amine

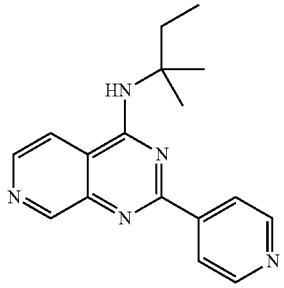 [SMILES: CCC(C)(C)Nc1nc(-c2ccncc2)nc2cnccc12]

1H NMR (500 MHz, Methanol-d4) δ 9.19-9.12 (m, 1H), 8.72 (ddt, J=6.3, 4.7, 1.6 Hz, 2H), 8.57 (dd, J=5.8, 2.6 Hz, 1H), 8.43 (tt, J=7.3, 3.4 Hz, 2H), 8.24-8.17 (m, 1H), 2.23 (qd, J=6.7, 6.0, 2.6 Hz, 2H), 1.66 (s, 6H), 0.94 (td, J=7.4, 1.6 Hz, 3H). LCMS (m/z [M+H]$^+$): 294.2.

Example 64: 2-(pyridin-4-yl)-N-[1-(trifluoromethyl)cyclopropyl]pyrido[3,4-d]pyrimidin-4-amine

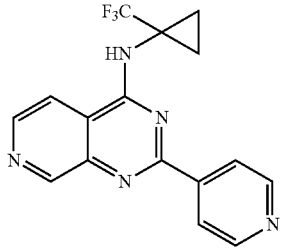 [SMILES: FC(F)(F)C1(Nc2nc(-c3ccncc3)nc3cnccc23)CC1]

1H NMR (500 MHz, DMSO-d6) δ 9.40 (s, 1H), 9.29 (d, J=0.9 Hz, 1H), 8.83-8.78 (m, 2H), 8.71 (d, J=5.6 Hz, 1H), 8.40-8.35 (m, 2H), 8.27 (dd, J=5.7, 1.0 Hz, 1H), 1.65-1.55 (m, 2H), 1.41-1.37 (m, 2H). LCMS (m/z [M+H]$^+$): 332.1.

Example 65: N-cyclopentyl-2-(pyridin-4-yl)pyrido[3,4-d]pyrimidin-4-amine

Example 67: 3,3,3-trifluoro-2-methyl-2-{[2-(pyridin-4-yl)pyrido[3,4-d]pyrimidin-4-yl]amino}propan-1-ol

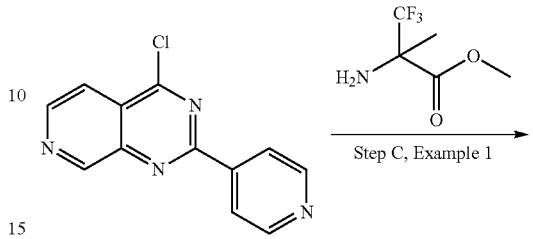

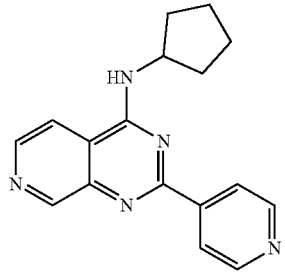 [SMILES: c1cc(-c2nc(NC3CCCC3)c3ccncc3n2)ccn1]

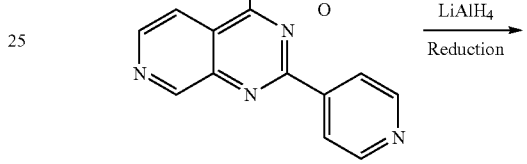

In a 20 mL vial 4-chloro-2-(pyridin-4-yl)pyrido[3,4-d]pyrimidine (intermediate 1c) (200 mg, 0.82 mmol) was stirred in DCM (5 mL) at room temperature and degassed with $N_2$. DIEA (324 microlitre, 1.85 mmol) was added and stirred for 5 minutes then KF (48 mg, 0.82 mmol). This mixture was stirred at room temperature for 15 minutes then cyclopentanamine (84 mg, 0.99 mmol) was added and degassed then stirred at 25° C. for 16 hours. The reaction was then concentrated and purified by flash chromatography on a COMBIFLASH® system (ISCO) using 0-10% MeOH/DCM to afford the title compound (51%). 1H NMR (400 MHz, DMSO-d6) 9.20 (s, 1H), 8.78 (d, 2H), 8.55 (d, 1H), 8.31 (d, 2H), 8.03 (d, 1H), 5.15-5.10 (m, 1H), 3.34 (s, 3H), 1.35 (s, 6H). LCMS (m/z [M+H]$^+$): 292.2.

Example 66: 2-methyl-2-{[2-(pyridin-4-yl)pyrido[3,4-d]pyrimidin-4-yl]amino}propan-1-ol

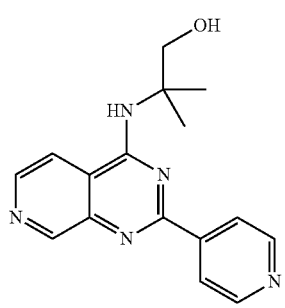 [SMILES: CC(C)(CO)Nc1nc(-c2ccncc2)nc2cnccc12]

1H NMR (500 MHz, DMSO-d6) δ 9.18 (d, J=0.8 Hz, 1H), 8.82-8.77 (m, 2H), 8.64 (d, J=5.6 Hz, 1H), 8.38 (dd, J=5.7, 0.9 Hz, 1H), 8.30 (dt, J=4.5, 1.7 Hz, 2H), 7.62 (s, 1H), 4.95-4.89 (m, 1H), 3.86 (d, J=6.1 Hz, 2H), 1.57 (s, 5H). LCMS (m/z [M+H]$^+$): 296.1.

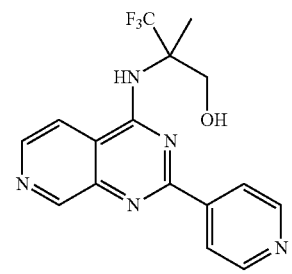

67

The title compound was prepared from methyl 2-amino-3,3,3-trifluoro-2-methylpropanoate hydrochloride and 4-chloro-2-(pyridin-4-yl)pyrido[3,4-d]pyrimidine as described in Step C, Example 1, followed by reduction of methyl ester to alcohol with lithium aluminum hydride.

Reduction: methyl 3,3,3-trifluoro-2-methyl-2-((2-(pyridin-4-yl)pyrido[3,4-d]pyrimidin-4-yl)amino)propanoate (12 mg, 0.032 mmol) was stirred with lithium aluminum hydride (4.8 mg, 0.127 mmol) in THF at 0° C. for 25 hours. No starting material was observed by TLC or LCMS. The reaction mixture was diluted with DCM/MeOH, washed by $H_2O$ and brine, then concentrated. The residue was purified by flash chromatography on a COMBIFLASH® system (ISCO) using 0-10% MeOH/DCM to give the title compound (17%).

1H NMR (500 MHz, DMSO-d6) δ 8.37 (d, J=1.0 Hz, 1H), 7.86-7.81 (m, 2H), 7.74 (d, J=5.7 Hz, 1H), 7.54-7.49 (m, 2H), 7.32 (dt, J=5.7, 1.3 Hz, 1H), 3.77 (d, J=11.6 Hz, 1H), 3.19-3.12 (m, 1H), 1.02 (d, J=1.2 Hz, 3H). LCMS (m/z [M+H]$^+$): 350.1.

Example 68: N-(butan-2-yl)-2-(pyridin-4-yl)pyrido[3,4-d]pyrimidin-4-amine

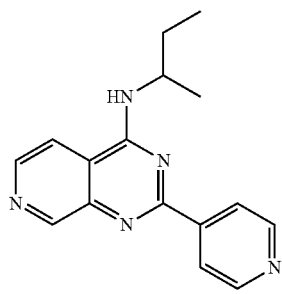 [SMILES: CCC(C)Nc1nc(-c2ccncc2)nc2cnccc12]

1H NMR (500 MHz, DMSO-d6) δ 9.18 (d, J=0.9 Hz, 1H), 8.80-8.74 (m, 2H), 8.65 (d, J=5.5 Hz, 1H), 8.43 (d, J=7.8 Hz, 1H), 8.36-8.27 (m, 3H), 4.56 (hept, J=6.4 Hz, 1H), 1.83-1.63 (m, 2H), 1.33 (d, J=6.6 Hz, 3H), 0.97 (t, J=7.4 Hz, 3H). LCMS (m/z [M+H]$^+$): 280.2.

Example 68a: (S)—N-(sec-butyl)-2-(pyridin-4-yl)pyrido[3,4-d]pyrimidin-4-amine (68a) and (R)—N-(sec-butyl)-2-(pyridin-4-yl)pyrido[3,4-d]pyrimidin-4-amine (68b)

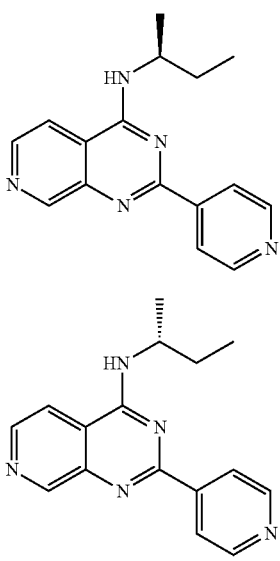

(68a)

(68b)

Compound N-(butan-2-yl)-2-(pyridin-4-yl)pyrido[3,4-d]pyrimidin-4-amine (26.7 mg) (Example 68) was subjected to chiral separation to get two enantiomers, peak 1 (T$_R$=1.44 min) isomer (11.7 mg) and peak 2 (T$_R$=1.94 min) isomer 11.6 mg. Chiral center assignments are tentative. Chiral separation conditions: solvent A CO$_2$ (85%), solvent B MeOH (15%), flow rate 2 ml/min, temp 30° C., column 21×250 mm AD-H, run time 3.5 minute stacked injections, 7 minute elution time.

Peak 1 (T$_R$=1.44 min) isomer: 1H NMR (500 MHz, DMSO-d6) δ 9.18 (s, 1H), 8.77 (d, J=5.5 Hz, 2H), 8.65 (d, J=5.6 Hz, 1H), 8.43 (d, J=7.8 Hz, 1H), 8.36-8.31 (m, 2H), 8.29 (d, J=5.6 Hz, 1H), 4.56 (p, J=7.2 Hz, 1H), 1.85-1.62 (m, 2H), 1.33 (d, J=6.6 Hz, 3H), 0.97 (t, J=7.4 Hz, 3H). LCMS (m/z [M+H]$^+$): 280.2.

Peak 2 (T$_R$=1.94 min) isomer: 1H NMR (500 MHz, DMSO-d6) δ 9.18 (s, 1H), 8.80-8.72 (m, 2H), 8.65 (d, J=5.6 Hz, 1H), 8.43 (d, J=7.8 Hz, 1H), 8.35-8.31 (m, 2H), 8.30 (dd, J=5.6, 0.8 Hz, 1H), 4.57 (hept, J=6.7 Hz, 1H), 1.82-1.63 (m, 2H), 1.33 (d, J=6.6 Hz, 3H), 0.97 (t, J=7.4 Hz, 3H). LCMS (m/z [M+H]$^+$): 280.2.

Example 69: N-(2-methylbut-3-yn-2-yl)-2-(pyridin-4-yl)pyrido[3,4-d]pyrimidin-4-amine

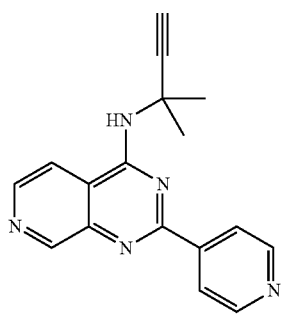 [SMILES: C#CC(C)(C)Nc1nc(-c2ccncc2)nc2cnccc12]

1H NMR (500 MHz, Methanol-d4) δ 9.25 (d, J=0.9 Hz, 1H), 8.77-8.71 (m, 2H), 8.64-8.58 (m, 3H), 8.23 (dd, J=5.7, 0.9 Hz, 1H), 2.81 (s, 1H), 1.93 (s, 6H). LCMS (m/z [M+H]$^+$): 290.1.

Example 70: (1r,3s)-3-methyl-3-{[2-(pyridin-4-yl)pyrido[3,4-d]pyrimidin-4-yl]amino}cyclobutan-1-ol

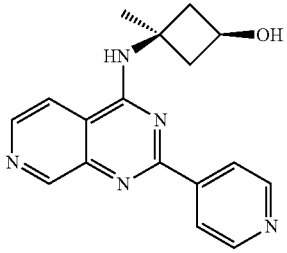 [SMILES: C[C@]1(Nc2nc(-c3ccncc3)nc3cnccc23)C[C@@H](O)C1]

1H NMR (400 MHz, DMSO-d6) 9.21 (s, 1H), 8.78 (d, 2H), 8.55 (d, 1H), 8.31 (d, 2H), 8.05 (d, 1H), 3.94 (q, 2H), 3.50 (s, 3H), 1.39 (t, 3H). LCMS (m/z [M+H]$^+$): 308.1.

Example 71: 2,3-dimethyl-3-{[2-(pyridin-4-yl)pyrido[3,4-d]pyrimidin-4-yl]amino}butan-2-ol

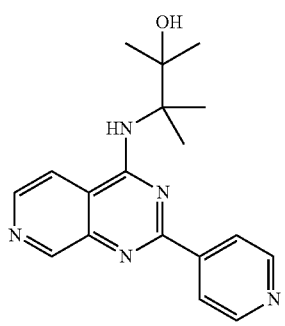 [SMILES: CC(C)(O)C(C)(C)Nc1nc(-c2ccncc2)nc2cnccc12]

1H NMR (500 MHz, DMSO-d6) δ 9.20 (d, J=0.8 Hz, 1H), 8.82-8.77 (m, 2H), 8.67 (d, J=5.6 Hz, 1H), 8.28-8.23 (m, 2H), 8.07 (dd, J=5.8, 0.9 Hz, 1H), 7.49 (s, 1H), 1.64 (s, 6H), 1.27 (s, 6H). LCMS (m/z [M+H]⁺): 324.2.

Example 72: 2-(pyridin-4-yl)-N-(2,4,4-trimethylpentan-2-yl)pyrido[3,4-d]pyrimidin-4-amine

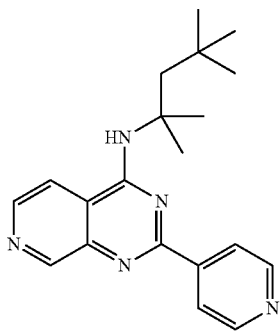 [SMILES: CC(C)(C)CC(C)(C)Nc1nc(-c2ccncc2)nc2cnccc12]

1H NMR (500 MHz, Methanol-d4) δ 9.19 (d, J=0.9 Hz, 1H), 8.78-8.72 (m, 2H), 8.58 (d, J=5.7 Hz, 1H), 8.50-8.45 (m, 2H), 8.22 (dd, J=5.8, 0.9 Hz, 1H), 2.33 (d, J=1.2 Hz, 2H), 1.77 (s, 6H), 1.01 (s, 9H). LCMS (m/z [M+H]⁺): 336.2.

Example 73: N-(pentan-3-yl)-2-(pyridin-4-yl)pyrido[3,4-d]pyrimidin-4-amine

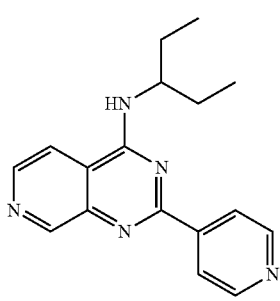 [SMILES: CCC(CC)Nc1nc(-c2ccncc2)nc2cnccc12]

1H NMR (500 MHz, DMSO-d6) δ 9.18 (d, J=0.8 Hz, 1H), 8.79-8.74 (m, 2H), 8.65 (d, J=5.6 Hz, 1H), 8.37-8.30 (m, 4H), 4.47 (dtd, J=13.2, 8.2, 5.1 Hz, 1H), 1.83-1.63 (m, 4H), 0.95 (t, J=7.4 Hz, 6H). LCMS (m/z [M+H]⁺): 294.2.

Example 74: (N-[2-methyl-1-(morpholin-4-yl)propan-2-yl]-2-(pyridin-4-yl)pyrido[3,4-d]pyrimidin-4-amine

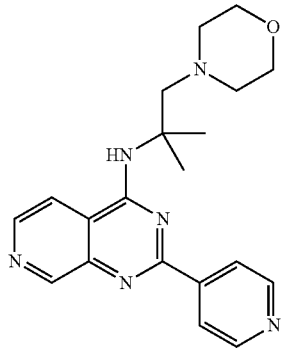 [SMILES: CC(C)(CN1CCOCC1)Nc1nc(-c2ccncc2)nc2cnccc12]

1H NMR (500 MHz, DMSO-d6) δ 9.18 (d, J=0.8 Hz, 1H), 8.83-8.77 (m, 2H), 8.65 (d, J=5.6 Hz, 1H), 8.35 (dd, J=5.8, 0.9 Hz, 1H), 8.32-8.28 (m, 2H), 7.79 (s, 1H), 3.55-3.49 (m, 4H), 2.99 (s, 2H), 2.51-2.45 (m, 4H), 1.62 (s, 6H). LCMS (m/z [M+H]⁺): 365.2.

Example 75: N-[1-(tert-butoxy)-2-methylpropan-2-yl]-2-(pyridin-4-yl)pyrido[3,4-d]pyrimidin-4-amine

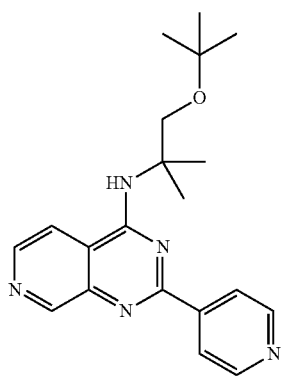 [SMILES: CC(C)(COC(C)(C)C)Nc1nc(-c2ccncc2)nc2cnccc12]

1H NMR (500 MHz, DMSO-d6) δ 9.18 (d, J=0.8 Hz, 1H), 8.82-8.77 (m, 2H), 8.65 (d, J=5.6 Hz, 1H), 8.38 (dd, J=5.7, 0.9 Hz, 1H), 8.33-8.28 (m, 2H), 7.66 (s, 1H), 3.84 (s, 2H), 1.60 (s, 6H), 1.05 (s, 9H). LCMS (m/z [M+H]⁺): 352.2.

Example 76: 4,4,4-trifluoro-2-{[2-(pyridin-4-yl)pyrido[3,4-d]pyrimidin-4-yl]amino}butan-1-ol

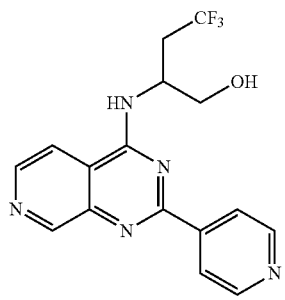 [SMILES: OCC(CC(F)(F)F)Nc1nc(-c2ccncc2)nc2cnccc12]

1H NMR (500 MHz, DMSO-d6) δ 9.23 (d, J=0.8 Hz, 1H), 8.81-8.76 (m, 2H), 8.70 (d, J=5.5 Hz, 1H), 8.62 (d, J=8.2 Hz, 1H), 8.36-8.31 (m, 2H), 8.22 (dd, J=5.7, 0.9 Hz, 1H), 5.19 (dd, J=6.3, 5.4 Hz, 1H), 4.98 (tq, J=9.6, 5.9 Hz, 1H), 3.72 (dt, J=10.9, 5.5 Hz, 1H), 3.61 (dt, J=11.0, 6.3 Hz, 1H), 2.87-2.71 (m, 2H). LCMS (m/z [M+H]⁺): 350.1.

Example 77: N-pentyl-2-(pyridin-4-yl)pyrido[3,4-d]pyrimidin-4-amine

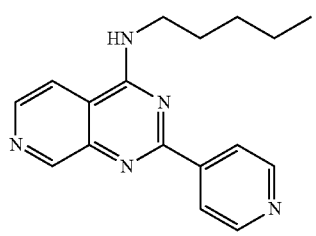 [SMILES: CCCCCNc1nc(-c2ccncc2)nc2cnccc12]

1H NMR (400 MHz, DMSO-d6) δ 9.18 (d, J=0.8 Hz, 1H), 8.83 (t, J=5.6 Hz, 1H), 8.79-8.73 (m, 2H), 8.64 (d, J=5.5 Hz, 1H), 8.36-8.29 (m, 2H), 8.18 (dd, J=5.6, 1.0 Hz, 1H), 3.70 (td, J=7.2, 5.6 Hz, 2H), 1.81-1.68 (m, 2H), 1.47-1.30 (m, 4H), 0.93-0.86 (m, 3H). LCMS (m/z [M+H]⁺): 294.2.

Example 78: 2-{[2-(pyridin-4-yl)pyrido[3,4-d]pyrimidin-4-yl]amino}butan-1-ol

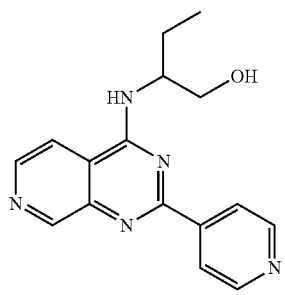 [SMILES: CCC(CO)Nc1nc(-c2ccncc2)nc2cnccc12]

1H NMR (400 MHz, DMSO-d6) δ 9.19 (d, J=0.8 Hz, 1H), 8.80-8.74 (m, 2H), 8.65 (d, J=5.6 Hz, 1H), 8.40-8.30 (m, 4H), 4.83 (t, J=5.7 Hz, 1H), 4.54 (td, J=8.4, 4.9 Hz, 1H), 3.72-3.56 (m, 2H), 1.84 (ddd, J=14.0, 7.4, 5.1 Hz, 1H), 1.68 (ddd, J=13.8, 8.8, 7.3 Hz, 1H), 0.96 (t, J=7.4 Hz, 3H). LCMS (m/z [M+H]⁺): 296.1.

Example 79: N-[1-(1H-indol-3-yl)-2-methylpropan-2-yl]-2-(pyridin-4-yl)pyrido[3,4-d]pyrimidin-4-amine

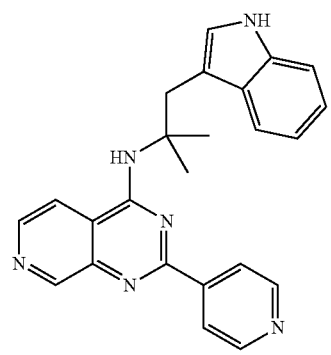 [SMILES: CC(C)(Cc1c[nH]c2ccccc12)Nc1nc(-c2ccncc2)nc2cnccc12]

1H NMR (400 MHz, DMSO-d6) δ 10.78 (d, J=2.6 Hz, 1H), 9.21 (d, J=0.8 Hz, 1H), 8.86-8.78 (m, 2H), 8.60 (d, J=5.6 Hz, 1H), 8.42-8.36 (m, 2H), 8.30 (dd, J=5.7, 0.9 Hz, 1H), 7.68 (s, 1H), 7.47-7.40 (m, 1H), 7.29 (dt, J=8.2, 0.9 Hz, 1H), 7.00 (ddd, J=8.1, 7.0, 1.1 Hz, 1H), 6.91-6.82 (m, 2H), 3.59 (s, 2H), 1.66 (s, 6H). LCMS (m/z [M+H]⁺): 395.2.

Example 80: N-[1-(4-fluorophenyl)-2-methylpropan-2-yl]-2-(pyridin-4-yl)pyrido[3,4-d]pyrimidin-4-amine

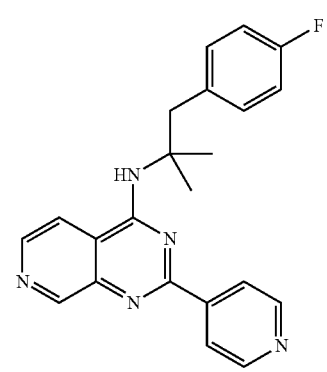 [SMILES: CC(C)(Cc1ccc(F)cc1)Nc1nc(-c2ccncc2)nc2cnccc12]

1H NMR (500 MHz, Methanol-d4) δ 9.23 (d, J=0.9 Hz, 1H), 8.80-8.75 (m, 2H), 8.58-8.51 (m, 3H), 8.13 (dd, J=5.7, 0.9 Hz, 1H), 7.11-7.04 (m, 2H), 6.95-6.87 (m, 2H), 3.56 (s, 2H), 1.69 (s, 6H). LCMS (m/z [M+H]⁺): 374.2.

Example 81: N-(2-phenylpropan-2-yl)-2-(pyridin-4-yl)pyrido[3,4-d]pyrimidin-4-amine

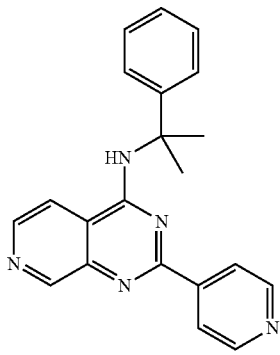 [SMILES: CC(C)(Nc1nc(-c2ccncc2)nc2cnccc12)c1ccccc1]

1H NMR (500 MHz, DMSO-d6) δ 9.16 (d, J=0.9 Hz, 1H), 8.69 (d, J=5.6 Hz, 1H), 8.66 (s, 1H), 8.61-8.56 (m, 2H), 8.53 (dd, J=5.6, 0.9 Hz, 1H), 7.80-7.75 (m, 2H), 7.55-7.48 (m, 2H), 7.35-7.28 (m, 2H), 7.20-7.12 (m, 1H), 1.89 (s, 6H). LCMS (m/z [M+H]$^+$): 342.2.

Example 82: N-(2-fluorophenyl)-2-(pyridin-4-yl)pyrido[3,4-d]pyrimidin-4-amine

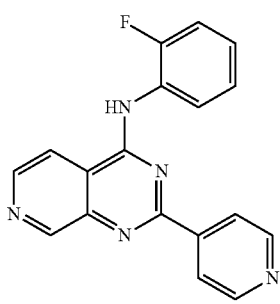 [SMILES: Fc1ccccc1Nc1nc(-c2ccncc2)nc2cnccc12]

1H NMR (500 MHz, Methanol-d4) δ 9.33 (d, J=1.0 Hz, 1H), 8.71 (d, J=5.7 Hz, 1H), 8.68-8.64 (m, 2H), 8.32 (ddd, J=9.5, 5.1, 1.3 Hz, 3H), 7.81 (td, J=8.0, 2.0 Hz, 1H), 7.41 (d, J=1.1 Hz, 1H), 7.38-7.31 (m, 2H). LCMS (m/z [M+H]$^+$): 318.1.

Example 83: N-[2-(4-fluorophenyl)propan-2-yl]-2-(pyridin-4-yl)pyrido[3,4-d]pyrimidin-4-amine

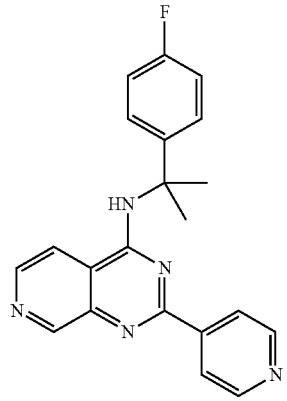 [SMILES: CC(C)(Nc1nc(-c2ccncc2)nc2cnccc12)c1ccc(F)cc1]

1H NMR (500 MHz, Methanol-d4) δ 9.18 (d, J=0.9 Hz, 1H), 8.63 (d, J=5.7 Hz, 1H), 8.59-8.53 (m, 2H), 8.36 (dd, J=5.7, 0.9 Hz, 1H), 7.97-7.92 (m, 2H), 7.61-7.53 (m, 2H), 7.11-7.02 (m, 2H), 1.96 (s, 6H). LCMS (m/z [M+H]$^+$): 360.2.

Example 84: 3,3,3-trifluoro-2-methyl-2-{[2-(pyridin-4-yl)pyrido[3,4-d]pyrimidin-4-yl]amino}propanoic acid

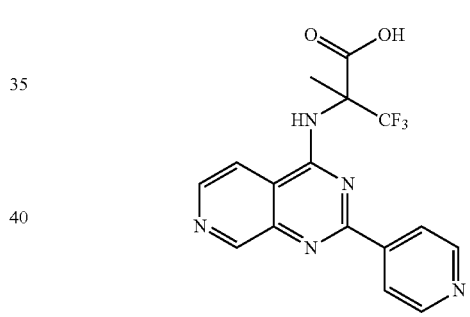

1H NMR (500 MHz, DMSO-d6) δ 9.38 (s, 1H), 9.24 (d, J=0.8 Hz, 1H), 8.81-8.75 (m, 2H), 8.71 (d, J=5.5 Hz, 1H), 8.34-8.29 (m, 2H), 7.84 (d, J=5.5 Hz, 1H), 7.07 (s, 1H), 2.03 (s, 3H). LCMS (m/z [M+H]$^+$): 364.1.

Example 85: 2-{[2-(pyridin-4-yl)pyrido[3,4-d]pyrimidin-4-yl]amino}ethan-1-ol

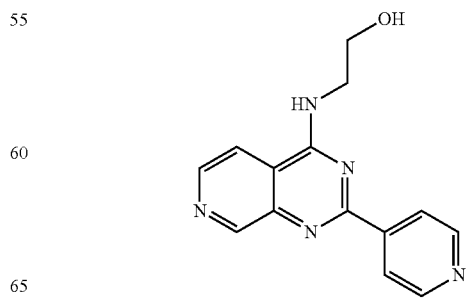

1H NMR (400 MHz, DMSO-d6) δ 9.20 (d, J=0.8 Hz, 1H), 8.88 (t, J=5.3 Hz, 1H), 8.82-8.73 (m, 2H), 8.65 (d, J=5.6 Hz, 1H), 8.38-8.31 (m, 2H), 8.21 (dd, J=5.6, 0.9 Hz, 1H), 4.90 (t, J=5.3 Hz, 1H), 3.76 (ttd, J=7.9, 5.5, 2.5 Hz, 4H). LCMS (m/z [M+H]+): 268.1.

Example 86: N-methyl-2-(pyridin-4-yl)pyrido[3,4-d]pyrimidin-4-amine

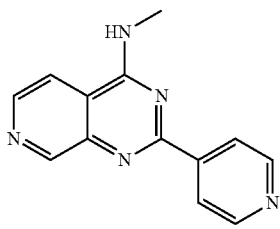 [SMILES: CNc1nc(-c2ccncc2)nc2cnccc12]

1H NMR (400 MHz, DMSO-d6) δ 9.19 (d, J=0.9 Hz, 1H), 8.88 (q, J=4.4 Hz, 1H), 8.80-8.73 (m, 2H), 8.65 (d, J=5.5 Hz, 1H), 8.40-8.33 (m, 2H), 8.12 (dd, J=5.6, 1.0 Hz, 1H), 3.18 (d, J=4.5 Hz, 3H). LCMS (m/z [M+H]+): 238.1.

Example 87: 1-({[2-(pyridin-4-yl)pyrido[3,4-d]pyrimidin-4-yl]amino}methyl)cyclopentan-1-ol

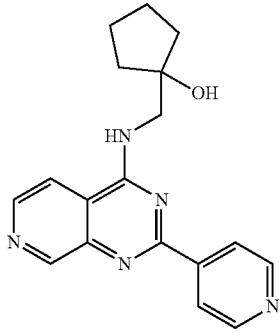 [SMILES: OC1(CNc2nc(-c3ccncc3)nc3cnccc23)CCCC1]

1H NMR (400 MHz, DMSO-d6) δ 9.19 (d, J=0.8 Hz, 1H), 8.81-8.74 (m, 2H), 8.67 (dd, J=11.8, 5.8 Hz, 2H), 8.37-8.33 (m, 2H), 8.30 (dd, J=5.6, 0.9 Hz, 1H), 4.70 (s, 1H), 3.89 (d, J=5.9 Hz, 2H), 1.78-1.50 (m, 8H). LCMS (m/z [M+H]+): 322.2.

Example 88: N,N-dimethyl-2-(pyridin-4-yl)pyrido[3,4-d]pyrimidin-4-amine

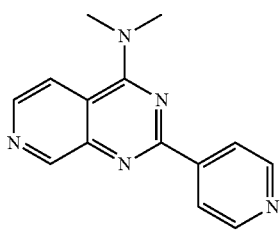 [SMILES: CN(C)c1nc(-c2ccncc2)nc2cnccc12]

1H NMR (400 MHz, DMSO-d6) δ 9.22 (d, J=0.8 Hz, 1H), 8.80-8.73 (m, 2H), 8.57 (d, J=5.8 Hz, 1H), 8.38-8.31 (m, 2H), 8.15 (dd, J=5.8, 0.8 Hz, 1H), 3.53 (s, 6H). LCMS (m/z [M+H]+): 252.1.

Example 89: N-(2-methylphenyl)-2-(pyridin-4-yl)pyrido[3,4-d]pyrimidin-4-amine

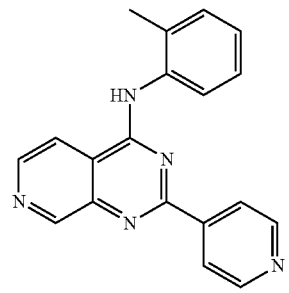 [SMILES: Cc1ccccc1Nc1nc(-c2ccncc2)nc2cnccc12]

1H NMR (500 MHz, DMSO-d6) δ 10.22 (s, 1H), 9.29 (d, J=0.9 Hz, 1H), 8.76 (d, J=5.5 Hz, 1H), 8.72-8.67 (m, 2H), 8.42 (dd, J=5.7, 1.0 Hz, 1H), 8.09-8.04 (m, 2H), 7.50 (dd, J=7.7, 1.5 Hz, 1H), 7.43 (dd, J=7.1, 1.8 Hz, 1H), 7.40-7.29 (m, 2H), 2.27 (s, 3H). LCMS (m/z [M+H]+): 314.1.

Example 90: N-(4-methylphenyl)-2-(pyridin-4-yl)pyrido[3,4-d]pyrimidin-4-amine

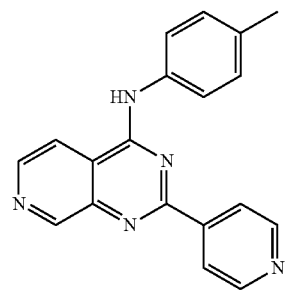 [SMILES: Cc1ccc(Nc2nc(-c3ccncc3)nc3cnccc23)cc1]

1H NMR (500 MHz, DMSO-d6) δ 10.25 (s, 1H), 9.29 (d, J=0.8 Hz, 1H), 8.81-8.73 (m, 3H), 8.49 (dd, J=5.7, 1.0 Hz, 1H), 8.30-8.25 (m, 2H), 7.87-7.80 (m, 2H), 7.36-7.30 (m, 2H), 2.38 (s, 3H). LCMS (m/z [M+H]+): 314.1.

Example 91: N-(4-methoxyphenyl)-2-(pyridin-4-yl)pyrido[3,4-d]pyrimidin-4-amine

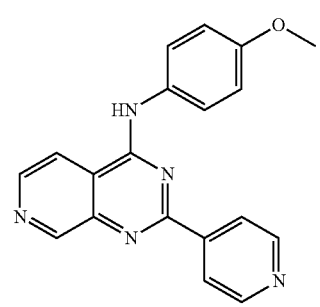 [SMILES: COc1ccc(Nc2nc(-c3ccncc3)nc3cnccc23)cc1]

1H NMR (400 MHz, DMSO-d6) δ 10.24 (s, 1H), 9.27 (d, J=0.8 Hz, 1H), 8.80-8.72 (m, 3H), 8.46 (dd, J=5.8, 1.0 Hz, 1H), 8.29-8.23 (m, 2H), 7.88-7.79 (m, 2H), 7.14-7.05 (m, 2H), 3.83 (s, 3H). LCMS (m/z [M+H]⁺): 330.1.

Example 92: N-phenyl-2-(pyridin-4-yl)pyrido[3,4-d]pyrimidin-4-amine

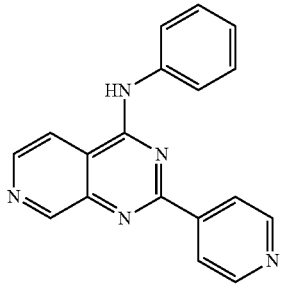 [SMILES: c1ccc(Nc2nc(-c3ccncc3)nc3cnccc23)cc1]

1H NMR (400 MHz, DMSO-d6) δ 10.31 (s, 1H), 9.30 (d, J=0.8 Hz, 1H), 8.82-8.74 (m, 3H), 8.51 (dd, J=5.8, 1.0 Hz, 1H), 8.31-8.24 (m, 2H), 8.00-7.92 (m, 2H), 7.58-7.48 (m, 2H), 7.26 (tt, J=7.3, 1.2 Hz, 1H). LCMS (m/z [M+H]⁺): 300.1.

Example 93: N-(3-methylphenyl)-2-(pyridin-4-yl)pyrido[3,4-d]pyrimidin-4-amine

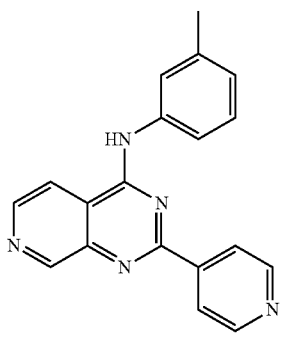 [SMILES: Cc1cccc(Nc2nc(-c3ccncc3)nc3cnccc23)c1]

1H NMR (500 MHz, DMSO-d6) δ 10.24 (s, 1H), 9.30 (d, J=0.8 Hz, 1H), 8.82-8.75 (m, 3H), 8.51 (dd, J=5.8, 0.9 Hz, 1H), 8.31-8.26 (m, 2H), 7.83-7.76 (m, 2H), 7.41 (t, J=7.8 Hz, 1H), 7.08 (ddt, J=7.6, 1.7, 0.9 Hz, 1H), 2.43 (s, 3H). LCMS (m/z [M+H]⁺): 314.1.

Example 94: 6-{[2-(pyridin-4-yl)pyrido[3,4-d]pyrimidin-4-yl]amino}hexanoic acid

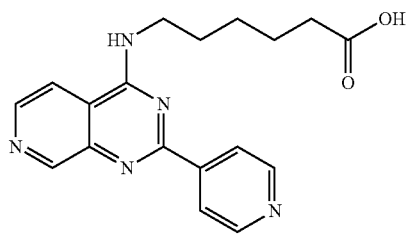 [SMILES: O=C(O)CCCCCNc1nc(-c2ccncc2)nc2cnccc12]

1H NMR (400 MHz, DMSO-d6) δ 12.02 (s, 1H), 9.19 (s, 1H), 8.84 (t, J=5.6 Hz, 1H), 8.80-8.73 (m, 2H), 8.65 (d, J=5.6 Hz, 1H), 8.37-8.31 (m, 2H), 8.18 (dd, J=5.6, 1.0 Hz, 1H), 3.76-3.66 (m, 2H), 2.23 (t, J=7.3 Hz, 2H), 1.81-1.69 (m, 2H), 1.61 (p, J=7.3 Hz, 2H), 1.43 (tt, J=9.6, 6.1 Hz, 2H). LCMS (m/z [M+H]⁺): 338.2.

Example 95: N-(3-fluorophenyl)-2-(pyridin-4-yl)pyrido[3,4-d]pyrimidin-4-amine

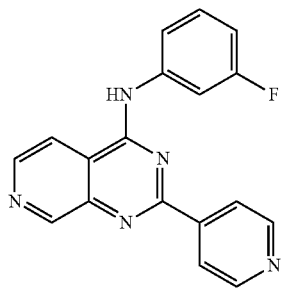 [SMILES: Fc1cccc(Nc2nc(-c3ccncc3)nc3cnccc23)c1]

1H NMR (500 MHz, DMSO-d6) δ 10.39 (s, 1H), 9.34 (d, J=0.8 Hz, 1H), 8.84-8.78 (m, 3H), 8.51 (dd, J=5.8, 0.9 Hz, 1H), 8.31-8.26 (m, 2H), 7.96 (dt, J=11.7, 2.3 Hz, 1H), 7.81 (ddd, J=8.2, 2.0, 0.9 Hz, 1H), 7.56 (td, J=8.2, 6.8 Hz, 1H), 7.08 (tdd, J=8.5, 2.6, 0.9 Hz, 1H). LCMS (m/z [M+H]⁺): 318.1.

Example 96: N-(4-fluorophenyl)-2-(pyridin-4-yl)pyrido[3,4-d]pyrimidin-4-amine

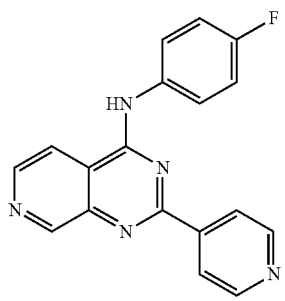 [SMILES: Fc1ccc(Nc2nc(-c3ccncc3)nc3cnccc23)cc1]

1H NMR (500 MHz, DMSO-d6) δ 10.34 (s, 1H), 9.31 (d, J=0.9 Hz, 1H), 8.81-8.75 (m, 3H), 8.47 (dd, J=5.7, 0.9 Hz, 1H), 8.31-8.24 (m, 2H), 7.99-7.92 (m, 2H), 7.41-7.33 (m, 2H). LCMS (m/z [M+H]⁺): 318.1.

Example 97: 4-{[2-(pyridin-4-yl)pyrido[3,4-d]pyrimidin-4-yl]amino}butanoic acid

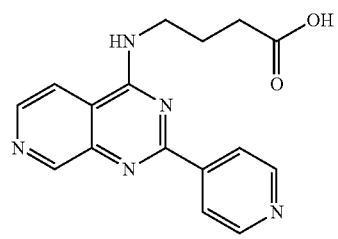 [SMILES: O=C(O)CCCNc1nc(-c2ccncc2)nc2cnccc12]

1H NMR (400 MHz, DMSO-d6) δ 10.43 (s, 1H), 9.16 (s, 1H), 8.79-8.72 (m, 2H), 8.62 (d, J=5.5 Hz, 1H), 8.39-8.32 (m, 2H), 8.19 (dd, J=5.6, 1.0 Hz, 1H), 3.67 (q, J=6.0 Hz, 2H), 2.33 (t, J=6.5 Hz, 2H), 1.94 (p, J=6.6 Hz, 2H). LCMS (m/z [M+H]$^+$): 365.2.

Example 98: N-(1-phenylethyl)-2-(pyridin-4-yl)pyrido[3,4-d]pyrimidin-4-amine

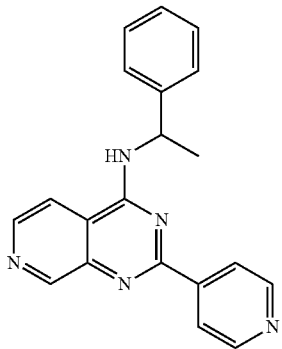 [SMILES: CC(Nc1nc(-c2ccncc2)nc2cnccc12)c1ccccc1]

1H NMR (DMSO-d6) δ 1.67 (d, J=6.8 Hz, 3H), 5.73 (m, 1H), 7.22 (m, 1H), 7.47 (m, 2H), 7.55 (m, 2H), 8.26 (d, J=5 Hz, 2H), 8.41 (d, J=5.6 Hz, 1H), 8.69 (d, J=5.6 Hz, 1H), 8.74 (d, J=5 Hz, 1H), 9.08 (d, J=7.2 Hz, 1H), 9.19 (s, 1H). LCMS (m/z [M+H]$^+$): 328.2.

Example 99: N-(1-methylcyclopropyl)-2-(pyridin-4-yl)pyrido[3,4-d]pyrimidin-4-amine

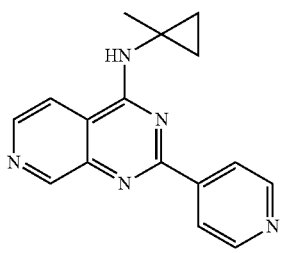

1H NMR (400 MHz, Methanol-d4) δ 9.19 (s, 1H), 8.73 (d, J=5.7 Hz, 2H), 8.55 (m, 3H), 8.01 (dd, J=5.7, 0.7 Hz, 1H), 1.64 (s, 3H), 0.99 (m, 2H), 0.93 (m, 2H). LCMS (m/z [M+H]$^+$): 278.1.

Example 100: Tert-butyl N-(2-methyl-2-{[2-(pyridin-4-yl)pyrido[3,4-d]pyrimidin-4-yl]amino}propyl)carbamate

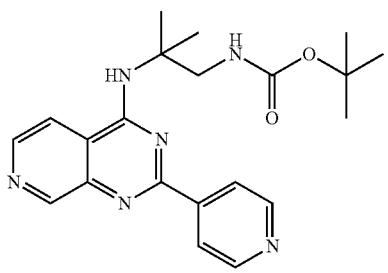 [SMILES: CC(C)(CNC(=O)OC(C)(C)C)Nc1nc(-c2ccncc2)nc2cnccc12]

1H NMR (400 MHz, DMSO-d6) δ 9.21 (s, 1H), 8.87 (s, 2H), 8.67 (d, J=5.6 Hz, 1H), 8.49 (d, J=4.6 Hz, 2H), 8.24 (d, J=5.6 Hz, 1H), 8.03 (s, 1H), 7.33 (t, J=6.4 Hz, 1H), 3.54 (d, J=6.4 Hz, 2H), 1.57 (s, 6H), 1.36 (s, 9H). LCMS (m/z [M+H]$^+$): 395.2.

Example 101: (1-{[2-(pyridin-4-yl)pyrido[3,4-d]pyrimidin-4-yl]amino}cyclobutyl)methanol

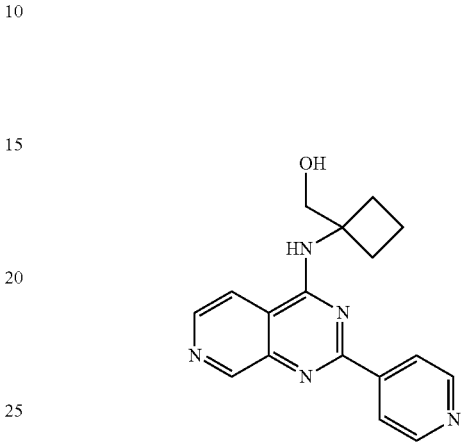

1H NMR (400 MHz, DMSO-d6) δ 9.16 (s, 1H), 8.78-8.72 (m, 2H), 8.68 (s, 1H), 8.62 (d, J=5.6 Hz, 1H), 8.36 (d, J=5.7 Hz, 1H), 8.31-8.20 (m, 2H), 4.94 (t, J=6.0 Hz, 1H), 3.96 (d, J=6.0 Hz, 2H), 2.41 (dt, J=12.5, 7.2 Hz, 4H), 1.89 (p, J=8.0 Hz, 2H). LCMS (m/z [M+H]$^+$): 308.1.

Example 102: methyl 2-(1-{[2-(pyridin-4-yl)pyrido[3,4-d]pyrimidin-4-yl]amino}cyclopropyl)acetate

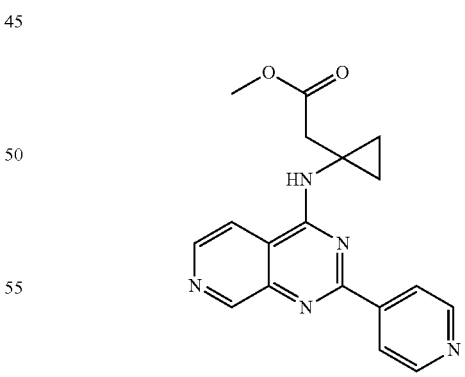

1H NMR (400 MHz, DMSO-d6) 9.25 (s, 1H), 9.05 (t, 1H), 8.90 (d, 2H), 8.70 (d, 1H), 8.60 (d, 2H), 8.24 (d, 1H), 3.90 (m, 2H), 3.79 (t, 2H), 3.59 (m, 2H), 3.55-3.49 (m, 4H), 3.45 (m, 2H), 3.41 (m, 2H), 2.40 (t, 2H). LCMS (m/z [M+H]$^+$): 336.1.

Example 103: N-(2-methylpropyl)-2-(pyridin-4-yl)pyrido[3,4-d]pyrimidin-4-amine

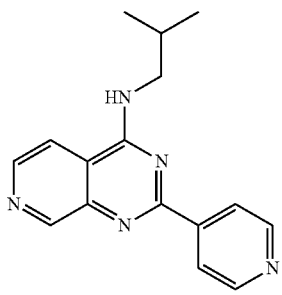 [SMILES: CC(C)CNc1nc(-c2ccncc2)nc2cnccc12]

1HNMR (400 MHz, CDCl₃) δ 9.35 (d, J=0.8 Hz, 1H), 8.79 (d, J=5.6 Hz, 2H), 8.64 (d, J=5.6 Hz, 1H), 8.39 (d, J=5.6 Hz, 2H), 7.52 (dd, J=5.6, 0.8 Hz, 1H), 6.00 (t, J=6.0 Hz, 1H), 3.66 (dd, J=6.8, 6.0 Hz, 2H), 2.09 (nonet, J=6.8 Hz, 1H), 1.12 (d, J=6.8 Hz, 6H). LCMS (m/z [M+H]⁺): 280.1.

Example 104: 3-methyl-3-{[2-(pyridin-4-yl)pyrido[3,4-d]pyrimidin-4-yl]amino}butanenitrile

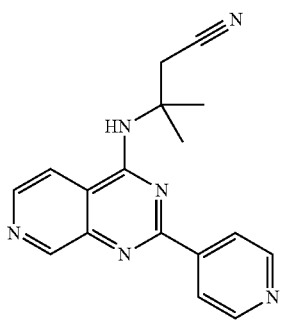 [SMILES: CC(C)(CC#N)Nc1nc(-c2ccncc2)nc2cnccc12]

1H NMR (500 MHz, Acetone-d6) δ 9.23 (d, J=0.9 Hz, 1H), 8.82-8.75 (m, 2H), 8.63 (d, J=5.6 Hz, 1H), 8.42-8.33 (m, 2H), 8.17 (dd, J=5.7, 0.9 Hz, 1H), 3.64 (s, 2H), 1.83 (s, 6H). LCMS (M/Z [M+H]⁺): 305.1.

Example 105: N-(6-aminohexyl)-2-(pyridin-4-yl)pyrido[3,4-d]pyrimidin-4-amine

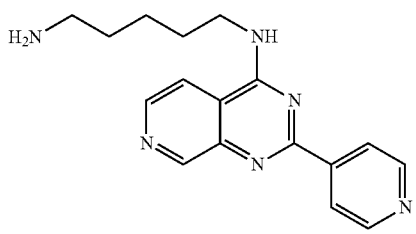 [SMILES: NCCCCCNc1nc(-c2ccncc2)nc2cnccc12]

1H NMR (400 MHz, DMSO-d6) δ 9.19 (s, 1H), 8.88-8.80 (m, 1H), 8.82-8.73 (m, 2H), 8.68-8.61 (m, 1H), 8.37-8.31 (m, 2H), 8.19 (d, J=5.6 Hz, 1H), 3.71 (q, J=6.5 Hz, 2H), 2.53 (d, J=1.6 Hz, 2H), 1.75 (dt, J=14.2, 7.1 Hz, 2H), 1.47-1.32 (m, 6H). LCMS (M/Z [M+H]⁺): 323.2.

Example 106: N-(4-aminobutyl)-2-(pyridin-4-yl)pyrido[3,4-d]pyrimidin-4-amine

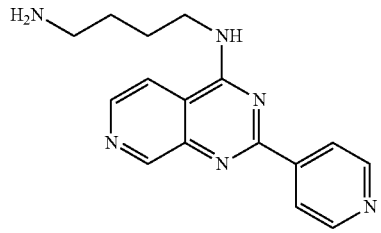 [SMILES: NCCCCNc1nc(-c2ccncc2)nc2cnccc12]

1H NMR (400 MHz, DMSO-d6) δ 9.23 (s, 1H), 8.96 (t, J=5.7 Hz, 1H), 8.88-8.82 (m, 2H), 8.70 (d, J=5.5 Hz, 1H), 8.51-8.44 (m, 2H), 8.20 (dd, J=5.6, 1.0 Hz, 1H), 7.65 (s, 2H), 3.80-3.72 (m, 2H), 2.86 (td, J=7.5, 5.5 Hz, 2H), 1.85-1.73 (m, 2H), 1.67 (ddt, J=12.8, 9.9, 5.8 Hz, 2H). LCMS (M/Z [M+H]⁺): 295.2.

Example 107: 2-methyl-2-{[2-(pyridin-4-yl)pyrido[3,4-d]pyrimidin-4-yl]amino}propanenitrile

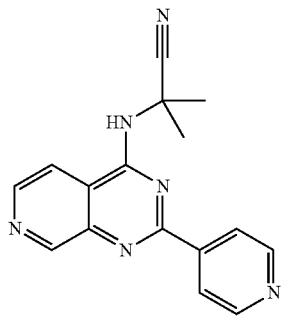 [SMILES: CC(C)(C#N)Nc1nc(-c2ccncc2)nc2cnccc12]

1H NMR (500 MHz, DMSO-d6) δ 9.31 (d, J=0.8 Hz, 1H), 8.85-8.80 (m, 2H), 8.78-8.72 (m, 2H), 8.45-8.40 (m, 2H), 8.37 (dd, J=5.7, 0.9 Hz, 1H), 1.93 (s, 6H). LCMS (M/Z [M+H]⁺): 291.1.

Example 108: N-[2-methyl-1-(2-methylpiperidin-1-yl)propan-2-yl]-2-(pyridin-4-yl)pyrido[3,4-d]pyrimidin-4-amine

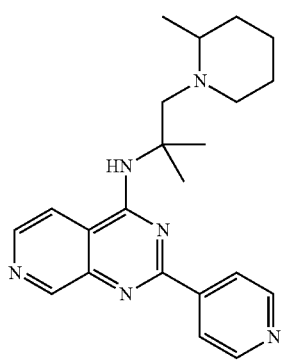 [SMILES: CC1CCCCN1CC(C)(C)Nc1nc(-c2ccncc2)nc2cnccc12]

1H NMR (500 MHz, Methanol-d4) δ 9.08 (d, J=0.9 Hz, 1H), 8.65-8.58 (m, 2H), 8.50 (d, J=5.7 Hz, 1H), 8.37-8.29

(m, 2H), 7.94 (dd, J=5.8, 1.0 Hz, 1H), 3.18 (d, J=14.7 Hz, 1H), 3.00-2.92 (m, 2H), 2.66 (s, 1H), 2.44 (dq, J=12.3, 5.9, 5.1 Hz, 1H), 1.86 (s, 1H), 1.69-1.43 (m, 10H), 1.38-1.25 (m, 2H), 0.97 (d, J=6.4 Hz, 3H). LCMS (M/Z [M+H]⁺): 377.2.

Example 109: dimethyl(3-methyl-3-{[2-(pyridin-4-yl)pyrido[3,4-d]pyrimidin-4-yl]amino}butyl)amine

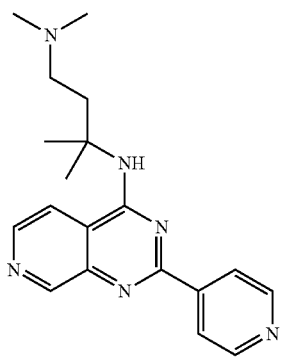 [SMILES: CN(C)CCC(C)(C)Nc1nc(-c2ccncc2)nc2cnccc12]

1H NMR (400 MHz, DMSO-d6) δ 9.23 (s, 1H), 8.96 (t, J=5.7 Hz, 1H), 8.88-8.82 (m, 2H), 8.70 (d, J=5.5 Hz, 1H), 8.51-8.44 (m, 2H), 8.20 (dd, J=5.6, 1.0 Hz, 1H), 7.65 (s, 2H), 3.80-3.72 (m, 2H), 2.86 (td, J=7.5, 5.5 Hz, 2H), 1.85-1.73 (m, 2H), 1.67 (ddt, J=12.8, 9.9, 5.8 Hz, 2H). LCMS (M/Z [M+H]⁺): 295.2.

Example 110: N-(1-amino-2-methylpropan-2-yl)-2-(pyridin-4-yl)pyrido[3,4-d]pyrimidin-4-amine

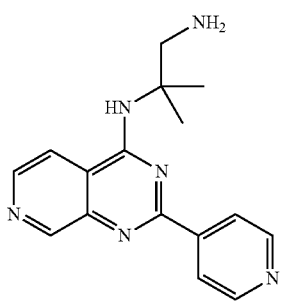 [SMILES: CC(C)(CN)Nc1nc(-c2ccncc2)nc2cnccc12]

1H NMR (400 MHz, DMSO-d6) δ 9.25 (s, 1H), 8.88 (s, 2H), 8.72 (d, J=5.6 Hz, 1H), 8.45 (d, J=5.7 Hz, 1H), 8.39 (d, J=4.9 Hz, 2H), 7.87 (s, 1H), 7.79 (s, 2H), 3.67 (d, J=5.9 Hz, 2H), 1.64 (s, 6H). LCMS (M/Z [M+H]⁺): 295.2.

Example 111: N-cyclopentyl-2-[3-(trifluoromethyl)-1H-pyrazol-4-yl]pyrido[3,4-d]pyrimidin-4-amine

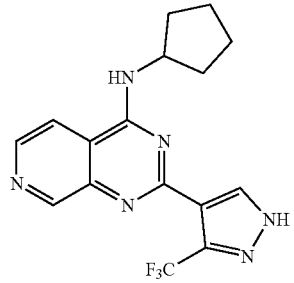

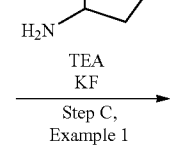

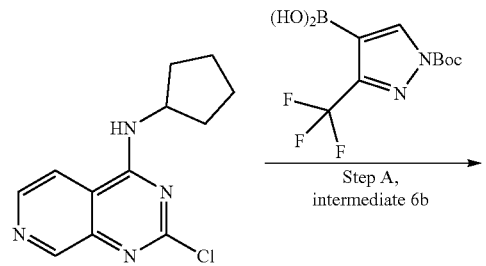

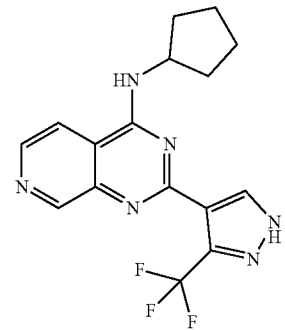

The title compound was prepared from 2,4-dichloropyrido[3,4-d]pyrimidine (intermediate 2c) as in Scheme 2 using Step C for Example 1 and Step A for Intermediate 6b. 1H NMR (400 MHz, DMSO-d6) δ 9.10 (d, J=0.8 Hz, 1H), 8.60 (d, J=5.6 Hz, 1H), 8.36 (dd, J=5.8, 0.9 Hz, 1H), 8.09 (dd, J=5.3, 0.8 Hz, 1H), 7.77 (s, 1H), 7.50 (dd, J=1.5, 0.8 Hz, 1H), 7.42 (dd, J=5.3, 1.5 Hz, 1H), 6.10 (s, 2H), 1.60 (s, 9H). LCMS (m/z [M+H]⁺): 349.1.

Examples 112-197

These compounds were synthesized according to the protocol described above using 2,4-dichloropyrido[3,4-d] pyrimidine (Intermediate 2c) and various amines and coupling partners respectively except specially stated.

Example 112: 4-[4-(tert-butylamino)pyrido[3,4-d]pyrimidin-2-yl]pyridin-2-amine

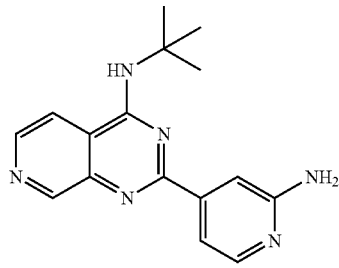 [SMILES: CC(C)(C)Nc1nc(-c2ccnc(N)c2)nc2cnccc12]

1H NMR (400 MHz, DMSO-d6) δ 9.10 (d, J=0.8 Hz, 1H), 8.60 (d, J=5.6 Hz, 1H), 8.36 (dd, J=5.8, 0.9 Hz, 1H), 8.09 (dd, J=5.3, 0.8 Hz, 1H), 7.77 (s, 1H), 7.50 (dd, J=1.5, 0.8 Hz, 1H), 7.42 (dd, J=5.3, 1.5 Hz, 1H), 6.10 (s, 2H), 1.60 (s, 9H). LCMS (m/z [M+H]$^+$): 295.2

Example 113: 2-[1-(benzenesulfonyl)-2-methyl-1H-pyrrolo[2,3-b]pyridin-3-yl]-N-tert-butylpyrido[3,4-d]pyrimidin-4-amine

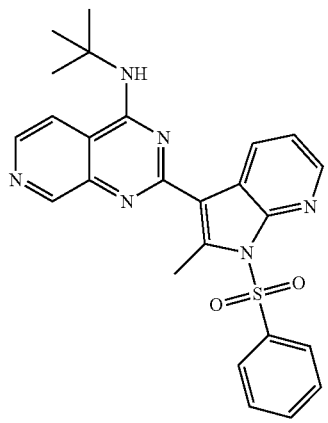 [SMILES: Cc1c(-c2nc(NC(C)(C)C)c3ccncc3n2)c2cccnc2n1S(=O)(=O)c1ccccc1]

1H NMR (400 MHz, DMSO-d6) δ 9.12 (d, J=0.8 Hz, 1H), 8.70 (dd, J=7.9, 1.7 Hz, 1H), 8.58 (d, J=5.6 Hz, 1H), 8.20 (m, 2H), 7.71 (m, 1H), 7.66-7.59 (m, 5H), 7.35 (dd, J=7.9, 4.7 Hz, 1H), 3.24 (s, 3H), 1.59 (s, 9H). LCMS (m/z [M+H]$^+$): 473.2.

Example 114: N-tert-butyl-2-{2-methyl-1H-pyrrolo[2,3-b]pyridin-3-yl}pyrido[3,4-d]pyrimidin-4-amine

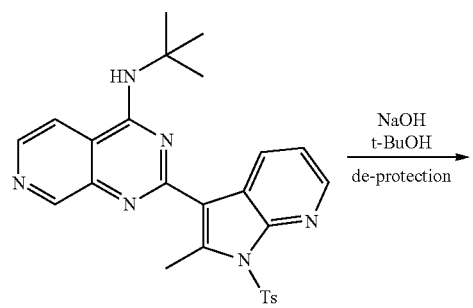

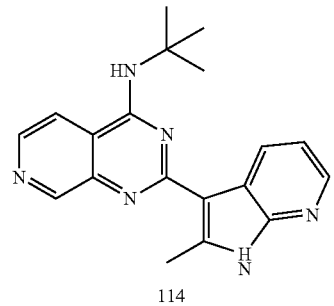
114

The title compound was prepared by de-protection of the tosyl group of Example 113.

De-protection: N-(tert-butyl)-2-(2-methyl-1-(phenylsulfonyl)-1H-pyrrolo[2,3-b]pyridin-3-yl)pyrido[3,4-d]pyrimidin-4-amine (32 mg, 0.068 mmol) was stirred in 1 mL of t-butanol at room temperature. Sodium hydroxide (270 microlitre (5M), 1.35 mmol) was then added and the reaction stirred at room temperature for two hours upon which time all starting material was consumed. The material was concentrated to an off white oil and purified by flash chromatography on a COMBIFLASH® system (ISCO) using 0-20% MeOH/DCM to afford the title product N-tert-butyl-2-{2-methyl-1H-pyrrolo[2,3-b]pyridin-3-yl}pyrido[3,4-d]pyrimidin-4-amine (55%).

1H NMR (400 MHz, DMSO-d6) δ 12.01 (s, 1H), 9.05 (d, J=0.8 Hz, 1H), 8.97 (dd, J=8.0, 1.7 Hz, 1H), 8.45 (d, J=5.5 Hz, 1H), 8.25 (ddd, J=23.7, 5.2, 1.3 Hz, 1H), 8.19 (m, 1H), 7.42 (s, 1H), 7.15 (dd, J=7.9, 4.7 Hz, 1H), 2.96 (s, 3H), 1.63 (s, 9H). LCMS (m/z [M+H]$^+$): 333.2.

Example 115: N-tert-butyl-2-[3-(trifluoromethyl)-1H-pyrazol-4-yl]pyrido[3,4-d]pyrimidin-4-amine

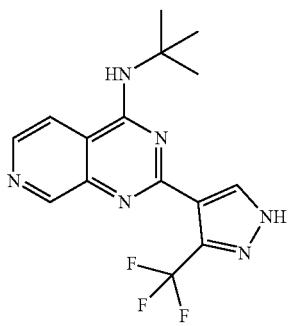 [SMILES: CC(C)(C)Nc1nc(-c2c[nH]nc2C(F)(F)F)nc2cnccc12]

1H NMR (400 MHz, DMSO-d6) δ 8.95 (d, J=0.8 Hz, 1H), 8.54 (d, J=5.6 Hz, 1H), 8.46 (s, 1H), 8.30 (dd, J=5.7, 0.9 Hz, 1H), 7.62 (s, 1H), 1.58 (s, 9H). LCMS (m/z [M+H]$^+$): 337.1.

Example 116: N-tert-butyl-2-(3-chloropyridin-4-yl)pyrido[3,4-d]pyrimidin-4-amine

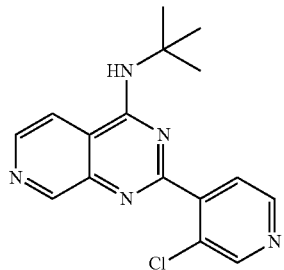 [SMILES: CC(C)(C)Nc1nc(-c2ccncc2Cl)nc2cnccc12]

1H NMR (400 MHz, DMSO-d6) δ 9.12 (d, J=0.8 Hz, 1H), 8.79 (d, J=0.5 Hz, 1H), 8.68 (m, 2H), 8.41 (dd, J=5.8, 0.9 Hz, 1H), 7.92 (s, 1H), 7.77 (dd, J=4.9, 0.6 Hz, 1H), 1.55 (s, 9H). LCMS (m/z [M+H]+): 314.1.

Example 117: N-tert-butyl-2-(3-methylpyridin-4-yl)pyrido[3,4-d]pyrimidin-4-amine

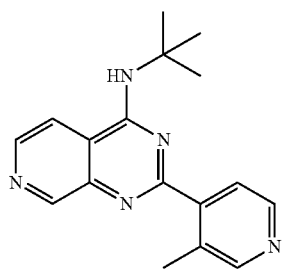 [SMILES: Cc1cnccc1-c1nc(NC(C)(C)C)c2ccncc2n1]

1H NMR (400 MHz, DMSO-d6) δ 9.11 (d, J=0.8 Hz, 1H), 8.63 (d, J=5.6 Hz, 1H), 8.55 (m, 2H), 8.39 (dd, J=5.7, 0.9 Hz, 1H), 7.79 (m, 1H), 7.76 (m, 1H), 2.59 (s, 3H), 1.58 (s, 9H). LCMS (m/z [M+H]+): 294.2.

Example 118: 2-(3-chloropyridin-4-yl)-N-(2-methylbutan-2-yl)pyrido[3,4-d]pyrimidin-4-amine

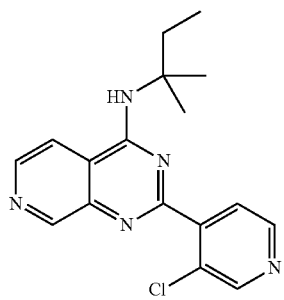 [SMILES: CCC(C)(C)Nc1nc(-c2ccncc2Cl)nc2cnccc12]

1H NMR (400 MHz, DMSO-d6) δ 9.12 (d, J=0.9 Hz, 1H), 8.78 (d, J=0.6 Hz, 1H), 8.68 (dd, J=5.3, 2.2 Hz, 1H), 8.66 (m, 2H), 8.41 (dd, J=5.7, 0.9 Hz, 1H), 7.74 (m, 1H), 2.00 (q, J=7.3 Hz, 2H), 1.49 (s, 6H), 0.80 (t, J=7.4 Hz, 3H). LCMS (m/z [M+H]+): 328.1.

Example 119: 2,4-dimethyl-4-({2-[3-(trifluoromethyl)-1H-pyrazol-4-yl]pyrido[3,4-d]pyrimidin-4-yl}amino)pentan-2-ol

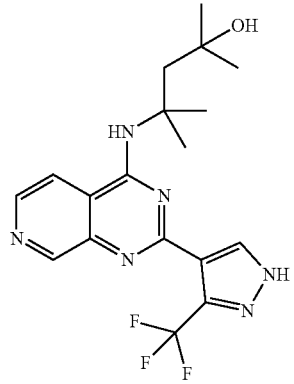 [SMILES: CC(C)(O)CC(C)(C)Nc1nc(-c2c[nH]nc2C(F)(F)F)nc2cnccc12]

1H NMR (400 MHz, DMSO-d6) δ 9.29 (s, 1H), 8.99 (d, J=0.8 Hz, 1H), 8.55 (d, J=5.6 Hz, 1H), 8.49 (s, 1H), 7.73 (dd, J=5.7, 0.9 Hz, 1H), 5.61 (s, 1H), 1.97 (s, 2H), 1.70 (s, 6H), 1.30 (s, 6H). LCMS (m/z [M+H]+): 395.2.

Example 120: N-ethyl-2-(3-fluoropyridin-4-yl)-N-(propan-2-yl)pyrido[3,4-d]pyrimidin-4-amine

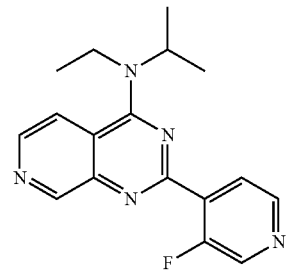

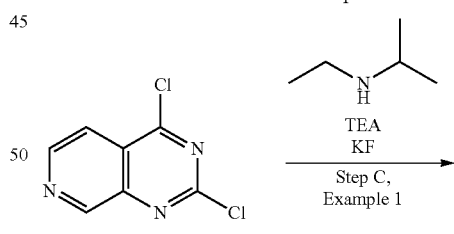

2c, Scheme 2

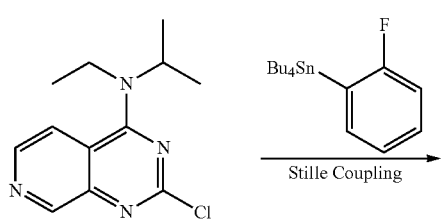

-continued

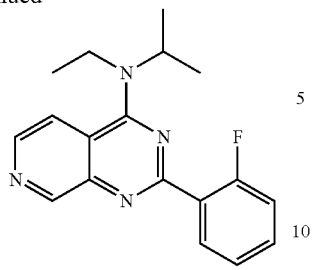

Title compound was prepared from 2,4-dichloropyrido[3,4-d]pyrimidine (intermediate 2c) similar as described in Example 111 except using Stille coupling as the second step.

Stille coupling: 2-chloro-N-ethyl-N-isopropylpyrido[3,4-d]pyrimidin-4-amine (30 mg, 0.12 mmol) was stirred in dry DMF (1 mL) at room temperature. 3-fluoro-4-(tributylstannyl)pyridine (50.8 mg, 0.13 mmol) was added then PdCl2(dppf).CH2Cl2 adduct (9.8 mg, 0.012 mmol) and CuI (2.3 mg, 0.012 mmol). The reaction was stirred for 1 hour at 130° C. The reaction was then concentrated and purified by flash chromatography on a COMBIFLASH® system (ISCO) using 0-10% MeOH/DCM to afford the title compound. 1H NMR (400 MHz, DMSO-d6) δ 9.20 (d, J=0.8 Hz, 1H), 8.72 (d, J=2.9 Hz, 1H), 8.61 (m, 1H), 8.59 (m, 1H), 8.08 (dd, J=6.7, 4.9 Hz, 1H), 7.90 (m, 1H), 4.92-4.88 (m, 1H), 3.79 (q, J=7.0 Hz, 2H), 1.37 (m, 6H), 1.32 (dd, J=23.7, 6.8 Hz, 3H). LCMS (m/z [M+H]+): 312.2.

Example 121: 2-methyl-1-[2-methyl-2-({2-[3-(trifluoromethyl)-1H-pyrazol-4-yl]pyrido[3,4-d]pyrimidin-4-yl}amino)propoxy]propan-2-ol

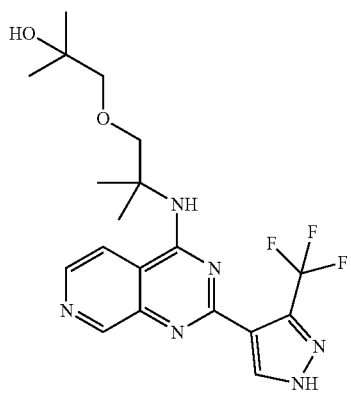 [SMILES: CC(C)(O)COCC(C)(C)Nc1nc(-c2c[nH]nc2C(F)(F)F)nc2cnccc12]

The title compound was prepared using procedures described in Example 111 and the amine as described in Example 12.

1H NMR (400 MHz, DMSO-d6) δ 13.80 (s, 1H), 8.99 (d, J=0.8 Hz, 1H), 8.55 (d, J=5.6 Hz, 1H), 8.44 (s, 1H), 8.25 (dd, J=5.8, 0.9 Hz, 1H), 7.53 (s, 1H), 4.35 (s, 1H), 3.82 (s, 2H), 3.17 (s, 2H), 1.54 (s, 6H), 1.00 (s, 6H). LCMS (m/z [M+H]+): 425.2.

Example 122: 2-(3-fluoropyridin-4-yl)-N-methyl-N-(propan-2-yl)pyrido[3,4-d]pyrimidin-4-amine

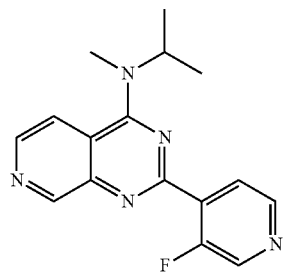 [SMILES: CC(C)N(C)c1nc(-c2ccncc2F)nc2cnccc12]

The title compound was prepared using procedures described in Example 120.

1H NMR (400 MHz, DMSO-d6) δ 9.21 (d, J=0.8 Hz, 1H), 8.74 (d, J=2.9 Hz, 1H), 8.60 (m, 2H), 8.11 (m, 1H), 8.09 (m, 1H), 5.11-5.06 (d, J=6.6 Hz, 1H), 3.37 (s, 3H), 1.34 (d, J=6.7 Hz, 6H). LCMS (m/z [M+H]+): 298.1.

Example 123: N-ethyl-2-(3-methylpyridin-4-yl)-N-(propan-2-yl)pyrido[3,4-d]pyrimidin-4-amine

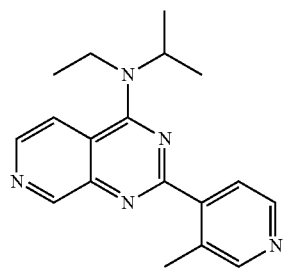 [SMILES: CCN(c1nc(-c2ccncc2C)nc2cnccc12)C(C)C]

1H NMR (400 MHz, DMSO-d6) δ 9.20 (d, J=0.8 Hz, 1H), 8.59 (m, 1H), 8.56 (m, 1H), 8.54 (m, 1H), 7.89 (m, 1H), 7.85 (m, 1H), 4.95-4.90 (d, J=6.6 Hz, 1H), 3.79 (q, J=7.0 Hz, 2H), 2.60 (s, 3H), 1.36 (d, J=6.6 Hz, 6H), 1.30 (t, J=7.0 Hz, 3H). LCMS (m/z [M+H]+): 308.2.

Example 124: 2-(3-chloropyridin-4-yl)-N-(1-methoxy-2-methylpropan-2-yl)pyrido[3,4-d]pyrimidin-4-amine

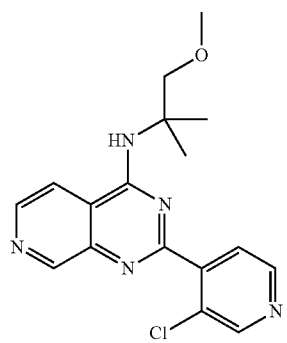 [SMILES: COCC(C)(C)Nc1nc(-c2ccncc2Cl)nc2cnccc12]

1H NMR (400 MHz, DMSO-d6) δ 9.12 (s, 1H), 8.79 (s, 1H), 8.69 (dd, J=5.2, 1.8 Hz, 2H), 8.40 (dd, J=5.8, 1.0 Hz, 1H), 7.78 (s, 1H), 7.75 (m, 1H), 3.73 (s, 2H), 3.22 (s, 3H), 1.50 (s, 6H). LCMS (m/z [M+H]⁺): 344.1.

Example 125: 4-{[2-(3-chloropyridin-4-yl)pyrido[3,4-d]pyrimidin-4-yl]amino}-2,4-dimethylpentan-2-ol

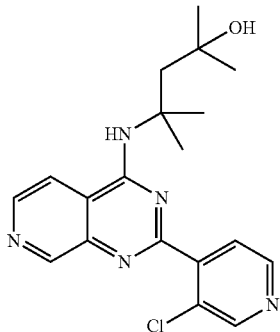 [SMILES: CC(C)(O)CC(C)(C)Nc1nc(-c2ccncc2Cl)nc2cnccc12]

1H NMR (400 MHz, DMSO-d6) δ 9.45 (s, 1H), 9.13 (d, J=0.7 Hz, 1H), 8.79 (s, 1H), 8.68 (dd, J=5.3, 3.4 z, 1H), 8.66 (m, 1H), 7.83 (dd, J=5.7, 0.9 Hz, 1H), 7.77 (dd, J=4.9, 0.6 Hz, 1H), 5.57 (s, 1H), 1.96 (s, 2H), 1.65 (s, 6H), 1.29 (s, 6H). LCMS (m/z [M+H]⁺): 372.2.

Example 126: 2-(3-chloropyridin-4-yl)-N-cyclopentylpyrido[3,4-d]pyrimidin-4-amine

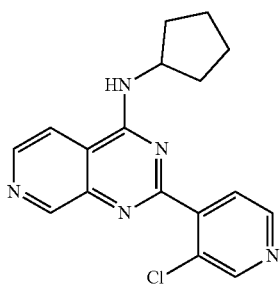 [SMILES: Clc1cnccc1-c1nc(NC2CCCC2)c2ccncc2n1]

1H NMR (400 MHz, DMSO-d6) δ 9.14 (d, J=0.9 Hz, 1H), 8.78 (d, J=0.6 Hz, 1H), 8.69 (dd, J=9.4, 5.2 Hz, 1H), 8.67 (d, J=6.9 Hz, 1H), 8.61 (d, J=6.8 Hz, 1H), 8.32 (dd, J=5.7, 0.9 Hz, 1H), 7.81 (m, 1H), 4.61-4.57 (m, 1H), 2.10-2.01 (m, 2H), 1.80-1.54 (m, 6H). LCMS (m/z [M+H]⁺): 326.1.

Example 127: 1-(2-{[2-(3-chloropyridin-4-yl)pyrido[3,4-d]pyrimidin-4-yl]amino}-2-methylpropoxy)-2-methylpropan-2-ol

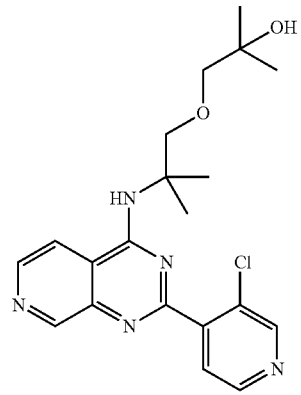 [SMILES: CC(C)(O)COCC(C)(C)Nc1nc(-c2ccncc2Cl)nc2cnccc12]

The title compound was prepared using procedures described in Example 111 and the amine as described in Example 12.

1H NMR (400 MHz, DMSO-d6) δ 9.13 (m, 1H), 8.80 (d, J=0.6 Hz, 1H), 8.69 (m, 2H), 8.40 (dd, J=5.8, 0.9 Hz, 1H), 7.83 (dd, J=4.9, 0.6 Hz, 1H), 7.76 (dd, J=4.9, 0.6 Hz, 1H), 4.38 (s, 1H), 3.80 (s, 2H), 3.16 (s, 2H), 1.51 (s, 6H), 1.00 (s, 6H). LCMS (m/z [M+H]⁺): 402.2.

Example 128: N-methyl-2-(3-methylpyridin-4-yl)-N-(propan-2-yl)pyrido[3,4-d]pyrimidin-4-amine

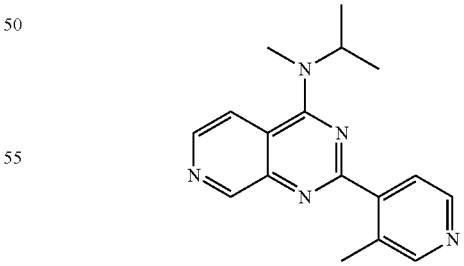

1H NMR (400 MHz, DMSO-d6) δ 9.19 (d, J=0.8 Hz, 1H), 8.58 (m, 2H), 8.53 (m, 1H), 8.03 (dd, J=5.8, 0.9 Hz, 1H), 7.87 (d, J=5.0 Hz, 1H), 5.09-5.00 (m, 1H), 3.29 (s, 3H), 2.60 (s, 3H), 1.31 (d, J=6.7 Hz, 6H). LCMS (m/z [M+H]⁺): 294.2.

Example 129: 2-(3-chloropyridin-4-yl)-N-(4-methanesulfonyl-2-methylbutan-2-yl)pyrido[3,4-d]pyrimidin-4-amine

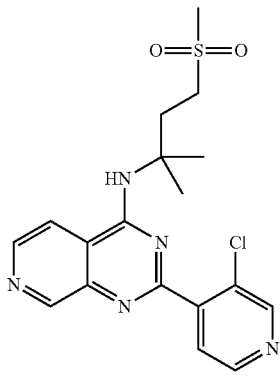 [SMILES: CC(C)(CCS(C)(=O)=O)Nc1nc(-c2ccncc2Cl)nc2cnccc12]

1H NMR (400 MHz, DMSO-d6) δ 9.15 (d, J=0.8 Hz, 1H), 8.79 (d, J=0.6 Hz, 1H), 8.69 (dd, J=21.3, 5.3 Hz, 1H), 8.65 (m, 1H), 8.40 (dd, J=5.8, 0.9 Hz, 1H), 7.80 (m, 1H), 7.78 (m, 1H), 3.12-3.08 (m, 2H), 2.87 (s, 3H), 2.49-2.46 (m, 2H), 1.53 (s, 6H). LCMS (m/z [M+H]+): 406.1.

Example 130: N-tert-butyl-2-[3-(trifluoromethyl)pyridin-4-yl]pyrido[3,4-d]pyrimidin-4-amine

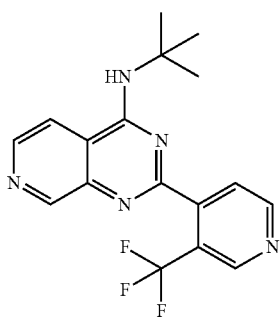 [SMILES: CC(C)(C)Nc1nc(-c2ccncc2C(F)(F)F)nc2cnccc12]

1H NMR (400 MHz, DMSO-d6) δ 8.92 (m, 1H), 8.89 (m, 1H), 8.08 (d, J=4.9 Hz, 1H), 7.76 (d, J=0.8 Hz, 1H), 7.70 (m, 1H), 7.67 (m, 1H), 7.56 (dd, J=5.0, 0.8 Hz, 1H), 1.49 (s, 9H). LCMS (m/z [M+H]+): 348.1.

Example 131: N-tert-butyl-2-[2-chloro-5-(trifluoromethyl)pyridin-4-yl]pyrido[3,4-d]pyrimidin-4-amine

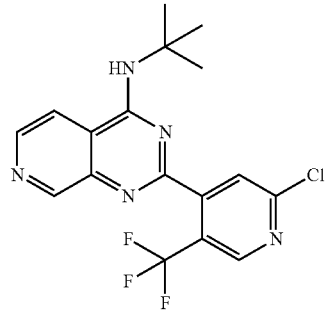 [SMILES: CC(C)(C)Nc1nc(-c2cc(Cl)ncc2C(F)(F)F)nc2cnccc12]

1H NMR (400 MHz, DMSO-d6) δ 9.08 (d, J=0.9 Hz, 1H), 8.87 (s, 1H), 8.61 (d, J=5.8 Hz, 1H), 8.22 (dd, J=5.8, 1.0 Hz, 1H), 7.83 (s, 1H), 1.20 (s, 9H). LCMS (m/z [M+H]+): 382.1.

Example 132: 2-(3-chloropyridin-4-yl)-N-[3-(1H-1,2,3,4-tetrazol-5-yl)propyl]pyrido[3,4-d]pyrimidin-4-amine

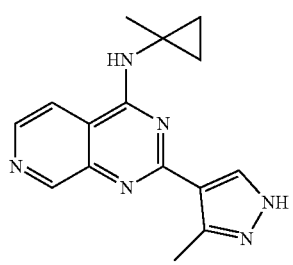 [SMILES: Cc1n[nH]cc1-c1nc(NC2(C)CC2)c2ccncc2n1]

1H NMR (400 MHz, DMSO-d6) δ 9.30 (s, 1H), 9.15 (d, J=0.8 Hz, 1H), 8.77 (s, 1H), 8.70 (dd, J=18.4, 5.2 Hz, 1H), 8.65 (m, 1H), 8.25 (dd, J=5.7, 0.9 Hz, 1H), 7.81 (d, J=4.9 Hz, 1H), 3.70-3.65 (td, J=6.8, 5.1 Hz, 2H), 2.90 (t, J=7.4 Hz, 2H), 2.12-2.07 (m, 2H). LCMS (m/z [M+H]+): 368.1.

Example 133: 2-(3-methyl-1H-pyrazol-4-yl)-N-(1-methylcyclopropyl)pyrido[3,4-d]pyrimidin-4-amine 1H NMR (500 MHz, Methanol-d4) δ 9.01 (s, 1H), 8.41 (d, J=5.7 Hz, 1H), 8.26 (s, 1H), 7.91 (dd, J=5.7, 0.9 Hz, 1H), 2.83 (s, 3H), 1.60 (s, 3H), 1.05-0.94 (m, 2H), 0.91-0.82 (m, 2H). LCMS (m/z [M+H]$^+$): 281.1.

Example 134: 2-(3-fluoropyridin-4-yl)-N-(1,1,1-trifluoro-2-methylpropan-2-yl)pyrido[3,4-d]pyrimidin-4-amine

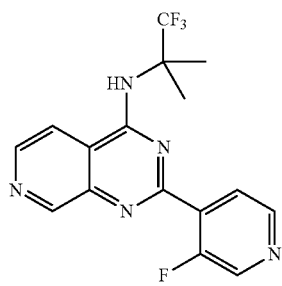 [SMILES: CC(C)(Nc1nc(-c2ccncc2F)nc2cnccc12)C(F)(F)F]

Title compound was prepared using procedures described in Example 120.

1H NMR (600 MHz, DMSO-d6) δ 9.24 (d, J=0.8 Hz, 1H), 8.77-8.73 (m, 2H), 8.62 (dd, J=4.9, 0.8 Hz, 1H), 8.52 (dd, J=5.8, 0.9 Hz, 1H), 8.04 (dd, J=6.7, 4.9 Hz, 1H), 7.99 (s, 1H), 1.86 (s, 6H). LCMS (m/z [M+H]$^+$): 352.1.

Example 135: 2-(3-methyl-1H-pyrazol-4-yl)-N-(1,1,1-trifluoro-2-methylpropan-2-yl)pyrido[3,4-d]pyrimidin-4-amine

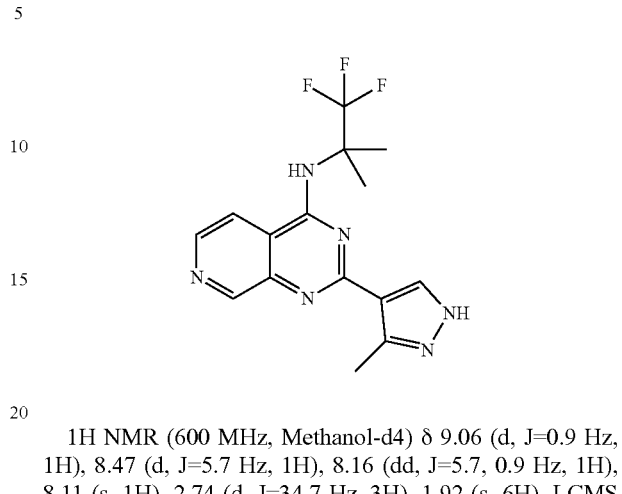

1H NMR (600 MHz, Methanol-d4) δ 9.06 (d, J=0.9 Hz, 1H), 8.47 (d, J=5.7 Hz, 1H), 8.16 (dd, J=5.7, 0.9 Hz, 1H), 8.11 (s, 1H), 2.74 (d, J=34.7 Hz, 3H), 1.92 (s, 6H). LCMS (m/z [M+H]$^+$): 337.1.

Example 136: 2-(3-fluoropyridin-4-yl)-N-methyl-N-[(2S)-1,1,1-trifluoropropan-2-yl]pyrido[3,4-d]pyrimidin-4-amine

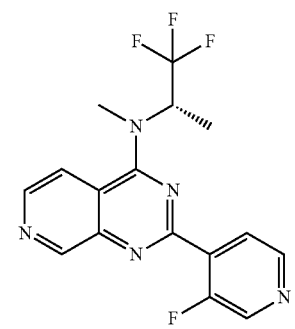

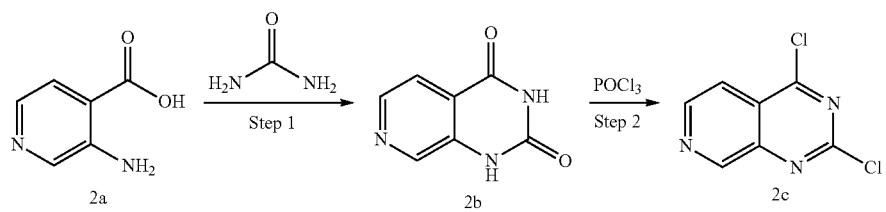

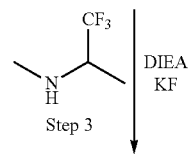

-continued

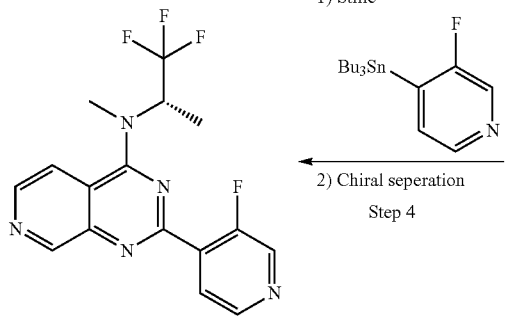
1) Stille

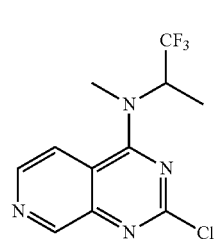
2) Chiral seperation
Step 4

Step 1

A mixture of urea (40.00 g, 666.00 mmol) and 3-aminoisonicotinic acid (2a, 18.40 g, 133.20 mmol) was heated at 210° C. for 1 hr (NOTE: no solvent was used). NaOH (2N, 320 mL) was added, and the mixture was stirred at 90° C. for 1 h. The solid was collected by filtration, and washed with water. The crude product thus obtained was suspended in HOAc (400 mL), and stirred at 100° C. for 1 h. The mixture was cooled to RT, filtered, and the solid was washed with a large amount of water, and then dried under the vacuum to give pyrido[3,4-d]pyrimidine-2,4(1H,3H)-dione (2b, 17.00 g, 78% yield) without further purification. LCMS (m/z [M+H]$^+$): 164.0.

Step 2

To a mixture of pyrido[3,4-d]pyrimidine-2,4(1H,3H)-dione (2b, 20.00 g, 122.60 mmol) and POCl$_3$ (328.03 g, 2.14 mol) in toluene (200 mL) was added DIEA (31.69 g, 245.20 mmol) dropwise and this reaction mixture stirred at 25° C. overnight (18 hr) to give suspension.

The solvent and POCl$_3$ was removed under vacuum, diluted with DCM (50 mL), neutralized with DIEA to pH=7 at −20° C. and concentrated again, the residue was purified by column (20-50% EA/PE) to give 2,4-dichloropyrido[3,4-d]pyrimidine (2c, 20.00 g, 99.99 mmol, 82% yield) as a yellow solid. 1H NMR (400 MHz, CHLOROFORM-d) b 9.52 (s, 1H), 8.92 (d, J=5.6 Hz, 1H), 8.04 (d, J=5.6 Hz, 1H). LCMS (m/z [M+H]$^+$): 200.0.

Step 3

In a 20 mL vial 2,4-dichloropyrido[3,4-d]pyrimidine (600 mg, 3.0 mmol) was stirred in DMSO (0.7 mL) at room temperature and degassed with N$_2$. DIEA (1 mL, 6 mmol) was added and stirred for 5 minutes then KF (174 mg, 3 mmol). This mixture was stirred at room temperature for 15 minutes then racemic 1,1,1-trifluoro-N-methylpropan-2-amine (419 mg, 3.3 mmol) was added and degassed then stirred at 60° C. for 4 hours. The reaction was then concentrated and purified by flash chromatography on a COMBIFLASH® system (ISCO) using 0-10% MeOH/DCM to afford 2-chloro-N-methyl-N-(1,1,1-trifluoropropan-2-yl)pyrido[3,4-d]pyrimidin-4-amine (680 mg, 74%). 1H NMR (500 MHz, Acetone-d6) δ 9.09 (d, J=0.9 Hz, 1H), 8.59 (d, J=5.9 Hz, 1H), 8.22 (dd, J=5.9, 0.9 Hz, 1H), 5.93 (dddd, J=15.3, 8.3, 7.0, 1.2 Hz, 1H), 3.61 (q, J=1.0 Hz, 3H), 1.63 (d, J=7.0 Hz, 3H). LCMS (m/z [M+H]$^+$): 291.7.

Step 4

Step 4: In a 20 mL vial 2-chloro-N-methyl-N-(1,1,1-trifluoropropan-2-yl)pyrido[3,4-d]pyrimidin-4-amine (100 mg, 0.34 mmol) was stirred in dry DMF (1 mL) at room temperature. 3-fluoro-4-(tributylstannyl)pyridine (133 mg, 0.34 mmol) was added then PdCl$_2$(dppf).CH$_2$Cl$_2$ adduct (28.1 mg, 0.034 mmol) and CuI (6.55 mg, 0.034 mmol). The reaction was stirred for 0.5 hour at 130° C. The crude mixture was diluted with DCM, H$_2$O, separated and extracted with DCM×3. Combined the organic layers and dried Na$_2$SO$_4$, filtered and concentrated. The residue was purified by flash chromatography on a COMBIFLASH® system (ISCO) using 0-10% MeOH/DCM to give the racemic product, then followed by chiral HPLC (21×250 mm OJ-H column with 85% CO$_2$ as phase A and 15% MeOH as phase B, flow rate 2 mL/min, 30° C., 2.75 min elution time) to separate the enantiomers to afford Examples 136 and 137

Examples 136

1H NMR (500 MHz, DMSO-d6) δ 9.30 (d, J=0.8 Hz, 1H), 8.75 (d, J=3.0 Hz, 1H), 8.66 (d, J=5.9 Hz, 1H), 8.62 (dd, J=4.9, 0.8 Hz, 1H), 8.24 (dd, J=5.9, 0.9 Hz, 1H), 8.15 (dd, J=6.8, 4.9 Hz, 1H), 6.12-5.98 (m, 1H), 3.51 (d, J=1.1 Hz, 3H), 1.57 (d, J=7.0 Hz, 3H). LCMS (m/z [M+H]$^+$): 352.1. Chiral HPLC T$_R$=0.88 min.

Example 137: 2-(3-fluoropyridin-4-yl)-N-methyl-N-[(2R)-1,1,1-trifluoropropan-2-yl]pyrido[3,4-d]pyrimidin-4-amine

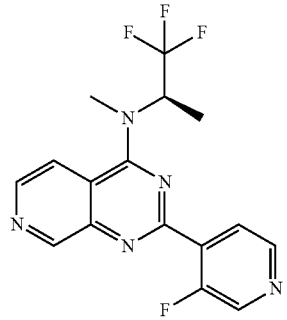 [SMILES: C[C@@H](N(C)c1nc(-c2ccncc2F)nc2cnccc12)C(F)(F)F]

1H NMR (500 MHz, DMSO-d6) δ 9.30 (d, J=0.8 Hz, 1H), 8.75 (d, J=3.0 Hz, 1H), 8.66 (d, J=5.9 Hz, 1H), 8.62 (dd,

J=4.9, 0.8 Hz, 1H), 8.24 (dd, J=5.9, 0.9 Hz, 1H), 8.15 (dd, J=6.8, 4.9 Hz, 1H), 6.12-5.98 (m, 1H), 3.51 (d, J=1.1 Hz, 3H), 1.57 (d, J=7.0 Hz, 3H). LCMS (m/z [M+H]$^+$): 352.1. Chiral HPLC TR=0.70 min.

Example 138: 4-{4-[(1-methylcyclopropyl)amino]pyrido[3,4-d]pyrimidin-2-yl}pyridin-2-amine

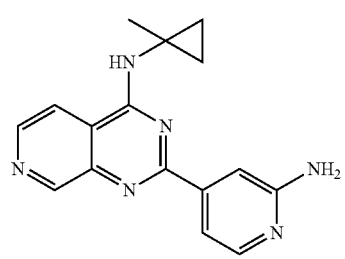 [SMILES: CC1(Nc2nc(-c3ccnc(N)c3)nc3cnccc23)CC1]

1H NMR (400 MHz, Acetone-d6) δ 9.15 (d, J=0.9 Hz, 1H), 8.55 (d, J=5.6 Hz, 1H), 8.17-8.09 (m, 2H), 7.98 (dd, J=5.6, 1.0 Hz, 1H), 7.81-7.70 (m, 2H), 1.61 (s, 3H), 1.00-0.94 (m, 2H), 0.91-0.84 (m, 2H). LCMS (m/z [M+H]$^+$): 293.1.

Example 139: 2-(3-chloropyridin-4-yl)-N-(1,1,1-trifluoro-2-methylpropan-2-yl)pyrido[3,4-d]pyrimidin-4-amine

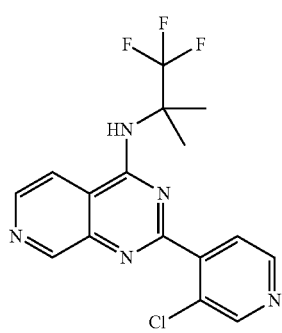 [SMILES: CC(C)(Nc1nc(-c2ccncc2Cl)nc2cnccc12)C(F)(F)F]

1H NMR (500 MHz, Methanol-d4) δ 9.20 (s, 1H), 8.74 (s, 1H), 8.68 (d, J=5.8 Hz, 1H), 8.63 (d, J=5.0 Hz, 1H), 8.33 (dd, J=5.8, 0.9 Hz, 1H), 7.79 (d, J=4.9 Hz, 1H), 1.88 (d, J=1.0 Hz, 6H). LCMS (m/z [M+H]$^+$): 368.1.

Example 140: 2,4-dimethyl-4-{[2-(3-methyl-1H-pyrazol-4-yl)pyrido[3,4-d]pyrimidin-4-yl]amino}pentan-2-ol

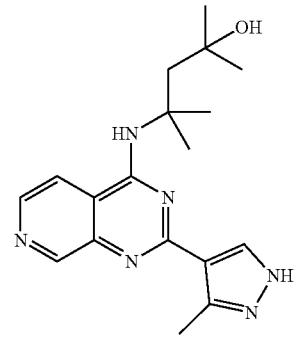 [SMILES: Cc1n[nH]cc1-c1nc(NC(C)(C)CC(C)(C)O)c2ccncc2n1]

1H NMR (400 MHz, Chloroform-d) δ 9.14 (s, 1H), 8.80 (s, 1H), 8.37 (t, J=5.8 Hz, 2H), 7.50-7.38 (m, 1H), 2.81 (s, 3H), 1.99 (s, 2H), 1.81 (s, 6H), 1.49 (s, 6H). LCMS (m/z [M+H]$^+$): 341.2.

Example 141: 4-{4-[(1-methylcyclopropyl)amino]pyrido[3,4-d]pyrimidin-2-yl}pyridine-3-carbonitrile

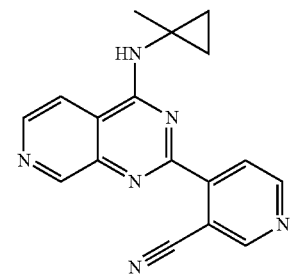 [SMILES: CC1(Nc2nc(-c3ccncc3C#N)nc3cnccc23)CC1]

1H NMR (400 MHz, Acetone-d6) δ 9.23 (d, J=0.9 Hz, 1H), 9.09 (d, J=0.8 Hz, 1H), 8.99 (d, J=5.2 Hz, 1H), 8.65 (d, J=5.6 Hz, 1H), 8.59-8.53 (m, 1H), 8.42 (s, 1H), 8.07 (dd, J=5.7, 0.9 Hz, 1H), 1.62 (s, 3H), 1.04-0.97 (m, 2H), 0.90-0.81 (m, 2H). LCMS (m/z [M+H]$^+$): 303.1.

Example 142: 2-{2-methyl-1H-pyrrolo[2,3-b]pyridin-3-yl}-N-propylpyrido[3,4-d]pyrimidin-4-amine

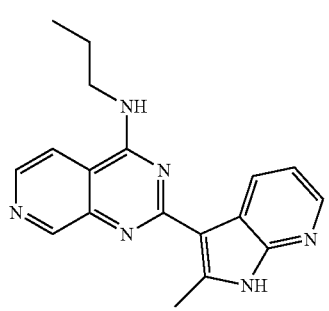 [SMILES: CCCNc1nc(-c2c(C)[nH]c3ncccc23)nc2cnccc12]

Title compound was prepared using procedures described in Example 114.

1H NMR (400 MHz, DMSO-d6) δ 12.02 (s, 1H), 9.06 (d, J=0.8 Hz, 1H), 8.98 (dd, J=7.9, 1.7 Hz, 1H), 8.50 (t, J=5.5 Hz, 1H), 8.46 (d, J=5.5 Hz, 1H), 8.19 (dd, J=4.7, 1.7 Hz, 1H), 8.06 (dd, J=5.6, 0.9 Hz, 1H), 7.16 (dd, J=7.9, 4.7 Hz, 1H), 3.62 (dt, J=8.1, 6.0 Hz, 2H), 2.96 (s, 3H), 1.90-1.69 (m, 2H), 1.00 (t, J=7.4 Hz, 3H). LCMS (m/z [M+H]⁺): 319.2.

Example 143: 2-(1H-indazol-5-yl)-N-(1-methylcyclopropyl)pyrido[3,4-d]pyrimidin-4-amine

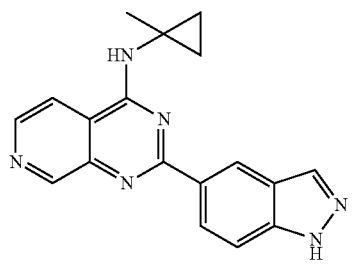 [SMILES: CC1(Nc2nc(-c3ccc4[nH]ncc4c3)nc3cnccc23)CC1]

1H NMR (400 MHz, DMSO-d6) δ 9.12 (d, J=0.9 Hz, 1H), 9.00 (dd, J=1.5, 0.8 Hz, 1H), 8.85 (s, 1H), 8.61 (dd, J=8.9, 1.5 Hz, 1H), 8.52 (d, J=5.5 Hz, 1H), 8.26 (s, 1H), 8.11 (dd, J=5.6, 0.9 Hz, 1H), 7.65 (d, J=8.8 Hz, 1H), 1.62 (s, 3H), 0.97-0.81 (m, 4H). LCMS (m/z [M+H]⁺): 317.1.

Example 144: 2-(3,5-dimethyl-1H-pyrazol-4-yl)-N-(1,1,1-trifluoro-2-methylpropan-2-yl)pyrido[3,4-d]pyrimidin-4-amine

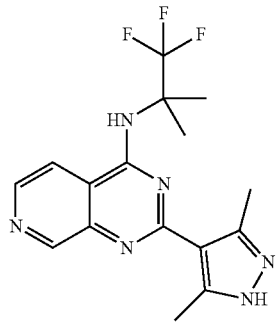 [SMILES: Cc1n[nH]c(C)c1-c1nc(NC(C)(C)C(F)(F)F)c2ccncc2n1]

1H NMR (500 MHz, Methanol-d4) δ 9.06 (d, J=0.9 Hz, 1H), 8.50 (d, J=5.8 Hz, 1H), 8.17 (dd, J=5.8, 0.9 Hz, 1H), 2.58 (s, 6H), 1.91 (d, J=1.1 Hz, 6H). LCMS (m/z [M+H]⁺): 3511.

Example 145: N-(1,1,1-trifluoro-2-methylpropan-2-yl)-2-[3-(trifluoromethyl)-1H-pyrazol-4-yl]pyrido[3,4-d]pyrimidin-4-amine

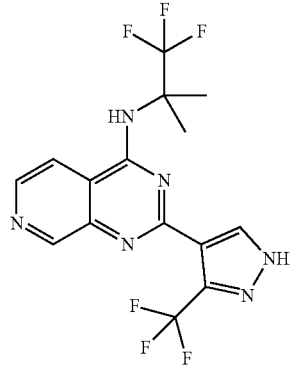 [SMILES: CC(C)(Nc1nc(-c2c[nH]nc2C(F)(F)F)nc2cnccc12)C(F)(F)F]

1H NMR (600 MHz, Methanol-d4) δ 9.06 (d, J=1.0 Hz, 1H), 8.54 (d, J=5.7 Hz, 1H), 8.38-8.36 (m, 1H), 8.20 (dd, J=5.7, 0.9 Hz, 1H), 1.90 (d, J=1.1 Hz, 6H). LCMS (m/z [M+H]⁺): 391.1.

Example 146: 4-{4-[(4-hydroxy-2,4-dimethylpentan-2-yl)amino]pyrido[3,4-d]pyrimidin-2-yl}pyridine-3-carbonitrile

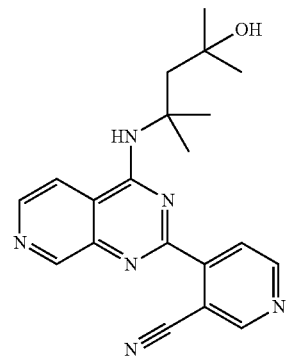 [SMILES: CC(C)(O)CC(C)(C)Nc1nc(-c2ccncc2C#N)nc2cnccc12]

1H NMR (400 MHz, Chloroform-d) δ 9.55 (s, 1H), 9.38 (s, 1H), 9.07 (d, J=0.8 Hz, 1H), 8.95 (d, J=5.2 Hz, 1H), 8.62 (d, J=5.9 Hz, 1H), 8.27 (dd, J=5.2, 0.8 Hz, 1H), 7.86-7.80 (m, 1H), 2.02 (s, 2H), 1.84 (s, 6H), 1.53 (s, 6H). LCMS (m/z [M+H]⁺): 363.2.

Example 147: 2-(3,5-difluoropyridin-4-yl)-N-(1-methylcyclopropyl)pyrido[3,4-d]pyrimidin-4-amine

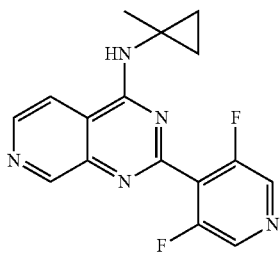 [SMILES: CC1(Nc2nc(-c3c(F)cncc3F)nc3cnccc23)CC1]

Title compound was prepared using procedures described in Example 120.

1H NMR (400 MHz, DMSO-d6) δ 9.16 (s, 1H), 9.14 (d, J=0.8 Hz, 1H), 8.71 (s, 2H), 8.68 (d, J=5.6 Hz, 1H), 8.19 (dd, J=5.7, 1.0 Hz, 1H), 1.45 (s, 3H), 0.87-0.77 (m, 2H), 0.75-0.64 (m, 2H). LCMS (m/z [M+H]$^+$): 314.1.

Example 148: 2-(2,3-difluoropyridin-4-yl)-N-(1-methylcyclopropyl)pyrido[3,4-d]pyrimidin-4-amine

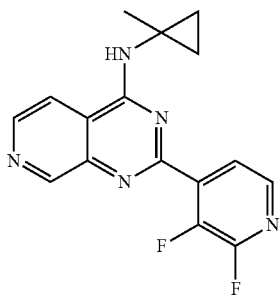 [SMILES: CC1(Nc2nc(-c3ccnc(F)c3F)nc3cnccc23)CC1]

Title compound was prepared using procedures described in Example 120.

1H NMR (400 MHz, Chloroform-d) δ 9.36 (s, 1H), 8.90 (dd, J=5.0, 0.9 Hz, 1H), 8.85 (dd, J=1.6, 0.9 Hz, 1H), 8.69 (dd, J=5.1, 1.6 Hz, 1H), 8.66 (d, J=5.7 Hz, 1H), 7.64-7.52 (m, 1H), 1.64 (s, 3H), 1.04-0.94 (m, 4H). LCMS (m/z [M+H]$^+$): 314.1.

Example 149: N-(1-methylcyclopropyl)-2-(1,3-thiazol-5-yl)pyrido[3,4-d]pyrimidin-4-amine

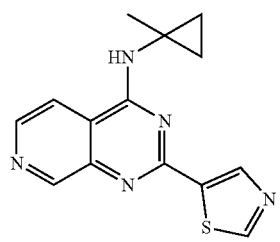 [SMILES: CC1(Nc2nc(-c3cncs3)nc3cnccc23)CC1]

1H NMR (400 MHz, DMSO-d6) δ 9.22 (d, J=0.8 Hz, 1H), 9.08 (d, J=0.8 Hz, 1H), 9.01 (s, 1H), 8.69-8.62 (m, 1H), 8.56 (d, J=5.5 Hz, 1H), 8.10 (dd, J=5.7, 0.9 Hz, 1H), 1.55 (s, 3H), 0.92-0.86 (m, 2H), 0.86-0.76 (m, 2H). LCMS (m/z [M+H]$^+$): 284.1.

Example 150: N-(1-methylcyclopropyl)-2-[2-(trifluoromethyl)pyridin-4-yl]pyrido[3,4-d]pyrimidin-4-amine

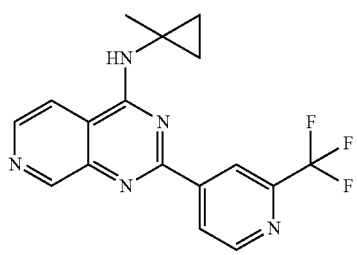 [SMILES: CC1(Nc2nc(-c3ccnc(C(F)(F)F)c3)nc3cnccc23)CC1]

1H NMR (400 MHz, Chloroform-d) δ 9.41 (s, 1H), 8.97-8.89 (m, 1H), 8.88 (dd, J=1.5, 0.8 Hz, 1H), 8.70-8.66 (m, 1H), 8.66-8.61 (m, 1H), 7.89-7.77 (m, 1H), 6.95-6.80 (m, 1H), 1.65 (s, 3H), 1.07-1.01 (m, 2H), 1.01-0.92 (m, 2H). LCMS (m/z [M+H]$^+$): 346.1.

Example 151: 4-{4-[(1-methylcyclopropyl)amino]pyrido[3,4-d]pyrimidin-2-yl}pyridine-2-carbonitrile

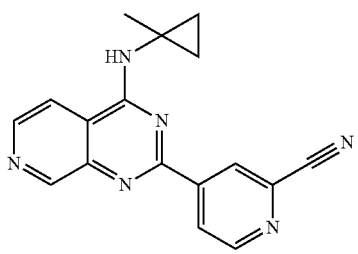 [SMILES: CC1(Nc2nc(-c3ccnc(C#N)c3)nc3cnccc23)CC1]

1H NMR (400 MHz, Chloroform-d) δ 9.36 (s, 1H), 8.90 (dd, J=5.0, 0.9 Hz, 1H), 8.85 (dd, J=1.6, 0.9 Hz, 1H), 8.69 (dd, J=5.1, 1.6 Hz, 1H), 8.66 (d, J=5.7 Hz, 1H), 7.64-7.52 (m, 1H), 1.64 (s, 3H), 1.04-0.94 (m, 4H). LCMS (m/z [M+H]$^+$): 303.1.

Example 152: N-(1-methylcyclopropyl)-2-(1,2-oxazol-4-yl)pyrido[3,4-d]pyrimidin-4-amine

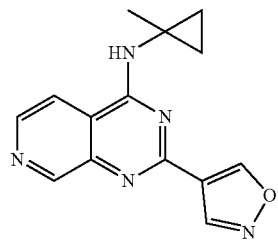 [SMILES: CC1(Nc2nc(-c3cnoc3)nc3cnccc23)CC1]

1H NMR (400 MHz, Chloroform-d) b 9.25 (s, 1H), 8.83 (s, 1H), 8.54 (dd, J=6.0, 0.7 Hz, 1H), 7.94-7.88 (br s, 1H), 7.32-7.27 (br s, 1H), 6.61 (dd, J=6.0, 0.7 Hz, 1H), 0.91 (s, 3H), 0.85-0.73 (m, 4H). LCMS (m/z [M+H]⁺): 268.1.

Example 153: 2-(dimethyl-1,2-oxazol-4-yl)-N-(1-methylcyclopropyl)pyrido[3,4-d]pyrimidin-4-amine

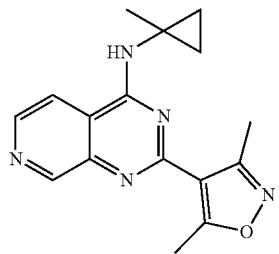 [SMILES: Cc1noc(C)c1-c1nc(NC2(C)CC2)c2ccncc2n1]

1H NMR (400 MHz, DMSO-d6) δ 9.05 (d, J=0.8 Hz, 1H), 8.89 (s, 1H), 8.54 (d, J=5.6 Hz, 1H), 8.10 (dd, J=5.7, 0.9 Hz, 1H), 2.90 (s, 3H), 2.65 (s, 3H), 1.51 (s, 3H), 0.96-0.84 (m, 2H), 0.83-0.71 (m, 2H). LCMS (m/z [M+H]⁺): 296.1.

Example 154: N-(1-methylcyclopropyl)-2-{1H-pyrrolo[2,3-b]pyridin-4-yl}pyrido[3,4-d]pyrimidin-4-amine

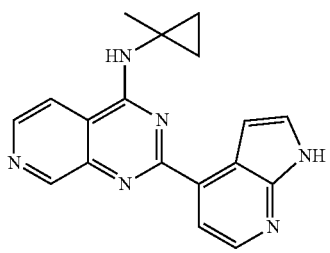 [SMILES: CC1(Nc2nc(-c3ccnc4[nH]ccc34)nc3cnccc23)CC1]

1H NMR (600 MHz, DMSO-d6) δ 11.77 (s, 1H), 9.23 (d, J=0.8 Hz, 1H), 8.92 (s, 1H), 8.59 (d, J=5.5 Hz, 1H), 8.38 (d, J=5.0 Hz, 1H), 8.22 (d, J=5.0 Hz, 1H), 8.16 (dd, J=5.7, 0.9 Hz, 1H), 7.69 (dd, J=3.4, 2.0 Hz, 1H), 7.61 (t, J=2.9 Hz, 1H), 1.61 (s, 3H), 0.99-0.94 (m, 2H), 0.92-0.87 (m, 2H). LCMS (m/z [M+H]⁺): 317.1.

Example 155: N-propyl-2-{1H-pyrrolo[2,3-b]pyridin-3-yl}pyrido[3,4-d]pyrimidin-4-amine

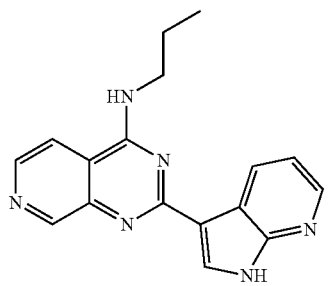 [SMILES: CCCNc1nc(-c2c[nH]c3ncccc23)nc2cnccc12]

1H NMR (400 MHz, DMSO-d6) δ 12.18 (s, 1H), 9.07 (d, J=0.8 Hz, 1H), 8.96 (dd, J=7.9, 1.6 Hz, 1H), 8.51 (dd, J=16.1, 5.5 Hz, 2H), 8.35-8.27 (m, 2H), 8.09 (dd, J=5.7, 1.0 Hz, 1H), 7.25 (dd, J=7.9, 4.6 Hz, 1H), 3.67 (dt, J=7.7, 5.9 Hz, 2H), 1.78 (h, J=7.4 Hz, 2H), 1.03 (t, J=7.4 Hz, 3H). LCMS (m/z [M+H]⁺): 305.1.

Example 156: N-propyl-2-{1H-pyrrolo[3,2-b]pyridin-1-yl}pyrido[3,4-d]pyrimidin-4-amine

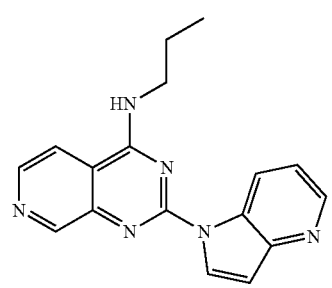 [SMILES: CCCNc1nc(-n2ccc3ncccc32)nc2cnccc12]

1H NMR (500 MHz, DMSO-d6) δ 9.19 (ddd, J=8.4, 1.5, 0.8 Hz, 1H), 9.13 (d, J=0.9 Hz, 1H), 9.02 (t, J=5.5 Hz, 1H), 8.65 (d, J=3.7 Hz, 1H), 8.55 (d, J=5.5 Hz, 1H), 8.48 (dd, J=4.6, 1.5 Hz, 1H), 8.16 (dd, J=5.5, 0.9 Hz, 1H), 7.35 (dd, J=8.4, 4.6 Hz, 1H), 6.88 (dd, J=3.8, 0.8 Hz, 1H), 3.71-3.63 (m, 2H), 1.85-1.74 (m, 2H), 1.04 (t, J=7.4 Hz, 3H). LCMS (m/z [M+H]⁺): 305.1.

Example 157: 2-(3-methylpyridin-4-yl)-N-(1,1,1-trifluoro-2-methylpropan-2-yl)pyrido[3,4-d]pyrimidin-4-amine

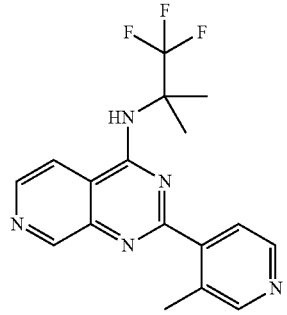 [SMILES: Cc1cnccc1-c1nc(NC(C)(C)C(F)(F)F)c2ccncc2n1]

1H NMR (400 MHz, DMSO-d6) δ 9.22 (d, J=0.8 Hz, 1H), 8.73 (d, J=5.7 Hz, 1H), 8.58 (d, J=5.8 Hz, 2H), 8.52 (dd, J=5.8, 1.0 Hz, 1H), 7.91 (s, 1H), 7.75 (d, J=5.0 Hz, 1H), 2.59 (s, 3H), 1.85 (s, 6H). LCMS (m/z [M+H]⁺): 348.1.

Example 158: N-(1-methylcyclobutyl)-2-(1H-pyrazol-4-yl)pyrido[3,4-d]pyrimidin-4-amine

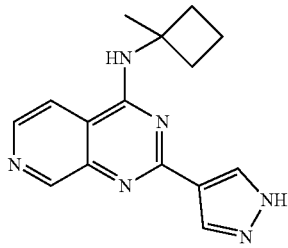 [SMILES: CC1(Nc2nc(-c3cn[nH]c3)nc3cnccc23)CCC1]

1H NMR (500 MHz, DMSO-d6) δ 13.11 (s, 1H), 8.98 (s, 1H), 8.47 (d, J=5.5 Hz, 1H), 8.38 (s, 1H), 8.27 (s, 1H), 8.14 (d, J=5.5 Hz, 1H), 8.07 (s, 1H), 2.48-2.41 (m, 2H), 2.25 (td, J=9.0, 4.3 Hz, 2H), 1.99-1.81 (m, 2H), 1.67 (s, 3H). LCMS (m/z [M+H]$^+$): 281.1.

Example 159: N-(1-methylcyclopropyl)-2-(pyrimidin-4-yl)pyrido[3,4-d]pyrimidin-4-amine

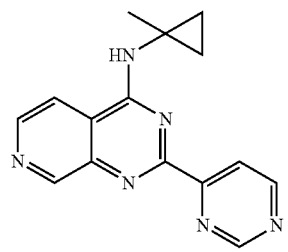 [SMILES: CC1(Nc2nc(-c3ccncn3)nc3cnccc23)CC1]

Title compound was prepared using procedures described in Example 120

1H NMR (400 MHz, Acetone-d6) δ 9.15 (d, J=0.9 Hz, 1H), 8.55 (d, J=5.6 Hz, 1H), 8.17-8.09 (m, 2H), 7.98 (dd, J=5.6, 1.0 Hz, 1H), 7.81-7.70 (m, 2H), 1.61 (s, 3H), 1.00-0.94 (m, 2H), 0.91-0.84 (m, 2H). LCMS (m/z [M+H]$^+$): 279.1.

Example 160: 4-{[2-(3,5-dimethyl-1H-pyrazol-4-yl)pyrido[3,4-d]pyrimidin-4-yl]amino}-2,4-dimethylpentan-2-ol

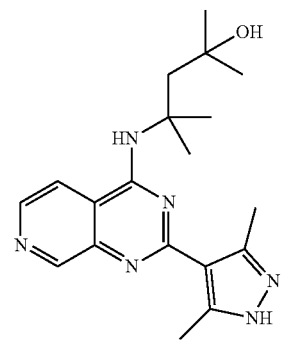 [SMILES: Cc1n[nH]c(C)c1-c1nc(NC(C)(C)CC(C)(C)O)c2ccncc2n1]

1H NMR (500 MHz, DMSO-d6) δ 12.43 (s, 1H), 9.15 (s, 1H), 8.96 (s, 1H), 8.46 (d, J=5.5 Hz, 1H), 7.69 (dd, J=5.7, 1.0 Hz, 1H), 5.61 (s, 1H), 2.61 (s, 3H), 2.55 (s, 3H), 1.95 (s, 2H), 1.70 (s, 6H), 1.32 (s, 6H). LCMS (m/z [M+H]$^+$): 355.2.

Example 161: 4 N-propyl-2-{7H-pyrrolo[2,3-d]pyrimidin-5-yl}pyrido[3,4-d]pyrimidin-4-amine

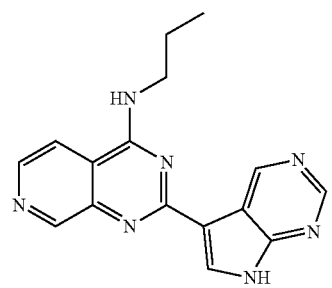 [SMILES: CCCNc1nc(-c2c[nH]c3ncncc23)nc2cnccc12]

1H NMR (500 MHz, DMSO-d6) δ 12.59 (d, J=2.5 Hz, 1H), 9.87 (s, 1H), 9.12 (d, J=0.9 Hz, 1H), 8.86 (s, 1H), 8.60 (t, J=5.6 Hz, 1H), 8.53 (d, J=5.5 Hz, 1H), 8.36 (d, J=2.6 Hz, 1H), 8.11 (dd, J=5.6, 0.9 Hz, 1H), 3.72-3.64 (m, 2H), 1.85-1.72 (m, 2H), 1.03 (t, J=7.4 Hz, 3H). LCMS (m/z [M+H]$^+$): 306.1.

Example 162: 2-(3-chloropyridin-4-yl)-N-propylpyrido[3,4-d]pyrimidin-4-amine

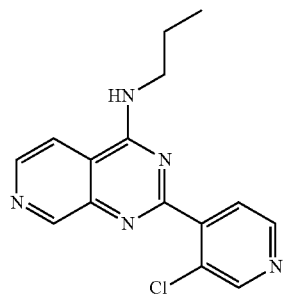 [SMILES: CCCNc1nc(-c2ccncc2Cl)nc2cnccc12]

1H NMR (500 MHz, DMSO-d6) δ 9.15 (d, J=0.8 Hz, 1H), 8.89 (t, J=5.5 Hz, 1H), 8.78 (d, J=0.6 Hz, 1H), 8.68 (dd, J=12.2, 5.2 Hz, 2H), 8.22 (dd, J=5.6, 0.9 Hz, 1H), 7.82 (dd, J=4.9, 0.6 Hz, 1H), 3.60-3.52 (m, 2H), 1.76-1.65 (m, 2H), 0.95 (t, J=7.4 Hz, 3H). LCMS (m/z [M+H]$^+$): 300.1.

Example 163: 2-(3-cyclopropyl-1H-pyrazol-4-yl)-N-propylpyrido[3,4-d]pyrimidin-4-amine

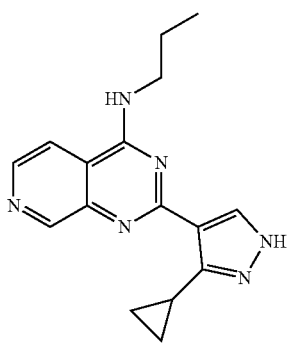 [SMILES: CCCNc1nc(-c2c[nH]nc2C2CC2)nc2cnccc12]

1H NMR (400 MHz, DMSO-d6) δ 12.47 (s, 1H), 8.98 (s, 1H), 8.54 (t, J=5.4 Hz, 1H), 8.48 (d, J=5.5 Hz, 1H), 8.06 (dd, J=5.6, 0.9 Hz, 1H), 3.55 (dt, J=7.8, 5.9 Hz, 2H), 3.24 (t, J=7.1 Hz, 1H), 3.17 (d, J=5.1 Hz, 1H), 1.77-1.63 (m, 2H), 0.93 (m, 7H). LCMS (m/z [M+H]⁺): 295.2.

Example 164: 2-(3-methylpyridin-4-yl)-N-propylpyrido[3,4-d]pyrimidin-4-amine

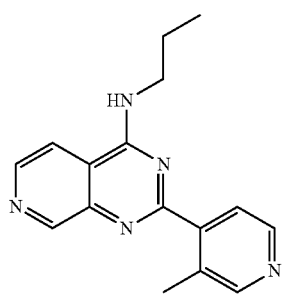 [SMILES: CCCNc1nc(-c2ccncc2C)nc2cnccc12]

1H NMR (500 MHz, DMSO-d6) δ 9.14 (d, J=0.9 Hz, 1H), 8.79 (t, J=5.6 Hz, 1H), 8.65 (d, J=5.5 Hz, 1H), 8.58-8.52 (m, 2H), 8.20 (dd, J=5.6, 1.0 Hz, 1H), 7.85 (d, J=5.0 Hz, 1H), 3.62-3.54 (m, 2H), 2.60 (s, 3H), 1.77-1.66 (m, 2H), 0.97 (t, J=7.4 Hz, 3H). LCMS (m/z [M+H]⁺): 280.2.

Example 165: 2-{1-methyl-1H-pyrrolo[2,3-b]pyridin-3-yl}-N-propylpyrido[3,4-d]pyrimidin-4-amine

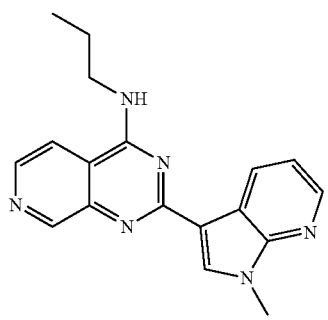 [SMILES: CCCNc1nc(-c2cn(C)c3ncccc23)nc2cnccc12]

1H NMR (500 MHz, DMSO-d6) δ 9.06 (d, J=0.9 Hz, 1H), 8.97 (dd, J=7.9, 1.7 Hz, 1H), 8.48 (d, J=5.5 Hz, 2H), 8.44 (s, 1H), 8.36 (dd, J=4.7, 1.7 Hz, 1H), 8.09 (d, J=5.7, 1.0 Hz, 1H), 7.29 (dd, J=7.9, 4.6 Hz, 1H), 3.94 (s, 3H), 3.72-3.64 (m, 2H), 1.85-1.73 (m, 2H), 1.04 (t, J=7.4 Hz, 3H). LCMS (m/z [M+H]⁺): 319.2.

Example 166: 2,4-dimethyl-4-{[2-(1H-pyrazol-4-yl)pyrido[3,4-d]pyrimidin-4-yl]amino}pentan-2-ol

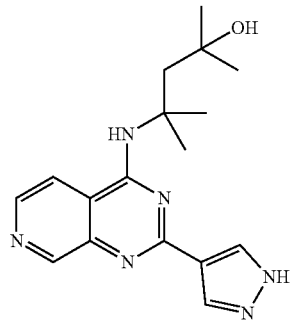 [SMILES: CC(C)(O)CC(C)(C)Nc1nc(-c2cn[nH]c2)nc2cnccc12]

1H NMR (DMSO-d6) δ 1.29 (s, 6H), 1.72 (s, 6H), 1.98 (s, 2H), 5.5 (s, 1H, NH), 7.69 (d, J=3.6 Hz, 1H), 8.09 (s, 1H), 8.30 (s, 1H), 8.48 (d, J=3.6 Hz, 1H), 8.99 (s, 1H), 9.13 (s, 1H). LCMS (m/z [M+H]⁺): 327.2.

Example 167: N-[(1R)-1-phenylethyl]-2-(1H-pyrazol-4-yl)pyrido[3,4-d]pyrimidin-4-amine

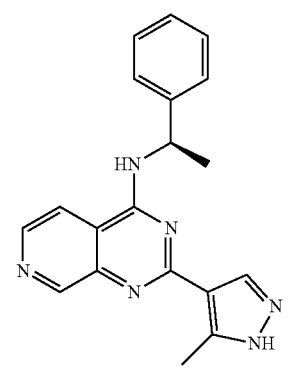 [SMILES: Cc1[nH]ncc1-c1nc(N[C@H](C)c2ccccc2)c2ccncc2n1]

1H NMR (MeOH-d4) d 1.70 (d, J=6.8 Hz, 3H), 5.63 (m, 1H), 7.21 (m, 1H), 7.32 (m, 2H), 7.49 (m, 2H), 8.17 (d, J=5.6 Hz, 1H), 8.20-8.23 (2H), 8.48 (d, J=5.6 Hz, 1H), 9.00 (s, 1H). LCMS (m/z [M+H]⁺): 317.2.

Example 168: 2-(5-methyl-1H-pyrazol-4-yl)-N-[(1R)-1-phenylethyl]pyrido[3,4-d]pyrimidin-4-amine 1H NMR (MeOH-d4) d1.70 (d, J=6.8 Hz, 3H), 2.54 (s, 3H), 5.65 (m, 1H), 7.20 (m, 1H), 7.32 (m, 2H), 7.44 (m, 2H), 8.14-8.18 (2H), 8.46 (s, 1H), 9.00 (s, 1H). LCMS (m/z [M+H]+): 331.2.

Example 169: N-methyl-2-(1-methyl-1H-pyrazol-5-yl)-N-(1-methylcyclopropyl)pyrido[3,4-d]pyrimidin-4-amine

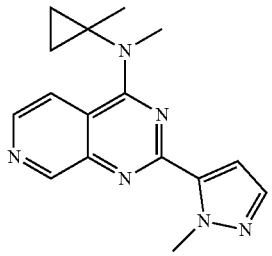 [SMILES: CN(c1nc(-c2ccnn2C)nc2cnccc12)C1(C)CC1]

1H NMR (DMSO-d6) δ 0.95 (s, 4H), 1.70 (s, 3H), 3.38 (s, 3H), 4.35 (s, 3H), 7.04 (d, J=2.0 Hz, 1H), 7.51 (d, J=2.0 Hz, 1H), 8.16 (d, J=5.6 Hz, 1H), 8.56 (d, J=5.6 Hz, 1H), 9.16 (s, 1H). LCMS (m/z [M+H]+): 295.2.

Example 170: 2-(1-methyl-1H-pyrazol-5-yl)-N-[(1R)-1-phenylethyl]pyrido[3,4-d]pyrimidin-4-amine

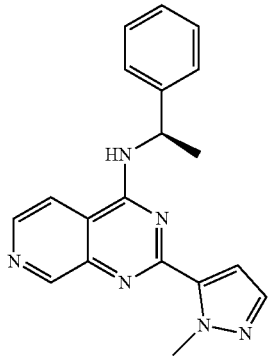 [SMILES: C[C@@H](Nc1nc(-c2ccnn2C)nc2cnccc12)c1ccccc1]

1H NMR (MeOH-d4) d 1.60 (d, J=7.2 Hz, 3H), 4.02 (s, 3H), 5.46 (m, 1H), 6.86 (d, J=2 Hz, 1H), 7.10 (m, 1H), 7.22 (m, 2H), 7.33 (m, 2H), 8.11 (d, J=5.6 Hz, 1H), 8.44 (d, J=5.6 Hz, 1H), 8.96 (s, 1H). LCMS (m/z [M+H]+): 331.2.

Example 171: N-methyl-N-(1-methylcyclopropyl)-2-(1H-pyrazol-4-yl)pyrido[3,4-d]pyrimidin-4-amine

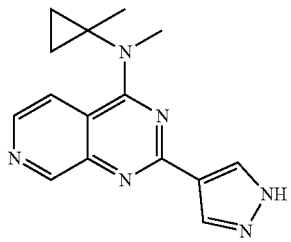 [SMILES: CN(c1nc(-c2cn[nH]c2)nc2cnccc12)C1(C)CC1]

1H NMR (DMSO-d6) δ 0.92 (s, 4H), 1.68 (s, 3H), 3.37 (s, 3H), 8.10 (d, J=5.6 Hz, 1H), 8.13 (s, 1H), 8.35 (s, 1H), 8.45 (m, 1H), 9.05 (s, 1H). LCMS (m/z [M+H]+): 281.1.

Example 172: 2-(1-methyl-1H-pyrazol-5-yl)-N-(1-methylcyclopropyl)pyrido[3,4-d]pyrimidin-4-amine

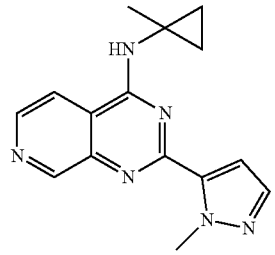 [SMILES: Cn1nccc1-c1nc(NC2(C)CC2)c2ccncc2n1]

1H NMR (400 MHz, Methanol-d4) δ 8.99 (s, 1H), 8.43 (d, J=5.7 Hz, 1H), 7.87 (dd, J=5.7, 0.8 Hz, 1H), 7.48 (d, J=2.0 Hz, 1H), 7.08 (d, J=2.0 Hz, 1H), 4.42 (s, 3H), 1.55 (s, 3H), 0.98-0.93 (m, 2H), 0.85-0.80 (m, 2H). LCMS (m/z [M+H]+): 281.1.

Example 173: 2-(1-ethyl-1H-pyrazol-5-yl)-N-(1-methylcyclopropyl)pyrido[3,4-d]pyrimidin-4-amine

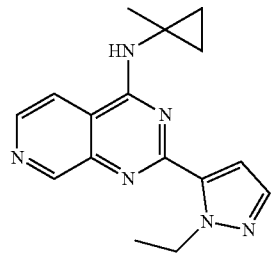 [SMILES: CCn1nccc1-c1nc(NC2(C)CC2)c2ccncc2n1]

1H NMR (400 MHz, Methanol-d4) δ 9.10 (s, 1H), 8.52 (s, 1H), 7.98 (d, J=5.5 Hz, 1H), 7.56 (d, J=2.0 Hz, 1H), 7.15 (d, J=2.0 Hz, 1H), 5.07 (q, J=7.1 Hz, 2H), 1.59 (s, 3H), 1.49 (t, J=7.1 Hz, 3H), 1.04-0.95 (m, 2H), 0.93-0.76 (m, 2H). LCMS (m/z [M+H]+): 295.2.

Example 174: N-(1-methylcyclopropyl)-2-(pyridazin-4-yl)pyrido[3,4-d]pyrimidin-4-amine

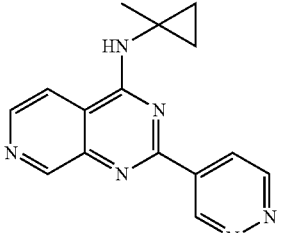

1H NMR (400 MHz, Methanol-d4) δ 10.19 (dd, J=2.1, 1.3 Hz, 1H), 9.39 (dd, J=5.3, 1.2 Hz, 1H), 9.20 (d, J=0.8 Hz, 1H), 8.70 (dd, J=5.3, 2.2 Hz, 1H), 8.57 (d, J=5.7 Hz, 1H), 8.01 (dd, J=5.7, 0.8 Hz, 1H), 1.64 (s, 3H), 1.04-0.98 (m, 2H), 0.97-0.91 (m, 2H). LCMS (m/z [M+H]⁺): 279.1.

Example 175: N-(1-methylcyclopropyl)-2-(1,3-oxazol-5-yl)pyrido[3,4-d]pyrimidin-4-amine

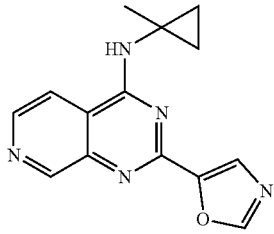 [SMILES: CC1(Nc2nc(-c3cnco3)nc3cnccc23)CC1]

1H NMR (400 MHz, Methanol-d4) δ 9.12 (s, 1H), 8.53 (d, J=5.7 Hz, 1H), 8.46 (s, 1H), 7.99-7.95 (m, 1H), 7.95 (s, 1H), 1.60 (s, 3H), 0.96 (m, 2H), 0.88 (m, 2H). LCMS (m/z [M+H]⁺): 268.1.

Example 176: N-(1-methylcyclopropyl)-2-(1H-pyrazol-5-yl)pyrido[3,4-d]pyrimidin-4-amine

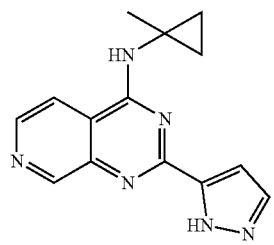 [SMILES: CC1(Nc2nc(-c3ccn[nH]3)nc3cnccc23)CC1]

1H NMR (400 MHz, Methanol-d4) δ 9.09 (d, J=0.8 Hz, 1H), 8.44 (s, 1H), 7.94 (dd, J=5.7, 0.8 Hz, 1H), 7.69 (d, J=2.1 Hz, 1H), 7.11 (d, J=2.1 Hz, 1H), 1.60 (s, 3H), 0.94 (m, 2H), 0.90-0.84 (m, 2H). LCMS (m/z [M+H]⁺): 267.1.

Example 177: 2-(1H-imidazol-5-yl)-N-(1-methylcyclopropyl)pyrido[3,4-d]pyrimidin-4-amine

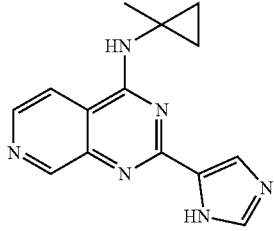 [SMILES: CC1(Nc2nc(-c3cnc[nH]3)nc3cnccc23)CC1]

1H NMR (400 MHz, Methanol-d4) δ 9.06 (s, 1H), 8.44 (d, J=5.7 Hz, 1H), 8.16 (s, 1H), 7.98-7.90 (m, 2H), 1.60 (s, 3H), 0.95 (m, 2H), 0.92-0.84 (m, 2H). LCMS (m/z [M+H]⁺): 267.1.

Example 178: 2-(1-methyl-1H-imidazol-5-yl)-N-(1-methylcyclopropyl)pyrido[3,4-d]pyrimidin-4-amine

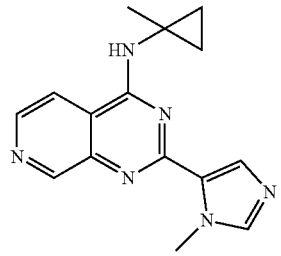 [SMILES: Cn1cncc1-c1nc(NC2(C)CC2)c2ccncc2n1]

1H NMR (400 MHz, Methanol-d4) δ 9.03 (s, 1H), 8.41 (d, J=5.7 Hz, 1H), 7.90 (dd, J=5.7, 0.8 Hz, 1H), 7.70 (d, J=0.8 Hz, 2H), 4.25 (s, 3H), 1.57 (s, 3H), 0.99-0.94 (m, 2H), 0.85-0.79 (m, 2H). LCMS (m/z [M+H]⁺): 281.1.

Example 179: N-(1-methylcyclopropyl)-2-{1H-pyrrolo[3,2-b]pyridin-1-yl}pyrido[3,4-d]pyrimidin-4-amine

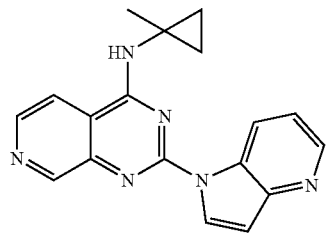 [SMILES: CC1(Nc2nc(-n3ccc4ncccc43)nc3cnccc23)CC1]

1H NMR (400 MHz, DMSO-d6) δ 9.69 (d, J=8.3 Hz, 1H), 9.39 (s, 1H), 9.18 (s, 1H), 8.88 (d, J=3.5 Hz, 1H), 8.72 (s, 1H), 8.58 (s, 1H), 8.18 (d, J=5.4 Hz, 1H), 7.71 (s, 1H), 7.10-7.02 (m, 1H), 1.59 (s, 3H), 0.99 (m, 2H), 0.98-0.95 (m, 2H). LCMS (m/z [M+H]⁺): 317.1.

Example 180: N-(1-methylcyclopropyl)-2-(1H-1,2,3-triazol-4-yl)pyrido[3,4-d]pyrimidin-4-amine

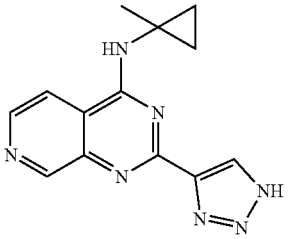 [SMILES: CC1(Nc2nc(-c3c[nH]nn3)nc3cnccc23)CC1]

1H NMR (400 MHz, DMSO-d6) δ 9.19 (s, 1H), 8.64 (d, J=5.0 Hz, 1H), 8.51 (s, 1H), 8.16 (d, J=5.5 Hz, 1H), 1.55 (s, 3H), 0.90 (m, 2H), 0.87 (m, 2H). LCMS (m/z [M+H]⁺): 268.1.

Example 181: 2-(3-methyl-1,2-oxazol-5-yl)-N-(1-methylcyclopropyl)pyrido[3,4-d]pyrimidin-4-amine

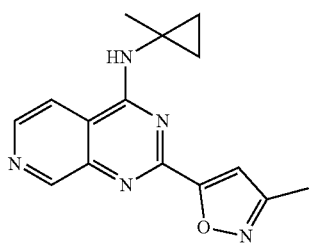 [SMILES: Cc1cc(-c2nc(NC3(C)CC3)c3ccncc3n2)on1]

1H NMR (400 MHz, Chloroform-d) δ 9.41 (s, 1H), 8.63 (d, J=5.6 Hz, 1H), 7.43 (d, J=5.6 Hz, 1H), 6.98 (s, 1H), 2.44 (s, 3H), 1.60 (s, 3H), 0.99-0.93 (m, 2H), 0.93-0.85 (m, 2H). LCMS (m/z [M+H]$^+$): 282.1.

Example 182: N-(1-methylcyclopropyl)-2-(2H-1,2,3,4-tetrazol-5-yl)pyrido[3,4-d]pyrimidin-4-amine

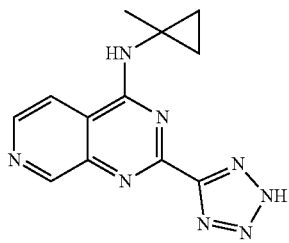 [SMILES: CC1(Nc2nc(-c3nn[nH]n3)nc3cnccc23)CC1]

1H NMR (400 MHz, DMSO-d6) δ 9.21 (s, 2H), 8.69 (s, 1H), 8.21 (d, J=5.2 Hz, 1H), 1.57 (s, 3H), 0.89 (m, 2H), 0.85 (m, 2H). LCMS (m/z [M+H]$^+$): 269.1.

Example 183: 2-(1H-pyrazol-4-yl)-N-[1-(pyridin-4-yl)ethyl]pyrido[3,4-d]pyrimidin-4-amine

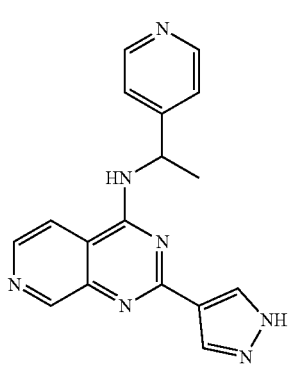 [SMILES: CC(Nc1nc(-c2cn[nH]c2)nc2cnccc12)c1ccncc1]

1H NMR (400 MHz, Methanol-d4) δ 9.17 (s, 1H), 8.75 (d, J=5.6 Hz, 3H), 8.37 (d, J=4.8 Hz, 1H), 8.32 (d, J=1.6 Hz, 2H), 8.14-8.09 (m, 2H), 5.89 (q, J=7.3 Hz, 1H), 1.84 (d, J=7.2 Hz, 3H). LCMS (m/z [M+H]$^+$): 318.1.

Example 184: N-tert-butyl-2-(1-methyl-1H-pyrazol-5-yl)pyrido[3,4-d]pyrimidin-4-amine

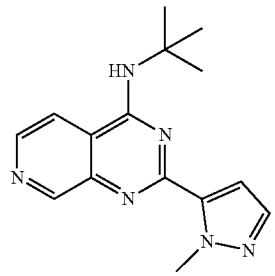 [SMILES: Cn1nccc1-c1nc(NC(C)(C)C)c2ccncc2n1]

1H NMR (400 MHz, DMSO-d6) δ 9.13 (d, J=2.5 Hz, 1H), 8.61 (d, J=5.6 Hz, 1H), 8.38 (t, J=5.2 Hz, 1H), 7.85 (d, J=7.9 Hz, 1H), 7.53 (d, J=1.9 Hz, 1H), 6.97 (d, J=1.9 Hz, 1H), 4.37 (s, 3H), 1.59 (s, 9H). LCMS (m/z [M+H]$^+$): 283.1.

Example 185: (1-{[2-(3-methyl-1H-pyrazol-4-yl)pyrido[3,4-d]pyrimidin-4-yl]amino}cyclobutyl)methanol

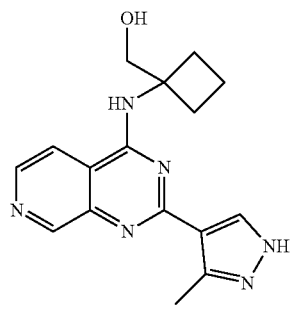 [SMILES: Cc1n[nH]cc1-c1nc(NC2(CO)CCC2)c2ccncc2n1]

1H NMR (400 MHz, DMSO-d6) δ 9.07 (s, 1H), 8.62 (s, 1H), 8.38 (d, J=5.6 Hz, 1H), 8.25-8.12 (m, 1H), 3.93 (s, 2H), 2.62 (s, 3H), 2.39 (t, J=7.8 Hz, 4H), 1.85 (dq, J=12.0, 8.4 Hz, 2H). LCMS (m/z [M+H]$^+$): 311.2.

Example 186: 2-(1-methyl-1H-pyrazol-5-yl)-N-(1-methylcyclobutyl)pyrido[3,4-d]pyrimidin-4-amine

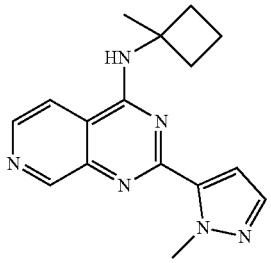 [SMILES: Cn1nccc1-c1nc(NC2(C)CCC2)c2ccncc2n1]

1H NMR (400 MHz, DMSO-d6) δ 9.12 (s, 1H), 8.78 (s, 1H), 8.62 (d, J=5.6 Hz, 1H), 8.31-8.24 (m, 1H), 7.53-7.46 (m, 1H), 6.97 (d, J=1.9 Hz, 1H), 4.38-4.31 (m, 3H), 2.48-2.41 (m, 2H), 2.22 (tt, J=8.4, 3.2 Hz, 2H), 1.98-1.78 (m, 2H), 1.65 (s, 3H). LCMS (m/z [M+H]$^+$): 295.2.

Example 187: (1-{[2-(1-methyl-1H-pyrazol-5-yl)pyrido[3,4-d]pyrimidin-4-yl]amino}cyclobutyl)methanol

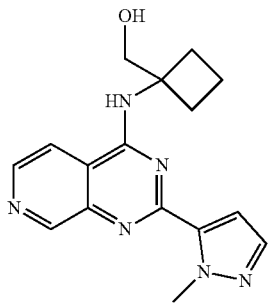 [SMILES: Cn1nccc1-c1nc(NC2(CO)CCC2)c2ccncc2n1]

1H NMR (400 MHz, DMSO-d6) δ 9.19-9.11 (m, 1H), 8.76 (s, 1H), 8.63 (d, J=5.7 Hz, 1H), 8.40 (dd, J=5.7, 0.7 Hz, 1H), 7.54-7.47 (m, 1H), 6.95 (d, J=1.9 Hz, 1H), 4.32 (s, 3H), 3.90 (s, 2H), 2.35 (t, J=7.2 Hz, 4H), 1.92-1.76 (m, 2H). LCMS (m/z [M+H]$^+$): 311.2.

Example 188: 2-(1H-pyrazol-4-yl)-N-[1-(trifluoromethyl)cyclopropyl]pyrido[3,4-d]pyrimidin-4-amine

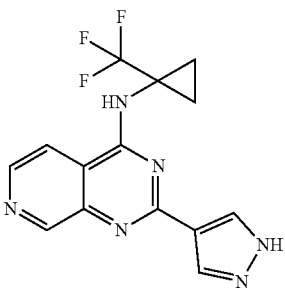 [SMILES: FC(F)(F)C1(Nc2nc(-c3cn[nH]c3)nc3cnccc23)CC1]

1H NMR (400 MHz, DMSO-d6) δ 9.21 (s, 1H), 9.10 (s, 1H), 8.56 (d, J=5.6 Hz, 1H), 8.27 (s, 2H), 8.16 (d, J=5.7 Hz, 1H), 1.61-1.53 (m, 2H), 1.33 (d, J=6.0 Hz, 2H). LCMS (m/z [M+H]$^+$): 321.1.

Example 189: 2-(1-methyl-1H-pyrazol-5-yl)-N-[1-(trifluoromethyl)cyclopropyl]pyrido[3,4-d]pyrimidin-4-amine

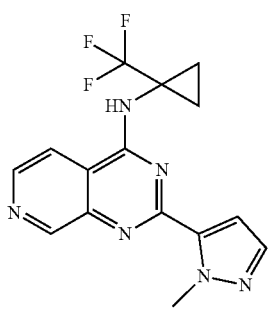 [SMILES: Cn1nccc1-c1nc(NC2(C(F)(F)F)CC2)c2ccncc2n1]

1H NMR (400 MHz, DMSO-d6) δ 9.32 (s, 1H), 9.19 (d, J=0.7 Hz, 1H), 8.65 (d, J=5.6 Hz, 1H), 8.23 (dd, J=5.7, 0.8 Hz, 1H), 7.58-7.47 (m, 1H), 7.07 (d, J=1.9 Hz, 1H), 4.37 (s, 3H), 1.64-1.49 (m, 2H), 1.37 (d, J=5.8 Hz, 2H). LCMS (m/z [M+H]$^+$): 335.1.

Example 190: 2-(3-methyl-1H-pyrazol-4-yl)-N-[1-(pyridin-4-yl)ethyl]pyrido[3,4-d]pyrimidin-4-amine

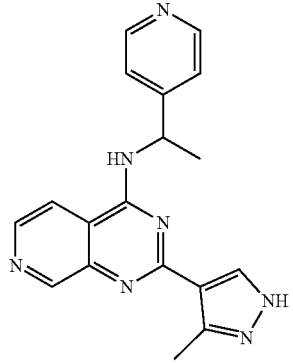 [SMILES: Cc1n[nH]cc1-c1nc(NC(C)c2ccncc2)c2ccncc2n1]

1H NMR (400 MHz, DMSO-d6) δ 9.00 (d, J=0.7 Hz, 1H), 8.77 (s, 1H), 8.54 (d, J=5.6 Hz, 1H), 8.51-8.47 (m, 2H), 8.30 (dd, J=5.6, 0.8 Hz, 1H), 7.99 (s, 1H), 7.50-7.40 (m, 2H), 5.54 (d, J=6.6 Hz, 1H), 2.48 (s, 3H), 1.63 (d, J=7.1 Hz, 3H). LCMS (m/z [M+H]$^+$): 332.2.

Example 191: (1-{[2-(1H-pyrazol-4-yl)pyrido[3,4-d]pyrimidin-4-yl]amino}cyclobutyl)methanol

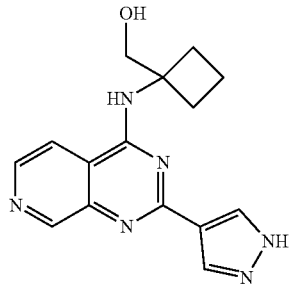 [SMILES: OCC1(Nc2nc(-c3cn[nH]c3)nc3cnccc23)CCC1]

1H NMR (400 MHz, DMSO-d6) δ9.11 (m, 2H), 8.69 (m, 2H), 8.39 (s, 2H), 3.92 (s, 2H), 2.39 (t, J=7.3 Hz, 4H), 1.87 (p, J=7.7, 6.6 Hz, 2H). LCMS (m/z [M+H]$^+$): 297.1.

Example 192: (1-{[2-(1H-pyrazol-4-yl)pyrido[3,4-d]pyrimidin-4-yl]amino}cyclopropyl)methanol

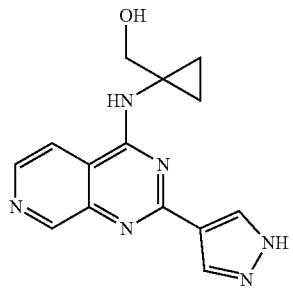 [SMILES: OCC1(Nc2nc(-c3cn[nH]c3)nc3cnccc23)CC1]

1H NMR (400 MHz, DMSO-d6) δ9.65 (s, 1H), 9.12 (s, 1H), 8.65 (d, J=5.4 Hz, 1H), 8.41 (s, 2H), 8.26 (d, J=5.5 Hz, 1H), 3.73 (m, 2H), 1.06-0.96 (m, 2H), 0.94-0.77 (m, 2H). LCMS (m/z [M+H]+): 283.1.

Example 193: 2-(1-methyl-1H-pyrazol-5-yl)-N-[1-(pyridin-4-yl)ethyl]pyrido[3,4-d]pyrimidin-4-amine

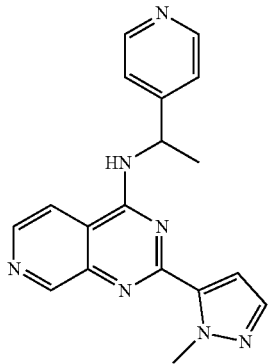 [SMILES: CC(Nc1nc(-c2ccnn2C)nc2cnccc12)c1ccncc1]

1H NMR (400 MHz, DMSO-d6) δ 8.37 (s, 1H), 7.93 (d, J=6.4 Hz, 2H), 7.85 (d, J=5.7 Hz, 1H), 7.51 (d, J=5.7 Hz, 1H), 7.31 (d, J=6.6 Hz, 2H), 6.63 (d, J=2.0 Hz, 1H), 6.01 (d, J=2.0 Hz, 1H), 4.89 (q, J=7.2 Hz, 1H), 3.43 (s, 3H), 1.00 (d, J=7.2 Hz, 3H). LCMS (m/z [M+H]+): 332.2.

Example 194: N-(1-methylcyclopropyl)-2-(1H-pyrazol-4-yl)pyrido[3,4-d]pyrimidin-4-amine

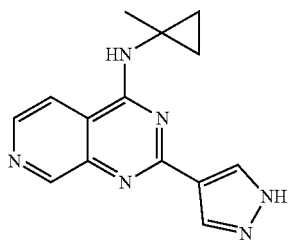 [SMILES: CC1(Nc2nc(-c3cn[nH]c3)nc3cnccc23)CC1]

1HNMR (400 MHz, CD3OD) d 9.03 (d, J=0.8 Hz, 1H), 8.43 (d, J=5.6 Hz, 1H), 8.24 (d, J=0.8 Hz, 1H), 8.20 (s, 1H), 7.93 (dd, J=5.6, 0.8 Hz, 1H), 1.61 (s, 3H), 0.99-0.95 (m, 2H), 0.90-0.85 (m, 2H). LCMS (m/z [M+H]+): 267.1.

Example 195: 2-(1-ethyl-1H-pyrazol-4-yl)-N-(2-methylpropyl)pyrido[3,4-d]pyrimidin-4-amine

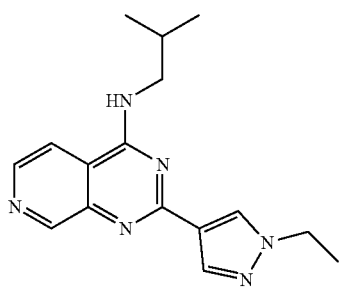 [SMILES: CCn1cc(-c2nc(NCC(C)C)c3ccncc3n2)cn1]

1HNMR (400 MHz, CDCl3) δ 9.20 (s, 1H), 8.50 (d, J=5.6 Hz, 1H), 8.24 (s, 1H), 8.20 (s, 1H), 7.43 (d, J=5.6 Hz, 1H), 5.87 (br s, 1H), 4.25 (q, J=7.2 Hz, 2H), 3.58 (dd, J=6.8, 6.0 Hz, 2H), 2.11 (nonet, J=6.8 Hz, 1H), 1.56 (t, J=7.2 Hz, 3H), 1.06 (d, J=6.8 Hz, 6H). LCMS (m/z [M+H]+): 297.2.

Example 196: 2-(1-methyl-1H-pyrazol-4-yl)-N-(1-methylcyclopropyl)pyrido[3,4-d]pyrimidin-4-amine

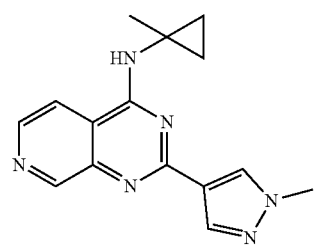 [SMILES: Cn1cc(-c2nc(NC3(C)CC3)c3ccncc3n2)cn1]

1HNMR (400 MHz, DMSO-d6) δ 8.99 (s, 1H), 8.72 (s, 1H), 8.46 (d, J=5.6 Hz, 1H), 8.33 (s, 1H), 8.05 (s, 1H), 8.03 (d, J=5.6 Hz, 1H), 3.93 (s, 3H), 1.54 (s, 3H), 0.90-0.80 (m, 4H). LCMS (m/z [M+H]+): 281.1.

Example 197: N-(1-amino-2-methylpropan-2-yl)-2-(1H-pyrazol-4-yl)pyrido[3,4-d]pyrimidin-4-amine

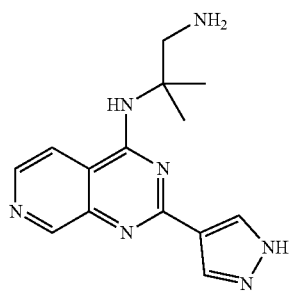 [SMILES: CC(C)(CN)Nc1nc(-c2cn[nH]c2)nc2cnccc12]

1H NMR (400 MHz, DMSO-d6) δ 9.05 (s, 1H), 8.56 (d, J=5.4 Hz, 1H), 8.32 (d, J=5.6 Hz, 1H), 8.28 (m, 1H), 7.76 (m, 3H), 3.63 (d, J=5.9 Hz, 2H), 1.59 (s, 6H). LCMS (M/Z [M+H]+): 284.2.

Example 198: 8-chloro-N-(1-methylcyclopropyl)-2-(pyridin-4-yl)pyrido[3,4-d]pyrimidin-4-amine

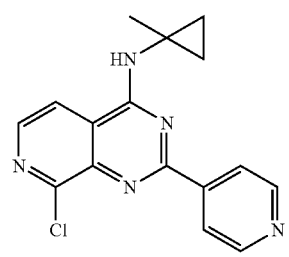 [SMILES: CC1(Nc2nc(-c3ccncc3)nc3c(Cl)nccc23)CC1]

Title compound was prepared from 4-chloro-2-(pyridin-4-yl)pyrido[3,4-d]pyrimidine (intermediate 3c) as in Scheme 3 using the procedure in Example 1 with 1-methylcyclopropanamine. 1H NMR (400 MHz, Methanol-d4) δ 8.78-8.66 (m, 2H), 8.61-8.49 (m, 2H), 8.30 (d, J=5.6 Hz, 1H), 7.94 (d, J=5.6 Hz, 1H), 1.63 (s, 3H), 1.04-0.96 (m, 2H), 0.95-0.86 (m, 2H). LCMS (m/z [M+H]⁺): 312.1.

Example 199: 8-methyl-N-(1-methylcyclopropyl)-2-(pyridin-4-yl)pyrido[3,4-d]pyrimidin-4-amine

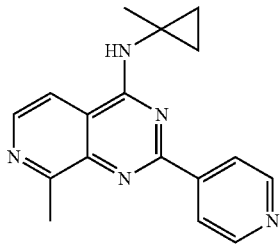 [SMILES: Cc1nccc2c(NC3(C)CC3)nc(-c3ccncc3)nc12]

Title compound was prepared from Example 198 using the procedure for intermediate 6b with 2,4,6-trimethyl-1,3,5,2,4,6-trioxatriborinane instead of 4-pyridine boronic acid. 1H NMR (500 MHz, DMSO-d6) δ 8.79 (d, J=5.1 Hz, 2H), 8.44 (d, J=5.6 Hz, 1H), 8.41 (d, J=5.0 Hz, 2H), 7.98 (dd, J=5.8, 0.8 Hz, 1H), 2.91 (s, 3H), 1.57 (s, 3H), 0.97-0.75 (m, 4H). LCMS (m/z [M+H]⁺): 292.2.

Example 251: N-(tert-butyl)-5-chloro-2-(pyridin-4-yl)pyrido[3,4-d]pyrimidin-4-amine

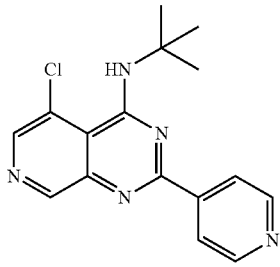 [SMILES: CC(C)(C)Nc1nc(-c2ccncc2)nc2cncc(Cl)c12]

Title compound was prepared from 4,5-dichloro-2-(pyridin-4-yl)pyrido[3,4-d]pyrimidine (intermediate 5d) as in Scheme 5 using Step C of Example 1 with tert-butyl amine. 1H NMR (400 MHz, Methanol-d4) δ 9.07 (s, 1H), 8.73 (s, 2H), 8.55 (s, 1H), 8.46-8.39 (m, 2H), 1.72 (s, 9H). LCMS (M/Z [M+H]⁺): 314.1.

Example 252: 5-chloro-N-(1-methylcyclopropyl)-2-(pyridin-4-yl)pyrido[3,4-d]pyrimidin-4-amine

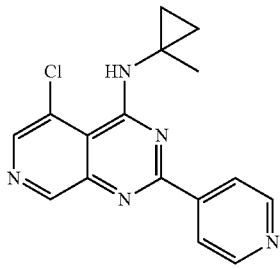 [SMILES: CC1(Nc2nc(-c3ccncc3)nc3cncc(Cl)c23)CC1]

Title compound was prepared as Example 251 using 4,5-dichloro-2-(pyridin-4-yl)pyrido[3,4-d]pyrimidine (intermediate 5d) and 1-methylcyclopropan-1-amine. 1HNMR (400 MHz, CDCl₃) δ 9.18 (s, 1H), 8.81 (br s, 2H), 8.50 (s, 1H), 8.42 (d, J=4.8 Hz, 2H), 8.00 (br s, 1H), 1.64 (s, 3H), 1.00-0.90 (m, 4H). LCMS (M/Z [M+H]⁺): 312.1.

Example 253: 5-chloro-N-(1-methylcyclopropyl)-2-(pyridin-4-yl)pyrido[3,4-d]pyrimidin-4-amine

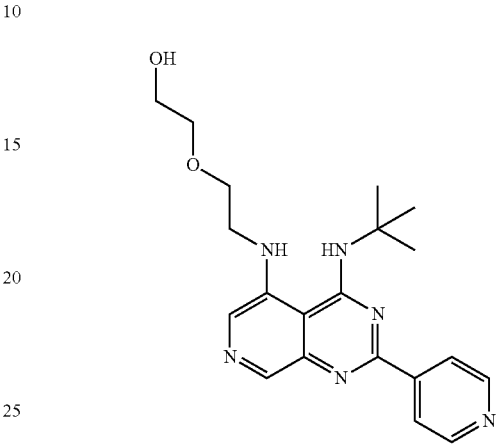

N-(tert-butyl)-5-chloro-2-(pyridin-4-yl)pyrido[3,4-d]pyrimidin-4-amine (Example 251, 10 mg, 0.032 mmol) and 2-(2-aminoethoxy)ethanol (670 mg, 6.37 mmol) were dissolved in NMP (1 mL) in a 2 ml microwave reactor. The reaction was heated at 160° C. for 1 hr (microwave irradiation). The reaction was cooled to rt and was diluted with water (20 ml), extracted with EtOAc (3×20 mL). The combined organic layers were dried over Na₂SO₄, filtered and evaporated. The residue was purified by mass-triggered HPLC to afford title compound (40%). 1H NMR (400 MHz, Methanol-d4) δ 8.63 (s, 1H), 8.23 (d, J=5.7 Hz, 2H), 8.18 (d, J=5.7 Hz, 2H), 8.08 (s, 1H), 3.4-3.8 (m, 8H), 1.72 (s, 9H). LCMS (M/Z [M+H]⁺): 383.2.

Example 254: N-(4-methoxy-2-methylbutan-2-yl)-2-(pyridin-4-yl)-1,7-naphthyridin-4-amine

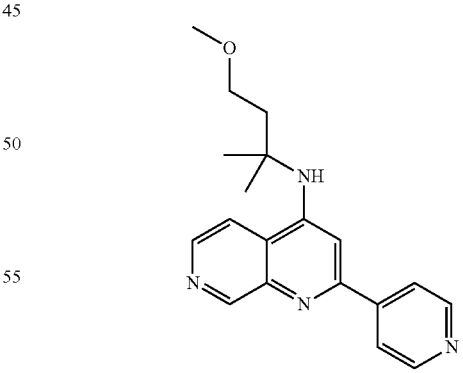

Title compound was prepared from 4-chloro-2-(pyridin-4-yl)-1,7-naphthyridine (intermediate 6b) using Step B as in Scheme 6.

Step B

In a 20 ml vial was added triethylamine (0.044 mL, 0.25 mmol), potassium fluoride (7.2 mg, 0.124 mmol), 4-chloro- 2-(pyridin-4-yl)-1,7-naphthyridine (intermediate 6b, 30 mg, 0.124 mmol), and 4-methoxy-2-methylbutan-2-amine (16 mg, 0.137 mmol) in DMSO (1 mL) to give a yellow suspension. The reaction mixture was stirred at 130° C. for 24 hrs. Solvent was evaporated under air flow. The residue was purified by flash chromatography on a COMBI-FLASH® system (ISCO) using 0-10% MeOH/DCM to give the title compound (21%). 1H NMR (400 MHz, DMSO-d6) δ 9.20 (d, J=0.7 Hz, 1H), 8.71 (m, 2H), 8.48 (d, J=5.8 Hz, 1H), 8.09 (ddd, J=12.9, 5.2, 1.3 Hz, 2H), 8.05 (m, 1H), 7.26 (s, 1H), 6.81 (s, 1H), 3.50 (t, J=6.5 Hz, 2H), 3.22 (s, 3H), 2.11 (t, J=6.5 Hz, 2H), 1.52 (s, 6H). LCMS (M/Z [M+H]+): 323.2.

Examples 255-268

These compounds were synthesized according to the protocol described for Example 1 using 4-chloro-2-(pyridin-4-yl)-1,7-naphthyridine (intermediate 6b) and various amines respectively except specially stated.

Example 255: N-[2-methyl-1-(propan-2-yloxy)propan-2-yl]-2-(pyridin-4-yl)-1,7-naphthyridin-4-amine

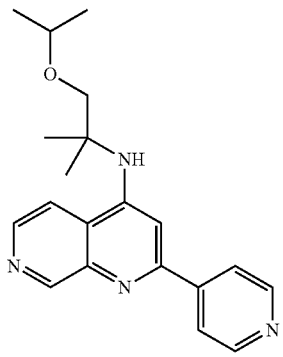 [SMILES: CC(C)OCC(C)(C)Nc1cc(-c2ccncc2)nc2cnccc12]

1H NMR (400 MHz, DMSO-d6) δ 9.18 (dd, J=7.4, 0.9 Hz, 1H), 8.80 (m, 2H), 8.64 (d, J=5.6 Hz, 1H), 8.39 (dd, J=5.7, 0.9 Hz, 1H), 8.29 (d, J=6.1 Hz, 2H), 7.70 (s, 1H), 3.90 (s, 2H), 3.55-3.50 (m, 1H), 1.61 (s, 6H), 1.00 (s, 6H). LCMS (M/Z [M+H]+): 337.2.

Example 256: N-[(2S)-butan-2-yl]-2-(pyridin-4-yl)-1,7-naphthyridin-4-amine

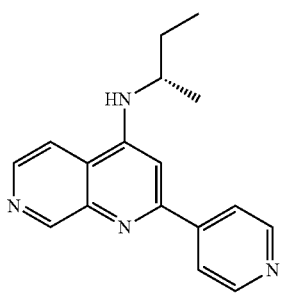 [SMILES: CC[C@H](C)Nc1cc(-c2ccncc2)nc2cnccc12]

1H NMR (400 MHz, DMSO-d6) δ 9.21 (d, J=7.4, 0.9 Hz, 1H), 8.73 (m, 2H), 8.49 (m, 1H), 8.29 (d, J=6.1 Hz, 1H), 8.20 (m, 2H), 7.24 (s, 1H), 7.19 (d, J=0.9 Hz, 1H), 4.02-3.99 (m, 1H), 1.79-1.75 (m, 1H), 1.69-1.65 (m, 1H), 1.29 (m, 3H), 0.09 (t, J=4.9 Hz, 3H). LCMS (M/Z [M+H]+): 279.1.

Example 257: N-[(2R)-butan-2-yl]-2-(pyridin-4-yl)-1,7-naphthyridin-4-amine

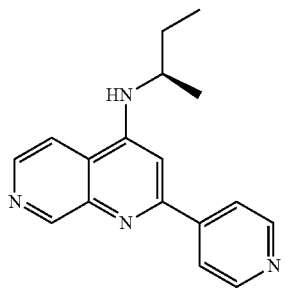 [SMILES: CC[C@@H](C)Nc1cc(-c2ccncc2)nc2cnccc12]

1H NMR (400 MHz, DMSO-d6) δ 9.21 (d, J=0.8 Hz, 1H), 8.73 (m, 2H), 8.49 (d, J=5.8 Hz, 1H), 8.29 (dd, J=5.9, 0.9 Hz, 1H), 8.20 (m, 2H), 7.24 (s, 1H), 7.19 (d, J=8.3 Hz, 1H), 4.02-3.99 (dt, J=13.6, 6.5 Hz, 1H), 1.79-1.75 (dq, J=14.4, 7.2 Hz, 1H), 1.69-1.65 (m, 1H), 1.29 (d, J=6.4 Hz, 3H), 0.09 (t, J=7.4 Hz, 3H). LCMS (M/Z [M+H]+): 279.3.

Example 258: N-(1-methoxy-2-methylpropan-2-yl)-2-(pyridin-4-yl)-1,7-naphthyridin-4-amine

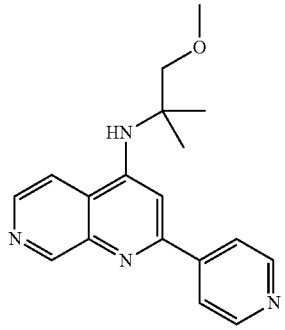 [SMILES: COCC(C)(C)Nc1cc(-c2ccncc2)nc2cnccc12]

1H NMR (400 MHz, DMSO-d6) δ 9.25 (dd, J=6.6, 0.8 Hz, 1H), 8.77 (m, 2H), 8.75 (s, 1H), 8.24 (dt, J=4.5, 1.9 Hz, 2H), 8.21 (s, 1H), 8.11 (m, 1H), 7.52 (s, 1H), 3.62 (s, 2H), 3.34 (s, 3H), 1.52 (s, 6H). LCMS (M/Z [M+H]+): 309.4.

Example 259: N-methyl-N-(propan-2-yl)-2-(pyridin-4-yl)-1,7-naphthyridin-4-amine

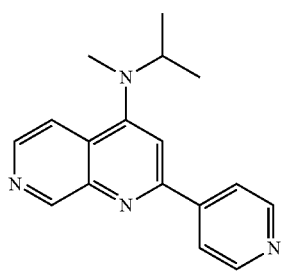 [SMILES: CC(C)N(C)c1cc(-c2ccncc2)nc2cnccc12]

1H NMR (400 MHz, DMSO-d6) δ 9.34 (dd, J=5.2, 0.9 Hz, 1H), 8.77 (ddd, J=6.2, 4.4, 1.7 Hz, 2H), 8.50 (dd, J=6.5, 5.8 Hz, 1H), 8.20 (m, 2H), 7.80 (s, 1H), 7.58 (s, 1H), 4.20-4.14 (m, 1H), 2.97 (s, 3H), 1.25 (s, 6H). LCMS (M/Z [M+H]+): 279.4.

Example 260: 3-methyl-3-{[2-(pyridin-4-yl)-1,7-naphthyridin-4-yl]amino}butan-1-ol

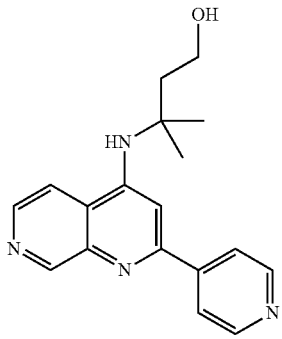 [SMILES: CC(C)(CCO)Nc1cc(-c2ccncc2)nc2cnccc12]

1H NMR (400 MHz, DMSO-d6) δ 9.40 (d, J=0.9 Hz, 1H), 8.79 (m, 2H), 8.60 (d, J=5.6 Hz, 1H), 8.26 (m, 2H), 7.95 (dd, J=5.6, 1.0 Hz, 1H), 7.89 (s, 1H), 4.55 (t, J=6.8 Hz, 2H), 4.08-4.04 (q, J=5.2 Hz, 1H), 1.95 (t, J=6.9 Hz, 2H), 1.14 (s, 6H). LCMS (M/Z [M+H]+): 309.3.

Example 261: N-(tert-butyl)-2-(pyridin-4-yl)-1,7-naphthyridin-4-amine

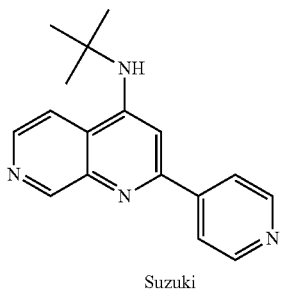

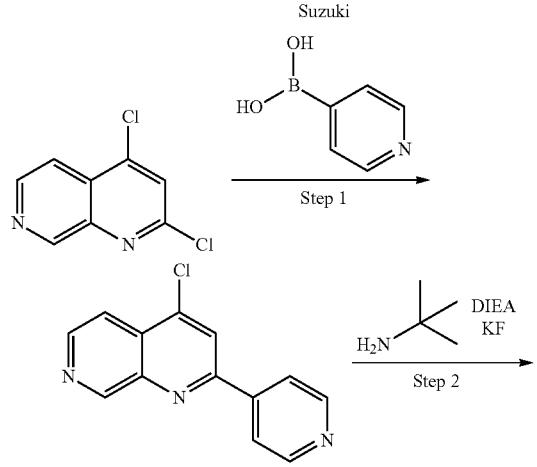

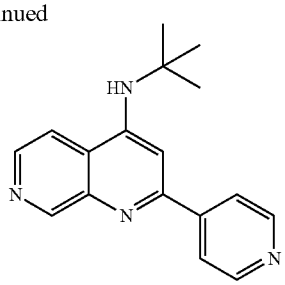

Step 1

In a 20 mL microwave reactor was added PalladiumTetrakis (58.1 mg, 0.050 mmol), potassium carbonate (1.256 mL, 2.51 mmol), and 2,4-dichloro-1,7-naphthyridine (200 mg, 1.005 mmol) and pyridin-4-ylboronic acid (130 mg, 1.055 mmol) in Acetonitrile (Volume: 2 mL) to give an orange suspension. The reaction mixture was stirred at 120° C. for 60 min under microwave. The crude mixture was diluted with DCM, H₂O, separated and extracted with DCM×3. Combined the organic layers and dried Na₂SO₄, filtered and concentrated. The residue was purified by flash chromatography on a COMBIFLASH® system (ISCO) using 0-10% MeOH/DCM to give the product (62%). 1H NMR (400 MHz, DMSO-d6) δ 9.58 (d, J=0.9 Hz, 1H), 8.85-8.78 (m, 4H), 8.32-8.29 (m, 2H), 8.11 (dd, J=5.8, 0.9 Hz, 1H). LCMS [M+H]=242.

Step 2

In a 40 ml vial was added potassium fluoride (11.54 mg, 0.199 mmol), 4-chloro-2-(pyridin-4-yl)-1,7-naphthyridine (40 mg, 0.166 mmol), and 2-methylpropan-2-amine (0.035 mL, 0.331 mmol) in DMSO (Volume: 2 mL) to give a yellow suspension. The reaction mixture was stirred at 130° C. for 24 hrs. Solvent was evaporated under air flow. The residue was purified by flash chromatography on a COMBIFLASH® system (ISCO) using 0-10% MeOH/DCM to give the product (82%). 1H NMR (400 MHz, DMSO-d6) δ 9.22 (d, J=0.7 Hz, 1H), 8.78-8.72 (m, 2H), 8.48 (d, J=5.8 Hz, 1H), 8.30 (dd, J=6.0, 0.9 Hz, 1H), 8.15-8.06 (m, 2H), 7.28 (s, 1H), 6.73 (s, 1H), 1.56 (s, 9H). LCMS [M+H]=279.2.

Example 262: 2,2-dimethyl-1-[2-(pyridin-4-yl)-1,7-naphthyridin-4-yl]piperidin-4-ol

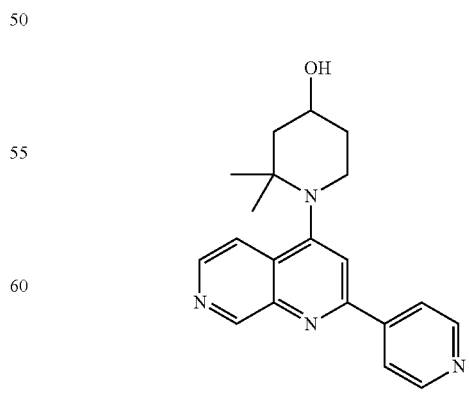

1H NMR (400 MHz, Acetone-d6) δ 9.41 (d, J=0.9 Hz, 1H), 8.80-8.75 (m, 2H), 8.60 (d, J=5.7 Hz, 1H), 8.23-8.20

(m, 2H), 8.18-8.14 (m, 1H), 8.11 (s, 1H), 4.15-3.99 (m, 1H), 3.52 (d, J=16.1 Hz, 1H), 3.16 (s, 1H), 1.86-1.68 (m, 2H), 1.46 (d, J=16.0 Hz, 3H), 1.16-1.00 (m, 3H), 0.87 (d, J=6.8 Hz, 2H). LCMS (M/Z [M+H]⁺): 335.2.

Example 263: 2,4-dimethyl-4-{[2-(pyridin-4-yl)-1,7-naphthyridin-4-yl]amino}pentan-2-ol

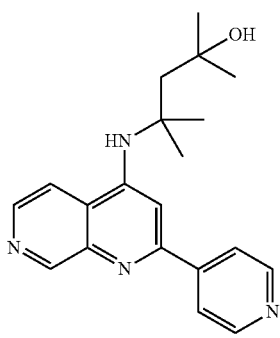

1H NMR (400 MHz, Acetone-d6) δ 9.22 (d, J=0.8 Hz, 1H), 8.78-8.67 (m, 2H), 8.63 (s, 1H), 8.40 (d, J=5.8 Hz, 1H), 8.19-8.09 (m, 2H), 7.81 (dd, J=5.9, 0.9 Hz, 1H), 7.36 (s, 1H), 2.08 (s, 2H), 1.75 (s, 6H), 1.47 (d, J=0.7 Hz, 6H). LCMS (M/Z [M+H]⁺): 337.2.

Example 264: N-cyclopentyl-2-(pyridin-4-yl)-1,7-naphthyridin-4-amine

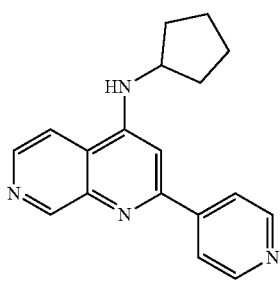 [SMILES: c1cc(-c2cc(NC3CCCC3)c3ccncc3n2)ccn1]

1H NMR (400 MHz, Acetone-d6) δ 9.26 (d, J=0.9 Hz, 1H), 8.77-8.66 (m, 2H), 8.44 (d, J=5.8 Hz, 1H), 8.23-8.15 (m, 2H), 8.06 (dd, J=5.8, 0.9 Hz, 1H), 7.34 (s, 1H), 6.70 (d, J=6.6 Hz, 1H), 4.40-4.25 (m, 1H), 2.29-2.19 (m, 2H), 1.86-1.68 (m, 6H). LCMS (M/Z [M+H]⁺): 279.1.

Example 265: dimethyl(3-methyl-3-{[2-(pyridin-4-yl)-1,7-naphthyridin-4-yl]amino}butyl)amine

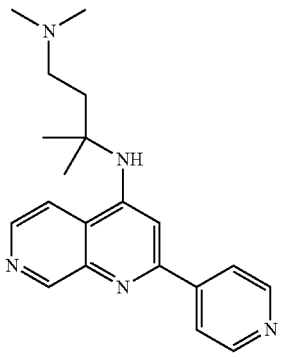 [SMILES: CN(C)CCC(C)(C)Nc1cc(-c2ccncc2)nc2cnccc12]

1H NMR (500 MHz, Methanol-d4) δ 9.40 (s, 1H), 8.91 (s, 2H), 8.62 (d, J=3.5 Hz, 1H), 8.48 (s, 2H), 8.40 (d, J=6.0 Hz, 1H), 7.46 (d, J=2.8 Hz, 1H), 3.28-3.23 (m, 2H), 2.92-2.81 (m, 6H), 2.48 (dd, J=8.3, 5.1 Hz, 2H), 1.71 (d, J=2.7 Hz, 6H). LCMS (M/Z [M+H]⁺): 336.2.

Example 266: N,N-diethyl-2-(pyridin-4-yl)-1,7-naphthyridin-4-amine

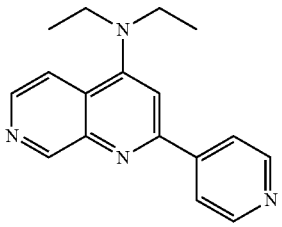 [SMILES: CCN(CC)c1cc(-c2ccncc2)nc2cnccc12]

1H NMR (400 MHz, Acetone-d6) δ 9.35 (d, J=0.9 Hz, 1H), 8.78-8.74 (m, 2H), 8.51 (d, J=5.8 Hz, 1H), 8.23-8.19 (m, 2H), 7.90 (dd, J=5.8, 0.9 Hz, 1H), 7.69 (s, 1H), 3.62 (q, J=7.1 Hz, 4H), 1.29 (t, J=7.1 Hz, 6H). LCMS (M/Z [M+H]⁺): 279.2.

Example 267: 2-methyl-1-(2-methyl-2-{[2-(pyridin-4-yl)-1,7-naphthyridin-4-yl]amino}propoxy)propan-2-ol

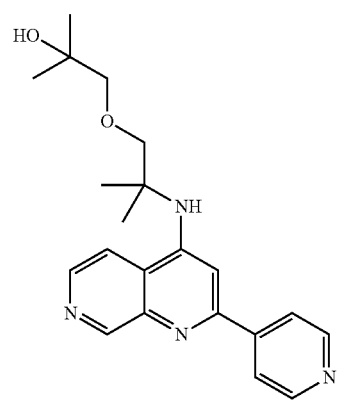 [SMILES: CC(C)(O)COCC(C)(C)Nc1cc(-c2ccncc2)nc2cnccc12]

1H NMR (500 MHz, Methanol-d4) δ 9.25 (s, 1H), 8.73 (d, J=5.2 Hz, 2H), 8.45 (d, J=5.9 Hz, 1H), 8.14-8.08 (m, 3H), 7.40 (s, 1H), 3.73 (s, 2H), 3.39 (s, 2H), 1.63 (s, 6H), 1.18 (s, 6H). LCMS (M/Z [M+H]⁺): 367.2.

Example 268: N-propyl-2-(pyridin-4-yl)-1,7-naphthyridin-4-amine

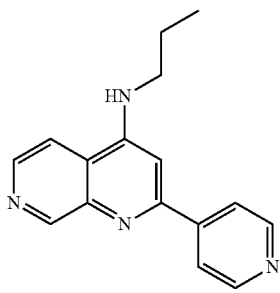 [SMILES: CCCNc1cc(-c2ccncc2)nc2cnccc12]

1H NMR (400 MHz, DMSO-d6) δ 9.22 (d, J=0.8 Hz, 1H), 8.77-8.70 (m, 2H), 8.48 (d, J=5.8 Hz, 1H), 8.22-8.16 (m, 3H), 7.60 (t, J=5.5 Hz, 1H), 7.21 (s, 1H), 3.43 (ddd, J=7.6, 6.6, 5.5 Hz, 2H), 1.79-1.67 (m, 2H), 1.01 (t, J=7.4 Hz, 3H). LCMS (M/Z [M+H]⁺): 265.1.

Example 269: N-tert-butyl-2-(3-methyl-1H-pyrazol-4-yl)-1,7-naphthyridin-4-amine

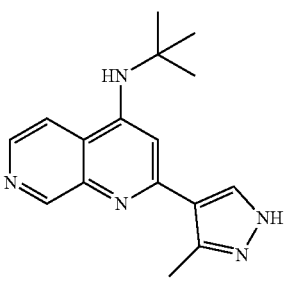 [SMILES: Cc1n[nH]cc1-c1cc(NC(C)(C)C)c2ccncc2n1]

Title compound was prepared from 2,4-dichloro-1,7-naphthyridine (intermediate 6a') as in Scheme 6 using tert-butyl 3-methyl-4-(4,4,5,5-tetramethyl-1,3,2-dioxaborolan-2-yl)-1H-pyrazole-1-carboxylate and tert-butyl amine. 1H NMR (400 MHz, DMSO-d6) 12.81 (s, 1H), 9.00 (d, J=0.7 Hz, 1H), 8.31 (d, J=5.8 Hz, 1H), 8.14 (dd, J=5.9, 0.8 Hz, 1H), 8.00 (s, 1H), 6.97 (s, 1H), 6.36 (s, 1H), 2.65 (s, 3H), 1.51 (s, 9H). LCMS (M/Z [M+H]⁺): 282.4.

Example 270: N-tert-butyl-2-(pyrimidin-4-yl)-1,7-naphthyridin-4-amine

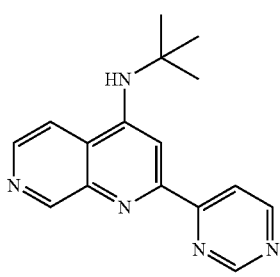

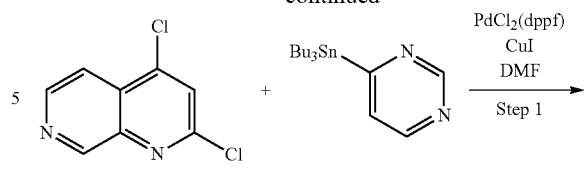

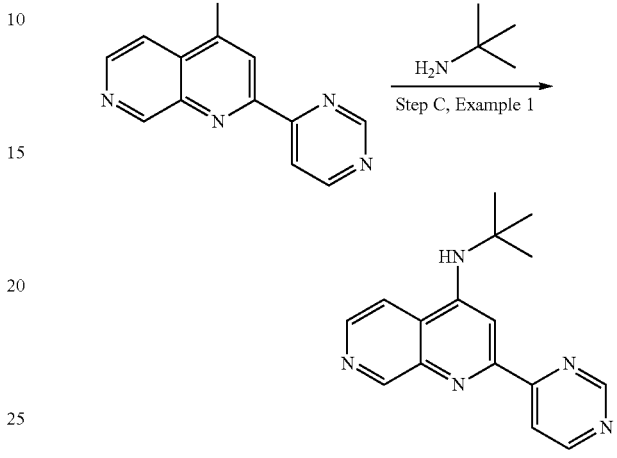

Step 1

2,4-dichloro-1,7-naphthyridine (6a, 100 mg, 0.502 mmol) was stirred in dry DMF at room temperature. 4-(tributylstannyl)pyrimidine (165 uL, 0.502 mmol) was added then 41 mg of PdCl₂(dppf).CH₂Cl₂ adduct (41 mg, 0.05 mmol, orange solid) and finally CuI (10 mg, 0.05 mmol, beige solid). The reaction was stirred for 1 hour at 130° C. The reaction was then concentrated and purified by flash chromatography on a COMBIFLASH® system (ISCO) using 0-10% MeOH/DCM to afford the product 4-chloro-2-(pyrimidin-4-yl)-1,7-naphthyridine (30%). LCMS (m/z [M+H]⁺): 243.6.

Title compound: was then prepared with 4-chloro-2-(pyrimidin-4-yl)-1,7-naphthyridine using the procedure detailed in Step C, Example 1.

1H NMR (400 MHz, DMSO-d6) δ 9.48 (d, J=1.4 Hz, 1H), 9.25 (d, J=0.8 Hz, 1H), 9.00 (d, J=5.3 Hz, 1H), 8.54 (m, 1H), 8.50 (m, 1H), 8.31 (dd, J=6.1, 0.9 Hz, 1H), 8.01 (s, 1H), 6.80 (s, 1H), 1.56 (s, 9H). LCMS (M/Z [M+H]+): 280.3.

Example 271: 2-(2-aminopyrimidin-4-yl)-N-tert-butyl-1,7-naphthyridin-4-amine

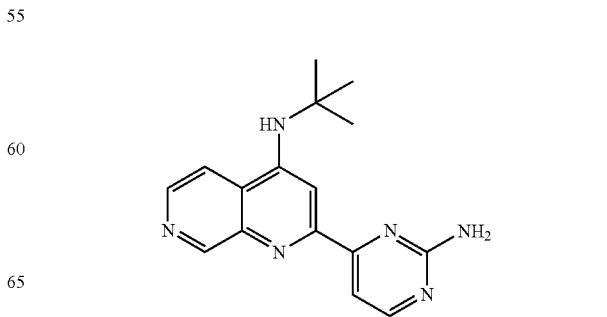

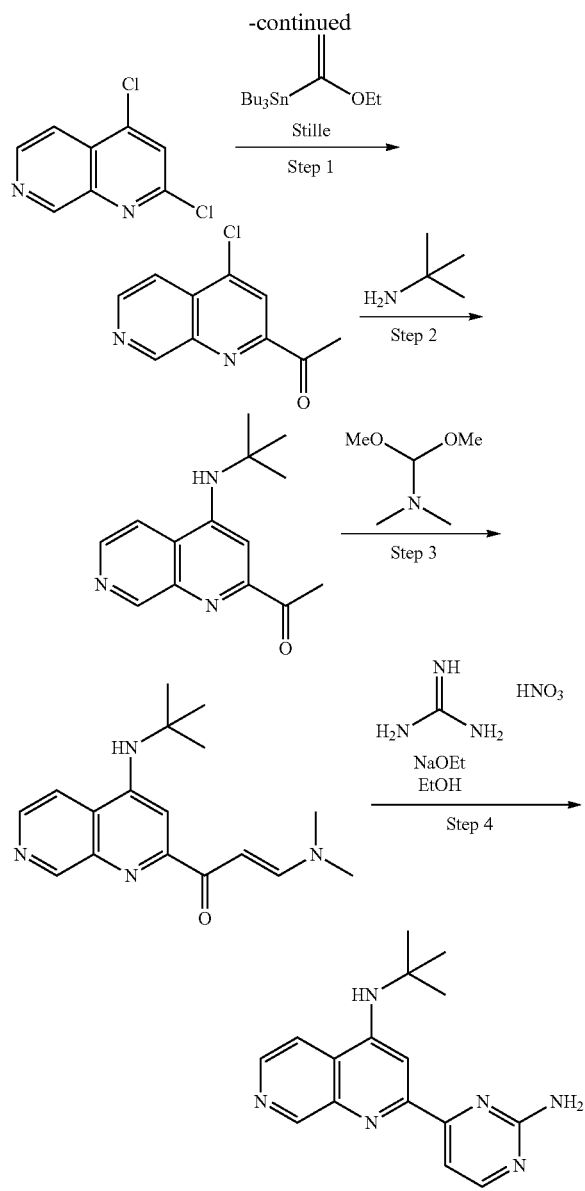

Step 1

2,4-dichloro-1,7-naphthyridine (6a', 400 mg, 2 mmol), Pd2(dba)3 (58 mg, 0.1 mmol) and PPh₃ (53 mg, 0.2 mmol) were stirred in 3 mL of toluene at room temperature for 15 minutes. 680 microlitre of tributyl(1-ethoxyvinyl)stannane (680 microlitre, 2 mmol) in 1.5 mL of toluene was then added and the reaction stirred at 110° C. for 1 hour. The reaction was cooled to room temperature. 4 mL of 1N HCl was added and the mixture stirred overnight. The reaction was then neutralized with NaOH and extracted with ether. The crude residue was then purified by flash chromatography on a COMBIFLASH® system (ISCO) using 0-70% EtOAc/Hexane to afford the product 1-(4-chloro-1,7-naphthyridin-2-yl)ethanone (40%). LCMS (m/z [M+H]+): 207.5.

Step 2

1-(4-chloro-1,7-naphthyridin-2-yl)ethanone (38 mg, 0.18 mmol) was stirred in DMF (2 mL) at room temperature and degassed with N₂. TEA (37 microlitre, 0.27 mmol) was added and stirred for 5 minutes then 14 mg of KF (14 mg, 0.27 mmol). This mixture was stirred at room temperature for 15 minutes then 2-methylpropan-2-amine (28 microlitre, 0.27 mmol) was added and degassed then stirred at 80° C. for two hrs. The reaction was then concentrated and purified by flash chromatography on a COMBIFLASH® system (ISCO) using 0-100% EtOAc/Hexane to afford the product 1-(4-(tert-butylamino)-1,7-naphthyridin-2-yl)ethanone (60%). LCMS (m/z [M+H]+): 244.3.

Step 3

1-(4-(tert-butylamino)-1,7-naphthyridin-2-yl)ethanone (25 mg, 0.1 mmol) was stirred in 0.8 mL of DMF/DMA at 110° C. for 6 hrs. The reaction was then concentrated and purified by flash chromatography on a COMBIFLASH® system (ISCO) using 0-100% EtOAc/Hexane to afford the product (E)-1-(4-(tert-butylamino)-1,7-naphthyridin-2-yl)-3-(dimethylamino)prop-2-en-1-one (30%). LCMS (m/z [M+H]$^+$): 299.4.

Step 4

(E)-1-(4-(tert-butylamino)-1,7-naphthyridin-2-yl)-3-(dimethylamino)prop-2-en-1-one (8 mg, 0.027 mmol) was stirred in EtOH (0.7 mL) at room temperature. Guanidine nitrate (4 mg, 0.034 mmol) was added and the reaction stirred at 100° C. for 20 minutes. Sodium ethoxide (in EtOH, 20 microlitre, 0.054 mmol) was then added and stirred at reflux overnight. Reaction was then concentrated and purified by flash chromatography on a COMBIFLASH® system (ISCO) using 0-20% MeOH/DCM to afford the title compound (30%). 1H NMR (400 MHz, DMSO-d6) δ 9.20 (d, J=0.8 Hz, 1H), 8.48 (m, 1H), 8.41 (m, 1H), 8.29 (dd, J=6.0, 0.9 Hz, 1H), 7.91 (s, 1H), 7.62 (d, J=5.0 Hz, 1H), 6.74 (s, 2H), 6.65 (s, 1H), 1.56 (s, 9H). LCMS (M/Z [M+H]+): 295.4.

Examples 272-274

These compounds were synthesized according to the protocol used for the preparation of Example 269 with 2,4-dichloro-1,7-naphthyridine (6a') and various boronic acids or esters respectively.

Example 272: N-tert-butyl-2-{1H-pyrrolo[2,3-b]pyridin-4-yl}-1,7-naphthyridin-4-amine

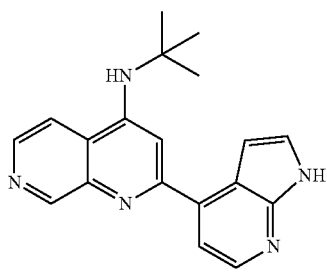 [SMILES: CC(C)(C)Nc1cc(-c2ccnc3[nH]ccc23)nc2cnccc12]

1H NMR (400 MHz, DMSO-d6) 11.86 (s, 1H), 9.23 (d, J=0.8 Hz, 1H), 8.50 (d, J=5.8 Hz, 1H), 8.39 (d, J=4.9 Hz, 1H), 8.30 (m, 1H), 7.63 (m, 1H), 7.61 (m, 1H), 7.32 (s, 1H), 6.96 (dd, J=3.4, 1.9 Hz, 1H), 6.67 (s, 1H), 1.56 (s, 9H). LCMS (M/Z [M+H]$^+$): 318.4.

Example 273: N-tert-butyl-2-(pyridazin-4-yl)-1,7-naphthyridin-4-amine

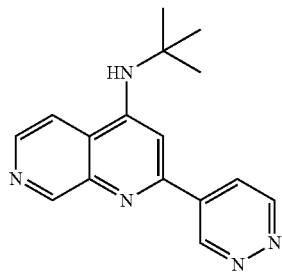 [SMILES: CC(C)(C)Nc1cc(-c2ccnnc2)nc2cnccc12]

1H NMR (400 MHz, DMSO-d6) δ 9.97 (s, 1H), 9.40 (d, J=0.8 Hz, 1H), 9.24 (s, 1H), 8.50 (d, J=4.6 Hz, 1H), 8.36 (d, J=0.8 Hz, 1H), 8.31 (m, 1H), 7.35 (s, 1H), 6.80 (s, 1H), 1.58 (s, 9H). LCMS (M/Z [M+H]⁺): 280.3.

Example 274: 2-(2-aminopyridin-4-yl)-N-tert-butyl-1,7-naphthyridin-4-amine

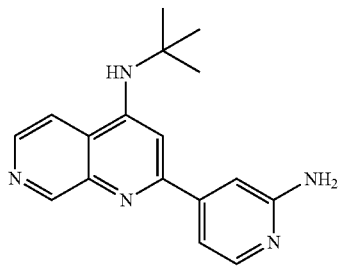 [SMILES: CC(C)(C)Nc1cc(-c2ccnc(N)c2)nc2cnccc12]

1H NMR (400 MHz, DMSO-d6) δ 9.18 (d, J=0.8 Hz, 1H), 8.45 (d, J=5.8 Hz, 1H), 8.26 (m, 1H), 8.05 (dd, J=5.3 0.7 Hz, 1H), 7.20 (m, 1H), 7.17 (m, 1H), 7.14 (m, 1H), 6.63 (s, 1H), 6.09 (s, 2H), 1.55 (s, 9H). LCMS (M/Z [M+H]⁺): 294.4.

Examples 275-286

These compounds were synthesized according to the protocol used for the preparation of Example 270 with 2,4-dichloro-1,7-naphthyridine (Intermediate 6a', Scheme 6) and various organotin reagents and amines respectively.

Example 275: N,N-diethyl-2-(3-fluoropyridin-4-yl)-1,7-naphthyridin-4-amine

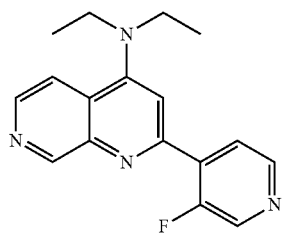 [SMILES: CCN(CC)c1cc(-c2ccncc2F)nc2cnccc12]

1H NMR (400 MHz, DMSO-d6) δ 9.33 (d, J=0.9 Hz, 1H), 8.78 (d, J=2.7 Hz, 1H), 8.62 (dd, J=4.9, 1.1 Hz, 1H), 8.55 (d, J=5.9 Hz, 1H), 8.02 (dd, J=6.8, 4.9 Hz, 1H), 7.88 (dd, J=5.8, 0.9 Hz, 1H), 7.42 (d, J=1.5 Hz, 1H), 3.50 (q, J=7.0 Hz, 4H), 1.21 (t, J=7.0 Hz, 6H). LCMS (M/Z [M+H]⁺): 297.1.

Example 276: (3-{[2-(3-fluoropyridin-4-yl)-1,7-naphthyridin-4-yl]amino}-3-methylbutyl)dimethylamine

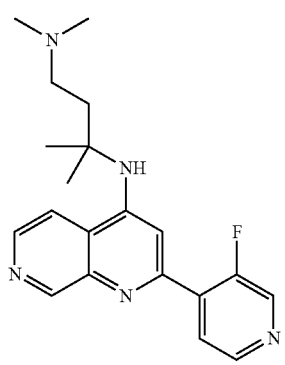 [SMILES: CN(C)CCC(C)(C)Nc1cc(-c2ccncc2F)nc2cnccc12]

1H NMR (400 MHz, DMSO-d6) δ 9.20 (d, J=0.8 Hz, 1H), 8.74 (d, J=2.8 Hz, 1H), 8.60 (dd, J=4.9, 1.1 Hz, 1H), 8.53 (d, J=5.8 Hz, 1H), 8.04 (dd, J=6.9, 4.9 Hz, 1H), 7.91-7.83 (s, 1H), 7.25 (d, J=1.4 Hz, 1H), 2.60-2.54 (m, 2H), 2.33-2.24 (m, 6H), 1.96-1.88 (m, 2H), 1.51 (s, 6H). LCMS (M/Z [M+H]+): 354.2.

Example 277: 2-(3-fluoropyridin-4-yl)-N-methyl-N-(propan-2-yl)-1,7-naphthyridin-4-amine

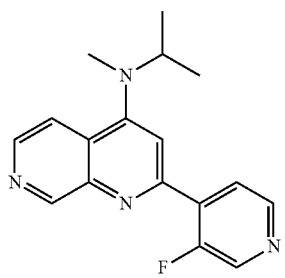 [SMILES: CC(C)N(C)c1cc(-c2ccncc2F)nc2cnccc12]

1H NMR (400 MHz, DMSO-d6) δ 9.33 (m, 1H), 8.78 (d, J=2.7 Hz, 1H), 8.61 (dd, J=4.9, 1.1 Hz, 1H), 8.55 (dd, J=5.9, 2.5 Hz, 1H), 8.05-8.01 (dd, J=6.8, 4.9 Hz, 1H), 7.85 (dd, J=5.8, 0.9 Hz, 1H), 7.41 (d, J=1.4 Hz, 1H), 4.20-4.14 (m, 1H), 2.93 (s, 3H), 1.28 (m, 6H). LCMS (M/Z [M+H]+): 297.1.

Example 278: 2-(3-fluoropyridin-4-yl)-4-(piperidin-1-yl)-1,7-naphthyridine

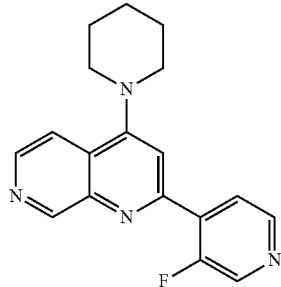 [SMILES: Fc1cnccc1-c1cc(N2CCCCC2)c2ccncc2n1]

1H NMR (400 MHz, DMSO-d6) δ 9.39 (d, J=0.8 Hz, 1H), 8.78 (d, J=2.7 Hz, 1H), 8.63 (m, 1H), 8.60 (m, 1H), 8.03 (dd, J=6.8, 4.9 Hz, 1H), 7.85 (dd, J=5.8, 0.9 Hz, 1H), 7.50 (d, J=1.5 Hz, 1H), 3.32-3.28 (m, 4H), 1.87-1.79 (m, 4H), 1.72-1.65 (m, 2H). LCMS (M/Z [M+H]+): 309.4.

Example 279: 2-(3-fluoropyridin-4-yl)-4-(morpholin-4-yl)-1,7-naphthyridine

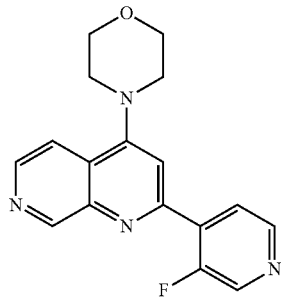 [SMILES: Fc1cnccc1-c1cc(N2CCOCC2)c2ccncc2n1]

1H NMR (400 MHz, DMSO-d6) δ 9.40 (d, J=0.8 Hz, 1H), 8.79 (d, J=2.6 Hz, 1H), 8.62 (m, 1H), 8.60 (m, 1H), 8.03 (dd, J=6.8, 4.9 Hz, 1H), 7.95 (dd, J=5.8, 0.9 Hz, 1H), 7.54 (d, J=1.4 Hz, 1H), 3.91-3.86 (m, 4H), 3.36-3.33 (m, 4H). LCMS (M/Z [M+H]+): 311.1.

Example 280: N-tert-butyl-2-(3-fluoropyridin-4-yl)-1,7-naphthyridin-4-amine

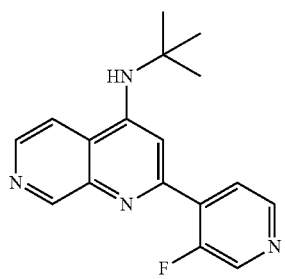

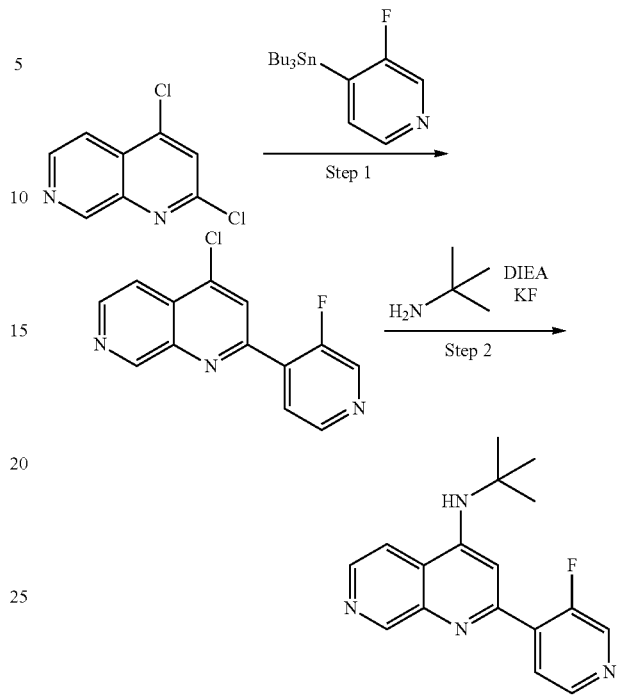

Step 1

In a 20 mL microwave reactor 2,4-dichloro-1,7-naphthyridine (6a, 100 mg, 0.502 mmol) was stirred in dry DMF (1 mL) at room temperature. 3-fluoro-4-(tributylstannyl)pyridine (194 mg, 0.502 mmol) was added then PdCl$_2$(dppf).CH$_2$Cl$_2$ adduct (41.0 mg, 0.050 mmol) and CuI (9.6 mg, 0.050 mmol). The reaction was stirred for 0.5 hour at 130° C. The crude mixture was diluted with DCM, H$_2$O, separated and extracted with DCM×3. Combined the organic layers and dried Na$_2$SO$_4$, filtered and concentrated. The residue was purified by flash chromatography on a COMBIFLASH® system (ISCO) using 0-10% MeOH/DCM to give the product 4-chloro-2-(3-fluoropyridin-4-yl)-1,7-naphthyridine (71%). 1H NMR (400 MHz, Acetone-d6) δ 9.56 (d, J=0.9 Hz, 1H), 8.83 (d, J=5.8 Hz, 1H), 8.74 (d, J=2.9 Hz, 1H), 8.67 (dd, J=5.0, 1.2 Hz, 1H), 8.44 (d, J=1.4 Hz, 1H), 8.18 (dd, J=6.7, 4.9 Hz, 1H), 8.14 (dd, J=5.8, 0.9 Hz, 1H). LCMS [M+H]=260.

Step 2:

In a 40 mL vial was added potassium fluoride (7 mg, 0.12 mmol), 4-chloro-2-(3-fluoropyridin-4-yl)-1,7-naphthyridine (26 mg, 0.10 mmol), and 2-methylpropan-2-amine (0.035 mL, 0.331 mmol) in DMSO (Volume: 1 mL) to give a yellow suspension. The reaction mixture was stirred at 130° C. for 24 hrs. Solvent was evaporated under air flow. The residue was purified by flash chromatography on a COMBIFLASH® system (ISCO) using 0-10% MeOH/DCM to give the product (42%). 1H NMR (400 MHz, Acetone-d6) b 9.24 (d, J=0.8 Hz, 1H), 8.65 (d, J=3.0 Hz, 1H), 8.59 (dd, J=4.9, 1.2 Hz, 1H), 8.46 (d, J=5.9 Hz, 1H), 8.15 (dd, J=6.8, 4.9 Hz, 1H), 8.06 (dd, J=5.9, 0.9 Hz, 1H), 7.48 (d, J=1.4 Hz, 1H), 6.30 (s, 1H), 1.61 (s, 9H). LCMS (M/Z [M+H]$^+$): 297.1.

Example 281: 2-(3-fluoropyridin-4-yl)-N-(2-methylbutan-2-yl)-1,7-naphthyridin-4-amine

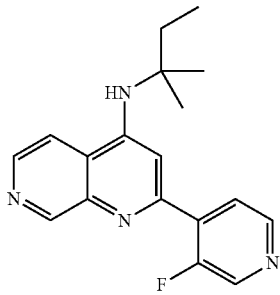 [SMILES: CCC(C)(C)Nc1cc(-c2ccncc2F)nc2cnccc12]

1H NMR (500 MHz, Acetone-d6) δ 9.24 (d, J=0.9 Hz, 1H), 8.64 (d, J=3.0 Hz, 1H), 8.58 (dd, J=4.9, 1.2 Hz, 1H), 8.47 (d, J=5.9 Hz, 1H), 8.15 (dd, J=6.8, 4.9 Hz, 1H), 8.07 (dd, J=5.9, 0.9 Hz, 1H), 7.47 (d, J=1.4 Hz, 1H), 6.12 (s, 1H), 2.03-1.98 (m, 2H), 1.56 (s, 6H), 0.94 (t, J=7.5 Hz, 3H). LCMS (M/Z [M+H]$^+$): 311.2.

Example 282: 2-{[2-(3-fluoropyridin-4-yl)-1,7-naphthyridin-4-yl]amino}-2-methylpropan-1-ol

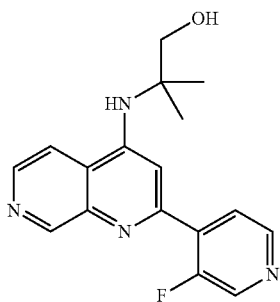 [SMILES: CC(C)(CO)Nc1cc(-c2ccncc2F)nc2cnccc12]

1H NMR (400 MHz, Acetone-d6) δ 9.24 (d, J=0.8 Hz, 1H), 8.59 (dd, J=4.9, 1.2 Hz, 1H), 8.49 (d, J=5.9 Hz, 1H), 8.15 (dd, J=6.8, 4.9 Hz, 1H), 7.97 (dt, J=5.8, 1.3 Hz, 1H), 7.50 (d, J=1.4 Hz, 1H), 6.29 (s, 1H), 3.78 (d, J=5.6 Hz, 2H), 1.56 (s, 6H). LCMS (M/Z [M+H]+): 313.1.

Example 283: 1-[2-(3-chloropyridin-4-yl)-1,7-naphthyridin-4-yl]-2,2-dimethylpiperidin-4-ol

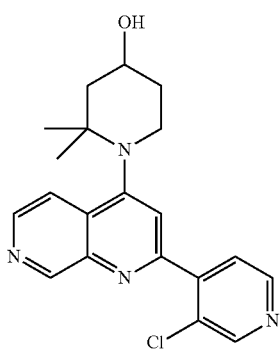 [SMILES: CC1(C)CC(O)CCN1c1cc(-c2ccncc2Cl)nc2cnccc12]

1H NMR (400 MHz, DMSO-d6) δ 9.40 (s, 1H), 8.79 (d, 1H), 8.62 (d, 1H), 8.60 (d, 1H), 8.03 (dd, 1H), 7.95 (d, 1H), 7.54 (s, 1H), 3.91-3.86 (m, 4H), 3.36-3.33 (m, 4H). LCMS (M/Z [M+H]+): 311.3.

Example 284: 2-(3-fluoropyridin-4-yl)-N-[2-methyl-1-(morpholin-4-yl)propan-2-yl]-1,7-naphthyridin-4-amine

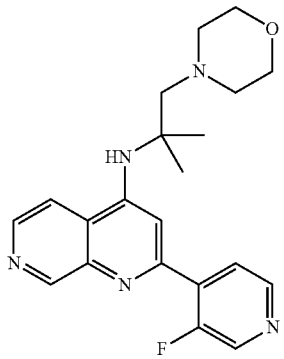 [SMILES: CC(C)(CN1CCOCC1)Nc1cc(-c2ccncc2F)nc2cnccc12]

1H NMR (500 MHz, Acetone-d6) δ 9.25 (d, J=0.9 Hz, 1H), 8.64 (d, J=3.0 Hz, 1H), 8.59 (dd, J=4.9, 1.2 Hz, 1H), 8.52 (d, J=5.8 Hz, 1H), 8.15 (dd, J=6.8, 4.9 Hz, 1H), 7.89 (dd, J=5.9, 0.8 Hz, 1H), 7.54 (d, J=1.4 Hz, 1H), 6.77 (s, 1H), 3.70-3.64 (m, 4H), 2.75 (s, 2H), 2.69-2.62 (m, 4H), 1.60 (s, 6H). LCMS (M/Z [M+H]+): 382.2.

Example 285: N-tert-butyl-2-(3-chloropyridin-4-yl)-1,7-naphthyridin-4-amine

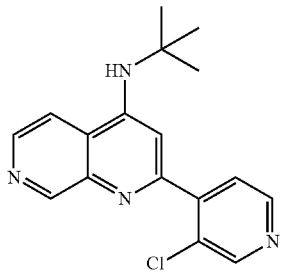 [SMILES: CC(C)(C)Nc1cc(-c2ccncc2Cl)nc2cnccc12]

1H NMR (400 MHz, Acetone-d6) δ 9.20 (d, J=0.9 Hz, 1H), 8.78-8.69 (m, 1H), 8.65 (d, J=4.9 Hz, 1H), 8.47 (d, J=5.9 Hz, 1H), 8.06 (dt, J=5.9, 1.0 Hz, 1H), 7.79-7.70 (m, 1H), 7.25 (s, 1H), 1.60 (s, 9H). LCMS (M/Z [M+H]+): 313.1.

Example 286: 2-(3-chloropyridin-4-yl)-N,N-diethyl-1,7-naphthyridin-4-amine

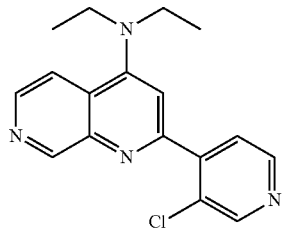 [SMILES: CCN(CC)c1cc(-c2ccncc2Cl)nc2cnccc12]

1H NMR (400 MHz, Acetone-d6) δ 9.31 (d, J=0.9 Hz, 1H), 8.75 (d, J=0.6 Hz, 1H), 8.67 (d, J=4.9 Hz, 1H), 8.54 (d, J=5.9 Hz, 1H), 7.93 (dd, J=5.8, 0.9 Hz, 1H), 7.76 (dd, J=4.9, 0.6 Hz, 1H), 7.39 (s, 1H), 3.58 (q, J=7.1 Hz, 4H), 1.29 (t, J=7.1 Hz, 6H). LCMS (M/Z [M+H]+): 313.1.

Example 287: N-propyl-2-(3-(trifluoromethyl)-1H-pyrazol-4-yl)pyrido[3,4-d]pyrimidin-4-amine

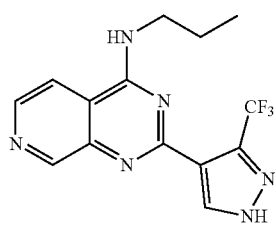 [SMILES: CCCNc1nc(-c2c[nH]nc2C(F)(F)F)nc2cnccc12]

The title compound was synthesized according to the protocol described for Example 111 using 2,4-dichloropyrido[3,4-d]pyrimidine (intermediate 2c) and propan-1-amine and tert-butyl 4-(4,4,5,5-tetramethyl-1,3,2-dioxaborolan-2-yl)-3-(trifluoromethyl)-1H-pyrazole-1-carboxylate. 1H NMR (500 MHz, DMSO-d6) δ 13.81 (s, 1H), 9.01 (d, J=0.9 Hz, 1H), 8.64 (t, J=5.7 Hz, 1H), 8.61-8.57 (m, 1H), 8.55 (d, J=5.5 Hz, 1H), 8.11 (dd, J=5.6, 1.0 Hz, 1H), 3.64-3.56 (m, 2H), 1.73-1.62 (m, 2H), 0.96 (t, J=7.4 Hz, 3H). LCMS (M/Z [M+H]⁺): 323.1.

Example 288: 3-(pyridin-4-yl)-N-(1-(trifluoromethyl)cyclopropyl)-2,6-naphthyridin-1-amine

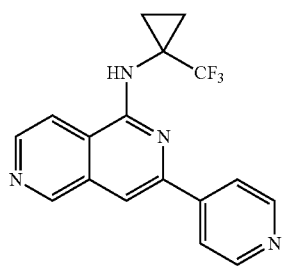

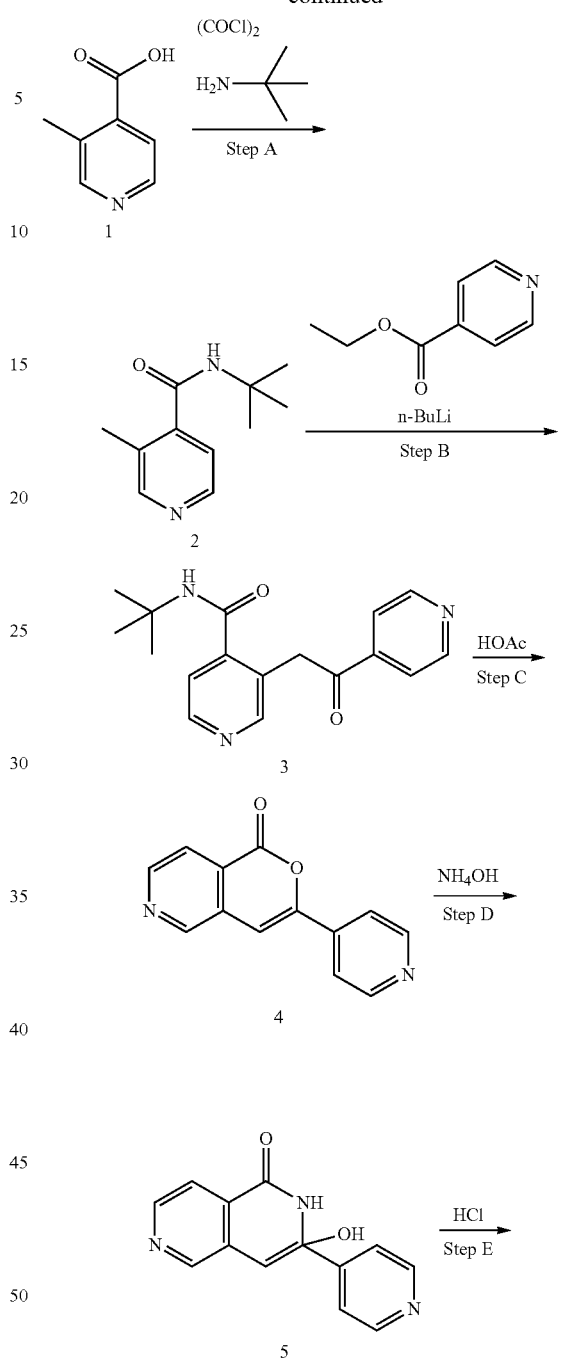

289

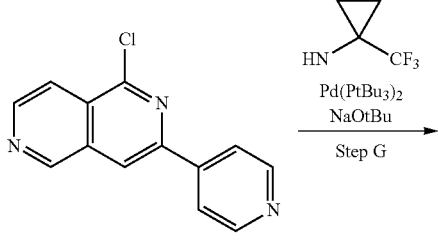

7

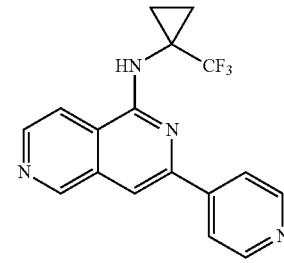

Step A

To a suspension of 3-methylisonicotinic acid (1) (10 g, 72.9 mmol) in dichloromethane (200 mL) was added DMF (200 mL) at 0° C. Ethyl chloroformate (8.6 mL, 12.5 g, 98.4 mmol) was added dropwise over 10 min at 0° C. to result in a mixture which was stirred at 0° C. for 15 min. tert-Butylamine (35.0 mL, 24.2 g, 330.0 mmol) was added dropwise over 15 min to the reaction mixture at 0° C., and the reaction mixture was concentrated under reduced pressure to result in a residue which was subjected to chromatography (hexanes:EtOAc) to give 2 (11.6 g, 83%). $^1$H NMR (400 MHz, DMSO-$d_6$) δ 8.46 (s, 1H), 8.43 (d, J=5.0 Hz, 1H), 7.20 (d, J=5.0 Hz, 1H), 2.29 (s, 3H), 1.37 (s, 9H). LCMS (m/z [M+H]$^+$): 193.

Step B

To a solution of 2 (11.6 g, 60.3 mmol) in THF (440 mL) was added a solution of n-BuLi (58.0 mL, 145.0 mmol, 2.5 M in hexanes) dropwise over 15 min at −45° C. under $N_2$ to result in a mixture which was stirred for 45 min at −45° C. Then a solution of ethyl isonicotinate (10.0 g, 66.3 mol) in THF (20 mL) was dropwise over 15 min at −45° C.

The reaction mixture was allowed to be warmed to room temperature over 2 h, and poured into a saturated aqueous $NH_4Cl$ solution (1000 mL). The organic layer was separated, and the aqueous layer was extracted with EtOAc (3×400 mL). The combined organic layers were washed with saturated aqueous NaCl solution (100 mL), dried over $MgSO_4$, and evaporated under reduced pressure to give crude 3. LCMS (m/z [M+H]$^+$): 298. The crude product was used in the next step without purification.

Step C

A solution of crude 3 of the Step B in acetic acid (200 mL) was heated at 100° C. for 16 h, cooled to room temperature and concentrated to ~80 mL under reduced pressure. Water (120 mL) was added, and the mixture was filtered to get a white precipitate which was washed with water (2×50 mL), and dried under reduced pressure to afford crude 4 (8.08 g).

290

LCMS (m/z [M+H]$^+$): 225. The crude product was used in the next step without purification.

Step D

To a suspension of crude 4 (8.08 g) in EtOH (100 mL) was added an aqueous $NH_4OH$ solution (80 mL, 28.5%) at room temperature to result in a mixture which was stirred for 2.5 h, and evaporated to afford crude 5. LCMS (m/z [M+H]$^+$): 242. The crude product was used in the next step without purification.

Step E

To a suspension of crude 5 of the Step D in EtOH (100 mL) was added water (20 mL) and then aqueous HCl solution (12 M, 25 mL) at 0° C. The reaction mixture was stirred for 19 h at room temperature, and filtered to get white solid which was dried under reduced pressure to afford crude 6 (10.2 g). LCMS (m/z [M+H]$^+$): 224. The crude product was used in the next step without purification.

Step F

A suspension of crude 6 (10.2 g) in $POCl_3$ (75 mL) in an open ChemGlass heavy wall round bottom pressure vessel (350 mL) was heated very slowly till the temperature reached 100° C., and stirred at 100° C. for 30 min. Then the pressure vessel was sealed, and the reaction mixture was heated at 135° C. for 14 h. The $POCl_3$ was removed under reduced pressure, and the residue was mixed with ice water (50 g of ice and 50 mL of water). The pH of the mixture was adjusted to 7 with aqueous NaOH solution (1 M), and then to ~10 with saturated aqueous $Na_2CO_3$ solution. Filtration of the mixture gave a while solid which was dried under reduce pressure to afford 7 (7.1 g, 49% yield for 5 steps from 2). $^1$H NMR (400 MHz, DMSO-$d_6$) δ 9.59 (s, 1H), 8.94 (s, 1H), 8.89 (d, J=5.6 Hz, 1H), 8.78 (d, J=4.8 Hz, 2H), 8.15 (d, J=4.8 Hz, 2H), 8.14 (d, J=5.6 Hz, 1H). LCMS (m/z [M+H]$^+$): 242.

Step G

To a solution of intermediate 7 (60.0 mg, 0.25 mmol) and 1-(trifluoromethyl)cyclopropan-1-amine (93.0 mg, 0.74 mmol) in dioxane (1.0 mL) was added bis(tri-tert-butylphosphine)palladium (13.0 mg, 0.2 micromol) and sodium tert-butoxide (71.0 mg, 0.74 mmol). The reaction mixture was heated under $N_2$ at 130° C. for overnight, and concentrated resulting in a residue which was subjected to chromatography (MeOH/DCM) to afford the title compound. $^1$H NMR (400 MHz, DMSO-$d_6$) δ 9.35 (s, 1H), 8.95 (d, J=8.0 Hz, 2H), 8.75 (d, J=4.0 Hz, 1H), 8.71 (s, 1H), 8.57 (d, J=8.0 Hz, 2H), 8.34 (s, 1H), 8.31 d, J=4.0 Hz, 1H), 1.57 (m, 2H), 1.31 (m, 2H). LCMS (m/z [M+H]$^+$): 331.

Example 289: N-(1-methylcyclopropyl)-7-(pyridin-4-yl)isoquinolin-5-amine

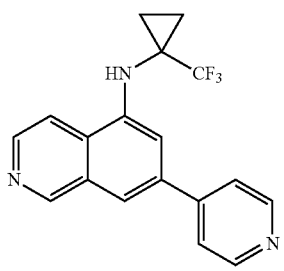

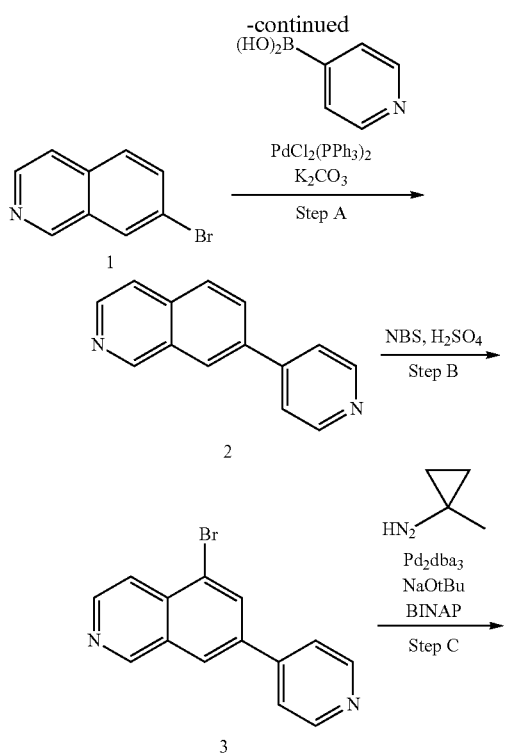

Step A

A suspension of 7-bromoisoquinoline (1) (300 mg, 1.44 mmol), pyridin-4-ylboronic acid (213 mg, 1.73 mmol), bis(triphenylphosphine)palladium(II) dichloride ($PdCl_2(PPh_3)_2$, 98 mg, 0.14 mmol) and potassium carbonate (2 N, 4.3 ml) in DMF (7 mL) was stirred and heated 100° C. for 3 hours. The reaction mixture was filtered through celite. The solution was diluted with water and extracted with EtOA×3. The combined organic layers were washed with saturated aqueous NaCl solution, dried over $MgSO_4$, and evaporated under reduced pressure. The resulted crude was purified by flash chromatography on a COMBIFLASH® system (ISCO) using 0-10% MeOH/DCM to afford 7-(pyridin-4-yl)isoquinoline (2, 282 mg) as a pale brown oil. LCMS (m/z $[M+H]^+$): 207.

Step B:

To a solution of 7-(pyridin-4-yl)isoquinoline (2) (282 mg, 1.37 mmol) in concentrated $H_2SO_4$ (3 mL) was added N-bromosuccinimide (NBS, 488 mg, 2.74 mmol) at 0° C. The reaction mixture was allowed to be warmed to room temperature over 2 h, and poured into ice-water (20 mL) and added saturated aqueous $NaHCO_3$ solution to pH ~8. The aqueous layer was extracted with EtOA×3. The combined organic layers were washed with saturated aqueous NaCl solution, dried over $MgSO_4$, and evaporated under reduced pressure. The resulted crude was purified by flash chromatography on a COMBIFLASH® system (ISCO) using 0-10% MeOH/DCM to afford 5-bromo-7-(pyridin-4-yl)isoquinoline (3, 110 mg). LCMS (m/z $[M+H]^+$): 285/287.

Step C

A suspension of 5-bromo-7-(pyridin-4-yl)isoquinoline (3) (30 mg, 0.105 mmol), 1-methylcyclopropan-1-amine hydrochloride (28.3 mg, 0.263 mmol), tris(dibenzylideneacetone)dipalladium(0) ($Pd_2dba_3$, 9.7 mg, 0.0105 mmol), 2,2'-bis(diphenylphosphino)-1,1'-binaphthyl (BINAP, 6.5 mg, 0.0105 mmol) and sodium tert-butoxide (44.3 mg, 0.462) in toluene (1.5 mL) was heated under $N_2$ at 90° C. for 16 h, cooled to room temperature and concentrated. The residue was diluted in MeOH and filtered, then purified by mass-triggered preparative reverse phase HPLC with 10-90% acetonitrile/water to afford the title compound (6 mg). 1H NMR (400 MHz, Chloroform-d) b 9.24 (s, 1H), 8.74 (s, 2H), 8.49 (s, 1H), 7.69-7.60 (m, 2H), 7.59-7.56 (m, 1H), 7.52-7.46 (m, 1H), 7.39-7.36 (m, 1H), 1.52 (s, 3H), 0.98-0.92 (m, 2H), 0.88-0.81 (m, 2H). LCMS (m/z $[M+H]^+$): 276.

Example 290: 2-(pyridin-4-yl)-4-(3-(trifluoromethyl)piperazin-1-yl)pyrido[3,4-d]pyrimidine

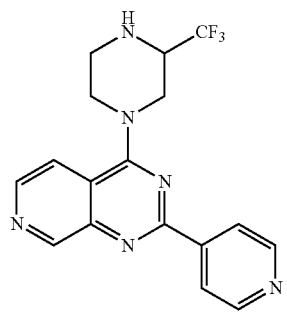

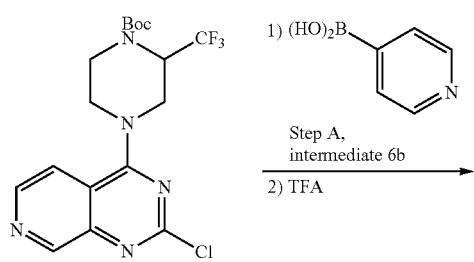

-continued

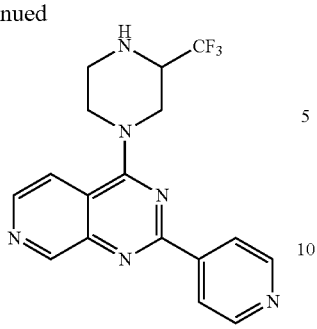

The title compound was synthesized according to the protocol described for example 111 using 2,4-dichloro-pyrido[3,4-d]pyrimidine (intermediate 2c) with tert-butyl 2-(trifluoromethyl)piperazine-1-carboxylate and pyridin-4-ylboronic acid followed by deprotection of the N-Boc group with TFA.

1H NMR (400 MHz, Chloroform-d) δ 9.46 (d, J=0.9 Hz, 1H), 8.83-8.78 (m, 2H), 8.63 (d, J=5.8 Hz, 1H), 8.35-8.30 (m, 2H), 7.74 (dd, J=5.8, 0.9 Hz, 1H), 5.80-5.67 (m, 1H), 4.07 (dt, J=24.3, 12.4 Hz, 2H), 3.65 (d, J=14.2 Hz, 1H), 3.34 (d, J=14.6 Hz, 1H), 3.18 (d, J=13.5 Hz, 1H), 2.89 (t, J=11.0 Hz, 1H). LCMS (m/z [M+H]$^+$): 361.1.

Example 291: 4-(4-methylpiperazin-1-yl)-2-(pyridin-4-yl)-1,7-naphthyridine

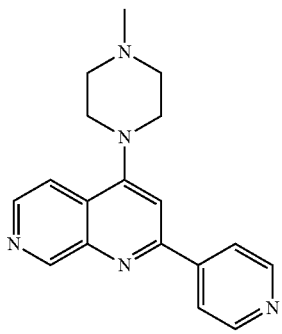 [SMILES: CN1CCN(c2cc(-c3ccncc3)nc3cnccc23)CC1]

The title compound was synthesized from 4-chloro-2-(pyridin-4-yl)-1,7-naphthyridine (Intermediate 6b) and 1-methylpiperazine as follows:

A solution of 4-chloro-2-(pyridin-4-yl)-1,7-naphthyridine (Intermediate 6b, 30 mg, 0.124 mmol), 1-methylpiperazine (50 mg, 0.499 mmol), potassium phosphate (132 mg, 0.621 mmol), RuPhos Pd G3 (16 mg, 0.019 mmol) and RuPhos (13 mg, 0.028 mmol) in dioxane (2 mL) was heated under argon in a microwave vial at 130° C. for 10 min. The solvent was evaporated under reduced pressure. The residue was purified by flash chromatography using 20-100% ethyl acetate/cyclohexane, followed by 2-30% methanol/dichloromethane to give the title compound (21%).

1H NMR (400 MHz, DMSO-d$_6$) δ 9.38 (s, 1H), 8.76 (d, J=4.8 Hz, 2H), 8.55 (d, J=5.7 Hz, 1H), 8.23 (d, J=4.8 Hz, 2H), 7.85 (d, J=5.7 Hz, 1H), 7.70 (s, 1H), 3.37 (s, 4H), 2.63 (s, 4H), 2.30 (s, 3H). LCMS (m/z [M+H]$^+$): 306.3, Rt$_1$=0.38 min.

Example 292: 4-(piperazin-1-yl)-2-(pyridin-4-yl)-1,7-naphthyridine

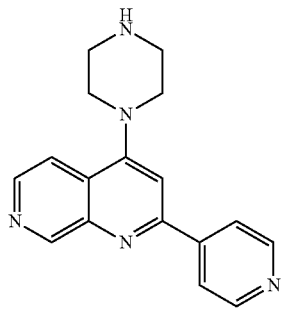 [SMILES: c1cc(-c2cc(N3CCNCC3)c3ccncc3n2)ccn1]

The title compound was synthesized in analogy of Example 291 in 2 steps from 4-chloro-2-(pyridin-4-yl)-1,7-naphthyridine (Intermediate 6b) and tert-butyl piperazine-1-carboxylate (step 1) and Boc-deprotection using HCl in diethylether (step 2).

Step 2 (Boc-Deprotection)

To a solution of tert-butyl 4-(2-(pyridin-4-yl)-1,7-naphthyridin-4-yl)piperazine-1-carboxylate (24 mg, 0.061 mmol) in dichloromethane (5 mL) was added 6M HCl in diethyl ether (2 mL, 12 mmol). The resulting yellow suspension was stirred at r.t. for 1 h. The yellow precipitate was filtered off and washed with dichloromethane. The hydrochloride salt was dissolved in MeOH and the solution was given on a PoraPak Rxn CX 20 cc (2 g) cartridge. The cartridge was then washed twice with 5 mL MeOH. Finally, the compound was eluted with 7N NH$_3$ in MeOH. The filtrate was evaporated under reduced pressure to give the title compound (76%).

1H NMR (400 MHz, DMSO-d$_6$) δ 9.37 (s, 1H), 8.76 (d, J=4.7 Hz, 2H), 8.55 (d, J=5.8 Hz, 1H), 8.22 (d, J=4.8 Hz, 2H), 7.86 (d, J=5.7 Hz, 1H), 7.67 (s, 1H), 3.28 (s, 4H), 2.99 (s, 4H). LCMS (m/z [M+H]$^+$): 292.3, Rt$_1$=0.38 min.

Example 293: 4-(2-methylpiperidin-1-yl)-2-(pyridin-4-yl)-1,7-naphthyridine

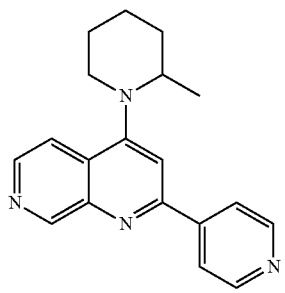 [SMILES: CC1CCCCN1c1cc(-c2ccncc2)nc2cnccc12]

The title compound was synthesized in analogy of Example 291 from 4-chloro-2-(pyridin-4-yl)-1,7-naphthyridine (Intermediate 6b) and 2-methylpiperidine.

1H NMR (400 MHz, DMSO-d$_6$) δ 9.48-9.32 (m, 1H), 8.86-8.74 (m, 2H), 8.56 (d, J=5.7 Hz, 1H), 8.30-8.16 (m, 2H), 7.86 (d, J=5.8 Hz, 1H), 7.72 (s, 1H), 4.10 (d, J=6.3 Hz, 1H), 3.53-3.41 (m, 1H), 3.21 (d, J=12.4 Hz, 1H), 2.05 (s,

1H), 1.86-1.74 (m, 3H), 1.62 (s, 2H), 1.06 (d, J=6.5 Hz, 3H). LCMS (m/z [M+H]+): 305.3, Rt₁=0.98 min.

Example 294: 2-(pyridin-4-yl)-N-(1-(trifluoromethyl)cyclobutyl)-1,7-naphthyridin-4-amine

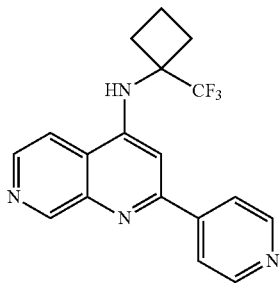 [SMILES: FC(F)(F)C1(Nc2cc(-c3ccncc3)nc3cnccc23)CCC1]

The title compound was synthesized from 4-chloro-2-(pyridin-4-yl)-1,7-naphthyridine (Intermediate 6b) and 1-(trifluoromethyl)cyclobutan-1-amine as follows: A solution of 4-chloro-2-(pyridin-4-yl)-1,7-naphthyridine (Intermediate 6b, 100 mg, 0.414 mmol), 1-(trifluoromethyl)cyclobutan-1-amine (115 mg, 0.828 mmol), potassium tert-butylate (139 mg, 1.241 mmol), Pd₂(dba)₃×CHCl₃ (43 mg, 0.042 mmol) and PhCPhos (36 mg, 0.085 mmol) in dioxane (5 mL) was heated under argon in a microwave vial at 100° C. for 30 min. The solvent was evaporated under reduced pressure. The residue was purified by flash chromatography using 20-100% ethyl acetate/cyclohexane, followed by 2-10% methanol/dichloromethane to give the title compound (9%).

1H NMR (600 MHz, DMSO-d₆) δ 9.30 (s, 1H), 8.78-8.74 (m, 2H), 8.57 (d, J=5.8 Hz, 1H), 8.40 (d, J=5.8 Hz, 1H), 8.08-8.04 (m, 2H), 7.89 (s, 1H), 6.94 (s, 1H), 2.85-2.78 (m, 2H), 2.74 (d, J=11.6 Hz, 2H), 2.04 (dd, J=18.6, 9.7 Hz, 2H). LCMS (m/z [M+H]+): 345.3, Rt₁=0.84 min.

Example 295: 2-methyl-N1-(2-(pyridin-4-yl)-1,7-naphthyridin-4-yl)propane-1,2-diamine

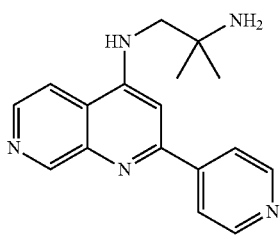 [SMILES: CC(C)(N)CNc1cc(-c2ccncc2)nc2cnccc12]

The title compound was synthesized in analogy of Example 254 in 2 steps from 4-chloro-2-(pyridin-4-yl)-1,7-naphthyridine (Intermediate 6b) and tert-butyl (1-amino-2-methylpropan-2-yl)carbamate (step 1) and Boc-deprotection using HCl in diethyl ether (step 2, described in Example 292).

1H NMR (400 MHz, DMSO-d₆) δ 9.24 (s, 1H), 8.75 (d, J=5.14 Hz, 2H), 8.51 (d, J=5.75 Hz, 1H), 8.26 (d, J=5.75 Hz, 1H), 8.21 (d, J=5.26 Hz, 2H), 7.40 (s, 1H), 7.29 (brs, 1H), 3.38 (br s, 2H), 1.63-2.22 (m, 2H), 1.16 (s, 6H). LCMS (m/z [M+H]+): 294.4, Rt₁=0.37 min.

Example 296: N-(oxetan-3-yl)-2-(pyridin-4-yl)-1,7-naphthyridin-4-amine

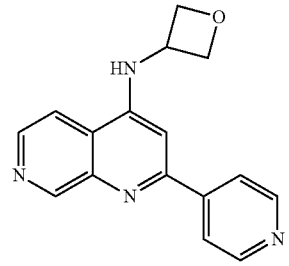 [SMILES: c1cc(-c2cc(NC3COC3)c3ccncc3n2)ccn1]

The title compound was synthesized in analogy of Example 254 from 4-chloro-2-(pyridin-4-yl)-1,7-naphthyridine (Intermediate 6b) and oxetan-3-amine.

1H NMR (400 MHz, DMSO-d₆) δ 9.28 (s, 1H), 8.76 (d, J=5.99 Hz, 2H), 8.57 (d, J=5.75 Hz, 1H), 8.29 (d, J=5.75 Hz, 1H), 8.21 (d, J=5.99 Hz, 2H), 8.11 (brd, J=5.75 Hz, 1H), 7.03 (s, 1H), 4.99-5.17 (m, 3H), 4.73 (t, J=5.93 Hz, 2H). LCMS (m/z [M+H]+): 279.3, Rt₁=0.49 min.

Example 297: N-(1-methylcycloropyl)-2-(pyridin-4-yl)-1,7-naphthyridin-4-amine

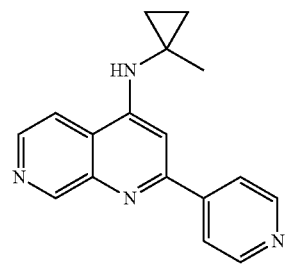 [SMILES: CC1(Nc2cc(-c3ccncc3)nc3cnccc23)CC1]

The title compound was synthesized in analogy of Example 254 from 4-chloro-2-(pyridin-4-yl)-1,7-naphthyridine (Intermediate 6b) and 1-methylcyclopropan-1-amine.

1H NMR (400 MHz, DMSO-d₆) δ 9.34 (s, 1H), 8.78 (d, J=5.75 Hz, 2H), 8.48 (d, J=5.87 Hz, 1H), 8.20 (d, J=5.87 Hz, 2H), 8.07 (d, J=5.87 Hz, 1H), 7.69 (s, 1H), 3.29 (s, 3H), 3.14-3.20 (m, 1H), 0.89-0.97 (m, 2H), 0.52-0.61 (m, 2H). LCMS (m/z [M+H]+): 277.3, Rt₁=0.73 min.

Example 298: 4-(3,3-dimethylpiperazin-1-yl)-2-(pyridin-4-yl)-1,7-naphthyridine

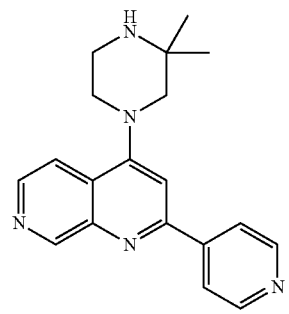 [SMILES: CC1(C)CN(c2cc(-c3ccncc3)nc3cnccc23)CCN1]

297

The title compound was synthesized in analogy of Example 291 in 2 steps from 4-chloro-2-(pyridin-4-yl)-1,7-naphthyridine (Intermediate 6b) and tert-butyl 2,2-dimethylpiperazine-1-carboxylate (step 1) and Boc-deprotection using HCl in diethylether (step 2, described in Example 292).

1H NMR (400 MHz, DMSO-$d_6$) δ 9.41 (s, 1H), 8.79 (d, J=6.0 Hz, 2H), 8.59 (d, J=5.7 Hz, 1H), 8.26 (d, J=6.0 Hz, 2H), 7.90 (d, J=5.8 Hz, 1H), 7.70 (s, 1H), 3.31 (s, 1H), 3.25 (d, J=4.9 Hz, 2H), 3.10 (s, 4H), 1.26 (s, 6H). LCMS (m/z [M+H]$^+$): 320.3, $Rt_1$=0.45 min.

Example 299: 2,2-dimethyl-4-(2-(pyridin-4-yl)-1,7-naphthyridin-4-yl)morpholine

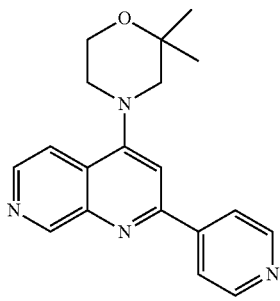 [SMILES: CC1(C)CN(c2cc(-c3ccncc3)nc3cnccc23)CCO1]

The title compound was synthesized in analogy of Example 291 from 4-chloro-2-(pyridin-4-yl)-1,7-naphthyridine (Intermediate 6b) and 2,2-dimethylmorpholine.

1H NMR (400 MHz, DMSO-$d_6$) δ 9.43 (s, 1H), 8.80 (d, J=5.9 Hz, 2H), 8.61 (d, J=5.8 Hz, 1H), 8.27 (d, J=6.0 Hz, 2H), 7.93 (d, J=5.8 Hz, 1H), 7.75 (s, 1H), 4.01-3.94 (m, 2H), 3.31 (s, 2H), 3.21 (s, 2H), 1.39 (s, 6H). LCMS (m/z [M+H]$^+$): 321.3, $Rt_1$=0.81 min.

Example 300: N-(1-methylcyclobutyl)-2-(pyridin-4-yl)-1,7-naphthyridin-4-amine

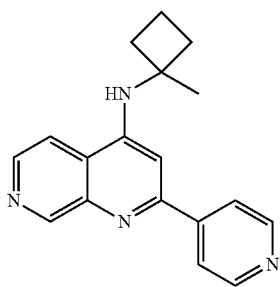 [SMILES: CC1(Nc2cc(-c3ccncc3)nc3cnccc23)CCC1]

The title compound was synthesized in analogy of Example 254 from 4-chloro-2-(pyridin-4-yl)-1,7-naphthyridine (Intermediate 6b) and 1-methylcyclobutan-1-amine.

1H NMR (400 MHz, DMSO-$d_6$) δ 9.23 (s, 1H), 8.75 (d, J=5.9 Hz, 2H), 8.49 (d, J=5.8 Hz, 1H), 8.26 (d, J=5.8 Hz, 1H), 8.08 (d, J=5.9 Hz, 2H), 7.64 (s, 1H), 6.83 (s, 1H), 2.45 (t, J=10.4 Hz, 2H), 2.32 (t, J=9.2 Hz, 2H), 1.97 (ddd, J=25.6, 20.0, 9.7 Hz, 2H), 1.62 (s, 3H). LCMS (m/z [M+H]$^+$): 291.3, $Rt_1$=0.70 min.

298

Example 301: 2,2-dimethyl-N1-(2-(pyridin-4-yl)-1,7-naphthyridin-4-yl)propane-1,3-diamine

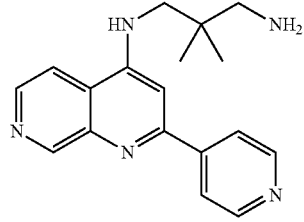 [SMILES: CC(C)(CN)CNc1cc(-c2ccncc2)nc2cnccc12]

The title compound was synthesized in analogy of Example 254 in 2 steps from 4-chloro-2-(pyridin-4-yl)-1,7-naphthyridine (Intermediate 6b) and tert-butyl (3-amino-2,2-dimethylpropyl)carbamate (step 1) and Boc-deprotection using HCl in diethyl ether (step 2, described in Example 292).

1H NMR (400 MHz, DMSO-$d_6$) δ 9.20 (s, 1H), 8.72 (d, J=5.9 Hz, 2H), 8.47 (d, J=5.7 Hz, 1H), 8.17 (d, J=6.0 Hz, 2H), 8.01 (d, J=5.8 Hz, 1H), 7.31 (s, 1H), 3.36 (s, 2H), 3.27 (s, 2H), 2.60 (s, 2H), 0.97 (s, 6H). LCMS (m/z [M+H]$^+$): 308.3, $Rt_1$=0.41 min.

Example 302: $N^2,N^2$,2-trimethyl-$N^1$-(2-(pyridin-4-yl)-1,7-naphthyridin-4-yl)propane-1,2-diamine

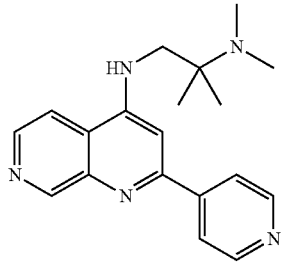 [SMILES: CN(C)C(C)(C)CNc1cc(-c2ccncc2)nc2cnccc12]

The title compound was synthesized in analogy of Example 254 from 4-chloro-2-(pyridin-4-yl)-1,7-naphthyridine (Intermediate 6b) and $N^2,N^2$,2-trimethylpropane-1,2-diamine.

1H NMR (400 MHz, DMSO-$d_6$) δ 9.27 (s, 1H), 8.76 (d, J=5.9 Hz, 2H), 8.54 (d, J=5.7 Hz, 1H), 8.23 (d, J=5.7 Hz, 2H), 8.05 (s, 1H), 7.33 (s, 1H), 6.75 (s, 1H), 3.42 (s, 2H), 2.29 (d, J=15.6 Hz, 6H), 1.16 (s, 6H). LCMS (m/z [M+H]$^+$): 322.3, $Rt_1$=0.39 min.

Example 303: 4-(2-methylpiperazin-1-yl)-2-(pyridin-4-yl)-1,7-naphthyridine

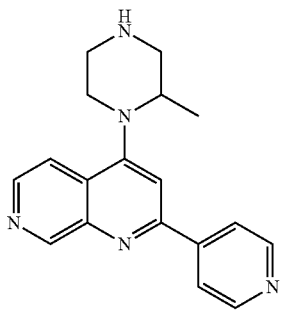 [SMILES: CC1CNCCN1c1cc(-c2ccncc2)nc2cnccc12]

The title compound was synthesized in analogy of Example 291 in 2 steps from 4-chloro-2-(pyridin-4-yl)-1,7-naphthyridine (Intermediate 6b) and tert-butyl 3-methylpiperazine-1-carboxylate (step 1) and Boc-deprotection using HCl in diethyl ether (step 2, described in Example 292).

1H NMR (400 MHz, DMSO-$d_6$) δ 9.44 (s, 1H), 8.80 (d, J=5.9 Hz, 2H), 8.60 (d, J=5.7 Hz, 1H), 8.28 (d, J=5.9 Hz, 2H), 7.98 (d, J=5.7 Hz, 1H), 7.84 (s, 1H), 4.08 (d, J=5.9 Hz, 1H), 3.60 (t, J=9.6 Hz, 1H), 3.42 (dd, J=12.3, 2.9 Hz, 1H), 3.29-3.17 (m, 2H), 3.12 (t, J=9.3 Hz, 1H), 2.98 (dd, J=12.3, 4.1 Hz, 1H), 1.10 (d, J=6.5 Hz, 3H). LCMS (m/z [M+H]$^+$): 306.3, $Rt_1$=0.43 min.

Example 304: 2-methyl-$N^1$-(2-(pyridin-4-yl)-1,7-naphthyridin-4-yl)propane-1,3-diamine

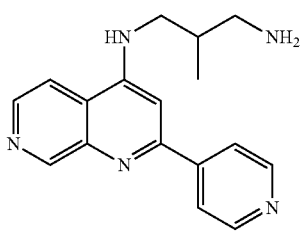 [SMILES: CC(CN)CNc1cc(-c2ccncc2)nc2cnccc12]

The title compound was synthesized in analogy of Example 254 in 2 steps from 4-chloro-2-(pyridin-4-yl)-1,7-naphthyridine (Intermediate 6b) and tert-butyl (3-amino-2-methylpropyl)carbamate (step 1) and Boc-deprotection using HCl in diethyl ether (step 2, described in Example 292).

1H NMR (400 MHz, DMSO-$d_6$) δ 9.25 (s, 1H), 8.76 (d, J=5.9 Hz, 2H), 8.51 (d, J=5.7 Hz, 1H), 8.24-8.16 (m, 3H), 7.96 (s, 1H), 7.27 (s, 1H), 5.14 (s, 2H), 3.50 (dd, J=13.4, 6.8 Hz, 1H), 3.40 (dd, J=13.8, 6.8 Hz, 1H), 2.80 (dd, J=12.6, 6.0 Hz, 1H), 2.70 (dd, J=12.5, 6.4 Hz, 1H), 2.11 (dq, J=13.2, 6.6 Hz, 1H), 1.04 (d, J=6.7 Hz, 3H). LCMS (m/z [M+H]$^+$): 294.3, $Rt_1$=0.37 min.

Example 305: (R)-2-(pyridin-4-yl)-4-(3-(trifluoromethyl)piperazin-1-yl)-1,7-naphthyridine

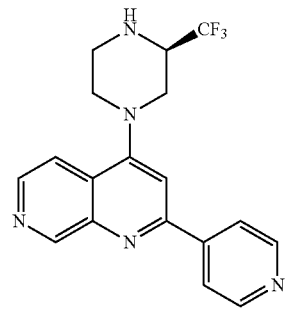 [SMILES: FC(F)(F)[C@H]1CN(c2cc(-c3ccncc3)nc3cnccc23)CCN1]

The title compound was synthesized in analogy of Example 291 from 4-chloro-2-(pyridin-4-yl)-1,7-naphthyridine (Intermediate 6b) and (R)-2-(trifluoromethyl)piperazine.

1H NMR (400 MHz, DMSO-$d_6$) δ 9.40 (s, 1H), 8.84-8.71 (m, 2H), 8.58 (d, J=5.7 Hz, 1H), 8.35-8.18 (m, 2H), 7.88 (d, J=5.8 Hz, 1H), 7.79 (s, 1H), 3.79 (s, 1H), 3.66 (d, J=11.9 Hz, 1H), 3.53 (d, J=10.3 Hz, 1H), 3.23-2.94 (m, 5H). LCMS (m/z [M+H]$^+$): 360.3, $Rt_1$=0.71 min.

Example 306: N-(tert-butyl)-N-methyl-2-(pyridin-4-yl)-1,7-naphthyridin-4-amine

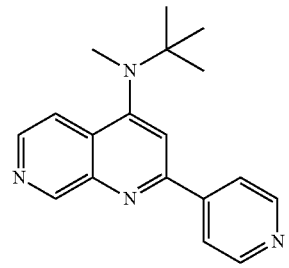 [SMILES: CN(c1cc(-c2ccncc2)nc2cnccc12)C(C)(C)C]

The title compound was synthesized in analogy of Example 254 from 4-chloro-2-(pyridin-4-yl)-1,7-naphthyridine (Intermediate 6b) and N,2-dimethylpropan-2-amine.

1H NMR (400 MHz, DMSO-$d_6$) δ 9.43 (s, 1H), 8.81 (d, J=5.6 Hz, 2H), 8.61 (d, J=5.7 Hz, 1H), 8.24 (d, J=5.7 Hz, 2H), 8.13 (d, J=6.2 Hz, 2H), 2.97 (s, 3H), 1.30 (s, 9H). LCMS (m/z [M+H]$^+$): 293.3, $Rt_1$=1.01 min.

Example 307: N-(1-methylcyclobutyl)-2-(pyrimidin-4-yl)-1,7-naphthyridin-4-amine

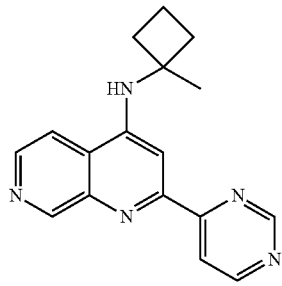 [SMILES: CC1(Nc2cc(-c3ccncn3)nc3cnccc23)CCC1]

The title compound was synthesized in analogy of Example 270 in 2 steps from 2,4-dichloro-1,7-naphthyridine (Intermediate 6a') and 4-(tributylstannyl)pyrimidine (step 1) and from 4-chloro-2-(pyrimidin-4-yl)-1,7-naphthyridine and 1-methylcyclobutan-1-amine (step 2).

1H NMR (400 MHz, DMSO-$d_6$) δ 9.37 (s, 1H), 9.27 (s, 1H), 9.01 (dd, J=5.2, 1.5 Hz, 1H), 8.59-8.48 (m, 2H), 8.29 (d, J=5.9 Hz, 1H), 7.69 (s, 1H), 7.58 (d, J=1.5 Hz, 1H), 2.46 (s, 2H), 2.27 (t, J=9.8 Hz, 2H), 1.98 (dq, J=31.9, 10.6, 10.2 Hz, 2H), 1.62 (s, 3H). LCMS (m/z [M+H]$^+$): 292.4, $Rt_1$=0.82 min.

Example 308: $N^1,N^1$,3-trimethyl-$N^3$-(2-(pyrimidin-4-yl)pyrido[3,4-d]pyrimidin-4-yl)butane-1,3-diamine

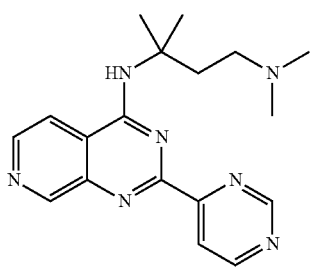 [SMILES: CN(C)CCC(C)(C)Nc1nc(-c2ccncn2)nc2cnccc12]

The title compound was synthesized in analogy of Example 159 in 2 steps from 2,4-dichloropyrido[3,4-d]pyrimidine (Intermediate 2c) and $N^1,N^1$,3-trimethylbutane-1,3-diamine (step 1) and from $N^3$-(2-chloropyrido[3,4-d]pyrimidin-4-yl)-$N^1,N^1$,3-trimethylbutane-1,3-diamine and 4-(tributylstannyl)pyrimidine (step 2).

¹H NMR (400 MHz, DMSO-$d_6$) δ ppm 9.29-9.48 (m, 2H), 9.22 (s, 1H), 9.05 (br d, J=5.01 Hz, 1H), 8.70 (br d, J=5.50 Hz, 1H), 8.38 (br d, J=5.01 Hz, 1H), 7.91 (br d, J=4.89 Hz, 1H), 2.21-2.43 (m, 8H), 2.05 (br s, 2H), 1.66 (s, 6H). LCMS (m/z [M+H]$^+$): 338.3, $Rt_1$=0.47 min.

Example 309: $N^1,N^1$,3-trimethyl-$N^3$-(2-(3-methyl-1H-pyrazol-4-yl)pyrido[3,4-d]pyrimidin-4-yl)butane-1,3-diamine

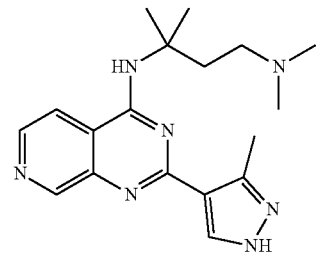 [SMILES: Cc1n[nH]cc1-c1nc(NC(C)(C)CCN(C)C)c2ccncc2n1]

The title compound was synthesized in analogy of Example 111 in 2 steps from 2,4-dichloropyrido[3,4-d]pyrimidine (Intermediate 2c) and $N^1,N^1$,3-trimethylbutane-1,3-diamine (step 1) and from $N^3$-(2-chloropyrido[3,4-d]pyrimidin-4-yl)-$N^1,N^1$,3-trimethylbutane-1,3-diamine and tert-butyl 3-methyl-4-(4,4,5,5-tetramethyl-1,3,2-dioxaborolan-2-yl)-1H-pyrazole-1-carboxylate (CAS no. 1009071-34-4, step 2).

1H NMR (400 MHz, DMSO-$d_6$) δ ppm 12.57-12.95 (m, 1H), 8.89-9.00 (m, 2H), 8.48 (d, J=5.50 Hz, 1H), 7.93-8.29 (m, 1H), 7.75 (br d, J=5.38 Hz, 1H), 2.55-2.84 (m, 5H), 2.25 (s, 6H), 1.99 (br s, 2H), 1.61 (s, 6H). LCMS (m/z [M+H]$^+$): 340.3, $Rt_1$=0.48 min.

Example 310: tert-butyl (2-methyl-1-((2-(pyridin-4-yl)pyrido[3,4-d]pyrimidin-4-yl)amino)propan-2-yl)carbamate

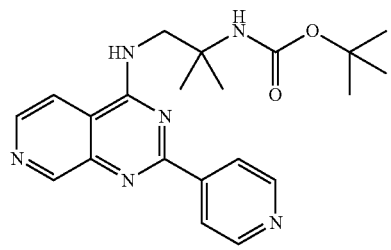 [SMILES: CC(C)(CNc1nc(-c2ccncc2)nc2cnccc12)NC(=O)OC(C)(C)C]

The title compound was synthesized in analogy of Example 1 from 4-chloro-2-(pyridin-4-yl)pyrido[3,4-d]pyrimidine (Intermediate 1c) and tert-butyl (1-amino-2-methylpropan-2-yl)carbamate.

1H NMR (400 MHz, DMSO-$d_6$) δ 9.21 (s, 1H), 8.78 (dd, J=8.9, 4.9 Hz, 3H), 8.68 (d, J=5.5 Hz, 1H), 8.44-8.34 (m, 2H), 8.22 (d, J=5.7 Hz, 1H), 6.88 (s, 1H), 3.90 (d, J=6.1 Hz, 2H), 1.35 (s, 6H), 1.27 (d, J=6.1 Hz, 9H). LCMS (m/z [M+H]$^+$): 395.2, $Rt_1$=0.97 min.

Example 311: tert-butyl (2-((2-(pyridin-4-yl)pyrido[3,4-d]pyrimidin-4-yl)amino)ethyl)carbamate

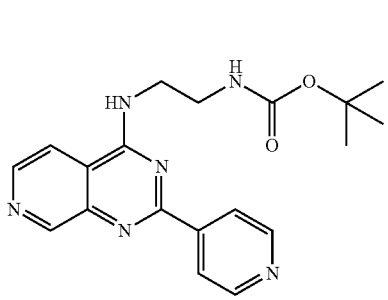 [SMILES: CC(C)(C)OC(=O)NCCNc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and tert-butyl (2-aminoethyl) carbamate.

1H NMR (400 MHz, DMSO-$d_6$) δ 9.19 (s, 1H), 8.93-8.81 (m, 1H), 8.79-8.68 (m, 2H), 8.64 (d, J=5.5 Hz, 1H), 8.39 (d, J=5.1 Hz, 2H), 8.13 (d, J=5.6 Hz, 1H), 7.03 (t, J=6.0 Hz, 1H), 3.73 (q, J=6.2 Hz, 2H), 3.40-3.32 (m, 2H), 1.33 (s, 9H). LCMS (m/z [M+H]$^+$): 367.2, $Rt_1$=0.78 min.

Example 312: 2-methyl-$N^1$-(2-(pyridin-4-yl)pyrido[3,4-d]pyrimidin-4-yl)propane-1,2-diamine

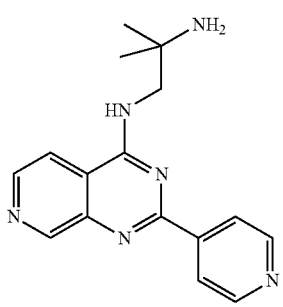 [SMILES: CC(C)(N)CNc1nc(-c2ccncc2)nc2cnccc12]

The title compound was synthesized in analogy of Example 1 in 2 steps from 4-chloro-2-(pyridin-4-yl)pyrido[3,4-d]pyrimidine (Intermediate 1c) and tert-butyl (1-amino-2-methylpropan-2-yl)carbamate (step 1) and Boc-deprotection using TFA (step 2).

1H NMR (400 MHz, DMSO-$d_6$) δ 9.18 (s, 1H), 8.83-8.74 (m, 2H), 8.65 (d, J=5.5 Hz, 1H), 8.38-8.33 (m, 2H), 8.31 (d, J=5.6 Hz, 1H), 3.70 (s, 2H), 1.13 (s, 6H). LCMS (m/z [M+H]$^+$): 295.2, $Rt_1$=0.41 min.

Example 313: N-(2-(pyridin-4-yl)pyrido[3,4-d]pyrimidin-4-yl)ethane-1,2-diamine

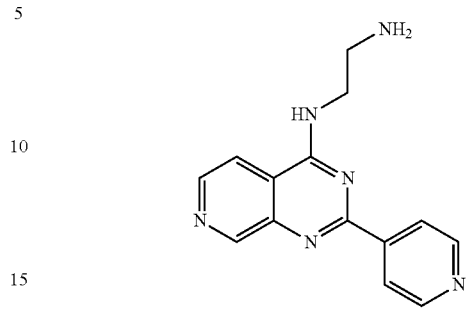

The title compound was synthesized in analogy of Example 1 in 2 steps from 4-chloro-2-(pyridin-4-yl)pyrido[3,4-d]pyrimidine (Intermediate 1c) and tert-butyl (2-aminoethyl)carbamate (step 1) and Boc-deprotection using TFA (step 2).

1H NMR (400 MHz, DMSO-$d_6$) δ 9.18 (s, 1H), 8.81-8.71 (m, 2H), 8.64 (d, J=5.5 Hz, 1H), 8.43-8.30 (m, 2H), 8.20 (d, J=5.6 Hz, 1H), 3.73 (t, J=6.4 Hz, 2H), 2.94 (t, J=6.4 Hz, 2H). LCMS (m/z [M+H]$^+$): 267.2, $Rt_1$=0.38 min.

Example 314: N,N,2-trimethyl-2-((2-(pyridin-4-yl)pyrido[3,4-d]pyrimidin-4-yl)amino)propanamide

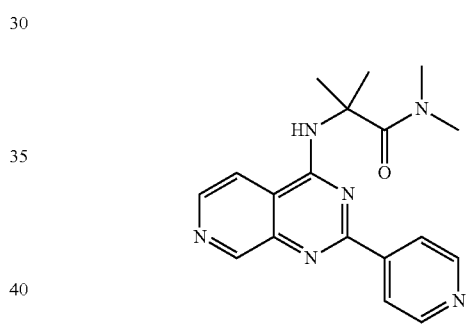

The title compound was synthesized in analogy of Example 1 from 4-chloro-2-(pyridin-4-yl)pyrido[3,4-d]pyrimidine (Intermediate 1c) and 2-amino-N,N,2-trimethylpropanamide.

1H NMR (400 MHz, DMSO-$d_6$) δ 9.22 (s, 1H), 8.74 (dd, J=6.9, 2.4 Hz, 3H), 8.68 (d, J=5.6 Hz, 1H), 8.38 (d, J=5.6 Hz, 1H), 8.36-8.31 (m, 2H), 2.95-2.69 (m, 6H), 1.6 (s, 6H). LCMS (m/z [M+H]$^+$): 337.2, $Rt_1$=0.58 min.

Example 315: $N^1$,3-dimethyl-$N^1$-(2-(pyridin-4-yl)pyrido[3,4-d]pyrimidin-4-yl)butane-1,3-diamine

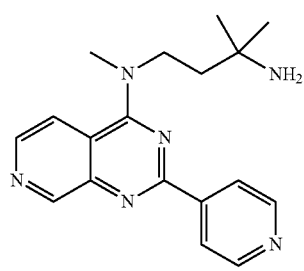 [SMILES: CN(CCC(C)(C)N)c1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and N¹,3-dimethylbutane-1,3-diamine.

1H NMR (400 MHz, DMSO-d$_6$) δ 9.20 (s, 1H), 8.83-8.69 (m, 2H), 8.55 (d, J=5.8 Hz, 1H), 8.40-8.29 (m, 2H), 8.12 (d, J=5.9 Hz, 1H), 4.04-3.92 (m, 2H), 3.52 (s, 3H), 1.87-1.74 (m, 2H), 1.56 (s, 2H), 1.15 (s, 6H). LCMS (m/z [M+H]$^+$): 323.2, Rt$_1$=0.49 min.

Example 316: tert-butyl (2,2-dimethyl-3-((2-(pyridin-4-yl)pyrido[3,4-d]pyrimidin-4-yl)amino)propyl)carbamate

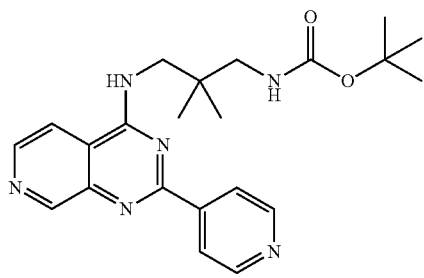 [SMILES: CC(C)(CNC(=O)OC(C)(C)C)CNc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and tert-butyl (3-amino-2,2-dimethylpropyl)carbamate.

1H NMR (600 MHz, DMSO-d$_6$) δ 9.20 (s, 1H), 8.77 (d, J=4.9 Hz, 2H), 8.68 (d, J=5.4 Hz, 1H), 8.61 (t, J=6.4 Hz, 1H), 8.43-8.30 (m, 2H), 8.17 (d, J=5.5 Hz, 1H), 7.01 (t, J=6.6 Hz, 1H), 3.62 (d, J=6.2 Hz, 2H), 2.93 (d, J=6.3 Hz, 2H), 1.38 (s, 9H), 0.92 (s, 6H). LCMS (m/z [M+H]$^+$): 409.3, Rt$_1$=1.06 min.

Example 317: 2,2-dimethyl-N¹-(2-(pyridin-4-yl)pyrido[3,4-d]pyrimidin-4-yl)propane-1,3-diamine

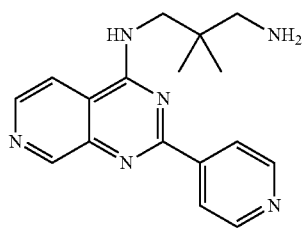 [SMILES: CC(C)(CN)CNc1nc(-c2ccncc2)nc2cnccc12]

The title compound was synthesized in analogy of Example 1 in 2 steps from 4-chloro-2-(pyridin-4-yl)pyrido[3,4-d]pyrimidine (Intermediate 1c) and tert-butyl (3-amino-2,2-dimethylpropyl)carbamate (step 1) and Boc-deprotection using TFA (step 2).

1H NMR (400 MHz, DMSO-d$_6$) δ 9.18 (s, 1H), 8.81-8.71 (m, 2H), 8.65 (d, J=5.6 Hz, 1H), 8.39-8.29 (m, 2H), 8.16 (d, J=5.6 Hz, 1H), 3.67 (s, 2H), 0.95 (s, 6H). LCMS (m/z [M+H]$^+$): 309.2, Rt$_1$=0.43 min.

Example 318: 3-methyl-3-((2-(pyridin-4-yl)pyrido[3,4-d]pyrimidin-4-yl)amino)butanamide

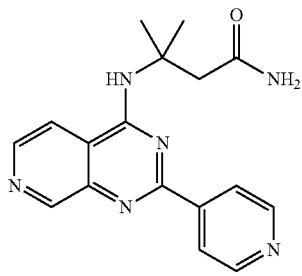 [SMILES: CC(C)(CC(N)=O)Nc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and 3-amino-3-methylbutanamide.

1H NMR (400 MHz, DMSO-d$_6$) δ 9.21 (s, 1H), 8.94-8.80 (m, 2H), 8.77-8.60 (m, 2H), 8.48-8.35 (m, 2H), 8.10 (d, J=5.6 Hz, 1H), 7.59 (s, 1H), 7.12 (s, 1H), 2.76 (s, 2H), 1.71 (s, 6H). LCMS (m/z [M+H]$^+$): 323.3, Rt$_1$=0.57 min.

Example 319: (R)-2-(pyridin-4-yl)-4-(3-(trifluoromethyl)piperazin-1-yl)pyrido[3,4-d]pyrimidine

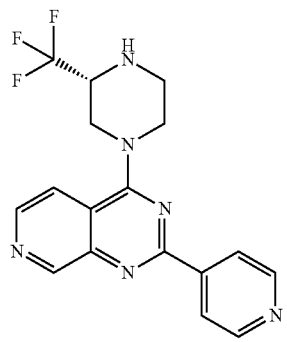 [SMILES: FC(F)(F)[C@H]1CN(c2nc(-c3ccncc3)nc3cnccc23)CCN1]

The title compound was synthesized in analogy of Example 1 from 4-chloro-2-(pyridin-4-yl)pyrido[3,4-d]pyrimidine (Intermediate 1c) and (R)-2-(trifluoromethyl)piperazine.

1H NMR (600 MHz, DMSO-d$_6$) δ 9.31 (s, 1H), 8.79 (d, J=5.3 Hz, 2H), 8.63 (d, J=5.6 Hz, 1H), 8.31 (d, J=4.9 Hz, 2H), 7.97 (d, J=5.7 Hz, 1H), 4.60-4.49 (m, 1H), 4.28-4.21 (m, 1H), 3.82-3.74 (m, 1H), 3.71-3.64 (m, 1H), 3.63-3.56 (m, 1H), 3.20-3.12 (m, 1H), 3.12-3.04 (m, 1H), 2.96-2.87 (m, 1H). LCMS (m/z [M+H]$^+$): 361.1, Rt$_1$=0.72 min.

Example 320: 2,3-dimethyl-N²-(2-(pyridin-4-yl)pyrido[3,4-d]pyrimidin-4-yl)butane-2,3-diamine

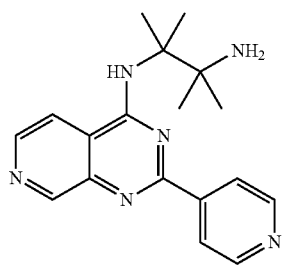 [SMILES: CC(C)(N)C(C)(C)Nc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and 2,3-dimethylbutane-2,3-diamine.

1H NMR (400 MHz, DMSO-d$_6$) δ 9.18 (s, 1H), 8.88-8.74 (m, 2H), 8.66 (d, J=5.5 Hz, 1H), 8.40-8.19 (m, 2H), 7.74 (d, J=5.5 Hz, 1H), 1.63 (s, 6H), 1.21 (s, 6H). LCMS (m/z [M+H]$^+$): 323.2, Rt$_1$=0.48 min.

Example 321: (S)-2-(pyridin-4-yl)-4-(3-(trifluoromethyl)piperazin-1-yl)pyrido[3,4-d]pyrimidine

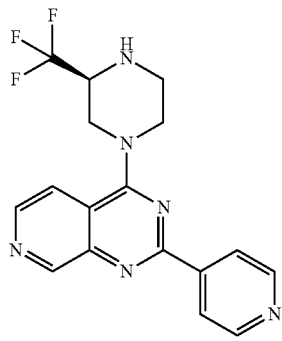 [SMILES: FC(F)(F)[C@@H]1CN(c2nc(-c3ccncc3)nc3cnccc23)CCN1]

The title compound was synthesized in analogy of Example 1 from 4-chloro-2-(pyridin-4-yl)pyrido[3,4-d]pyrimidine (Intermediate 1c) and (S)-2-(trifluoromethyl)piperazine.

1H NMR (600 MHz, DMSO-d$_6$) δ 9.31 (s, 1H), 8.81-8.77 (m, 2H), 8.63 (d, J=5.7 Hz, 1H), 8.34-8.29 (m, 2H), 7.97 (d, J=5.6 Hz, 1H), 4.57-4.52 (m, 1H), 4.28-4.21 (m, 1H), 3.83-3.74 (m, 1H), 3.71-3.65 (m, 1H), 3.63-3.57 (m, 1H), 3.20-3.14 (m, 1H), 3.11-3.05 (m, 1H), 2.95-2.88 (m, 1H). LCMS (m/z [M+H]$^+$): 361.1, Rt$_1$=0.72 min.

Example 322: ethyl 2-methyl-2-((2-(pyridin-4-yl)pyrido[3,4-d]pyrimidin-4-yl)amino)propanoate

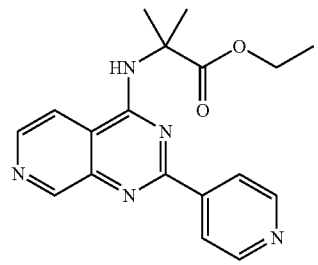 [SMILES: CCOC(=O)C(C)(C)Nc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and ethyl 2-amino-2-methylpropanoate.

1H NMR (400 MHz, DMSO-d$_6$) δ 9.23 (s, 1H), 8.83 (s, 1H), 8.80-8.74 (m, 2H), 8.69 (d, J=5.6 Hz, 1H), 8.39 (d, J=5.6 Hz, 1H), 8.28-8.23 (m, 2H), 3.99 (q, J=7.1 Hz, 2H), 1.69 (s, 6H), 0.91 (t, J=7.1 Hz, 3H). LCMS (m/z [M+H]$^+$): 338.2, Rt$_1$=0.78 min.

Example 323: N¹,N¹,2,2-tetramethyl-N³-(2-(pyridin-4-yl)pyrido[3,4-d]pyrimidin-4-yl)propane-1,3-diamine

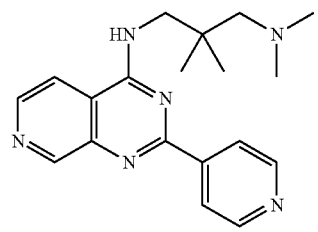 [SMILES: CN(C)CC(C)(C)CNc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and N¹,N¹,2,2-tetramethylpropane-1,3-diamine.

1H NMR (600 MHz, DMSO-d$_6$) δ 9.20-9.17 (m, 1H), 9.04 (t, J=5.6 Hz, 1H), 8.80-8.74 (m, 2H), 8.68-8.63 (m, 1H), 8.38-8.31 (m, 2H), 8.13-8.08 (m, 1H), 3.72-3.65 (m, 2H), 2.36-2.28 (m, 8H), 0.99 (s, 6H). LCMS (m/z [M+H]$^+$): 337.2, Rt$_1$=0.46 min.

Example 324: 4-(4-(tert-butylamino)pyrido[3,4-d]pyrimidin-2-yl)-1,2,5-oxadiazol-3-amine

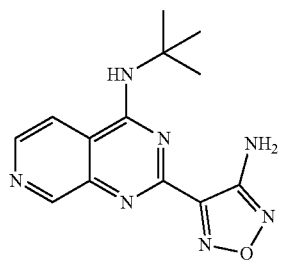 [SMILES: CC(C)(C)Nc1nc(-c2nonc2N)nc2cnccc12]

The title compound was synthesized according to the scheme below from 3-aminoisonicotinamide and 4-amino-1,2,5-oxadiazole-3-carboxylic acid.

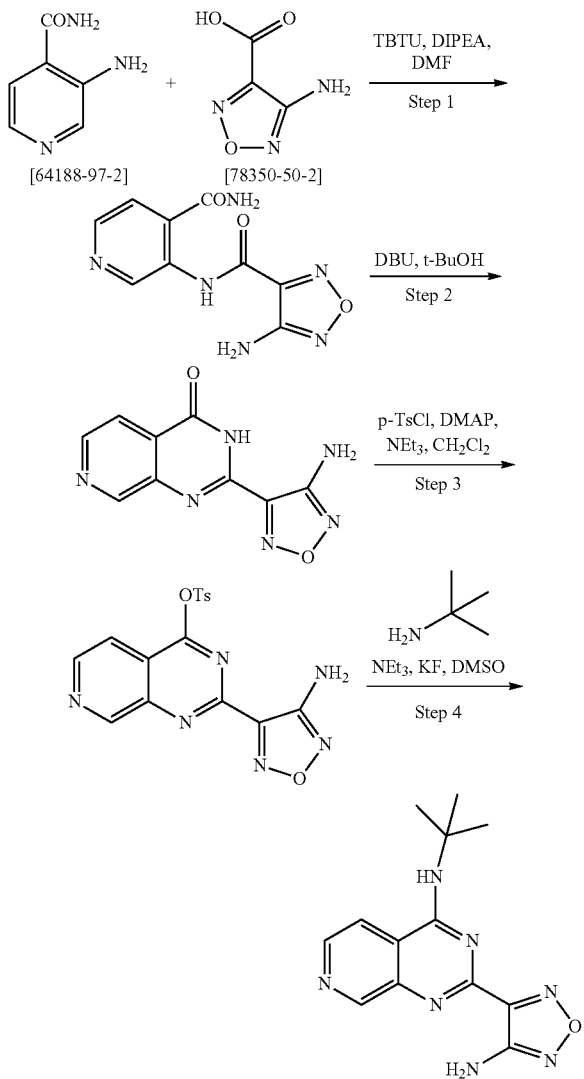

Step 1: 4-amino-N-(4-carbamoylpyridin-3-yl)-1,2,5-oxadiazole-3-carboxamide

In a two necked R.B. flask fitted with thermometer pocket and nitrogen inlet, TBTU (4.75 g, 14.8 mmol) and N,N-diisopropylethylamine (2.6 mL, 14.8 mmol) were added to a stirred solution of 3-aminoisonicotinamide (1.7 g, 12.4 mmol) and 4-amino-1,2,5-oxadiazole-3-carboxylic acid (1.92 g, 14.8 mmol) in DMF (40 mL) at 25-30° C. Resulting reaction mixture was stirred for 72 h at 25-30° C. Reaction mixture was poured over water (200 mL) and precipitated solid was collected by filtration. Washed with water (100 mL). Purification was done by trituration by using 20% ethyl acetate in n-Hexane to get 4-amino-N-(4-carbamoylpyridin-3-yl)-1,2,5-oxadiazole-3-carboxamide (0.84 g, 27.45%) as Off-white solid. $^1$H-NMR (400 MHz, DMSO-d$_6$): δ 12.60 (s, 1H, Exchangeable with D$_2$O), 9.70 (s, 1H), 8.64 (s, 1H, Exchangeable with D$_2$O), 8.52 (d, J=4.4 Hz, 1H), 8.81 (s, 1H, Exchangeable with D$_2$O), 7.80 (d, J=4.8 Hz, 1H), 6.25 (s, 2H, Exchangeable with D$_2$O). LCMS (m/z [M+H]$^+$): 249.1, Rt$_2$=1.312 min.

Step 2: 2-(4-amino-1,2,5-oxadiazol-3-yl)pyrido[3,4-d]pyrimidin-4(3H)-one

In a sealed tube, DBU (0.98 g, 6.45 mmol) was added to a stirred suspension of 4-amino-N-(4-carbamoylpyridin-3-yl)-1,2,5-oxadiazole-3-carboxamide (0.8 g, 3.22 mmol) in tert-butanol (8.0 mL). Sealed the cap and heated reaction mixture to 100° C. for 16 h. Solvent was evaporated, resulting residue was diluted with water (20 mL) and stirred for 0.5 h at 25-30° C. Precipitated solid was collected by filtration, washed solid with water (2×10 mL) and n-hexane (10 mL). The obtained solid were dried at a 55° C. in rotating flask to obtain (0.421 g, 56.73%) of 2-(4-amino-1,2,5-oxadiazol-3-yl)pyrido[3,4-d]pyrimidin-4(3H)-one as off-white solid.
$^1$H-NMR (400 MHz, DMSO-d$_6$): b 13.31 (s, 1H, Exchangeable with D$_2$O), 9.36 (s, 1H), 8.74 (d, J=5.2 Hz, 1H), 8.01 (d, J=5.2 Hz, 1H), 6.95 (s, 2H, Exchangeable with D$_2$O). LCMS (m/z [M+H]$^+$): 231.2, Rt$_2$=1.279 min.

Step 3: 2-(4-amino-1,2,5-oxadiazol-3-yl)pyrido[3,4-d]pyrimidin-4-yl 4-methylbenzenesulfonate In a two necked R.B. flask fitted with, thermometer pocket and nitrogen inlet, DMAP (0.015 g, 0.116 mmol) was added to a stirred solution of 2-(4-amino-1,2,5-oxadiazol-3-yl)pyrido[3,4-d]pyrimidin-4(3H)-one (0.27 g, 1.168 mmol) and triethylamine (0.245 mL, 1.752 mmol) in dichloromethane (10 mL) at 0° C. p-TsCl (0.245 g, 1.168 mmol) was added and stirred resulting reaction mixture for 0.5 h. Allowed reaction mixture to warm to 25-30° C. by removing ice bath and stirred at 25-30° C. for 1.5 h. The mixture was diluted with DCM (20 mL), washed with water (2×20 mL) and brine (20 mL). Dried organic layers over anhydrous sodium sulphate and filtered. Filtrate was concentrated on rotavapor to get 2-(4-amino-1,2,5-oxadiazol-3-yl)pyrido[3,4-d]pyrimidin-4-yl 4-methylbenzenesulfonate (0.285 g, 63.21%) as crude. Crude was used for next step without purification. LCMS (m/z [M+H]$^+$): 385.1, Rt$_2$=1.779 min.

Step 4: 4-(4-(tert-butylamino)pyrido[3,4-d]pyrimidin-2-yl)-1,2,5-oxadiazol-3-amine In a two necked R.B. flask fitted with, thermometer pocket and nitrogen inlet, tert-Butyl amine (0.0714 g, 0.976 mmol) was added to a stirred solution of the 2-(4-amino-1,2,5-oxadiazol-3-yl)pyrido[3,4-d]pyrimidin-4-yl 4-methylbenzenesulfonate (0.25 g, 0.651 mmol) in DMSO (2.5 mL) followed by added KF (0.0566 g, 0.976 mmol) and triethylamine (0.18 mL, 1.304 mmol) at 25-30° C. After being stirred at rt for 45 min reaction mixture was poured over water (25 mL). Precipitated solid was collected by filtration. Washed solid with water (25 mL) and n-hexane (10 mL). Purification was done by trituration in n-hexane: diethyl ether; 1:1(5 mL) to get 4-(4-(tert-butylamino)pyrido[3,4-d]pyrimidin-2-yl)-1,2,5-oxadiazol-3-amine (0.135 g, 72.75%) as Off-white solid.
$^1$H NMR (400 MHz, DMSO-d$_6$) δ ppm 9.30 (s, 1H), 8.67 (d, J=5.57 Hz, 1H), 8.39 (d, J=5.58 Hz, 1H), 8.00 (s, 1H), 6.89 (s, 2H), 1.60 (s, 9H). LCMS (m/z [M+H]$^+$): 286.1, Rt$_1$=0.92 min.

Example 325: N²,N²,2-trimethyl-N¹-(2-(pyridin-4-yl)pyrido[3,4-d]pyrimidin-4-yl)propane-1,2-diamine

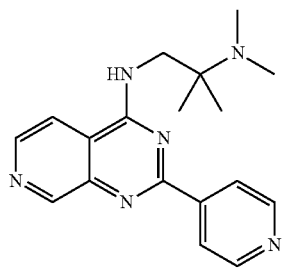 [SMILES: CN(C)C(C)(C)CNc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and N²,N²,2-trimethylpropane-1,2-diamine.

1H NMR (400 MHz, DMSO-d6) δ 9.19 (s, 1H), 8.85-8.72 (m, 2H), 8.65 (d, J=5.6 Hz, 1H), 8.36-8.31 (m, 2H), 8.27 (t, J=6.4 Hz, 2H), 3.79 (d, J=5.6 Hz, 2H), 2.27 (s, 6H), 1.09 (s, 6H). LCMS (m/z [M+H]⁺): 323.2, Rt₁=0.44 min.

Example 326: 2-methyl-2-((2-(pyridin-4-yl)pyrido[3,4-d]pyrimidin-4-yl)amino)propanamide

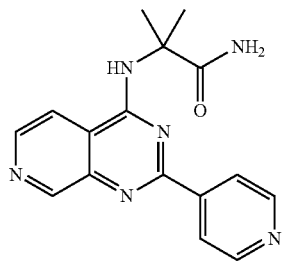 [SMILES: CC(C)(Nc1nc(-c2ccncc2)nc2cnccc12)C(N)=O]

The title compound was synthesized in analogy of Example 1 from 4-chloro-2-(pyridin-4-yl)pyrido[3,4-d]pyrimidine (Intermediate 1c) and 2-amino-2-methylpropanamide.

1H NMR (400 MHz, DMSO-d6) δ 9.20 (s, 1H), 8.77-8.71 (m, 2H), 8.67 (d, J=5.5 Hz, 1H), 8.49 (s, 1H), 8.39 (d, J=5.7 Hz, 1H), 8.36-8.30 (m, 2H), 7.29 (s, 1H), 6.84 (s, 1H), 1.63 (s, 6H). LCMS (m/z [M+H]⁺): 309.2, Rt₁=0.50 min.

Example 327: (S)-1,1,1-trifluoro-2-methyl-3-((2-(pyridin-4-yl)-1,7-naphthyridin-4-yl)amino)propan-2-ol

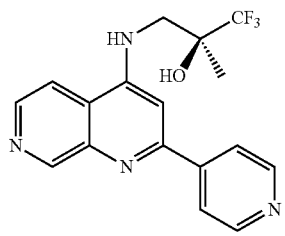 [SMILES: C[C@](O)(CNc1cc(-c2ccncc2)nc2cnccc12)C(F)(F)F]

The title compound was synthesized according to the scheme below from 2,4-dibromo-1,7-naphthyridine.

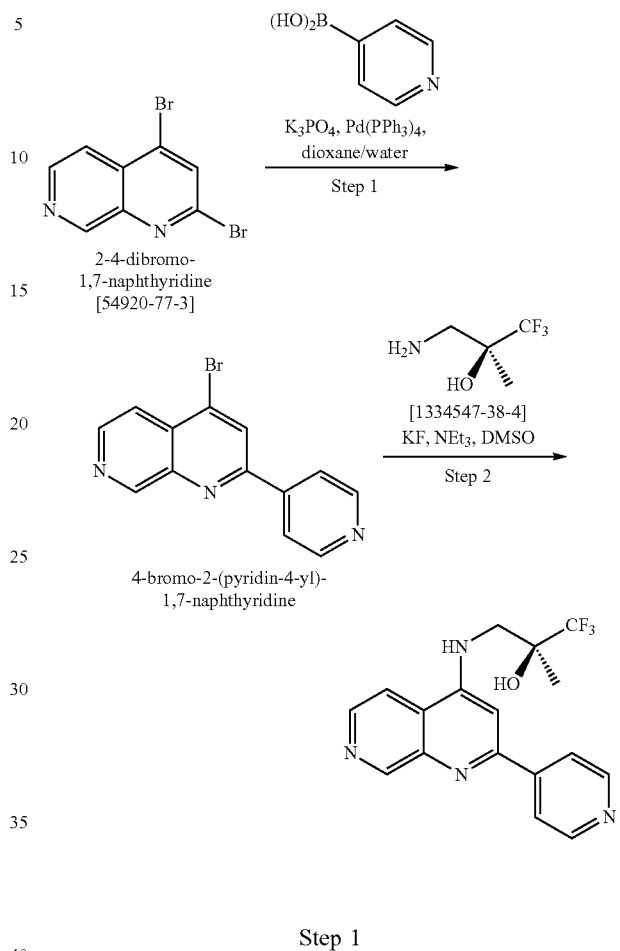

Step 1

A solution of 2,4-dibromo-1,7-naphthyridine (350 mg, 1.22 mmol), 4-pyridinylboronic acid (194 mg, 1.58 mmol), potassium phosphate (1032 mg, 4.86 mmol) and Pd(PPh₃)₄ (140 mg, 0.122 mmol) in dioxane (6 mL)/water (1.5 mL) was heated under argon in a microwave vial at 110° C. for 60 min. Water was added at r.t. and the reaction mixture was extracted 3 times with dichloromethane. The combined organic phases were washed with brine, dried with sodium sulfate and the solvent was evaporated under reduced pressure. The residue was purified by flash chromatography using 0-100% ethyl acetate/cyclohexane to give 4-bromo-2-(pyridin-4-yl)-1,7-naphthyridine (44%). LCMS (m/z [M+H]⁺): 286.0/288.0, Rt₁=0.83 min.

Step 2

The title compound was synthesized in analogy of Example 254 from 4-bromo-2-(pyridin-4-yl)-1,7-naphthyridine and (S)-3-amino-1,1,1-trifluoro-2-methylpropan-2-ol [1334547-38-4].

¹H NMR (600 MHz, DMSO-d₆) b ppm 9.26 (s, 1H), 8.77 (d, J=5.69 Hz, 2H), 8.53 (d, J=5.87 Hz, 1H), 8.20 (d, J=5.69 Hz, 1H), 8.14-8.18 (m, 2H), 7.48-7.55 (m, 2H), 6.34 (s, 1H), 3.82 (dd, J=14.58, 6.33 Hz, 1H), 3.69-3.76 (m, 1H), 1.40 (s, 3H). LCMS (m/z [M+H]⁺): 349.3, Rt=0.62 min.

Example 328: tert-butyl (3-methyl-3-((2-(pyridin-4-yl)pyrido[3,4-d]pyrimidin-4-yl)amino)butyl)carbamate

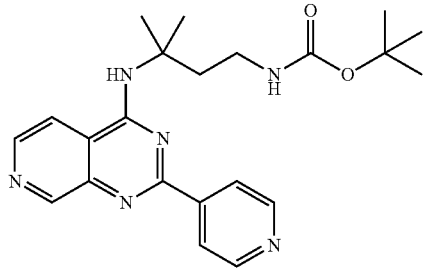 [SMILES: CC(C)(CCNC(=O)OC(C)(C)C)Nc1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and tert-butyl (3-amino-3-methylbutyl)carbamate.

1H NMR (400 MHz, DMSO-d6) δ 9.18 (s, 1H), 8.88-8.73 (m, 2H), 8.64 (d, J=5.6 Hz, 1H), 8.37 (d, J=5.7 Hz, 1H), 8.33-8.25 (m, 2H), 7.73 (s, 1H), 6.75 (s, 1H), 2.97 (t, J=7.6 Hz, 2H), 2.31-2.19 (m, 2H), 1.60 (s, 6H), 1.25 (s, 9H). LCMS (m/z [M+H]$^+$): 409.2, Rt$_1$=0.96 min.

Example 329: $N^1,N^1,N^3$,2,2-pentamethyl-$N^3$-(2-(pyridin-4-yl)pyrido[3,4-d]pyrimidin-4-yl)propane-1,3-diamine

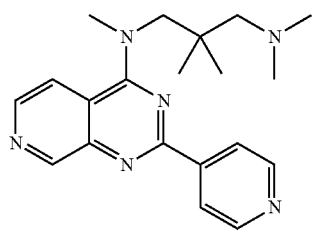 [SMILES: CN(C)CC(C)(C)CN(C)c1nc(-c2ccncc2)nc2cnccc12]

The title compound was synthesized in analogy of Example 1 from 4-chloro-2-(pyridin-4-yl)pyrido[3,4-d]pyrimidine (Intermediate 1c) and $N^1,N^1,N^3$,2,2-pentamethyl-propane-1,3-diamine.

1H NMR (400 MHz, DMSO-d6) δ 9.18 (s, 1H), 8.76 (d, 2H), 8.54 (d, J=5.9 Hz, 1H), 8.34 (d, 2H), 8.23 (d, J=5.9 Hz, 1H), 4.11 (s, 2H), 3.66 (s, 3H), 2.30 (s, 6H), 2.23 (s, 2H), 0.96 (s, 6H). LCMS (m/z [M+H]$^+$): 351.2, Rt$_1$=0.50 min.

Example 330: N,N-diethyl-3-methyl-$N^3$-(2-(pyridin-4-yl)pyrido[3,4-d]pyrimidin-4-yl)butane-1,3-diamine

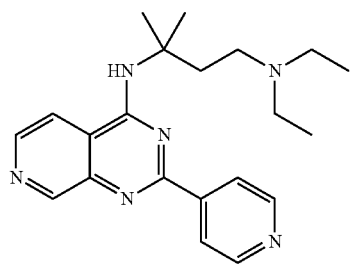 [SMILES: CCN(CC)CCC(C)(C)Nc1nc(-c2ccncc2)nc2cnccc12]

The title compound was synthesized according to the scheme below from Example 328 (tert-butyl (3-methyl-3-((2-(pyridin-4-yl)pyrido[3,4-d]pyrimidin-4-yl)amino)butyl)carbamate).

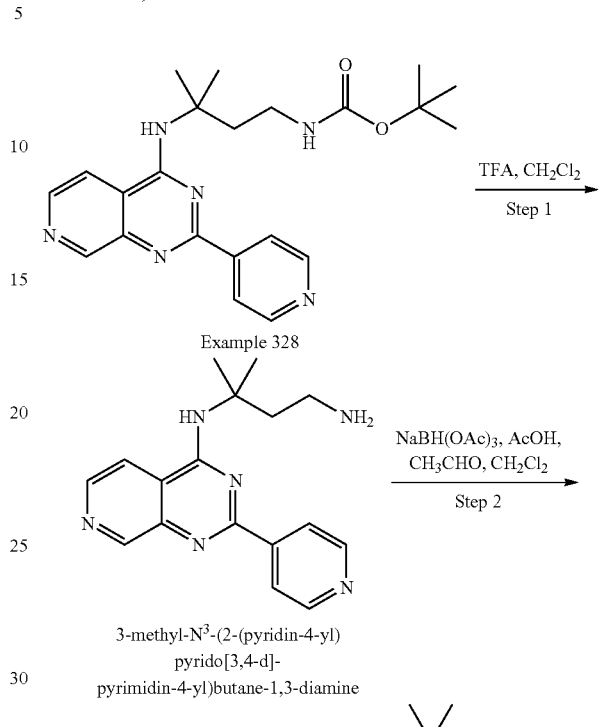

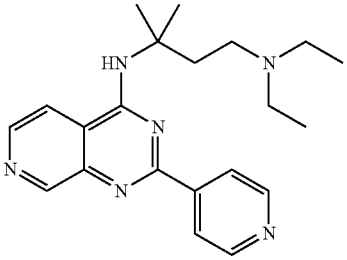

Step 1

To a solution of tert-butyl (3-methyl-3-((2-(pyridin-4-yl)pyrido[3,4-d]pyrimidin-4-yl)amino)butyl)carbamate (80 mg, 0.196 mmol) in dichloromethane (2 mL) was added TFA (0.377 mL, 4.90 mmol) and the resulting yellow solution was stirred at r.t. for 2 h. Then the solution was evaporated to dryness. The residue was dissolved in MeOH and the solution was given on a PoraPak Rxn CX 20 cc (2 g) cartridge. The cartridge was then washed twice with 5 mL MeOH. Finally, the compound was eluted with 7N NH$_3$ in MeOH. The filtrate was evaporated under reduced pressure to give 3-methyl-$N^3$-(2-(pyridin-4-yl)pyrido[3,4-d]pyrimidin-4-yl)butane-1,3-diamine (66%). LCMS (m/z [M+H]$^+$): 309.1, Rt$_1$=0.53 min.

Step 2

A solution of 3-methyl-$N^3$-(2-(pyridin-4-yl)pyrido[3,4-d]pyrimidin-4-yl)butane-1,3-diamine (40 mg, 0.130 mmol), acetic acid (0.037 mL, 0.649 mmol) and acetaldehyde (57 mg, 1.297 mmol) in dichloromethane (5 mL) was stirred at r.t. for 1 h. Then NaBH(OAc)$_3$ (137 mg, 0.649 mmol) was added and the mixture was stirred for further 1 h at r.t.

Saturated NaHCO₃-solution was added and the aqueous phase was extracted 3 times with dichloromethane (3×20 mL). The combined organic phases were washed with brine, dried with sodium sulfate and the solvent was evaporated under reduced pressure. The residue was purified by flash chromatography using a gradient of 12-100% ethyl acetate/cyclohexane followed by a gradient of 2-30% methanol (+10% 7N NH₃ in methanol)/dichloromethane to give a yellow oil. The oil was taken up in dichloromethane (2 mL) and 4N HCL in dioxane (0.2 mL) was added. The precipitate was filtered off and washed with pentane to give the title compound as HCL salt (17%).

1H NMR (400 MHz, Methanol-d4) δ 9.52 (s, 1H), 9.22-9.02 (m, 4H), 8.82 (d, J=6.2 Hz, 1H), 8.74 (dd, J=6.2, 0.9 Hz, 1H), 3.27 (dd, J=8.4, 4.7 Hz, 2H), 3.21 (q, J=7.3 Hz, 4H), 2.84-2.70 (m, 2H), 1.79 (s, 6H), 1.23 (t, J=7.3 Hz, 6H). LCMS (m/z [M+H]⁺): 365.2, Rt₁=0.59 min.

Example 331: N³-(2-(2-fluoropyridin-4-yl)pyrido[3,4-d]pyrimidin-4-yl)-N¹,N¹,3-trimethylbutane-1,3-diamine

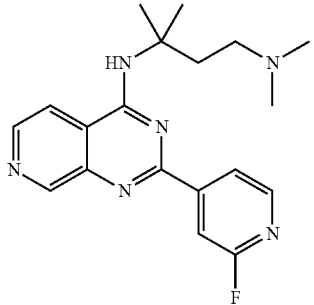 [SMILES: CN(C)CCC(C)(C)Nc1nc(-c2ccnc(F)c2)nc2cnccc12]

The title compound was synthesized in analogy of Example 111 in 2 steps from 2,4-dichloropyrido[3,4-d]pyrimidine (Intermediate 2c) and N¹,N¹,3-trimethylbutane-1,3-diamine (step 1) and from N³-(2-chloropyrido[3,4-d]pyrimidin-4-yl)-N¹,N1,3-trimethylbutane-1,3-diamine and (2-fluoropyridin-4-yl)boronic acid (CAS no. 401815-98-3, step 2).

1H NMR (400 MHz, DMSO-d6) δ 9.53 (s, 1H), 9.18 (s, 1H), 8.69 (d, J=5.5 Hz, 1H), 8.46 (d, J=5.2 Hz, 1H), 8.26 (dd, J=4.7, 2.0 Hz, 1H), 7.92 (s, 1H), 7.85 (d, J=5.6 Hz, 1H), 2.26 (s, 6H), 2.00 (t, J=6.4 Hz, 2H), 1.66 (s, 6H), remark: one CH2 signal is overlapping with DMSO signal. LCMS (m/z [M+H]⁺): 355.2, Rt₁=0.67 min.

Example 332: N³-(2-(3,5-dimethyl-1H-pyrazol-4-yl)pyrido[3,4-d]pyrimidin-4-yl)-N¹,N¹,3-trimethylbutane-1,3-diamine

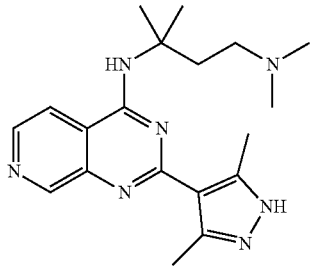 [SMILES: Cc1n[nH]c(C)c1-c1nc(NC(C)(C)CCN(C)C)c2ccncc2n1]

The title compound was synthesized in analogy of Example 111 in 2 steps from 2,4-dichloropyrido[3,4-d]pyrimidine (Intermediate 2c) and N¹,N¹,3-trimethylbutane-1,3-diamine (step 1) and from N³-(2-chloropyrido[3,4-d]pyrimidin-4-yl)-N¹,N1,3-trimethylbutane-1,3-diamine and tert-butyl 3,5-dimethyl-4-(4,4,5,5-tetramethyl-1,3,2-dioxaborolan-2-yl)-1H-pyrazole-1-carboxylate (CAS no. 1073354-70-7, step 2).

1H NMR (400 MHz, DMSO-d6) δ 12.41 (s, 1H), 9.11 (s, 1H), 8.95 (s, 1H), 8.49 (d, J=5.5 Hz, 1H), 7.68 (d, J=5.6 Hz, 1H), 2.56 (s, 6H), 2.27 (s, 6H), 1.92 (t, J=6.1 Hz, 2H), 1.61 (s, 6H). remark: one CH2 signal is overlapping with DMSO signal. LCMS (m/z [M+H]⁺): 354.2, Rt₁=0.50 min.

Example 333: N¹,N,3-trimethyl-N³-(2-(3-(trifluoromethyl)-1H-pyrazol-4-yl)pyrido[3,4-d]pyrimidin-4-yl)butane-1,3-diamine

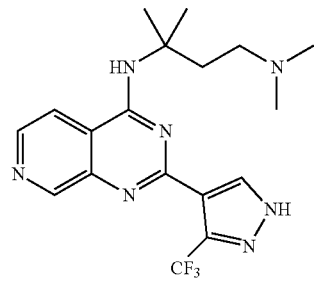 [SMILES: CN(C)CCC(C)(C)Nc1nc(-c2c[nH]nc2C(F)(F)F)nc2cnccc12]

The title compound was synthesized in analogy of Example 111 in 2 steps from 2,4-dichloropyrido[3,4-d]pyrimidine (Intermediate 2c) and N¹,N¹,3-trimethylbutane-1,3-diamine (step 1) and from N³-(2-chloropyrido[3,4-d]pyrimidin-4-yl)-N¹,N¹,3-trimethylbutane-1,3-diamine and 4-(4,4,5,5-tetramethyl-1,3,2-dioxaborolan-2-yl)-3-(trifluoromethyl)-1H-pyrazole (CAS no. 1218790-40-9, step 2).

1H NMR (400 MHz, DMSO-d6) δ 13.80 (s, 1H), 9.25 (s, 1H), 8.96 (s, 1H), 8.57 (d, J=5.5 Hz, 1H), 8.46 (s, 1H), 7.75 (d, J=5.6 Hz, 1H), 2.25 (s, 6H), 1.93 (t, J=6.3 Hz, 2H), 1.60 (s, 6H). remark: one CH2 signal is overlapping with DMSO signal. LCMS (m/z [M+H]⁺): 394.3, Rt₁=0.62 min.

Example 334: N³-(2-(2-aminopyridin-4-yl)pyrido[3,4-d]pyrimidin-4-yl)-N¹,N¹,3-trimethylbutane-1,3-diamine

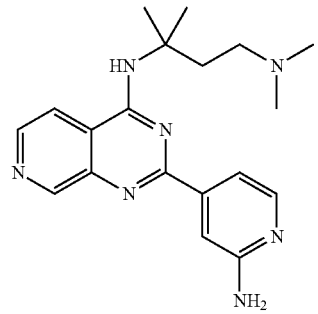 [SMILES: CN(C)CCC(C)(C)Nc1nc(-c2ccnc(N)c2)nc2cnccc12]

The title compound was synthesized in analogy of Example 111 in 3 steps from 2,4-dichloropyrido[3,4-d]pyrimidine (Intermediate 2c) and N¹,N¹,3-trimethylbutane- 1,3-diamine (step 1), from $N^3$-(2-chloropyrido[3,4-d]pyrimidin-4-yl)-$N^1$,$N^1$,3-trimethylbutane-1,3-diamine and tert-butyl (4-(4,4,5,5-tetramethyl-1,3,2-dioxaborolan-2-yl)pyridin-2-yl)carbamate CAS no. 1095708-32-9 (step 2) and Boc-deprotection using TFA (step 3).

1H NMR (400 MHz, DMSO-d6) δ 9.30 (s, 1H), 9.11 (s, 1H), 8.62 (d, J=5.6 Hz, 1H), 8.07 (d, J=5.3 Hz, 1H), 7.82 (d, J=5.6 Hz, 1H), 7.49 (s, 1H), 7.43 (dd, J=5.3, 1.4 Hz, 1H), 6.11 (s, 2H), 2.47 (d, J=8.1 Hz, 2H), 2.24 (s, 6H), 1.99 (t, J=6.4 Hz, 2H), 1.66 (s, 6H). LCMS (m/z [M+H]$^+$): 352.2, $Rt_1$=0.48 min.

Example 335: 3-methyl-$N^1$-(2-(pyridin-4-yl)pyrido[3,4-d]pyrimidin-4-yl)butane-1,3-diamine

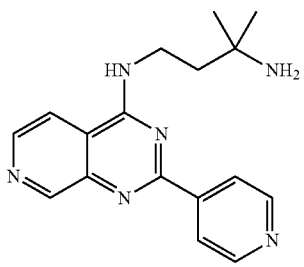 [SMILES: CC(C)(N)CCNc1nc(-c2ccncc2)nc2cnccc12]

The title compound was synthesized in analogy of Example 1 in 2 steps from 4-chloro-2-(pyridin-4-yl)pyrido[3,4-d]pyrimidine (Intermediate 1c) and tert-butyl (4-amino-2-methylbutan-2-yl)carbamate (step 1) and Boc-deprotection using TFA (step 2).

1H NMR (400 MHz, DMSO-d6) δ 9.18 (s, 1H), 8.80-8.71 (m, 2H), 8.63 (d, J=5.5 Hz, 1H), 8.37-8.31 (m, 2H), 8.07 (d, J=5.5 Hz, 1H), 3.83-3.73 (m, 2H), 1.80-1.68 (m, 2H), 1.15 (s, 6H), 3 exchangeable protons. LCMS (m/z [M+H]$^+$): 309.2, $Rt_1$=0.45 min.

Ex-Vivo Cell Population Expansion and Use in Therapy
Starting Material to Prepare an Expanded Population of Cells:
Autologous Method The seeding population of cells for use in the method of cell population expansion to obtain an expanded population of cells may be obtained from a recipient himself/herself. In patients where tissue, organ, or cell deficiency is partial, for example healthy cells are present, the seeding population of cells may be obtained from non-affected tissue or organ or cell source. For example, in the case of unilateral ocular cell deficiency, the seeding population may be obtained from a biopsy on the non-affected eye. It may also be obtained from healthy tissue remaining in an organ that is partially damaged.

Allogenic Method

In a preferred embodiment, the seeding population of cells for use in the method of cell population expansion to obtain an expanded population of cells may be obtained from cells originally derived from donor tissue (e.g. human, rabbit, monkey etc, preferably human). For example a source of human tissue is from cadaveric donors or tissues from living donors, including living relatives.

From autologous or allogenic tissue derived as described above under autologous and allogenic methods which has been removed from the body, the cells may, for example, be extracted and prepared as follows: The desired area may be dissected, for example, using scalpels and the cells then dissociated (e.g. using collagenase, dispase, trypsin, accutase or TripLE; for example 1 mg/ml collagenase at 37° C.), until cell detachment becomes apparent by microscopic observation (e.g. using a Zeiss Axiovert inverted microscope) from 45 minutes to 3 hours.

For use in the cell population expansion method according to the invention the isolated cells are then added to medium, for example by pipetting, as described below in the section "Cell population expansion".

In a preferred embodiment according to the invention, an assessment of the quality of cellular material harvested from the donor is performed. For example, approximately 24 hours after harvesting the cells and beginning culturing in medium (growth or cell proliferation medium, as described below), a visual assessment under brightfield microscope to look for floating cells present (as an indicator of dead cells) may be performed. Ideally this assessment is to show that there is approximately less than 10% as floating cells for the material to be suitable for use to generate an expanded population of cells according to the invention.

The number of cells suitable for use in the method of cell population expansion according to the invention is not limited, but as an example for illustrative purposes, the seeding cell population suitable for use in the method of cell population expansion according to the invention may comprise approximately 1000 cells.

If it is desired to measure the cell numbers in the seeding cell population, this may be done for example by manual or automated cell counting using a light microscope, immuno-histochemistry or FACS according to standard protocols well known in the art.

Ex-Vivo Ocular Cell Population Expansion and Use in Therapy

Described below in more detail is a description of the methodology relating to expansion of ocular cell populations (preparation of starting material, followed by cell population expansion phase, storage of cells) as applied to ocular cells with the specific examples of limbal stem cells and corneal endothelial cells.

Starting Material to Prepare an Expanded Population of Limbal Stem Cells: Corneal Epithelial and Limbal Cells
Autologous Method The seeding population of cells for use in the method of cell population expansion to obtain an expanded population of limbal stem cells may be obtained from the recipient himself/herself. In patients where limbal stem cell deficiency is partial, the seeding population of cells may be obtained from non-affected parts of the limbus. For example, in the case of unilateral limbal stem cell deficiency, the seeding population may be obtained from a biopsy on the non-affected eye. It may also be obtained from healthy tissue remaining in a limbus that is partially damaged.

Allogenic Method

In a preferred embodiment, the seeding population of cells for use in the method of cell population expansion to obtain an expanded population of limbal stem cells may be obtained from cells originally derived from donor mammalian corneal tissue (e.g. human, rabbit, monkey etc, preferably human).

For example a source of human corneal tissue is from cadaveric donors (for example sourced through eye banks) or tissues from living donors, including living relatives. A range of donor limbal tissue is suitable for use according to the invention. In a preferred embodiment limbal tissue is obtained from living relatives or donors with a compatible HLA profile.

The tissue that is used to obtain the LSCs may, for example, be a ring of limbal tissue of approximately 4 mm in width and 1 mm in height.

From the corneal tissue as described above under autologous and allogenic methods which has been removed from the body, the LSCs may, for example, be extracted and prepared as follows: The limbal epithelial area may be dissected, for example, using scalpels and the cells then dissociated (e.g. using collagenase, dispase, trypsin, accutase or TripLE; for example 1 mg/ml collagenase at 37° C.), until cell detachment becomes apparent by microscopic observation (e.g. using a Zeiss Axiovert inverted microscope) from 45 minutes to 3 hours.

For use in the cell population expansion method according to the invention the isolated cells are then added to medium, for example by pipetting, as described below in the section "Cell population expansion".

In a preferred embodiment according to the invention, an assessment of the quality of cellular material harvested from the donor cornea is performed. For example, approximately 24 hours after harvesting the cells and beginning culturing in medium (growth or cell proliferation medium, as described below), a visual assessment under brightfield microscope to look for floating cells present (as an indicator of dead cells) may be performed. Ideally this assessment is to show that there is approximately less than 10% as floating cells for the material to be suitable for use to generate an expanded population of cells according to the invention.

The number of cells suitable for use in the method of cell population expansion according to the invention is not limited, but as an example for illustrative purposes, the seeding cell population suitable for use in the method of cell population expansion according to the invention may comprise approximately 1 000 limbal stem cells.

If it is desired to measure the cell numbers in the seeding cell population, this may be done for example by manual or automated cell counting using a light microscope, immunohistochemistry or FACS according to standard protocols well known in the art.

Starting Material to Prepare an Expanded Population of Corneal Endothelial Cells The seeding population of corneal endothelial cells (CECs) for use in the method of cell population expansion may be obtained from cells originally derived from mammalian corneal tissue (e.g. human, rabbit, monkey etc, preferably human). For example, a source of human corneal tissue is from cadaveric human donors (which may be sourced through eye banks).

The age of the donors can range, for example, from infancy to 70 years of age. Preferably also suitable donors are those who have no history of corneal disease or trauma. In one embodiment according to the invention, preferred donor corneas are those where the corneal endothelial cell count is above 2 000 cells/mm$^2$ (area). In a more preferred embodiment according to the invention the corneal endothelial cell count is 2 000 to 3 500 cells/mm$^2$ (area). This is measured for example by examining the cornea of the donor material under a direct light microscope or a specular microscope as per standard Eye Bank techniques known in the art for evaluation of donor tissue before transplantation to patients (see Tran et al (2016) Comparison of Endothelial Cell Measurements by Two Eye Bank Specular Micorscopes; International Journal of Eye Banking; vol 4, no 2; 1-8, which is herein incorporated by reference).

The surface of cornea that is used to obtain the CECs is not limited, but may, for example, be an area of approx. 8-10 mm in diameter.

The CECs may, for example, be extracted and prepared as follows from the donor corneal tissue: The corneal endothelial cell layer and Descemet's membrane (DM) are scored, for example with a surgical-grade reverse Sinsky endothelial stripper. The DM-endothelial cell layer is peeled off the corneal stroma and cells are dissociated from the DM, for example using 1 mg/ml collagenase at 37° C. until cell detachment becomes apparent by microscopic observation (e.g. using a Zeiss Axiovert inverted microscope) (from 45 minutes to 3 hours). As the DM only carries corneal endothelial cells in the cornea, the cell population isolated in this manner is a population of CECs, which is suitable for use as a seeding population of cells according to the invention.

For use in the method of cell population expansion according to the invention the isolated corneal endothelial cells may be added to medium as described below in the section "Cell population expansion".

In a preferred embodiment according to the invention, an assessment of the quality of cellular material harvested from the donor cornea is performed. For example, approximately 24 hours after harvesting the cells and beginning culturing in medium (growth or cell proliferation medium, as described below), a visual assessment under brightfield microscope to look for floating cells present (as an indicator of dead cells) may be performed. Ideally this assessment is to show that there is approximately less than 10% as floating cells for the material to be suitable for use to generate an expanded population of cells according to the invention.

The starting number of cells suitable for use in the method of cell population expansion according to the invention is not limited, but as an example for illustrative purposes, the seeding population of corneal endothelial cells suitable for use in the method of cell population expansion according to the invention may be 100 000 to 275 000 cells.

If it is desired to measure the cell numbers in the seeding cell population, this may be done for example by taking an aliquot and performing immunocytochemistry (e.g. to count nuclei stained with Sytox Orange) or by live cell imaging under brightfield microscope to count the number of cells.

The Sytox Orange assay may be performed according to standard protocols known in the art. In brief, after cells have attached to the cell culture dish (typically 24 h after cell plating), the cells are fixed in paraformaldehyde. The cells are then permeabilized (e.g. using a solution of 0.3% Triton X-100) and they are then labeled in a solution of Sytox Orange (e.g. using 0.5 micromolar of Sytox Orange in PBS). The number of nuclei stained with Sytox Orange per surface area are then counted under a Zeiss epifluorescence microscope.

Cell Population Expansion

In one embodiment of the invention, a population of cells comprising cells from a patient or a donor, can be grown in medium in a culture container known in the art, such as plates, multi-well plates, and cell culture flasks. For example, a culture dish may be used which is non-coated or coated with collagen, synthemax, gelatin or fibronectin. A preferred example of a suitable culture container is a non-coated plate. Standard culturing containers and equipment such as bioreactors known in the art for industrial use may also be used.

The medium used may be a growth medium or a cell proliferation medium. In general, a growth medium is a culture medium supporting the growth and maintenance of a population of cells. Those of skill in art can readily determine an appropriate growth medium for a particular type of cell population. Suitable growth mediums are known in the art for stem cell culture or epithelial cell culture are for example: DMEM (Dulbecco's Modified Eagle's Medium) supplemented with FBS (Fetal Bovine Serum) (Invitrogen), human endothelial SF (serum free) medium (Invitrogen) supplemented with human serum, X-VIVO15 medium (Lonza), or DMEM/F12 (Thermo Fischer Scientific) (optionally supplemented with calcium chloride). These may be additionally supplemented with growth factors (e.g. bFGF), and/or antibiotics such as penicillin and streptomycin.

Alternatively, isolated cells may be added first to a cell proliferation medium according to the invention. The cell proliferation medium as defined herein comprises a growth medium and a LATS inhibitor according to the invention.

In certain embodiments, a cell proliferation medium of the invention comprises a growth medium and a LATS inhibitor according to the invention. The LATS inhibitor is preferably selected from the group comprising compounds according to Formula A1 or subformulae thereof and as further described under the section "LATS inhibitors".

In a preferred embodiment the LATS inhibitors according to Formula A1 or subformulae thereof are added at a concentration of about 0.5 to 100 micromolar, preferably about 0.5 to 25 micromolar, more preferably about 1 to 20 micromolar. In a specific embodiment the LATS inhibitors according to Formula A1 or subformulae thereof are added at a concentration of about 3 to 10 micromolar.

In one embodiment, the stock solution of the compound according to Formula A1 or subformulae thereof may be prepared by dissolving the compound powder to a stock concentration of 10 mM in DMSO.

In one aspect of the invention the LATS inhibitor according to the invention inhibits LATS1 and/or LATS2 activity in the cell population. In a preferred embodiment the LATS inhibitor inhibits LATS1 and LATS2.

The cells may go through a round or rounds of addition of fresh growth medium and/or cell proliferation medium. The cells do not need to be passaged in order for fresh medium to be added, but passaging cells is also a way to add fresh medium.

A series of mediums may be also used, in various combinations of orders: for example a cell proliferation medium, followed by addition of a growth medium (which is not supplemented with LATS inhibitors according to the invention, and may be different to the growth medium used as the base for the cell proliferation medium).

The cell population expansion phase according to the invention occurs during the period the cells are exposed to the cell proliferation medium.

Standard temperature conditions known in the art for culturing cells may be used, for example preferably about 30° C. to 40° C. Particularly preferably cell growth, as well as the cell population expansion phase is carried out at about 37° C. A conventional cell incubator with 5-10% $CO_2$ levels may be used. Preferably the cells are exposed to 5% $CO_2$.

The cells may be passaged during the culturing in the growth or cell proliferation medium as necessary. Cells may be passaged when they are sub-confluent or confluent. Preferably the cells are passaged when they reach approximately 90%-100% confluency, although lower percentage confluency levels may also be performed. The passaging of cells is done according to standard protocols known in the art. For example, in brief cells are passaged by treating cultures with Accutase (e.g. for 10 minutes), rinsing the cell suspension by centrifugation and plating cells in fresh growth medium or cell proliferation medium as desired. Cell splitting ratios range, for example, from 1:2 to 1:5.

For the cell population expansion phase of the method of cell population expansion according to the invention, the expansion of the seeding cell population in the cell proliferation medium may be performed until the required amount of cellular material is obtained.

The cells may be exposed to the cell proliferation medium for a range of time periods in order to expand the cell population.

In a preferred embodiment the seeding cell population is exposed to the LATS inhibitors according to the invention (such as those compounds according to Formula A1 or subformulae thereof) directly after cell isolation from the patient or donor tissue and maintained for the entire time that cell proliferation is required, for example 12 to 16 days.

In one embodiment according to the invention, a gene editing technique may optionally be performed to genetically modify cells and/or to express a biotherapeutic compound. For example, the cells may be modified to reduce or eliminate the expression and/or function of an immune response mediating gene, which may otherwise contribute to immune rejection when the cell population is delivered to the patient. The application of gene editing techniques in the method of cell population expansion according to the invention is optional, and the administration to the patient of topical immunosuppressants and/or anti-inflammatory agents (as described further under the section Immunosuppressant and Anti-inflammatory agent) may instead be used if desired to mitigate issues with immunorejection of the transplanted material in the patient.

According to one aspect of the invention, genetically modifying comprises reducing or eliminating the expression and/or function of a gene associated with facilitating a host versus graft immune response. In a preferred embodiment, genetically modifying comprises introducing into an isolated stem cell or stem cell population a gene editing system which specifically targets a gene associated with facilitating a host versus graft immune response. In a specific embodiment, said gene editing system is selected from the group consisting of CRISPR (CRISPR: clustered regularly interspaced short palindromic repeats, also known as CRISPR/Cas systems), ZFN (Zinc-finger nucleases), TALEN (transcription activator-like effector based nucleases), engineered meganucleases (e.g. ARCUS nucleases, such as the ARC nuclease), AAV vector (adeno-associated virus) and lentiviral vectors-based genome editing technologies.

A gene editing technique, if it is to be used, may be performed at different points, such as for example (1) on tissue, before cell isolation or (2) at the time of cell isolation or (3) during the cell population expansion phase in vitro (when the cells are exposed to a LATS inhibitor according to the invention in vitro) or (4) in vitro at the end of the cell population expansion phase (after the cells are exposed to a LATS inhibitor according to the invention in vitro). In a specific embodiment, CRISPR is used after two weeks of in vitro expansion of the cell population in the presence of the LATS inhibitor according to the invention.

The gene editing techniques suitable for use in the method of cell population expansion are further described under the section "reduction of immunorejection".

In the method of cell population expansion according to the invention the LATS inhibitors, which are preferably compounds, produce greater than 2 fold expansion of the seeded population of cells.

In one aspect of the method of cell population expansion according to the invention the compounds according to Formula A1 or subformulae thereof produce greater than 30 fold expansion of the seeded population of isolated cells (i.e., cells obtained from a patient or a donor). In a specific embodiment of the method of cell population expansion according to the invention, the LATS inhibitors according to Formula A1 or subformulae thereof produce 100 fold to 2200 fold expansion of the seeded population of isolated cells. In a more specific embodiment of the method of cell population expansion according to the invention, the LATS inhibitors according to Formula A1 or subformulae thereof produce 600 fold to 2200 fold expansion of the seeded population of isolated cells. The fold expansion factor achieved by the method of cell population expansion according to the invention may be achieved in one or more passages of the cells. In another aspect of the invention the fold expansion factor achieved by the method of cell population expansion according to the invention may be achieved after exposure to the compound according to Formula A1 or subformulae thereof for about 12 to 16 days, preferably about 14 days.

If it is desired to measure the cell number or expansion of the cell population, this may be done for example by taking an aliquot and performing immunocytochemistry (e.g. to count nuclei stained with Sytox Orange) or by live cell imaging under brightfield microscope to count the number of cells or by performing real-time quantitative live-cell analysis of cell confluence at various time points during the cell population expansion phase of the method according to the invention.

The Sytox Orange assay may be performed according to standard protocols known in the art. In brief, after cells have attached to the cell culture dish (typically 24 h after cell plating), the cells are fixed in paraformaldehyde. The cells are then permeabilized (e.g. using a solution of 0.3% Triton X-100) and they are then labeled in a solution of Sytox Orange (e.g. using 0.5 micromolar of Sytox Orange in PBS). The number of nuclei stained with Sytox Orange per surface area are then counted under a Zeiss epifluorescence microscope. The cell population expanded by the method of cell population expansion according to the invention may be added to a solution and then stored, for example in a preservation or cryopreservation solution (such as those described below), or added directly to a composition suitable for delivery to a patient. The preservation, cryopreservation solution or composition suitable for ocular delivery may optionally comprise a LATS inhibitor according to the invention.

In a more preferred embodiment according to the invention, the cell population preparation which is delivered to a patient comprises very low to negligible levels of a LATS inhibitor compound. Thus in a specific embodiment, the method of cell population expansion according to the invention comprises the further step of rinsing to substantially remove the compound according to the invention (such as the compound according to Formula A1 or subformulae thereof). This may involve rinsing the cells after the cell population expansion phase according to the invention. To rinse the cells, the cells are detached from the culture dish (e.g. by treating with Accutase), the detached cells are then centrifuged, and a cell suspension is made in PBS or growth medium according to the invention. This step may be performed multiple times, e.g. one to ten times, to rinse out the cells. Finally the cells may be resuspended in a preservation solution, cryopreservation solution, a composition suitable for ocular delivery, growth medium or combinations thereof as desired.

The expanded population of cells prepared by the method of cell population expansion and rinsed of cell proliferation medium comprising a LATS inhibitor according the invention may be transferred to a composition suitable for delivery to a patient, such as for example a localising agent. Optionally the cell population is stored for a period before addition to a localising agent suitable for delivery to a patient. In a preferred embodiment, the expanded cell population may first be added to a solution suitable for preservation or cryopreservation, which preferably does not comprise a LATS inhibitor, and the cell population stored (optionally with freezing) before addition to a localising agent suitable for delivery to a patient, which also preferably does not comprise a LATS inhibitor.

Typical solutions suitable for cryopreservation, glycerol, dimethyl sulfoxide, propylene glycol or acetamide may be used in the cryopreservation solution of the present invention. The cryopreserved preparation of cells is typically kept at −20° C. or −80° C.

Cell Population Expansion: To Prepare an Expanded Population of Limbal Stem Cells In one embodiment of the invention, a population of cells comprising corneal epithelial and limbal cells, including limbal stem cells, for example obtained as described in the section "Starting material to prepare an expanded population of limbal stem cells: Corneal epithelial and limbal cells", can be grown in medium in a culture container known in the art, such as plates, multi-well plates, and cell culture flasks. For example, a culture dish may be used which is non-coated or coated with collagen, synthemax, gelatin or fibronectin. A preferred example of a suitable culture container is a non-coated plate. Standard culturing containers and equipment such as bioreactors known in the art for industrial use may also be used.

The medium used may be a growth medium or a cell proliferation medium. A growth medium is defined herein as a culture medium supporting the growth and maintenance of a population of cells. Suitable growth mediums are known in the art for stem cell culture or epithelial cell culture are for example: DMEM (Dulbecco's Modified Eagle's Medium) supplemented with FBS (Fetal Bovine Serum) (Invitrogen), human endothelial SF (serum free) medium (Invitrogen) supplemented with human serum, X-VIVO15 medium (Lonza), or DMEM/F12 (Thermo Fischer Scientific) (optionally supplemented with calcium chloride). These may be additionally supplemented with growth factors (e.g. bFGF), and/or antibiotics such as penicillin and streptomycin. A preferred growth medium according to the invention is X-VIVO15 medium (which is not additionally supplemented with growth factors).

Alternatively, the isolated cells may be added first to a cell proliferation medium according to the invention. The cell proliferation medium as defined herein comprises a growth medium and a LATS inhibitor according to the invention. In the cell proliferation medium according to the invention the growth medium component is selected from the group consisting of DMEM (Dulbecco's Modified Eagle's Medium) supplemented with FBS (Fetal Bovine Serum) (Invitrogen), human endothelial SF (serum free) medium (Invitrogen) supplemented with human serum, X-VIVO15 medium (Lonza or DMEM/F12 (Thermo Fischer Scientific) (optionally supplemented with calcium chloride). These may be additionally supplemented with growth factors (e.g. bFGF), and/or antibiotics such as penicillin and streptomycin.

A preferred cell proliferation medium according to the invention is X-VIVO15 medium (Lonza) with a LATS inhibitor according to the invention. This cell proliferation medium has the advantage that it does not need additional growth factors or feeder cells to facilitate the proliferation of the LSCs. X-VIVO medium comprises inter alia pharmaceutical grade human albumin, recombinant human insulin, and pasteurized human transferrin. Optionally antibiotics may be added to X-VIVO15 medium. In a preferred embodiment, X-VIVO15 medium is used without the addition of antibiotics.

The cell proliferation medium comprises a growth medium and a LATS inhibitor according to the invention. The LATS inhibitor is preferably selected from the group comprising compounds according to Formula A1 or subformulae thereof and as further described under the section "LATS inhibitors".

In a preferred embodiment the LATS inhibitors according to Formula A1 or subformulae thereof are added at a concentration of about 0.5 to 100 micromolar, preferably about 0.5 to 25 micromolar, more preferably about 1 to 20 micromolar. In a specific embodiment the LATS inhibitors according to Formula A1 or subformulae thereof are added at a concentration of about 3 to 10 micromolar.

In one embodiment, the stock solution of the compound according to Formula A1 or subformulae thereof may be prepared by dissolving the compound powder to a stock concentration of 10 mM in DMSO.

In one aspect of the invention the LATS inhibitor according to the invention inhibits LATS1 and/or LATS2 activity in the limbal cells. In a preferred embodiment the LATS inhibitor inhibits LATS1 and LATS2.

The cells may go through a round or rounds of addition of fresh growth medium and/or cell proliferation medium. The cells do not need to be passaged in order for fresh medium to be added, but passaging cells is also a way to add fresh medium.

A series of mediums may be also used, in various combinations of orders: for example a cell proliferation medium, followed by addition of a growth medium (which is not supplemented with LATS inhibitors according to the invention, and may be different to the growth medium used as the base for the cell proliferation medium).

The cell population expansion phase according to the invention occurs during the period the cells are exposed to the cell proliferation medium.

Standard temperature conditions known in the art for culturing cells may be used, for example preferably about 30° C. to 40° C. Particularly preferably cell growth, as well as the cell population expansion phase is carried out at about 37° C. A conventional cell incubator with 5-10% $CO_2$ levels may be used. Preferably the cells are exposed to 5% $CO_2$.

The cells may be passaged during the culturing in the growth or cell proliferation medium as necessary. Cells may be passaged when they are sub-confluent or confluent. Preferably the cells are passaged when they reach approximately 90%-100% confluency, although lower percentage confluency levels may also be performed. The passaging of cells is done according to standard protocols known in the art. For example, in brief cells are passaged by treating cultures with Accutase (e.g. for 10 minutes), rinsing the cell suspension by centrifugation and plating cells in fresh growth medium or cell proliferation medium as desired. Cell splitting ratios range, for example, from 1:2 to 1:5.

For the cell population expansion phase of the method of cell population expansion according to the invention, the expansion of the seeding cell population in the cell proliferation medium may be performed until the required amount of cellular material is obtained.

The cells may be exposed to the cell proliferation medium for a range of time periods in order to expand the cell population. For example this may include the entire time that the LSCs are kept in culture, or for the first week after LSC isolation or for 24 hours after dissection of the limbus from the cornea.

In a preferred embodiment the seeding cell population is exposed to the LATS inhibitors according to the invention (such as those compounds according to Formula A1 or subformulae thereof) directly after cell isolation from the cornea and maintained for the entire time that LSC proliferation is required, for example 12 to 16 days.

In one embodiment according to the invention, a gene editing technique may optionally be performed to genetically modify cells, to reduce or eliminate the expression and/or function of an immune response mediating gene which may otherwise contribute to immune rejection when the cell population is delivered to the patient. The application of gene editing techniques in the method of cell population expansion according to the invention is optional, and the administration to the patient of topical immunosuppressants and/or anti-inflammatory agents (as described further under the section Immunosuppressant and Anti-inflammatory agent) may instead be used if desired to mitigate issues with immunorejection of the transplanted material in the patient.

According to one aspect of the invention, genetically modifying comprises reducing or eliminating the expression and/or function of a gene associated with facilitating a host versus graft immune response. In a preferred embodiment, genetically modifying comprises introducing into a limbal stem cell a gene editing system which specifically targets a gene associated with facilitating a host versus graft immune response. In a specific embodiment, said gene editing system is selected from the group consisting of CRISPR (CRISPR: clustered regularly interspaced short palindromic repeats, also known as CRISPR/Cas systems), ZFN (Zinc-finger nucleases), TALEN (transcription activator-like effector based nucleases), engineered meganucleases (e.g. ARCUS nucleases, such as the ARC nuclease), AAV vector (adeno-associated virus) gene editing (e.g., AAV vector driven homologous recombination) and lentiviral vectors-based genome editing technologies. AAV vector driven gene delivery, such as driven by homologous recombination, can be achieved by an AAV selected from the group consisting of: AAV2, AAV3, AAV4, AAV5, AAV6, AAV7, AAV8, AAV9, or a derivative thereof.

A gene editing technique, if it is to be used, may be performed at different points, such as for example (1) on limbal epithelial tissue, before LSC isolation or (2) at the time of cell isolation or (3) during the cell population expansion phase in vitro (when the cells are exposed to a LATS inhibitor according to the invention in vitro) or (4) in vitro at the end of the cell population expansion phase (after the cells are exposed to a LATS inhibitor according to the invention in vitro). In a specific embodiment CRISPR is used after two weeks of in vitro expansion of the cell population in the presence of the LATS inhibitor according to the invention.

The gene editing techniques suitable for use in the method of cell population expansion are further described under the section "reduction of immunorejection".

In the method of cell population expansion according to the invention the LATS inhibitors, which are preferably compounds, produce greater than 2 fold expansion of the seeded population of cells.

In one aspect of the method of cell population expansion according to the invention the compounds according to Formula A1 or subformulae thereof produce greater than 30 fold expansion of the seeded population of limbal cells. In a specific embodiment of the method of cell population expansion according to the invention, the LATS inhibitors according to Formula A1 or subformulae thereof produce 100 fold to 2200 fold expansion of the seeded population of limbal cells. In a more specific embodiment of the method of cell population expansion according to the invention, the LATS inhibitors according to Formula A1 or subformulae thereof produce 600 fold to 2200 fold expansion of the seeded population of limbal cells. The fold expansion factor achieved by the method of cell population expansion according to the invention may be achieved in one or more passages of the cells. In another aspect of the invention the fold expansion factor achieved by the method of cell population expansion according to the invention may be achieved after exposure to the compound according to Formula A1 or subformulae thereof for about 12 to 16 days, preferably about 14 days.

In one aspect of the method of cell population expansion according to the invention, the LATS inhibitors according to Formula A1 or subformulae thereof produce a cell population with more than 6% of p63alpha positive cells compared to the total amount of cells. In a specific embodiment of the method of cell population expansion according to the invention, the LATS inhibitors according to Formula A1 or subformulae thereof produce a cell population with more than 20% of p63alpha positive cells compared to the total amount of cells. In another specific embodiment of the method of cell population expansion according to the invention, the LATS inhibitors according to Formula A1 or subformulae thereof produce a cell population with more than 70% of p63alpha positive cells compared to the total amount of cells. In yet another specific embodiment of the method of cell population expansion according to the invention the LATS inhibitors according to Formula A1 or subformulae thereof produce a cell population with more than 95% of p63alpha positive cells compared to the total amount of cells. The increase in the percentage of p63alpha positive cells achieved by the method of cell population expansion according to the invention may be achieved in one or more passages of the cells. In another aspect of the invention the increase in the percentage of p63alpha positive cells achieved by the method of cell population expansion according to the invention may be achieved after exposure to the compound according to Formula A1 or subformulae thereof for about 12 to 16 days, preferably about 14 days.

If it is desired to measure the cell number or expansion of the cell population, this may be done for example by taking an aliquot and performing immunocytochemistry (e.g. to count nuclei stained with Sytox Orange) or by live cell imaging under brightfield microscope to count the number of cells or by performing real-time quantitative live-cell analysis of cell confluence at various time points during the cell population expansion phase of the method according to the invention.

The Sytox Orange assay may be performed according to standard protocols known in the art. In brief, after cells have attached to the cell culture dish (typically 24 h after cell plating), the cells are fixed in paraformaldehyde. The cells are then permeabilized (e.g. using a solution of 0.3% Triton X-100) and they are then labeled in a solution of Sytox Orange (e.g. using 0.5 micromolar of Sytox Orange in PBS). The number of nuclei stained with Sytox Orange per surface area are then counted under a Zeiss epifluorescence microscope.

In one aspect according to the invention the LSC population obtainable or obtained by the method of cell population expansion according to the invention preferably shows at least one of the following characteristics. More preferably, it shows two or more, more preferably all, of the following characteristics.

(1) The cell preparation is positive for p63alpha cells. The expression of p63alpha may be estimated by standard techniques known in the art, such as for example immunohistochemistry and quantitative RT-PCR.

(2) The cell preparation comprises more than 6% p63alpha positive cells. Preferably the cell preparation comprises more than 10%, 20%, 30%, 40%, 50%, 60%, 70%, 80% or 90% p63alpha positive cells. In a preferred embodiment the cell preparation comprises more than 95% p63alpha positive cells. The percentage of p63alpha cells may be measured by immunohistochemistry or FACS.

(3) The cells express one or more of ABCB5, ABCG2, and C/EBPδ. The expression of ABCB5, ABCG2, and C/EBPδ may be estimated by standard techniques known in the art, such as for example immunohistochemistry and quantitative RT-PCR.

(4) The cells can differentiate into corneal epithelium cells as observed by keratin-12 expression. These characteristics can be observed by immunohistochemistry or FACS.

The cell population expanded by the method of cell population expansion according to the invention may be added to a solution and then stored, for example in a preservation or cryopreservation solution (such as those described below), or added directly to a composition suitable for ocular delivery. The preservation, cryopreservation solution or composition suitable for ocular delivery may optionally comprise a LATS inhibitor according to the invention.

In a more preferred embodiment according to the invention, the cell population preparation which is delivered to the eye comprises very low to negligible levels of a LATS inhibitor compound. Thus in a specific embodiment, the method of cell population expansion according to the invention comprises the further step of rinsing to substantially remove the compound according to the invention (such as the compound according to Formula A1 or subformulae thereof). This may involve rinsing the cells after the cell population expansion phase according to the invention. To rinse the cells, the cells are detached from the culture dish (e.g. by treating with Accutase), the detached cells are then centrifuged, and a cell suspension is made in PBS or growth medium according to the invention. This step may be performed multiple times, e.g. one to ten times, to rinse out the cells. Finally the cells may be resuspended in a preservation solution, cryopreservation solution, a composition suitable for ocular delivery, growth medium or combinations thereof as desired.

The expanded population of cells prepared by the method of cell population expansion and rinsed of cell proliferation medium comprising a LATS inhibitor according the invention may be transferred to a composition suitable for ocular delivery, such as for example a localising agent. Optionally the cell population is stored for a period before addition to a localising agent suitable for ocular delivery. In a preferred embodiment, the expanded cell population may first be added to a solution suitable for preservation or cryopreservation, which preferably does not comprise a LATS inhibitor, and the cell population stored (optionally with freezing) before addition to a localising agent suitable for ocular delivery, which also preferably does not comprise a LATS inhibitor.

Typical solutions suitable for preservation of LSCs are Optisol or PBS, preferably Optisol. Optisol is a corneal storage medium comprising chondroitin sulfate and dextran to enhance corneal dehydration during storage (see for example Kaufman et al., (1991) Optisol corneal storage medium; Arch Ophthalmol June; 109(6): 864-8). For cryopreservation, glycerol, dimethyl sulfoxide, propylene glycol or acetamide may be used in the cryopreservation solution of the present invention. The cryopreserved preparation of cells is typically kept at −20° C. or −80° C.

In one aspect the invention relates to a preserved or cryopreserved preparation of limbal stem cells obtainable by the method of cell population expansion according to the invention. In an alternative aspect the invention relates to a fresh cell preparation where limbal stem cells obtainable by the method of cell population expansion according to the invention are in suspension in PBS and/or growth medium or combined with a localising agent. The fresh cell preparation is typically kept at about 15 to 37° C. Standard cell cultures containers known in the art may be used to store the cells, such as a vial or a flask.

In a preferred embodiment according to the invention, before use in the eye, a cryopreserved preparation of cells is thawed (for example by incubating at a temperature of about 37° C. in an incubator or waterbath). Preferably 10 volumes of PBS or growth medium may be added to rinse off the cells from the cryopreservant solution. Cells may then be rinsed by centrifugation, and a cell suspension may be made in PBS and/or growth medium, before combination with a localising agent for ocular delivery, which also preferably does not comprise a LATS inhibitor.

In one aspect of the invention the expanded population of cells prepared by the method of cell population expansion, are prepared as a suspension (for example in PBS and/or growth medium, such as for example X-VIVO medium) and combined with a localising agent suitable for ocular delivery, (such as a biomatrix like GelMA). In a specific embodiment of the method of treatment according to the invention, this combination of cells, PBS and/or growth medium, and biomatrix is delivered to the eye via a carrier (such as a contact lens). In yet another specific embodiment this combination of cells, PBS and/or growth medium, and biomatrix comprises at most only trace levels of a LATS inhibitor.

The term "trace levels" as used herein means less than 5% w/v (e.g., no more than 5% w/v, 4% w/v, 3% w/v, 2% w/v, or 1% w/v), and preferably less than 0.01% w/v (e.g., no more than 0.01% w/v, 0.009% w/v, 0.008% w/v, 0.007% w/v, 0.006% w/v, 0.005% w/v, 0.004% w/v, 0.003% w/v, 0.002% w/v, or 0.001% w/v), which can be measured, for example using high-resolution chromatography as described in the Examples herein. In certain embodiments, trace levels of a LATS inhibitor compound of the invention are the levels of residual compounds present after one or more wash steps, which collectively are below the cellular potency of such compounds, and accordingly they do not induce biological effect in vivo. Accordingly, residual levels of compounds are below the amount expected to have a biological effect on cell population expansion in cell culture or in a subject (e.g., after transplantation of an expanded cell population to the subject). Trace levels can be measured, for example, as the wash-off efficiency, which can be calculated as follows: Wash-off efficiency=100−(average concentration in post-wash pellet×pellet volume×molecule weight)/(compound concentration×culture media volume×molecule weight). As used herein, "rinsing to substantially remove" a LATS inhibitor compound of the invention from cells refers to steps for establishing trace levels of the LATS inhibitor compound.

Alternatively, the cells may be cultured and the cell population proliferation phase may occur in cell proliferation medium on a localising agent suitable for cell delivery to the ocular surface (for example fibrin, collagen).

Cell Population Expansion: To Prepare an Expanded Population of Corneal Endothelial Cells In a preferred embodiment of the invention, corneal endothelial cells, for example isolated and obtainable as described in the section "Starting material to prepare an expanded population of corneal endothelial cells", can be grown in medium in a culture container known in the art, such as plates, multi-well plates, and cell culture flasks. For example, a culture dish may be used which is non-coated or coated with collagen, synthemax, gelatin or fibronectin. A preferred example of a suitable culture container is a non-coated plate. Standard culturing containers and equipment such as bioreactors known in the art for industrial use may also be used.

The medium used may be a growth medium or a cell proliferation medium. A growth medium is defined herein as a culture medium supporting the growth and maintenance of a population of cells. Suitable growth mediums are known in the art for corneal endothelial cell culture are for example: DMEM (Dulbecco's Modified Eagle's Medium) supplemented with FBS (Fetal Bovine Serum) (Invitrogen), human endothelial SF (serum free) medium (Invitrogen) supplemented with human serum, X-VIVO15 medium (Lonza) or mesenchymal stem cell-conditioned medium. These may be additionally supplemented with growth factors (e.g. bFGF), and/or antibiotics such as penicillin and streptomycin. A preferred growth medium according to the invention is X-VIVO15 medium (which is not additionally supplemented with growth factors).

Alternatively, the isolated cells may be added first to a cell proliferation medium according to the invention. The cell proliferation medium as defined herein comprises a growth medium and a LATS inhibitor according to the invention. In the cell proliferation medium according to the invention the growth medium component is selected from the group consisting of DMEM (Dulbecco's Modified Eagle's Medium) supplemented with FBS (Fetal Bovine Serum) (Invitrogen), human endothelial SF (serum free) medium (Invitrogen) supplemented with human serum, X-VIVO15 medium (Lonza) or mesenchymal stem cell-conditioned medium. These may be additionally supplemented with growth factors (e.g. bFGF), and/or antibiotics such as penicillin and streptomycin.

A preferred cell proliferation medium according to the invention is X-VIVO15 medium (Lonza) with a LATS inhibitor according to the invention. This cell proliferation medium has the advantage that it does not need additional growth factors or feeder cells to facilitate the proliferation of the CECs. X-VIVO medium comprises inter alia pharmaceutical grade human albumin, recombinant human insulin, and pasteurised human transferrin. Optionally antibiotics may be added to X-VIVO15 medium. In a preferred embodiment, X-VIVO15 medium is used without the addition of antibiotics.

The cell proliferation medium comprises a growth medium and a LATS inhibitor according to the invention. The LATS inhibitor is preferably selected from the group comprising compounds according to Formula A1 or subformulae thereof and as further described under the section "LATS Inhibitors".

In a preferred embodiment the LATS inhibitors according to Formula A1 or subformulae thereof are added at a concentration of about 0.5 to 100 micromolar, preferably about 0.5 to 25 micromolar, more preferably about 1 to 20 micromolar. In a specific embodiment the LATS inhibitors according to Formula A1 or subformulae thereof are added at a concentration of about 3 to 10 micromolar.

In one embodiment, the stock solution of the compound according to Formula A1 or subformulae thereof may be prepared by dissolving the compound powder to a stock concentration of 10 mM in DMSO.

In one aspect of the invention the LATS inhibitor according to the invention inhibits LATS1 and/or LATS2 activity in the corneal endothelial cells. In a preferred embodiment the LATS inhibitor inhibits LATS1 and LATS2.

The cells may go through a round or rounds of addition of fresh growth medium and/or cell proliferation medium. The cells do not need to be passaged in order for fresh medium to be added, but passaging cells is also a way to add fresh medium.

A series of mediums may be also used, in various combinations of orders: for example a cell proliferation medium, followed by addition of a growth medium (which is not supplemented with LATS inhibitors according to the invention, and may be different to the growth medium used as the base for the cell proliferation medium).

The cell population expansion phase according to the invention occurs during the period the cells are exposed to the cell proliferation medium.

Standard temperature conditions known in the art for culturing cells may be used, for example preferably about 30° C. to 40° C. Particularly preferably cell growth, as well as the cell population expansion phase is carried out at about 37'C. A conventional cell incubator with 5-10% $CO_2$ levels may be used. Preferably the cells are exposed to 5% $CO_2$.

The cells may be passaged during the culturing in the growth or cell proliferation medium as necessary. Cells may be passaged when they are sub-confluent or confluent. Preferably the cells are passaged when they reach approximately 90%-100% confluency, although lower percentage confluency levels may also be performed. The passaging of cells is done according to standard protocols known in the art. For example, in brief the cells are detached from the culture container, for example using collagenase. The cells are then centrifuged and rinsed in PBS or the cell growth medium according to the invention and plated in fresh growth or cell proliferation medium as desired at a dilution of, for example, 1:2 to 1:4.

For the cell population expansion phase of the method of cell population expansion according to the invention, the expansion of the seeding cell population in the cell proliferation medium may be performed until the required amount of cellular material is obtained.

The cells may be exposed to the cell proliferation medium for a range of time periods in order to expand the cell population. For example, this may include the entire time that the CECs are kept in culture, or only for the first one to two weeks after CEC isolation or only for 24 hours after dissection of the cornea.

In a preferred embodiment, the corneal endothelial cells are exposed to the LATS inhibitors according to the invention (such as those compounds according to Formula A1 or subformulae thereof) directly after cell isolation from the cornea, and maintained for the entire time that CEC proliferation is required, for example one to two weeks.

In a more preferred embodiment of the invention, after the cell population expansion phase in vitro (i.e. after the cells are exposed to a LATS inhibitor according to the invention for a period of time to expand the population of cells), the method of cell population expansion according to the invention comprises a further step wherein the cells may be grown for a period of time (e.g. two weeks) in growth medium without supplementation of a LATS inhibitor, to enable a mature corneal endothelium to form. A mature corneal endothelium is defined herein as a monolayer of CECs with hexagonal morphology, ZO-1-positive tight junctions and expression of Na/K ATPase. In a preferred embodiment the cells are not passaged while the mature corneal endothelium is formed.

In one embodiment according to the invention, a gene editing technique may optionally be performed to genetically modify cells, to reduce or eliminate the expression and/or function of an immune response mediating gene which may otherwise contribute to immune rejection when the cell population is delivered to the patient. The application of gene editing techniques in the method of cell population expansion according to the invention is optional, and the administration to the patient of topical immunosuppressants and/or anti-inflammatory agents (as described further under the section Immunosuppressant and Anti-inflammatory agent) may instead be used if desired to mitigate issues with immunorejection of the transplanted material in the patient.

According to one aspect of the invention, for the scenario that a gene editing technique is used, genetically modifying comprises reducing or eliminating the expression and/or function of a gene associated with facilitating a host versus graft immune response. In a preferred embodiment, genetically modifying comprises introducing into a corneal endothelial cell a gene editing system which specifically targets a gene associated with facilitating a host versus graft immune response. In a specific embodiment, said gene editing system is selected from the group consisting of CRISPR (CRISPR: clustered regularly interspaced short palindromic repeats, also known as CRISPR/Cas systems), ZFN (Zinc-finger nucleases), TALEN (transcription activator-like effector based nucleases), engineered meganucleases (e.g. ARCUS nucleases, such as the ARC nuclease), AAV vector (adeno-associated virus) gene editing (e.g. AAV vector driven homologous recombination) and lentiviral vectors-based genome editing technologies. AAV vector driven gene delivery, such as driven by homologous recombination, can be achieved by an AAV selected from the group consisting of: AAV2, AAV3, AAV4, AAV5, AAV6, AAV7, AAV8, AAV9, or a derivative thereof.

A gene editing technique, if it is to be used, may be performed at different points, such as for example (1) on corneal tissue, before CEC isolation or (2) at the time of cell isolation or (3) during the cell population expansion phase in vitro (when the cells are exposed to a LATS inhibitor according to the invention in vitro) or (4) in vitro at the end of the cell population expansion phase (after the cells are exposed to a LATS inhibitor according to the invention in vitro).

The gene editing techniques suitable for use in the method of cell population expansion are further described under the section "reduction of immunorejection".

In the method of cell population expansion according to the invention the LATS inhibitors, which are preferably compounds, produce greater than 2 fold expansion of the seeded population of cells.

In one aspect of the method of cell population expansion according to the invention the compounds according to Formula A1 or subformulae thereof produce greater than 10 fold expansion of the seeded population of corneal endothelial cells. In a specific embodiment of the method of cell population expansion according to the invention, the LATS inhibitors according to Formula A1 or subformulae thereof produce 15 fold to 600 fold expansion of the seeded population of corneal endothelial cells. In a more specific embodiment of the method of cell population expansion according to the invention, the LATS inhibitors according to Formula A1 or subformulae thereof produce 20 fold to 550 fold expansion of the seeded population of corneal endothelial cells. The fold expansion factor achieved by the method of cell population expansion according to the invention may be achieved in one or more passages of the cells. In another aspect of the invention the fold expansion factor achieved by the method of cell population expansion according to the invention may be achieved after exposure to the compound according to Formula A1 or subformulae thereof for one to two weeks, preferably after about 10 days.

If it is desired to measure the cell number or expansion of the cell population, this may be done for example by taking an aliquot and performing immunocytochemistry (e.g. to count nuclei stained with Sytox Orange) or by live cell imaging under brightfield microscope to count the number of cells or by performing real-time quantitative live-cell analysis of cell confluence at various time points during the cell population expansion phase of the method according to the invention.

In one aspect according to the invention the CEC population obtainable or obtained by the method of cell population expansion according to the invention preferably shows at least one of the following characteristics. More preferably, it shows two or more, particularly preferably all, of the following characteristics.

(1) The cells express Na/K ATPase. The expression of Na/K ATPase may be estimated by standard techniques known in the art, such as for example immunohistochemistry, quantitative RT-PCR or by FACS analysis.

(2) The cells express one or more of Collagen 8a2, AQP1 (aquaporin 1) and SLC4A11 (Solute Carrier Family 4 Member 11). Preferably the relative expression levels are higher than cells which do not typically express collagen 8a2, AQP1 and SLC4A11, such as, for example, in dermal fibroblasts. The expression of Collagen 8a2, AQP1 or SLC4A11 may be estimated by standard techniques known in the art, such as for example immunohistochemistry, quantitative RT-PCR or by FACS analysis.

(3) The cells do not express (or at most express relatively low levels of) RPE65 (a marker of retinal pigmented epithelium) and/or CD31 (a marker of vascular endothelium). The relative expression levels are similar to cells which do not typically express RPE65, CD31, such as in dermal fibroblasts. The expression of RPE65 and CD31 may be estimated by standard techniques known in the art, such as for example quantitative RT-PCR, immunohistochemistry or FACS analysis.

(4) The cells express relatively low levels of CD73. The relative expression levels are lower than cells which have undergone endothelial to mesenchymal transition. The expression of CD73 may be estimated by standard techniques known in the art, such as for example FACS analysis or immunohistochemistry.

In another aspect according to the invention, when in a layer, for example when cultured on a plate, the CEC population obtainable by the method of cell population expansion according to the invention preferably shows at least one of the following characteristics.

More preferably, it shows two or more, particularly preferably all, of the following characteristics:

(1) The cells are able to form a single layer structure. This is one of the characteristics of the corneal endothelial cell layer in the body. This may be observed by nuclear staining (e.g. with nuclear dye such as Sytox, Hoechst) followed by examination by microscopy.

(2) The cells are able to form tight junctions. This may be checked by a standard technique known in the art, immunofluorescence staining of tight-junction marker Zonula Occludens-1 (ZO-1).

(3) The cells are able to be regularly arranged in the cell layer. This may be checked by a standard technique known in the art, immunofluorescence staining of tight-junction marker Zonula Occludens-1 (ZO-1). In the healthy corneal endothelial cell layer in the body, the cells constituting the layer are regularly arrayed, due to which corneal endothelial cells are considered to maintain normal function and high transparency and the cornea is considered to appropriately exhibit water control function.

The cell population expanded by the method of cell population expansion according to the invention may be added to a solution and then stored, for example in a preservation or cryopreservation solution (such as those described below), or added directly to a composition suitable for ocular delivery. The preservation, cryopreservation solution or composition suitable for ocular delivery may optionally comprise a LATS inhibitor according to the invention.

In a more preferred embodiment according to the invention, the cell population preparation which is delivered to the eye comprises very low to negligible levels of a LATS inhibitor compound. Thus in a specific embodiment, the method of cell population expansion according to the invention comprises the further step of rinsing to substantially remove the compound according to the invention (such as the compound according to Formula A1 or subformulae thereof). This may involve rinsing the cells after the cell population expansion phase according to the invention (directly after the cell population expansion phase and/or after the cells have been cultured to form a mature corneal endothelium in growth medium which has not been supplemented by a LATS inhibitor). To rinse the cells, the cells are centrifuged, and a cell suspension is made in PBS or growth medium according to the invention. This step may be performed multiple times, e.g. one to ten times, to rinse out the cells. Finally the cells may be resuspended in a preservation solution, cryopreservation solution, a composition suitable for ocular delivery, growth medium or combinations thereof as desired.

The expanded population of cells prepared by the method of cell population expansion and rinsed of cell proliferation medium comprising a LATS inhibitor according the invention may be transferred to a composition suitable for ocular delivery, such as for example a localising agent. Optionally the cell population is stored for a period before addition to a localising agent suitable for ocular delivery. In a preferred embodiment, the expanded cell population may first be added to a solution suitable for preservation or cryopreservation, which preferably does not comprise a LATS inhibitor, and the cell population stored (optionally with freezing) before addition to a localising agent suitable for ocular delivery, which also preferably does not comprise a LATS inhibitor.

Typical solutions for suitable for preservation of CECs are Optisol or PBS, preferably Optisol. Optisol is a corneal storage medium comprising chondroitin sulfate and dextran to enhance corneal dehydration during storage (see for example Kaufman et al., (1991) Optisol corneal storage medium; Arch Ophthalmol June; 109(6): 864-8). For cryopreservation, glycerol, dimethyl sulfoxide, propylene glycol or acetamide may be used in the cryopreservation solution of the present invention. The cryopreserved preparation of cells is typically kept at −20° C. or −80° C.

In one aspect the invention relates to a preserved or cryopreserved preparation of corneal endothelial cells obtainable by the method of cell population expansion according to the invention. In an alternative aspect the invention relates to a fresh cell preparation where corneal endothelial cells obtainable by the method of cell population expansion according to the invention are in suspension in PBS and/or growth medium or combined with a localising agent. The fresh cell preparation is typically kept at about 37° C. Standard cell cultures containers known in the art may be used to store the cells, such as a vial or a flask.

In a preferred embodiment according to the invention, before use in the eye, a cryopreserved preparation of cells is thawed (for example by incubating at a temperature of about 37° C. in an incubator or waterbath). Preferably 10 volumes of PBS or growth medium may be added to rinse off the cells from the cryopreservant solution. Cells may then be rinsed by centrifugation, and a cell suspension may be made in PBS and/or growth medium, before combination with a localising agent for ocular delivery, which also preferably does not comprise a LATS inhibitor.

In one aspect of the invention the expanded population of cells prepared by the method of cell population expansion, (preferably also including the step of growth in medium without supplementation with LATS inhibitor to form a mature corneal endothelium), are prepared as a suspension (for example in PBS and/or growth medium, such as for example X-VIVO medium) and combined with a localising agent suitable for ocular delivery, (such as a biomatrix like GelMA). In a specific embodiment of the method of treatment according to the invention, this combination of cells, PBS and/or growth medium, and biomatrix is delivered as a suspension to the eye. In yet another specific embodiment this combination of cells, PBS and/or growth medium, and biomatrix comprises at most only trace levels of a LATS inhibitor.

Alternatively, the cells may be cultured and the cell population proliferation phase may occur in cell proliferation medium on a localising agent suitable for cell delivery to the ocular surface.

In an embodiment of the invention the cell population expanded according to the invention may be isolated as a contiguous cell sheet for delivery to the cornea, using methods known in the art (for examples, see Kim et al, *JSM Biotechnol. Bioeng.*, 2016, p. 1047). Cell sheets may be mechanically supported on a material or materials for delivery to the cornea.

Reduction of Immunorejection

Upon transplantation, allogeneic limbal stem cells are at risk of rejection by the recipient's immune system. Immunosuppression regimens can be used to reduce the risk of immunorejection of transplanted cells, such as LSCs.

Suitable systemic immunosuppressant agents used in recipients of allogeneic LSCs include tacrolimus, mycophenolate mofetil, prednisone and prophylactic valganciclovir and trimethoprim/sulfamethoxazole. (See: Holland E J, Mogilishetty G, Skeens H M, Hair D B, Neff K D, Biber J M, Chan C C (2012) Systemic immunosuppression in ocular surface stem cell transplantation: results of a 10-year experience. Cornea. 2012 June; 31(6):655-61).

As the methods of cell population expansion according the present invention provide high expansion capabilities of a population of cells, optionally gene-editing technologies may be used to remove drivers of immunorejection or add genes that reduce the recipient's immune response.

In one aspect of the invention gene editing is carried out on a cell population "ex vivo". In another aspect of the invention gene-editing technologies may optionally be used to reduce or eliminate the expression of a gene associated with facilitating a host versus graft immune response. In a preferred embodiment the gene is selected from the group consisting of: B2M, HLA-A, HLA-B and HLA-C. In a specific embodiment the gene is B2M. B2M is beta 2 microglobulin and is a component of the class I major histocompatibility complex (MHC). It has the HUGO Gene Nomenclature Committee (HGNC) identifier 914. HLA-A is major histocompatibility complex, class I, A (HGNC ID 4931). HLA-B is major histocompatibility complex, class I, B (HGNC ID 4932). HLA-C is major histocompatibility complex, class I, C (HGNC ID 4933).

Several gene editing methods may be used, including, but not limited to methods selected from the group consisting of CRISPR (CRISPR: clustered regularly interspaced short palindromic repeats, also known as CRISPR/Cas systems), ZFN (Zinc-finger nucleases), TALEN (transcription activator-like effector based nucleases), engineered meganucleases (e.g. ARCUS nucleases, such as the ARC nuclease), AAV vector (adeno-associated virus) gene delivery (e.g., AAV vector driven homologous recombination) and lentiviral vectors-based genome editing technologies. AAV vector driven gene delivery, such as driven by homologous recombination, can be achieved by an AAV selected from the group consisting of: AAV2, AAV3, AAV4, AAV5, AAV6, AAV7, AAV8, AAV9, or a derivative thereof. In one aspect of the invention gene editing is carried out on a cell population "ex vivo".

Gene Editing System

As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site. As described herein, gene editing can be carried out ex vivo.

AAV Gene Editing Systems

The use of vectors derived from AAVs to transfer genes in vitro and in vivo is well known in the art (see U.S. Pat. No. 9,707,304, for example). The use of viral vectors for editing genes in a cell has been described, for example, in Chen et al., 2016, Molecular Therapy, 24:447-457; Gornalusse et al., Nature Biotechnology, 2017, 35(8):765-772; and WO2017087961.

An AAV vector can be made using methods known in the art. Such methods are described, for example, in Flotte T R. Adeno-associated virus-based gene therapy for inherited disorders. Pediatr Res. 2005 December; 58(6):1143-7; Goncalves M A. Adeno-associated virus: from defective virus to effective vector, Virol J. 2005 May 6; 2:43; Surace E M, Auricchio A. Adeno-associated viral vectors for retinal gene transfer. Prog Retin Eye Res. 2003 November; 22(6):705-19; Mandel R J, Manfredsson F P, Foust K D, Rising A, Reimsnider S, Nash K, Burger C. Recombinant adeno-associated viral vectors as therapeutic agents to treat neurological disorders. Mol Ther. 2006 March; 13(3):463-83.

CRISPR Gene Editing Systems

"CRISPR" as used herein refers to a set of clustered regularly interspaced short palindromic repeats, or a system comprising such a set of repeats. "Cas," as used herein, refers to a CRISPR-associated protein. The diverse CRISPR-Cas systems can be divided into two classes according to the configuration of their effector modules: class 1 CRISPR systems utilize several Cas proteins and the crRNA to form an effector complex, whereas class 2 CRISPR systems employ a large single-component Cas protein in conjunction with crRNAs to mediate interference. One example of class 2 CRISPR-Cas system employs Cpf1 (CRISPR from *Prevotella* and *Francisella* 1). See, e.g., Zetsche et al., Cell 163:759-771 (2015), the content of which is herein incorporated by reference in its entirety. The term "Cpf1" as used herein includes all orthologs, and variants that can be used in a CRISPR system.

Naturally-occurring CRISPR systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) Science 322: 1843-1845.

The CRISPR system has been modified for use in gene editing (silencing, enhancing or changing specific genes) in eukaryotes such as mice, primates and humans. Wiedenheft et al. (2012) *Nature* 482: 331-8. This is accomplished by, for example, introducing into the eukaryotic cell one or more vectors encoding a specifically engineered guide RNA (gRNA) (e.g., a gRNA comprising sequence complementary to sequence of a eukaryotic genome) and one or more appropriate RNA-guided nucleases, e.g., Cas proteins. The RNA guided nuclease forms a complex with the gRNA, which is then directed to the target DNA site by hybridization of the gRNA's sequence to complementary sequence of a eukaryotic genome, where the RNA-guided nuclease then induces a double or single-strand break in the DNA. Insertion or deletion of nucleotides at or near the strand break creates the modified genome.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs.

A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

In some embodiments, the RNA-guided nuclease is a Cas molecule, e.g., a Cas9 molecule. The "Cas9 molecule," can interact with a gRNA molecule (e.g., sequence of a domain of a tracr, also known as tracrRNA or trans activating CRISPR RNA) and, in concert with the gRNA molecule, localize (e.g., target or home) to a site which comprises a target sequence and PAM (protospacer adjacent motif) sequence.

According to the present invention, Cas9 molecules of, derived from, or based on the Cas9 proteins of a variety of species can be used in the methods and compositions described herein. For example, Cas9 molecules of, derived from, or based on, e.g., *S. pyogenes, S. thermophilus, Staphylococcus aureus* and/or *Neisseria meningitidis* Cas9 molecules, can be used in the systems, methods and compositions described herein. Additional Cas9 species include: *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhiz obium* sp., *Brevibacillus latemsporus, Campylobacter coli, Campylobacter jejuni, Campylobacter lad, Candidatus Puniceispirillum, Clostridiu cellulolyticum, Clostridium perfringens, Corynebacterium accolens, Corynebacterium diphtheria, Corynebacterium matruchotii, Dinoroseobacter sliibae, Eubacterium dolichum*, gamma proteobacterium, *Gluconacetobacler diazotrophicus, Haemophilus parainfluenzae, Haemophilus sputorum, Helicobacter canadensis, Helicobacter cinaedi, Helicobacter mustelae, Ilyobacler polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae.*

In some embodiments, the ability of an active Cas9 molecule to interact with and cleave a target nucleic acid is PAM sequence dependent. A PAM (protospacer adjacent motif) sequence is a sequence in the target nucleic acid. It is typically short, for example 2 to 7 base pairs long. In an embodiment, cleavage of the target nucleic acid occurs upstream from the PAM sequence. Active Cas9 molecules from different bacterial species can recognize different sequence motifs (e.g., PAM sequences). In an embodiment, an active Cas9 molecule of *S. pyogenes* recognizes the sequence motif NGG and directs cleavage of a target nucleic acid sequence 1 to 10, e.g., 3 to 5, base pairs upstream from that sequence. See, e.g., Mali el al, SCIENCE 2013; 339 (6121): 823-826. In an embodiment, an active Cas9 molecule of *S. thermophilus* recognizes the sequence motif NGGNG (SEQ ID NO: 4) and NNAG AAW (SEQ ID NO: 5) (W=A or T and N is any nucleobase) and directs cleavage of a core target nucleic acid sequence 1 to 10, e.g., 3 to 5, base pairs upstream from these sequences. See, e.g., Horvath et al., SCIENCE 2010; 327(5962): 167-170, and Deveau et al, J BACTERIOL 2008; 190(4): 1390-1400. In an embodiment, an active Cas9 molecule of *S. mutans* recognizes the sequence motif NGG or NAAR (R-A or G) and directs cleavage of a core target nucleic acid sequence 1 to 10, e.g., 3 to 5 base pairs, upstream from this sequence. See, e.g., Deveau et al., J BACTERIOL 2008; 190(4): 1390-1400.

In an embodiment, an active Cas9 molecule of *S. aureus* recognizes the sequence motif NNGRR (SEQ ID NO: 6) (R=A or G) and directs cleavage of a target nucleic acid sequence 1 to 10, e.g., 3 to 5, base pairs upstream from that sequence. See, e.g., Ran F. et al., NATURE, vol. 520, 2015, pp. 186-191. In an embodiment, an active Cas9 molecule of *N. meningitidis* recognizes the sequence motif NNNNGATT (SEQ ID NO: 7) and directs cleavage of a target nucleic acid sequence 1 to 10, e.g., 3 to 5, base pairs upstream from that sequence. See, e.g., Hou et al., PNAS EARLY EDITION 2013, 1-6. The ability of a Cas9 molecule to recognize a PAM sequence can be determined, e.g., using a transformation assay described in Jinek et al, SCIENCE 2012, 337:816.

Exemplary naturally occurring Cas9 molecules are described in Chylinski et al, RNA Biology 2013; 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS 10270, MGAS 10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA 159, NN2025), *S. macacae* (e.g., strain NCTC1 1558), *S. gallolyticus* (e.g., strain UCN34, ATCC BAA-2069), *S. equines* (e.g., strain ATCC 9812, MGCS 124), *S. dysdalac-tiae* (e.g., strain GGS 124), *S. bovis* (e.g., strain ATCC 700338), *S. cmginosus* (e.g.; strain F021 1), *S. agalactia*\* (e.g., strain NEM316, A909), *Listeria monocytogenes* (e.g., strain F6854), *Listeria innocua* (*L. innocua*, e.g., strain Clip 11262), *EtUerococcus italicus* (e.g., strain DSM 15952), or *Enterococcus faecium* (e.g., strain 1,23,408). Additional exemplary Cas9 molecules are a Cas9 molecule of *Neisseria meningitidis* (Hou et al. PNAS Early Edition 2013, 1-6) and a *S. aureus* Cas9 molecule.

In an embodiment, a Cas9 molecule, e.g., an active Cas9 molecule comprises an amino acid sequence: having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, 10 or 20 amino acids but by no more than 100, 80, 70, 60, 50, 40 or 30 amino acids from; or is identical to; any Cas9 molecule sequence described herein or a naturally occurring Cas9 molecule sequence, e.g., a Cas9 molecule from a species listed herein or described in Chylinski et al., RNA Biology 2013, 10:5, 'I2'I-T, 1 Hou et al. PNAS Early Edition 2013, 1-6.

In an embodiment, a Cas9 molecule comprises an amino acid sequence having 60%, 65%, 70%, 75%, 80%, 85%, 90%, 95%, 96%, 97%, 98%, or 99% homology with; differs at no more than 1%, 2%, 5%, 10%, 15%, 20%, 30%, or 40% of the amino acid residues when compared with; differs by at least 1, 2, 5, 10 or 20 amino acids but by no more than 100, 80, 70, 60, 50, 40 or 30 amino acids from; or is identical to; *S. pyogenes* Cas9 (UniProt Q99ZW2). In embodiments, the Cas9 molecule is a *S. pyogenes* Cas9 variant, such as a variant described in Slaymaker et al., *Science Express*, available online Dec. 1, 2015 at Science DOI: 10.1126/science.aad5227; Kleinstiver et al., Nature, 529, 2016, pp. 490-495, available online Jan. 6, 2016 at doi:10.1038/nature16526; or US2016/0102324, the contents of which are incorporated herein in their entirety.

In some embodiments, the Cas9 molecule, e.g., a Cas9 of *S. pyogenes*, may additionally comprise one or more amino acid sequences that confer additional activity. In some aspects, the Cas9 molecule may comprise one or more nuclear localization sequences (NLSs), such as at least 1, 2, 3, 4, 5, 6, 7, 8, 9, 10, or more NLSs. Typically, an NLS consists of one or more short sequences of positively charged lysines or arginines exposed on the protein surface, but other types of NLS are known. Non-limiting examples of NLSs include an NLS sequence comprising or derived from: the NLS of the SV40 virus large T-antigen, having the amino acid sequence PKKKRKV (SEQ ID NO: 8). Other suitable NLS sequences are known in the art (e.g., Sorokin, Biochemistry (Moscow) (2007) 72:13, 1439-1457; Lange J Biol Chem. (2007) 282:8, 5101-5). In any of the aforementioned embodiments, the Cas9 molecule may additionally (or alternatively) comprise a tag, e.g., a His tag, e.g., a His(6) tag (SEQ ID NO: 25) or His(8) tag (SEQ ID NO: 26), e.g., at the N terminus or the C terminus.

Thus, engineered CRISPR gene editing systems, e.g., for gene editing in eukaryotic cells, typically involve (1) a guide RNA molecule (gRNA) comprising a targeting domain (which is capable of hybridizing to the genomic DNA target sequence), and a sequence which is capable of binding to a Cas, e.g., Cas9 enzyme, and (2) a Cas, e.g., Cas9, protein. The sequence which is capable of binding to a Cas protein may comprise a domain referred to as a tracr domain or tracrRNA. The targeting domain and the sequence which is capable of binding to a Cas, e.g., Cas9 enzyme, may be disposed on the same (sometimes referred to as a single gRNA, chimeric gRNA or sgRNA) or different molecules (sometimes referred to as a dual gRNA or dgRNA). If disposed on different molecules, each includes a hybridization domain which allows the molecules to associate, e.g., through hybridization. gRNA molecule formats are known in the art. An exemplary gRNA molecule, e.g., dgRNA molecule, as disclosed herein comprises, e.g., consists of, a first nucleic acid having the sequence:

(SEQ ID NO: 9)
5'nnnnnnnnnnnnnnnnnnnnGUUUUAGAGCUAUGCUGUUUUG 3', where the "n'"s refer to the residues of the targeting domain, e.g., as described herein, and may consist of 15-25 nucleotides, e.g., consists of 20 nucleotides;
and a second nucleic acid sequence having the exemplary sequence:
5'AACUUACCAAGGAACAG-CAUAGCAAGUUAAAAUAAGGCUAGUCCGUUAU-CAACUUG AAAAAGUGGCACCGAGUCGGUGC 3', optionally with 1, 2, 3, 4, 5, 6, or 7 (e.g., 4 or 7, e.g., 7) additional U nucleotides at the 3' end (SEQ ID NO: 10).

The second nucleic acid molecule may alternatively consist of a fragment of the sequence above, wherein such fragment is capable of hybridizing to the first nucleic acid. An example of such second nucleic acid molecule is:
5'AACAGCAUAGCAAGUUAAAAUAAGGCUAGU-CCGUUAUCAAC U UGAAAAAGUGGCAC CGAGU-CGGUGC 3', optionally with 1, 2, 3, 4, 5, 6, or 7 (e.g., 4 or 7, e.g., 7) additional U nucleotides at the 3' end (SEQ ID NO:11).

Another exemplary gRNA molecule, e.g., a sgRNA molecule, as disclosed herein comprises, e.g., consists of a first nucleic acid having the sequence:
5'nnnnnnnnnnnnnnnnnnnnGUUUUAGAGCUA-GAAAUAGCAAGUUAAAAUAAGGCUAGUCC GUUAUCAACUUGAAAAAGUGGCACCGAGUCG-GUGC 3'(SEQ ID NO:12), where the "n"s refer to the residues of the targeting domain, e.g., as described herein, and may consist of 15-25 nucleotides, e.g., consist of 20 nucleotides, optionally with 1, 2, 3, 4, 5, 6, or 7 (e.g., 4 or 7, e.g., 4) additional U nucleotides at the 3' end.

Additional components and/or elements of CRISPR gene editing systems known in the art, e.g., are described in U.S. Publication No. 2014/0068797, WO2015/048577, and Cong (2013) Science 339: 819-823, the contents of which are hereby incorporated by reference in their entirety. Such systems can be generated which inhibit a target gene, by, for example, engineering a CRISPR gene editing system to include a gRNA molecule comprising a targeting domain that hybridizes to a sequence of the target gene. In embodiments, the gRNA comprises a targeting domain which is fully complementarity to 15-25 nucleotides, e.g., 20 nucleotides, of a target gene. In embodiments, the 15-25 nucleotides, e.g., 20 nucleotides, of the target gene, are disposed immediately 5' to a protospacer adjacent motif (PAM) sequence recognized by the RNA-guided nuclease, e.g., Cas protein, of the CRISPR gene editing system (e.g., where the system comprises a S. pyogenes Cas9 protein, the PAM sequence comprises NGG, where N can be any of A, T, G or C).

In some embodiments, the gRNA molecule and RNA-guided nuclease, e.g., Cas protein, of the CRISPR gene editing system can be complexed to form a RNP (ribonucleoprotein) complex. Such RNP complexes may be used in the methods described herein. In other embodiments, nucleic acid encoding one or more components of the CRISPR gene editing system may be used in the methods described herein.

In some embodiments, foreign DNA can be introduced into the cell along with the CRISPR gene editing system, e.g., DNA encoding a desired transgene, with or without a promoter active in the target cell type. Depending on the sequences of the foreign DNA and target sequence of the genome, this process can be used to integrate the foreign DNA into the genome, at or near the site targeted by the CRISPR gene editing system. For example, 3' and 5' sequences flanking the transgene may be included in the foreign DNA which are homologous to the gene sequence 3' and 5' (respectively) of the site in the genome cut by the gene editing system. Such foreign DNA molecule can be referred to as "template DNA."

In an embodiment, the CRISPR gene editing system of the present invention comprises Cas9, e.g., S. pyogenes Cas9, and a gRNA comprising a targeting domain which hybridizes to a sequence of a gene of interest. In an embodiment, the gRNA and Cas9 are complexed to form a RNP (ribonucleoprotein). In an embodiment, the CRISPR gene editing system comprises nucleic acid encoding a gRNA and nucleic acid encoding a Cas protein, e.g., Cas9, e.g., S. pyogenes Cas9. In an embodiment, the CRISPR gene editing system comprises a gRNA and nucleic acid encoding a Cas protein, e.g., Cas9, e.g., S. pyogenes Cas9.

In some embodiments, inducible control over Cas9, sgRNA expression can be utilized to optimize efficiency while reducing the frequency of off-target effects thereby increasing safety. Examples include, but are not limited to, transcriptional and post-transcriptional switches listed as follows; doxycycline inducible transcription Loew et al. (2010) BMC Biotechnol. 10:81, Shield1 inducible protein stabilization Banaszynski et al. (2016) Cell 126: 995-1004, Tamoxifen induced protein activation Davis et al. (2015) Nat. Chem. Biol. 11: 316-318, Rapamycin or optogenetic induced activation or dimerization of split Cas9 Zetsche (2015) Nature Biotechnol. 33(2): 139-142, Nihongaki et al. (2015) Nature Biotechnol. 33(7): 755-760, Polstein and Gersbach (2015) Nat. Chem. Biol. 11: 198-200, and SMASh tag drug inducible degradation Chung et al. (2015) Nat. Chem. Biol. 11: 713-720.

In general, the CRISPR-Cas or CRISPR system refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA (s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments it may be preferred in a CRISPR complex that the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme. In embodiments of the invention the terms guide sequence and guide RNA are used interchangeably. In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies); ELAND (Illumina, San Diego, Calif.), and SOAP. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MM M MMMNNNNNNNNNNNNXGG (SEQ ID NO: 13), where NNN NNN NN XGG (N is A, G, T, or C; and X can be anything) has a single occurrence in the genome. A unique target sequence in a genome may include an S. pyogenes Cas9 target site of the form MMM MMMMMNNNNNNNNNNNXGG (SEQ ID NO: 14), where N N N N XGG (N is A, G, T, or C; and X can be anything) has a single occurrence in the genome. For the S. thermophilus CRISPRI Cas9, a unique target sequence in a genome may include a Cas9 target site of the form MMMMMMMMNN N N NN XXAGAAW (SEQ ID NO: 15), where NNN NN N XXAGAAW (SEQ ID NO: 29) (N is A, G, T, or C; X can be anything; and W is A or T) has a single occurrence in the genome. A unique target sequence in a genome may include an S. thermophilus CRISPRI Cas9 target site of the form MMMMMM MN N NNN NNXX-AGAAW (SEQ ID NO: 16), where NNNNNNNNNNNXX-AGAAW (SEQ ID NO: 30) (N is A, G, T, or C; X can be anything; and W is A or T) has a single occurrence in the genome. For the S. pyogenes Cas9, a unique target sequence in a genome may include a Cas9 target site of the form MMMMMMMMMNNNN NNNNNNXGGXG (SEQ ID NO: 17), where NNNNNNNNNNNNXGGXG (N is A, G, T, or C; and X can be anything) has a single occurrence in the genome. A unique target sequence in a genome may include an S. pyogenes Cas9 target site of the form MMMMMMMMMMNNNNNNNNNNNXGGXG (SEQ ID NO: 31) where NNNNNNNNNNNXGGXG (SEQ ID NO: 18), (N is A, G, T, or C; and X can be anything) has a single occurrence in the genome. In each of these sequences, N is any nucleobase and "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1 151-62).

Methods for Designing gRNA Molecules

Methods for selecting, designing, and validating targeting domains for use in the gRNAs described herein are provided. Exemplary targeting domains for incorporation into gRNAs are also provided herein.

Methods for selection and validation of target sequences as well as off-target analyses have been described (see, e.g., Mali 2013; Hsu 2013; Fu 2014; Heigwer 2014; Bae 2014; and Xiao 2014). For example, target sequences can be chosen by identifying the PAM sequence for a Cas9 molecule (for example, relevant PAM e.g., NGG PAM for S. pyogenes, NNNNGATT (SEQ ID NO: 19), or NNNNGCTT PAM (SEQ ID NO: 20), for N. meningitides, and NNGRRT (SEQ ID NO: 21), or NNGRRV PAM (SEQ ID NO: 22), for S. aureus), and identifying the adjacent sequence as the target sequence for a CRISPR system using that Cas9 molecule. A software tool can be used to further refine the choice of potential targeting domains corresponding to a user's target sequence, e.g., to minimize total off-target activity across the genome. Candidate targeting domains and gRNAs comprising those targeting domains can be functionally evaluated by using methods known in the art and/or as set forth herein.

As a non-limiting example, targeting domains for use in gRNAs for use with S. pyogenes, N. meningiitidis and S. aureus Cas9s are identified using a DNA sequence searching algorithm. 17-mer, 18-mer, 19-mer, 20-mer, 21-mer, 22-mer, 23-mer, and/or 24-mer targeting domains are designed for each Cas9. With respect to S. pyogenes Cas9, preferably, the targeting domain is a 20-mer. gRNA design is carried out using a custom gRNA design software based on the public tool cas-offinder (Bae 2014). This software scores guides after calculating their genome-wide off-target propensity.

Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule have been described previously (Jinek 2012). Each technique described herein may be used alone or in combination with one or more techniques to evaluate the candidate molecule. The techniques disclosed herein may be used for a variety of methods including, without limitation, methods of determining the stability of a Cas9 molecule/gRNA molecule complex, methods of determining a condition that promotes a stable Cas9 molecule/gRNA molecule complex, methods of screening for a stable Cas9 molecule/gRNA molecule complex, methods of identifying an optimal gRNA to form a stable Cas9 molecule/gRNA molecule complex, and methods of selecting a Cas9/gRNA complex for administration to a subject.

Binding and Cleavage Assay: Testing the endonuclease activity of Cas9 molecule The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and −3-6 pmol (−20-40 mCi) [γ-32P]-ATP in IX T4 polynucleotide kinase reaction buffer at 37° C. for 30 min, in a 50 microlitre reaction. After heat inactivation (65° C. for 20 min), reactions are purified through a column to remove unincorporated label. Duplex localising agents (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM $MgCl_2$, 1 mM DTT, 5% glycerol) in a total volume of 9 microlitre. Reactions are initiated by the addition of 1 microlitre target DNA (10 nM) and incubated for 1 h at 37° C. Reactions are quenched by the addition of 20 microlitre of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Indel Detection and Identification. Targeted genome modifications can also be detected by either Sanger or deep sequencing. For the former, genomic DNA from the modified region can be amplified with either primers flanking the target sequence of the gRNA. Amplicons can be subcloned into a plasmid such as pUC19 for transformation, and individual colonies should be sequenced to reveal the clonal genotype.

Alternatively, deep sequencing is suitable for sampling a large number of samples or target sites. NGS primers are designed for shorter amplicons, typically in the 100-200-bp size range. For the detection of indels, it is important to design primers situated at least 50 bp from the Cas9 target site to allow for the detection of longer indels. Amplicons may be assessed using commercially-available instruments, for example, the Illumina system. Detailed descriptions of NGS optimization and troubleshooting can be found in the Illumina user manual.

TALEN Gene Editing Systems

TALENs are produced artificially by fusing a TAL effector DNA binding domain to a DNA cleavage domain. Transcription activator-like effects (TALEs) can be engineered to bind any desired DNA sequence, e.g., a target gene. By combining an engineered TALE with a DNA cleavage domain, a restriction enzyme can be produced which is specific to any desired DNA sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is, for example, a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A TALEN (or pair of TALENs) can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN, e.g., DNA encoding a transgene, and depending on the sequences of the foreign DNA and chromosomal sequence, this process can be used to integrate the transgene at or near the site targeted by the TALEN. TALENs specific to a target gene can be constructed using any method known in the art, including various schemes using modular components. Zhang et al. (2011) *Nature Biotech.* 29: 149-53; Geibler et al. (2011) *PLoS ONE* 6: e19509; U.S. Pat. Nos. 8,420,782; 8,470,973, the contents of which are hereby incorporated by reference in their entirety.

Zinc Finger Nuclease (ZFN) Gene Editing System

"ZFN" or "Zinc Finger Nuclease" refer to a zinc finger nuclease, an artificial nuclease which can be used to modify, e.g., delete one or more nucleic acids of, a desired nucleic acid sequence.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of the target gene in a cell. ZFNs can also be used with homologous recombination to mutate the target gene or locus, or to introduce nucleic acid encoding a desired transgene at a site at or near the targeted sequence.

ZFNs specific to sequences in a target gene can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; and Guo et al. (2010) J. Mol. Biol. 400: 96; U.S. Patent Publication 2011/0158957; and U.S. Patent Publication 2012/0060230, the contents of which are hereby incorporated by reference in their entirety. In embodiments, The ZFN gene editing system may also comprise nucleic acid encoding one or more components of the ZFN gene editing system.

Meganuclease Gene Editing System

"Meganuclease" refers to a meganuclease, an artificial nuclease which can be used to edit a target gene.

Meganucleases are derived from a group of nucleases which recognize 15-40 base-pair cleavage sites. Meganucleases are grouped into families based on their structural motifs which affect nuclease activity and/or DNA recognition. Members of the LAGLIDADG (SEQ ID NO: 23) family are characterized by having either one or two copies of the conserved LAGLIDADG motif (SEQ ID NO: 23) (see Chevalier et al. (2001), *Nucleic Acids Res.* 29(18): 3757-3774). The LAGLIDADG (SEQ ID NO: 23) meganucleases with a single copy of the LAGLIDADGmotif (SEQ ID NO: 23) form homodimers, whereas members with two copies of the LAGLIDADG motif (SEQ ID NO: 23) are found as monomers. The GIY-YIG family members have a GIY-YIG module, which is 70-100 residues long and includes four or five conserved sequence motifs with four invariant residues, two of which are required for activity (see Van Roey et al. (2002), Nature Struct. Biol. 9: 806-811). The His-Cys box meganucleases are characterized by a highly conserved series of histidines and cysteines over a region encompassing several hundred amino acid residues (see Chevalier et al. (2001), Nucleic Acids Res. 29(18): 3757-3774). The NHN family, the members are defined by motifs containing two pairs of conserved histidines surrounded by asparagine residues (see Chevalier et al. (2001), Nucleic Acids Res. 29(18): 3757-3774).

Strategies for engineering a meganuclease with altered DNA-binding specificity, e.g., to bind to a predetermined nucleic acid sequence are known in the art. E.g., Chevalier et al. (2002), Mol. Cell, 10:895-905; Epinat et al. (2003) Nucleic Acids Res 31: 2952-62; Silva et al. (2006) J Mol Biol 361: 744-54; Seligman et al. (2002) Nucleic Acids Res 30: 3870-9; Sussman et al. (2004) J Mol Biol 342: 31-41; Rosen et al. (2006) Nucleic Acids Res; Doyon et al. (2006) J. Am Chem Soc 128: 2477-84; Chen et al. (2009) Protein Eng Des Sel 22: 249-56; Arnould S (2006) J Mol Biol. 355: 443-58; Smith (2006) Nucleic Acids Res. 363(2): 283-94.

A meganuclease can create a double-stranded break in the DNA, which can create a frame-shift mutation if improperly repaired, e.g., via non-homologous end joining, leading to a decrease in the expression of a target gene in a cell. Alternatively, foreign DNA can be introduced into the cell along with the Meganuclease; depending on the sequences of the foreign DNA and chromosomal sequence, this process can be used to modify a target gene, e.g., correct a defect in the target gene, thus causing expression of a repaired target gene, or e.g., introduce such a defect into a wt gene, thus decreasing expression of a target gene, e.g., as described in Silva et al. (2011) Current Gene Therapy 11:11-27.

Ocular Administration of the Expanded Cell Population

In one aspect of the invention the expanded cell population obtainable by the methods according to the invention as described above is delivered to the eye. The delivery is performed under aseptic conditions.

In one embodiment relating to use for limbal stem cell therapy after a 360° limbal peritomy the fibrovascular corneal pannus may be carefully removed from the surface.

In one aspect of the invention, the cell population is combined with a localising agent suitable for ocular delivery (as described further below) and delivered to the eye. In a preferred embodiment the cells and localising agent suitable for ocular delivery are combined and administered to the eye via a carrier such as for example a therapeutic contact lens or amniotic membrane. In an alternative embodiment the cells and localising agent suitable for use in the eye, such as a light curable biomatrix, like GelMA, are delivered to the eye via bioprinting.

In one embodiment, the invention provides a method of transplanting a population of cells comprising corneal endothelial cells onto the cornea of a subject, the method comprising expanding a population of cells comprising corneal endothelial cells by culturing said population with cell proliferation medium comprising a LATS inhibitor according to the invention, rinsing the expanded population of cells to substantially remove the LATS inhibitor, and administering said cells onto the cornea of said subject. Preferably said cells are combined with a biomatrix prior to said administration. In a specific embodiment said cells are combined with a biomatrix which is GelMA prior to said administration. In a more specific embodiment said corneal endothelial cells are combined with a biomatrix which is bioprinted onto the ocular surface. Particularly preferably said corneal endothelial cells are combined with a biomatrix which is GelMA and bioprinted onto the ocular surface by polymerising the GelMA by a light triggered reaction.

In another embodiment, the invention provides a method of transplanting a population of cells to the eye of a subject, comprising combining the cells with a biomatrix to form a cell/biomatrix mixture, injecting the mixture into the eye of the subject or applying the mixture onto the surface of the eye of the subject, and bioprinting the cells in or on the eye by guiding and fixing the cells, such as on the cornea, using a light source, such as an Ultraviolet A or white light source. In certain embodiments, the light source produces light of a wavelength that is at least 350 nm. In certain embodiments, the light source produces light in the 350 nm to 420 nm range. For example, an LED light source can be used to produce a light having a wavelength of 365 nm or 405 nm, or any other wavelength above 350 nm, or a mercury lamp with a bandpass filter can be used to produce a light having a wavelength of 365 nm. In another embodiment, the light source produces visible, white light having a wavelength, for example, in the 400 nm to 700 nm range. In certain embodiments, the cells are ocular cells, such as corneal cells (e.g., corneal endothelial cells), lens cells, trabecular mesh cells, or cells found in the anterior chamber. In a particular embodiment, the cells are corneal endothelial cells. Certain embodiments of such method include:

Embodiment x1

A method of transplanting a population of isolated cells to the eye of a subject, comprising combining the cells with a biomatrix to form a cell/biomatrix mixture, injecting the mixture into the eye of the subject, (e.g., into the anterior chamber) and bioprinting the cells in the eye by guiding and fixing the cells in the eye using a light source.

Embodiment x2

The method of Embodiment x1, wherein the isolated cells are combined with a biomatrix which is GelMA and bioprinted onto the cornea by polymerising the GelMA by a light triggered reaction.

Embodiment x3

The method of Embodiment x1 or Embodiment x2, wherein the light source produces a light having a wavelength in the 350 nm to 700 nm range.

Embodiment x4

The method of any one of Embodiments x1 to x3, wherein the wavelength is 350 nm to 420 nm.

Embodiment x5

The method of any one of Embodiments x1 to x4, wherein the wavelength is 365 nm.

Embodiment x6

The method of any one of Embodiments x1 to x5, wherein the isolated cells are corneal endothelial cells.

Embodiment x7

A method of transplanting a population of isolated cells to the eye of a subject, comprising combining the cells with a biomatrix to form a cell/biomatrix mixture, applying the mixture onto the eye of the subject, and bioprinting the cells on the eye by guiding and fixing the cells on the eye using a light source.

Embodiment x8

The method of Embodiment x7, wherein the isolated cells are combined with a biomatrix which is GelMA and bioprinted onto the ocular surface by polymerising the GelMA by a light triggered reaction.

Embodiment x9

The method of Embodiment x7 or Embodiment x8, wherein the light source produces a light having a wavelength in the 350 nm to 700 nm range.

Embodiment x10

The method of any one of Embodiments x7 to x9, wherein the wavelength is 350 nm to 420 nm.

Embodiment x11

The method of any one of Embodiments x7 to x10, wherein the wavelength is 365 nm.

Embodiment x12

The method of any one of Embodiments x7 to x11, wherein the isolated cells are limbal stem cells.

In an alternative embodiment the expanded cell population obtainable by the methods according to the invention as described above may be delivered directly via a therapeutic contact lens to the eye, without use of a localising agent suitable for ocular delivery (such as GelMA).

Localising Agent Suitable for Ocular Delivery

In an embodiment of the invention the cell preparation may be delivered to the eye via a localising agent suitable for ocular use. The cells may be embedded within the localising agent or adhered to the surface of the localising agent, or both.

The type of localising agent is not limited as long as it is able to carry LSCs or CECs and is suitable for use in the eye. In a preferred embodiment, the localising agent is degradable and biocompatible. Where CECs are delivered, preferably the localising agent can facilitate CEC attachment to the cornea after surgical delivery to the surface of the eye.

In a preferred embodiment the cells are only combined with the localising agent after cell population expansion. In a particularly preferred embodiment the expanded cell population is combined with the localising agent suitable for ocular delivery after rinsing the cell population to substantially remove the presence of the LATs inhibitor according to the invention. In one embodiment, the LSCs or CECs and localising agent are combined and stored in a form suitable for ocular use. In another embodiment, the LSCs or CECs and localising agent are stored separately and combined immediately prior to ocular use.

The localising agent is preferably selected from the list consisting of fibrin, collagen, gelatin, cellulose, amniotic membrane, fibrin glue, polyethylene (glycol) diacrylate (PEGDA), GelMA, (which is methacrylamide modified gelatin, and is also known as gelatin methacrylate), localising agents comprising a polymer, cross-linked polymer, or hydrogel comprising one or more of hyaluronic acid, polyethylene glycol, polypropylene glycol, polyethylene oxide, polypropylene oxide, poloxamer, polyvinyl alcohol, polyacrylic acid, polymethacrylic acid, polyvinyl pyrrolidone, poly(lactide-co-glycolide), alginate, gelatin, collagen, fibrinogen, cellulose, methylcellulose, hydroxyethylcellulose, hydroxypropyl cellulose, hydroxypropylmethylcellulose, hydroxypropyl-guar, gellan gum, guar gum, xanthan gum and carboxymethylcellulose, as well as derivatives thereof, co-polymers thereof, and combinations thereof.

In a more preferred embodiment the localising agent is selected from the list consisting of fibrin, collagen, gelatin, amniotic membrane, fibrin glue, polyethylene (glycol) diacrylate (PEGDA), GelMA, localising agents comprising a polymer, cross-linked polymer, or hydrogel comprising one or more of hyaluronic acid, polyethylene glycol, polypropylene glycol, polyethylene oxide, polypropylene oxide, poloxamer, polyacrylic acid, poly(lactide-co-glycolide), alginate, gelatin, collagen, fibrinogen, hydroxypropylmethylcellulose and hydroxypropyl-guar, as well as derivatives thereof, co-polymers thereof, and combinations thereof.

In a preferred embodiment the expanded cell population according to the invention may be delivered to a recipient via a localising agent which is a biomatrix. In a more preferred embodiment the localising agent is a light curable, degradable biomatrix. Preferably this is able to be injected into the eye. A specific example of a biomatrix is GelMA, which is methacrylamide modified gelatin, and is also known as gelatin methacrylate.

GelMA may be prepared according to standard protocols known in the art (Van Den Bulcke et al., *Biomacromolecules,* 2000, p.31-38; Yue et al., *Biomaterials,* 2015, p.254-271). For example, gelatin from porcine skin (gel strength 300 g Bloom, Type A) is dissolved in PBS without calcium and magnesium (Dulbeccos PBS), and methacrylic anhydride may be added with strong agitation into the gelatin solution to reach the desired concentration (e.g. 8% (vol/vol). The mixture may be stirred before and after adding further DPBS. The diluted mixture may be purified via dialysis against Milli-Q water using dialysis tubing to remove methacrylic acid. The purified samples may optionally be lyophilized and the solid stored at $-80°$ C., $-20°$ C., or 4° C. until further use.

A GelMA stock solution is prepared by dissolving lyophilized GelMA in a formulation suitable for ocular use comprising pharmaceutically acceptable excipients. To prepare a GelMA stock solution, lyophilized GelMA may be dissolved in DPBS. After the GelMA is fully dissolved, a photoinitiator (for example such as lithium phenyl-2,4,6-trimethylbenzoylphosphinate) may be introduced into the GelMA solution. To adjust the pH to neutral, NaOH may be added to the solution before filtering using 0.22 micrometre sterile membranes. The final filtrate may be separated into aliquots and stored at 4° C. until further use.

In one aspect according to the invention, the cells are encapsulated within the biomatrix using a photoinitiator to polymerise the biomatrix, which is preferably GelMa. Suitable photoinitiator agents are Irgacure 2959, lithium phenyl-2,4,6-trimethylbenzoylphosphinate, sodium phenyl-2,4,6-trimethylbenzoylphosphinate, lithium bis(2,4,6-trimethylbenzoyl)phosphinate, sodium bis(2,4,6-trimethylbenzoyl)phosphinate, Diphenyl(2,4,6-trimethylbenzoyl)phosphine oxide, eosin Y, riboflavin phosphate, camphorquinone, Quantacure BPQ, Irgacure 819, Irgacure 1850, and Darocure 1173. In a preferred embodiment, the photoiniator is lithium phenyl-2,4,6-trimethylbenzoylphosphinate, sodium phenyl-2,4,6-trimethylbenzoylphosphinate, riboflavin phosphate. In another embodiment the photoinitiator is lithium phenyl-2,4,6-trimethylbenzoylphosphinate.

Prior to polymerization, the light curable biomatrix is combined with a suitable photoinitiator in a formulation suitable for ocular use comprising pharmaceutically acceptable excipients in suitable containers known in the art such as vials. The photoinitiator may be combined with the biomatrix prior to mixing with cells; alternatively the photoinitiator may be combined with the biomatrix after mixing with cells; alternatively the photoiniator may be added to the cells first, then combined with the biomatrix. The concentration of biomatrix and photoinitiator is dependent on the specific biomatrix and specific photoinitiator used, but is chosen to provide polymerization within a convenient light exposure duration, typically less than about 5 minutes; preferably less than about 2 minutes; more preferably less than about one minute.

In one embodiment the photoinitiator is lithium phenyl-2,4,6-trimethylbenzoylphosphinate and its concentration in the formulation for cell delivery to the eye is about 0.01% w/v to about 0.15% w/v. In another aspect the lithium phenyl-2,4,6-trimethylbenzoylphosphinate concentration in the formulation for cell delivery to the eye is about 0.05% w/v or about 0.075% w/v. LAP may be synthesized using published procedure (Biomaterials 2009, 30, 6702-6707) and is also available from TCI (Prod. #L0290) and Biobots (BioKey).

The cells may be added to the GelMA in suitable containers known in the art such as vials or tubes. The cells may for example be added by pipetting into the GelMA and mixing by gentle pipetting up and down. In one embodiment the GelMA concentration in the composition suitable for ocular delivery is about 10 to about 200 mg/mL, or about 25 to about 150 mg/mL, or about 25 to about 75 mg/mL. In a preferred embodiment the GelMA concentration in the composition suitable for ocular delivery is about 25 mg/mL, about 50 mg/mL or about 75 mg/mL.

To polymerise the light curable biomatrix, the biomatrix, photoinitiator, and cells are exposed to a light source for a preferred duration, as described above. The wavelength of light used for polymerization will depend on the photochemical properties of the specific photoinitiator used. For example, photoinitation of polymerization for Irgacure 2959 will occur with light of wavelength between 300-370 nm; photoinitation of polymerization for lithium phenyl-2,4,6-trimethylbenzoylphosphinate will occur with light of wavelength between 300-420 nm; photoinitation of polymerization for riboflavin-5'-phosphate will occur with light of wavelength between 300-500 nm. The light source used may emit a range of wavelengths, like that achieved with incandescent lamps, gas discharge lamps, or metal vapor lamps; alternatively, the light source used may emit a narrow range of wavelengths, like that achieved with optical filters or with an light emitting diode (LED). Preferably, the light source used does not emit light with wavelength less than 315 nm to avoid the damaging effects of UV irradiation on cells. In one embodiment, the light source is a white light source with a spectral range of 415-700 nm. In another embodiment the light source is a LED light source with spectral range of about 365±5 nm, about 375±5 nm, about 385±5 nm, about 395±5 nm, about 405±5 nm, about 415±5 nm, about 425±5 nm, about 435±5 nm, about 445±5 nm, about 455±5 nm, or about 465±5 nm. The intensity of light is chosen to minimize phototoxicity and provide polymerization within a convenient light exposure duration, typically less than about 5 minutes; preferably less than about 2 minutes; more preferably less than about one minute. One indication of polymerization is an increase in solution viscosity. Another indication of polymerization is the onset of gelation.

The polymerization of the biomatrix may occur on the ocular surface via bioprinting techniques, or alternatively on a carrier that is then transplanted to the ocular surface. Optionally the polymerization of the biomatrix may occur on the cornea surface in the anterior chamber, or alternatively on a carrier that is then transplanted to the cornea surface in the anterior chamber.

Carrier

The cells and localising agent suitable for ocular delivery are preferably delivered via a carrier such as a contact lens or amniotic membrane.

Contact lenses suitable for use according to the invention are preferably those which conform to the patient's corneal curvature and are able to be well tolerated by the patient in clinical practice for continuous use as bandage contact lenses for several days.

Examples of suitable types of contact lens according to the invention are consistent with what has been extensively validated in clinical use for long-term bandage contact lens use with Boston keratoprosthesis type 1 (which can be also used in patients with limbal stem cell deficiency) and described in: Thomas, Merina M. D.; Shorter, Ellen O. D.; Joslin, Charlotte E. O. D., Ph.D.; McMahon, Timothy J. O. D.; Cortina, M. Soledad M. D. Contact Lens Use in Patients With Boston Keratoprosthesis Type 1: Fitting, Management, and Complications. Eye Contact Lens. 2015 November; 41(6):334-40.

A contact lens can be of any appropriate material known in the art or later developed, and can be a soft lens, a hard lens, or a hybrid lens, preferably a soft lens, more preferably a conventional hydrogel contact lens or a silicone hydrogel (SiHy) contact lens.

A "conventional hydrogel contact lens" refers to a contact lens comprising a hydrogel bulk (core) material which is a water-insoluble, crosslinked polymeric material, is theoretically free of silicone, and can contain at least 10% by weight of water within its polymer matrix when fully hydrated. A conventional hydrogel contact lens typically is obtained by copolymerization of a conventional hydrogel lens formulation (i.e., polymerizable composition) comprising silicone-free, hydrophilic polymerizable components known to a person skilled in the art.

Examples of conventional hydrogel lens formulation for making commercial hydrogel contact lenses include, without limitation, alfafilcon A, acofilcon A, deltafilcon A, etafilcon A, focofilcon A, helfilcon A, helfilcon B, hilafilcon B, hioxifilcon A, hioxifilcon B, hioxifilcon D, methafilcon A, methafilcon B, nelfilcon A, nesofilcon A, ocufilcon A, ocufilcon B, ocufilcon C, ocufilcon D, omafilcon A, phemfilcon A, polymacon, samfilcon A, telfilcon A, tetrafilcon A, and vifilcon A.

A "SiHy contact lens" refers to a contact lens comprising a silicone hydrogel bulk (core) material which is a water-insoluble, crosslinked polymeric material containing silicone and can contains at least 10% by weight of water within its polymer matrix when fully hydrated. A silicone hydrogel contact lens typically is obtained by copolymerization of a silicone hydrogel lens formulation comprising at least silicone-containing polymerizable component and hydrophilic polymerizable components known to a person skilled in the art.

Examples of SiHy lens formulation for making commercial SiHy contact lenses include, without limitation, asmofilcon A, balafilcon A, comfilcon A, delefilcon A, efrofilcon A, enfilcon A, fanfilcon A, galyfilcon A, lotrafilcon A, lotrafilcon B, narafilcon A, narafilcon B, senofilcon A, senofilcon B, senofilcon C, smafilcon A, somofilcon A, and stenfilcon A.

In a preferred embodiment the carrier is a contact lens selected from the group consisting of Balafilcon A, Lotrafilcon A, Lotrafilcon B, Senofilcon A and methafilcon A.

In a particularly preferred embodiment the carrier is a contact lens, which is Lotrafilcon B.

The carrier may be held in place on the ocular surface using fibrin glue or sutures to prevent eye movements from dislodging the construct.

The carrier combined with biomatrix and cells may be left on the eye for a range of times in order to deliver the cells, for example a few days to one week, preferably one week.

Other Delivery Methods:

In an alternative embodiment the LSCs may be delivered as a cell suspension to the ocular surface (without a localising agent such as a biomatrix and with/or without a carrier such as a contact lens). Compounds and excipients known in the art to improve tissue adhesion such as mucoadhesive agents, viscosity enhancers, or reverse thermal gelators may be included in the formulation.

Bioprinting Step

The population of ocular cells, e.g. corneal endothelial cells, obtainable according to the method of cell population expansion according to the invention may be grafted to the eye of a subject, e.g., to the cornea of a subject.

The cell population according to the invention may be delivered via a localising agent suitable for ocular use which is a light curable, degradable biomatrix such as GelMA. The following methods describe procedures for controlling the delivery to the inner wall of the cornea.

Method 1. Bubble Depression Method (Shown in FIG. 22)

The dysfunctional endothelial cells may first be detached from the inner wall of the cornea by peeling/scraping or in a controlled manner using photodisruption with a femtosecond laser. A small bolus of the cell-laden biomatrix is then injected near the interior surface of the cornea. This may be done manually using a standard syringe or custom applicator. It can also be controlled through a surgical system (e.g. constellation) or syringe pumps. A gas bubble is then injected beneath the bolus. The gas bubble squeezes the bolus against the posterior cornea, creating a thin coating. The entire gel is then cured using a using a UV or near UV light source, or any other spectral band needed to cure the biomatrix. Alternatively, the dysfunctional tissue may be left, and the biomatrix cured over top of it. The light source can be focused into different sizes using other optical focusing methods to control the curing area. The remaining uncured area can be flushed out using irrigating/aspirating canula.

Method 2. Subtractive Method Using Femtosecond Laser (Shown in FIG. 23)

The dysfunctional endothelial cells may first be detached from the inner wall of the cornea by peeling/scraping or in a controlled manner using photodisruption with a femtosecond laser. Alternatively, they may be left in place. The cell-laden biomatrix is then injected onto the interior surface of the cornea covering the void where tissue was removed or over the dysfunctional tissue. This may be done manually using a standard syringe or custom applicator. It can also be controlled through a surgical system (e.g. constellation) or syringe pumps. The biomatrix is then cured using a using a UV or near UV light source, or any other spectral band needed to cure the biomatrix. The femtosecond laser is then used to detach excess material, controlling the thickness and area to a desired distribution. The excess material is then removed with forceps through a corneal incision.

Method 3. Stain Mask and Absorption Based Thickness Control (Shown in FIG. 24)

A biocompatible stain (Trypan Blue, Brilliant Blue, etc.) is firstly used to dye the inner surface of the cornea. The dysfunctional endothelial cells are then detached from the inner wall of the cornea by peeling/scraping. The cell-laden biomatrix containing the biocompatible stain is then injected onto the interior surface of the cornea covering the void where tissue was removed. The biomatrix is then cured using a using a UV or near UV light source, or any other spectral band needed to cure the biomatrix. The stain in the corneal tissue increases the light absorption acting as a mask to control the area of the cured biomatrix. Similarly, the stain in the biomatrix increases the absorption of light thereby controlling the depth/thickness of the cured material. Uncured gel material is then flushed from the anterior chamber using an irrigating/aspirating cannula.

Method 4. Dry Anterior Chamber Application (Shown in FIG. 25)

The dysfunctional endothelial cells may first be detached from the inner wall of the cornea by peeling/scraping or in a controlled manner using photodisruption with a femtosecond laser. Alternatively it may be left in place. The anterior chamber of the anterior segment is then drained of aqueous and replaced with gas (e.g. air). The cell-laden biomatrix is then applied to interior surface of the cornea in small controlled droplets (allowing surface tension to disperse the drops), or painted using a brush or soft tip cannula. Hyaluronic acid may be applied to the biomatrix to alter its viscous properties and enable better control over dispensing/application. The entire biomatrix is then cured using a using a UV or near UV light source, or any other spectral band needed to cure the biomatrix. Finally, the anterior chamber is then filled again with balanced salt solution.

Method 5. Naturally Buoyant Formulation

The dysfunctional endothelial cells may first be detached from the inner wall of the cornea by peeling/scraping or in a controlled manner using photodisruption with a femtosecond laser. A small bolus of the cell-laden biomatrix is then injected near the interior surface of the cornea. The biomatrix is formulated to be naturally buoyant relative to aqueous humor or aerated to achieve the same effect. This causes the biomatrix to naturally rise to posterior cornea, creating a thin coating. The entire biomatrix is then cured using a using a UV or near UV light source, or any other spectral band needed to cure the biomatrix. Alternatively, the dysfunctional tissue may be left, and the biomatrix cured over top of it. The UV light source can be focused into different sizes using optical focusing methods to control the curing area. The remaining uncured area can be flushed out using aspiration canula.

Other Delivery Methods

In an alternative embodiment an expanded cell population, such as CECs as described herein, may be delivered as a cell suspension (without a localising agent such as a light curable, degradable biomatrix) and left to attach by gravity by having the patient look down for 3 hours. Compounds and excipients known in the art to improve tissue adhesion such as adhesive agents, viscosity enhancers, or reverse thermal gelators may be included in the formulation.

In yet another alternative embodiment an expanded cell population, such as CECs as described herein can also be delivered by using magnetic beads. A suspension of CECs/beads in a medium suitable for ocular delivery is prepared and this is then injected into the eye. Cell attachment is promoted by a magnet applied to the eye. (Magnetic field-guided cell delivery with nanoparticle-loaded human corneal endothelial cells. Moysidis S N, Alvarez-Delfin K, Peschansky V J, Salero E, Weisman A D, Bartakova A, Raffa G A, Merkhofer R M Jr, Kador K E, Kunzevitzky N J, Goldberg J L. Nanomedicine. 2015 April; 11(3):499-509. doi: 10.1016/j. nano.2014.12.002.)

Other Methods of Use of the LATS Inhibitors According to the Invention

In one aspect according to the invention it is possible to directly add the LATS inhibitors according to the invention directly to the surface of the eye to achieve cell population expansion. For example this can be done if the cell loss was not total and there is a remaining seeding population of cells to be expanded. For example if there are remaining limbal stem cells in the eye of the patient or if there are remaining corneal endothelial cells in the cornea of the patient as the case may be. For example, this can be achieved by preparing the compounds as disclosed herein in a formulation suitable for ocular use comprising pharmaceutically acceptable excipients and applying by eye drops to the eye. Alternatively, compounds as disclosed herein in a formulation suitable for ocular use comprising pharmaceutically acceptable excipients can be applied intraocularly, for example, intracamerally.

Pharmaceutically acceptable excipients enhance or stabilize the composition, or facilitate preparation of the composition. Pharmaceutically acceptable excipients include solvents, dispersion media, coatings, antibacterial and antifungal agents, isotonic and absorption delaying agents, and the like that are physiologically compatible.

The LATS inhibitor according to the invention may be combined with ophthalmologically acceptable preservatives, co-solvents, surfactants, viscosity enhancers, penetration enhancers, buffers, sodium chloride, or water to form an aqueous ophthalmic suspension or solution. Topical ophthalmic products may be packaged, for example, in multi-dose form. Preservatives may thus be required to prevent microbial contamination during use. Suitable preservatives include: chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v.

In an embodiment of the invention the LATS inhibitors according to the invention could be used to preserve cells, e.g. corneal epithelial and limbal cells until transplantation. After postmortem dissection by eye-bank specialists, corneas are preserved in media such as Optisol or PBS until transplantation. In a specific embodiment of the invention a LATS inhibitor may be added to a solution generally used for corneal transplantation, such as Optisol or PBS. Preferably the concentration of the LATS inhibitor in the preservation solution is 0.5 to 100 micromolar, more preferably 0.5 to 25 micromolar, particularly preferably 1 to 20 micromolar. In a specific embodiment the LATS inhibitors according to Formula I are added at a concentration of about 3 to 10 micromolar.

Immunosuppressant, Anti-Inflammatory and Antibiotic Agents

In addition to, or as an alternative to, the use of a gene editing technique performed in vitro on a cell population, as described for limbal stem cells or corneal endotheal cells, to mitigate the risk of immune rejection of the transplanted cells to the patient, the cell population according to the invention may be administered simultaneously or sequentially with an immunosuppressant and/or anti-inflammatory agents or agents. Standard agents for immunosuppression or anti-inflammatory agents or agents may be used including, but not limited to, dexamethasone or cyclosporine.

Antibiotics may also be administered to the patient in conjunction with an expanded cell population (e.g. the limbal stem cells or corneal endotheal cells as described herein), such as the antibiotics cefazolin and tobramycin.

When the cell population of the present invention is administered together with another agent or agents, the cell population and the agent(s) can be administered sequentially in any order or simultaneously. In some embodiments, an expanded cell population according to the invention is administered in conjunction with surgical treatments. In other embodiments, the limbal stem cell population according to the invention is administered in conjunction with surgical treatments. In other embodiments, the corneal endothelial cell population according to the invention is administered in conjunction with surgical treatments.

Therapeutic Uses

The ocular cell population according to the invention may be used in a method of treatment or prophylaxis of an ocular disease or disorder comprising administering to a subject in need thereof of a therapeutically effective amount of a cell population comprising ocular cells.

The limbal stem cell population according to the invention may be used in a method of treatment or prophylaxis of an ocular disease or disorder comprising administering to a subject in need thereof of a therapeutically effective amount of a cell population comprising limbal stem cells. Preferably the ocular disease or disorder is associated with limbal stem cell deficiency.

Limbal stem cell deficiency may arise as a result of several diverse conditions including but not limited to:
  direct stem cell damage from chemical or thermal burns or radiation injury;
  congenital conditions such as aniridia, sclerocornea, multiple endocrine neoplasia;
  autoimmune disorders such as Stevens Johnson syndrome or ocular cicatricial pemphigoid or collagen vascular diseases;
  chronic non-auto-immune inflammatory disorders such as contact lens use, dry eye disease, rosacea, staph marginal, keratitis (bacterial, fungal & viral), pterygia or neoplasm;
  iatrogenic, such as after multiple eye surgeries, excision of pterygia or neoplasm, cryotherapy;
  as a result of medication toxicity such as preservatives (thimerosal, benzalkonium), topical anesthetics, pilocarpine, beta blockers, mitomycin, 5-fluorouracil, silver nitrate, and oral medications causing Stevens Johnson syndrome.

(See: Dry Eye: a practical guide to ocular surface disorders and stem cell surgery. SLACK 2006—Rzany B, Mockenhaupt M, Baur S et al. J. Clin. Epidemiol. 49, 769-773 (1996)).

The most commonly encountered causes of limbal stem cell deficiency in clinical practice are chemical burns, aniridia, Stevens Johnson Syndrome and contact lens use.

More preferably the ocular disease or disorder is limbal stem cell deficiency which arises due an injury or disease or disorder selected from the group consisting of chemical burns, thermal burns, radiation injury, aniridia, sclerocornea, multiple endocrine neoplasia, Stevens Johnson syndrome, ocular cicatricial pemphigoid, collagen vascular diseases, chronic non-auto-immune inflammatory disorders arising from contact lens use, dry eye disease, rosacea, staph marginal, keratitis (including bacterial, fungal & viral keratitis), pterygia or neoplasm, limbal stem cell deficiency arising after multiple eye surgeries or excision of pterygia or neoplasm or cryotherapy; and limbal stem cell deficiency arising as a result of medication toxicity from a medication selected from the group consisting of preservatives (thimerosal, benzalkonium), topical anaesthetics, pilocarpine, beta blockers, mitomycin, 5-fluorouracil, silver nitrate, and oral medications causing Stevens Johnson syndrome.

In a specific embodiment, the present invention provides a method of treating limbal stem cell deficiency by administering to a subject in need thereof an effective amount of a limbal stem cell population obtainable by the method of cell population expansion according to the invention.

In a more specific embodiment, the present invention provides a method of treating limbal stem cell deficiency which arises due an injury or disorder selected from the group consisting of chemical burns, thermal burns, radiation injury, aniridia, sclerocornea, multiple endocrine neoplasia, Stevens Johnson syndrome, ocular cicatricial pemphigoid, collagen vascular diseases, chronic non-auto-immune inflammatory disorders arising from contact lens use, dry eye disease, rosacea, staph marginal, keratitis (including bacterial, fungal & viral keratitis), pterygia or neoplasm, limbal stem cell deficiency arising after multiple eye surgeries, or excision of pterygia or neoplasm or cryotherapy; and limbal stem cell deficiency arising as a result of medication toxicity from a medication selected from the group consisting of preservatives (thimerosal, benzalkonium), topical anesthetics, pilocarpine, beta blockers, mitomycin, 5-fluorouracil, silver nitrate, and oral medications causing Stevens Johnson syndrome by administering to a subject in need thereof a therapeutically effective amount of a limbal stem cell population obtainable by the method of cell population expansion according to the invention.

In yet a more specific embodiment, the present invention provides a method of treating limbal stem cell deficiency which arises due an injury or disease or disorder selected from the group consisting of chemical burns, aniridia, Stevens Johnson Syndrome and contact lens use by administering to a subject in need thereof a therapeutically effective amount of a limbal stem cell population obtainable by the method of cell population expansion according to the invention.

When an adult is a recipient (transplant recipient), preferably greater than 1 000 p63alpha expressing cells may be administered to a patient in the methods of treatment according to the invention. In a preferred embodiment, 1 000 to 100

000 p63alpha expressing cells may be administered to a patient in the methods of treatment according to the invention.

The corneal endothelial cell population according to the invention may be used in a method of treatment or prophylaxis of an ocular disease or disorder comprising administering to a subject in need thereof of a therapeutically effective amount of a cell population comprising corneal endothelial cells. Preferably the ocular disease or disorder is associated with decreased corneal endothelial cell density. In a preferred embodiment the ocular disease or disorder is corneal endothelial dysfunction.

More preferably the ocular disease or disorder is corneal endothelial dysfunction which is selected from the group consisting of Fuchs endothelial corneal dystrophy, bullous keratopathy (including pseudophakic bullous keratopathy and aphakic bullous keratopathy), corneal transplant failure, posterior polymorphous corneal dystrophy, congenital hereditary endothelial dystrophy, X-linked endothelial corneal dystrophy, aniridia, and corneal endothelitis. In a specific embodiment the ocular disease or disorder is selected from the group consisting of Fuchs endothelial corneal dystrophy, bullous keratopathy (including pseudophakic bullous keratopathy and aphakic bullous keratopathy) and corneal transplant failure.

In a specific embodiment, the present invention provides a method of treating corneal endothelial dysfunction by administering to a subject in need thereof an effective amount of a corneal endothelial cell population obtainable by the method of cell population expansion according to the invention.

In a more specific embodiment, the present invention provides a method of treating corneal endothelial dysfunction which is selected from the group consisting of Fuchs endothelial corneal dystrophy, bullous keratopathy (including pseudophakic bullous keratopathy and aphakic bullous keratopathy), corneal transplant failure, posterior polymorphous corneal dystrophy, congenital hereditary endothelial dystrophy, X-linked endothelial corneal dystrophy, aniridia, and corneal endothelitis by administering to a subject in need thereof an effective amount of a corneal endothelial cell population obtainable by the method of cell population expansion according to the invention.

In yet a more specific embodiment, the present invention provides a method of treating corneal endothelial dysfunction selected from the group consisting of Fuchs endothelial corneal dystrophy, bullous keratopathy (including pseudophakic bullous keratopathy and aphakic bullous keratopathy) and corneal transplant failure by administering to a subject in need thereof an effective amount of a corneal endothelial cell population obtainable by the method of cell population expansion according to the invention.

When an adult is a recipient (transplant recipient), the corneal endothelial cell layer for use in the method of treatment according to the invention preferably has a final cell density in the eye of about at least 500 cells/mm² (area), preferably 1 000 to 3 500 cells/mm² (area), more preferably 2 000 to about 4 000 cells/mm² (area).

Example Sections A-C

The following examples are provided to further illustrate the invention but not to limit its scope. Other variants of the invention will be readily apparent to one of ordinary skill in the art and are encompassed by the appended claims.

Unless defined otherwise, the technical and scientific terms used herein have the same meaning as that usually understood by a specialist familiar with the field to which the disclosure belongs.

Example A1: LATS1 Biochemical Assay: Homogenous Time Resolved Fluorescence (HTRF) Assay (Compound Examples 1-290)

The LATS1 biochemical HTRF assay was performed using the HTRF KinEASE-STK S1 kit (CisBio, catalogue number 62ST1PEC) according to manufacturer's instructions. Human LATS1 kinase domain protein was purchased from Carnabio (catalogue number 01-123), which harbors the catalytic domain of amino acids 589-1130, and was co-purified with human His-tagged MOBKL1A (NP_775-739). Compounds were added by ECHO liquid handler (Labcyte) into 384-well plates. Then 5 microlitre of the following solution was added into the wells (50 mM HEPES, 0.01% BSA, 100 nM Orthaovanadate, 1 mM MgCl2, 1 mM DTT, 0.6 ng/microlitre LATS1 enzyme (Carnabio, 01-123), 2 micromolar STK1 localising aid (CisBio)), followed with 5 microlitre of 2 mM ATP in the kinase buffer (50 mM HEPES, 0.01% BSA, 100 nM Orthaovanadate, 1 mM MgCl2, 1 mM DTT) and incubated for 30 minutes at room temperature. 10 microlitre of detection mix (50 mM HEPES, 0.01% BSA, 100 nM Orthaovanadate, 1 mM MgCl2, 1 mM DTT, STK Antibody-Cryptate (CisBio), Streptavidin-XL665 (CisBio), 500 micromolar potassium fluoride, 50 nM EDTA) was added to each well and incubated for 1 hour at room temperature. Plates were read on Pherastar (BMG Labtech) for HTRF (665 nm/620 nm). The $IC_{50}$ is measured when the effect of the compound reduces the HTRF signal by 50%. LATS1 $IC_{50}$ values for the exemplified compounds are shown in Table 1A.

Example A2: LATS1 Biochemical Caliper Assay

Human LATS1 kinase domain protein was purchased from Carnabio (catalogue number 01-123), which harbors the catalytic domain of amino acids 589-1130, and was co-purified with human His-tagged MOBKL1A (NP_775-739). 5 microlitre of enzyme buffer, 100 nL of compounds and 5 microlitre of localising aid buffer were added into 384-well plates. The final assay reaction mix contains 100 mM HEPES, pH7.5, 0.1% BSA, 0.01% Triton X-100, 1 mM DTT, 10 mM MgCl2, 10 micromolar Sodium Orthovanadate, 10 micromolar Beta-Glycerophosphate, 400 micromolar ATP, 1% DMSO, 1.1 nM LATS1 enzyme (Carnabio, 01-123), 1 micromolar localising aid of FAM-KKLRRTLSVA-COOH (SEQ ID NO: 24) (NanoSyn). The plates were incubated at 25° C. for 3 hours. 40 microlitre of stop buffer with 25 mM EDTA (NanoSyn) was added to each well to terminate the reaction. Localising aids and products were separated electrophoretically using the microfluidic-based Caliper Labchip 3000 Drug Discovery System (Caliper Life Sciences). Plates were read using blue laser excitation and green fluorescence detection and quantified by fluorescence intensity. The $IC_{50}$ is measured when the effect of the compound reduces the product fluorescence signal by 50%. According to this assay the LATS1 $IC_{50}$ values in micromolar for the following compounds are:

Ex. 49: 0.012, Ex. 14: 0.034, Ex. 65: 0.022, Ex, 139: 0.028, Ex. 133: 0.004.

Example A3: LATS2 Biochemical Caliper Assay (Compound Examples 1-290)

Human LATS2 kinase domain protein was purchased from Carnabio (catalogue number 01-124), which harbors the catalytic domain of amino acids 553-1088, and was co-purified with human His-tagged MOBKL1A (NP_775-739). 5 microlitre of enzyme buffer, 100 nL of compounds and 5 microlitre of localising aid buffer were added into 384-well plates. The final assay reaction mix contains 100 mM HEPES, pH7.5, 0.1% BSA, 0.01% Triton X-100, 1 mM DTT, 10 mM MgCl2, 10 micromolar Sodium Orthovanadate, 10 micromolar Beta-Glycerophosphate, 400 micromolar ATP, 1% DMSO, 1.1 nM LATS2 enzyme (Carnabio, 01-124), 1 micromolar localising aid of FAM-KKLRRTLSVA-COOH (SEQ ID NO: 24) (NanoSyn). The plates were incubated at 25° C. for 3 hours. 40 microlitre of stop buffer with 25 mM EDTA (NanoSyn) was added to each well to terminate the reaction. Localising aids and products were separated electrophoretically using the microfluidic-based Caliper Labchip 3000 Drug Discovery System (Caliper Life Sciences). Plates were read using blue laser excitation and green fluorescence detection and quantified by fluorescence intensity. The IC$_{50}$ is measured when the effect of the compound reduces the product fluorescence signal by 50%. LATS2 IC$_{50}$ values for the exemplified compounds 1-290 are shown in Table 1A.

TABLE 1A

Inhibitory Activity against LATS1 and LATS2

| Example No. | LATS1 IC$_{50}$ (µM) | LATS2 IC$_{50}$ (µM) |
|---|---|---|
| 1 | 0.001 | n.d. |
| 2 | 0.001 | n.d. |
| 3 | 0.001 | n.d. |
| 4 | 0.001 | 0.001 |
| 5 | 0.002 | n.d. |
| 6 | 0.001 | 0.008 |
| 7 | 0.002 | n.d. |
| 8 | 0.003 | n.d. |
| 9 | 0.003 | n.d. |
| 10 | 0.003 | n.d. |
| 11 | 0.003 | 0.012 |
| 12 | 0.004 | 0.015 |
| 13 | 0.004 | n.d. |
| 14 | 0.002 | 0.05 |
| 15 | 0.004 | n.d. |
| 16 | 0.005 | n.d. |
| 17 | 0.005 | n.d. |
| 17a | 0.003 | n.d. |
| 17b | 0.0009 | n.d. |
| 17c | 0.003 | n.d. |
| 17d | 0.001 | n.d. |
| 18 | 0.006 | n.d. |
| 19 | 0.006 | n.d. |
| 20 | 0.006 | n.d. |
| 21 | 0.007 | n.d. |
| 22 | 0.007 | n.d. |
| 23 | 0.01 | n.d. |
| 24 | 0.017 | n.d. |
| 25 | 0.03 | n.d. |
| 26 | 0.031 | n.d. |
| 27 | 0.035 | n.d. |
| 28 | 0.036 | n.d. |
| 29 | 0.036 | n.d. |
| 30 | 0.039 | n.d. |
| 31 | 0.041 | n.d. |
| 32 | 0.047 | n.d. |
| 33 | 0.071 | n.d. |
| 34 | 0.095 | n.d. |
| 35 | 0.118 | n.d. |
| 36 | 0.199 | n.d. |
| 37 | 0.233 | n.d. |
| 38 | 0.24 | n.d. |
| 39 | 0.244 | n.d. |
| 40 | 0.328 | n.d. |
| 41 | 0.708 | n.d. |
| 42 | 0.711 | n.d. |
| 43 | >1.97 | n.d. |
| 44 | >2.5 | n.d. |
| 45 | >2.5 | n.d. |
| 46 | >2.5 | n.d. |
| 47 | 0.002 | 0.006 |
| 48a | 0.002 | 0.002 |
| 48b | 0.006 | 0.018 |
| 49 | 0.001 | 0.021 |
| 50 | 0.005 | n.d. |
| 51 | 0.006 | n.d. |
| 52 | 0.012 | n.d. |
| 53 | 0.04 | n.d. |
| 54 | 0.078 | n.d. |
| 55 | 0.46 | n.d. |
| 56 | 1.16 | n.d. |
| 57 | 1.44 | n.d. |
| 58 | 0.001 | 0.17 |
| 59 | 0.001 | 0.004 |
| 60 | 0.001 | n.d. |
| 61 | 0.001 | n.d. |
| 62 | 0.001 | 0.002 |
| 63 | 0.001 | n.d. |
| 64 | 0.001 | n.d. |
| 65 | 0.002 | 0.03 |
| 66 | 0.002 | 0.011 |
| 67 | 0.002 | n.d. |
| 68 | 0.002 | n.d. |
| 68a | 0.001 | n.d. |
| 68b | 0.002 | n.d. |
| 69 | 0.003 | n.d. |
| 70 | 0.003 | n.d. |
| 71 | 0.004 | n.d. |
| 72 | 0.004 | n.d. |
| 73 | 0.006 | n.d. |
| 74 | 0.006 | n.d. |
| 75 | 0.008 | n.d. |
| 76 | 0.009 | n.d. |
| 77 | 0.009 | n.d. |
| 78 | 0.011 | n.d. |
| 79 | 0.011 | n.d. |
| 80 | 0.011 | n.d. |
| 81 | 0.011 | n.d. |
| 82 | 0.013 | n.d. |
| 83 | 0.017 | n.d. |
| 84 | 0.021 | n.d. |
| 85 | 0.025 | n.d. |
| 86 | 0.026 | n.d. |
| 87 | 0.03 | n.d. |
| 88 | 0.037 | n.d. |
| 89 | 0.044 | n.d. |
| 90 | 0.126 | n.d. |
| 91 | 0.148 | n.d. |
| 92 | 0.304 | n.d. |
| 93 | 0.809 | n.d. |
| 94 | 1.15 | n.d. |
| 95 | >1.44 | n.d. |
| 96 | >1.70 | n.d. |
| 97 | >2.5 | n.d. |
| 98 | 1.35 | n.d. |
| 99 | 0.001 | n.d. |
| 100 | 0.004 | n.d. |
| 101 | 0.005 | 0.03 |
| 102 | 0.126 | n.d. |
| 103 | 0.002 | n.d. |
| 104 | 0.005 | n.d. |
| 105 | 0.001 | n.d. |
| 106 | 0.003 | n.d. |
| 107 | 0.008 | n.d. |
| 108 | 0.027 | n.d. |
| 109 | 0.001 | n.d. |
| 110 | 0.002 | n.d. |
| 111 | 0.001 | n.d. |
| 112 | 0.002 | n.d. |
| 113 | 0.235 | n.d. |
| 114 | 0.002 | n.d. |

TABLE 1A-continued

Inhibitory Activity against LATS1 and LATS2

| Example No. | LATS1 IC$_{50}$ (μM) | LATS2 IC$_{50}$ (μM) |
|---|---|---|
| 115 | 0.002 | n.d. |
| 116 | 0.003 | n.d. |
| 117 | 0.004 | n.d. |
| 118 | 0.005 | n.d. |
| 119 | 0.009 | n.d. |
| 120 | 0.01 | n.d. |
| 121 | 0.014 | n.d. |
| 122 | 0.015 | n.d. |
| 123 | 0.018 | n.d. |
| 124 | 0.022 | n.d. |
| 125 | 0.023 | n.d. |
| 126 | 0.053 | n.d. |
| 127 | 0.055 | n.d. |
| 128 | 0.077 | n.d. |
| 129 | 0.187 | n.d. |
| 130 | 1.153 | n.d. |
| 131 | >0.833 | n.d. |
| 132 | >2.5 | n.d. |
| 133 | 0.002 | 0.004 |
| 134 | 0.001 | n.d. |
| 135 | 0.002 | n.d. |
| 136 | 0.002 | n.d. |
| 137 | 0.022 | n.d. |
| 138 | 0.002 | n.d. |
| 139 | 0.003 | 0.02 |
| 140 | 0.004 | n.d. |
| 141 | 0.004 | n.d. |
| 142 | 0.006 | n.d. |
| 143 | 0.007 | n.d. |
| 144 | 0.01 | n.d. |
| 145 | 0.012 | n.d. |
| 146 | 0.033 | n.d. |
| 147 | 0.069 | n.d. |
| 148 | 0.168 | n.d. |
| 149 | 0.171 | n.d. |
| 150 | 4.27 | n.d. |
| 151 | >10 | n.d. |
| 152 | >2.5 | n.d. |
| 153 | >5 | n.d. |
| 154 | 0.0 | n.d. |
| 155 | 0.001 | n.d. |
| 156 | 0.006 | n.d. |
| 157 | 0.006 | n.d. |
| 158 | 0.008 | n.d. |
| 159 | 0.016 | n.d. |
| 160 | 0.024 | n.d. |
| 161 | 0.025 | n.d. |
| 162 | 0.049 | n.d. |
| 163 | 0.051 | n.d. |
| 164 | 0.159 | n.d. |
| 165 | >2.5 | n.d. |
| 166 | 0.014 | n.d. |
| 167 | 0.143 | n.d. |
| 168 | 0.028 | n.d. |
| 169 | 0.098 | n.d. |
| 170 | 1.28 | n.d. |
| 171 | 0.054 | n.d. |
| 172 | 0.017 | n.d. |
| 173 | 0.061 | n.d. |
| 174 | 0.197 | n.d. |
| 175 | 0.324 | n.d. |
| 176 | >2.5 | n.d. |
| 177 | >2.5 | n.d. |
| 178 | >2.5 | n.d. |
| 179 | 0.002 | n.d. |
| 180 | 0.322 | n.d. |
| 181 | 9.0 | n.d. |
| 182 | >10 | n.d. |
| 183 | 0.797 | n.d. |
| 184 | 0.004 | n.d. |
| 185 | 0.009 | n.d. |
| 186 | 0.009 | 0.05 |
| 187 | 0.016 | n.d. |
| 188 | 0.017 | n.d. |
| 189 | 0.083 | n.d. |
| 190 | 0.099 | n.d. |
| 191 | 0.189 | n.d. |
| 192 | 0.201 | n.d. |
| 193 | >10 | n.d. |
| 194 | 0.005 | n.d. |
| 195 | >10 | n.d. |
| 196 | >2.5 | n.d. |
| 197 | 0.023 | n.d. |
| 198 | 0.001 | n.d. |
| 199 | 0.001 | n.d. |
| 251 | 0.004 | n.d. |
| 252 | 0.002 | n.d. |
| 253 | 0.085 | n.d. |
| 254 | 0.005 | n.d. |
| 255 | 0.008 | n.d. |
| 256 | 0.008 | n.d. |
| 257 | 0.022 | n.d. |
| 258 | 0.023 | n.d. |
| 259 | 0.061 | n.d. |
| 260 | 0.459 | n.d. |
| 261 | 0.001 | 0.004 |
| 262 | 0.003 | n.d. |
| 263 | 0.007 | n.d. |
| 264 | 0.007 | n.d. |
| 265 | 0.008 | n.d. |
| 266 | 0.009 | n.d. |
| 267 | 0.013 | n.d. |
| 268 | 0.018 | n.d. |
| 269 | 0.001 | n.d. |
| 270 | 0.002 | n.d. |
| 271 | 0.002 | n.d. |
| 272 | 0.002 | n.d. |
| 273 | 0.463 | n.d. |
| 274 | 0.013 | n.d. |
| 275 | 0.011 | n.d. |
| 276 | 0.017 | n.d. |
| 277 | 0.065 | n.d. |
| 278 | 0.09 | n.d. |
| 279 | >2.5 | n.d. |
| 280 | 0.003 | n.d. |
| 281 | 0.004 | n.d. |
| 282 | 0.01 | n.d. |
| 283 | 0.02 | n.d. |
| 284 | 0.03 | n.d. |
| 285 | 0.19 | n.d. |
| 286 | 0.56 | n.d. |
| 287 | 0.002 | 0.015 |
| 288 | 0.004 | 0.034 |
| 289 | 0.004 | n.d. |
| 290 | 0.004 | 0.008 | n.d. means not determined

Example A4: LATS1 Biochemical Caliper Assay (Compound Examples 291-335)

The LATS1 biochemical Caliper assay was performed as following.

Human LATS1 kinase domain protein was purchased from Carnabio (catalogue number 01-123; lot 15CBS-0098D). Human LATS1, catalytic domain [589-1130(end) amino acids of accession number NP_004681.1] was co-expressed as N-terminal GST-fusion protein (90 kDa) with human His-tagged MOBKL1A [1-216(end) amino acids of accession number NP_775739.1] using baculovirus expression system. GST-LATS1 was purified by using glutathione sepharose chromatography. The substrate (Fluo-SGKtide; Peptide for LATS1; lot BS-41067) has the following sequence: 5-Fluo-Nva-KKRNRRLSVA-amide (SEQ ID NO: 27) x TFA and was purchased from Biosyntan.

The reaction is performed in reaction buffer containing 50 mM Hepes pH 7,5; 0.02% Tween20; 0.02% BSA; 1 mM DTT; 10 uM $Na_3VO_4$ and 10 mM beta-Glycerolphosphat and fresh added 1 mM $MgCl_2$ and qsp $H_2O$.

The substrate solution (2× conc.) in Reaction Buffer contains 300 µM ATP and 4 µM Fluo-SGKtide.

The kinase solution (2× conc.) in Reaction Buffer contains 20 nM LATS1 kinase. 4.5 µL of 2× conc. Kinase solution, 50 nL of 1.8 mM compounds and 4.5 µL of substrate solution were added into 384-well plates black small volume from Greiner and incubated at 32° C. for 1 hour. 15 µL of stop buffer containing 100 mM Hepes pH 7,5; 5% DMSO; 0.1% Coating reagent; 10 mM EDTA and 0.02% Brij35 and qsp $H_2O$ to each well to terminate the reaction.

Substrates and products were electrophoretically separated using the microfluidic-based Caliper EZ Reader System (Caliper Life Sciences) using a 12 sipper chip (cat 760404). The separation takes place in Coating Buffer (idem Stop buffer) and containing 0.1% Coating reagent CR3 and 0.5% coating reagent CR8 (Perkin Elmer).

Plates were read using a LED with an excitation at 488 nm and a detection at 520 nm to 5 quantify the fluorescence intensity. The $IC_{50}$ is measured when the effect of the compound reduces the product fluorescence signal by 50%. LATS1 $IC_{50}$ values for the exemplified compounds 291-335 are shown in Table 1B.

TABLE 1B

Inhibitory Activity against LATS1

| Example No. | LATS1 $IC_{50}$ (µM) |
|---|---|
| 291 | 0.4570 |
| 292 | 0.0433 |
| 293 | 0.0160 |
| 294 | 0.0045 |
| 295 | 0.0100 |
| 296 | 0.2089 |
| 297 | 0.0075 |
| 298 | 0.0590 |
| 299 | 0.0971 |
| 300 | 0.0012 |
| 301 | 0.0052 |
| 302 | 0.0595 |
| 303 | 0.0102 |
| 304 | 0.0096 |
| 305 | 0.6629 |
| 306 | 0.0012 |
| 307 | 0.0019 |
| 308 | 0.0687 |
| 309 | 0.0008 |
| 310 | 0.1639 |
| 311 | 1.0336 |
| 312 | 0.0024 |
| 313 | 0.0038 |
| 314 | 0.4667 |
| 315 | 0.0050 |
| 316 | 0.0425 |
| 317 | 0.0008 |
| 318 | 0.0018 |
| 319 | 0.0581 |
| 320 | 0.0007 |
| 321 | 0.0038 |
| 322 | 0.0292 |
| 323 | 0.0045 |
| 324 | 0.0104 |
| 325 | 0.0037 |
| 326 | 0.0572 |
| 327 | 0.1251 |
| 328 | 0.0189 |
| 329 | 0.0030 |
| 330 | 0.0031 |
| 331 | 0.0105 |
| 332 | 0.0076 |
| 333 | 0.0023 |
| 334 | 0.0061 |
| 335 | n.t. | n.t.: not tested

Example A5: Mouse Hepatic Progenitor Cell Proliferation Assay

The proliferation assay consists in measuring the compound induced three-dimensional growth of hepatic progenitor cells (HPC) into small organoids by means of high content imaging methods. The progenitor cells were isolated from C57Bl/6 wild type mice and expanded as described (Lu, W. Y. et al., Nat. Cell Biol. 17, 971-983 (2015)). Cells are stocked in liquid nitrogen, thawed on need and tested using the following protocol: HPC are harvested from their collagen I coated culture vessel (Corning; cat. Number 354487), counted and assessed for viability using a CEDEX cell counter (Roche). After centrifugation, 12 million cells are re-suspended in 2 ml of William's E Medium (Life Technologies; cat. Number 22551089) supplemented with 10% Fetal Bovine Serum (Amimed; cat. Number 2-01F10-I); 1% Penicillin/Streptomycin (Sigma; cat. Number 15140-122); 17.6 mM of $NaHCO_3$ (Sigma; cat. Number S8761); 20 mM HEPES (Gibco; cat. Number H3375); 10 mM Nicotinamide (Sigma; cat. Number N0636-100); 14 mM glucose (Sigma; cat. Number G7021); 1 mM Sodium Pyruvate (Sigma; cat. Number TMS-005); Insulin Transferrin Selenium (ITS) diluted 100 times from stock solution (Sigma; cat. Number 13148); 100 nM Dexamethasone (Sigma; cat. Number D4902); 0.2 mM ascorbic acid (Sigma; cat. Number A7506-100G); 10 ng/ml recombinant human IL-6 (Preprotech; cat. Number 200-06); 10 ng/ml murine HGF (Preprotech; cat. Number 315-23; Lot. 0711S527); 10 ng/ml murine EGF (Preprotech; cat. Number 315-09; Lot. 0217179-1). Six milliliters of Matrigel (Corning; cat. Number 354277; Lot: 5187006) are added to the cell/media solution, thus the final cell concentration is 1.5 million HPC per milliliter, in 25% culture medium and 75% Matrigel. Five microliter (p1) of the cell/Matrigel suspension are transferred in each well of the clear bottom 96 well assay plate (Corning; cat. Number 356649) using the Star dispenser (Hamilton). After 20 minutes incubation at 37° C. and 5% $CO_2$ to allow for Matrigel polymerization, 45 µl of cell culture media are dispensed on top.

In the compound source plate, 300 µl of cell culture media are dispensed on 1.2 µl of compounds dissolved in 90% DMSO. After proper mixing, 50 µl of the compound solution is transferred to the assay plate using a CyBi Well (CyBio). Each compound is tested in 8-point concentration curves having a dilution factor of 3.16 between each concentration. The maximum compound concentration tested is 20 µM and the lowest is 9 nM. The assay plates are incubated for 4 days at 37° C. and 5% $CO_2$.

Following the incubation, the organoids are fixed with phosphate buffer saline (PBS) (Gibco; cat. Number 10010-015) containing 4% Paraformaldehyde (Electron Microscopy Sciences; cat. Number 15714-S) and Hoechst 33342 (Life Technologies; cat. Number H3570) diluted 1/5000 of the stock solution to stain the nuclei. The plates are incubated 90 minutes at room temperature and washed once with 300 µl PBS containing 1% Penicillin/Streptomycin.

Plates are imaged with the CV7000 imager (Yokogawa) at a 10 fold magnification using the bright field lamp (lamp power: 10%; exposure time: 20 ms) and the 405 nanometer laser (laser power: 100%; exposure time 200 ms). Four different images per well were acquired and analyzed with the Yokogawa image analysis software (YAS). The output feature used to determine organoid size is the mean number of nuclei per organoid, averaged on the well.

The mean number of nuclei per organoid (x) is normalized to the neutral control treatment (DMSO), using the following calculation: [xn=+100 (x−NC)/NC]. The neutral control-normalized data are used for automated curve fitting to derive curve parameters per compound, including EC50 values.

The mouse hepatic progenitor cell proliferation assay may easily be used to test whether a compound is effective at inducing hepatic progenitor cell proliferation. Certain compounds of the invention were tested in the mouse hepatic progenitor cell proliferation assay and found to have $EC_{50}$ values of less than 20 µM, e.g. Examples 48a and 58 were found to have $EC_{50}$ values of 0.26 and 0.84 µM respectively. Certain other compounds of the invention were tested in the mouse hepatic progenitor cell proliferation assay and found to have $EC_{50}$ values of greater than 20 µM, e.g. Example 303.

Example A6: pYAP HTRF Assay (HaCaT Cells)

The pYAP HTRF assay was performed using the Phospho-YAP (SER127) 10000 test kit (CisBio, catalogue number 64YAPPEH) according to manufacturer's instructions. Briefly, HaCaT cells were suspended at $1.1 \times 10^6$ cells/mL in DMEM (no phenol red)+10% FBS with penicillin-streptomycin-glutamine. 5 µL of cells were dispensed into 1536 well white solid bottom, tissue culture treated plates (5500 cells/well), and incubated for 48 hours at 37° C. 50 nL test compound was transferred into the assay plates containing HaCaT cells using Pintool (GNF) and incubated for 2 hours. Lysis buffer (CisBio) was added to the assay wells and incubated for 5 minutes at room temperature, followed by the addition of 2 µL detection antibodies (1:40 dilution of each pYAP d2 ab and pYAP cryptate antibody stocks). The plates were incubated overnight (20 hrs) at room temperature covered with metal lids. Plates were read on Pherastar (BMG Labtech) for HTRF (665 nm/620 nm). The $IC_{50}$ is measured when the effect of the compound reduces the HTRF signal by 50%. Results are shown in Table 1C.

Example A7: YAP Translocation Assay (HaCaT Cells)

HaCaT cells were suspended at $0.4 \times 10^6$ cells/ml in DMEM+10% FBS with penicillin-streptomycin-glutamine. 50 µl of cells were dispensed into 384-well clear bottom assay plates (20,000 cells/well), and incubated overnight at 37° C. 100 nL test compound was transferred into the assay wells containing HaCaT cells using ECHO (Labcyte). After 24 hours incubation at 37° C., 7 µL of 32% PFA was dispensed into each well and incubated for 45 minutes at room temperature. Plates were washed 3 times with PBS, leaving 20 µL of PBS per well, then treated with 0.1% Triton and 1.5% BSA in PBS for 45 minutes at room temperature. Plates were washed for 5 times with PBS, leaving 20 µL of PBS per well. 20 µL of 1:1000 primary YAP ab (Santa Cruz Biotechnology, catalogue number 63.7) and 1:1500 Draq5 in PBS with 1.5% BSA was added to each well and incubated for 4 hrs at room temperature. After 3 times PBS wash, leaving 20 µL of PBS per well, each well was incubated with 20 µL of 1:2000 AlexaFluor 488_A21202 secondary antibody (Molecular Probes) for 4 hrs at room temperature. Plates were further washed 3 time with PBS, sealed and imaged on the high-content Opera imaging system (PerkinElmer). Results are shown in Table 1C.

TABLE 1C

| | Inhibitor of phosphorylation of YAP and YAP Nuclear Translocation | |
|---|---|---|
| Example No. | HaCaT pYAP $IC_{50}$ (µM) | HaCaT nuclear translocation $EC_{50}$ (µM) |
| 1 | 0.019 | 0.326 |
| 2 | 0.067 | 0.584 |
| 3 | 0.853 | 0.641 |
| 4 | 1.15 | 2.53 |
| 5 | 2.19 | 2.48 |
| 6 | 1.24 | 1.70 |
| 7 | 0.165 | 0.733 |
| 8 | 0.198 | 1.20 |
| 9 | 2.10 | 2.42 |
| 10 | 2.96 | 3.55 |
| 11 | 0.646 | 1.43 |
| 12 | 1.15 | 1.75 |
| 13 | 13.45 | 8.51 |
| 14 | 7.31 | 4.25 |
| 15 | 0.66 | 3.48 |
| 16 | 9.79 | 15.8 |
| 17 | 0.606 | 2.63 |
| 17a | 4.95 | 4.1 |
| 17b | 0.765 | 1.22 |
| 17c | 4.28 | 4.68 |
| 17d | 0.402 | 1.72 |
| 18 | 1.52 | 3.46 |
| 19 | 24.8 | 17.6 |
| 20 | 1.77 | 5.18 |
| 21 | 19.2 | 8.81 |
| 22 | 11.4 | 13.0 |
| 23 | 9.58 | 11.8 |
| 24 | 34.7 | 33.1 |
| 25 | n.d. | >20 |
| 26 | 54.6 | >100 |
| 27 | n.d. | >14.4 |
| 28 | n.d. | >20 |
| 29 | n.d. | >20 |
| 30 | n.d. | >20 |
| 31 | n.d. | >20 |
| 32 | >10 | >20 |
| 33 | >20 | >20 |
| 34 | n.d. | >20 |
| 35 | n.d. | >20 |
| 36 | n.d. | >20 |
| 37 | n.d. | >6.67 |
| 38 | >10 | >20 |
| 39 | n.d. | >11.6 |
| 40 | >10 | >20 |
| 41 | >10 | >20 |
| 42 | n.d. | 11.6 |
| 43 | n.d. | >20 |
| 44 | >10 | >20 |
| 45 | n.d. | >20 |
| 46 | n.d. | >20 |
| 47 | 0.55 | 1.31 |
| 48a | 0.37 | 0.80 |
| 48b | 7.25 | 7.22 |
| 49 | 0.607 | 1.17 |
| 50 | 17.0 | 3.81 |
| 51 | 57.8 | 4.39 |
| 52 | 11.3 | >20 |
| 53 | n.d. | >20 |
| 54 | n.d. | >20 |
| 55 | >10 | >20 |
| 56 | >10 | >20 |

TABLE 1C-continued

Inhibitor of phosphorylation of YAP and YAP Nuclear Translocation

| Example No. | HaCaT pYAP IC$_{50}$ (μM) | HaCaT nuclear translocation EC$_{50}$ (μM) |
|---|---|---|
| 57 | n.d. | >20 |
| 58 | 0.185 | 0.302 |
| 59 | 0.019 | 0.341 |
| 60 | n.d. | 0.44 |
| 61 | 0.141 | 0.517 |
| 62 | 0.040 | 0.538 |
| 63 | 0.131 | 0.338 |
| 64 | 0.063 | 0.479 |
| 65 | 0.895 | 1.99 |
| 66 | 0.534 | 1.01 |
| 67 | n.d. | 0.685 |
| 68 | 1.23 | 3.39 |
| 68a | 1.43 | 1.68 |
| 68b | 4.27 | 2.92 |
| 69 | 4.72 | 11.5 |
| 70 | 0.422 | 1.68 |
| 71 | 0.026 | 1.57 |
| 72 | 1.17 | 3.65 |
| 73 | 9.07 | 8.26 |
| 74 | 3.4 | 12.7 |
| 75 | 3.8 | 6.91 |
| 76 | 6.42 | 9.41 |
| 77 | >100 | 13.4 |
| 78 | 12.1 | 14.3 |
| 79 | 0.765 | 3.87 |
| 80 | 21.6 | 12.9 |
| 81 | 42.8 | 17.0 |
| 82 | >100 | >20 |
| 83 | 42.1 | 28.2 |
| 84 | 65.2 | >20 |
| 85 | 31.0 | 9.81 |
| 86 | 56.0 | >20 |
| 87 | 51.6 | >20 |
| 88 | 69.8 | 29.3 |
| 89 | >100 | >100 |
| 90 | n.d. | >20 |
| 91 | >10 | >20 |
| 92 | n.d. | >20 |
| 93 | n.d. | >20 |
| 94 | n.d. | >20 |
| 95 | >10 | >20 |
| 96 | n.d. | >20 |
| 97 | n.d. | >20 |
| 98 | n.d. | n.d. |
| 99 | 0.113 | 0.606 |
| 100 | 11.6 | 4.83 |
| 101 | 5.4 | >20 |
| 102 | n.d. | n.d. |
| 103 | 2.64 | 2.27 |
| 104 | 2.6 | 5.19 |
| 105 | 19.9 | >20 |
| 106 | 14.2 | >20 |
| 107 | 31.2 | 20.0 |
| 108 | 11.8 | >19.3 |
| 109 | 0.977 | 4.71 |
| 110 | 2.97 | 15.29 |
| 111 | 0.33 | 2.70 |
| 112 | 1.21 | 3.52 |
| 113 | n.d. | >20 |
| 114 | 0.565 | 1.33 |
| 115 | 1.05 | 1.66 |
| 116 | 0.782 | 2.18 |
| 117 | 2.31 | 4.47 |
| 118 | 2.05 | 5.01 |
| 119 | n.d. | 5.18 |
| 120 | 2.14 | 2.93 |
| 121 | n.d. | 8.17 |
| 122 | 7.4 | 5.8 |
| 123 | 9.45 | 9.2 |
| 124 | 8.01 | 12.0 |
| 125 | n.d. | 8 |
| 126 | n.d. | >20 |
| 127 | n.d. | >20 |
| 128 | n.d. | >20 |
| 129 | n.d. | >20 |
| 130 | n.d. | >20 |
| 131 | n.d. | >20 |
| 132 | n.d. | >20 |
| 133 | 0.414 | 1.67 |
| 134 | 0.539 | 1.19 |
| 135 | 0.488 | 0.85 |
| 136 | 1.14 | 2.96 |
| 137 | 35.5 | >17.8 |
| 138 | 3.37 | 9.07 |
| 139 | 0.38 | 2.66 |
| 140 | 1.24 | 2.26 |
| 141 | 13.56 | >10 |
| 142 | >100 | >28.02 |
| 143 | >10 | >20 |
| 144 | 0.606 | 4.44 |
| 145 | >100 | 9.31 |
| 146 | n.d. | >20 |
| 147 | >10 | >20 |
| 148 | n.d. | >20 |
| 149 | >10 | >20 |
| 150 | n.d. | n.d. |
| 151 | n.d. | n.d. |
| 152 | n.d. | >20 |
| 153 | >10 | >20 |
| 154 | 2.53 | 1.06 |
| 155 | 1.58 | 1.05 |
| 156 | >100 | 90.1 |
| 157 | 4.05 | 3.78 |
| 158 | 11.2 | 6.29 |
| 159 | >10 | >20 |
| 160 | 6.8 | >20 |
| 161 | >100 | >20 |
| 162 | n.d. | >20 |
| 163 | n.d. | >20 |
| 164 | n.d. | >20 |
| 165 | n.d. | >20 |
| 166 | n.d. | 8.45 |
| 167 | n.d. | >20 |
| 168 | 26.5 | 11.6 |
| 169 | n.d. | n.d. |
| 170 | >10 | >20 |
| 171 | n.d. | 17.2 |
| 172 | >10 | >20 |
| 173 | n.d. | >20 |
| 174 | >10 | >20 |
| 175 | >10 | >20 |
| 176 | n.d. | >20 |
| 177 | n.d. | >20 |
| 178 | n.d. | >20 |
| 179 | >10 | >20 |
| 180 | >10 | >20 |
| 181 | n.d. | >10 |
| 182 | n.d. | >20 |
| 183 | n.d. | >20 |
| 184 | 2.51 | 2.81 |
| 185 | n.d. | 11.5 |
| 186 | n.d. | >20 |
| 187 | >100 | >20 |
| 188 | >100 | 12.0 |
| 189 | n.d. | >10 |
| 190 | n.d. | >20 |
| 191 | n.d. | n.d. |
| 192 | >10 | >20 |
| 193 | n.d. | n.d. |
| 194 | 11.3 | 4.24 |
| 195 | n.d. | n.d. |
| 196 | >10 | >20 |
| 197 | n.d. | n.d. |
| 198 | 2.18 | 3.23 |
| 199 | n.d. | 9.1 |
| 251 | 1.96 | 10.87 |

TABLE 1C-continued

Inhibitor of phosphorylation of
YAP and YAP Nuclear Translocation

| Example No. | HaCaT pYAP IC$_{50}$ (µM) | HaCaT nuclear translocation EC$_{50}$ (µM) |
| --- | --- | --- |
| 252 | 6.98 | >10 |
| 253 | 16.67 | >20 |
| 254 | 2.91 | 4.63 |
| 255 | 3.18 | 5.39 |
| 256 | 11.07 | 15.6 |
| 257 | n.d. | >20 |
| 258 | n.d. | 9.92 |
| 259 | n.d. | 17.31 |
| 260 | n.d. | >20 |
| 261 | 0.202 | 1.22 |
| 262 | n.d. | 0.311 |
| 263 | 3.22 | 5.99 |
| 264 | 14.8 | 11.2 |
| 265 | 22.3 | >20 |
| 266 | n.d. | 5.35 |
| 267 | 7.19 | 9.75 |
| 268 | n.d. | >20 |
| 269 | 0.294 | 0.438 |
| 270 | 0.423 | 0.873 |
| 271 | 0.187 | 1.07 |
| 272 | 3.51 | 5.97 |
| 273 | >100 | >20 |
| 274 | n.d. | 17.3 |
| 275 | n.d. | 15.1 |
| 276 | n.d. | >20 |
| 277 | n.d. | >20 |
| 278 | n.d. | >20 |
| 279 | n.d. | >20 |
| 280 | 0.476 | 2.73 |
| 281 | 0.656 | 2.89 |
| 282 | 8.27 | 11.32 |
| 283 | 8.25 | 14.19 |
| 284 | 46.46 | >41.19 |
| 285 | n.d. | >20 |
| 286 | n.d. | >20 |
| 287 | 2.99 | 3.88 |
| 288 | 18.3 | 7.42 |
| 289 | 34.1 | 6.50 |
| 290 | n.d. | 1.39 | n.d. means not determined

Example A8: Target Identification siRNA against MST1/2 or LATS1/2 were transfected into human HaCaT cells. Forty-eight hours later, cells were treated with 1 µM of Okadaic acid for two hours to enhance pYAP signals. Cell lysates were subjected to western blot analysis for pYAP (Ser127) described below. The results of the experiment are reported in FIGS. 33A to 33C.

Western Blot Analysis

Cell lysates (25 µg per lane) were mixed with XT sample buffer and reducing agent (Bio-Rad), separated by 4-12% gradient SDS Criterion precast gel (Bio-Rad), and transferred to a nitrocellulose membrane (Bio-Rad). Proteins were detected with primary antibodies and horseradish peroxidase-conjugated secondary antibodies by using an enhanced chemiluminescence kit (ThermoFisher). Primary antibodies used were anti-pYAP antibody (Cell Signaling, catalogue number 13008S) and anti ACTIN antibody (Abcam, catalogue number ab8227)

Example A9: In Vivo Pharmacodynamics (PD)

8-10 week old male C$_{57}$BL6 mice (Envigo) were used for the in vivo PD study. A sterile surgical 6 mm punch biopsy tool was used to make two full-thickness excisional wounds on the dorsum of the anesthetized mouse. LATS inhibitors were formulated in 49.5% propylene glycol/0.5% Tween80/49% PBS/1% HPMC, and administered topically at a dosing volume of 3 µL. The wound area was covered with an adhesive dressing (Tegaderm). The animals were then wrapped with self-adhesive bandage. After two daily doses, the skin samples around the wound edge (2 mm ring-shaped samples) were collected using scissors 7 hour after the last dose.

The harvested samples were subjected to RNA extraction using the RNeasy kit (Qiagen), according to the manufacturer's instruction. Two-Step TaqMan RT-PCR analysis was performed on a PTC-200 peltier thermal cycler (MJ Research) and an ABI PRISM 7900HT Sequence Detection system (Applied Biosystems). cDNA was synthesized using a High-Capacity cDNA Archive kit (Applied Biosystems) according to the manufacturer's instructions. TaqMan analyses were performed using TaqMan Universal Master mix (Applied Biosystems) and Cyr61 and Gapdh probes (Applied Biosystems) according to the manufacturer's instructions. mRNA expression levels for the target genes were normalized to Gapdh mRNA levels and data analyzed using SDS 2.0 software (Applied Biosystems) to calculate relative RNA quantities.

All animal studies were conducted at the Genomics Institute of the Novartis Research Foundation (GNF). The experimental protocols were in compliance with animal welfare regulations and approved by the Institutional Animal Care and Use Committee at GNF.

Figure 34:
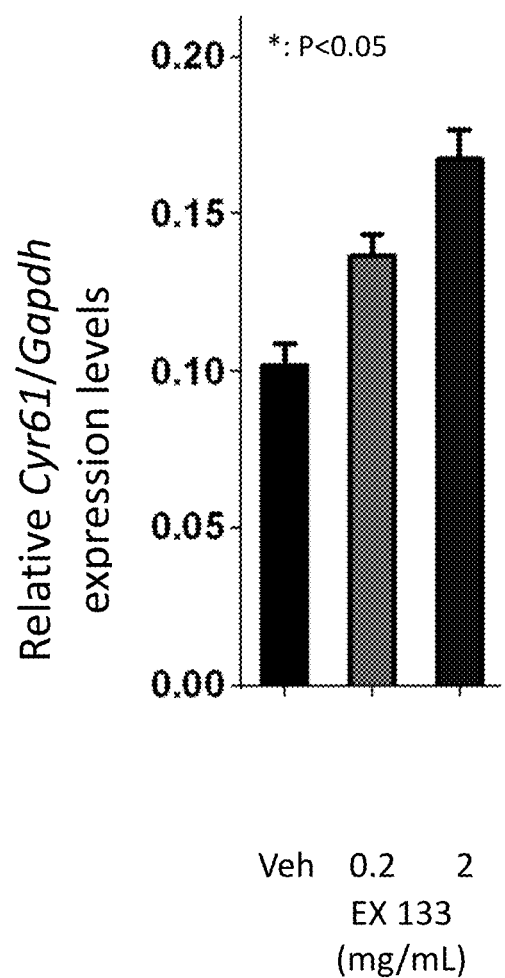
FIG. 34: is a bar graph of relative Cyr61/Gapdh expression levels versus concentration of Example 133 at 0, 0.2 and 2 mg/mL.

The resulted relative Cyr61/Gapdh expression levels against test compound concentrations were plotted as a bar graph in FIG. 34.

Example A10: In Vivo Histology and Ki67 Staining 7 week old male C$_{57}$BL6 mice were used for the in vivo histology study. LATS inhibitors were formulated in 70% PG/30% EtOH, and administered topically at a dosing volume of 25 µL (250 µg per dosge) to the shaved dorsal surface. After 3 days of twice a day dosing, the skin samples were collected, subjected to immuno-histology staining for Ki67 (ThermoFisher Scientific, Catalogue number RM-9106). The sections were observed visually, and Ki67 positive cells were counted by an in-house imaging algorithm. Representative micrographs of Ki67 staining were shown in FIG. 35A. The abundance of Ki67 positive cells in untreated and treated mouse skin cell were plotted as a scatter plot in FIG. 35B.

Example A11: pYAP HTRF Assay (JHH-5 cells)

The pYAP HTRF assay is performed using compound-treated JHH-5 cells (Fujise et al., *Hepatogastroenterology*. 1990 October; 37(5):457-60) that are analyzed with the Phospho-YAP (Ser127) 50000 test kit (CisBio catalog number 64YAPPEI) according to manufacturer's instructions. Briefly, JHH-5 cells are suspended at 0.48×10^6 cells/ml in William's E medium without phenol-red (Thermo Fisher Scientific Gibco catalog number A1217601) supplemented with 10% (v/v) heat-inactivated fetal bovine serum (Thermo Fisher Scientific Gibco catalog number 16140071) and penicillin-streptomycin at 100 U/ml each (Thermo Fisher Scientific Gibco catalog number 15140122). Cells are dispensed into 384well clear bottom culture plates (50 ul/well, at 24000 cells per well, Greiner catalog number 781091), and incubated for 24 hours in a cell culture incubator at 37° C. Test compounds are transferred into culture plates containing JHH-5 cells using an Echo550 (Labcyte) acoustic dispenser (50 nl/well), followed by incubation for 2 hours at 37° C. Lysis buffer (part of CisBio kit catalog number 64YAPPEI) is added to the assay plates as a four-fold concentrate (corresponding to 16 ul/well) and incubated for 30 minutes at room temperature with agitation. Lysate is transferred from culture plates into white low-volume 384well assay plates (12 ul/well, Greiner catalog number 784075), followed by the addition of 3 ul/well of detection antibodies (part of CisBio kit catalog number 64YAPPEI: 1:40 dilution of each pYAP d2 antibody and pYAP cryptate antibody stocks). The plates are sealed and incubated overnight (18 hours) at room temperature protected from light. Plates are read on an EnVision plate reader (Perkin Elmer) at emission wavelengths of 665 nm and 620 nm. The HTRF signal ratio x per well is calculated as [x=Signal(665 nm)/Signal(620 nm)×10000] as specified in the manufacturer's protocol. The signal ratio x per well is normalized to active control and neutral control treatment (DMSO), scoring median NC as 0% and median AC as −100% to calculate normalized signal ratio xn per well as [xn=±100 (x−NC)/(AC−NC)]. The control-normalized data is used for automated curve fitting to derive curve parameters per compound, including $IC_{50}$ values. pYAP $IC_{50}$ values in JHH-5 cells for the exemplified compounds are shown in Table 1D.

TABLE 1D

Inhibition of phosphorylation of YAP in JHH5 cells

| Example No. | JHH-5 pYAP $IC_{50}$ (µM) |
|---|---|
| 1 | |
| 2 | >10 |
| 3 | 1.0 |
| 4 | >10 |
| 5 | 2.3 |
| 6 | 2.6 |
| 7 | 1.6 |
| 8 | 1.9 |
| 9 | n.d. |
| 10 | 8.7 |
| 11 | n.d. |
| 12 | 2.9 |
| 13 | n.d. |
| 14 | >10 |
| 15 | 4.1 |
| 16 | n.d. |
| 17 | n.d. |
| 18 | n.d. |
| 19 | n.d. |
| 20 | n.d. |
| 21 | n.d. |
| 22 | n.d. |
| 23 | n.d. |
| 24 | n.d. |
| 25 | n.d. |
| 26 | n.d. |
| 27 | n.d. |
| 28 | n.d. |
| 29 | n.d. |
| 30 | >10 |
| 31 | n.d. |
| 32 | n.d. |
| 33 | n.d. |
| 34 | n.d. |
| 35 | n.d. |
| 36 | n.d. |
| 37 | n.d. |
| 38 | n.d. |
| 39 | n.d. |
| 40 | >10 |
| 41 | n.d. |
| 42 | n.d. |
| 43 | n.d. |
| 44 | n.d. |
| 45 | n.d. |
| 46 | n.d. |
| 47 | n.d. |
| 48a | 0.6 |
| 48b | n.d. |
| 49 | 1.6 |
| 50 | >10 |
| 51 | n.d. |
| 52 | n.d. |
| 53 | n.d. |
| 54 | n.d. |
| 55 | n.d. |
| 56 | n.d. |
| 57 | n.d. |
| 58 | 0.6 |
| 59 | 1.1 |
| 60 | n.d. |
| 61 | 1.4 |
| 62 | 0.6 |
| 63 | n.d. |
| 64 | 2.1 |
| 65 | 5.8 |
| 66 | 6.2 |
| 67 | n.d. |
| 68 | 3.5 |
| 69 | n.d. |
| 70 | 4.0 |
| 71 | >10 |
| 72 | 4.6 |
| 73 | n.d. |
| 74 | n.d. |
| 75 | n.d. |
| 76 | n.d. |
| 77 | n.d. |
| 78 | n.d. |
| 79 | 2.1 |
| 80 | n.d. |
| 81 | n.d. |
| 82 | n.d. |
| 83 | n.d. |
| 84 | >10 |
| 85 | >10 |
| 86 | n.d. |
| 87 | n.d. |
| 88 | n.d. |
| 89 | n.d. |
| 90 | n.d. |
| 91 | n.d. |
| 92 | n.d. |
| 93 | n.d. |
| 94 | n.d. |
| 95 | n.d. |
| 96 | n.d. |
| 97 | n.d. |
| 98 | n.d. |
| 99 | 5.7 |
| 100 | n.d. |
| 101 | 3.3 |
| 102 | n.d. |
| 103 | n.d. |
| 104 | n.d. |
| 105 | n.d. |
| 106 | n.d. |
| 107 | n.d. |
| 108 | n.d. |
| 109 | 1.5 |
| 110 | 1.5 |
| 111 | 2.4 |
| 112 | 3.2 |
| 113 | n.d. |
| 114 | n.d. |
| 115 | 3.4 |
| 116 | 2.2 |

TABLE 1D-continued

Inhibition of phosphorylation of YAP in JHH5 cells

| Example No. | JHH-5 pYAP IC$_{50}$ (μM) |
| --- | --- |
| 117 | >10 |
| 118 | 4.0 |
| 119 | n.d. |
| 120 | n.d. |
| 121 | n.d. |
| 122 | 8.0 |
| 123 | n.d. |
| 124 | n.d. |
| 125 | n.d. |
| 126 | n.d. |
| 127 | n.d. |
| 128 | n.d. |
| 129 | n.d. |
| 130 | n.d. |
| 131 | n.d. |
| 132 | n.d. |
| 133 | 1.7 |
| 134 | 1.0 |
| 135 | n.d. |
| 136 | 1.3 |
| 137 | n.d. |
| 138 | n.d. |
| 139 | 1.7 |
| 140 | 2.2 |
| 141 | n.d. |
| 142 | n.d. |
| 143 | n.d. |
| 144 | n.d. |
| 145 | n.d. |
| 146 | n.d. |
| 147 | n.d. |
| 148 | n.d. |
| 149 | n.d. |
| 150 | n.d. |
| 151 | n.d. |
| 152 | n.d. |
| 153 | n.d. |
| 154 | n.d. |
| 155 | 2.6 |
| 156 | n.d. |
| 157 | 9.2 |
| 158 | n.d. |
| 159 | n.d. |
| 160 | n.d. |
| 161 | n.d. |
| 162 | n.d. |
| 163 | n.d. |
| 164 | n.d. |
| 165 | n.d. |
| 166 | n.d. |
| 167 | n.d. |
| 168 | n.d. |
| 169 | n.d. |
| 170 | n.d. |
| 171 | n.d. |
| 172 | n.d. |
| 173 | n.d. |
| 174 | n.d. |
| 175 | n.d. |
| 176 | n.d. |
| 177 | n.d. |
| 178 | n.d. |
| 179 | n.d. |
| 180 | n.d. |
| 181 | n.d. |
| 182 | n.d. |
| 183 | n.d. |
| 184 | 6.5 |
| 185 | n.d. |
| 186 | n.d. |
| 187 | n.d. |
| 188 | n.d. |
| 189 | n.d. |
| 190 | n.d. |
| 191 | n.d. |
| 192 | n.d. |
| 193 | n.d. |
| 194 | n.d. |
| 195 | n.d. |
| 196 | n.d. |
| 197 | n.d. |
| 198 | 1.3 |
| 199 | 3.2 |
| 251 | 1.5 |
| 252 | n.d. |
| 253 | n.d. |
| 254 | 1.3 |
| 255 | 7.1 |
| 256 | >10 |
| 257 | >10 |
| 258 | >10 |
| 259 | n.d. |
| 260 | n.d. |
| 261 | 0.6 |
| 262 | n.d. |
| 263 | >10 |
| 264 | >10 |
| 265 | >10 |
| 266 | n.d. |
| 267 | 5.9 |
| 268 | >10 |
| 269 | 0.8 |
| 270 | 0.8 |
| 271 | 0.8 |
| 272 | 8.1 |
| 273 | >10 |
| 274 | >10 |
| 275 | >10 |
| 276 | >10 |
| 277 | n.d. |
| 278 | n.d. |
| 279 | n.d. |
| 280 | 3.8 |
| 281 | 5.9 |
| 282 | n.d. |
| 283 | >10 |
| 284 | n.d. |
| 285 | n.d. |
| 286 | n.d. |
| 287 | 9.0 |
| 288 | n.d. |
| 289 | n.d. |
| 290 | 3.0 |
| 291 | n.d. |
| 292 | n.d. |
| 293 | n.d. |
| 294 | 1.1 |
| 295 | >10 |
| 296 | n.d. |
| 297 | >10 |
| 298 | n.d. |
| 299 | n.d. |
| 300 | 0.9 |
| 301 | >10 |
| 302 | n.d. |
| 303 | >10 |
| 304 | >10 |
| 305 | n.d. |
| 306 | 1.0 |
| 307 | 1.3 |
| 308 | >10 |
| 309 | 2.0 |
| 310 | n.d. |
| 311 | n.d. |
| 312 | 7.7 |
| 313 | 7.8 |
| 314 | n.d. |
| 315 | 5.7 |
| 316 | n.d. |
| 317 | 3.2 |

TABLE 1D-continued

Inhibition of phosphorylation of YAP in JHH5 cells

| Example No. | JHH-5 pYAP IC$_{50}$ (µM) |
|---|---|
| 318 | 3.1 |
| 319 | >10 |
| 320 | 1.0 |
| 321 | n.d. |
| 322 | n.d. |
| 323 | n.d. |
| 324 | n.d. |
| 325 | n.d. |
| 326 | n.d. |
| 327 | n.d. |
| 328 | n.d. |
| 329 | n.d. |
| 330 | n.d. |
| 331 | n.d. |
| 332 | n.d. |
| 333 | n.d. |
| 334 | n.d. |
| 335 | n.d. | n.d. means not determined

Example A12: YAP Nuclear Translocation Assay (JHH-5 Cells)

The YAP nuclear translocation assay is performed using compound-treated JHH-5 cells (Fujise et al., *Hepatogastroenterology*. 1990 October; 37(5):457-60) that are analyzed by high-content imaging following an anti-YAP1 antibody stain. Briefly, JHH-5 cells are suspended at 0.48×10^6 cells/ml in William's E medium without phenol-red (Thermo Fisher Scientific Gibco catalog number A1217601) supplemented with 10% (v/v) heat-inactivated fetal bovine serum (Thermo Fisher Scientific Gibco catalog number 16140071) and penicillin-streptomycin at 100 U/ml each (Thermo Fisher Scientific Gibco catalog number 15140122). Cells are dispensed into 384well clear bottom culture plates (50 ul/well, at 24000 cells per well, Greiner catalog number 781091), and incubated for 24 hours in a cell culture incubator at 37° C. Test compounds are transferred into culture plates containing JHH-5 cells using an Echo550 (Labcyte) acoustic dispenser (50 nl/well). Following an incubation of 4 hours at 37° C., 12.5 ul of 20% PFA stock solution (Electron Microscopy Sciences catalog number 15713S) is dispensed into each well for a final concentration of 4% (v/v) and incubated for 20 minutes at room temperature. Plates are washed with TBS (prepared from ten-fold concentrate, Sigma Aldrich catalog number T5912) and then permeabilized with 0.1% (v/v) Triton X-100 solution (Sigma Aldrich catalog number 93443) in DPBS for 15 minutes at room temperature. Plates are again washed with TBS, followed by addition of anti-YAP1 antibody (Novus Biologicals catalog number NB110-58358) to each well at a dilution of 1:500 in 3% (w/v) BSA in DPBS (prepared from 35% stock solution, Sigma Aldrich catalog number A7979) and incubation overnight at 4° C. After removal of primary antibody solution and washing with TBS, each well is incubated for 2 hours at room temperature with a 1:1000 dilution of goat anti-rabbit secondary antibody conjugated to Alexa Fluor 647 (Thermo Fisher Scientific catalog number A-21244) in 3% (w/v) BSA in DPBS (prepared from 35% stock solution, Sigma Aldrich catalog number A7979) supplemented with Hoechst 33342 solution (Thermo Fisher Scientific catalog number 3570) at a 1:10000 dilution. Plates are again washed with TBS and then sealed and imaged on the IN Cell Analyzer High-Content Analysis System (GE Healthcare Life Sciences). By comparison of Hoechst nuclear stain to total intracellular YAP Alexa Flour 647 stain using the CellProfiler image analysis software (Carpenter et al., Genome Biol. 2006; 7(10):R100), the signal corresponding to nuclear YAP is derived. Nuclear YAP signal x is normalized to active control and neutral control treatment (DMSO), scoring median NC as 0% and median AC as +100% to calculate normalized nuclear YAP signal xn per well as [xn=±100 (x−NC)/(AC−NC)]. The control-normalized data were used for automated curve fitting to derive curve parameters per compound, including EC$_{50}$ values.

Example A13: In Vivo Treatment of Mice

All animal studies were carried out in accordance with federal, state, local and institutional guidelines governing the use of laboratory animals in research. Male C57BL/6J mice (age 8-10 weeks) were purchased from Jackson Labs (Bar Harbor, Me.). Example 46 was formulated for oral dosing at 3 mg/ml, and Example 261 at 1 mg/ml, in a suspension of methylcellulose:Tween80:Water (0.5:0.5:99). Single oral dose of either compound was at 10 mL/kg body weight. Blood and liver tissue were collected under deep anesthesia (isoflurane) at either 2 h post-dose (for mRNA analysis) or 24 h post-dose (for immunohistochemistry).

Phospho-YAP (pYAP) HTRF in Liver Tissue

Frozen liver tissue was transferred into a Lysing Matrix tube (MP, cat #6913-500) with a 1:50 solution of Protease inhibitor (Sigma-Aldrich, cat #P8340) in Phosphosafe extraction buffer (Novagen, cat #71296-3) and homogenized using the FastPrep-24 (MP biomedicals). The mixture was kept on ice for 20 min and then centrifuged at 14000 rpm for 20 min. The supernatant was transferred to a new tube. The protein concentration was measured using the BCA Protein Assay Kit (Pierce cat. 23227) following the manufacturer's protocol. All samples were normalized to a final concentration of 5 µg/µl in a total volume of 180 µl of Phosphosafe and plated in a 96well plate for the HTRF assay. pYAP was assayed by HTRF using the Phospho-YAP (SER127) 50000 test kit (Cisbio, catalogue number 64YAPPEI). Mouse liver lysates in extraction buffer alone (Phosphosafe) or 1:1 mix of Phosphosafe with HTRF Lysis buffer (Cisbio) were assayed in duplicate wells of 384-well assay plates (12 µL/well). The same input quantity was used for each sample, based on total protein content (30-60 ug per sample per well). Detection antibodies phospho-YAP d2 and phospho-YAP cryptate each diluted 1:40 in Detection buffer (Cisbio) were added (3 µL/well, final dilution 1:200 for each antibody) after which the plates were sealed and incubated overnight (18 hrs) at room temperature protected from light. Plates were read on an EnVision (PerkinElmer) with emission wavelengths of 665 nm & 620 nm. The HTRF signal ratio was calculated as Signal(665 nm)/Signal(620 nm))× 10000 as specified in the manufacturer's protocol. One HTRF signal value (mean of duplicate wells) was used for each lysate sample in treatment group plots.

Quantitative RT-PCR

Total liver RNA was isolated from tissue after storage in RNAlater reagent (Qiagen), using a TRIzol method according to the manufacturer's instructions (Life Technologies). Relative mRNA abundance was measured by quantitative RT-PCR using TaqMan gene expression assays and reagents according to standard protocols (Applied Biosystems). Mouse probes for YAP target genes were CTGF (Mm01192933_g1) and Cyr61 (Mm00487498_m1). Mouse GAPDH was used as an internal control (probe 4351309).

Relative changes in mRNA were calculated by the ΔΔCt method. Changes in gene expression with compound treatment are expressed as fold-change relative to the vehicle group.

Immunohistochemistry (IHC) for Ki67

Liver tissue was fixed in 10% neutral buffered formalin for 24-48 h. Processing and embedding in paraffin was by standard procedures. Sections were cut at 5 microns thickness and stained using a Ventana automated system. Primary antibody for mouse Ki67 was a rabbit IgG (Bethyl Labs). Ki67-positive hepatocytes were quantified by image analysis using the HALO platform. At least 3 sections per animal were analyzed, from the middle of the medial lobe.

TABLE 1E

Results of compound treatment in mouse

| | pYAP (% of control) | CTGF mRNA (fold-change) | Cyr61 mRNA (fold-change) | Ki67 IHC (fold-change) |
|---|---|---|---|---|
| Example 46 30 mg/kg | 64 | 2.1 (+/−0.4) | 3.5 (+/−0.5) | 3.3 (+/−0.2) |
| Example 261 10 mg/kg | 60 | 2.5 (+/−0.2) | 3.9 (+/−0.6) | 3.1 (+/−0.5) | mRNAs for YAP target genes CTGF and Cyr61 were increased 2 h and proliferation indicated by Ki67 immunohistochemistry (IHC) was increased 24 h post single oral dose of LATS kinase inhibitors. Values are expressed as fold-change relative to the vehicle group with (mean+/− SEM).

Example B1: Human Limbal Epithelial Cell Isolation

Research-consented cadaveric human corneas were obtained from eye banks. Limbal rims were dissected and partially dissociated in a 1.2 mg/ml dispase solution for 2 hours at 37° C. followed by 10 minutes in TrypLE (Life Technologies). Pieces of limbal crypts were then carefully cut out of the partially dissociated limbal rims and rinsed by centrifugation). Cells obtained in this manner were used in the Examples B2-B11 below.

Example B2: Exposure of Cells to LATS Inhibitors and Measurement of Intracellular YAP Distribution Cells obtained as described in Example B1 were plated in glass-bottom black wall 24-well dishes in limbal epithelium cell culture medium (DMEM F12 supplemented with 10% human serum and 1.3 mM calcium chloride) supplemented with LATS inhibitor compound example no. 133 or 49 at a concentration of 10 micromolar or supplemented in DMSO as a negative control. Cells were cultured under these conditions for 24 hours at 37° C. in 5% CO2.

To measure the effect of the LATS inhibitors on the downstream target YAP, intracellular YAP distribution was analyzed by immunohistochemistry. Cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibody used was anti-YAP from Santa Cruz Biotechnology. Samples were washed in PBS three times and donkey-raised secondary antibody Alexa Fluor 488 (Molecular Probes) at 1:500 dilution were applied for 30 minutes at room temperature. Negative control was omitted primary antibody (data not shown). Fluorescence was observed using a Zeiss LSM 880 confocal microscope.

Only weak YAP immunostaining was observed in the nucleus of LSCs cultured without the LATS inhibitors (DMSO control). YAP immunostaining was stronger in the nucleus of LSCs exposed to the LATS inhibitor compound example no. 133 or 49 (data not shown).

Example B3: Exposure of Cells to LATS Inhibitors and Measurement of YAP Phosphorylation Cells obtained as described in Example B1 were detached from the culture dish with Accutase for 10 minutes at 37° C., cell suspensions were rinsed by centrifugation and plated in DMEM F12 supplemented with 10% human serum and 1.3 mM calcium chloride in 6-well plates (Corning) and cultured without LATS inhibitor compounds for 2-4 days.

The medium was then replaced by fresh limbal epithelium cell culture medium (DMEM F12 supplemented with 10% human serum and 1.3 mM calcium chloride) supplemented with LATS inhibitor compound example no. 133 or 49 at a concentration of 10 micromolar or supplemented in DMSO as a negative control. Cells were cultured under these conditions for 1 hour at 37° C. in 5% CO2.

To measure the effect of the LATS inhibitors on the downstream target YAP, the YAP phosphorylation levels were measured by western blot as follows. The cell pellets were obtained by trypsin dissociation and centrifugation and washed with PBS. The pellets were lysed with 30 microlitres of RIPA lysis buffer containing protease inhibitor cocktail (Life Technologies) for 30 minutes, with vortexing every 10 minutes. The cell debris were then pelleted at 4° C. for 15 minutes at 14 k rpm and the protein lysate was collected. Protein concentration was quantified using a micro BCA kit (Pierce). Fifteen micrograms of total protein was loaded in each well of 4-20% TGX gels (BioRad) and Western blotting was performed according to the manufacturer's instructions. Membranes were probed with phospho-YAP (ser127) (CST, 1:500) or total Yap (Abnova, 1:500) antibody and actin (Abcam) labelling was used as loading control. Membranes were stained with HRP-conjugated secondary antibodies, rinsed and imaged using a ChemiDoc system (Biorad) according to the manufacturer's instructions.

Western blot analysis (see FIG. 1) showed that both compound example no. 133 and 49 caused a reduction in YAP phosphorylation levels in human LSCs. These results suggest that the LATS inhibitor compound example no. 133 and 49 can activate YAP signaling in human LSCs.

Example B4: Human Limbal Stem Cell Population Expansion and Immunohistochemical Observation of Cellular Phenotype Cells obtained as described in Example B1 were plated in 24-well plates (Corning) in limbal epithelium cell culture medium (DMEM F12 supplemented with 10% human serum and 1.3 mM calcium chloride) supplemented with LATS inhibitor compound example no. 133 or 49 at a concentration of 10 micromolar or supplemented in DMSO as a negative control. Cells were first cultured at 37° C. in 5% CO2 for 6 days after isolation without passaging (FIGS. 2A, 2B and 2C).

To evaluate the ability of the compounds to enable LSC expansion after two passages, LSCs were passaged and cultured for two weeks in the presence of compound example 49 to enable expansion (FIG. 2D). Limbal stem cells (LSCs) were passaged by treating cultures with Accutase for 10 minutes at 37° C., rinsing the cell suspension by centrifugation and plating cells in fresh LSC culture medium supplemented with LATS inhibitor compound example 49.

In order to observe that the expanded cell population expressed p63alpha, this was measured by immunohistochemistry as follows. Cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibody used was p63alpha from Cell Signalling. Samples were washed in PBS three times and donkey-raised secondary antibody Alexa Fluor 488 (Molecular Probes) at 1:500 dilution were applied for 30 minutes at room temperature. Cells were counter-stained with a human nuclear antigen antibody (Millipore) at a 1:500 dilution in order to label all cells in the culture and confirm their human identity. Negative control was omitted primary antibody (data not shown). Fluorescence was observed using a Zeiss LSM 880 confocal microscope.

FIG. 2A shows that in the presence of growth medium and DMSO, only a few isolated cells attach to the culture dish and survive up to 6 days. Most cells expressed the human nuclear marker, but few expressed p63alpha. In contrast, in the presence of LATS inhibitors compound example no. 133 (FIG. 2B) and compound example no. 49 (FIG. 2C), the cells formed colonies and expressed p63alpha. This result indicated that the LATS inhibitors promote the expansion of the population of cells with the p63alpha-positive phenotype. FIG. 2D: Passaging cells and culturing them in the presence of LATS inhibitor compound example no. 49 for two weeks enabled cell population expansion and the formation of confluent cultures expressing p63alpha.

Example B5: Human Limbal Stem Cell Population Expansion and Measurement Thereof

Cells obtained as described in Example B1 were plated in 48-well plates (Corning) in XVIVO15 medium (Lonza) supplemented with LATS inhibitors (as listed in Table 2 and 3 below) at a concentration of 10 micromolar or supplemented in DMSO as a negative control. Cells were cultured at 37° C. in 5% CO2.

For each compound, two sets of cultures were generated. A first set of cultures was fixed in 4% PFA for 20 minutes at room temperature after cells isolated from the cornea had attached to the cell culture dish (typically 24 h after cell plating). A second set of cultures was fixed in 4% PFA for 20 minutes at room temperature after being cultured for two passages. Cells were passaged when they reached 90-100% confluence.

In order to observe that the expanded cell population expressed p63alpha, this was measured by immunohistochemistry as follows. The fixed cell cultures were permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibody used was p63alpha from Cell Signalling. Samples were washed in PBS three times and donkey-raised secondary antibody Alexa Fluor 488 (Molecular Probes) at 1:500 dilution were applied for 30 minutes at room temperature. Cell nuclei were then labeled in a solution of 0.5 micromolar of Sytox Orange (ThermoFisher) in PBS for 5 minutes at room temperature.

To evaluate the percentage of p63alpha-positive cells, the number of cells labeled by the anti-p63alpha antibody was counted and the total number of cells was determined by counting the number of nuclei stained by Sytox Orange. The proportion of p63alpha-positive cells was then determined by calculating the percentage of Sytox-orange-positive nuclei that also expressed p63alpha.

To evaluate cell expansion ratios, nuclei were counted using a Zeiss LSM 880 confocal microscope. The expansion factor was then determined by calculating the ratio of the expanded population of cells to population of seeded cells.

Results in the Tables below indicate that the LATS inhibitors enabled cell population expansion. In the presence of the LATS inhibitors, 57 to 97 percent of the cells express the p63alpha-positive phenotype.

TABLE 2

| Compound Example No. | Expansion factor |
| --- | --- |
| Ex. 47 | 2137 |
| Ex. 12 | 2087 |
| Ex. 49 | 2029 |
| Ex. 261 | 1717 |
| Ex. 62 | 1712 |
| Ex. 14 | 1423 |
| Ex. 6 | 1275 |
| Ex. 288 | 1241 |
| Ex. 133 | 1205 |
| Ex. 66 | 1160 |
| Ex. 290 | 1051 |
| Ex. 65 | 1048 |
| Ex. 287 | 991 |
| Ex. 17 | 976 |
| Ex. 139 | 961 |
| Ex. 11 | 705 |
| Ex. 289 | 681 |
| Ex. 33 | 39 |
| DMSO | 35 |

TABLE 3

| Compound Example No. | Percentage of p63a-positive cells | Compound Example No. | Percentage of p63a-positive cells |
| --- | --- | --- | --- |
| Ex. 47 | 97 | Ex. 290 | 90 |
| Ex. 12 | 95 | Ex. 65 | 87 |
| Ex. 49 | 92 | Ex. 287 | 86 |
| Ex. 261 | 93 | Ex. 17 | 86 |
| Ex. 62 | 95 | Ex. 139 | 87 |
| Ex. 14 | 93 | Ex. 11 | 86 |
| Ex. 6 | 93 | Ex. 289 | 80 |
| Ex. 288 | 95 | Ex. 33 | 6 |
| Ex. 133 | 89 | DMSO | 3 |
| Ex. 66 | 89 | | |

Example B6: siRNA Knockdown of LATS1 and LATS2 in Human Limbal Cells

Cells obtained as described in Example B1 were plated in 24-well plates (Corning) in XVIVO15 medium (Lonza). Cells were cultured at 37° C. in 5% CO2. LATS1 and LATS2 were knocked down by transfection (lipofection, using RNAiMax, Thermofisher). Each well of the cell culture plate was transfected with 0.5 micrograms of pools of 4 siRNAs targeting each gene. siRNAs used in this study were Qiagen's LATS1 siRNA S100067172 and LATS2 siRNA S100106925. Scrambled siRNAs were used as negative controls according to the manufacturer's protocol (Qiagen).

In order to measure cell proliferation, EdU staining was performed according to the manufacturer's instructions (Life Technologies) 48 hours after transfection with LATS1 and LATS2 siRNAs or scrambled siRNA controls. Cell nuclei were labeled with Sytox Orange. EdU and Sytox Orange fluorescence was observed using a Zeiss LSM 880 confocal microscope in order to measure the percentage of EdU-positive cell nuclei.

Figure 3:
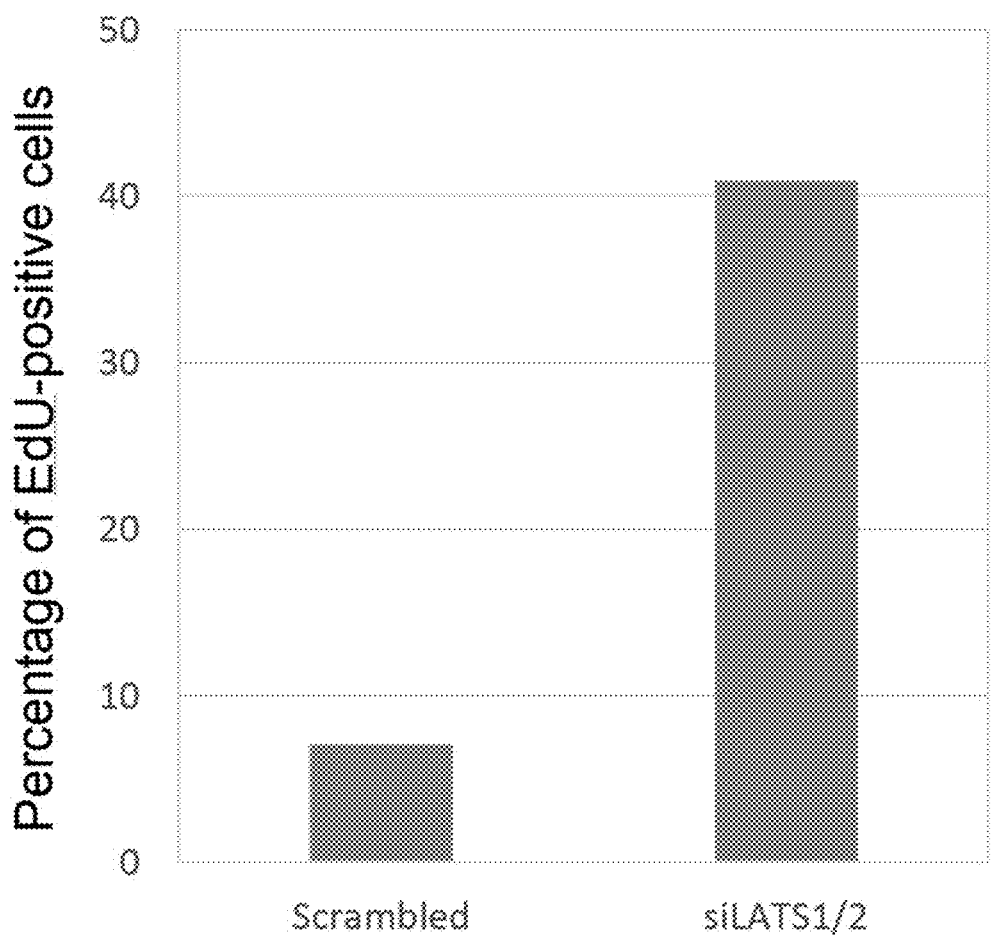
FIG. 3: LATS1 and LATS2 knockdown by siRNA activates LSC proliferation in culture as shown by percentage of EdU positive cells.

FIG. 3 shows that the percentage of EdU-positive cells increased upon LATS1 and LATS2 knockdown, showing that knockdown of LATS leads to cell proliferation.

Example B7: Human Limbal Stem Cell Population Expansion and Immunohistochemical Observation of Markers DeltaN-p63 Alpha/Beta/Gamma, ABCG2 and C/EBP Delta Cells obtained as described in Example B1 were plated in 48-well plates (Corning) in XVIVO15 medium (Lonza) supplemented with LATS inhibitors (Compound ex. 49 and compound ex. 133) at a concentration of 10 micromolar or supplemented in DMSO as a negative control. Cells were cultured at 37° C. in 5% CO2 for 8 to 10 days.

In order to observe that the expanded cell population expresses markers normally expressed by limbal stem cells, the ability of the cells to express DeltaN-p63 alpha/beta/gamma, ABCG2 and C/EBP delta was measured by immunohistochemistry as follows. Cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibodies used were p63a (Cell Signaling Technology), ABCG2 (EMD Millipore), and C/EBPO (Abcam), cytokeratin 15, cytokeratin 12 (Abcam). Samples were washed in PBS three times and donkey-raised secondary antibody Alexa Fluor 488 (Molecular Probes) at 1:500 dilution were applied for 30 minutes at room temperature. Cell nuclei were then labeled in a solution of 0.5 micromolar of Sytox Orange (ThermoFisher) in PBS for 5 minutes at room temperature. Samples were then observed using a Zeiss LSM 880 confocal microscope.

Figure 4:
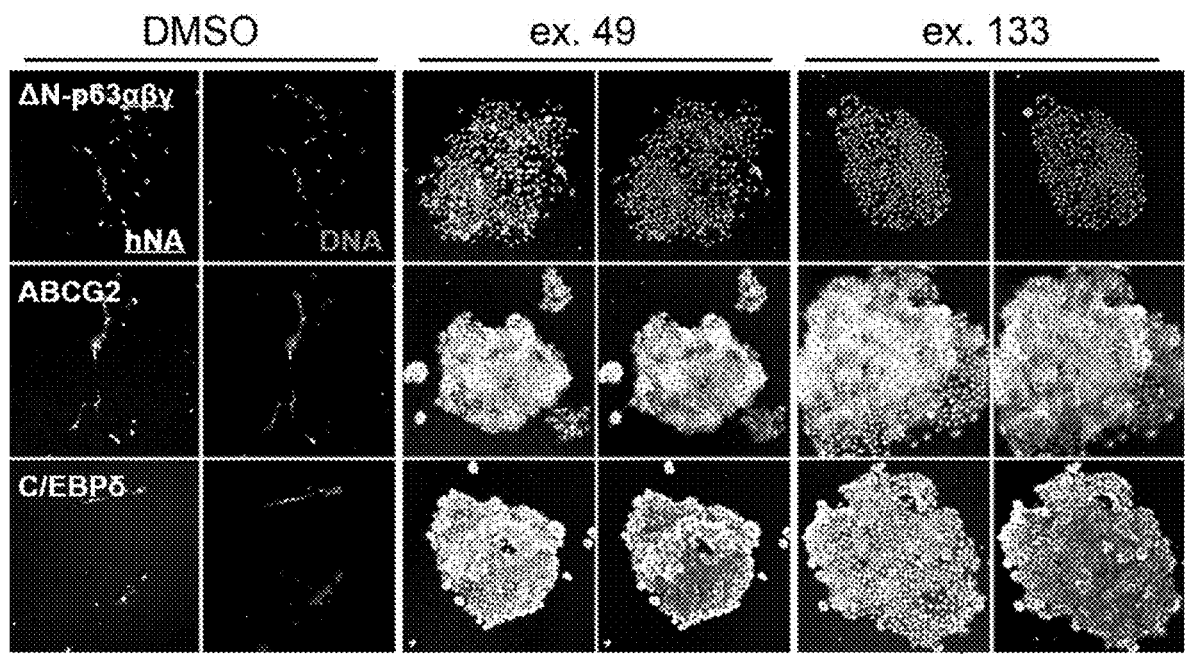
FIG. 4: Immunolabelling of LSC markers DeltaN-p63 alpha/beta/gamma, ABCG2 and C/EBP delta indicates that LSCs maintained in a culture medium containing the LATS inhibitors (compound ex. 49 and ex. 133) express typical markers of LSCs. Results indicate that cells cultured in DMSO do not typically express markers such as DeltaN-p63 alpha/beta/gamma, ABCG2 and C/EBP delta, normally expressed by LSCs. In contrast, cells cultured in the presence of LATS inhibitors express markers such as DeltaN-p63 alpha/beta/gamma, ABCG2 and C/EBP delta, normally expressed by LSCs.

Results indicated (see FIG. 4) that cells cultured in XVIVO medium supplemented with DMSO alone (no LATS inhibitor compound) do not typically express markers normally expressed by LSCs. In contrast, cells cultured in the presence of LATS inhibitors express markers normally expressed by LSCs.

Example B8: Human Limbal Stem Cell Differentiation into Corneal Epithelial Cells Cells obtained as described in Example B1 were plated in 48-well plates (Corning) in XVIVO15 medium supplemented with LATS inhibitors compound example no. 49, 47, 12 or 261 at a concentration of 10 micromolar or supplemented in DMSO as a negative control. Cells were cultured at 37° C. in 5% CO2 for 8 to 10 days.

Analysis was then conducted to determine whether a population of p63alpha-positive LSCs expanded in the presence of LATS inhibitors retained the ability to differentiate into keratin-12-positive corneal epithelial cells, which is required for corneal clarity to be restored in the patients that receive the LSC transplant.

To promote LSC differentiation into corneal epithelium cells, the culture medium was changed to DMEM (Invitrogen) without serum or LATS inhibitors and cells were cultured for 4-8 days. In order to observe LSC differentiation into corneal epithelium cells, the cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibodies used were p63a (Cell Signaling Technology) and cytokeratin 12 (Abcam). Samples were washed in PBS three times and donkey-raised secondary antibody conjugated to Alexa Fluor 488 or Alexa Fluor 647 (Molecular Probes) at 1:500 dilution were applied for 30 minutes at room temperature. Samples were then observed using a Zeiss LSM 880 confocal microscope.

Figures 5A, 5B, 5C, 5D:
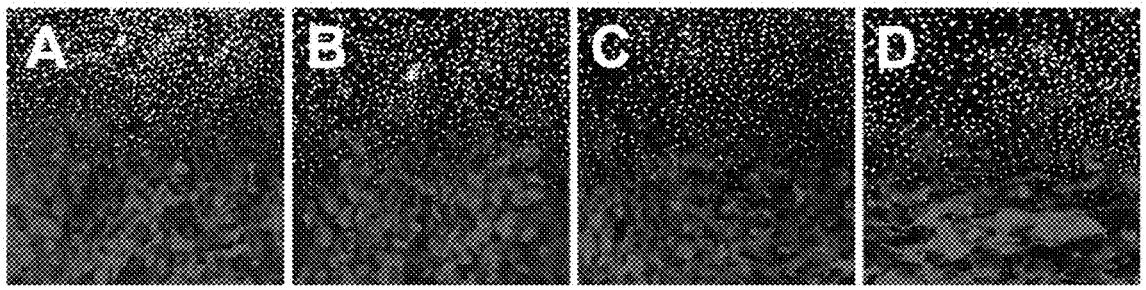
FIG. 5: Immunolabelling of undifferentiated LSC marker p63alpha and corneal epithelium cell marker keratin 12 shows that LSC populations expanded using a culture medium comprising the LATS inhibitors (FIG. 5A: compound ex. 49, FIG. 5B: compound ex. 47, FIG. 5C: compound ex. 12, FIG. 5D: compound ex. 261) can differentiate into corneal epithelium cells when transferred to conditions that enable differentiation. Shown are views where the transition from the p63alpha-positive cell identity to the keratin-12 identity are occurring.

Results indicated that cultures maintained in the presence of LATS inhibitors and then induced to differentiate, contained areas where clusters of p63alpha-positive cells are contiguous to clusters of cells that are p63alpha-negative, but keratin-12-positive (FIG. 5). Therefore limbal cells expanded in the presence of LATS inhibitors can differentiate into keratin-12-positive cells when under appropriate conditions.

Example B9: Delivery of LSC-Biomatrix Preparation to Rabbit Eyes Rabbit Model of Limbal Stem Cell Deficiency Limbal stem cell deficiency (LSCD) was unilaterally created in the right eye of NZA rabbits by debridement of epithelial cells and ablation of limbal stem cells (LSC) with Whatman paper soaked with a solution of 1M of sodium hydroxide. Limbal conjunctiva was treated with Mitomycin C to reduce corneal neovascularization. The left eye was left intact. The cell population expanded in LATS inhibitor compound example no. 12 was delivered as described below. After cell delivery, rabbits received analgesic treatment (Tramadol 10 mg/kg PO BID in first 2 weeks, Meloxicam 0.3 mg/kg PO SID in first 2 weeks or as long as the animal showed signs of ocular discomfort), anti-inflammatory treatment (Ancef® (cefazolin) 50 mg sub-Tenon immediate post-procedure, Tobrex® ophthalmic solution t.i.d in 1st week and b.i.d thereafter, ampicillin 80 mg/kg/day (40 mg BID) SQ for first week) and immunosuppression (Cyclosporine A (0.5%) top oc. t.i.d 1st week and b.i.d. thereafter, Gentocin®-Durafilm® (Gentamicin sulfate and betamethasone, MERCK) top oc. t.i.d 1st week and b.i.d. thereafter, Cyclosporine A (5 mg/kg/day) SQ in 1st week and then % dosage thereafter).

Biomatrix Preparation.

Gelatin methacrylate (GelMA) was synthesized according to a previously published protocol. (Nichol, J. W. et al. Cell-laden microengineered gelatin methacrylate hydrogels. Biomaterials 31, 5536-5544, doi:10.1016/j.biomaterials.2010.03.064 (2010). In brief, 20 grams of porcine derived gelatin (Cat #G2500, Sigma) was dissolved overnight at 50° C. in 200 ml of PBS without calcium and magnesium (DPBS, Cat#21-031, Corning). With strong agitation, methacrylic anhydride (Cat#276685, Sigma) was added dropwise (approximately 1 ml/min) into the gelatin solution to reach the concentration of 8% (vol/vol). The mixture was stirred at 60° C. in an oil bath for 3 hours before adding 200 ml of the DPBS and followed by thorough mixing for additional 15 minutes. The diluted mixture was purified via dialysis against Milli-Q water using dialysis tubings (15 kDa MWCO, Spetrua/Por) for 1 week at 45° C. to remove methacrylic acid. The purified samples were lyophilized and stored at −80° C. until further use.

To prepare a 15% GelMA stock solution, 1.5 gram of the freeze-dried GelMA foam was dissolved in 10 ml of pre-warmed DPBS at 37° C. After the GelMA foam was fully dissolved, the photoinitiator was introduced by adding into the GelMA solution 15 mg of lithium phenyl-2,4,6-trimethylbenzoylphosphinate (LAP). 500 microlitre of 1N NaOH (Cat #BDH-7222-1, VWR) was added to the solution to adjust the pH to neutral before the solution was filtered using 0.22 micrometre sterile membranes (Millipore). The final filtrate was separated into 500 microlitre aliquots and stored at 4° C. until further use.

LSC Transplantation In Vivo.

Cells obtained as described in Example B1 were plated in 6-well plates (Corning) in XVIVO15 medium supplemented with LATS inhibitor compound example no 12 at a concentration of 10 micromolar. Cells were cultured at 37° C. in 5% CO2 for two passges (two weeks).

Cell suspensions for transplantation were prepared as follows. Cells were detached from the culture dish with Accutase for 10 minutes at 37° C. Cells were then rinsed by centrifugation and resuspended in 16 microlitres of XVIVO15 medium without LATS inhibitors.

A 5% GelMA solution was prepared by mixing 16 microlitres of the LSC suspension or saline control with 8 microlitres of the 15% GelMA stock solution and followed by adding all the mixture to the therapeutic contact lens (Lotrafilcon B, Alcon) on a supporting glass slide. The final solution contained 300 000 cells and 5% GelMA. The power of the UV LED light source (365 nm, Hamamatsu) was adjusted to 15% with a UV intensity reading of 30 mW/cm2. A brief UVA exposure of 25 seconds was used for the photopolymerization process to bioprint the human LSCs to the inner surface of the contact lens. After the polymerization process, the LSC loaded contact lens was applied to a dissected rabbit eye ex vivo or to the rabbit eye in vivo.

For experiments where the LSC-loaded contact lens was applied ex vivo, samples were observed under a Zeiss epifluorescence microscope within two hours.

For in vivo experiments, the LSC-loaded contact lens was applied to the right eye of the rabbit model of LSCD described above and tarsorrhaphy was performed to keep the contact lens on the ocular surface for 1 week. After one week, the contact lens was removed and rabbits were kept alive for an additional 4 weeks.

Rabbits were sacrificed five weeks after cell delivery, corneas were dissected and fixed in 4% PFA. Samples were embedded in paraffin and sectioned. Immunohistochemistry was performed to detect the presence of keratin-12, a marker of corneal epithelium cells and keratin-19, a marker of conjunctival cells. The anti-keratin 12 and 19 primary antibodies were from Abcam. Human mitochondrial protein was used to confirm the human origin of the cells. The anti-human mitochondrial protein primary antibody was from Novus. Samples were then stained with HRP-conjugated secondary antibodies (ThermoFisher) and observed under a Zeiss microscope.

Figure 6:
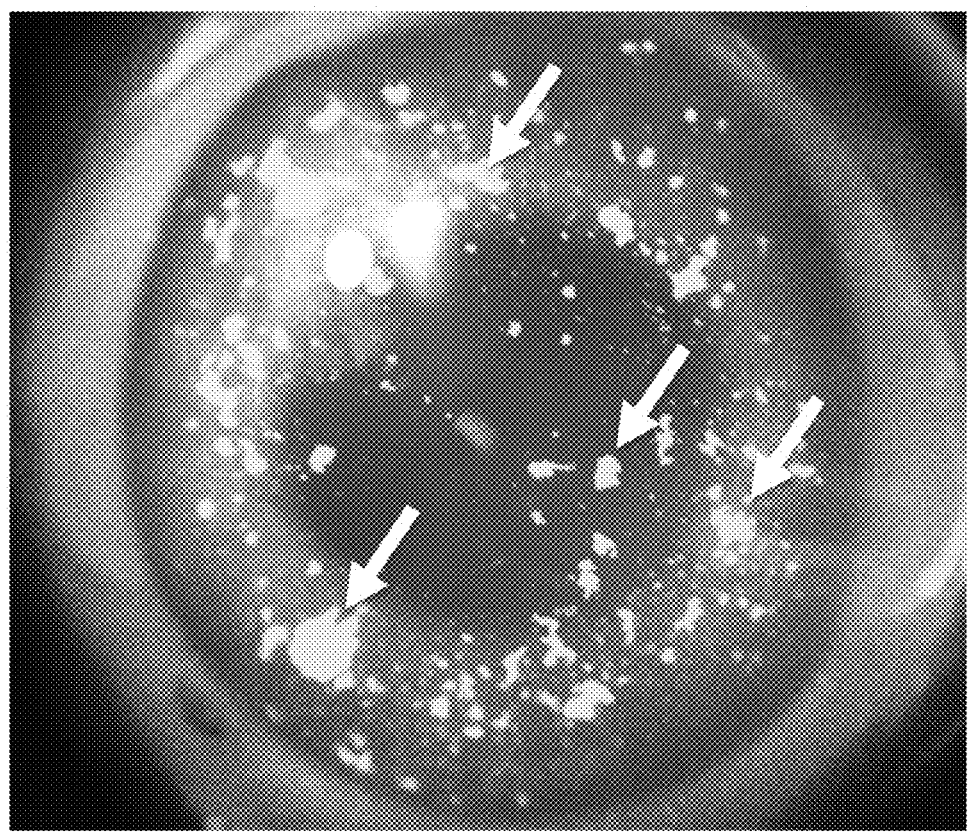
FIG. 6: LSCs were labeled using a fluorescent protein in order to confirm that LSCs attached to a contact lens using GelMA polymerization can be delivered to the surface of the rabbit eye ex vivo. Arrows show site of attachment of LSCs.

Results indicated that LSCs attached to a contact lens using GelMA polymerization can be delivered to the surface of the rabbit eye ex vivo (FIG. 6).

FIG. 7 shows that in a rabbit model of limbal stem cell deficiency, a LSC population expanded in the presence of the LATS inhibitor (compound ex. 12), attached to a contact lens using GelMA polymerization and delivered in vivo to the rabbit's corneal surface, lead to regeneration of the a keratin-12-positive corneal epithelium and prevented conjunctivalization by keratin-19-positive conjunctival cells in the transplanted eye (FIGS. 7A and B respectively). In contrast, non-transplanted rabbit eyes showed absence of keratin-12-positive corneal epithelium restoration. Instead, signs of conjunctivalization were observed, as showed by the presence of keratin-19 staining (FIGS. 7C and D respectively).

Figure 8A:
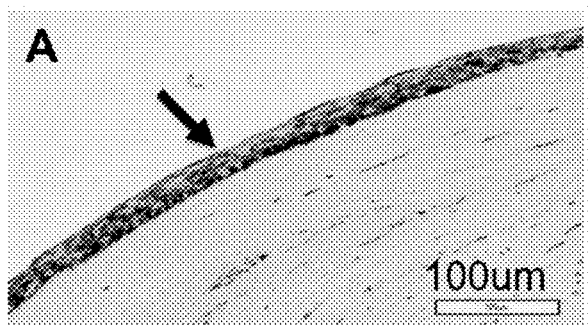
FIG. 8A: Rabbit eye transplanted with human LSCs.
Figure 8B:
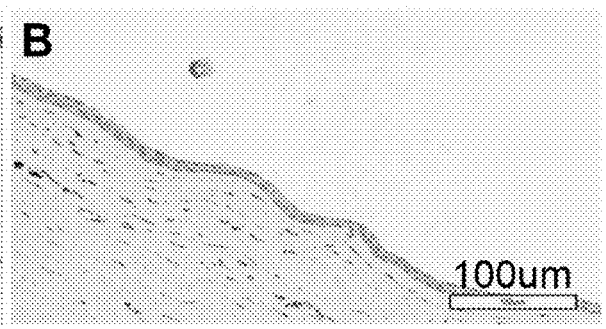
FIG. 8B: Control rabbit eye, non-transplanted with human LSCs. These Figures show that the cells that restored the corneal epithelium of transplanted eyes were human (FIG. 8A), as demonstrated by the presence of human mitochondrial protein (arrow shows the human mitochondrial marker is present). In contrast, the ocular surface of non-transplanted eyes did not exhibit human mitochondrial protein staining (FIG. 8B: human mitochondrial marker is absent).

FIG. 8 shows that the cells that restored the corneal epithelium of transplanted eyes were human, as demonstrated by the presence of human mitochondrial protein (FIG. 8A). In contrast, the ocular surface of non-transplanted eyes did not exhibit human mitochondrial protein staining (FIG. 8B).

Example B10: Delivery of LSC Ex Vivo Using TISSEEL

To prepare TISSEEL (Baxter, cat #NDC 0944-4301-02) working solution, manufacturer's instructions were followed to reconstitute the supplied ingredients. Further dilution of the reconstituted fibrinogen solution can be done by adding sterile water to reach desired concentration of fibrinogen. Thrombin working solution was diluted 500 times with Dulbecco's phosphate-buffered saline (DPBS, GIBCO, Thermo Fisher Scientific, Waltham, Mass.) to achieve 1 unit/ml solution.

LSC Delivery to Culture Surface In Vitro.

Cells obtained as described in Example B1 were plated in 6-well plates (Corning) in XVIVO15 medium supplemented with LATS inhibitor compound example no 12 at a concentration of 10 micromolar. Cells were cultured at 37° C. in 5% $CO_2$ for two passages (two weeks).

Cell suspensions for transplantation were prepared as follows. Cells were detached from the culture dish with Accutase for 10 minutes at 37° C. Cells were then rinsed by centrifugation and resuspended in the thrombin working solution mentioned above and the final cell densities were adjusted by serial dilution to between 0.1 million per ml and 30 million per ml.

Figure 9:
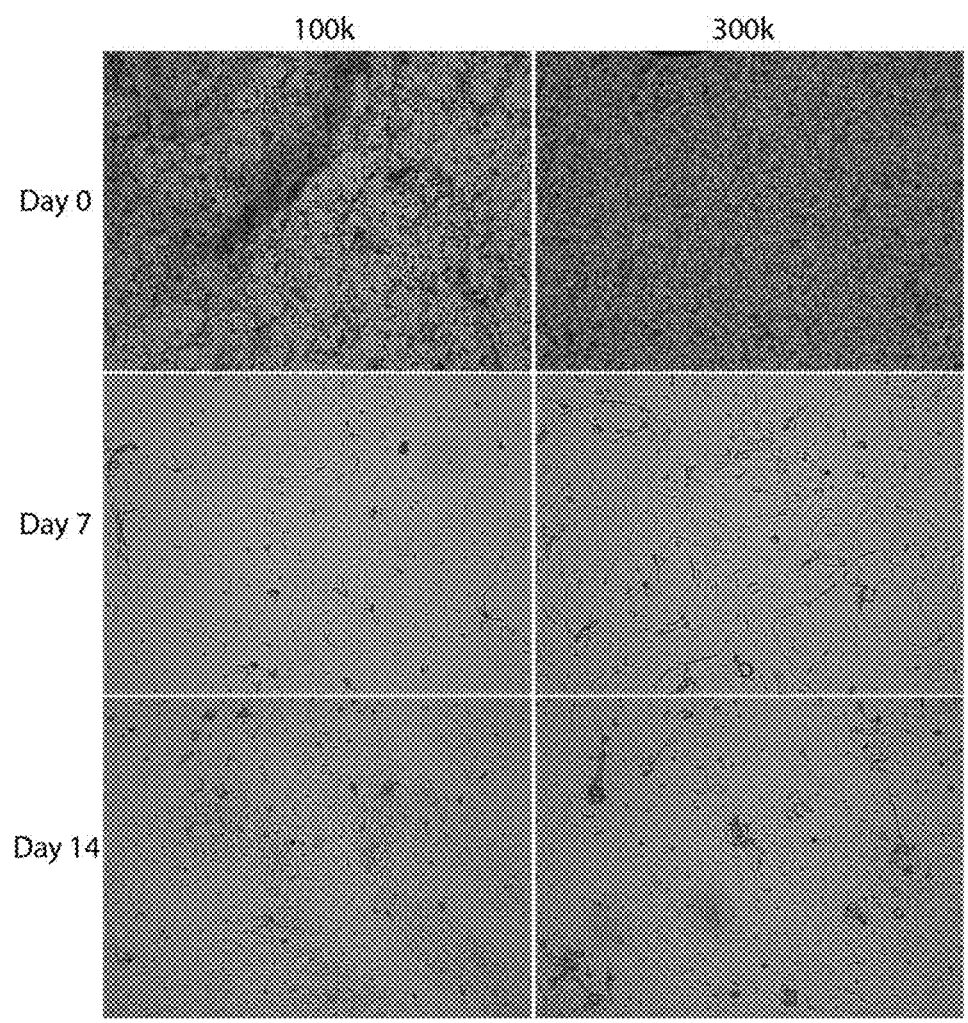
FIG. 9: Microscopic images of LSCs delivered via TISSEEL to collagen coated 24 well plate show repopulation of the cells to cover the culture surface within 2 weeks.

Immediately after mixing the cell suspension with fibrinogen solution, 10 ul of the mixture were plated to the center of a collagen coated 24 well plate and incubated at room temperature for 5 minutes to solidify the fibrin. After replenishing each well with XVIVO15 medium without LATS inhibitors, all the samples were monitored for 2 weeks for fibrin degradation and cell repopulation. The results (FIG. 9) suggested that TISSEEL was used successfully to deliver LSCs, and the culture area, similar size to human cornea, can be covered between 1 week and 2 weeks in the samples with 100k and 300k LSCs delivered initially.

LSC Delivery to Human Cornea Ex Vivo.

Cells obtained as described in Example B1 were plated in 6-well plates (Corning) in XVIVO15 medium supplemented with LATS inhibitor compound example no 12 at a concentration of 10 micromolar. Cells were cultured at 37° C. in 5% $CO_2$ for two passages (two weeks). One day before the delivery experiment, cells were labeled with CellTracker green CMFDA dye (Thermo Fisher Scientific, Waltham, Mass.) according to the manufacturer's protocol.

Cell suspensions for transplantation were prepared as follows. Cells were detached from the culture dish with Accutase for 10 minutes at 37° C. Cells were then rinsed by centrifugation and resuspended in the thrombin working solution mentioned above to reach the final cell density of 30 million per ml.

Figure 10:
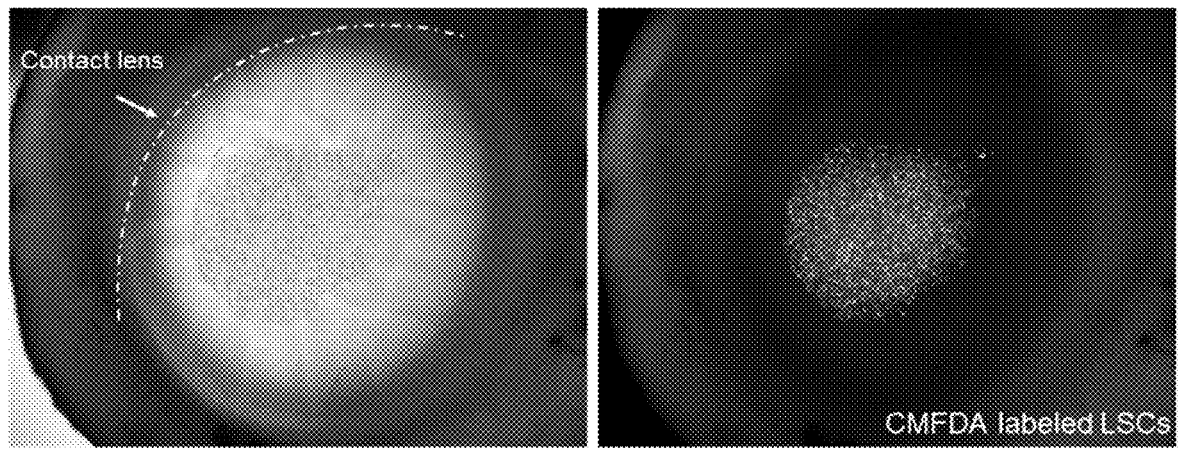
FIG. 10: CellTracker Green CMFDA labeled LSCs were delivered to human cornea ex vivo and covered with protective contact lens.

Immediately after mixing the cell suspension with fibrinogen solution, 10 ul of the mixture were plated to the center of a human cornea and incubated at room temperature for 5 minutes to solidify the fibrin. A LotraB contact lens (Air Optix Night and Day, Alcon) was used to cover the LSC-fibrin construct on the human cornea to mimic the real clinical procedure. Fluorescence images were taken by a Nikon fluorescence stereomicroscope. The data (FIG. 10) demonstrated that TISSEEL was successfully used to deliver high number of LSCs onto corneal surface ex vivo and the LSC-fibrin construct appears robust to tolerate further manipulation such as applying protective contact lens.

Example B11: Delivery of Multiple Cell Populations to Ocular Surface into Designated Patterns Via Bioprinting A customized bioprinter was built based on DOPsL technology as published in Advanced Materials (2015, DOI: 10.1002/adma.201202024).

Cell suspensions for bioprinting were prepared as follows. HEK-293 cells were pre-labelled with Celltracker green CMFDA dye or red CMTPX dye (Thermo Fisher Scientific, Waltham, Mass.) before harvest. 25 µl of the cell suspension was mixed with 25 µl of the 15% GelMA stock solution to reach a final cell density of 200 million cells/ml.

Rabbit eye balls were placed onto a petri dish filled with 1% low melting point agarose and the epithelium was carefully debrided by a surgical scalpel immediately before the bioprinting process. The cell-GelMA mixture was then applied to the top of the cornea with a Polydimethylsiloxane (PDMS) o-ring (Specialty Silicone Products, Inc., Ballston Spa, N.Y.) placed on the limbus to prevent the cell-GelMA mixture dripping from the curved ocular surface.

Figure 11:
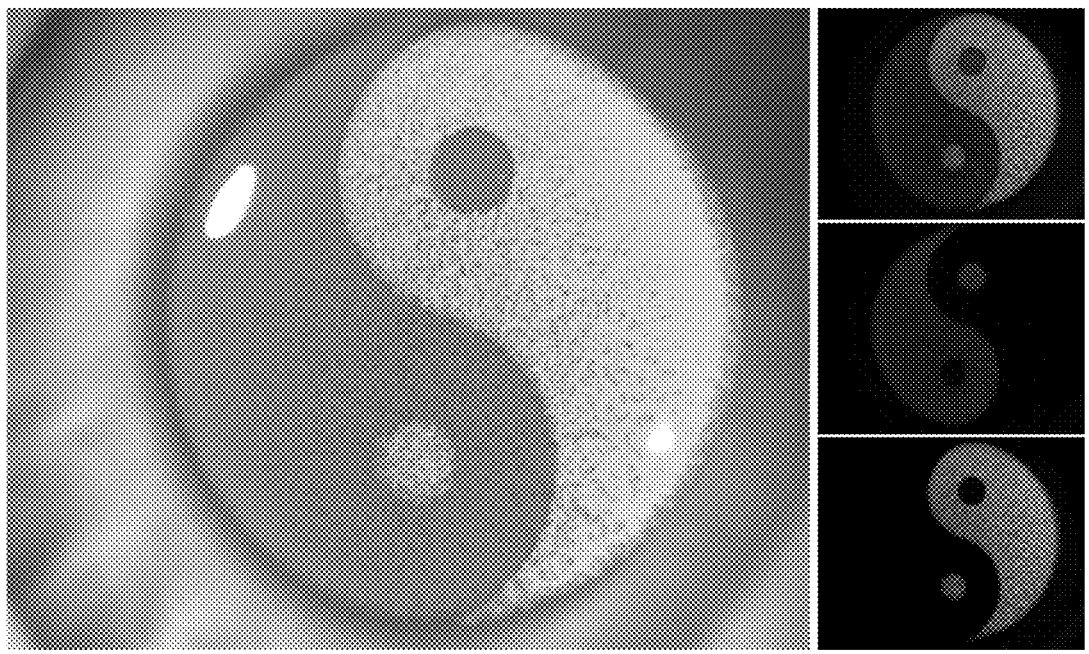
FIG. 11: Red and green dye labeled HEK-293 cells were bioprinted into a Yin-Yang pattern on top of a rabbit cornea ex vivo (shown as dark and light gray pattern).

A customized light pattern (i.e. half of the Yin-Yang pattern) was projected to the cell(green)-GelMA mixture on top of the rabbit eye for 4 seconds before the unpolymerized mixture was rinsed away. Another light pattern (i.e. the other half of the Yin-Yang pattern) was projected to the sample for 4 seconds after a new cell (red)-GelMA mixture was applied to the top of the same rabbit cornea. Several rinses with PBS were performed before imaging. See FIG. 11.

Example B12: Reducing Immune Rejection by CRISPR/Cas9-Mediated Deletion of the Beta-2-Microglobulin Gene in LSCs In the example below, HLA class I expression was eliminated from the LSC surface by CRISPR-mediated deletion of the beta-2-microglobulin gene.

Cell transfection: LSCs obtained as described in Example B1 were cultured in X-VIVO15 medium supplemented with the LATS inhibitor compound example no 48a to a confluency of 50-60% in a 35 mm petri dish eight days after LSC isolation. LSCs were transfected with a mixture of tracrRNA-crRNA-Cas9 mRNA. To obtain the mixture for the size of a 35 mm petri dish, 12.5 microlitre of 10 micromolar tracrRNA (Dharmacon, Cat #U-002000-20), 12.5 microlitre of 10 micromolar crRNA targeting human B2M (Dharmacon, Cat #CR-004366-01), 50 microlitre of 0.1 microgram/microlitre Cas9 mRNA (Dharmacon, Cat #CAS11195), and 15 microlitre of DharmaFECT Duo Transfection Reagent (Dharmacon, Cat #T-2010-02) were combined and incubated for 20 minutes at room temperature. The mixture was added drop wise to the culture dish in 2.5 ml the medium (XVIVO15 supplemented with the LATS inhibitor compound example no 48a) (w/o antibiotics). In order to reduce mRNA cytotoxicity, 0.2 microgram/ml B18R (eBioscience, Cat #34-8185-81) was added to the medium. The transfection reagent alone represents the transfection negative control.

After 6 h incubation in 5% $CO_2$ at 37° C. medium was replaced with fresh X-VIVO15 medium supplemented with compound example no 48a (w/o antibiotics) including compound and B18R. After 72 h in a 5% CO2 incubator cells were passaged 1:2 and expanded for additional 72 h in LSC medium (w/o antibiotics) including compound and B18R on synthemax coated petri dishes to obtain more cells for FACS sorting.

FACS analysis: LSCs were treated with Accutase (ThermoFisher, Cat #A1110501) for 20 minutes in 5% CO2 at 37° C. After scraping the cells, the reaction was stopped by using cell culture medium containing 10% Serum and transferred to a falcon tube for a centrifugation step (1000 rpm, 5 minutes). After aspirating the medium cells were resuspended in 200 microlitre FACS buffer (PBS/10% FBS).

To analyze the expression of B2M and HLA-ABC, 5 microlitre APC mouse anti-human 32-microglobulin antibody (Biolegend, Cat #316312) and 20 microlitre PE mouse anti-human HLA-ABC antibody (BD Bioscience, Cat #560168) were added to the cell suspension and incubated for 30 minutes on ice. Cells were washed 3 times after antibody labelling with FACS buffer and resuspended in 500 microlitres in FACS buffer. Before FACS sorting, cells were filtered through a 70 micrometre filter and stored on ice until sorting.

In order to prevent cells sticking to the wall, collection tubes were filled with the serum for 30 minutes before the sort. Cells were sorted on a BD FACSAria II instrument into prepared collection tubes, using human serum enriched LSC medium including compound and B18R. FACS data were analyzed using BD FACSDiva software.

Figure 12:
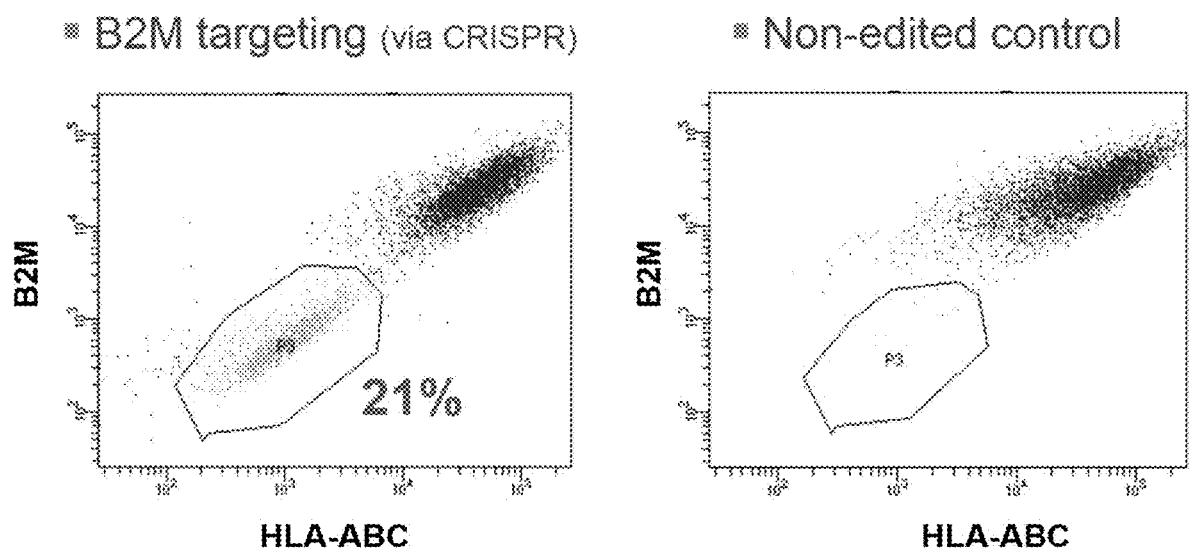
FIG. 12: Reducing immune rejection by CRISPR/Cas9-mediated deletion of the beta-2-microglobulin (B2M) gene in LSCs: FACS analyses show that CRISPR-mediated deletion of B2M and subsequent elimination of HLA A, B and C occurred in 21 percent of the LSCs.
Figure 13:
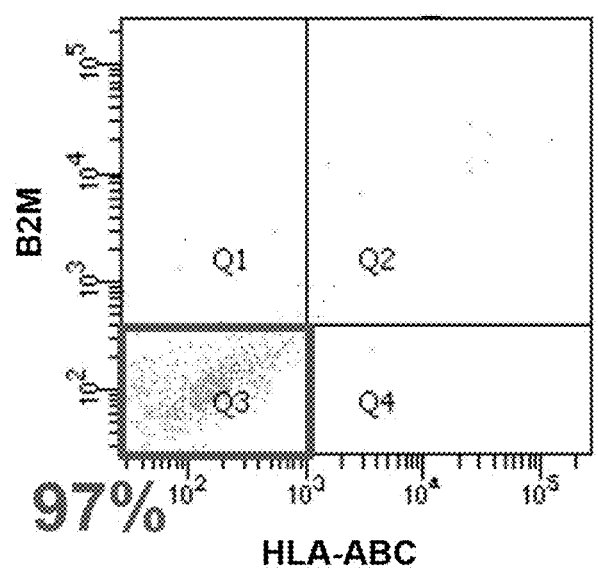
FIG. 13: The population of B2M-negative/HLA A,B,C-negative LSCs was expanded using compound example no. 48a to produce a cell preparation where 97 percent of the cells do not express HLA A, B, C.
Figure 13:
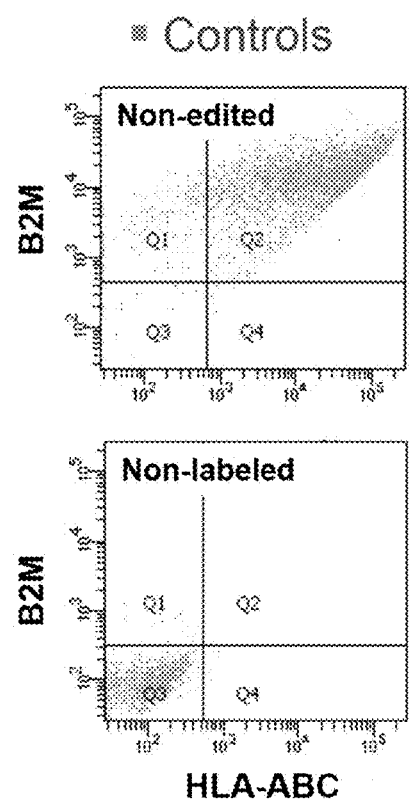

Results presented in FIG. 12 show that CRISPR-mediated deletion of B2M and subsequent elimination of HLA A, B and C occurred in 21 percent of the LSCs. As the XVIVO15 medium supplemented with the LATS inhibitor compound example no 48a enables efficient expansion of LSCs, the 21 percent B2M-negative/HLA A,B,C-negative population of LSCs could then be expanded to produce a cell preparation where 97 percent of the cells do not express HLA class-I drivers of immune rejection (FIG. 13).

Example B13: Residual Compound Estimation Study Standard Curve Preparation

A dilution series of stock standards were made at concentrations of 100 micromolar, 10 micromolar, 1 micromolar, 500 nM, 100 nM, and 0 micromolar. Compound example no. 48a (10 mM in DMSO) stock was spiked into 50% acetonitrile 50% water to make the spike standards. The spiking standards were used to spike the blank media samples. 10 microlitres of spiking standard was added to 90 microlitres of media to create the spiked media standards. 10,000 nM, 1000 nM, 100 nM, 50 nM, 10 nM, and 0 nM media standards were used to generate the compound example no. 48a standard curve. 50 microlitres of each media sample was treated with 400 microlitres of the extraction solution. The extraction solution consists of acetonitrile/methanol (3:1). The standard curve samples were extracted using the same volumes and conditions as the unknown media samples. The extracted samples were centrifuged at 10,000 rpm for 5 min. After centrifugation, 200 microlitres of each sample supernatant was transferred to a clean 96-well plate. The extracted samples were analyzed by High Resolution LC-MS. Thermo Xcalibur Software and Quan Browser were used to generate the standard curve and calculate the concentration values. An external calibration method was used to calculate the concentration of compound example no. 48a in the culture media samples.

LC-MS Analysis

High-resolution chromatography was performed using the Thermo Ultimate UPLC and a Kinetex 2.1×50 mM $C_{1-8}$ RP column (2.6 micron particles). The mobile phases consisted of 5 mM Ammonium Acetate in H2O for Buffer A, and 0.1% Formic Acid in Acetonitrile for Buffer B. A standard binary linear gradient was used for Reverse Phase Chromatography. The Thermo Q Exactive mass spectrometer was used for this study. The UPLC effluent was directed into the Q Exactive Mass Spectrometer which was equipped with an ESI ion source. The mass spectrometer was programmed to perform in High Resolution Full Scan mode and MS2 mode.

Test System

Cell preparation for the LSC washout: the washout experiment was performed in triplicates, where each sample contained 0.5 million cells. All samples (media only, media with cells, supplemented with compound example no. 48a and cells in media supplemented with compound example no. 48a) were cultured at 37 degree incubator for the duration of the experiment. The medium used for the experiment was X-VIVO 15.

The cells were cultured to passage 2 in X-VIVO-15 medium supplemented with 3 micromolar compound example no. 48a. When the culture reached 70% confluency, the medium was removed by aspiration and replaced with fresh medium supplemented with 3 micromolar compound example no. 48a; the cells were cultured for an additional six days. On day seven, the following samples were generated:
1. 2 ml of "blank" medium (not supplemented with the compound)
2. 2 ml of medium cultured in the presence of the compound (pre-wash)
3. 2 ml of media for each wash sample 1-10
4. Cell pellets (post-wash)

The cells were collected by using the sell lifter (Costar, cat #3008).

The media and cell pellet samples were analyzed and quantified using High Resolution LC-MS.

To estimate the residual levels of compound example no. 48a, cell pellets and supernatent were collected. The amount of compound example no. 48a was determined by LC-MS. Estimation of compound example no. 48a concentrations in the Pre-wash Media, Wash Media (Table 4) and the Cell Pellet are summarized (Table 5). Pre-wash Media samples have the highest levels of compound example no. 48a (approx. 9,830 nM to 10,837 nM range). Post-wash Pellet levels have low, but detectable levels of compound example no. 48a (nanomolar).

TABLE 4

Estimation of concentrations for compound example no. 48a in the Pre-wash Media and Wash Media

| Sample | Volume (mL) | compound example no. 48a (nM) in Triplicate #1 | compound example no. 48a (nM) in Triplicate #2 | compound example no. 48a (nM) in Triplicate #3 |
|---|---|---|---|---|
| Pre-wash Media | 2 | 9829.547 | 10374.463 | 10837.706 |
| Wash Media 1 | 2 | 461.271 | 401.058 | 354.547 |
| Wash Media 2 | 2 | 31.933 | 38.721 | 18.400 |
| Wash Media 3 | 2 | BLQ | BLQ | BLQ |
| Wash Media 4 | 2 | BLQ | BLQ | BLQ |
| Wash Media 5 | 2 | BLQ | BLQ | BLQ |
| Wash Media 6 | 2 | BLQ | BLQ | BLQ |
| Wash Media 7 | 2 | BLQ | BLQ | BLQ |
| Wash Media 8 | 2 | BLQ | BLQ | BLQ |
| Wash Media 9 | 2 | BLQ | BLQ | BLQ |
| Wash Media 10 | 2 | BLQ | BLQ | BLQ |

BLQ = Beneath Limit of Quantification

TABLE 5

Estimation of concentrations for compound example no. 48a in the Cell Pellet

| Sample | compound example no. 48a (nM) | compound example no. 48a (pg/cell) | Avg of compound example no. 48a (pg/cell) | # of cells in Pellet | Total compound example no. 48a (pg) |
|---|---|---|---|---|---|
| PostWash_Pellet 1 | 20.342 | 0.00068 | 0.00068 | $0.5 \times 10^6$ | 340 |
| PostWash_Pellet 2 | 19.908 | 0.00066 | | | |
| PostWash_Pellet 3 | 20.787 | 0.00069 | | | |

The amount of compound example no. 48a in the Pre-wash Media from three incubations ranges from 9,830-10,838 nM. The concentration of compound example no. 48a in the Post-wash Cell Pellet was in the range of 19.9-20.8 nM.

Residual Amount of Other Compound Examples after Wash-Out

For compound example numbers 12, 261, and 5, residual amounts in expanded LSCs were measured using the same method as for compound example no. 48a.

TABLE 6

Estimation of concentrations for compound ex. 12 in the Cell Pellet

| Sample | compound ex. 12 (nM) | compound ex. 12 (pg/cell) | Avg of compound ex. 12 (pg/cell) | # of cells in Pellet | Total compound ex. 12 (pg) |
|---|---|---|---|---|---|
| PostWash_Pellet 1 | 7.370 | 0.000136 | 0.000178 | $1 \times 10^6$ | 178 |
| PostWash_Pellet 2 | 14.443 | 0.000264 | | | |
| PostWash_Pellet 3 | 7.319 | 0.000134 | | | |

TABLE 7

Estimation of concentrations for compound example no. 261 in the Cell Pellet

| Sample | compound example no. 261 (nM) | compound example no. 261 (pg/cell) | Avg of compound example no. 261 (pg/cell) | # of cells in Pellet | Total compound example no. 261 (pg) |
|---|---|---|---|---|---|
| PostWash_Pellet 1 | 0.315 | 0.0000043 | 0.000083 | $1 \times 10^6$ | 83 |
| PostWash_Pellet 2 | 6.941 | 0.000095 | | | |
| PostWash_Pellet 3 | 11.008 | 0.00015 | | | |

TABLE 8

Estimation of concentrations for compound example no. 5 in the Cell Pellet

| Sample | compound example no. 5 (nM) | compound example no. 5 (pg/cell) | Avg of compound example no. 5 (pg/cell) | # of cells in Pellet | Total compound example no. 5 (pg) |
|---|---|---|---|---|---|
| PostWash_Pellet 1 | 21.733 | 0.00061 | 0.00083 | $0.5 \times 10^6$ | 415 |
| PostWash_Pellet 2 | 13.454 | 0.00038 | | | |
| PostWash_Pellet 3 | 46.529 | 0.0015 | | | |

Example C1: Human Corneal Endothelial Cell Isolation

Research-consented cadaveric human corneas were obtained from eye banks. The corneal endothelium cell (CEC) layer and Descemet's membrane (DM) were scored with a surgical-grade reverse Sinsky endothelial stripper. The DM-endothelium cell layer was carefully peeled off the corneal stroma and cells were dissociated from the DM using 1 mg/ml collagenase at 370° C. until cell detachment became apparent by microscopic observation (45 minutes to 3 hours). Cells obtained in this manner were used in the Examples C1-C17-below.

Example C2: Exposure of Cells to LATS Inhibitors and Measurement of Intracellular YAP Distribution Cells obtained as described in Example C1 were plated in glass-bottom black wall 24-well dishes in corneal endothelial cell culture medium (human endothelial SF (serum free) medium (Invitrogen) with human serum) supplemented with LATS inhibitor compound example no. 133 or compound example no. 49 at a concentration of 10 micromolar or supplemented in DMSO as a negative control. Cells were cultured under these conditions for 24 hours at 37° C. in 5% CO2.

To measure the effect of the LATS inhibitors on the downstream target YAP, intracellular YAP distribution was analyzed by immunohistochemistry. Cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibody used was anti-YAP from Santa Cruz Biotechnology. Samples were washed in PBS three times and donkey-raised secondary antibody Alexa Fluor 488 (Molecular Probes) at 1:500 dilution were applied for 30 minutes at room temperature. Negative control was omitted primary antibody (data not shown). Fluorescence was observed using a Zeiss LSM 880 confocal microscope.

Figure 14:
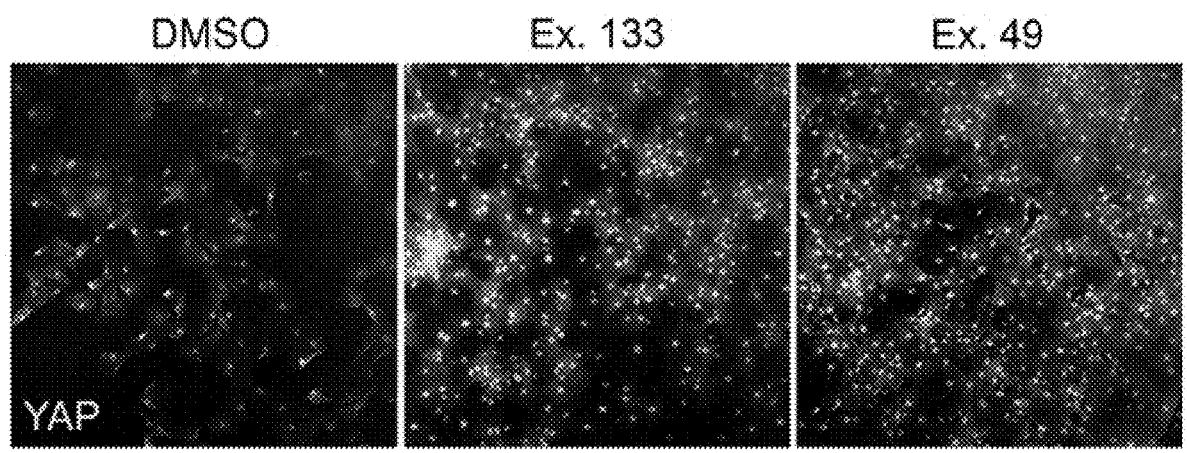
FIG. 14: LATS inhibitors (compounds ex. 133 and ex. 49) induce translocation of YAP into the nucleus in Corneal Endothelial Cells (CECs).

YAP immunostaining is stronger in CECs exposed to cell proliferation medium with the LATS inhibitor compound example no. 133 or example 49 as indicated by immunofluorescence staining of YAP, as shown in FIG. 14. These compounds therefore had an effect on the intracellular localisation of the downstream target YAP.

Example C3: Exposure of Cells to LATS Inhibitors and Measurement of YAP Phosphorylation Cells obtained as described in Example C1 were detached from the culture dish with 1 mg/ml collagenase for 15 minutes at 37° C., cell suspensions were rinsed by centrifugation and plated in corneal endothelial cell culture medium (human endothelial SF medium (Invitrogen) with human serum) in 6-well plates (Corning) and cultured for 2 to 4 days. The medium was then replaced by fresh corneal endothelial cell culture medium (human endothelial SF medium (Invitrogen) with human serum) supplemented with LATS inhibitor, compound example no. 133 or example no 49 (diluted in DMSO) at a concentration of 10 micromolar or as a negative control DMSO alone without compound. Cells were cultured under these conditions for 1 hour at 37° C. in 5% CO2.

Cell pellets were obtained by trypsin dissociation and centrifugation and washed with PBS. The pellets were lysed with 30 micromolar of RIPA lysis buffer containing protease inhibitor cocktail (Life Technologies) for 30 minutes, with vortexing every 10 minutes. The cell debris were then pelleted at 4° C. for 15 minutes at 14k rpm and the protein lysate was collected. Protein concentration was quantified using a micro BCA kit (Pierce). Fifteen (15) micrograms of total protein was loaded in each well of 4-20% TGX gels (BioRad) and Western blotting was performed according to the manufacturer's instructions. Membranes were probed with phospho-YAP (ser127) (CST, 1:500) or total Yap (Abnova, 1:500) antibody and actin (Abcam) labelling was used as loading control. Membranes were stained with HRP-conjugated secondary antibodies, rinsed and imaged using a ChemiDoc system (Biorad) according to the manufacturer's instructions.

Figure 15A:
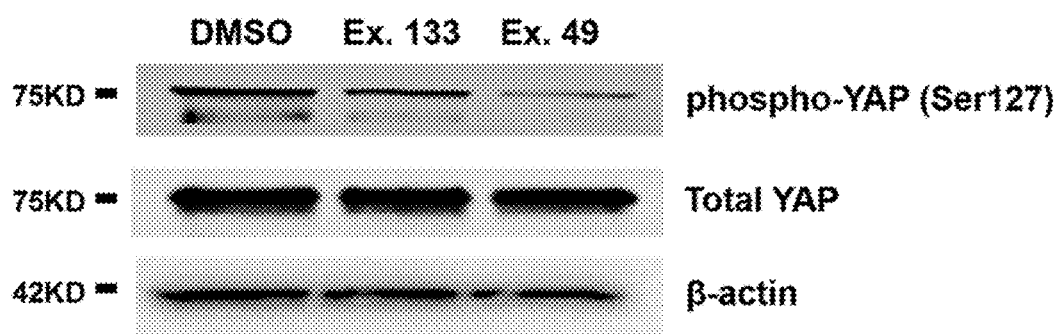
As shown in FIG. 15a by Western blot.
Figure 15B:
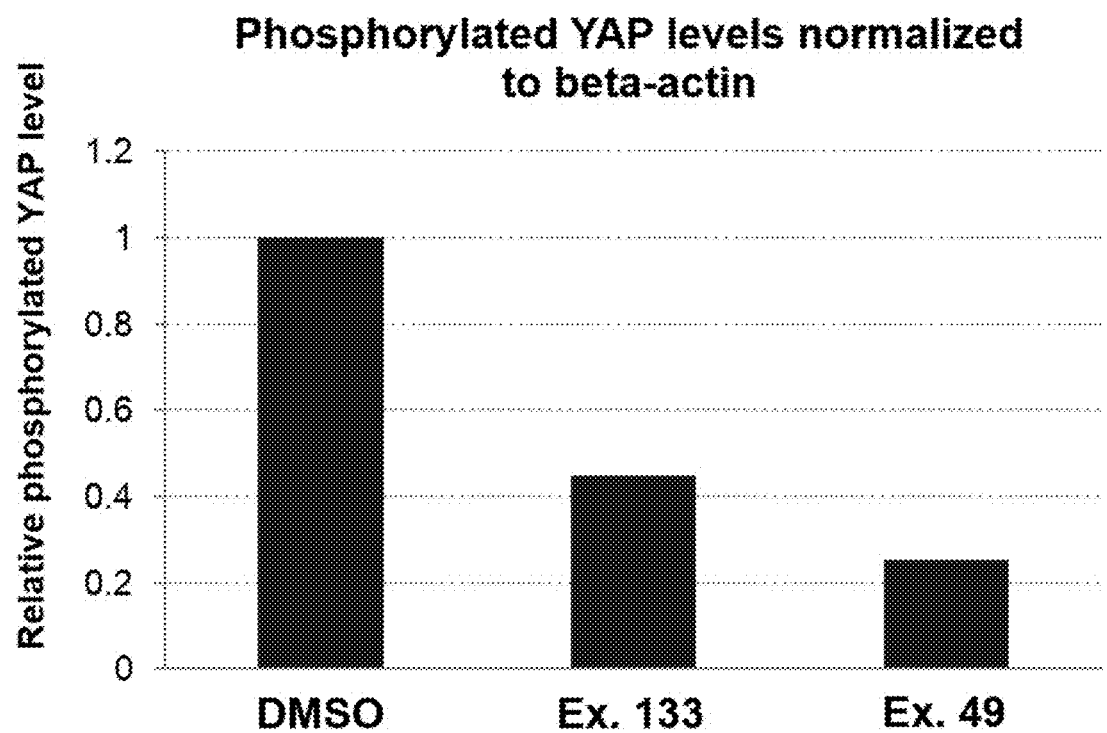
FIG. 15b: graph showing phosphorylated YAP levels normalized to beta-actin.
Figure 15C:
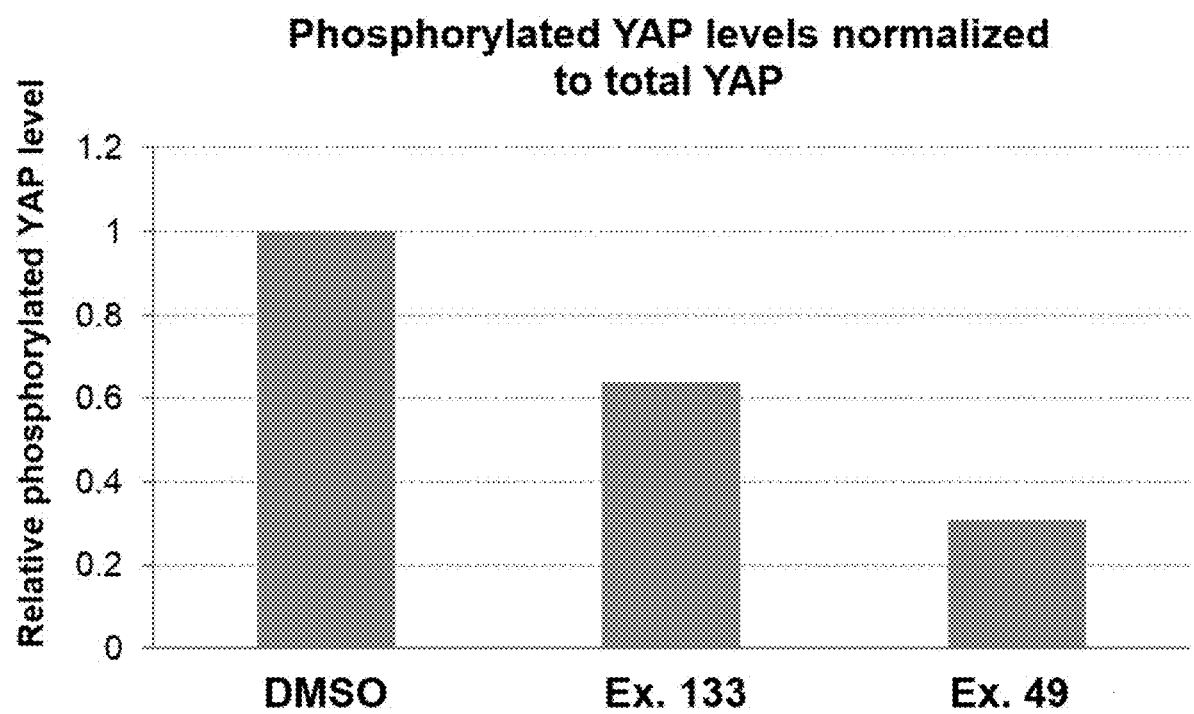
FIG. 15c: graph showing phosphorylated YAP levels normalized to total YAP.

Western blot analysis showed that both compound example no. 133 and example no 49 caused a reduction in YAP phosphorylation levels in human CECs. A marked difference was observed after one hour of treatment with compound example no. 133 and example no 49 in human CECs, as shown by Western Blot in FIG. 15a. FIG. 15b shows by graphical representation the phosphorylated YAP levels normalized to beta-actin and FIG. 15c shows phosphorylated YAP levels normalized to total YAP.

These results suggest that the LATS inhibitors compound example no 133 and example no 49 can activate YAP signaling in human CECs.

Example C4: Human Corneal Endothelial Cell Population Expansion and Measurement of Cell Density Cells obtained as described in Example C1 were detached from the culture dish with 100 microlitres of Accutase (ThermoFisher) for 10 minutes at 37° C., cell suspensions were rinsed by centrifugation and plated in corneal endothelial cell culture medium (human endothelial SF medium (Invitrogen) with human serum) in 6-well plates (Corning) supplemented with LATS inhibitor compound example no. 133 or example no 49 (diluted in DMSO) at a concentration of 10 micromolar or as a negative control DMSO alone without compound. Cells were cultured at 37° C. in 5% CO2.

To measure cell proliferation, an Incucyte machine was used following the manufacturer's instructions (Essen Biosciences) to perform real-time quantitative live-cell analysis of cell confluence every 3 hours for 10 days.

Figure 16:
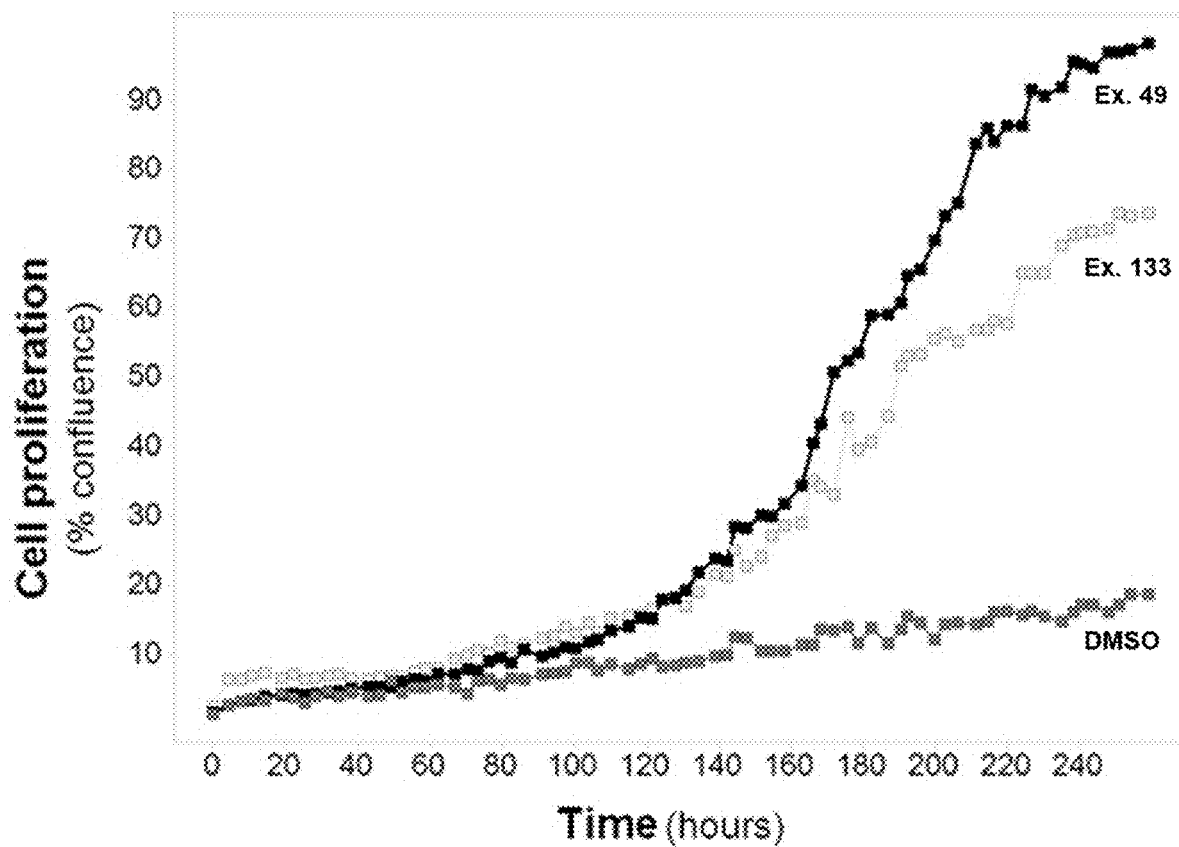
FIG. 16: CECs grown in presence or absence of LATS inhibitors. An Incucyte system (Essen Biosciences) was used to measure CEC confluence by real-time quantitative live-cell analysis over a time course. Compound ex. 49 (black squares) and ex. 133 (light grey squares) induced strong CEC proliferation; whereas CEC proliferation was minimal in the vehicle (DMSO, dark grey squares).

FIG. 16 shows the percentage confluence of the cell population over time after exposure to LATS inhibitor or DMSO alone. Although human CECs are normally non-proliferative, the results show that both LATS inhibitors compound example no. 133 and example no 49 could activate proliferation in these cells.

Example C5: Human Corneal Endothelial Cell Population Expansion and Measurement of Cell Density Cells obtained as described in Example C1 were plated in 48-well plates (Corning) in X-VIVO15 medium supplemented with LATS inhibitors as listed in Tables 9 and 10 (diluted in DMSO) at a concentration of 10 micromolar or as a negative control DMSO alone without compound. Cells were cultured at 37° C. in 5% CO2.

For each compound, two sets of cultures were generated. A first set of cultures was fixed in 4% PFA for 20 minutes at room temperature after cells isolated from the cornea had attached to the cell culture dish (typically 24 h after cell plating). A second set of cultures was fixed in 4% PFA for 20 minutes at room temperature 10 days after the first one.

To measure cell density in all fixed cultures, the number of nuclei stained with Sytox Orange (ThermoFisher) were counted per surface area as follows: fixed cell cultures fixed were permeabilized in a solution of 0.3% Triton X-100 (Sigma-Aldrich). Cells were then labeled in a solution of 0.5 micromolar of Sytox Orange in PBS for 5 minutes at room temperature. Nuclei were counted under a Zeiss epifluorescence microscope. The expansion factor was then determined by calculating the ratio of the expanded population of cells to population of seeded cells.

The cell population expansion achieved with the tested compounds is shown by Tables 9 and 10 below.

TABLE 9

Fold Cell expansion

| Compound example no. | Expansion factor |
| --- | --- |
| Ex. 12 | 521 |
| Ex. 261 | 461 |
| Ex. 47 | 449 |
| Ex. 48a | 446 |
| Ex. 49 | 426 |
| Ex. 5 | 408 |
| Ex. 62 | 402 |
| Ex. 6 | 391 |
| Ex. 14 | 337 |
| Ex. 288 | 302 |
| Ex. 66 | 280 |
| Ex. 133 | 273 |
| Ex. 287 | 237 |
| Ex. 290 | 221 |
| Ex. 65 | 203 |
| Ex. 17 | 187 |
| Ex. 139 | 107 |
| Ex. 289 | 84 |
| Ex. 11 | 79 |
| Ex. 48b | 21 |
| Ex. 33 | 12 |
| DMSO | 7 |

TABLE 10

Endothelial Cell density in vitro (cells/mm$^2$ area)

| Compound example number | Cell density: cells/mm$^2$ | Compound example number | Cell density: cells/mm$^2$ |
| --- | --- | --- | --- |
| Ex. 12 | 4226 | Ex. 133 | 2028 |
| Ex. 261 | 4308 | Ex. 287 | 1893 |
| Ex. 47 | 4294 | Ex. 290 | 2071 |
| Ex. 48a | 4021 | Ex. 65 | 1702 |
| Ex. 49 | 3873 | Ex. 17 | 1628 |
| Ex. 5 | 3911 | Ex. 139 | 1179 |
| Ex. 62 | 3301 | Ex. 289 | 1421 |
| Ex. 6 | 3378 | Ex. 11 | 1121 |
| Ex. 14 | 3271 | Ex. 48b | 869 |
| Ex. 288 | 2779 | Ex. 33 | 25 |
| Ex. 66 | 2503 | DMSO | 13 |

Example C6: siRNA Knockdown of LATS1 and LATS2 in Human Corneal Endothelial Cells Cells obtained as described in Example C1 were plated in 24-well plates (Corning) in X-VIVO15 medium (Lonza). Cells were cultured at 37° C. in 5% CO2. LATS1 and LATS2 were knocked down by transfection (lipofection, using RNAiMax, Thermofisher). Each well of the cell culture plate was transfected with 0.5 micrograms of pools of 4 siRNAs targeting each gene. siRNAs used in this study were Qiagen's LATS1 siRNA S100067172 and LATS2 siRNA S100106925. Scrambled siRNAs were used as negative controls according to the manufacturer's protocol (Qiagen).

In order to measure cell proliferation, EdU staining was performed 48 hours after transfection with LATS1 and LATS2 siRNAs or scrambled siRNA controls according to the manufacturer's instructions (Life Technologies). Cell nuclei were labeled with Sytox Orange. EdU and Sytox Orange fluorescence was observed using a Zeiss LSM 880 confocal microscope in order to measure the percentage of EdU-positive cell nuclei.

Figure 17:
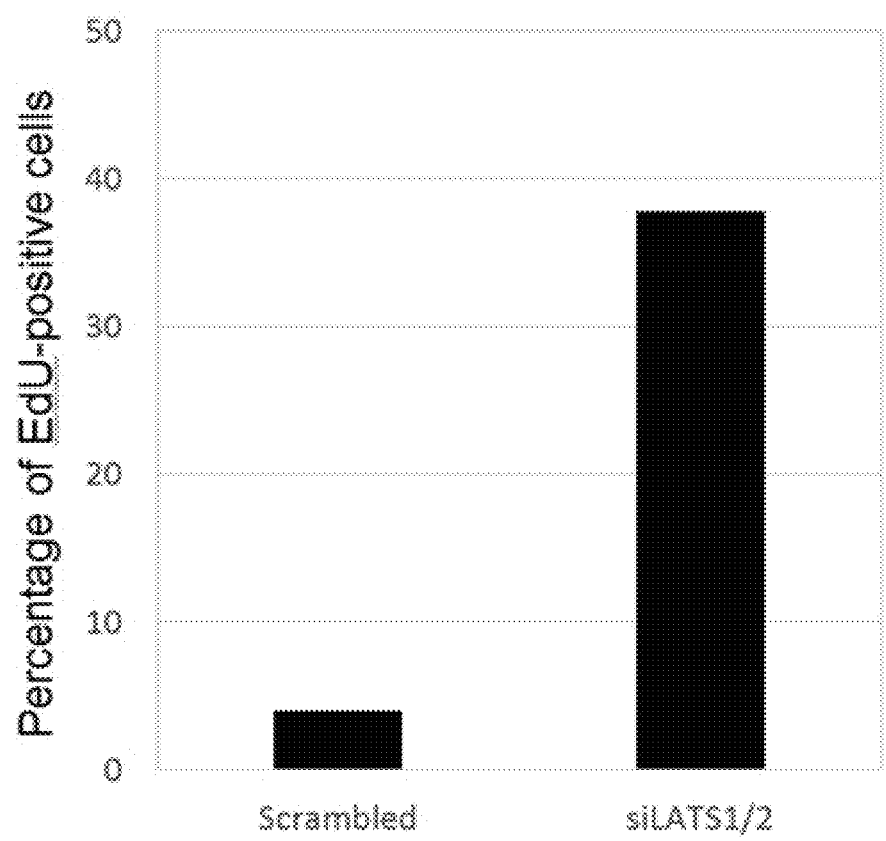
FIG. 17: LATS1 and LATS2 knockdown by siRNA activates corneal endothelial cell proliferation in culture as shown by percentage of EdU positive cells.

FIG. 17 shows that the percentage of EdU-positive CEC increased upon LATS1 and LATS2 knockdown, showing that knockdown of LATS leads to CEC proliferation.

Example C7: Human Corneal Endothelial Cell Population Expansion and Immunohistochemical Observation of Cellular Morphology Cells obtained as described in Example C1 were plated in 24-well plates (Corning) in corneal endothelial cell culture medium (human endothelial SF medium (Invitrogen) with human serum) supplemented with LATS inhibitor compound example no 49 (diluted in DMSO) at a concentration of 10 micromolar or supplemented with a negative control of DMSO without compound. Cells were cultured at 37° C. in 5% CO2 for 10 days.

In order to observe that the expanded cell population has the required cellular morphology for use in vivo, the ability of the cells to form tight junctions was measured by immunohistochemistry as follows. Cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibody in the blocking solution for 12 hours at 4° C. Primary antibody used was ZO-1 from Invitrogen. Samples were washed in PBS three times and donkey-raised secondary antibody Alexa Fluor 488 (Molecular Probes) at 1:500 dilution were applied for 30 minutes at room temperature. Cells were washed three times in PBS and nuclei (DNA) were stained with Sytox Orange (567 nm, Life Technologies). Negative control was omitted primary antibody (data not shown). Fluorescence was observed using a Zeiss LSM 880 confocal microscope.

CECs proliferated in the presence of medium and DMSO control show signs of polymegatism characteristic of dysfunctional CECs (FIG. 18A). CECs exposed to cell proliferation medium with the LATS inhibitor example no 49 retained a normal corneal endothelial cell morphology and the ability to form tight junctions as indicated by immunofluorescence staining of tight-junction marker Zonula Occludens-1 (ZO-1), as shown in FIG. 18B. Both a normal corneal endothelial cell morphology and the ability to form tight junctions are crucial for the maintenance of corneal endothelium functions.

Example C8: Human Corneal Endothelial Cell Population Expansion and Measurement of Markers Collagen 8a2, AQP1, SLC4A11, RPE65, CD31, and Na/K ATPase In order to verify that the expanded cell population expresses genes normally expressed by corneal endothelial cells in vivo, cells were cultured and RT-PCR analysis was then performed to measure the expression levels of Collagen 8a2, AQP1, SLC4A11, RPE65 and CD31. Immunohistochemical analysis was also performed to analyse the levels of Na/K ATPase and Collagen 8a2 as follows.

Cells obtained as described in Example C1 were plated in 24-well plates (Corning) in corneal endothelial cell culture medium (human endothelial SF medium (Invitrogen) with human serum) supplemented with LATS inhibitor compound example no 49 (diluted in DMSO) at a concentration of 10 micromolar or supplemented with a negative control of DMSO without compound. Cells were cultured at 37° C. in 5% CO2 for 10 days. For the negative control, dermal fibroblasts (Lonza) were cultured in DMEM-F12 (LifeTechnologies) without LATS inhibitors.

To perform the RT-PCR analysis, total RNA was extracted using Trizol (Invitrogen), RNeasy Mini and QIA Shredder (Qiagen) according to manufacturer's protocol. RNA quality and quantity were measured using Nanodrop 100 (Thermo-Fisher Scientific) and Bioanalyzer 2100 (Agilent Technologies). cDNA was prepared by reverse transcription and relative mRNA expression was assessed by quantitative RT-PCR using an 7900HT system (Applied Biosystems). The following cycling parameters were used:
1) 50° C. for 2 minutes; 2) 95° C. for 10 minutes; 3) 95° C. for 15 seconds 4) 60° C. for 1 minute. Steps 3-4 were repeated 40 times.

Actin mRNA levels were measured and used as a endogenous controls to normalize gene expression levels and calculate delta Ct values according to the formula $dCt=Ct$ for gene of interest−Ct for endogenous control. Primers were obtained from Applied Biosystems.

Figure 19:
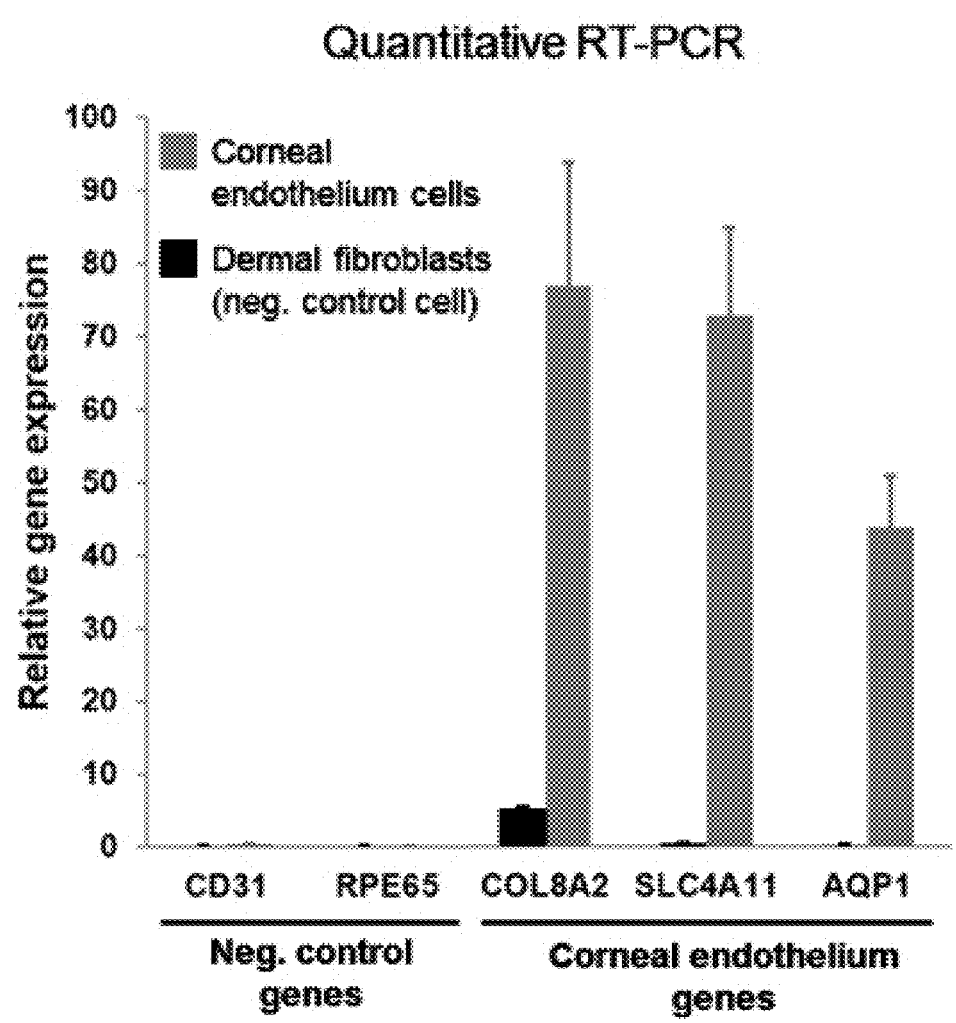
FIG. 19: Quantitative RT-PCR analysis indicates that a corneal endothelial cell population expanded with the LATS inhibitor, compound ex. 49, express genes normally expressed by corneal endothelial cells in vivo, including Collagen 8a2, AQP1, SLc4A11. The cells do not express markers of other epithelia present in the eye, including RPE65 (a marker of retinal pigmented epithelium) and CD31 (a marker of vascular epithelium).

RT-PCR analysis as shown in FIG. 19 indicates that a corneal endothelial cell population expanded with LATS inhibitor compound example no 49 express genes normally expressed by corneal endothelial cells in vivo, including Collagen 8a2, AQP1, SLC4A11. The cells do not express markers of other epithelia present in the eye, including RPE65 (a marker of retinal pigmented epithelium) and CD31 (a marker of vascular epithelium).

To check the expression of Na/K ATPase and Collagen 8a2 by immunohistochemistry the cell cultures were fixed with 4% PFA for 20 minutes, permeabilized and blocked in a blocking solution of 0.3% Triton X-100 (Sigma-Aldrich) and 3% donkey serum in PBS for 30 minutes. Cells were then labeled with primary antibodies in the blocking solution for 12 hours at 4° C. Primary antibodies used were Na/K ATPase and Collagen 8a2 (Santa Cruz Biotechnology). Samples were washed in PBS three times and donkey-raised secondary antibody Alexa Fluor 488 or 647 (Molecular Probes) at 1:500 dilution were applied for 30 minutes at room temperature. Cells were washed three times in PBS and nuclei (DNA) were stained with Sytox Orange (567 nm, Life Technologies). Negative controls were either omitted primary antibody or isotype control antibody (data not shown). Fluorescence was observed using a Zeiss LSM 880 confocal microscope.

Figure 20A:
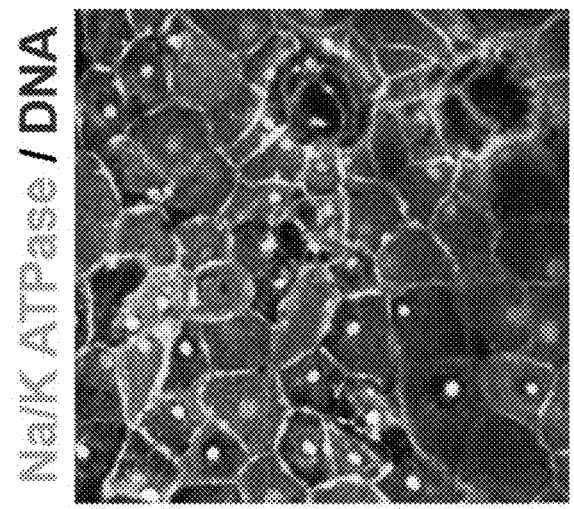
FIG. 20: Immunohistochemical analysis indicates that a corneal endothelial cell population expanded with the LATS inhibitor, compound ex. 49, express genes normally expressed by corneal endothelial cells in vivo, including Na/K ATPase (FIG. 20a) and Collagen 8a2 (FIG. 20b).
Figure 20B:
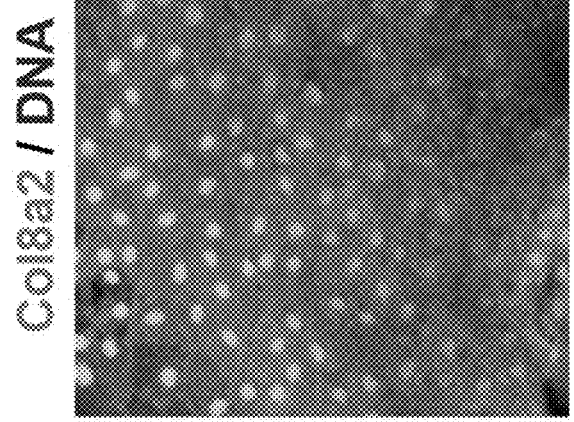
Figure 21A:
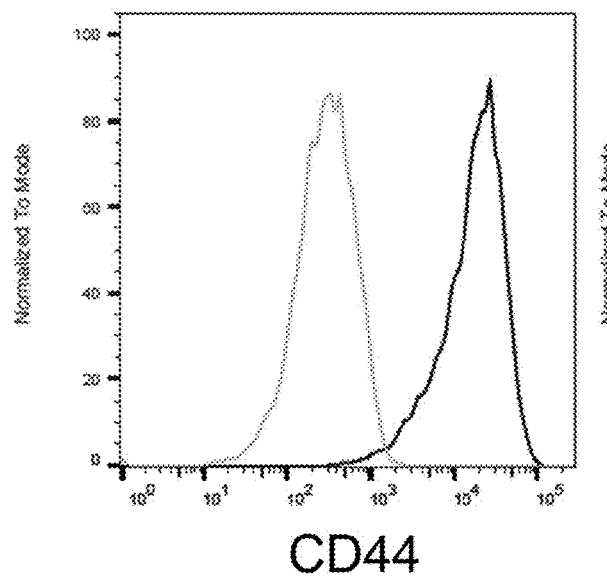
FIG. 21: FACS analysis of the corneal endothlelium cell population expanded in the presence of the LATS inhibitor, compound ex. 47, and CECs cultured in the absence of a LATS inhibitor. The cell population expanded in the presence of the LATS inhibitor expresses low levels of CD73 (FIG. 21a, grey line), CD44 (FIG. 21b, grey line), CD166 (FIG. 21c, grey line) and CD105 (FIG. 21d, grey line); while the cell population cultured without the LATS inhibitor expresses high levels of CD44, CD73, CD105 and CD166 (black lines).
Figure 21B:
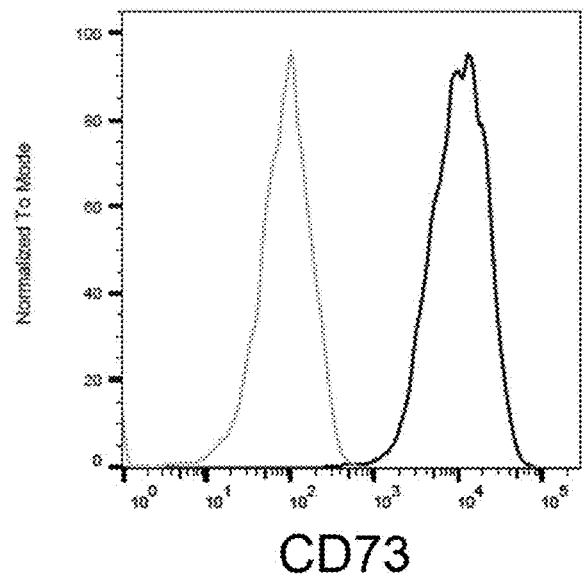
Figure 21C:
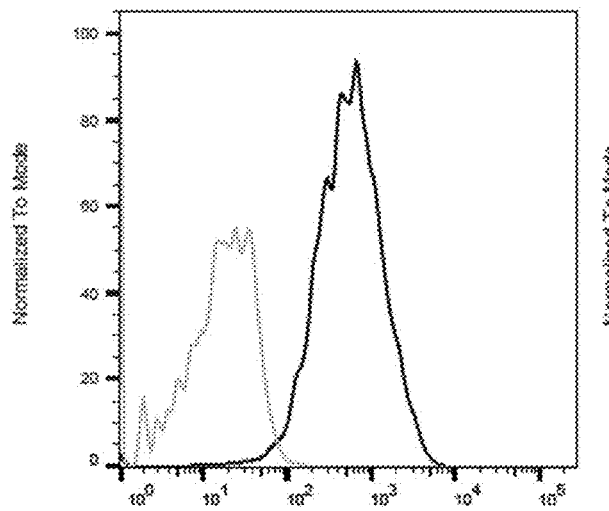
Figure 21D:
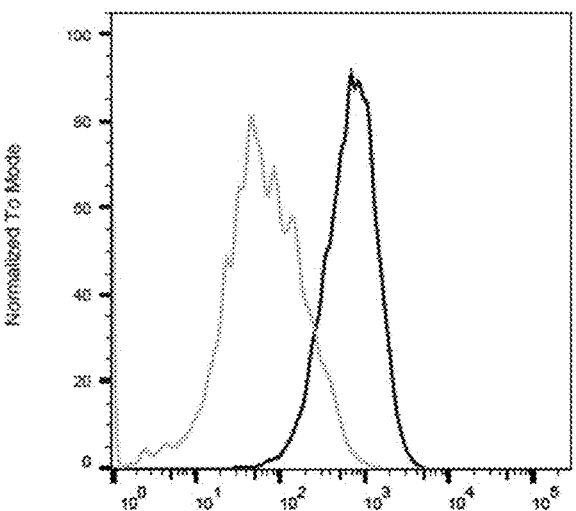
Figure 22A:
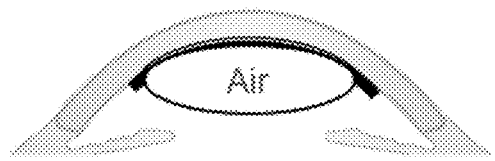
FIG. 22a. Inject bolus of biomatrix.
Figure 22B:
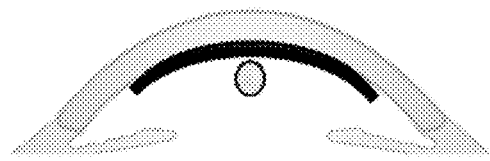
FIG. 22b Inject bubble beneath biomatrix to spread over cornea.
Figure 22C:
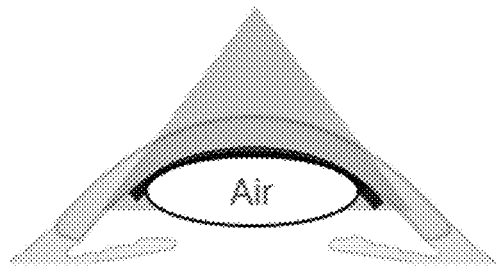
FIG. 22c Cure biomatrix with UV or blue light source.
Figure 22D:
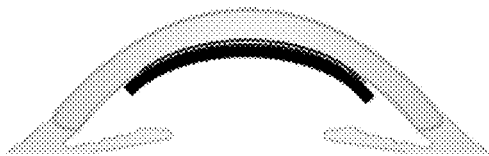
FIG. 22d Remove bubble and replace with balanced salt solution.
Figure 23A:
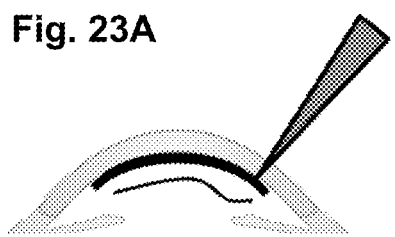
FIG. 23a Remove dysfunctional endothelium with FS.
Figure 23B:
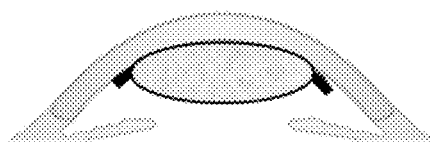
FIG. 23b Inject biomatrix in anterior chamber.
Figure 23C:
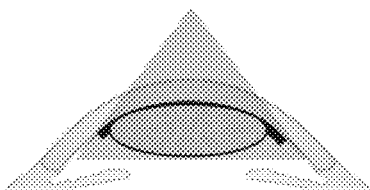
FIG. 23c Cure biomatrix with UV or blue light source.
Figure 23D:
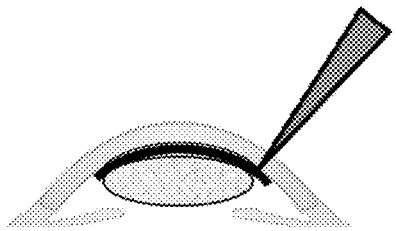
FIG. 23d Detach unwanted biomatrix with FS.
Figure 23E:
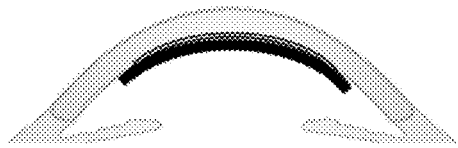
FIG. 23e Remove detached biomatrix with forceps.
Figure 24A:
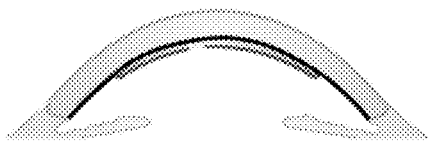
FIG. 24a Stain the endothelium with dye (e.g. Typan Blue)
Figure 24B:
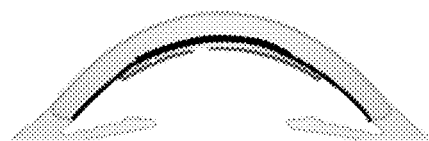
FIG. 24b Peel the dysfunctional endothelium.
Figure 24C:
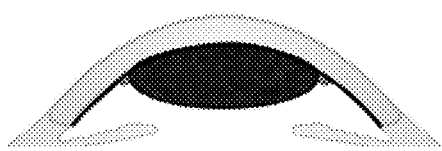
FIG. 24c Inject dyed biomatrix.
Figure 24D:
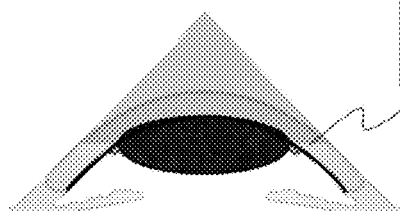
FIG. 24d Cure biomatrix with UV or blue light source.
Figure 24E:
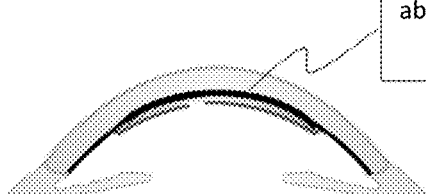
FIG. 24e Flush uncured biomatrix.
Figure 25A:
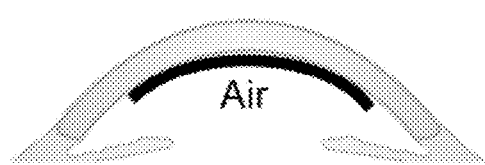
FIG. 25a Drain anterior chamber.
Figure 25B:
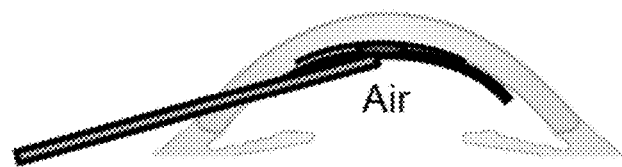
FIG. 25b Dispense biomatrix to posterior cornea with soft tip/brush cannula.
Figure 25C:
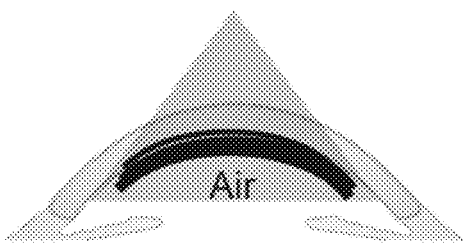
FIG. 25c Cure biomatrix with UV or blue light source.
Figure 25D:
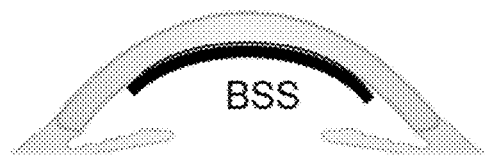
FIG. 25d Refill eye with balanced salt solution.

Immunohistochemical analysis as shown in FIG. 20 indicates that a corneal endothelial cell population expanded with LATS inhibitor compound example no 49 express genes normally expressed by corneal endothelial cells in vivo, including Na/K ATPase (FIG. 20a) and Collagen 8a2 (FIG. 20b).

Example C9: Human Corneal Endothelial Cell Population Expansion and Measurement of Markers CD44, CD105, CD166 and CD73

In order to verify that the expanded cell population does not undergo endothelial to mesenchymal transition, CECs were cultured as follows and FACS analysis was then performed to analyse the levels of CD44, CD105, CD166 and CD73.

To generate mature CEC cultures, cells obtained as described in Example C1 were plated in X-VIVO15 supplemented with LATS inhibitor compound example no. 48a (diluted in DMSO) at a concentration of 3 micromolar. Cells were cultured in 48 well plates (corning) at 37° C. in 5% CO2 for two weeks. Cells were passaged twice during this time by detaching cells with 1 mg/ml collagenase for 15 minutes at 37° C., rinsing cell suspensions by centrifugation and plating in fresh medium. These cells were then grown in XVIVO medium without a LATS inhibitor for a further 2 weeks.

To measure the levels of CD44, CD105, CD166 and CD73 by FACS the CECs were treated with Accutase (ThermoFisher, Cat #A1110501) for 20 minutes in 5% CO2 at 37° C. The reaction was stopped by using cell culture medium containing 10% Serum and transferred to a falcon tube for a centrifugation step (1000 rpm, 5 minutes). After aspirating the medium cells were resuspended in 200 microlitre FACS buffer (PBS/10% FBS).

Antibodies against CD44, CD105, CD166 and CD73 (BD Biosciences) were added to the cell suspension and incubated for 30 minutes on ice. Cells were washed 3 times after antibody labelling with FACS buffer and resuspended in 500 microlitre in FACS buffer. Before FACS sorting, cells were filtered through a 70 micrometre filter and stored on ice until sorting. Cells were sorted on a BD FACSAria II instrument. FACS data were analyzed using BD FACSDiva software.

FACS analysis as shown in FIG. 21 indicates that the FACS marker expression profile of the cell population expanded in the presence of the LATS inhibitor is different from the FACS marker expression profile of cells that have undergone endothelial to mesenchymal transition. Specifically, cells cultured in the presence of the LATS inhibitor express lower levels of CD44, CD73, CD105 and CD166 compared to cells grown in the absence of the LATS inhibitor. Importantly, CD73 is a marker of endothelial to mesenchymal transition, therefore these results indicate that CECs cultured in the presence of LATS inhibitors do not undergo endothelial to mesenchymal transition.

Example C10: Cell Bioprinting: GelMA Preparation Synthesis of GelMA

Gelatin methacrylate (GelMA) with approximately 100% of Lys residues methacrylated was synthesized according to a previously published protocol (Nichol, J. W. et al. *Biomaterials*, 2010, p.5536-5544). 20 grams of porcine derived gelatin (Cat #G2500, Sigma) was dissolved overnight at 50° C. in 200 ml of PBS without calcium and magnesium (DPBS, Cat#21-031, Corning). With strong agitation, methacrylic anhydride (Cat#276685, Sigma) was added dropwise (approximately 1 ml/min) into the gelatin solution to reach the concentration of 8% (vol/vol). The mixture was stirred at 60° C. in an oil bath for 3 hours before adding 200 ml of the DPBS and followed by thorough mixing for an additional 15 minutes. The diluted mixture was purified via dialysis against Milli-Q water (used 15 kDa MWCO Spectra/Por dialysis tubing) for 1 week at 45° C. to remove methacrylic acid. The purified samples were lyophilized and stored at −80° C. until further use.

$^1$H NMR (400 MHz, $D_2O$, 35° C.) was used to determine the degree of methacrylation for a 15 mg/mL solution of GelMA. The peak area ratio of Phe to methacrylamide was found to be 1.00:0.82 by comparing the area of the multiplet at 7.25-7.50 ppm (assumed to be Phe protons, 5H per Phe in GelMA) to the sum of the areas of four singlets at 5.47 ppm, 5.51 ppm, 5.71 ppm, and 5.76 ppm (assumed to be vinyl protons, 2H per methacrylamide in GelMA). The molar Phe:Lys ratio in the gelatin used in this reaction was determined to be 1.00:2.06 by amino acid analysis. Therefore, the molar ratio of Phe:Lys:methacrylamide in GelMA is 1.00:2.06:2.05. Assuming that the primary site of gelatin methacrylation is at Lys residues, the 1H NMR analysis indicates the degree of methacrylation is ~100% (2.05/2.06×100%=99.5%).

Stock solutions of GelMA and LAP were prepared in DPBS, pH-adjusted, sterile filtered, and stored at 4° C. until further use as described below. The following protocol exemplifies the preparation of a 15% w/v GelMA and 0.15% w/v LAP stock, but other strengths were prepared following an identical procedure. To prepare a 15% w/v GelMA stock solution, 1.5 gram of the freeze-dried GelMA prepared as described above was dissolved in 10 ml of pre-warmed DPBS at 37° C. After the GelMA was fully dissolved, the photoinitiator was introduced by adding into the GelMA solution 15 mg of lithium phenyl-2,4,6-trimethylbenzoylphosphinate (LAP), resulting in a stock solution containing 15% w/v GelMA and 0.15% w/v LAP. LAP was synthesized using published procedure (Biomaterials 2009, 30, 6702-6707). 500 microlitres of 1N NaOH (Cat #BDH-7222-1, VWR) was added to the solution to adjust the pH to neutral before the solution was filtered using 0.22 micrometre sterile membranes (Millipore). The final filtrate was separated into 500 ul aliquots and stored at 4° C. until further use.

Example C11: Bioprinters: design and operation

In order to develop a cell therapy where the location of cell delivery is precisely controlled, a bioprinting technology is used to precisely position CECs on the posterior side of the cornea.

Bioprinting experiments were performed on glass coverslips using HEK293 cells. Red-fluorescent protein-labeled HEK293 cells were cultured to confluence in 6-well culture plates in DMEM-F12 with 5% fetal bovine serum. Cells were then detached from the culture dish with 100 microlitre of TripLE (Invitrogen) for 10 minutes at 37° C., cell suspensions were rinsed by centrifugation and resuspended in DMEM-F12 at a concentration of 80 million cells per ml.

Figure 26:
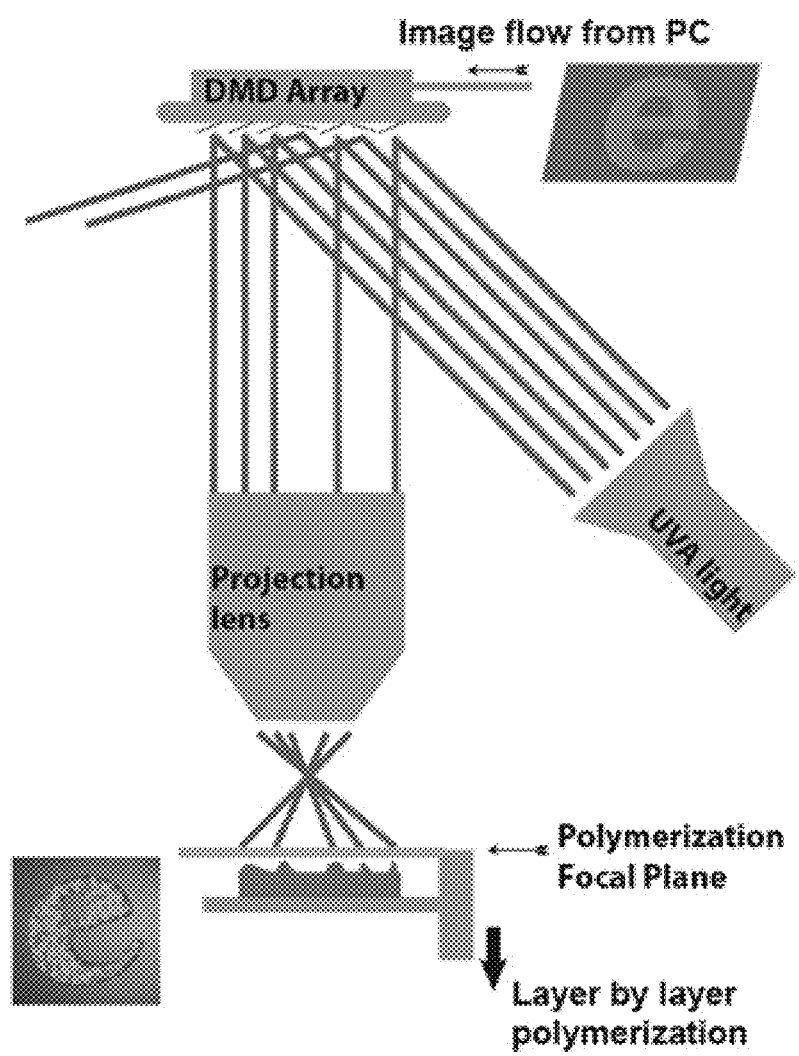
FIG. 26 Schematic showing bioprinting device as described further in Example C11.

A first bioprinter was designed based on dynamic light projection (DLP) technology and the schematic of the system is illustrated in FIG. 26. The system consists of five main components: 1. A UVA light source (365 nm, S2000, EXPO); 2. A digital micromirror array device (DMD, DLP-07 XGA; Texas Instruments) to modulate light to generate light patterns; 3. An optical system to project the light pattern towards the sample; 4. An automated stage to move in all three axes in a synchronized manner with the corresponding light patterns generated by the DMD; 5. A computer which feeds the DMD chip image flows and controls all the components.

For bioprinting, a HEK293 cell/biomatrix mixture was prepared by mixing 50 microlitre of the 15% GelMA stock solution containing 0.15% LAP with the same volume of HEK293 cell suspension to reach a final cell density of 40 million per ml. The cell/GelMA mixture was then added to the center of a glass coverslip and polymerized in the shape of the letter "e" by applying 365 nm UVA light mask for 30 seconds. Images were then acquired using a Zeiss LSM 880 confocal microscope.

Results showed that cell-laden constructs could be precisely bioprinted in the form of the letter "e" (actual results are shown on the bottom left hand side of FIG. 26: the "e"). This indicated that the bioprinting technology could enable precise control of the location of cell delivery.

In order to facilitate in vivo animal work, the core technology of the bioprinter described above was converted into a compact portable handheld design as follows. A light emitting head was composed of a high power LED emitter (365 nm, LED Engin) and an aspherical lens to provide collimated light beam. The light emitting head was built in a customized aluminum case for better heat dissipation. A rechargeable battery, power switch and other electronics were accommodated in a 3D printed plastic handle, which was assembled together with the light emitting head via a pivot to enable more freedom to turn the head. 3D printed adaptors allowed attaching to the head light guides of different dimensions to control the size of the illumination area. Inspired by the DMD based system, this handheld device can use masks printed on transparency sheet attached to the front of the head to generate customized light pattern to control photopolymerization.

Example C12: Bioprinting Cell Laden Constructs on the Posterior Side of the Human Cornea Ex Vivo In order to determine whether the portable handheld bioprinting device would enable the precise positioning of cells on the posterior side of the human cornea, bioprinting experiments were preformed ex vivo using HEK293 cells and human corneas obtained from eye banks. Red-fluorescent protein-labeled HEK293 cells were cultured to confluence in 6-well culture plates in DMEM-F12 with 5% fetal bovine serum. Cells were then detached from the culture dish with 100 microlitres of TripLE (Invitrogen) for 10 minutes at 37° C., cell suspensions were rinsed by centrifugation and resuspended in DMEM-F12 at a concentration of 80 million cells per ml.

For bioprinting, a HEK293 cell/biomatrix mixture was prepared by mixing 50 microlitre of the 15% GelMA stock solution containing 0.15% LAP with the same volume of HEK293 cell suspension to reach a final cell density of 40 million per ml.

The cell/GelMA mixture was then added to the center of a glass coverslip and polymerized in the shape of the letter "e" by applying 365 nm UVA light mask for 30 seconds. Images were then acquired using a Zeiss LSM 880 confocal microscope.

Human donor corneas obtained from eye banks were removed from their storage solution (Optisol) and rinsed briefly with DPBS. Under the dissecting microscope, the Descement membrane was carefully scraped before the corneas were further rinsed with DPBS. One cornea was then placed on a plastic lid of a 35 mm petri dish with the inner surface facing up.

A cell/biomatrix mixture was prepared freshly by mixing 50 microlitres of the 15% GelMA stock solution containing 0.15% LAP with the same volume of HEK-293-RFP cell suspension to reach the final cell density of 40 million per ml. The cell/GelMA mixture was then added to the center of the cornea and then a convex shaped plastic holder was applied to form a closed chamber mimicking the eye's anterior chamber. The whole construct was then carefully flipped and the handheld bioprinting device was used to project a 5.5-mm diameter circular pattern of 365 nm UVA light through the cornea for 30 seconds. This pattern of UV light was expected to polymerize the cell/GelMA mixture in the form of a disk attached to the posterior side of the cornea. In order to determine whether this occurred, we separated the cornea from the lid, rinsed any unpolymerized and unattached material by pipetting DPBS on the posterior side of the cornea and images were acquired using a Zeiss LSM 880 confocal microscope.

Figure 27:
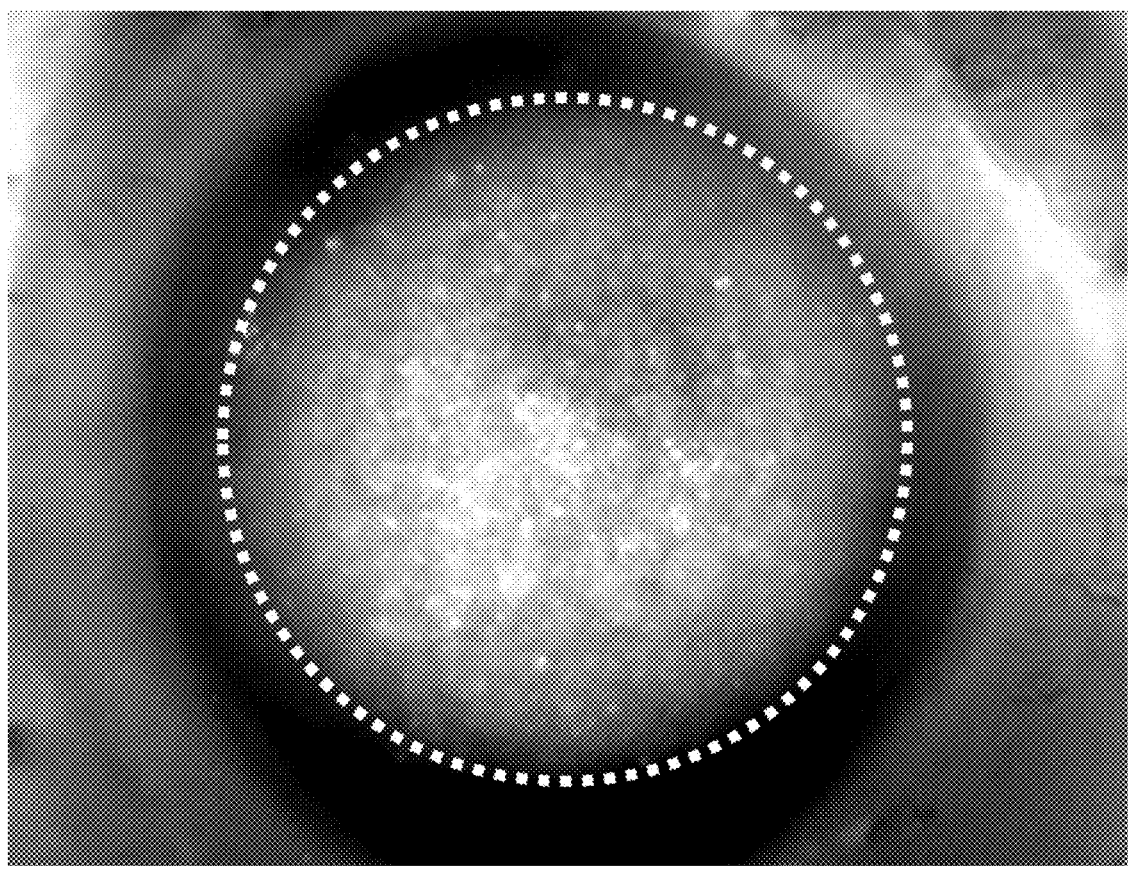
FIG. 27 Results showing cells can be bioprinted on the posterior side of the cornea by using a handheld device that projects 365 nm UVA light through the cornea. After unpolymerized and unattached material was rinsed, a circular pattern of fluorescent protein-labelled cells was retained on the posterior side of the cornea.

Results show that after unpolymerized and unattached material was rinsed, a circular pattern of red-fluorescent protein-labelled cells was retained on the posterior side of the cornea (FIG. 27). This confirmed that cells could be bioprinted on the posterior side of the cornea by using a handheld device that projects 365 nm UVA light through the cornea.

Example C13: Bioprinting Cell Laden Constructs on the Posterior Side of the Rabbit Cornea In Vivo CEC Preparation Cells obtained as described in Example C1 were detached from the culture dish with 100 microlitres of Accutase (ThermoFisher) for 10 minutes at 37° C., cell suspensions were rinsed by centrifugation and plated in X-VIVO15 supplemented with LATS inhibitor compound example no. 48a (diluted in DMSO) at a concentration of 3 micromolar. Cells were cultured in 6-well plates (corning) at 37° C. in 5% $CO_2$ for two weeks. Cells were passaged twice during this time by detaching cells with 1 mg/ml collagenase for 15 minutes at 37° C., rinsing cell suspensions by centrifugation and plating in fresh medium. These cells were then grown in XVIVO medium without a LATS inhibitor for a further 2 weeks to create mature CECs.

In order to prepare CECs for bioprinting inside the rabbit eye, a cell/biomatrix mixture was generated by mixing 15 microlitres of the 15% GelMA stock solution containing 0.15% LAP with 30 microlitres of CEC suspension to reach the final cell density from 0.625 million per ml to 25 million per ml. The cell/GelMA mixture was then added to the center of the cornea.

Rabbit Model of Corneal Endothelial Cell Deficiency

Corneal endothelial cell deficiency was unilaterally created in the right eye of NZA rabbits by scraping off the whole cornea endothelium using a silicon tip needle. The anterior chamber was rinsed using an aspiration cannula to remove floating debris. Forty microliters of freshly prepared cell/GelMA mixture was injected into the anterior chamber and followed by 365 nm UVA exposure for 30 seconds using the handheld bioprinter equipped with a 3 mm light guide about 1 cm away from the ocular surface. Gentle rinsing was performed using a small cannula to inject 500 microlitres of heparin supplemented balanced salt solution to remove unpolymerized material and floating cells. The left eye of each rabbit was left intact and served as a control. After cell delivery, rabbits received analgesic treatment (Tramadol 10 mg/kg PO BID in first 2 weeks, Meloxicam 0.3 mg/kg PO SID in first 2 weeks or as long as the animal showed signs of ocular discomfort), anti-inflammatory treatment (Ancef® (cefazolin) 50 mg sub-Tenon immediate post-procedure, Tobrex® ophthalmic solution t.i.d in 1st week and b.i.d thereafter, ampicillin 80 mg/kg/day (40 mg BID) SQ for first week) and immunosuppression (Cyclosporine A (0.5%) top oc. t.i.d 1st week and b.i.d. thereafter, Gentocin®-Durafilm® (Gentamicin sulfate and betamethasone, MERCK) top oc. t.i.d 1st week and b.i.d. thereafter, Cyclosporine A (5 mg/kg/day) SQ in 1st week and then % dosage thereafter).

Rabbits were sacrificed three weeks after cell delivery, corneas were dissected and fixed in 4% PFA. Immunohistochemistry was performed to detect the presence of human nuclear antigen (Millipore) to confirm the presence of human cells and ZO-1 (Invitrogen) to determine whether bioprinted CECs could form tight junctions observed in a normal corneal endothelioum. Images were then acquired using a Zeiss LSM 880 confocal microscope.

Figures 28A, 28B, 28C, 28D, 28E, 28F:
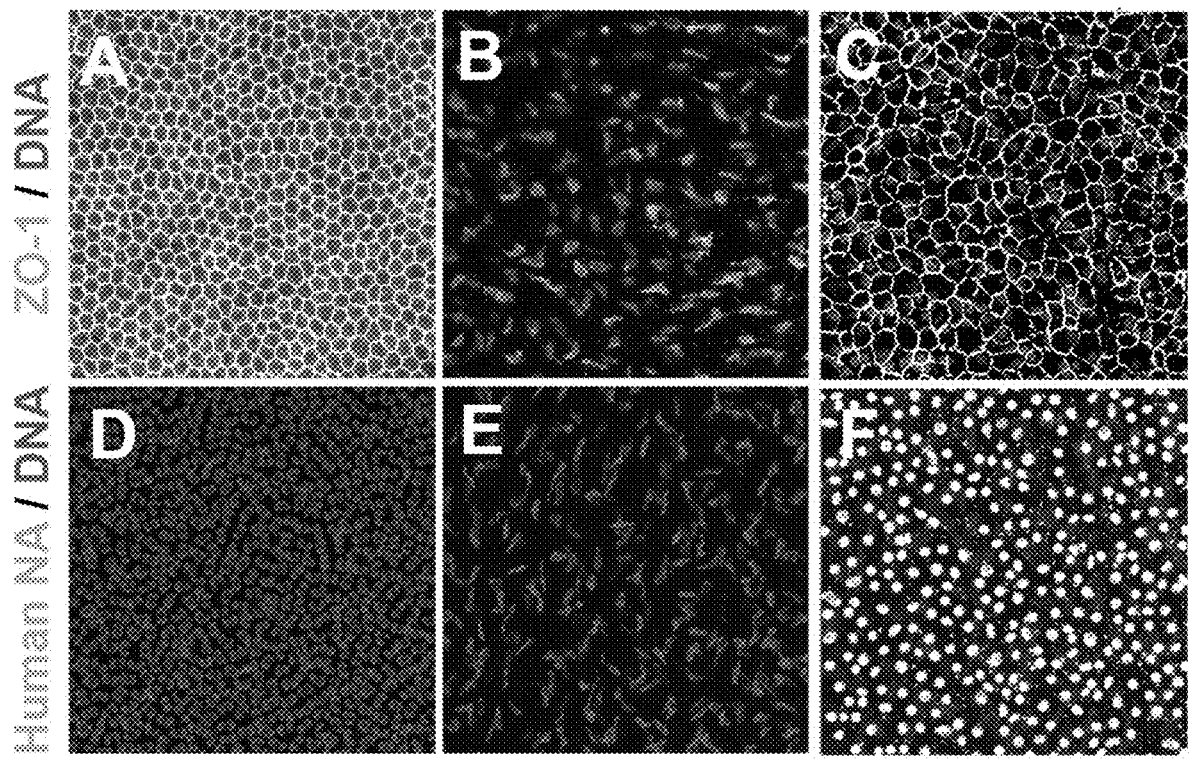
FIG. 28D and FIG. 28E show that human nuclear antigen immunostaining is absent in eyes that did not receive any human CECs. In contrast, human nuclear antigen-positive cells cover the imaged field in eyes where human CECs were bioprinted (FIG. 28F), indicating that the ZO-1-labeled corneal endothelium structure shown in FIG. 28C is composed of the human CECs bioprinted on the posterior side of the rabbit cornea.

Results indicated that in experimental rabbits, the corneal endothelium structure can be detected using ZO-1 immunohistochemistry (FIG. 28, panel A). In the right eye of a rabbit where the corneal endothelium was surgically removed and no CEC was bioprinted, the ZO-1 staining is absent, indicating an absence of normal corneal endothelium structure (FIG. 28, panel B). In the right eye of a rabbit where the corneal endothelium was surgically removed and CEC were bioprinted, the ZO-1 staining is present, indicating that a corneal endothelium structure has been rebuilt (FIG. 28, panel C).

Human nuclear antigen staining was used to confirm that the cells that rebuilt the corneal endothelium in FIG. 28, panel C are the human CECs delivered by bioprinting. FIG. 28, panels D and E show that human nuclear antigen immunostaining is absent in eyes that did not receive any human CECs. In contrast, human nuclear antigen-positive cells cover the imaged field in eyes where human CECs were bioprinted (FIG. 28, panel F), indicating that the ZO-1-labeled corneal endothelium structure shown in FIG. 28, panel C is composed of the human CECs bioprinted on the posterior side of the rabbit cornea.

Example C14: Bioprinting Cell Laden Constructs of Highly Customizable Shapes on the Posterior Side of the Human Cornea Ex Vivo Human donor corneas obtained from eye banks were removed from their storage solution (Optisol) and rinsed briefly with DPBS. Under the dissecting microscope, the Descement membrane was carefully scraped before the corneas were further rinsed with DPBS. One cornea was then placed on a plastic lid of a 35 mm petri dish with the inner surface facing up.

A cell/biomatrix mixture was prepared freshly by mixing 50 µl of the 15% GelMA stock solution containing 0.15% LAP with the same volume of HEK-293-RFP cell suspension to reach the final cell density of 40 million per ml. The cell/GelMA mixture was then added to the center of the cornea and then a convex shaped plastic holder was applied to form a closed chamber mimicking the eye's anterior chamber. The whole construct was then carefully flipped and the DLP bioprinting device mentioned in Example C11 was used to project customizable patterns of 365 nm UVA light through the cornea for 7.5 seconds. Any unpolymerized and unattached material was then rinsed by DPBS on the posterior side of the cornea and images were acquired using a Zeiss fluorescence stereomicroscope.

Figure 29:
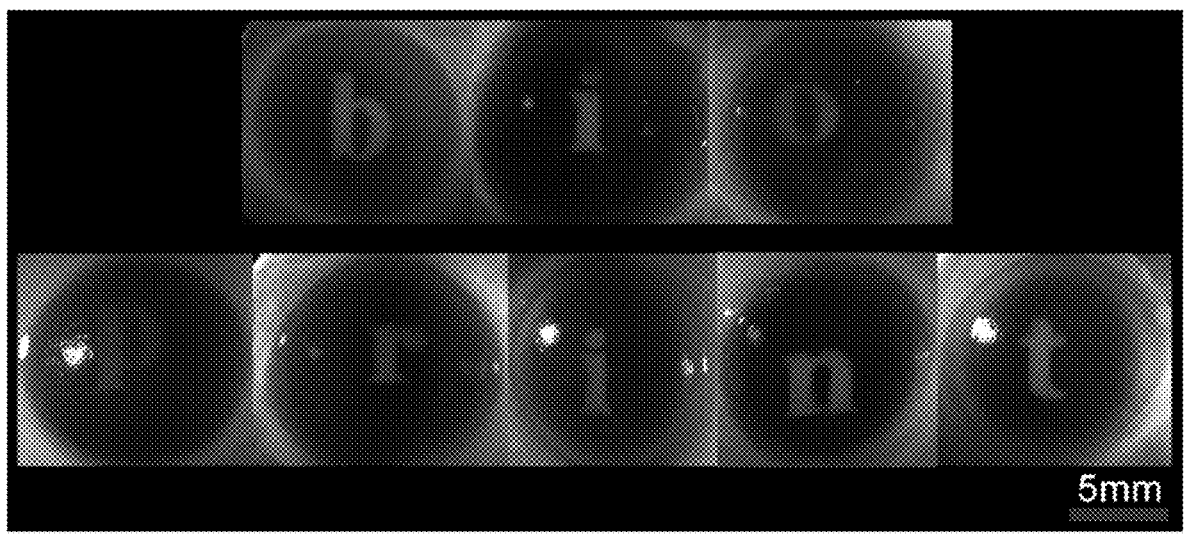
FIG. 29: Red-fluorescent-protein labeled HEK-293 cells were bioprinted into constructs of different letters on the posterior side of human cornea ex vivo.

In order to demonstrate the reproducibility and customizability of our bioprinting technology, light patterns in the design of different letters, which can be easily recognized, were projected to the samples. Results (FIG. 29) show that customizable cell laden constructs with high precision can be bioprinted to the posterior side of the cornea determined by the light patterns through the cornea.

Example C15: Residual Compound Estimation Study Standard Curve Preparation

A dilution series of stock standards were made at concentrations of 30 micromolar, 3 micromolar, 300 nM, 30 nM, 3 nM, 0.3 nM and 0 micromolar. Compound example 48a (10 mM in DMSO) stock was spiked into 50% acetonitrile 50% water to make the spike standards. The spiking standards were used to spike the blank media samples. 10 microlitre of spiking standard was added to 90 microlitres of media to create the spiked media standards. 3000 nM, 300 nM, 30 nM, 3 nM, 300 µM, 30 µM, and 0 nM media standards were used to generate the compound example no. 48a standard curve.

50 microlitre of each media sample was treated with 300 microlitre of the extraction solution. The extraction solution consists of acetonitrile/methanol (3:1). The standard curve samples were extracted using the same volumes and conditions as the unknown media samples. The extracted samples were centrifuged at 10,000 rpm for 5 min. After centrifugation, 200 microlitres of each sample supernatant was transferred to a clean 96-well plate. The extracted samples were analyzed by High Resolution LC-MS. Thermo Xcalibur Software and Quan Browser were used to generate the standard curve and calculate the concentration values. An external calibration method using linear log-log scaling was used to calculate the concentration of compound example no. 48a in the culture media samples.

LC-MS Analysis

High-resolution chromatography was performed using the Thermo Ultimate UPLC and a Kinetex 2.1×50 mM $C_{1-8}$ RP column (2.6 micron particles). The mobile phases consisted of 5 mM Ammonium Acetate in $H_2O$ for Buffer A, and 0.1% Formic Acid in Acetonitrile for Buffer B. A standard binary linear gradient was used for Reverse Phase Chromatography. The Thermo Q Exactive mass spectrometer was used for this study. The UPLC effluent was directed into the Q Exactive Mass Spectrometer which was equipped with an ESI ion source. The mass spectrometer was programmed to perform in High Resolution Full Scan mode. Extracted Ion Chromatograms were used for chromatographic integration.

Test System

Cell preparation for the CEC washout: the washout experiment was performed in triplicates, where each sample contained 0.5 million cells. All samples (media only, media with cells, supplemented with compound example no. 48a and cells in media supplemented with compound example no. 48a) were cultured at 37 degree incubator for the duration of the experiment. The medium used for the experiment was X-VIVO 15 (Lonza, cat no. 04-744Q).

The cells were cultured to passage 2 in X-VIVO-15 medium supplemented with 3 micromolar of compound example no. 48a. Upon reaching confluency, the medium was removed by aspiration and replaced with fresh medium not supplemented with compound example no. 48a. The cells were cultured for an additional week in the absence of compound example no. 48a. After one week of culture in the absence of the compound, the medium was removed by aspiration, refreshed with the medium without the compound and cell culture was continued in the absence of the compound for another six days. On day 7, the following samples were generated:

5. 2 ml of "blank" medium (not supplemented with the compound)
6. 2 ml of medium cultured in the presence of the compound (pre-wash)
7. 2 ml of media for each wash sample 1-10
8. Cell pellets (post-wash)

The cells were collected by using the cell lifter (Costar, cat #3008).

The media and cell pellet samples were analyzed and quantified using High Resolution LC-MS.

To estimate the residual levels of compound example no. 48a, cell pellets and supernatant were collected. The amount of compound example no. 48a was determined by LC-MS. Estimation of compound example no. 48a concentrations in the Pre-wash Media, Wash Media (Table 11) and the Cell Pellet are summarized (Table 12). Pre-wash Media samples have the highest levels of compound example no. 48a (approx. 35 nM to 122 nM range). Post-wash Pellet levels have low, but detectable levels of compound example no 48a (picomolar).

TABLE 11

Estimation of concentrations for compound example no. 48a in the Pre-wash Media and Wash Media

| Sample | Volume (mL) | compound example no. 48a (nM) in Triplicate #1 | compound example no. 48a (nM) in Triplicate #2 | compound example no. 48a (nM) in Triplicate #3 |
|---|---|---|---|---|
| Pre-wash Media | 2 | 35.344 | 66.248 | 121.863 |
| Wash Media 1 | 2 | 0.408 | 0.614 | 0.712 |
| Wash Media 2 | 2 | BLQ | 0.003 | 0.002 |
| Wash Media 3 | 2 | BLQ | BLQ | BLQ |
| Wash Media 4 | 2 | BLQ | BLQ | BLQ |
| Wash Media 5 | 2 | BLQ | BLQ | BLQ |
| Wash Media 6 | 2 | BLQ | BLQ | BLQ |
| Wash Media 7 | 2 | BLQ | BLQ | BLQ |
| Wash Media 8 | 2 | BLQ | BLQ | BLQ |
| Wash Media 9 | 2 | BLQ | BLQ | BLQ |
| Wash Media 10 | 2 | BLQ | BLQ | BLQ |

TABLE 12

Estimation of concentrations for compound example no. 48a in the Cell Pellet

| Sample | compound example no. 48a (nM) | compound example no. 48a (pg/cell) | Avg of compound example no. 48a (pg/cell) | # of cells in Pellet | Total of compound example no. 48a (pg) |
|---|---|---|---|---|---|
| PostWash_Pellet 1 | 0.004 | $0.13 \times 10^{-6}$ | $1.5 \times 10^{-6}$ | $0.5 \times 10^{6}$ | 0.75 |
| PostWash_Pellet 2 | 0.071 | $2.3 \times 10^{-6}$ | | | |
| PostWash_Pellet 3 | 0.065 | $2.1 \times 10^{-6}$ | | | |

The amount of compound example no. 48a in the Pre-wash Media from three incubations ranges from 35.344-121.863 nM. The average amount of compound example no. 48a in the Cell Pellet was 0.75 picograms for 500,000 cells.

Figure 30:
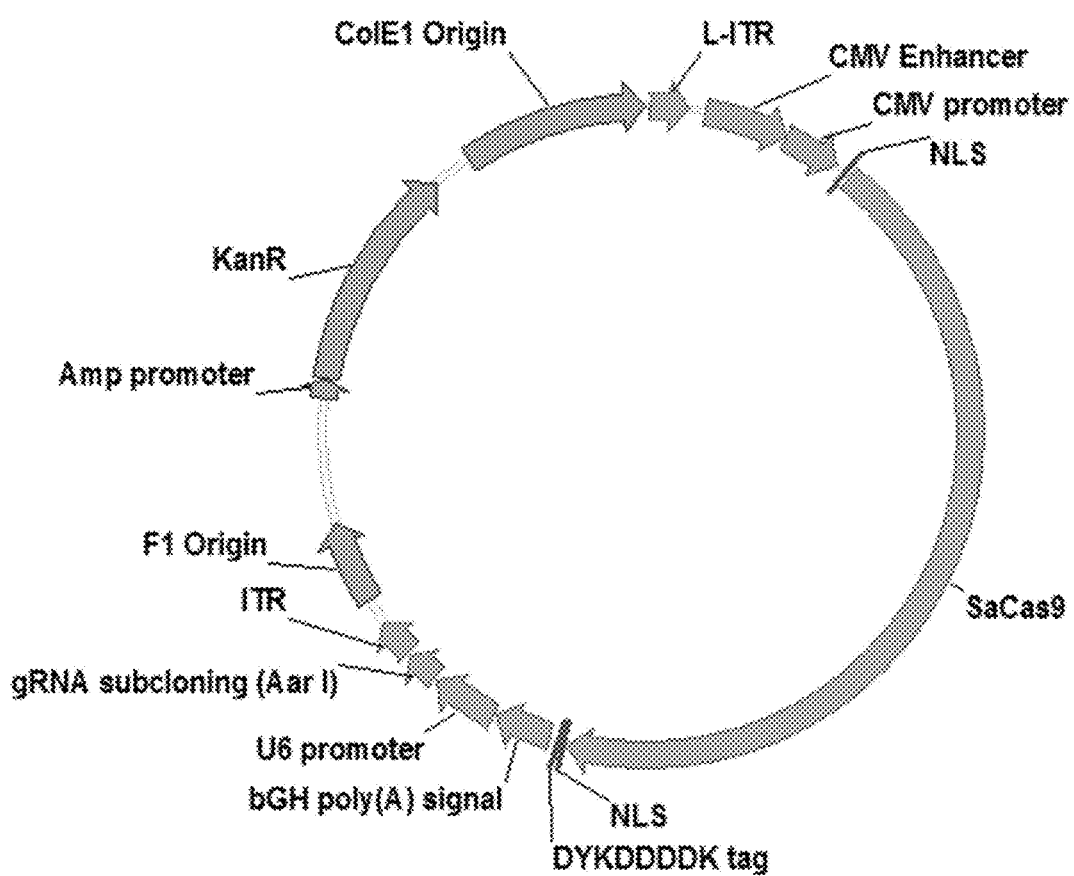
FIG. 30: Vector map shows the design of the AAV2 vector used to express the CRISPR system in LSCs and CECs.

Example C16: Reducing Immune Rejection by AAV-Mediated Deletion of the Beta-2-Microglobulin Gene in LSCs AAV Vector Design:

The vector map shown in FIG. 30 provides the design of the AAV vector used to express the CRISPR system in LSCs. The vector expressed *Staphylococcus aureus* Cas9 (Ran et al, *Nature*. 2015 Apr. 9; 520(7546):186-191) and a B2M-specific guide RNA inserted in the Aar I restriction site.

Cell Transduction:

LSCs obtained as described in Example B1 were cultured in X-VIVO15 medium supplemented with the LATS inhibitor compound example no 48a. LSC were transduced either in suspension immediately after isolation from human corneas or after isolation, attachment and expansion in the LATS inhibitor compound to a confluency of 50-60% in a 35 mm petri dish eight days after LSC isolation. LSCs were transduced at MOIs of 10K, 50K, 100K or 200K. The vector particles were diluted in a buffer composed of IxPBS+ 0.001% Pluronic and pipetted into the culture dish. The viral particle storage buffer alone represented the transduction negative control. Cells were cultured for 72 hours in a 5% $CO_2$ incubator before FACS analysis and sorting was performed.

FACS Analysis:

LSCs were treated with Accutase (ThermoFisher, Cat #A1110501) for 20 minutes in 5% $CO_2$ at 37° C. After scraping the cells, the reaction 5 was stopped by using cell culture medium containing 10% serum and transferred to a falcon tube for a centrifugation step (1000 rpm, 5 minutes). After aspirating the medium, cells were resuspended in 200 microlitre FACS buffer (PBS/10% FBS).

To analyze the expression of B2M and HLA-ABC, 5 microlitre APC mouse anti-human Beta2-microglobulin antibody (Biolegend, Cat #316312) and 20 microlitre PE mouse antihuman HLA-ABC antibody (BD Bioscience, Cat #560168) were added to the cell suspension and incubated for 30 minutes on ice. Cells were washed 3 times after antibody labelling with FACS buffer and resuspended in 500 microlitres in FACS buffer. Before FACS sorting, cells were filtered through a 70 micrometre filter and stored on ice until sorting. In order to prevent cells sticking to the wall, collection tubes were filled with the serum for 30 minutes before the sort. Cells were sorted on a BD FACSAria II instrument into 20 prepared collection tubes, using human serum enriched LSC medium. FACS data were analyzed using BD FACSDiva software.

Figure 31:
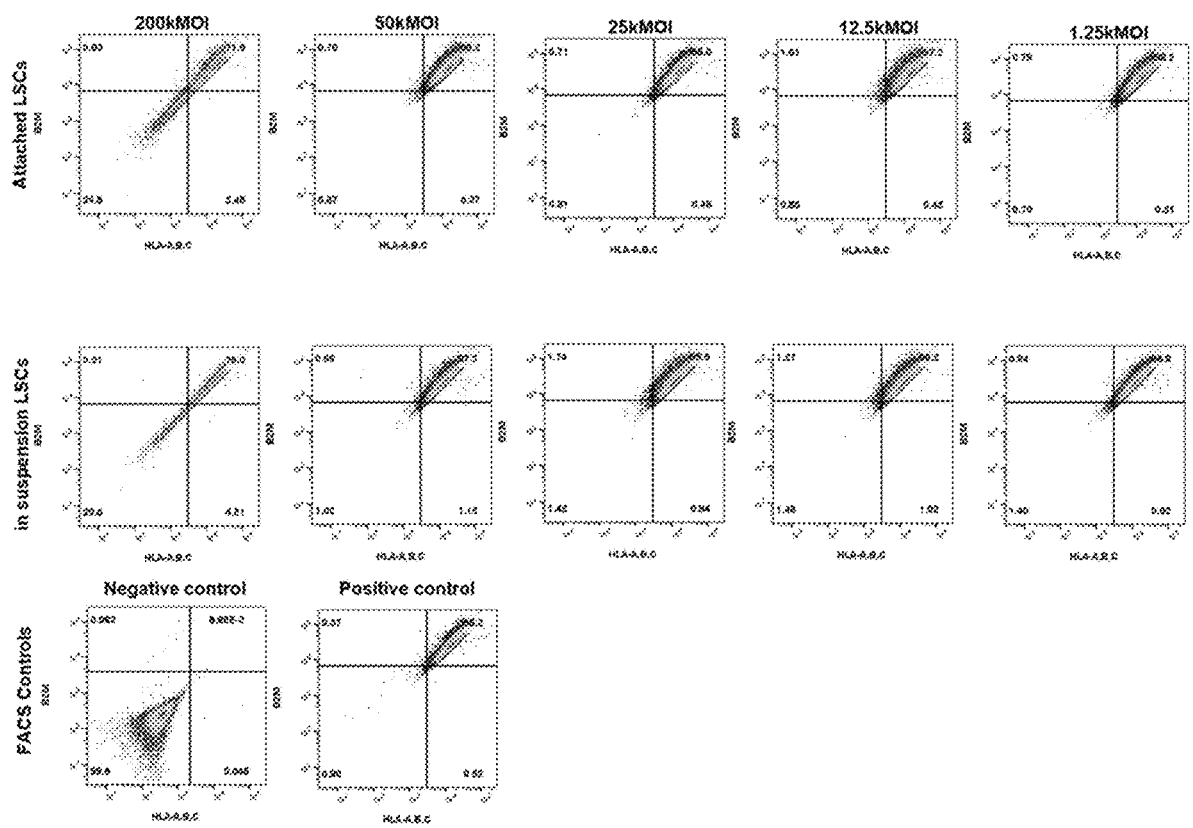
FIG. 31: FACS analysis of AAV-mediated expression of the CRISPR system enabled deletion of B2M and subsequent elimination of HLA A, B and C in LSCs.

Results presented in FIG. 31 show at an MOI of 200K, AAV-mediated expression of the CRISPR system enabled deletion of B2M and subsequent elimination of HLA A, B and C occurred in 24.9 percent of the LSCs when attached cells were transfected and 20.0 percent of LSCs when cells in suspension were transduced.

Example C17: Reducing Immune Rejection by AAV-Mediated Deletion of the Beta-2-Microglobulin Gene in CECs AAV Vector Design:

The vector map shown in FIG. 30 provides the design of the AAV vector used to express the CRISPR system in CECs. The vector expressed *Staphylococcus aureus* Cas9 (Ran et al, *Nature*. 2015 Apr. 9; 520(7546):186-191) and a B2M-specific guide RNA inserted in the Aar I restriction site.

Cell Transduction:

Cells obtained as described in Example C1 were detached from the culture dish with 100 microlitres of Accutase (ThermoFisher) for 10 minutes at 37° C., cell suspensions were rinsed by centrifugation and plated in corneal endothelial cell culture medium (human endothelial SF medium (Invitrogen) with human serum) in 6-well plates (Corning) supplemented with LATS inhibitor compound example no. 133 or example no 49 (diluted in DMSO) at a concentration of 10 micromolar or as a negative control DMSO alone without compound. Cells were cultured at 37° C. in 5% $CO_2$.

CECs were cultured in corneal endothelial cell culture medium (human endothelial SF medium (Invitrogen) with human serum) in 6-well plates (Corning) supplemented with LATS inhibitor compound example no. 133 or example no 49 (diluted in DMSO) at a concentration of 10 micromolar. CEC were transduced after isolation, attachment and expansion in the LATS inhibitor compound to a confluency of 50-60% in a 6-well plate eight days after CEC isolation. CECs were transduced at MOIs of 0.1K, 1K, 5K, 10K, 20K or 40K. The vector particles were diluted in a buffer composed of 1×PBS+0.001% Pluronic and pipetted into the culture dish. The viral particle storage buffer alone represented the transduction negative control. Cells were cultured for 72 hours in a 5% $CO_2$ incubator before FACS analysis and sorting was performed.

FACS Analysis:

CECs were treated with Accutase (ThermoFisher, Cat #A1110501) for 20 minutes in 5% $CO_2$ at 37° C. After scraping the cells, the reaction 5 was stopped by using cell culture medium containing 10% serum and transferred to a falcon tube for a centrifugation step (1000 rpm, 5 minutes). After aspirating the medium cells were resuspended in 200 microlitre FACS buffer (PBS/10% FBS).

To analyze the expression of B2M and HLA-ABC, 5 microlitre APC mouse anti-human Beta2-microglobulin antibody (Biolegend, Cat #316312) and 20 microlitre PE mouse antihuman HLA-ABC antibody (BD Bioscience, Cat #560168) were added to the cell suspension and incubated for 30 minutes on ice. Cells were washed 3 times after antibody labelling with FACS buffer and resuspended in 500 microlitres in FACS buffer.

Before FACS sorting, cells were filtered through a 70 micrometre filter and stored on ice until sorting. In order to prevent cells sticking to the wall, collection tubes were filled with the serum for 30 minutes before the sort. Cells were sorted on a BD FACSAria II instrument into 20 prepared collection tubes, using human serum enriched CEC culture medium. FACS data were analyzed using BD FACSDiva software.

Figure 32:
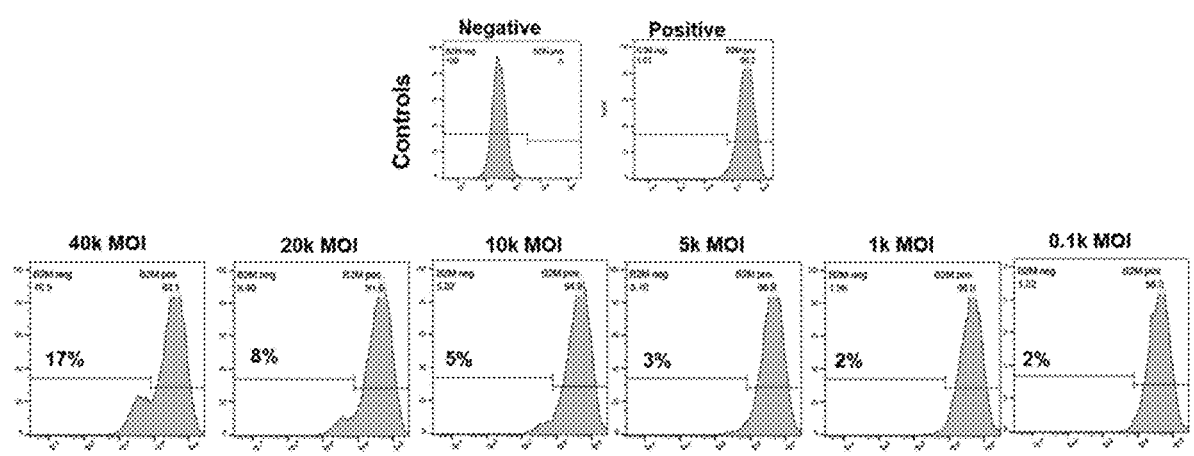
FIG. 32: FACS analysis of AAV-mediated expression of the CRISPR system enabled deletion of B2M and subsequent elimination of HLA A, B and C in CECs.

Results presented in FIG. 32 show that AAV-mediated expression of the CRISPR system enabled deletion of B2M and subsequent elimination of HLA A, B and C. At an MOI of 40K, B2M deletion occurred in 17 percent of the CECs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below. Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other embodiments, advantages, and modifications are considered to be within the scope of the following claims. Those skilled in the art will recognize or be able to ascertain, using no more than routine experimentation, many equivalents of the specific embodiments of the invention described herein.

What is claimed is:

1. A compound of Formula II:

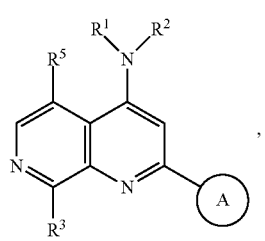

or a pharmaceutically acceptable salt thereof
wherein
Ring A is
(a) a 5- or 6-membered monocyclic heteroaryl that is linked to the remainder of the molecule through a carbon ring member and comprises, as ring member, 1 to 4 heteroatoms that are independently selected from the group consisting of N, O and S, provided that at least one of the heteroatom ring member is an unsubstituted nitrogen (—N═) positioned at the 3- or the 4-position relative to the linking carbon ring member of the 5-membered heteroaryl or at the para ring position of the 6-membered heteroaryl; or (b) a 9-membered fused bicyclic heteroaryl that is selected from the group consisting of:

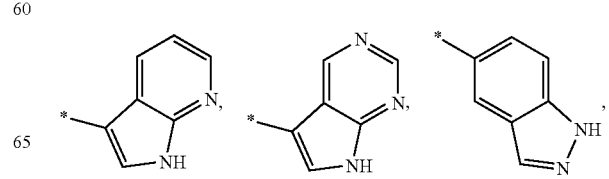

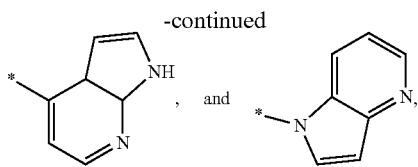

wherein "*" represents the point of attachment of ring A to the remainder of the molecule; and wherein ring A is unsubstituted or substituted by 1 to 2 substituents independently selected from the group consisting of halogen, cyano, $C_{1-6}$alkyl, $C_{1-6}$haloalkyl, —$NH_2$, $C_{1-6}$alkylamino, di-($C_{1-6}$alkyl)amino, $C_{3-6}$cycloalkyl, and phenylsulfonyl;

$R^0$ is hydroxyl or $C_{1-6}$alkoxy;

$R^1$ is hydrogen or $C_{1-6}$alkyl;

$R^2$ is selected from the group consisting of (a) $C_{1-8}$alkyl that is unsubstituted or substituted by 1 to 3 substituents independently selected from the group consisting of:
  (i) halogen;
  (ii) cyano;
  (iii) oxo;
  (iv) $C_2$alkenyl;
  (v) $C_2$alkynyl;
  (vi) $C_{1-6}$haloalkyl;
  (vii) —$OR^6$, wherein $R^6$ is selected from hydrogen, $C_{1-6}$alkyl that is unsubstituted or substituted by $R^0$ or —$C(O)R^0$;
  (viii) —$NR^{7a}R^{7b}$, wherein $R^{7a}$ is hydrogen or $C_{1-6}$alkyl, and $R^{7b}$ is selected from hydrogen, —$C(O)R^0$, $C_{1-6}$alkyl that is unsubstituted or substituted by —$C(O)R^0$;
  (ix) —$C(O)R^8$, wherein $R^8$ is $R^0$ or —NH—$C_{1-6}$alkyl-$C(O)R^0$;
  (x) —$S(O)_2C_{1-6}$alkyl;
  (xi) monocyclic $C_{3-6}$cycloalkyl or polycyclic $C_{7-10}$cycloalkyl that are each unsubstituted or substituted by 1 to 2 substituents independently selected from the group consisting of halogen, $C_{1-6}$alkyl, hydroxy$C_{1-6}$alkyl, $C_{1-6}$haloalkyl, $R^0$, —$NH_2$, $C_{1-6}$alkylamino, and di-($C_{1-6}$alkyl)amino;
  (xii) 6-membered heterocycloalkyl comprising, as ring members, 1 to 2 heteroatoms independently selected from the group consisting of N, O and S and that is unsubstituted or substituted by 1 to 2 substituents independently selected from the group consisting of hydroxyl, halogen, $C_{1-6}$alkyl, $C_{1-6}$alkylamino, and di-(Ci-6alkyl)amino;
  (xiii) phenyl that is unsubstituted or substituted by halogen;
  (xiv) 5- or 6-membered monocyclic heteroaryl comprising, as ring members, 1 to 4 heteroatoms independently selected from the group consisting of N and O; and
  (xv) 9- or 10-membered fused bicyclic heteroaryl comprising, as ring member, 1 to 2 heteroatoms independently selected from the group consisting of N and O;

(b) —$S(O)_2C_{1-6}$alkyl;

(c) phenyl that is unsubstituted or substituted by 1 to 2 substituents independently selected from the group consisting of halogen, $C_{1-6}$alkyl and $R^0$;

(d) $C_{3-6}$cycloalkyl that is unsubstituted or substituted by 1 to 2 substituents independently selected from the group consisting of $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$; and (e) 4-membered heterocycloalkyl comprising, as ring members, 1 to 2 heteroatoms selected from the group consisting of N, O and S and that is unsubstituted or substituted by 1 to 2 substituents independently selected from the group consisting of $C_{1-6}$haloalkyl, $R^0$, $C_{1-6}$alkylamino, di-($C_{1-6}$alkyl)amino, —$C(O)R^0$, and $C_{1-6}$alkyl that is unsubstituted or substituted by $R^0$ or —$C(O)R^0$;

or, $R^1$ and $R^2$ can be taken together with the nitrogen atom to which both are bound to form a 4- to 6-membered heterocycloalkyl that can include, as ring members, 1 to 2 additional heteroatoms independently selected from the group consisting of N, O, and S, wherein the 4- to 6-membered heterocycloalkyl formed by $R^1$ and $R^2$ taken together with the nitrogen atom to which both are bound is unsubstituted or substituted by 1 to 3 substituents independently selected from the group consisting of halogen, $C_{1-6}$alkyl, $C_{1-6}$haloalkyl, and $R^0$;

$R^3$ is selected from the group consisting of hydrogen, halogen and $C_{1-6}$alkyl; and $R^5$ is selected from the group consisting of hydrogen, halogen and —NH-(3- to 8-membered heteroalkyl), wherein the 3- to 8-membered hetero$C_{3-8}$alkyl of the —NH-(3- to 8-membered heteroalkyl) comprises 1 to 2 oxygen atoms as chain members and is unsubstituted or substituted by $R^0$.

2. The compound according to claim 1, wherein ring A is selected from the group consisting of

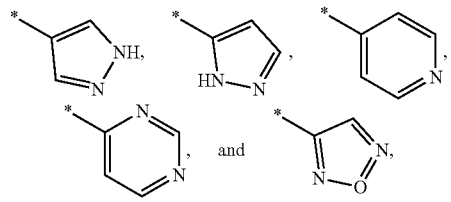

which are each unsubstituted or substituted by a substituent selected from the group consisting of halogen, cyano, $C_{1-6}$alkyl, $C_{1-6}$haloalkyl, and —$NH_2$; or is

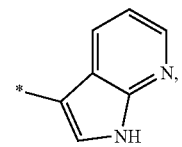

which is unsubstituted or substituted by $C_{1-6}$alkyl.

3. The compound according to claim 1, wherein ring A is

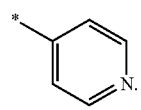

4. The compound according to claim 1, wherein $R^2$ is selected from the group consisting of:
(a) $C_{1-8}$alkyl that is unsubstituted or substituted by A1 to A3 substituents independently selected from the group consisting of (i) cyano;

(ii) C₂alkynyl;

(iii) C_{1-6}haloalkyl;

(iv) —OR⁶, wherein R⁶ is selected from the group consisting of hydrogen, and C_{1-6}alkyl that is unsubstituted or substituted by R⁰ or —C(O)R⁰;

(v) —NR^{7a}R^{7b}, wherein R^{7a} is hydrogen or C_{1-6}alkyl, and R^{7b} is selected from the group consisting of hydrogen, —C(O)R⁰, and C_{1-6}alkyl that is unsubstituted or substituted by —C(O)R⁰;

(vi) —C(O)R⁸, wherein R⁸ is R⁰;

(vii) —S(O)2C_{1-4}alkyl;

(viii) monocyclic C_{3-6}cycloalkyl that is unsubstituted or substituted by a substituent selected from the group consisting of C_{1-6}alkyl, hydroxyC_{1-6}alkyl and R⁰;

(ix) 6-membered heterocycloalkyl comprising, as ring members, 1 to 2 heteroatoms independently selected from the group consisting of N and O, and wherein the 6-membered heterocycloalkyl is unsubstituted or substituted by C_{1-6}alkyl;

(x) phenyl that is unsubstituted or substituted by halogen; and (b) C_{3-6}cycloalkyl that is unsubstituted or substituted by 1 to 2 substituents independently selected from C_{1-6}haloalkyl, R⁰, C_{1-6}alkylamino, —C(O)R⁰, C_{1-6}alkyl that is unsubstituted or substituted by —R⁰ or —C(O)R⁰.

5. The compound according to claim 1, wherein R² is selected from the group consisting of:

n-propyl, isopropyl, t-butyl,

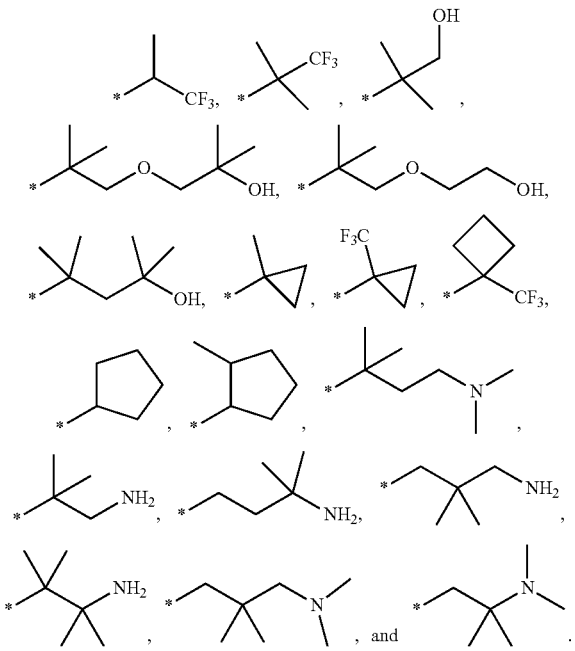

6. The compound according to claim 1, wherein the compound is of Formula A3:

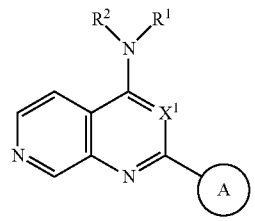

wherein
X¹ is CH;
Ring A is

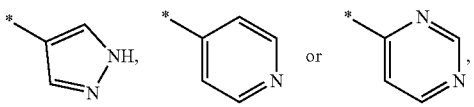 [SMILES: *c1cn[nH]c1 ; *c1ccncc1 ; *c1ccncn1]

each of which is unsubstituted or substituted by a substituent selected from the group consisting of halogen, C_{1-6}alkyl, C_{1-6}haloalkyl, and —NH₂;

R¹ is hydrogen or unsubstituted C_{1-6}alkyl; and

R² is (a) C_{1-8}alkyl that is unsubstituted or substituted by 1 substituents selected from the group consisting of
(i) C_{1-4}haloalkyl; and
(ii) —OR⁶, wherein R⁶ is selected from the group consisting of hydrogen and C_{1-6}alkyl that is unsubstituted or substituted by hydroxyl; or (b) monocyclic C_{3-6}cycloalkyl that is unsubstituted or substituted by C_{1-6}alkyl or C_{1-6}haloalkyl and R⁰.

7. A compound, or a salt thereof, selected from the group consisting of: N (4 methoxy-2-methylbutan-2-yl)-2-(pyridin-4-yl)-1,7-naphthyridin-4-amine; N-[2-methyl-1-(propan-2-yloxy)propan-2-yl]-2-(pyridin-4-yl)-1,7-naphthyridin-4-amine; N-[(2S)-butan-2-yl]-2-(pyridin-4-yl)-1,7-naphthyridin-4-amine; N-[(2R)-butan-2-yl]-2-(pyridin-4-yl)-1,7-naphthyridin-4-amine; N-(1-methoxy-2-methylpropan-2-yl)-2-(pyridin-4-yl)-1,7-naphthyridin-4-amine; N-methyl-N-(propan-2-yl)-2-(pyridin-4-yl)-1,7-naphthyridin-4-amine; 3-methyl-3-{[2-(pyridin-4-yl )-1,7-naphthyridin-4-yl]amino}butan-1-ol; N-tert-butyl-2-(pyridin-4-yl)-1,7-naphthyridin-4-amine; 2,2-dimethyl-1-[2-(pyridin-4-yl)-1,7-naphthyridin-4-yl]piperidin-4-ol; 2,4-dimethyl-4-{[2-(pyridin-4-yl)-1,7-naphthyridin-4-yl]amino pentan-2-ol; N-cyclopentyl-2-(pyridin-4-yl)-1,7-naphthyridin-4-amine; dimethyl(3-methyl-3-{[2-(pyridin-4-yl)-1,7-naphthyridin-4-yl]amino}butyl)amine; N,N-diethyl-2-(pyridin-4-yl)-1,7-naphthyridin-4-amine; 2-methyl-1-(2-methyl-2-{[2-(pyridin-4-yl)-1,7-naphthyridin-4-yl]amino}propoxy)propan-2-ol; N-propyl-2-(pyridin-4-yl)-1,7-naphthyridin-4-amine; N-tert-butyl-2-(3-methyl-1H-pyrazol-4-yl)-1,7-naphthyridin-4-amine; N-tert-butyl-2-(pyrimidin-4-yl)-1,7-naphthyridin-4-amine; 2-(2-aminopyrimidin-4-yl)-N-tert-butyl-1,7-naphthyridin-4-amine; N-tert-butyl-2-{1H-pyrrolo[2,3-b]pyridin-4-yl}-1,7-naphthyridin-4-amine; N-tert-butyl-2-(pyridazin-4-yl)-1,7-naphthyridin-4-amine; 2-(2-aminopyridin-4-yl)-N-tert-butyl-1,7-naphthyridin-4-amine; N,N-diethyl-2-(3-fluoropyridin-4-yl)-1,7-naphthyridin-4-amine; (3-{[2-(3-fluoropyridin-4-yl)-1,7-naphthyridin-4-yl]amino}-3-methylbutyl)dimethylamine; 2-(3-fluoropyridin-4-yl)-N-methyl-N-(propan-2-yl)-1,7-naphthyridin-4-amine; N-tert-butyl-2-(3-fluoropyridin-4- yl)-1,7-naphthyridin-4-amine; 2-(3-fluoropyridin-4-yl)-N-(2-methylbutan-2-yl)-1,7-naphthyridin-4-amine; 2-{[2-(3-fluoropyridin-4-yl)-1,7-naphthyridin-4-yl]amino}-2-methylpropan-1-ol; 2 (3 fluoropyridin-4-yl)-N-[2-methyl-1-(morpholin-4-yl)propan-2-yl]-1,7-naphthyridin-4-amine; N-tert-butyl-2-(3-chloropyridin-4-yl)-1,7-naphthyridin-4-amine; 2 (pyridin-4-yl)-N-(1-(trifluoromethyl)cyclobutyl)-1,7-naphthyridin-4-amine; 2-methyl-N1-(2-(pyridin-4-yl)-1,7-naphthyridin-4-yl)propane-1,2-diamine; N-(oxetan-3-yl)-2-(pyridin-4-yl)-1,7-naphthyridin-4-amine; N-(1-methylcyclopropyl)-2-(pyridin-4-yl)-1,7-naphthyridin-4-amine; N-(1 methylcyclobutyl)-2-(pyridin-4-yl)-1,7-naphthyridin-4-amine; 2,2-dimethyl-N1-(2-(pyridin-4-yl)-1,7-naphthyridin-4-yl)propane-1,3-diamine; $N^2,N^2$,2-trimethyl-$N^1$-(2-(pyridin-4-yl)-1,7-naphthyridin-4-yl)propane-1,2-diamine; 4-(2-methylpiperazin-1-yl)-2-(pyridin-4-yl)-1,7-naphthyridine; 2-methyl-$N^1$-(2-(pyridin-4-yl)-1,7-naphthyridin-4-yl)propane-1,3-diamine; N-(tert-butyl)-N-methyl-2-(pyridin-4-yl)-1,7-naphthyridin-4-amine; N-(1-methylcyclobutyl)-2-(pyrimidin-4-yl)-1,7-naphthyridin-4-amine; and (S)-1,1,1-trifluoro-2-methyl-3-((2-(pyridin-4-yl)-1,7-naphthyridin-4-yl)amino)propan-2-ol; 2-(3-chloropyridin-4-yl)-N,N-diethyl-1,7-naphthyridin-4-amine.

8. A pharmaceutical composition comprising a compound of claim 1 as an active ingredient and at least one pharmaceutically acceptable excipient.

9. The compound according to claim 1, wherein Ring A is a 5- or 6-membered monocyclic heteroaryl that is linked to the remainder of the molecule through a carbon ring member and comprises, as ring member, 1 to 2 heteroatoms that are selected from N, provided that at least one of the nitrogen atom ring member is an unsubstituted nitrogen (—N═) positioned at the 3- or the 4-position relative to the linking carbon ring member of the 5-membered heteroaryl or at the para ring position of the 6-membered heteroaryl.

10. The compound according to claim 1, wherein ring A is selected from

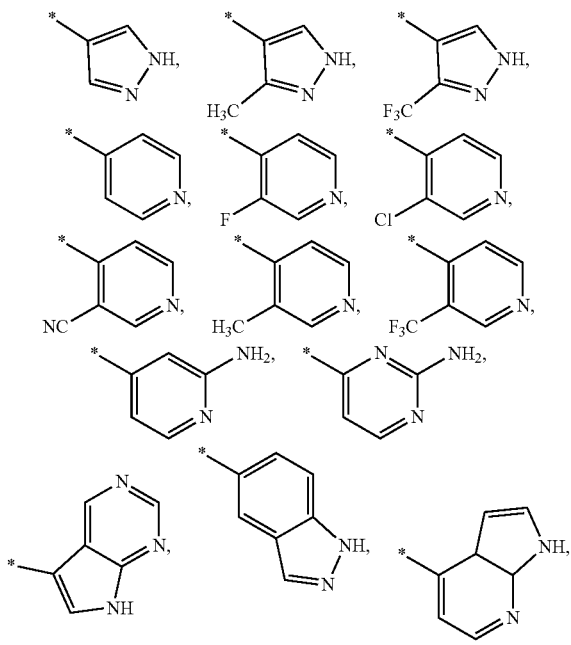

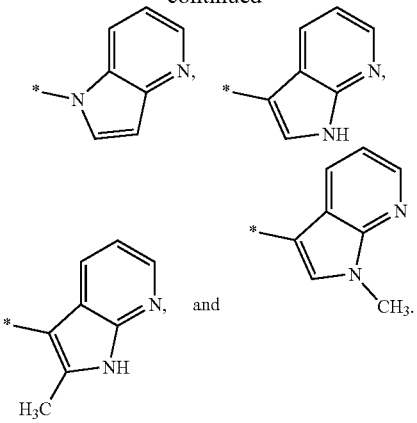

11. The compound according to claim 1, wherein R² is selected from
(a) $C_{1-8}$alkyl that is unsubstituted or substituted by 1 to 2 substituents independently selected from
  (i) cyano;
  (ii) $C_2$alkynyl;
  (iii) $C_{1-6}$haloalkyl;
  (iv) —OR⁶, wherein R⁶ is selected from hydrogen, $C_{1-6}$alkyl that is unsubstituted or substituted by hydroxyl or —C(O)H;
  (v) —NR$^{7a}$R$^{7b}$, wherein R$^{7a}$ is hydrogen or $C_{1-6}$alkyl, and R$^{7b}$ is selected from hydrogen, —C(O)—$C_{1-6}$ alkoxy, and $C_{1-6}$alkyl that is unsubstituted or substituted by — C(O)OH; and
  (vi) monocyclic $C_{3-6}$cycloalkyl that is unsubstituted or substituted by a hydroxyl; and
(b) $C_{3-6}$cycloalkyl that is unsubstituted or substituted by 1 to 2 substituents independently selected from $C_{1-6}$haloalkyl, R⁰, $C_{1-6}$alkylamino, and $C_{1-6}$alkyl that is unsubstituted or substituted by hydroxyl or —C(O)—$C_{1-6}$alkoxy.

12. The compound according to claim 1, wherein R² is selected from
(a) $C_{1-8}$alkyl that is unsubstituted or substituted by 1 to 2 substituents independently selected from
  (i) $C_{1-6}$haloalkyl;
  (ii) —OR⁶, wherein R⁶ is selected from hydrogen, and $C_{1-6}$alkyl that is unsubstituted or substituted by hydroxyl; and
  (iii) monocyclic $C_{3-6}$cycloalkyl that is unsubstituted or substituted by hydroxyl; and
(b) $C_{3-6}$cycloalkyl that is unsubstituted or substituted by 1 to 2 substituents independently selected from $C_{1-6}$haloalkyl, R⁰, $C_{1-6}$alkylamino, and $C_{1-6}$alkyl that is unsubstituted or substituted by hydroxyl.

13. The compound according to claim 1, wherein ring A is

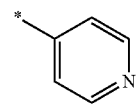 [SMILES: *c1ccncc1]

and R² is selected from ethyl,
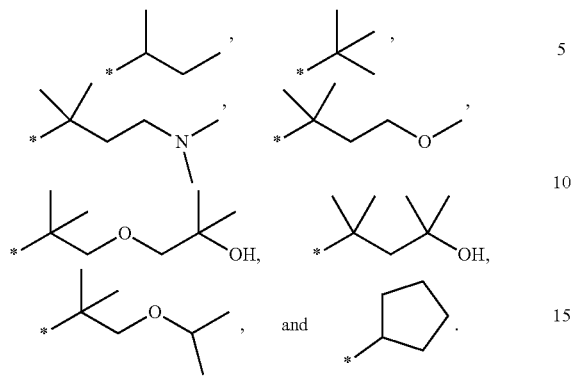
14. The compound according to claim 1, wherein R² is tert-butyl.